United States Patent
Kajino et al.

(10) Patent No.: US 7,399,759 B2
(45) Date of Patent: Jul. 15, 2008

(54) 1,3-BENZOTHIAZINONE DERIVATIVES AND USE THEREOF

(75) Inventors: Masahiro Kajino, Osaka (JP); Akira Kawada, Osaka (JP); Yutaka Nakayama, Tsukuba (JP); Haruhide Kimura, Osaka (JP); Taisuke Tawaraishi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 205 days.

(21) Appl. No.: 10/488,384

(22) PCT Filed: Sep. 2, 2002

(86) PCT No.: PCT/JP02/08866

§ 371 (c)(1),
(2), (4) Date: Sep. 13, 2004

(87) PCT Pub. No.: WO03/020719

PCT Pub. Date: Mar. 13, 2003

(65) Prior Publication Data

US 2005/0032786 A1 Feb. 10, 2005

(30) Foreign Application Priority Data

Sep. 3, 2001 (JP) .............................. 2001-265743
Jun. 20, 2002 (JP) .............................. 2002-180528

(51) Int. Cl.
C07D 417/04 (2006.01)
A61K 31/538 (2006.01)

(52) U.S. Cl. ..................... 514/226.5; 544/50

(58) Field of Classification Search ............... 544/50; 514/226.5
See application file for complete search history.

(56) References Cited

U.S. PATENT DOCUMENTS

2003/0186971 A1 10/2003 Kimura et al.
2006/0034832 A1 2/2006 Kimura et al.

FOREIGN PATENT DOCUMENTS

EP 1325918 A1 7/2003
WO WO 02/18356 3/2002

OTHER PUBLICATIONS

Chemical abstracts, vol. 51, Col. 17927-17930.*
Conti et al. Bollettino Scientifico della Facolta di Chimica Industriale di Bologna (1957), 15, 37-9 (Abstract in English, STN printout 2 pages).*
XP002295355, 6001 Chemical Abstracts, Columbus, Ohio, US, (1978), p. 621, vol. 89, No. 5.
Chemical Abstracts, vol. 51, Col. 17927-17930, (1957), Conti et al.
Examination Report in EPO Application 02 762 953 dated Sep. 6, 2007.
S. Pallazzo and L.I. Giannola, *Atti Accad. Sci., Lett. Arti Palermo. Parte I* (1976) 34(2), 73-82.
L. Conti and G. Leandri, *Boll. Sci. Fac. Chim. Ind. Bologna* 15:37-39 (1957).
S. Pallazzo and L.I. Giannola, *Attl Accad. Sci., Lett. Arti Palermo, Parte I* (1976) 34(2), 73-82 (with English translation).

* cited by examiner

*Primary Examiner*—Kahsay Habte
(74) *Attorney, Agent, or Firm*—Edwards Angell Palmer & Dodge LLP; David G. Conlin; Mark D. Russett

(57) ABSTRACT

This invention provides a compound represented by the formula (I):

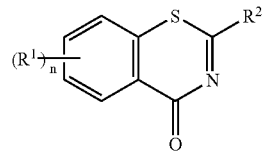

wherein $R^1$ is a hydrogen atom, a halogen atom, hydroxy, nitro, optionally halogenated alkyl, alkoxy optionally having substituents, acyl or amino optionally having substituents; $R^2$ is pyridyl, furyl, thienyl, pyrrolyl, quinolyl, pyrazinyl, pyrimidinyl, pyridazinyl, indolyl, tetrahydroquinolyl or thiazolyl, each of which may have substituents; n is 1 or 2; or a salt. And this invention provides a safe pharmaceutical comprising the compound of the formula (I), which has an excellent apoptosis inhibitory effect and MIF binding effect, for preventing and/or treating heart disease, nervous degenerative disease, cerebrovascular disease, central nervous infectious disease, traumatorathy, demyelinating disease, bone and articular disease, kidney disease, liver disease, osteomyelodysplasia, AIDS, cancer, and the like.

11 Claims, No Drawings

1,3-BENZOTHIAZINONE DERIVATIVES AND USE THEREOF

This application is the National Phase filing of International Patent Application No. PCT/JP02/08866, filed Sep. 2, 2002.

TECHNICAL FIELD

This invention relates to 1,3-benzothiazinone derivatives, the production thereof and the use thereof, which are useful as drugs.

BACKGROUND ART

Apoptosis is closely involved in morphogenesis and histogenesis in the development process, maintenance of homeostasis, and bio-defense, and it is cell death having an important role in maintaining individual lives. When the death process regulated by genes is congenitally or postnatally hindered, apoptosis is excessively induced or inhibited to cause functional disorders in various organs, and thus diseases (Saishin Igaku, vol. 54, p. 825, 1999).

Lately, it has been come out that apoptosis plays an important role in occurrence or development of several diseases (The New England Journal of Medicine, vol. 341, p. 759, 1999). In a mammalian heart, it is considered that heart muscle cells are finally differentiated cells, and lose proliferation activity. Accordingly, when heart muscle cells disappear by apoptosis, the heart contraction should be maintained only by remaining cells. Disappearance of heart muscle cells beyond threshold necessary for maintaining the heart contraction would result in abnormal heart functions and diseases. Apoptosis of heart muscle cells is actually observed in various animal models with cardiac insufficiency or in human patients with cardiac insufficiency, and it is noted that disappearance or lack of heart muscle cells by apoptosis may be involved in onset and progress of cardiac insufficiency (The New England Journal of Medicine, vol. 335, p. 1182, 1996). It is further recognized that in heart muscle cells of human patients with cardiac insufficiency, an apoptosis-inhibitory factor Bcl-2 is expressed in excess, which is a possible compensation mechanism for cardiac insufficiency (The New England Journal of Medicine, vol. 336, p. 1131, 1997); that serum levels of soluble Fas (sFas has an inhibitory activity on apoptosis) which lacks a membrane penetration domain in the Fas receptor known as an apoptosis inducing receptor, are increased significantly in proportion to severeness in NYHA class (New York Heart Association Functional Class) but independently of fundamental diseases, and thus an increase in serum levels of sFas is considered to be a compensatory mechanism to inhibit promotion of apoptosis in cardiac insufficiency (Journal of the American College of Cardiology, vol. 29, p. 1214, 1997); and that in the heart with congestive cardiomyopathy, deoxyribonuclease I (DNase I) considered as a indicator of apoptosis is increased 7-fold or more than in healthy persons (Journal of Molecular & Cell Cardiology, vol. 28, p. 95, 1996).

When considered at the level of internal organs, the functions of the heart muscle are lowered in human cardiac diseases, and insufficient heart muscle contraction often endangers the maintenance of the life. Abnormalities, for example, myocardial disorders, abnormal heart pumping, pressure burden due to high blood pressure, volume burden due to acute nephritis, and insufficient blood pumping caused by these abnormalities lead to the onset of cardiac insufficiency. Against these abnormalities, the sympathetic nervous system, the internal secretion system, and the like work together to start a compensating mechanism, resulting in cardiac hypertrophy accompanied by hypertrophy of myocardial cells. However, when these abnormalities occur alone or in combination persistently and chronically, the hypertrophied myocardial cells are not sufficiently supplied with blood, and thus the myocardial cells disappear due to apoptosis, etc. As a result, the compensating mechanism fails to work, leading to a cardiac insufficiency syndrome accompanied by myocardial disorders such as insufficient heart contraction, a reduction in pumped blood, circulatory disorders in internal organs, venostasis, and body fluid retention.

At present, the cardiac insufficiency syndrome is treated by using cardiotonic glycosides such as digoxin, sympathetic agents such as dobutamine, phosphodiesterase inhibitors such as amrinone, vasodilators such as hydralazine, calcium antagonist, angiotensin converting enzyme inhibitor and angiotensin receptor antagonist, and dilated cardiomyopathy is treated by β-blockers, etc.

On the other hand, 1,3-benzothiazinone compound whose 2-position is substituted by pyridyl is described in Chemical Abstract 51:17927g, however, the activity thereof is not described on it.

Furthermore, 1,3-benzothiazinone compound having heart muscle cells apoptosis inhibitory effect are disclosed on WO 02/18356, which is an earlier application of this applicant.

The drugs for treating cardiac insufficiency syndrome don't possess efficient effect. Therefore the excellent drug for preventing and/or treating cardiac insufficiency syndrome is desired.

DISCLOSURE OF THE INVENTION

The inventors assumed that inhibiting heart muscle cells apoptosis is useful for preventing and treating cardiac insufficiency syndrome and examined several ways. After that they produced a compound represented by the formula:

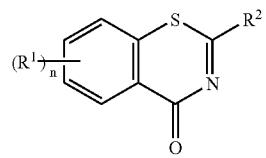

wherein $R^1$ is a hydrogen atom, a halogen atom, hydroxy, nitro, optionally halogenated alkyl, alkoxy optionally having substituents, acyl or amino optionally having substituents; $R^2$ is pyridyl, furyl, thienyl, pyrrolyl, quinolyl, pyrazinyl, pyrimidinyl, pyridazinyl, indolyl, tetrahydroquinolyl or thiazolyl, each of which may have substituents; n is 1 or 2; or a salt thereof (hereinafter sometimes abbreviated as Compound (I)); whose character is having pyridyl, furyl, thienyl, pyrrolyl, quinolyl, pyrazinyl, pyrimidinyl, pyridazinyl or indolyl, each of which may have substituents, on 2-position of 1,3-benzothiazinone skeleton for the first time. And they found that Compound (I) possesses an excellent apoptosis inhibitory effect and macrophage migration-inhibitory factor binding ability, and it possesses the excellent property as a drug for preventing and/or treating cardiac insufficiency syndrome. On the basis of the above findings, the inventors completed this invention.

That is, this invention relates to
[1] Compound (I);
[2] Compound (I) described in the above [1], wherein $R^2$ is pyridyl, furyl, thienyl, pyrrolyl, quinolyl, pyrazinyl, pyrimidinyl, pyridazinyl or indolyl, each of which may have substituents;
[3] the compound described in the above [1], wherein the compound is represented by the formula:

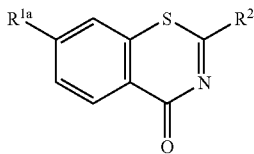

wherein $R^{1a}$ is a hydrogen atom, a halogen atom, optionally halogenated alkyl or optionally halogenated alkoxy; $R^2$ has the same meaning as described in the above [1];
[4] Compound (I) described in the above [1], wherein $R^1$ is a halogen atom, hydroxy, nitro, optionally halogenated alkyl, alkoxy optionally having substituents, acyl or amino optionally having substituents;
[5] Compound (I) described in the above [1], wherein $R^1$ is a hydrogen atom;
[6] Compound (I) described in the above [1], wherein the "pyridyl which may have substituents" is pyridyl which has substituents;
[7] Compound (I) described in the above [1], wherein $R^1$ is a hydrogen atom; the "pyridyl which may have substituents" is pyridyl which has substituents;
[8] Compound (I) described in the above [1], wherein $R^1$ is a halogen atom;
[9] Compound (I) described in the above [1], wherein $R^2$ is pyridyl which may have substituents;
[10] Compound (I) described in the above [1], wherein $R^2$ is pyridyl which has substituents;
[11] Compound (I) described in the above [1], wherein $R^2$ is 2- or 4-pyridyl which may have substituents;
[12] Compound (I) described in the above [1], wherein $R^2$ is pyridyl, furyl, thienyl, pyrrolyl, quinolyl, pyrazinyl, pyrimidinyl, indolyl, tetrahydroquinolyl or thiazolyl, each of which may have substituents;
[13] Compound (I) described in the above [1], wherein $R^2$ is pyridyl, furyl, thienyl, pyrrolyl, quinolyl, pyrazinyl, pyrimidinyl, pyridazinyl, indolyl, tetrahydroquinolyl or thiazolyl, each of which may have 1 to 3 substituent(s) selected from the group consisting of
(1) a halogen atom,
(2) a $C_{1-6}$ alkyl which may have 1 to 5 substituent(s) selected from the group consisting of (i) a halogen atom, (ii) hydroxy, (iii) carboxy, (iv) cyano, (v) carboxy-$C_{1-6}$ alkoxy, (vi) $C_{1-6}$ alkoxy-$C_{1-6}$ alkoxy, (vii) $C_{1-6}$ alkoxy-carbonyl-$C_{1-6}$ alkoxy, (viii) $C_{1-6}$ alkyl-carbonyloxy, (ix) $C_{1-6}$ alkoxy-carbonyl, (x) carbamoyl which may have 1 or 2 substituent(s) selected from the group consisting of(a) mono- or di-$C_{1-6}$ alkyl which may have carboxy, (b) $C_{1-6}$ alkylsulfonyl and (c) $C_{6-10}$ arylsulfonyl, (xi) 5- or 6-membered saturated cyclic amino-carbonyl which may have carboxy, (xii) $C_{1-6}$ alkylthio which may have $C_{1-6}$ alkoxy-carbonyl, (xiii) $C_{1-6}$ alkylsulfinyl which may have $C_{1-6}$ alkoxy-carbonyl, (xiv) $C_{1-6}$ alkylsulfonyl which may have $C_{1-6}$ alkoxy-carbonyl, (xv) $C_{7-12}$ aralkylthio, (xvi) $C_{7-12}$ aralkylsulfinyl, (xvii) $C_{7-12}$ aralkylsulfonyl, (xviii) (5- or 6-membered aromatic heterocycle)-thio, (xix) amino which may have 1 or 2 substituent(s) selected from the group consisting of(a) $C_{1-6}$ alkyl, (b) $C_{1-6}$ alkoxy-carbonyl, (c) optionally halogenated $C_{1-6}$ alkyl-carbonyl, (d) $C_{6-10}$ aryl-carbonyl, (e) thienylcarbonyl, (f) $C_{1-6}$ alkylthio-$C_{1-6}$ alkyl-carbonyl, (g) mono- or di-$C_{1-6}$ alkyl-carbamoyl, (h) $C_{1-6}$ alkylsulfonyl, (i) $C_{6-10}$ arylsulfonyl, (j) di-$C_{1-6}$ alkylphosphono, (k) di-$C_{1-6}$ alkylthiophosphono and (l) $C_{6-10}$ aryl-carbamoyl, (xx) phthalimido, (xxi) $C_{1-6}$ alkylsulfonyloxy, (xxii) 5- or 6-membered aromatic heterocyclic group, (xxiii) phosphono which may have $C_{1-6}$ alkyl, (xxiv) 5- to 7-membered saturated cyclic amino which may have 1 or 2 substituent(s) selected from the group consisting of (a) $C_{7-12}$ aralkyl, (b) optionally halogenated $C_{6-10}$ aryl and (c) hydroxy and (xxv) (5- to 7-membered cyclic amino)-carbonyl,
(3) $C_{2-7}$ alkenyl which may have carboxy or $C_{1-6}$ alkoxy-carbonyl,
(4) $C_{6-10}$ aryl which may have $C_{1-6}$ alkoxy,
(5) $C_{1-6}$ alkoxy which may have substituents selected from the group consisting of $C_{1-6}$ alkoxy, $C_{1-6}$ alkoxy-carbonyl, phthalimido, di-$C_{1-6}$ alkylsulfonamido and di-$C_{1-6}$ alkylaminomethylenesulfonamido,
(6) $C_{6-10}$ aryloxy which may have $C_{1-6}$ alkylthio,
(7) $C_{7-12}$ aralkyloxy,
(8) $C_{1-6}$ alkylthio which may have substituents selected from the group consisting of mono- or di-$C_{1-6}$ alkylamino, carboxy, carbamoyl and $C_{1-6}$ alkoxy-carbonyl,
(9) $C_{1-6}$ alkylsulfinyl which may have substituents selected from the group consisting of mono- or di-$C_{1-6}$ alkylamino, carboxy, carbamoyl and $C_{1-6}$ alkoxy-carbonyl,
(10) $C_{1-6}$ alkylsulfonyl which may have substituents selected from the group consisting of mono- or di-$C_{1-6}$ alkylamino, carboxy, and $C_{1-6}$ alkoxy-carbonyl,
(11) $C_{6-10}$ arylthio which may have substituents selected from the group consisting of halogen atom, $C_{1-6}$ alkyl and $C_{1-6}$ alkoxy-carbonyl,
(12) $C_{6-10}$ arylsulfinyl which may have $C_{1-6}$ alkyl,
(13) $C_{6-10}$ arylsulfonyl which may have $C_{1-6}$ alkyl,
(14) carboxy,
(15) $C_{1-6}$ alkoxy-carbonyl,
(16) $C_{7-12}$ aralkylthio,
(17) $C_{7-12}$ aralkylsulfinyl,
(18) $C_{7-12}$ aralkylsulfonyl,
(19) amino which may have 1 or 2 substituent(s) selected from the group consisting of $C_{1-6}$ alkyl, $C_{7-12}$ aralkyl, $C_{1-6}$ alkoxy-$C_{1-6}$ alkyl, $C_{1-6}$ alkoxy-carbonyl, $C_{1-6}$ alkoxy-carbonyl-$C_{1-6}$ alkyl, carboxy-$C_{1-6}$ alkyl, $C_{1-6}$ alkyl-carbonyl, $C_{6-10}$ aryl-carbonyl, $C_{3-6}$ cycloalkyl-carbonyl, thienylcarbonyl, furylcarbonyl and mono- or di-$C_{1-6}$ alkylaminocarbonyl,
(20) 5- to 7-membered saturated cyclic amino which may have substituents selected from the group consisting of (i) optionally halogenated $C_{6-10}$ aryl, (ii) $C_{7-12}$ aralkyl, (iii) hydroxy, (iv) $C_{1-6}$ alkyl which may have $C_{1-6}$ alkoxy-carbonyl or carboxy, (v) oxo, (vi) $C_{1-6}$ alkyl-carbonyl, (vii) $C_{6-10}$ aryl-carbonyl and (viii) $C_{1-6}$ alkoxy-carbonyl,
(21) carbamoyl which may have substituents selected from the group consisting of (i) $C_{1-6}$ alkyl which may have substituents selected from the group consisting of halogen atom, $C_{1-6}$ alkoxy, amino, $C_{1-6}$ alkoxy-carboxamido and hydroxy, (ii) $C_{7-12}$ aralkyl and (iii) mono- or di-$C_{1-6}$ alkylamino-carbonyl,
(22) (5- to 7-membered cyclic amino)-carbonyl,
(23) 5- or 6-membered aromatic heterocyclic group which may have $C_{1-6}$ alkyl,
(24) cyano,

(25) (5- to 10-membered aromatic heterocycle)-thio which may have $C_{1-6}$ alkyl,
(26) $C_{1-6}$ alkylcarbonyl and
(27) oxo;

[14] Compound (I) described in the above [1] or [3], wherein $R^2$ is optionally N-oxidized pyridyl which may have 1 to 3 substituent(s) selected from the group consisting of
(1) a halogen atom,
(2) a $C_{1-6}$ alkyl which may have substituents selected from the group consisting of a halogen atom, $C_{1-6}$ alkyl-carbonyloxy, $C_{1-6}$ alkoxy-$C_{1-6}$ alkoxy, hydroxy, $C_{1-6}$ alkoxy-carbonyl-$C_{1-6}$ alkoxy, carboxy-$C_{1-6}$ alkoxy, carboxy, $C_{1-6}$ alkoxy-carbonyl, $C_{1-6}$ alkylthio, $C_{1-6}$ alkylsulfinyl, $C_{1-6}$ alkylsulfonyl, $C_{1-6}$ alkylsulfonyloxy, 5- or 6-membered saturated cyclic amino, $C_{1-6}$ alkylsulfonyl-carbamoyl, $C_{6-10}$ arylsulfonyl-carbamoyl and (5- to 7-membered cyclic amino)-carbonyl,
(3) $C_{2-6}$ alkenyl which may have carboxy or $C_{1-6}$ alkoxy-carbonyl,
(4) $C_{6-10}$ aryl,
(5) $C_{1-6}$ alkoxy which may have substituents selected from the group consisting of $C_{1-6}$ alkoxy, $C_{1-6}$ alkoxy-carbonyl, phthalimido, di-$C_{1-6}$ alkylsulfonamido and di-$C_{1-6}$ alkylaminomethylenesulfonamido,
(6) $C_{6-10}$ aryloxy which may have $C_{1-6}$ alkylthio,
(7) $C_{7-12}$ aralkyloxy,
(8) $C_{1-6}$ alkylthio which may have mono- or di-$C_{1-6}$ alkylamino or $C_{1-6}$ alkoxy-carbonyl,
(9) $C_{1-6}$ alkylsulfinyl which may have mono- or di-$C_{1-6}$ alkylamino,
(10) $C_{1-6}$ alkylsulfonyl which may have mono- or di-$C_{1-6}$ alkylamino,
(11) $C_{6-10}$ arylthio which may have substituents selected from the group consisting of halogen atom, $C_{1-6}$ alkyl and $C_{1-6}$ alkoxy-carbonyl,
(12) $C_{6-10}$ arylsulfinyl which may have $C_{1-6}$ alkyl,
(13) $C_{6-10}$ arylsulfonyl which may have $C_{1-6}$ alkyl,
(14) carboxy,
(15) $C_{1-6}$ alkoxy-carbonyl,
(16) $C_{7-12}$ aralkylthio,
(17) $C_{7-12}$ aralkylsulfinyl,
(18) $C_{7-12}$ aralkylsulfonyl,
(19) amino which may have substituents selected from the group consisting of $C_{1-6}$ alkyl, $C_{7-12}$ aralkyl, $C_{1-6}$ alkoxy-$C_{1-6}$ alkyl, $C_{1-6}$ alkoxy-carbonyl, $C_{1-6}$ alkyl-carbonyl, $C_{6-10}$ aryl-carbonyl, $C_{3-6}$ cycloalkyl-carbonyl, thienylcarbonyl, furylcarbonyl and mono- or di-$C_{1-6}$ alkylamino-carbonyl,
(20) 5- to 7-membered saturated cyclic amino which may have substituents selected from the group consisting of optionally halogenated $C_{6-10}$ aryl, $C_{1-6}$ alkyl-carbonyl, $C_{6-10}$ aryl-carbonyl and $C_{1-6}$ alkoxy-carbonyl,
(21) carbamoyl which may have substituents selected from the group consisting of (i) $C_{1-6}$ alkyl which may have substituents selected from the group consisting of halogen atom, $C_{1-6}$ alkoxy, amino and $C_{1-6}$ alkoxy-carboxamido, (ii) $C_{7-12}$ aralkyl and (iii) mono- or di-$C_{1-6}$ alkylamino-carbonyl,
(22) (5- to 7-membered cyclic amino)-carbonyl,
(23) pyridyl, thienyl, furyl, pyrazolyl or oxazolyl, each of which may have $C_{1-6}$ alkyl and (24) oxo;

[15] Compound (I) described in the above [1], wherein $R^2$ is furyl, thienyl, pyrrolyl, quinolyl, pyrazinyl, pyrimidinyl, indolyl, tetrahydroquinolyl or thiazolyl, each of which may have 1 or 2 substituent(s) selected from (1) $C_{1-6}$ alkyl, (2) amino which may have 1 or 2 substituent (s) selected from the group consisting of $C_{1-6}$ alkyl, $C_{1-6}$ alkoxy-carbonyl, $C_{1-6}$ alkoxy-carbonyl-$C_{1-6}$ alkyl and carboxy-$C_{1-6}$ alkyl, (3) $C_{1-6}$ alkylsulfonyl and (4) mono- or di-$C_{1-6}$ alkylamino-$C_{1-6}$ alkylthio;

[16] Compound (I) described in the above [1], wherein $R^2$ is pyridyl which may have 1 or 2 substituent(s) selected from the group consisting of
(1) $C_{1-6}$ alkyl which may have substituents selected from the group consisting of $C_{1-6}$ alkoxy-carbonyl-$C_{1-6}$ alkoxy, carboxy-$C_{1-6}$ alkoxy, carboxy, $C_{1-6}$ alkoxy-carbonyl and $C_{1-6}$ alkylsulfonyloxy,
(2) $C_{2-6}$ alkenyl which may have carboxy or $C_{1-6}$ alkoxy-carbonyl,
(3) $C_{1-6}$ alkylthio which may have mono- or di-$C_{1-6}$ alkylamino or $C_{1-6}$ alkoxy-carbonyl,
(4) $C_{1-6}$ alkylsulfinyl which may have mono- or di-$C_{1-6}$ alkylamino,
(5) $C_{1-6}$ alkylsulfonyl which may have mono- or di-$C_{1-6}$ alkylamino,
(6) $C_{7-12}$ aralkylthio,
(7) $C_{7-12}$ aralkylsulfinyl,
(8) $C_{7-12}$ aralkylsulfonyl,
(9) carbamoyl which may have substituents selected from the group consisting of (i) $C_{1-6}$ alkyl which may have substituents selected from the group consisting of halogen atom, $C_{1-6}$ alkoxy and amino, (ii) $C_{7-12}$ aralkyl and (iii) mono- or di-$C_{1-6}$ alkylamino-carbonyl and
(10) (5- to 7-membered cyclic amino)-carbonyl;

[17] Compound (I) described in the above [1], wherein $R^1$
(1) a hydrogen atom, (2) a halogen atom, (3) hydroxy, (4) optionally halogenated $C_{1-6}$ alkyl, (5) $C_{1-6}$ alkoxy which may have substituents selected from the group consisting of carboxy, hydroxy, $C_{1-6}$ alkoxy-carbonyl and $C_{6-10}$ aryl, (6) $C_{1-6}$ alkyl-carbamoyl, (7) $C_{3-6}$ cycloalkyl-carbamoyl, (8) (5- or 6-membered saturated cyclic amino)-carbonyl or (9) carboxy;

[18] Compound (I) described in the above [16], wherein $R^1$ is a hydrogen atom or a halogen atom;

[19] Compound (I) described in the above [1], wherein $R^1$ is a halogen atom or a hydrogen atom, $R^2$ is pyridyl which may have 1 or 2 substituent(s) selected from the group consisting of $C_{1-6}$ alkyl, carboxy-$C_{1-6}$ alkyl and $C_{1-6}$ alkylsulfonyl;

[20] 3-[6-(4-oxo-4H-1,3-benzothiazin-2-yl)-2-pyridyl]propionic acid,
3-[6-(7-chloro-4-oxo-4H-1,3-benzothiazin-2-yl)-4-methyl-2-pyridyl]propionic acid,
3-[2-(7-chloro-4-oxo-4H-1,3-benzothiazin-2-yl)-4-pyridyl]propionic acid,
3-[2-methyl-6-(4-oxo-4H-1,3-benzothiazin-2-yl)-4-pyridyl]propionic acid,
3-[2-(7-chloro-4-oxo-4H-1,3-benzothiazin-2-yl)-6-methyl-4-pyridyl]propionic acid or salts thereof;

[21] Compound (I) described in the above [1], which has an ability to bind macrophage migration-inhibitory factor;

[22] a pharmaceutical, which comprises a compound described in
[1], a salt thereof or prodrug thereof;

[23] the pharmaceutical described in the above [22], which is a pharmaceutical for inhibition of apoptosis or protection of cells;

[24] the pharmaceutical described in the above [22], which is a pharmaceutical for inhibition of apoptosis;

[25] the pharmaceutical described in the above [23], which is a pharmaceutical for inhibition of heart muscle cells apoptosis;

[26] the pharmaceutical described in the above [22], which is a pharmaceutical for preventing and/or treating apoptosis derived diseases;

[27] the pharmaceutical described in the above [22], which is a pharmaceutical for preventing and/or treating macrophage migration-inhibitory factor derived diseases;

[28] the pharmaceutical described in the above [22], which is a pharmaceutical for preventing and/or treating circulatory disease, bone and articular disease, infectious disease, inflammatory bowel disease or kidney disease;

[29] a method for preventing and/or treating circulatory disease, bone and articular disease, infectious disease, inflammatory bowel disease or kidney disease, which comprises administering an effective amount of the compound described in the above [1], a salt thereof or a prodrug thereof to a mammal;

[30] use of the compound described in the above [1], a salt thereof or a prodrug thereof for producing a pharmaceutical for preventing and/or treating circulatory disease, bone and articular disease, infectious disease, inflammatory bowel disease or kidney disease; and the like.

BEST MODE FOR CARRYING OUT THE INVENTION

In the above formula, $R^1$ represents a hydrogen atom, a halogen atom, hydroxy, nitro, optionally halogenated alkyl, alkoxy which may have substituents, acyl or amino which may have substituents.

Examples of the "halogen atom" represented by $R^1$ are fluorine, chlorine, bromine, iodine and the like.

Examples of the "optionally halogenated alkyl" represented by $R^1$ are alkyl (e.g., $C_{1-6}$ alkyl such as methyl, ethyl, propyl, isopropyl, butyl, isobutyl, sec-butyl, tert-butyl, pentyl, hexyl and the like) which may have 1 to 5, preferably 1 to 3 halogen atoms (e.g., fluorine, chlorine, bromine, iodine and the like), and the like. Concrete examples are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the "alkoxy" of "alkoxy which may have substituents" represented by $R^1$ are $C_{1-8}$ alkoxy such as methoxy, ethoxy, propoxy, isopropoxy, butoxy, isobutoxy, sec-butoxy, pentyloxy, hexyloxy, and the like.

Examples of the "substituent" of "alkoxy which may have substituents" represented by $R^1$ are the same as the "substituent" of "hydrocarbon group which may have substituents" represented by $R^3$ described below and the like. And the number of the substituent is 1 to 3 and the substitution can be occurred at the position which is possible to be substituted.

Examples of "acyl" represented by $R^1$ are acyl represented by the formula: —(C=O)—$R^3$, —(C=O)—$OR^3$, —(C=O)—$NR^3R^4$, —(C=S)—$NHR^3$, —SO—$R^5$, —$SO_2$—$R^5$ or —$SO_2$—$NHR^3$ wherein $R^3$ is a hydrogen atom, hydrocarbon group which may have substituents or heterocyclic group which nay have substituents; $R^4$ is a hydrogen atom or $C_{1-6}$ alkyl; $R^5$ is hydrocarbon group which may have substituents or heterocyclic group which may have substituents, and the like.

In the above formula, examples of the "hydrocarbon group" of the "hydrocarbon group which may have substituents" are chain or cyclic hydrocarbon group (e.g., alkyl, alkenyl, alkynyl, cycloalkyl, aryl, aralkyl, and the like), and the like. Among them, chain or cyclic hydrocarbon group having 1 to 16 carbon atoms and the like are preferable.

AS the "alkyl", $C_{1-6}$ alkyl (e.g., methyl, ethyl, propyl, isopropyl, butyl, isobutyl, sec-butyl, tert-butyl, pentyl, hexyl, and the like) and the like are preferable.

As the "alkenyl", $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, and the like) and the like are preferable.

As the "alkynyl", $C_{2-6}$ alkynyl (e.g., ethynyl, propargyl, 1-butynyl, 2-butynyl, 3-butynyl, 1-hexynyl, and the like) and the like are preferable.

As the "cycloalkyl", $C_{3-6}$ cycloalkyl (e.g., cyclopropyl, cyclobutyl, cyclopentyl, cyclohexyl, and the like) and the like are preferable.

As the "aryl", $C_{6-14}$ aryl (e.g., phenyl, 1-naphthyl, 2-naphthyl, 2-biphenylyl, 3-biphenylyl, 4-biphenylyl, 2-anthryl, and the like), and the like are preferable.

As the "aralkyl", $C_{7-16}$ aralkyl (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, and the like) and the like are preferable.

Examples of the "substituent" of "hydrocarbon group which may have substituents" represented by $R^3$ are halogen atom (e.g., fluorine, chlorine, bromine, iodine, and the like), $C_{1-3}$ alkylenedioxy (e.g., methylenedioxy, ethylenedioxy, and the like), nitro, cyano, optionally halogenated $C_{1-6}$ alkyl, optionally halogenated $C_{2-6}$ alkenyl, carboxy-$C_{2-6}$ alkenyl (e.g., 2-carboxyethenyl, 2-carboxy-2-methylethenyl, and the like), optionally halogenated $C_{2-6}$ alkynyl, optionally halogenated $C_{3-6}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, and the like), optionally halogenated $C_{1-8}$ alkoxy, $C_{1-6}$ alkoxy-carbonyl-$C_{1-6}$ alkoxy (e.g., ethoxycarbonylmethyloxy, and the like), hydroxy, $C_{6-14}$ aryloxy (e.g., phenyloxy, 1-naphthyloxy, 2-naphthyloxy, and the like), $C_{7-16}$ aralkyloxy (e.g., benzyloxy, phenethyloxy, and the like), mercapto, optionally halogenated $C_{1-6}$ alkylthio, $C_{6-14}$ arylthio (e.g., phenylthio, 1-naphthylthio, 2-naphthylthio, and the like), $C_{7-16}$ aralkylthio (e.g., benzylthio, phenethylthio, and the like), amino, mono-$C_{1-6}$ alkylamino (e.g., methylamino, ethylamino, and the like), mono-$C_{6-14}$ arylamino (e.g., phenylamino, 1-naphthylamino, 2-naphthylamino, and the like), di-$C_{1-6}$ alkylamino (e.g., dimethylamino, diethylamino, ethylmethylamino, and the like), di-$C_{6-14}$ arylamino (e.g., diphenylamino, and the like), formyl, carboxy, $C_{1-6}$ alkyl-carbonyl (e.g., acetyl, propionyl, and the like), $C_{3-6}$ cycloalkyl-carbonyl (e.g., cyclopropylcarbonyl, cyclopentylcarbonyl, cyclohexylcarbonyl, and the like), $C_{1-6}$ alkoxy-carbonyl (e.g., methoxycarbonyl, ethoxycarbonyl, propoxycarbonyl, tert-butoxycarbonyl, and the like), $C_{6-14}$ aryl-carbonyl (e.g., benzoyl, 1-naphthoyl, 2-naphthoyl, and the like), $C_{7-16}$ aralkyl-carbonyl (e.g., phenylacetyl, 3-phenylpropionyl, and the like), $C_{6-14}$ aryloxy-carbonyl (e.g., phenoxycarbonyl, and the like), $C_{7-16}$ aralkyloxy-carbonyl (e.g., benzyloxycarbonyl, phenethyloxycarbonyl, and the like), (5- or 6-membered heterocycle)-carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, and the like), carbamoyl, mono-$C_{1-6}$ alkyl-carbamoyl (e.g., methylcarbamoyl, ethylcarbamoyl, and the like), di-$C_{1-6}$ alkyl-carbamoyl (e.g., dimethylcarbamoyl, diethylcarbamoyl, ethylmethylcarbamoyl, and the like), $C_{6-14}$ aryl-carbamoyl (e.g., phenylcarbamoyl, 1-naphthylcarbamoyl, 2-naphthylcarbamoyl, and the like), (5- or 6-membered heterocycle)-carbamoyl (e.g., 2-pyridylcarbamoyl, 3-pyridylcarbamoyl, 4-pyridylcarbamoyl, 2-thienylcarbamoyl, 3-thienylcarbamoyl, and the like), $C_{1-6}$ alkylsulfonyl (e.g., methylsulfonyl, ethylsulfonyl, and the like), $C_{6-14}$ arylsulfonyl (e.g., phenylsulfonyl, 1-naphthylsulfonyl, 2-naphthylsulfonyl, and the like), formylamino, $C_{1-6}$ alkyl-carbonylamino (e.g., acetylamino, and the like), $C_{6-14}$ aryl-carbonylamino (e.g., benzoylamino, naphthoylamino, and the like), $C_{1-6}$ alkoxy-carbonylamino (e.g., methoxycarbonylamino, ethoxycarbonylamino, propoxycarbonylamino, butoxycarbonylamino, and the like), $C_{1-6}$ alkylsulfonylamino (e.g., methylsulfonylamino, ethylsulfonylamino, and the like), $C_{6-14}$ arylsulfonylamino (e.g., phenylsulfonylamino, 2-naphthylsulfonylamino, 1-naphthylsulfonylamino, and the like), $C_{1-6}$ alkyl-carbonyloxy (e.g., acetoxy, propionyloxy, and the like), $C_{6-14}$ aryl-carbonyloxy (e.g., benzoyloxy, naphthylcarbonyloxy, and the like), $C_{1-6}$ alkoxy-carbonyloxy (e.g., methoxycarbonyloxy, ethoxycarbonyloxy, propoxycarbonyloxy, butoxycarbonyloxy, and the like), mono-$C_{1-6}$ alkyl-carbamoyloxy (e.g., methylcarbamoyloxy, ethylcarbamoyloxy, and the like), di-$C_{1-6}$ alkyl-carbamoyloxy (e.g., dimethylcarbamoyloxy, diethylcarbamoyloxy, and the like), $C_{6-14}$ aryl-carbamoyloxy (e.g., phenylcarbamoyloxy, naphthylcarbamoyloxy, and the like), nicotinoyloxy, 5- to 7-membered saturated cyclic amino which may have substituents, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, and the like), sulfo, and the like.

The "hydrocarbon group" may have 1 to 5, preferably 1 to 3 substituent(s) at the position which is possible to be substituted. And when the number of the substituents 2 or more, each substituent can be same or different.

Examples of the "optionally halogenated $C_{1-6}$ alkyl" described above are alkyl (e.g., $C_{1-6}$ alkyl such as methyl, ethyl, propyl, isopropyl, butyl, isobutyl, sec-butyl, tert-butyl, pentyl, hexyl and the like) which may have 1 to 5, preferably 1 to 3 halogen atom(s) (e.g., fluorine, chlorine, bromine, iodine, and the like), and the like. Concrete examples are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the "optionally halogenated $C_{2-6}$ alkenyl" described above are $C_{2-6}$ alkenyl (e.g., vinyl, propenyl, isopropenyl, 2-buten-1-yl, 4-penten-1-yl, 5-hexen-1-yl, and the like) which may have 1 to 5, preferably 1 to 3 halogen atom(s) (e.g., fluorine, chlorine, bromine, iodine, and the like), and the like.

Examples of the "optionally halogenated $C_{2-6}$ alkynyl" described above are $C_{2-6}$ alkynyl (e.g., 2-butyn-1-yl, 4-pentyn-1-yl, 5-hexyn-1-yl, and the like) which may have 1 to 5, preferably 1 to 3 halogen atom(s) (e.g., fluorine, chlorine, bromine, iodine, and the like), and the like.

Examples of the "optionally halogenated $C_{3-6}$ cycloalkyl" described above are $C_{3-6}$ cycloalkyl (e.g., cyclopropyl, cyclobutyl, cyclopentyl, cyclohexyl, and the like) which may have 1 to 5, preferably 1 to 3 halogen atom(s) (e.g., fluorine, chlorine, bromine, iodine, and the like), and the like. Concrete examples are cyclopropyl, cyclobutyl, cyclopentyl, cyclohexyl, 4,4-dichlorocyclohexyl, 2,2,3,3-tetrafluorocyclopentyl, 4-chlorocyclohexyl, and the like.

Examples of the "optionally halogenated $C_{1-8}$ alkoxy" are $C_{1-8}$ alkoxy (e.g., methoxy, ethoxy, propoxy, isopropoxy, butoxy, isobutoxy, sec-butoxy, pentyloxy, hexyloxy, and the like) which may have 1 to 5, preferably 1 to 3 halogen atom(s) (e.g., fluorine, chlorine, bromine, iodine, and the like), and the like. Concrete examples are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

Examples of the "optionally halogenated $C_{1-6}$ alkylthio" are $C_{1-6}$ alkylthio (e.g., methylthio, ethylthio, propylthio, isopropylthio, butylthio, sec-butylthio, tert-butylthio, and the like) which may have 1 to 5, preferably 1 to 3 halogen atom(s) (e.g., fluorine, chlorine, bromine, iodine, and the like), and the like. Concrete examples are methylthio, difluoromethylthio, trifluoromethylthio, ethylthio, propylthio, isopropylthio, butylthio, 4,4,4-trifluorobutylthio, pentylthio, hexylthio, and the like.

Examples of the "5- to 7-membered saturated cyclic amino" of the "5- to 7-membered saturated cyclic amino which may have substituents" described above are 5- to 7-membered saturated cyclic amino which may contain 1 to 4 heteroatom(s) selected 1 or 2 kind(s) from nitrogen atom, sulfur atom and oxygen atom in addition to one nitrogen atom and carbon atom(s). Concrete examples are pyrrolidin-1-yl, piperidino, piperadin-1-yl, morpholino, thiomorpholino, tetrahydroazepin-1-yl, and the like.

Examples of the "substituent" of the "5- to 7-membered saturated cyclic amino which may have substituents" described above are $C_{1-6}$ alkyl (e.g., methyl, ethyl, propyl, isopropyl, butyl, isobutyl, sec-butyl, tert-butyl, pentyl, hexyl, and the like), $C_{6-14}$ aryl (e.g., phenyl, 1-naphthyl, 2-naphthyl, 2-biphenylyl, 3-biphenylyl, 4-biphenylyl, 2-anthryl, and the like), $C_{1-6}$ alkyl-carbonyl (e.g., acetyl, propionyl, and the like), 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, and the like), oxo and the like. The number of the substituent is 1 to 3.

Examples of the "heterocyclic group" of the "heterocyclic group which may have substituents" represented by $R^3$ are monovalent group produced by removing any one of hydrogen atom from 5- to 14-membered (monocyclic, bicyclic or tricyclic) heterocycle containing 1 to 4 heteroatom(s) selected 1 or 2 kind(s) from nitrogen atom, sulfur atom and oxygen atom in addition to carbon atom(s), and the like. Preferable examples are monovalent groups produced by removing any one of hydrogen atom from (i) 5- to 14-membered (preferably 5- to 10-membered) aromatic heterocycle, (ii) 5- to 10-membered non-aromatic heterocycle and (iii) 7- to 10-membered bridged heterocycle.

Examples of the "5- to 14-membered (preferably 5- to 10-membered) aromatic heterocycle" described above are aromatic heterocycle such as thiophene, benzo[b]thiophene, benzo[b]furan, benzimidazole, benzoxazole, benzthiazole, benzoisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, and the like; or the ring produced by condensing the aromatic heterocycle (preferably monocyclic heterocycle) with 1 or more (preferably 1 or 2) aromatic ring(s) (e.g., benzene ring, and the like); and the like.

Examples of the "5- to 10-membered non-aromatic heterocycle" described above are pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, and the like.

Examples of the "7- to 10-membered bridged heterocycle" described above are quinuclidine, 7-azabicyclo[2.2.1]heptane, and the like.

Preferable examples of the "heterocyclic group" are 5 to 14-membered (preferably 5- to 10-membered) (monocyclic or bicyclic) heterocyclic group containing 1 to 4 heteroatom(s) selected 1 or 2 kind(s) from nitrogen atom, sulfur atom and oxygen atom in addition to carbon atom(s). Concrete examples are aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b)thienyl, 2-benzo[b]furanyl, 3-benzo[b]furanyl, and the like; non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, and the like.

Among them, 5- or 6-membered heterocyclic group containing 1 to 3 heteroatom(s) selected from nitrogen atom, sulfur atom and oxygen atom in addition to carbon atom(s) and the like are more preferable. Concrete examples are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

The "substituent" of the "heterocyclic group which may have substituents" has the same meaning as the "substituent" of the "hydrocarbon group which may have substituents" represented by $R^3$ described above.

The "heterocyclic group" may have 1 to 5, preferably 1 to 3 substituent(s) described above at the position where the substitution can be possible. When the number of the substituent is 2 or more, each of substituents may be same or different.

Examples of the "$C_{1-6}$ alkyl" represented by $R^4$ are methyl, ethyl, propyl, isopropyl, butyl, isobutyl, sec-butyl, tert-butyl, pentyl, hexyl and the like.

The "hydrocarbon group which may have substituents" and "heterocyclic group which may have substituents" represented by $R^5$ have the same meaning as "hydrocarbon group which may have substituents" and "heterocyclic group which may have substituents" represented by $R^3$ described above, respectively.

As the "substituent" of "amino which may have substituents" represented by $R^1$, 1 or 2 of the "substituent" of the "hydrocarbon group which may have substituents" represented by $R^3$ described above can be exemplified.

Concrete examples of $R^1$ are (1) a hydrogen atom, (2) a halogen atom, (3) hydroxy, (4) optionally halogenated $C_{1-6}$ alkyl, (5) $C_{1-6}$ alkoxy which may have substituents selected from the group consisting of carboxy, hydroxy, $C_{1-6}$ alkoxycarbonyl and $C_{6-10}$ aryl, (6) $C_{1-6}$ alkyl-carbamoyl, (7) $C_{3-6}$ cycloalkyl-carbamoyl, (8) (5- or 6-membered saturated cyclic amino)-carbonyl, and the like.

Preferable examples of $R^1$ are a hydrogen atom, a halogen atom, optionally halogenated alkyl (preferably $C_{1-6}$ alkyl), optionally halogenated alkoxy (preferably $C_{1-6}$ alkoxy), and the like. Especially, the preferable example of $R^1$ is a hydrogen atom.

$R^2$ is pyridyl, furyl, thienyl, pyrrolyl, quinolyl, pyrazinyl, pyrimidinyl, pyridazinyl, indolyl, tetrahydroquinolyl or thiazolyl, each of which may have substituents.

Examples of the "substituent" of the "pyridyl, furyl, thienyl, pyrrolyl, quinolyl, pyrazinyl, pyrimidinyl, pyridazinyl, indolyl, tetrahydroquinolyl or thiazolyl, each of which may have substituents" represented by $R^2$ are (1) halogen atom (e.g., fluorine, chlorine, bromine, iodine, and the like), (2) $C_{1-6}$ alkyl (e.g., methyl, ethyl, propyl, isopropyl, butyl, isobutyl, sec-butyl, tert-butyl, pentyl, hexyl, and the like) which may have substituents, (3) $C_{2-6}$ alkenyl (e.g., vinyl, propenyl, isopropenyl, 2-buten-1-yl, 4-penten-1-yl, 5-hexen-1-yl, and the like) which may have substituents, (4) $C_{6-10}$ aryl (e.g., phenyl, 1-naphthyl, 2-naphthyl, and the like) which may have substituents, (5) $C_{1-6}$ alkoxy (e.g., methoxy, ethoxy, propoxy, isopropoxy, butoxy, isobutoxy, sec-butoxy, pentyloxy, hexyloxy, and the like) which may have substituents, (6) $C_{6-10}$ aryloxy (e.g., phenyloxy, 1-naphthyloxy, 2-naphthyloxy, and the like) which may have substituents, (7) $C_{7-12}$ aralkyloxy (e.g., benzyloxy, phenethyloxy, and the like) which may have substituents, (8) $C_{1-6}$ alkylthio (e.g., methylthio, ethylthio, propylthio, isopropylthio, butylthio, sec-butylthio, tert-butylthio, and the like) which may have substituents, (9) $C_{1-6}$ alkylsulfinyl (e.g., methylsulfinyl, ethylsulfinyl, propylsulfinyl, isopropylsulfinyl, butylsulfinyl, sec-butylsulfinyl, tert-butylsulfinyl, and the like) which may have substituents, (10) $C_{1-6}$ alkylsulfonyl (e.g., methylsulfonyl, ethylsulfonyl, propylsulfonyl, isopropylsulfonyl, butylsulfonyl, sec-butylsulfonyl, tert-butylsulfonyl, and the like) which may have substituents, (11) $C_{6-10}$ arylthio (e.g., phenylthio, 1-naphthylthio, 2-naphthylthio, and the like) which may have substituents, (12) $C_{6-10}$ arylsulfinyl (e.g., phenylsulfinyl, 1-naphthylsulfinyl, 2-naphthylsulfinyl, and the like) which may have substituents, (13) $C_{6-10}$ arylsulfonyl (e.g., phenylsulfonyl, 1-naphthylsulfonyl, 2-naphthylsulfonyl, and the like) which may have substituents, (14) carboxy, (15) $C_{1-6}$ alkoxy-carbonyl (e.g., methoxycarbonyl, ethoxycarbonyl, propoxycarbonyl, butoxycarbonyl, and the like) which may have substituents, (16) $C_{7-12}$ aralkylthio (e.g., benzylthio, phenethylthio, and the like) which may have substituents, (17) $C_{7-12}$ aralkylsulfinyl (e.g., benzylsulfinyl, phenethylsulfinyl, and the like) which may have substituents, (18) $C_{7-12}$ aralkylsulfonyl (e.g., benzylsulfonyl, phenethylsulfonyl, and the like) which may have substituents, (19) amino which may have substituents, (20) 5- to 7-membered (preferably 5- or 6-membered) saturated cyclic amino (e.g., pyrrolidin-1-yl, piperidino, piperazin-1-yl, morpholino, thiomorpholino, imidazolidinyl, and the like) which may have substituents, (21) carbamoyl which may have substituents, (22) (5- to 7-membered cyclic amino)-carbonyl (e.g., pyrrolidin-1-ylcarbonyl, and the like) which may have substituents, (23) 5- to 10-membered (preferably 5- or 6-membered) aromatic heterocyclic group (e.g., 2-thienyl, 3-thienyl, 2-furyl, 3-furyl, 1-pyrazolyl, 3-pyrazolyl, 2-pyridyl, 3-pyridyl, 4-pyridyl, 5-oxazolyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, and the like) which may have substituents, (24) (5- to 10-membered aromatic heterocyclic group)-thio (e.g., 4-pyridylthio, 2-pyrimidinylthio, and the like) which may have substituents, (25) $C_{1-6}$ alkylcarbonyl which may have substituents, (26) oxo, (27) cyano, and the like. And the number of the substituent is 1 to 5, preferably, 1 to 3. The preferable substituent is $C_{1-6}$ alkyl which may have substituents.

Examples of the "substituent" of the above described (2)-(13), (15)-(25) are (i) halogen atom (e.g., fluorine, chlorine, bromine, iodine, and the like),
(ii) hydroxy,
(iii) carboxy,
(iv) cyano,
(v) $C_{1-6}$ alkyl which may have 1 to 3 substituent(s) selected from the group consisting of (a) halogen atom, (b) $C_{1-6}$ alkoxy, (c) amino, (d) $C_{1-6}$ alkoxy-carboxamido, (e) $C_{1-6}$ alkoxy-carbonyl, (f) hydroxy and (g) carboxy (e.g., methyl, chloromethyl, difluoromethyl, trichloromethyl, trifluoromethyl, ethyl, 2-bromoethyl, 2,2,2trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, aminomethyl, 2-aminoethyl, 3-aminopropyl, 4-aminobutyl, 5-aminopentyl, 6-aminohexyl, methoxyethyl, 2,2-dimethoxyethyl, 6,6-dimethoxyhexyl, methoxycarbonylmethyl, hydroxymethyl, carboxymethyl, butoxycarbonylmethyl, and the like),
(vi) optionally halogenated $C_{6-10}$ aryl (e.g., phenyl, 4-fluorophenyl, 4-chlorophenyl, and the like),
(vii) $C_{7-12}$ aralkyl (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, and the like),
(viii) $C_{1-6}$ alkoxy (e.g., methoxy, ethoxy, propoxy, butoxy, and the like),
(ix) $C_{1-6}$ alkoxy-$C_{1-6}$ alkoxy (e.g., methoxymethoxy, ethoxymethoxy, propoxymethoxy, butoxymethoxy, and the like),
(x) $C_{1-6}$ alkyl-carbonyloxy (e.g., acetoxy, propionyloxy, and the like),
(xi) carboxy-$C_{1-6}$ alkoxy (e.g., carboxymethoxy, 2-carboxyethoxy, and the like),
(xii) $C_{1-6}$ alkoxy-carbonyl-$C_{1-6}$ alkoxy (e.g., methoxycarbonylmethoxy, methoxycarbonylethoxy, ethoxycarbonylethoxy, butoxycarbonylethoxy, tert-butoxycarbonylethoxy, and the like),
(xiii) $C_{1-6}$ alkylsulfonyloxy (e.g., methylsulfonyloxy, ethylsulfonyloxy, propylsulfonyloxy, isopropylsulfonyloxy, butylsulfonyloxy, sec-butylsulfonyloxy, tert-butylsulfonyloxy, and the like),
(xiv) $C_{1-6}$ alkyl-carbonyl (e.g., acetyl, propionyl, and the like),
(xv) $C_{6-10}$ aryl-carbonyl (e.g., benzoyl, naphthylcarbonyl, and the like),
(xvi) $C_{3-6}$ cycloalkyl-carbonyl (e.g., cyclopropylcarbonyl, cyclopentylcarbonyl, cyclohexylcarbonyl, and the like),
(xvii) $C_{1-6}$ alkoxy-carbonyl (e.g., methoxycarbonyl, ethoxycarbonyl, propoxycarbonyl, butoxycarbonyl, tert-butoxycarbonyl, and the like),
(xviii) mono- or di-$C_{1-6}$ alkylaminocarbonyl (e.g., methylaminocarbonyl, ethylaminocarbonyl, dimethylaminocarbonyl, diethylaminocarbonyl, and the like),
(xix) (5- or 6-membered aromatic heterocycle)-carbonyl (e.g., thienylcarbonyl, furylcarbonyl, and the like),
(xx) mono- or di-$C_{1-6}$ alkyl-carbamoyl which may have carboxy (e.g., methylcarbamoyl, ethylcarbamoyl, dimethylcarbamoyl, diethylcarbamoyl, ethylmethylcarbamoyl, carboxymethylcarbamoyl, carboxymethyl(methyl)carbamoyl, and the like),
(xxi) (5- or 6-membered saturated cyclic amino)-carbonyl which may have carboxy (e.g., carboxypyrrolidinylcarbonyl, and the like), $C_{6-10}$ arylamino-carbonyl or (5- to 7-membered cyclic ammo)-carbonyl,
(xxii) $C_{1-6}$ alkylthio which may have $C_{1-6}$ alkoxy-carbonyl or mono- or di-$C_{1-6}$ alkylamino (e.g., methylthio, ethylthio, propylthio, isopropylthio, butylthio, sec-butylthio, tert-butylthio, methoxycarbonylmethylthio, and the like),
(xxiii) $C_{1-6}$ alkylsulfinyl which may have $C_{1-6}$ alkoxy-carbonyl (e.g., methylsulfinyl, ethylsulfinyl, propylsulfinyl, isopropylsulfinyl, butylsulfinyl, sec-butylsulfinyl, tert-butylsulfinyl, methoxycarbonylmethylsulfinyl, and the like),
(xxiv) $C_{1-6}$ alkylsulfonyl which may have $C_{1-6}$ alkoxy-carbonyl (e.g., methylsulfonyl, ethylsulfonyl, propylsulfonyl, isopropylsulfonyl, butylsulfonyl, sec-butylsulfonyl, tert-butylsulfonyl, methoxycarbonylmethylsulfonyl, and the like),
(xxv) $C_{7-12}$ aralkylthio (e.g., benzylthio, phenethylthio, and the like),
(xxvi) $C_{742}$ aralkylsulfinyl (e.g., benzylsulfinyl, phenethylsulfinyl, and the like),
(xxvii) $C_{7-12}$ aralkylsulfonyl (e.g., benzylsulfonyl, phenethylsulfonyl, and the like),
(xxviii) (5- or 6-membered aromatic heterocycle)-thio (e.g., 2-pyridylthio, 3-pyridylthio, 4-pyridylthio, and the like),
(xxix) amino which may have 1 or 2 substituent(s) selected from the group consisting of (a) $C_{1-6}$ alkyl, (b) $C_{1-6}$ alkoxy-carbonyl, (c) optionally halogenated $C_{1-6}$ alkyl-carbonyl, (d) $C_{6-10}$ aryl-carbonyl, (e) thienylcarbonyl, (f) $C_{1-6}$ alkylthio-$C_{1-6}$ alkyl-carbonyl, (g) mono- or di-$C_{1-6}$ alkyl-carbamoyl, (h) $C_{1-6}$ alkylsulfonyl, (i) $C_{6-10}$ arylsulfonyl, (j) di-$C_{1-6}$ alkylphosphono, (k) di-$C_{1-6}$ alkylthiophosphono and (l) $C_{6-10}$ aryl-carbamoyl (e.g., amino, methylamino, ethylamino, dimethylamino, diethylamino, ethylmethylamino, tert-butoxycarbonylamino, acetylamino, propionylamino, butyrylamino, isobutyrylamino, trifluoroacetylamino, benzoylamino, naphthylcarbonylamino, thienylcarbonylamino, 3-methylthiopropionylamino, 3-methylureido, 3,3-dimethylureido, methylsulfamoyl, ethylsulfamoyl, phenylsulfamoyl, diethylphosphonoamino, diethylthiophosphonoamino, 3-phenylureido, 3,3-diethylureido, methylcarbonylamino, ethylcarbonylamino, propylcarbonylamino, phenylcarbonylamino, thiophenylcarbonylamino, trifluoromethylcarbonylamino, methylthioethylcarbonylamino, dimethylaminocarbonylamino, methylsulfonylamino, ethylsulfonylamino, phenylsulfonylamino, methylaminocarbonylamino, ethylaminocarbonylamino, phenylaminocarbonylamino, thiophenylcarbonylamino, and the like),
(xxx) 5- to 7-membered (preferably 5- or 6-membered) saturated cyclic amino (e.g., pyrrolidin-1-yl, piperidino, piperazin-1-yl, morpholino, thiomorpholino, and the like) which may have 1 or 2 substituent(s) selected from the group consisting of (a) $C_{7-12}$ aralkyl, (b) optionally halogenated $C_{6-10}$ aryl and (c) hydroxy,
(xxxi) phthalimido,
(xxxii) carbamoyl which may have 1 or 2 substituent(s) selected from the group consisting of (a) $C_{1-6}$ alkylsulfonyl and (b) $C_{6-10}$ arylsulfonyl,
(xxxiii) di-$C_{1-6}$ alkylsulfonamido (e.g., dimethylsulfonamido, and the like) or di-$C_{1-6}$ alkylamino-$C_{1-6}$ alkylenesulfonamido (e.g., dimethylaminomethylenesulfonamido, and the like),
(xxxiv) 5- or 6-membered aromatic heterocyclic group (e.g., tetrazolyl, oxazolyl, isoxazolyl, and the like),
(xxxv) phosphono which may have $C_{1-6}$ alkyl (e.g., phosphono, diethylphosphono, and the like), (xxxvi) oxo, and the like. The number of the substituent is 1 to 3.

The "pyridyl, furyl, thienyl, pyrrolyl, quinolyl, pyrazinyl, pyrimidinyl, pyridazinyl, indolyl, tetrahydroquinolyl or thiazolyl, each of which may have substituents" represented by $R^2$ may have 1 to 3 substituent(s) at any position which can be substituted. When the number of the substituent is 2 or more, each substituent may be same or different.

Preferable examples of $R^2$ are pyridyl, furyl, thienyl, pyrrolyl, quinolyl, pyrazinyl, pyrimidinyl, pyridazinyl, indolyl, tetrahydroquinolyl or thiazolyl (preferably pyridyl, more preferably 2- or 4-pyridyl), each of which has 1 to 3 substituent(s) selected from the group consisting of (1) halogen atom,
(2) $C_{1-6}$ alkyl which may have 1 to 5 substituent(s) selected from the group consisting of (i) halogen atom, (ii) hydroxy, (iii) carboxy, (iv) cyano, (v) carboxy-$C_{1-6}$ alkoxy, (vi) $C_{1-6}$ alkoxy-$C_{1-6}$ alkoxy, (vii) $C_{1-6}$ alkoxy-carbonyl-$C_{1-6}$ alkoxy, (viii) $C_{1-6}$ alkyl-carbonyloxy, (ix) $C_{1-6}$ alkoxy-carbonyl, (x) carbamoyl which may have 1 or 2 substituent(s) selected from the group consisting of (a) mono-or di-$C_{1-6}$ alkyl which may have carboxy, (b) $C_{1-6}$ alkylsulfonyl and (c) $C_{6-10}$ arylsulfonyl (xi) (5- or 6-membered saturated cyclic amino)-carbonyl which may have carboxy, (xii) $C_{1-6}$ alkylthio which may have $C_{1-6}$ alkoxy-carbonyl, (xiii) $C_{1-6}$ alkylsulfinyl which may have $C_{1-6}$ alkoxy-carbonyl, (xiv) $C_{1-6}$ alkylsulfonyl which may have $C_{1-6}$ alkoxy-carbonyl, (xv) $C_{7-12}$ aralkylthio, (xvi) $C_{7-12}$ aralkylsulfinyl, (xvii) $C_{7-12}$ aralkylsulfonyl, (xviii) (5- or 6-membered aromatic heterocycle)-thio, (xix) amino which may have 1 or 2 substituent(s) selected from the group consisting of (a) $C_{1-6}$ alkyl, (b) $C_{1-6}$ alkoxy-carbonyl, (c) optionally halogenated $C_{1-6}$ alkyl-carbonyl, (d) $C_{6-10}$ aryl-carbonyl, (e) thienylcarbonyl, (f) $C_{1-6}$ alkylthio-$C_{1-6}$ alkyl-carbonyl, (g) mono- or di-$C_{1-6}$ alkyl-carbamoyl, (h) $C_{1-6}$ alkylsulfonyl, (i) $C_{6-10}$ arylsulfonyl, (j) di-$C_{1-6}$ alkylphosphono, (k) di-$C_{1-6}$ alkylthiophosphono and (l) $C_{6-10}$ aryl-carbamoyl, (xx) phthalimido, (xxi) $C_{1-6}$ alkylsulfonyloxy, (xxii) 5- or 6-membered aromatic heterocyclic group, (xxiii) phosphono which may have $C_{1-6}$ alkyl, (xxiv) 5- to 7-membered saturated cyclic amino which may have 1 or 2 substituent(s) selected from the group consisting of (a) $C_{7-12}$ aralkyl, (b) optionally halogenated $C_{6-10}$ aryl and (c) hydroxy and (xxv) (5- to 7-membered cyclic amino)-carbonyl,
(3) $C_{1-6}$ alkenyl which may have carboxy or $C_{1-6}$ alkoxy-carbonyl,
(4) $C_{6-10}$ aryl which may have $C_{1-6}$ alkoxy,
(5) $C_{1-6}$ alkoxy which may have substituents selected from the group consisting of $C_{1-6}$ alkoxy, $C_{1-6}$ alkoxy-carbonyl, phthalimido, di-$C_{1-6}$ alkylsulfonamido and di-$C_{1-6}$ alkylaminomethylenesulfonamido,
(6) $C_{6-10}$ aryloxy which may have $C_{1-6}$ alkylthio,
(7) $C_{7-12}$ aralkyloxy,
(8) $C_{1-6}$ alkylthio which may have substituents selected from the group consisting of mono- or di-$C_{1-6}$ alkylamino, carboxy, carbamoyl and $C_{1-6}$ alkoxy-carbonyl,
(9) $C_{1-6}$ alkylsulfinyl which may have substituents selected from the group consisting of mono- or di-$C_{1-6}$ alkylamino, carboxy, carbamoyl and $C_{1-6}$ alkoxy-carbonyl,
(10) $C_{1-6}$ alkylsulfonyl which may have substituents selected from the group consisting of mono- or di-$C_{1-6}$ alkylamino, carboxy and $C_{1-6}$ alkoxy-carbonyl,
(11) $C_{6-10}$ arylthio which may have substituents selected from the group consisting of halogen atom, $C_{1-6}$ alkyl and $C_{1-6}$ alkoxy-carbonyl,
(12) $C_{6-10}$ arylsulfinyl which may have $C_{1-6}$ alkyl,
(13) $C_{6-10}$ arylsulfonyl which may have $C_{1-6}$ alkyl,
(14) carboxy,
(15) $C_{1-6}$ alkoxy-carbonyl,
(16) $C_{7-12}$ aralkylthio,
(17) $C_{7-12}$ aralkylsulfinyl,
(18) $C_{7-12}$ aralkylsulfonyl,
(19) amino which may have 1 or 2 substituent(s) selected from the group consisting of $C_{1-6}$ alkyl, $C_{7-12}$ aralkyl, $C_{1-6}$ alkoxy-$C_{1-6}$ alkyl, $C_{1-6}$ alkoxy-carbonyl, $C_{1-6}$ alkoxy-carbonyl-$C_{1-6}$ alkyl, carboxy-$C_{1-6}$ alkyl, $C_{1-6}$ alkyl-carbonyl, $C_{6-10}$ aryl-carbonyl, $C_{3-6}$ cycloalkyl-carbonyl, thienylcarbonyl, furylcarbonyl and mono- or di-$C_{1-6}$ alkylaminocarbonyl,
(20) 5- to 7-membered saturated cyclic amino which may have substituents selected from the group consisting of (i) optionally halogenated $C_{6-10}$ aryl, (ii) $C_{7-12}$ aralkyl, (iii) hydroxy, (iv) $C_{1-6}$ alkyl which may have $C_{1-6}$ alkoxy-carbonyl or carboxy, (v) oxo, (vi) $C_{1-6}$ alkyl-carbonyl, (vii) $C_{6-10}$ aryl-carbonyl and (viii) $C_{1-6}$ alkoxy-carbonyl,
(21) carbamoyl which may have substituents selected from the group consisting of (i) $C_{1-6}$ alkyl which may have substituents selected from the group consisting of halogen atom, $C_{1-6}$ alkoxy, amino, $C_{1-6}$ alkoxy-carboxamido and hydroxy, (ii) $C_{7-12}$ aralkyl and (iii) mono- or di-$C_{1-6}$ alkylamino-carbonyl,
(22) (5- to 7-membered cyclic amino)-carbonyl,
(23) 5- or 6-membered aromatic heterocyclic group which may have $C_{1-6}$ alkyl,
(24) cyano,
(25) (5- to 10-membered aromatic heterocyclic group)-thio which may have $C_{1-6}$ alkyl,
(26) $C_{1-6}$ alkylcarbonyl and
(27) oxo. The "pyridyl" may be N-oxidized.

And also, preferable examples of $R^2$ are pyridazinyl or pyrazinyl, each of which may have substituents selected from the group consisting of (1) $C_{1-6}$ alkylthio, (2) $C_{1-6}$ alkylsulfinyl, (3) $C_{1-6}$ alkyl sulfonyl and (4) amino which may have 1 or 2 $C_{1-6}$ alkyl (s) which may have $C_{1-6}$ alkoxy-carbonyl or carboxy, and the like.

And also, preferable examples of $R^2$ are furyl, thienyl, pyrrolyl, quinolyl, pyrazinyl, pyrimidinyl, indolyl, tetrahydroquinolyl or thiazolyl, each of which may have 1 or 2 substituent(s) selected from the group consisting of (1) $C_{1-6}$ alkyl, (2) amino which may have substituent(s) selected from the group consisting of $C_{1-6}$ alkyl, $C_{1-6}$ alkoxy-carbonyl, $C_{1-6}$ alkoxy-carbonyl-$C_{1-6}$ alkyl and carboxy-$C_{1-6}$ alkyl, (3) $C_{1-6}$ alkylsulfonyl and (4) mono- or di-$C_{1-6}$ alkylamino-$C_{1-6}$ alkylthio, and the like.

More preferable examples of $R^2$ are pyridyl, furyl, thienyl, pyrrolyl, quinolyl, pyrazinyl, pyrimidinyl, pyridazinyl, indolyl, tetrahydroquinolyl or thiazolyl (preferably pyridyl, more preferably 2- or 4-pyridyl), each of which has 1 to 3 substituent(s) selected from the group consisting of (1) $C_{1-6}$ alkyl which may have substituents selected from the group consisting of $C_{1-6}$ alkoxy-carbonyl-$C_{1-6}$ alkoxy, carboxy-$C_{1-6}$ alkoxy, carboxy, $C_{1-6}$ alkoxy-carbonyl and $C_{1-6}$ alkylsulfonyloxy, (2) $C_{2-6}$ alkenyl which may have carboxy or $C_{1-6}$ alkoxy-carbonyl, (3) $C_{1-6}$ alkylthio which may have mono- or di-$C_{1-6}$ alkylamino or $C_{1-6}$ alkoxy-carbonyl, (4) $C_{1-6}$ alkylsulfinyl which may have mono- or di-$C_{1-6}$ alkylamino, (5) $C_{1-6}$ alkylsulfonyl which may have mono- or di-$C_{1-6}$ alkylamino, (6) $C_{7-12}$ aralkylthio, (7) $C_{7-12}$ aralkylsulfinyl, (8) $C_{7-12}$ aralkylsulfonyl, (9) carbamoyl which may have substituents selected from the group consisting of (i) $C_{1-6}$ alkyl which may have substituents selected from the group consisting of halogen atom, $C_{1-6}$ alkoxy and amino, (ii) $C_{7-12}$ aralkyl and (iii) mono-or di-$C_{1-6}$ alkylamino-carbonyl and (10) (5- to 7-membered cyclic amino)-carbonyl, and the like. The "pyridyl" may be N-oxidized.

The most preferable examples of $R^2$ are pyridyl (preferably 2- or 4-pyridyl) which has 1 or 2 substituent(s) selected from the group consisting of (1) $C_{1-6}$ alkyl which may have carboxy and/or hydroxy and (2) $C_{1-6}$ alkylsulfonyl, and the like.

Preferable substituted position is 5-, 6- or 7-position.

Examples of Compound (I) are (1) the compound wherein $R^1$ is a halogen atom, hydroxy, nitro, optionally halogenated alkyl, alkoxy which may have substituents, acyl or amino which may have substituents; $R^2$ is pyridyl, furyl, thienyl, pyrrolyl, quinolyl, pyrazinyl, pyrimidinyl, pyridazinyl, indolyl, tetrahydroquinolyl or thiazolyl, each of which has substituents respectively; n is 1 or 2, (2) the compound wherein $R^1$ is a hydrogen atom; $R^2$ is pyridyl, furyl, thienyl, pyrrolyl, quinolyl, pyrazinyl, pyrimidinyl, pyridazinyl, indolyl, tetrahydroquinolyl or thiazolyl, each of which has substituents respectively, and the like.

The example of Compound (I) is a compound represented by the formula:

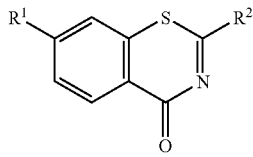

wherein $R^1$ and $R^2$ have the same meaning described above, or a salt thereof. Preferably $R^1$ is a hydrogen atom, a halogen atom, optionally halogenated alkyl or optionally halogenated alkoxy, and the like.

Especially, the most preferable compounds of this invention are, for example, 3-[6-(4-oxo-4H-1,3-benzothiazin-2-yl)-2-pyridyl]propionic acid, 3-[6-(7-chloro-4-oxo-4H-1,3-benzothiazin-2-yl)-4-methyl-2-pyridyl]propionic acid, 3-[2-(7-chloro-4-oxo-4H-1,3-benzothiazin-2-yl)-4-pyridyl]propionic acid, 3-[2-methyl-6-(4-oxo-4H-1,3-benzothiazin-2-yl)-4-pyridyl]propionic acid, 3-[2-(7-chloro-4-oxo-4H-1,3-benzothiazin-2-yl)-6-methyl-4-pyridyl]propionic acid or salts thereof.

Examples of a salt of Compound (I) and intermediates thereof are metal salts, ammonium salts, salts with organic bases, salts with inorganic acids, salts with organic acids, salts with basic or acidic amino acids, and the like. Suitable examples of metal salts are alkali metal salts such as sodium salt, potassium salt; alkali-earth metal salts such as calcium salt, magnesium salt, barium salt; aluminum salts; and the like. Suitable examples of the salt with organic bases are salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine, and the like. Suitable examples of the salt with inorganic acids are salts with hydrochloric acid, hydrobromic acid, nitric acid, sulfuric acid, phosphoric acid, and the like. Suitable examples of the salt with organic acids are salts with formic acid, acetic acid, trifluoroacetic acid, phthalic acid, fumalic acid, oxalic acid, tartaric acid, maleic acid, citric acid, succinic acid, malic acid, methanesulfonic acid, benzenesulfonic acid, p-toluenesulfonic acid, and the like. Suitable examples of the salt with basic amino acid are salts with arginine, lysine, ornithine, and the like. Suitable examples of the salt with acidic amino acids are salts with aspartic acid, glutamic acid, and the like.

Among them, pharmaceutically acceptable salts are preferable. And in the case of the compound having an acidic functional group, examples of the salt are in organic salts such as alkali metal salts (e.g., sodium salt, potassium salt, and the like), alkali-earth metal salts (e.g., calcium salt, magnesium salt, barium salt, and the like); ammonium salt; and the like. And in the case of the compound having a basic functional group, examples of the salt are salts with inorganic acids such as hydrobromic acid, nitric acid, sulfuric acid, phosphoric acid; and salts with organic acids such as acetic acid, phthalic acid, fumalic acid, tartaric acid, maleic acid, citric acid, succinic acid, methanesulfonic acid, p-toluenesulfonic acid, and the like.

Compound (I) may be a hydrate or a non-hydrate. The hydrate is exemplified by semihydrate, monohydrate, sesquihydrate and dihydrate.

When compound (I) is obtained as a mixture of optically active substances (racemic body), it can be resolved into the objective (R)- and (S)-forms by per se known optical resolution techniques.

A prodrug of Compound (I) is a compound which is converted into Compound (I) under a physiological condition as a result of a reaction with an enzyme or gastric acid, thus a compound undergoing enzymatic oxidation, reduction or hydrolysis to form Compound (I) and a compound hydrolyzed by gastric acid, etc. to form Compound (I). A prodrug of Compound (I) may for example be a compound obtained by subjecting amino group in Compound (I) to acylation, alkylation or phosphorylation (e.g., a compound obtained by subjecting amino group in Compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, and the like); a compound obtained by subjecting hydroxy group in Compound (I) to acylation, alkylation, phosphorylation or boration (e.g., a compound obtained by subjecting hydroxy group in Compound (I) to acetylation, palmitoylation, propanoylation, pivaloylation, succinylation, fumarylation, alanylation, dimethylaminomethylcarbonylation, and the like); a compound obtained by subjecting carboxy group in Compound (I) to esterification or amidation (e.g., a compound obtained by subjecting carboxy group in Compound (I) to ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation, and the like) and the like. Any of these compounds can be produced from Compound (I) by a method known per se.

A prodrug of Compound (I) may also be one which is converted into Compound (I) under a physiological condition, such as those described in "IYAKUHIN NO KAIHATSU (Development of Pharmaceuticals)", Vol. 7, Design of Molecules, p. 163-198, Published by HIROKAWA SHOTEN (1990).

The production method of Compound (I) is described below.

Compound (I) can be produced by the method represented by Scheme 1 or its analogous methods.

Each symbol in Scheme 1 described below has the same meaning described above. In the scheme, the compound may contain salt forms, and examples of the salts are the same as salts of Compound (I), and the like.

Scheme 1

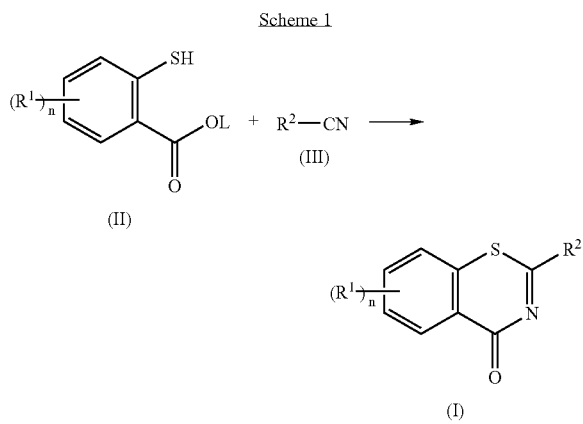

Compound (I) can be produced by reacting Compound (II) and Compound (III).

In Compound (II), L is a hydrogen atom or a leaving group. Examples of the leaving group are alkyl and the like.

This reaction may be performed in the presence of base.

The amount of Compound (III) is about 0.4 to 2 moles, preferably about 0.8 to 1.2 moles per 1 mole of Compound (II).

The amount of base is about 1 to 2.5 moles, preferably about 0.8 to 1.5 moles per 1 mole of Compound (II).

Examples of the "base" are basic salts such as sodium carbonate, potassium carbonate, cesium carbonate, and the like; inorganic bases such as sodium hydroxide, potassium hydroxide, and the like; aromatic amines such as pyridine, lutidine, and the like; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, and the like; metal hydrides such as sodium hydride, potassium hydride and the like; metal amides such as sodium amide, lithium diisopropyl amide, lithium hexamethyldisilazide, and the like; metal alkoxides such as sodium methoxide, sodium ethoxide, potassium tert-butoxide, and the like; and the like.

It is advantageous to perform this reaction without using solvent or in the solvent inert to this reaction. The solvent is not limited as long as the reaction is proceeded. Examples of the solvent are aromatic amines, halgenated hydrocarbons, aliphatic hydrocarbons, aromatic hydrocarbons, ethers, amides, or mixture of 2 or more thereof. Among them, pyridine and toluene and the like are preferable. And when the reaction is performed in pyridine, base is not always necessary.

The reaction temperature is normally about 100 to 150° C., preferably 120 to 130° C. The reaction time is normally about 3 hours to 72 hours, preferably about 8 to 24 hours at the boiling point of the solvent used.

This reaction is performed under reflux at the boiling point of the solvent used.

Compound (II) can be used as it is when it can be commercially available. And it can be produced in accordance with the known methods per se or analogous methods thereof. For example, Compound (II) can be obtained from anthrailic acid derivatives corresponding to Compound (II) by the known method (e.g., Journal of organic Chemistry, Vol. 18, pp. 1380, 1953, etc.) and from salicylic acid derivatives corresponding to Compound (II) by the known method (e.g., Journal of organic Chemistry, Vol. 31, pp. 3980, 1966, etc.).

Compound (III) can be used as it is when it can be commercially available. And it can be produced in accordance with the known methods per se or analogous methods thereof. For example, Compound (III), wherein $R^2$ is pyridyl which may have substituents, can be obtained from pyridine derivatives corresponding to Compound (III) by the known method (e.g., Journal of organic Chemistry, Vol. 48, pp. 1375, 1983; Synthesis, Vol. 316, pp. 316, 1983, etc.).

In the reaction described above, a starting compound having an amino, carboxy or hydroxy as its substituent may be present as a compound in which a protective group employed ordinarily in a peptide chemistry has been introduced into such a substituent, and an intended compound can be obtained by deprotection if necessary after the reaction.

A protective group for an amino may for example be a formyl or each optionally substituted $C_{1-6}$ alkyl-carbonyl (e.g., acetyl, propionyl, and the like), phenylcarbonyl, $C_{1-6}$ alkoxy-carbonyl (e.g., methoxycarbonyl, ethoxycarbonyl, and the like), phenyloxycarbonyl, $C_{7-10}$ aralkyloxy-carbonyl (e.g., benzyloxycarbonyl, and the like), trityl, phthaloyl and the like. Its substituent may for example be a halogen atom (e.g., fluorine, chlorine, bromine, iodine, and the like), $C_{1-6}$ alkyl-carbonyl (e.g., acetyl, propionyl, valeryl, and the like), nitro and the like, and the number of the substituents may be 1 to 3.

A protective group for a carboxy may for example be each optionally substituted $C_{1-6}$ alkyl (e.g., methyl, ethyl, propyl, isopropyl, butyl, tert-butyl, and the like), phenyl, trityl, silyl and the like. Its substituent may for example be a halogen atom (for example, fluorine, chlorine, bromine, iodine, and the like), formyl, $C_{1-6}$ alkyl-carbonyl (e.g., acetyl, propionyl, butylcarbonyl, and the like), nitro, $C_{1-6}$ alkyl (e.g.:, methyl, ethyl, tert-butyl, and the like) and $C_{6-10}$ aryl (e.g., phenyl, naphthyl, and the like), and the number of the substituents may be 1 to 3.

A protective group for a hydroxy may for example be each optionally substituted $C_{1-6}$ alkyl (e.g., methyl, ethyl, propyl, isopropyl, butyl, tert-butyl, and the like), phenyl, $C_{7-11}$ aralkyl (e.g., benzyl, and the like), formyl, $C_{1-6}$ alkyl-carbonyl (e.g., acetyl, propionyl, and the like), phenyloxycarbonyl, $C_{7-11}$ aralkyloxy-carbonyl (e.g., benzyloxycarbonyl, and the like), tetrahydropyranyl, tetrahydrofuranyl, silyl and the like. Its substituent may for example be a halogen atom (e.g., fluorine, chlorine, bromine, iodine, and the like), $C_{1-6}$ alkyl (e.g., methyl, ethyl, tert-butyl, and the like), $C_{7-11}$ aralkyl (e.g., benzyl, and the like), $C_{6-10}$ aryl (e.g., phenyl, naphthyl, and the like), nitro, and the like, and the number of the substituents may be 1 to 4.

A deprotection method may be a method known per se such as a treatment with an acid, base, UV, hydrazine, phenylhydrazine, sodium N-methyldithiocarbamate, tetrabutylammonium fluoride, palladium acetate and the like, as well as a reduction.

In any case, a deprotection, acylation, alkylation, hydrogenation, oxidation, reduction, carbon chain elongation and substituent exchange reaction are further employed if necessary alone or in combination with each other to synthesize Compound (I). These reactions may employ the methods described for example in SHINJIKKENKAGAKUKOZA, Vols. 14 and 15, 1977 (MARUZEN) and the like.

Examples of the "aromatic amines" described above are pyridine, lutidine, quinoline, and the like.

Examples of the "halogenated hydrocarbons" described above are dichloromethane, chloroform, 1,2-dichloroethane, and the like.

Examples of the "aliphatic hydrocarbons" described above are hexane, pentane, cyclohexane, and the like.

Examples of the "aromatic hydrocarbons" described above are benzene, toluene, xylene, chlorobenzene, and the like.

Examples of the "ethers" described above are diethyl ether, diisopropyl ether, diphenyl ether, tetrahydrofuran, dioxane, 1,2-dimethoxyethane, and the like.

Examples of the "amides" described above are N,N-dimethylformamide, N,N-dimethylacetamide, hexamethylphosphoric triamide, and the like.

When an objective product is obtained in a free form by a reaction described above, then it may be converted in accordance with an ordinary method into a salt, and when it is obtained as a salt then it may be converted in accordance with an ordinary method into a free form or another salt. Compound (I) thus obtained can be isolated and purified from a reaction solution by a known method such as a partition, concentration, solvent extraction, fraction distillation, crystallization, recrystallization, chromatography and the like.

When Compound (I) is present as a configuration isomer, diastereomer, conformer and the like, then it can be isolated if desired by a separation or purification procedure described above. When Compound (I) is present as a racemate, it can be resolved into S form and R form by an ordinary optical resolution method.

When Compound (I) has its stereoisomers, then individual isomers or a mixture thereof may also encompassed in this invention.

Compound (I) of this invention has an excellent inhibitory action on apoptosis (e.g., inhibitory action on apoptosis and heart muscle cells, and the like) to an animal, especially to a mammal (e.g., human, monkey, dog, cat, rabbit, guinea pig, rat, mouse, and the like) and a low toxicity. Furthermore, Compound (I) of this invention has an ability to bind macrophage migration-inhibitory factor (MIF) and inhibits the apoptosis based on oxidation-stress, removal of serum, lack of growth factor, HMG-CoA reductase inhibitor, anti-cancer drug, NO, amyloid β protein, and the like. For example, the apoptosis derived from several factors is observed as an elimination of heart muscle cells from heart muscle, which gives a malignant effect on heart function. Therefore, the compound having apoptosis inhibitory effect on heart muscle cells can prevent the malignant effect on heart function derived from the elimination of heart muscle cells. And Compound (I) of this invention also has an inhibitory effect on the proliferation of tumor and the arterialization.

On the basis of that, Compound (I) is useful as a safe pharmaceutical and can be used as a pharmaceutical for preventing and/or treating heart disease [e.g., cardiomyopathy (e.g., congestive cardiomyopathy, hypertrophic obstructive cardiomyopathy, hypertrophic cardiomyopathy, idiopathic cardiomyopathy, constrictive cardiomyopathy, diabetic cardiomyopathy, and the like), heart failure (e.g., chronic heart failure, chronic congestive heart failure, acute heart failure, cardiac decompensation, left cardic failure, right heart failure, congestive heart failure, acute congestive heart failure, metabolic heart failure, congestive heart failure, high output heart failure, low output heart failure, intractable heart failure, muscle infarction prognosis failure, and the like), angina pectoris, myocardial infarction, and the like], nervous degenerative disease [e.g., Parkinson's disease, Alzheimer disease, triplet repeat disease (e.g., Huntington's chorea, spinocerebellar imbalance type-I, Machado-Joseph disease, dentate rubro pallido luysian atrophy, and the like), prion disease (e.g., Creutzfeldt-Jakob disease, bovine spongiform encephalopathy, and the like), amyotrophic lateral sclerosis (ALS), cerebellum degeneration, retinitis pigmentosa, and the like], cerebrovascular disease (e.g., cerebral infarction, and the like), central nervous infectious disease (e.g., HIV encephalitis, bacterial meningitis, and the like), traumatorathy (e.g., spine damage, cerebral damage, and the like), demyelinating disease (e.g., multiple scleroma, and the like), bone and articular disease (e.g., osteoporosis, osteoarthritis, rheumatism, and the like), kidney disease (e.g., ischemic acute renal failure, hemolytic uremic syndrome, acute tubulorrhexis, hydronephrosis, glomerular nephritis, diabetic nephropathy, transplantation rejection kidney, and the like), liver disease (e.g., viral hepatitis, alcoholic hepatitis, and the like), osteomyelodysplasia (e.g., aplastic anemia, and the like), AIDS, arteriosclerosis, diabetes, pulmonary hypertension, sepsis, septicaemia, inflammatory bowel disease, autoimmune disease (e.g., systematic lupus erythematosus, atopic dermatitis, and the like), transplanted organ disorder in rejection, cancer (e.g., colon cancer, breast cancer, lung cancer, prostatic cancer, esophageal carcinoma, stomach cancer, liver cancer, carcinoma of biliary tract, lienal cancer, renal cancer, bladder cancer, uterine cancer, testoid cancer, thyroid cancer, pancreatic cancer, brain tumor, hematic cancer, and the like), and the like.

When Compound (I) is used as a pharmaceutical for preventing and/or treating diseases described above, the administration route may be oral or parenteral in accordance with the known method per se. And it may be administered orally as a solid preparation such as tablet, capsule, granule, powder, and the like or parenterally as an intravenous, subcutaneous or intramuscular injection formulation, a suppository or a troche. And it may be administered hypoglossaly, subcutaneously or intramuscularly as a sustained formulation such as troche, microcapsule, and the like The dosage of Compound (I) may vary depending on administration target, administration route, condition, and the like, and is not limited especially, a daily dose in an adult having heart failure is usually 0.001 to 10 mg/kg, preferably 0.001 to 0.2 mg/kg, more preferably 0.001 to 0.02 mg/kg, which is given once to in three portions a day.

The amount of Compound (I) in a pharmaceutical of this invention is usually about 0.01 to 100% by weight based on the entire pharmaceutical.

The pharmaceutically acceptable carriers include a wide variety of organic or inorganic carrier materials conventionally used for pharmaceutical preparations, and are mixed, for example, as excipients, lubricants, binders, disintegrators in solid preparation; solvents, solubilizers, suspending agents, isotonizing agents, buffers and painkillers in liquid preparation. If necessary, additives such as preservatives, antioxidants, coloring agents, sweeteners, etc. can also be used.

Preferable examples of the excipient are lactose, sucrose, D-mannitol, starch, crystalline cellulose, light silicic anhydride, and the like. Preferable examples of the lubricant are magnesium stearate, calcium stearate, talc, colloidal silica, and the like. Preferable examples of the binder are crystalline cellulose, sucrose, D-mannitol, dextrin, hydroxypropylcellulose, hydroxypropylmethylcellulose, polyvinylpyrrolidone, and the like. Preferable examples of the disintegrator are starch, carboxymethylcellulose, calcium carboxymethylcellulose, sodium croscarmellose, sodium carboxymethyl starch, and the like. Preferable examples of the solvent are water for injection, alcohol, propylene glycol, Macrogol, sesame oil, corn oil, and the like. Preferable examples of the solubilizer are polyethylene glycol, propylene glycol, D-mannitol, benzyl benzoate, ethanol, trisaminomethane, cholesterol, triethanolamine, sodium carbonate, sodium citrate, and the like. Preferable examples of the suspending agent are surfactant such as stearyl triethanolamine, sodium laurylsulfate, lauryl aminopropionic acid, lecithin, benzalconium chloride, benzetonium chloride, glycerine monostearate, and the like; and hydrophilic polymers such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like. Preferable examples of the isotonizing agent are sodium chloride, glycerine, D-mannitol, and the like. Preferable examples of the buffer are buffer such as phosphate, acetate, carbonate, citrate, and the like. Preferable examples of the painkiller are benzyl alcohol, and the like. Preferable examples of the preservative are p-hydroxybenzoic acid ester, chlorobutanol, benzyl alcohol, phenethyl alcohol, dehydroacetic acid, sorbic acid, and the like. Preferable examples of the antioxidant are sulfite, ascorbic acid, and the like.

An intravenous, subcutaneous or intramuscular injection formulation can be produced by the adding suspending agents, solubilizers, stabilizers, isotonizing agents, preservatives to Compound (I) in accordance with known method per se. The intravenous, subcutaneous or intramuscular injection formulation can be converted to freeze-dried formulation. When the compound of this invention is administered to human, it can be converted as a pharmaceutical composition as it is or combining with pharmaceutically acceptable carriers, excipients, diluents and administered orally or parenterally.

Examples of the pharmaceutical composition are oral drug (e.g., powder, granule, capsule, tablet), injection formulation, drop, external preparation (e.g., nose drop, endermism, and the like), suppository (e.g., rectum suppository, vagina suppository), and the like.

These pharmaceutical preparations can be produced by a method known per se which is employed usually in a pharmaceutical process.

Compound (I) can be formulated with dispersant (e.g., Tween 80 (ATLAS POWDER, USA), HCO60 (NIKKO CHEMICALS), polyethylene glycol, carboxymethyl cellulose, sodium alginate, and the like), preservative (e.g., methylparabene, propylparabene, benzyl alcohol, and the like), isotonicity agent (e.g., sodium chloride, mannitol, sorbitol, glucose, etc.), and the like into aqueous formulation for injection, or dissolved, suspended or emulsified in a vegetable oil such as olive oil, sesame oil, cottonseed oil and corn oil, etc. and in propylene glycol, etc. to form an oily formulation, whereby producing an injection formulation.

In order to obtain an oral dosage form, a method known per se is employed to compress compound (I) for example with excipient (e.g., lactose, sugar, starch, and the like), disintegrator (e.g., starch, calcium carbonate, etc.), binder (e.g., starch, gum arabic, carboxymethyl cellulose, polyvinyl pyrrolidone, hydroxypropyl cellulose, and the like) or lubricant (e.g., talc, magnesium stearate, polyethylene glycol 6000, and the like), and the like into a desired shape, which is then subjected to taste masking, covered with enteric coating or imparted with a sustained release performance if necessary by means of a coating method known per se, whereby obtaining an oral dosage form. Examples of the coating are hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (Rohm, German, methacrylic/acrylic acid copolymer) and colorant (e.g., iron oxide red, titanium dioxide, etc.). When Compound (I) is produced as an enteric coating formulation, the intermediate phase can be located between enteric coating phase and drug containing phase in order to isolate the two phases.

In order to obtain external preparation, a method known per se is employed to convert Compound (I) or salt thereof into a solid, semi-solid or liquid external preparation. For example, the solid external preparation can be produced by Compound (I) or salt thereof as it is or by combining Compound (I) with excipient (e.g., glycol, mannitol, starch, micro crystalline cellulose, and the like), thickener (e.g., natural gum, cellulose derivatives, acrylic acid polymer, and the like), and the like. The liquid external preparation such as oily or aqueous suspension can be produced in accordance with the method for producing the injection formulation. Examples of the semi-solid external preparation are aqueous or oily gel, or ointment. And each of them can be combined with pH adjusting agent (e.g., carbonic acid, phosphoric acid, citric acid, hydrochloric acid, sodium hydroxide, and the like), antiseptics (e.g., p-hydroxybenzoic acid ester, chlorobutanol, benzalconium chloride, and the like), and the like.

In order to obtain for example suppository, a method known per se is employed to convert Compound (I) into an oily or aqueous solid, semi-solid or liquid suppository. The oily base employed in a composition described above may for example be a higher fatty acid glyceride [e.g., cocoa butter, UITEPSOL (DYNAMITE NOVEL, Germany), etc.], a medium fatty acid [e.g., MIGRIOL (DYNAMITE NOVEL, Germany), etc.], or vegetable oil (e.g., sesame oil, soybean oil, cottonseed oil, and the like), and the like. The aqueous base may for example be polyethylene glycol and propylene glycol, and the aqueous gel base may for example be natural gums, cellulose derivatives, vinyl polymers and acrylic acid polymers, and the like.

Examples of the drug which can be administered together with Compound (I) are described below. Each of the drugs may be administered orally or parenterally (e.g., nose drop, injection formulation, suppository, and the like). And each of the drugs can be blended into one formulation. And each of the drugs can be formulated by combining with pharmacologically acceptable carriers, excipients, binders, diluents, and the like respectively and administered respectively or simultaneously. In case that each of the drugs is formulated respectively, each of the drugs can be administered to the same target simultaneously or separately as well as they can be administered by mixing them and diluents when they are used.

Examples of the drug obtaining synergism effects together with Compound (I) are inotropic agents (e.g., cardiac glycosides such as digoxin, and the like; β-agonist such as dopamine, dobutamine, and the like; phosphodiesterase inhibitor such as amrinone, milrinone, and the like); anti heart failure drug (e.g., class I of anti heart failure drug such as disopyramide, lidocaine, procainamide, and the like; class III of anti heart failure drug such as amiodarone, sotalol and the like; β-blocker such as propranolol, and the like); vasodilator (e.g., angiotensin converting enzyme inhibitor such as captopril, enalapril, and the like; nitrous acid drug such as nitroprusside, isosorbide dinitrate, and the like; calcium receptor inhibitor such as verapamil, diltiazem, nicardipine, nifedipine, and the like; angiotensin II receptor inhibitor such as losartan, candesartan, and the like); diuretic (e.g., loop diuretic such as furosemide, bumetanide, and the like; thiazide diuretic such as chlorothiazide, bendrofluazide, and the like; potassium sparing diuretic such as amiloride, spironolactone, and the like); and the like.

And when Compound (I) is used together with HMG-CoA reductase inhibitor (e.g., simvastatin, atorvastatin, and the like), fibrate-type drug for hyperlipemia (e.g., gemfibrozil, and the like), anti cancer drug (e.g., ifosfamide, UFT, adriamycin, doxorubicin, peplomycin, cisplatin, cyclophosphamide, 5-FU, methotrexate, mitomycin C, mitoxantrone, and the like), and the like, the side-effect derived from HMG-CoA reductase inhibitor, fibrate-type drug for hyperlipemia, anti cancer drug and the like, which gives wounds to normal cells, can be reduced.

This invention will be now further described specifically with reference to the following Reference Examples, Examples, Formulation examples and Experimental Examples, which are however not intended to limit the scope of the present invention.

In the following Reference Examples, "%" means % by weight unless otherwise specified. $^1$H-NMR spectra were measured by Bruker AVANCE DPX-300 (300 MHz) spectrometer with tetramethyl silane as the internal standard. All δ values are expressed in ppm.

The abbreviations as used herein have the following meanings.

s: singlet
d: doublet
dd: double doublet
t: triplet
tt: triple triplet
q: quartet
m: multiplet
br: broad
J: coupling constant
Hz: Hertz
DMF: N,N-dimethylformamide
CDCl$_3$: deuterated chloroform
DMSO-d$_6$: dimethylsulfoxide-d$_6$
IR: infrared absorption spectrum
WSC: 1-ethyl-3-(dimethylaminopropyl)carbodiimide hydrochloride
HOBt: 1-hydroxybenzotriazole The "room temperature" usually means about 10° C. to 35° C., however, that is not limited strictly.

EXAMPLES

Example 1

2-(2-Furyl)-4H-1,3-benzothiazine-4-one

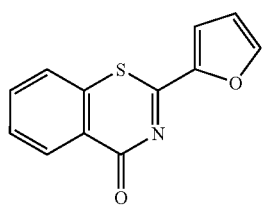

A mixture of methyl thiosalicylate (1.01 g, 6.0 mmol), 2-furonitrile (0.57 g, 6.0 mmol), triethylamine (1.5 ml, 10.7 mmol) and toluene (20 ml) was refluxed for 24 hrs. After cooling, the precipitated crystals were collected by filtration and recrystallized from hexane-ethanol to give the titled compound (0.26 g, 19%).

mp. 170.0-171.5° C. IR (KBr): 3132, 3072, 1653, 1572, 1508, 1456, 1296, 1271, 1101, 1014, 860, 744, 592 cm$^{-1}$. $^1$H-NMR (CDCl$_3$) δ: 6.65 (1H, dd, J=1.8, 3.5 Hz), 7.48-7.71 (5H, m), 6.51 (1H, dd, J=1.5, 5.0 Hz). Elemental Analysis for C$_{12}$H$_7$NO$_2$S Calcd. C, 62.87; H, 3.08; N, 6.11. Found C, 62.84; H, 2.92; N; 6.23.

Example 2

2-(2-Thienyl)-4H-1,3-benzothiazine-4-one

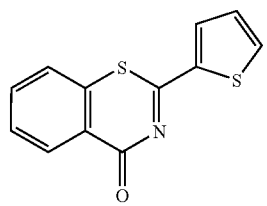

A mixture of methyl thiosalicylate (1.60 g, 9.5 mmol), 2-thiophenecarboxylic acid (1.04 g, 9.5 mmol), triethylamine (2.0 ml, 14.3 mmol) and toluene (2 ml) was refluxed for 12 hrs. After cooling, the precipitated crystals were collected by filtration and recrystallized from methanol-ether to give the titled compound (1.71 g, 73%).

mp. 157.7-158.2° C. IR (KBr): 3084, 1649, 1521, 1500, 1408, 1292, 1248, 1099, 841, 760, 731 cm$^{-1}$. $^1$H-NMR (CDCl$_3$) δ: 7.21 (1H, m), 7.49 (1H, m), 7.58-7.73 (3H, m), 7.96 (1H, m), 8.50 (1H, m). Elemental Analysis for C$_{12}$H$_7$NOS$_2$ Calcd. C, 58.75; H, 2.88; N, 5.71. Found C, 58.74; H, 2.67; N, 5.90.

Example 3

2-(2-Quinolinyl)-4H-1,3-benzothiazine-4-one

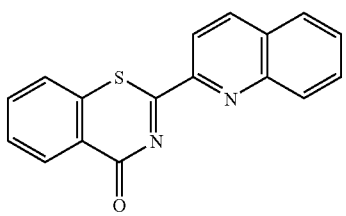

The titled compound was obtained by the reaction of methyl thiosalicylate (1.00 g, 5.9 mmol) and 2-quinolinecarbonitrile (0.95 g, 6.2 mmol) in accordance with the method described in Example 1 (1.54 g, 89%).

mp. 262.7-263.4° C. (recrystallized from chloroform) IR (KBr): 3055, 1651, 1593, 1570, 1529, 1440, 1292, 1097, 929, 837, 740 cm$^{-1}$. $^1$H-NMR (CDCl$_3$) δ: 7.63-7.70 (4H, m), 7.81 (1H, m), 7.90 (1H, d), 8.23 (1H, d), 8.34 (1H, d), 8.58-8.62 (2H, m). Elemental Analysis for C$_{17}$H$_{10}$N$_2$OS Calcd. C, 70.33; H, 3.47; N, 9.65. Found C, 70.27; H, 3.48; N, 9.80.

Example 4

2-(3-Quinolinyl)-4H-1,3-benzothiazine-4-one

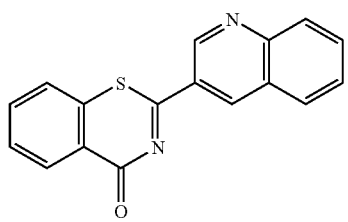

The titled compound was obtained by the reaction of methyl thiosalicylate (1.00 g, 5.9 mmol) and 3-quinolinecarbonitrile (0.92 g, 6.0 mmol) in accordance with the method described in Example 1 (0.30 g, 17%).

mp. 216.0-217.0° C. (recrystallized from chloroform-hexane) IR (KBr): 3045, 1657, 1591, 1572, 1518, 1458, 1439, 1292, 1236, 1097, 920, 738 cm$^{-1}$. $^1$H-NMR (CDCl$_3$) δ: 7.59-7.73 (4H, m), 7.87 (1H, m), 8.00 (1H, d, J=8.0 Hz), 8.20 (1H, d, J=8.4 Hz), 8.58 (1H, dd, J=1.3, 7.6 Hz), 9.02 (1H, d, J=2.1 Hz), 9.64 (1H, d, J=2.1 Hz). Elemental Analysis for C$_{17}$H$_{10}$N$_2$OS Calcd. C, 70.33; H, 3.47; N, 9.65. Found C, 70.36; H, 3.44; N, 9.78.

Reference Example 1

2-Cyano-6-methylpyridine

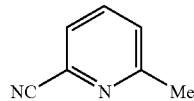

2-Methylpyridinium-N-oxide (2.00 g, 18.3 mmol) was dissolved in nitroethane (10 ml). Trimethylsilylcyanide (2.7 ml, 20.2 mmol) and dimethylcarbamyl chloride (1.7 ml, 18.5 mmol) were added thereto and the mixture was stirred at room temperature for 22 hrs. After evaporation of the solvent, the residue was combined with ethyl acetate and saturated aqueous sodium hydrogen carbonate solution and stirred. The water layer was extracted with ethyl acetate once. The combined organic layer was washed with saturated brine once, dried over anhydrous magnesium sulfate and concentrated under reduced pressure. The obtained crystals were washed with isopropyl ether and dried to give the titled compound (0.61 g, 28%). $^1$H-NMR (CDCl$_3$) δ: 2.62 (3H, s), 7.38 (1H, d, J=7.9 Hz), 7.52 (1H, d, J=7.8 Hz), 7.71 (1H, t, J=7.8 Hz).

Example 5 tert-Butyl 3-[6-(7-chloro-4-oxo-4H-1,3-benzothiazin-2-yl)-2-pyridyl]propanoate

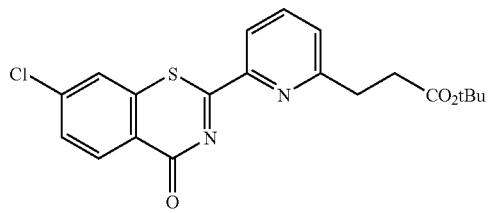

4-Chloro-2-mercaptobenzoic acid (2.60 g, 13.7 mmol) and tert-butyl 3-(6-cyano-2-pyridyl)propanoate (1.60 g, 6.9 mmol) were dissolved in pyridine (15 ml), and the mixture was refluxed for 13 hrs. The reaction mixture was concentrated under reduced pressure, subjected to silica gel column chromatography and eluted with hexane-ethyl acetate (3:1, v/v) to give the titled compound (1.42 g, 51%).

mp. 167.9-168.2° C. IR (KBr): 2976, 2932, 1726, 1678, 1585, 1570, 1535, 1379, 1271, 1149, 1093, 995, 814, 733 cm$^{-1}$. $^1$H-NMR (CDCl$_3$) δ: 1.42 (9H, s), 2.87 (2H, t, J=7.2 Hz), 3.20 (2H, t, J=7.2 Hz), 7.43 (1H, d, J=7.3 Hz), 7.56 (1H, dd, J=2.0, 8.5 Hz), 7.62 (1H, d, J=2.0 Hz), 7.80 (1H, dd, J=7.3, 7.5 Hz), 8.34 (1H, d, J=7.5 Hz), 8.47 (1H, d, J=8.5 Hz). Elemental Analysis for C$_{20}$H$_{19}$N$_2$O$_3$SCl Calcd. C, 59.62; H, 4.75; N, 6.95. Found C, 59.65; H, 4.96; N, 7.15.

Example 6

3-[6-(7-Chloro-4-oxo-4H-1,3-benzothiazin-2-yl)-2-pyridyl]propionic acid

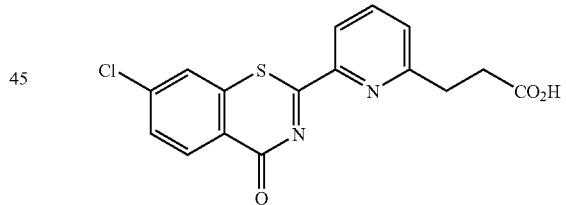

A mixture of tert-butyl 3-[6-(7-chloro-4-oxo-4H-1,3-banzothiazin-2-yl)-2-pyridyl]propanoate obtained in Example 5 (0.60 g, 1.5 mmol) and trifluoroacetic acid (5.0 ml) was stirred at 0° C. for 2 hrs. The reaction mixture was concentrated under reduced pressure. Diisopropyl ether was added thereto to precipitate crystals, which were collected by filtration and dried to give the titled compound (0.49 g, 96%).

mp. 224.4-224.7° C. IR (KBr): 3051, 2922, 1709, 1664, 1585, 1566, 1529, 1379, 1261, 1230, 1095, 846, 804 cm$^{-1}$. $^1$H-NMR (DMSO-d$_6$) δ: 2.80 (2H, t, J=7.1 Hz), 3.13 (2H, t, J=7.1 Hz), 7.65 (1H, d, J=7.7 Hz), 7.73 (1H, dd, J=2.0, 8.5 Hz), 8.00 (1H, m), 8.13-8.17 (2H, m), 8.31 (1H, d, J=8.5 Hz), 12.20 (1H, br s). Elemental Analysis for C$_{16}$H$_{11}$N$_2$O$_3$SCl.0.25H$_2$O Calcd. C, 54.71; H, 3.30; N, 7.97. Found C, 54.85; H, 3.14; N, 7.82.

Example 7

2-Pyrazinyl-4H-1,3-benzothiazine-4-one

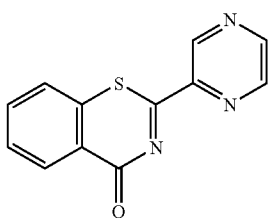

A mixture of methyl thiosalicylate (1.68 g, 10.0 mmol), cyanopyrazine (1.06 g, 10.1 mmol), triethylamine (2.10 ml, 15.1 mmol) and toluene (10.0 ml) was refluxed at 120° C. for 8 hrs. The solvent was evaporated and the residue was recrystallized from dioxane-hexane to give the titled compound (0.54 g, 22%) as crystals.

mp. 240.7-241.7° C. IR(KBr):3069, 1668, 1574, 1537, 1464, 1439, 1404, 1280, 1267, 1255, 1232, 1165, 1124, 1095, 1062, 1053, 1033, 1018, 939, 864, 825, 798, 760, 744 cm$^{-1}$. $^1$H-NMR(CDCl$_3$) δ: 7.61-7.75 (4H, m), 8.55-8.58 (1H, m), 8.70-8.72 (1H, m), 8.85 (1H, d, J=2.4 Hz), 9.72 (1H, d, J=1.3 Hz). Elemental Analysis for C$_{12}$H$_7$N$_3$OS Calcd. C, 59.74; H, 2.92; N, 17.42. Found C, 59.47; H, 2.82; N, 17.21.

Example 8

2-(3-Methyl-2-pyridyl)-4H-1,3-benzothiazine-4-one

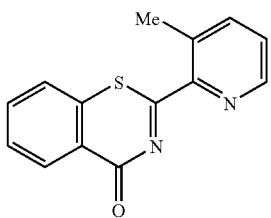

The titled compound was obtained by the reaction of methyl thiosalicylate (1.68 g, 10.0 mmol) and 3-methyl-2-cyanopyridine (1.19 g, 10.0 mmol) in accordance with the method described in Example 1 (0.09 g, 4%).

mp. 149.9-151.6° C. IR(KBr): 3061, 1664, 1574, 1537, 1440, 1413, 1404, 1386, 1321, 1302, 1256, 1236, 1209, 1186, 1134, 1120, 1095, 1060, 1030, 1033, 999, 985, 964, 931, 868, 825, 790, 763, 740 cm$^{-1}$. $^1$H-NMR(CDCl$_3$) δ: 2.87 (3H, s), 7.39-7.42 (1H, m), 7.56-7.71 (4H, m), 8.50-8.60 (2H, m). Elemental Analysis for C$_{14}$H$_{10}$N$_2$OS Calcd. C, 66.12; H, 3.96; N, 11.02. Found C, 65.94; H, 3.92; N, 11.23.

Example 9

6-Chloro-2-(2-pyridyl)-4H-1,3-benzothiazine-4-one

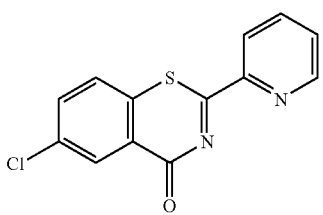

A mixture of 5-chloro-2-mercaptobenzoic acid (2.00 g, 10.6 mmol), 2-cyanopyridine (1.10 g, 10.5 mmol) and pyridine (50.0 ml) was refluxed for 9 hrs. After cooling, the precipitated crystals were collected by filtration and recrystallized from hexane-chlorobenzene to give the titled compound (0.78 g, 27%).

mp. 269.4-270.1° C. IR(KBr): 3086, 3061, 1660, 1568, 1531, 1313, 1234, 945, 790 cm$^{-1}$. $^1$H-NMR(CDCl$_3$+DMSO-d$_6$) δ: 7.57-7.70 (3H, m,), 7.95 (1H, m, 8.49-8.51 (2H, m), 8.75 (1H, m). Elemental Analysis for C$_{13}$H$_7$N$_2$OSCl Calcd. C, 56.83; H, 2.57; N, 10.20. Found C, 56.95; H, 2.41; N, 10.31.

Example 10

7-Chloro-2-(2-pyridyl)-4H-1,3-benzothiazine-4-one

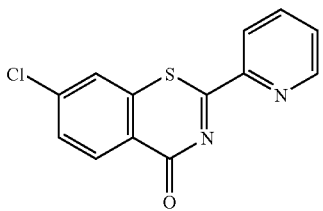

A mixture of 4-chloro-2-mercaptobenzoic acid (6.00 g, 31.8 mmol), 2-cyanopyridine (1.90 g, 17.7 mmol) and pyridine (50.0 ml) was refluxed for 9 hrs as described in Example 9. After cooling, the precipitated crystals were collected by filtration and recrystallized from hexane-chlorobenzene to give the titled compound (2.30 g, 48%).

mp. 245.3-245.6° C. IR(KBr): 1666, 1589, 1564, 1535, 1458, 1429, 1379, 1302, 1273, 1234, 1107, 1087, 860, 790, 740 cm$^{-1}$. $^1$H-NMR(CDCl$_3$) δ: 7.54-7.60 (3H, m,), 7.92 (1H, m,), 8.47 (1H, d), 8.52 (1H, d), 8.74 (1H, dd) Elemental Analysis for C$_{13}$H$_7$N$_2$OSCl Calcd. C, 56.83; H, 2.57; N, 10.20. Found C, 56.82; H, 2.76; N, 10.07.

Example 11

6-Bromo-2-(2-pyridyl)-4H-1,3-benzothiazine-4-one

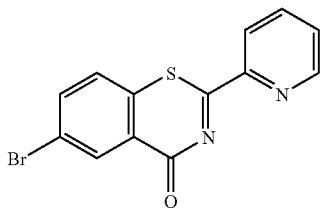

5-Bromo-2-mercaptobenzoic acid (4.10 g, 17.6 mmol), 2-cyanopyridine (1.70 g, 16.3 mmol) and pyridine (50.0 ml) were refluxed for 9 hrs as described in Example 9. After cooling, the precipitated crystals were collected and recrystallized from hexane-chlorobenzene to give the titled compound (2.40 g, 45%).

mp. 253.0-253.7° C. IR(KBr): 3061, 1658, 1566, 1527, 1388, 1311, 1232, 945, 846, 788, 736 cm$^{-1}$. $^1$H-NMR (CDCl$_3$) δ: 7.50 (1H, d, J=8.4 Hz), 7.56 (1H, dd, J=4.8, 7.5 Hz), 7.79 (1H, dd, J=2.2, 8.4 Hz), 7.92 (1H, m), 8.53 (1H, d, J=7.5 Hz), 8.70-8.75 (2H, m). Elemental Analysis for C$_{13}$H$_7$N$_2$OSBr Calcd. C, 48.92; H, 2.21; N, 8.78. Found C, 49.05; H, 2.27; N, 8.89.

Example 12

8-Methyl-2-(2-pyridyl)-4H-1,3-benzothiazine-4-one

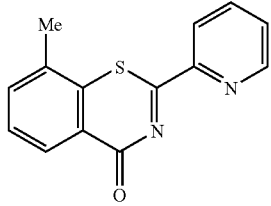

A mixture of 3-methyl-2-mercaptobenzoic acid (2.40 g, 14.3 mmol), 2-cyanopyridine (1.20 g, 11.9 mmol) and pyridine (50.0 ml) was refluxed for 9 hrs as described in Example 9. After cooling, the precipitated crystals were collected by filtration and recrystallized from hexane-tetrahydrofuran to give the titled compound (1.60 g, 52%).

mp. 197.8-198.5° C. IR(KBr): 3468, 3063, 1649, 1577, 1537, 1311, 1282, 1232, 1099, 1086, 995, 939, 787, 750, 738 cm$^{-1}$. $^1$H-NMR(CDCl$_3$) δ: 2.59 (3H, s), 7.50-7.57 (3H, m), 7.92 (1H, m), 8.42 (1H, m), 8.57 (1H, d, J=7.9 Hz), 8.77 (1H, d, J=4.6 Hz). Elemental Analysis for C$_{14}$H$_{10}$N$_2$OS Calcd. C, 66.12; H, 3.96; N, 11.02. Found C, 66.00; H, 3.94; N, 11.14.

Example 13

6-Methyl-2-(2-pyridyl)-4H-1,3-benzothiazine-4-one

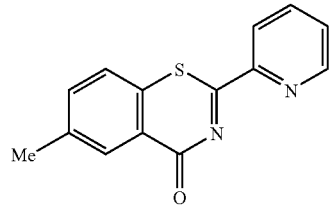

A mixture of 5-methyl-2-mercaptobenzoic acid (1.60 g, 9.5 mmol), 2-cyanopyridine (1.10 g, 10.1 mmol) and pyridine (20.0 ml) was refluxed for 8 hrs as described in Example 9. After cooling, the precipitated crystals were collected by filtration and recrystallized from hexane-ethanol to give the titled compound (1.04 g, 43%).

mp. 219.8-220.8° C. IR(KBr): 3049, 2916, 1651, 1568, 1537, 1466, 1317, 1280, 1234, 1188, 997, 788, 734, 617, 515 cm$^{-1}$. $^1$H-NMR(CDCl$_3$) δ: 2.50 (3H, s), 7.51-7.59 (3H, m), 7.91 (1H, m) 8.38 (1H, s), 8.54 (1H, d, J=7.9 Hz), 8.73 (1H, d, J=4.4 Hz). Elemental Analysis for C$_{14}$H$_{10}$N$_2$OS Calcd. C, 66.12; H, 3.96; N, 11.02. Found C, 66.02; H, 3.93; N, 11.13.

Example 14

6,7-Dimethoxy-2-(2-pyridyl)-4H-1,3-benzothiazine-4-one

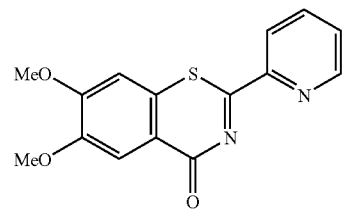

A mixture of 4,5-dimethoxy-2-mercaptobenzoic acid (2.20 g, 10.2 mmol), 2-cyanopyridine (1.10 g, 10.2 mmol) and pyridine (15.0 ml) was refluxed for 20 hrs as described in Example 9. After cooling, the precipitated crystals were collected by filtration and recrystallized from hexane-chlorobenzene to give the titled compound (1.70 g, 55%).

mp. 236.3-237.5° C. IR(KBr): 3059, 2970, 1641, 1603, 1531, 1504, 1466, 1398, 1280, 1267, 1043, 910, 794, 734, 723 cm$^{-1}$. $^1$H-NMR(CDCl$_3$) δ: 4.01 (3H, s), 4.03 (3H, s), 6.96 (1H, s), 7.52 (1H, m), 7.90 (1H, m), 7.97 (1H, s), 8.54 (1H, d, J=7.9 Hz), 8.71 (1H, d, J=4.5 Hz). Elemental Analysis for C$_{15}$H$_{12}$N$_2$O$_3$S Calcd. C, 59.99; H, 4.03; N, 9.33. Found C, 60.11; H, 4.02; N, 9.35.

Example 15

2-(1H-Pyrrol-2-yl)-4H-1,3-benzothiazine-4-one

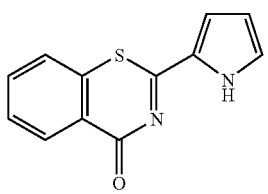

A mixture of methyl thiosalicylate (2.00 g, 11.8 mmol), pyrrole-2-carbonitrile (1.10 g, 11.9 mmol), triethylamine (2.00 ml, 14.3 mmol) and toluene (4.0 ml) was refluxed for 15 hrs as described in Example 1. After cooling, the precipitated crystals were collected by filtration and recrystallized from hexane-ethanol to give the titled compound (1.90 g, 73%).

mp. 202.4-203.2° C. IR(KBr): 3269, 1631, 1572, 1543, 1493, 1454, 1396, 1302, 1124, 1101, 1049, 887, 742 cm$^{-1}$. $^1$H-NMR(CDCl$_3$) δ: 6.39 (1H, s), 7.14-7.16 (2H, m), 7.43-7.63 (3H, m), 8.49 (1H, dd, J=1.5, 7.7 Hz), 10.10 (1H, br s). Elemental Analysis for C$_{12}$H$_8$N$_2$OS Calcd. C, 63.14; H, 3.53; N, 12.27. Found C, 63.11; H, 3.49; N, 12.35.

Example 16

2-(1,5-Dimethyl-1H-pyrrol-2-yl)-4H-1,3-benzothiazine-4-one

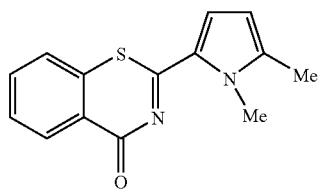

A mixture of methyl thiosalicylate (2.20 g, 13.3 mmol), 1,5-dimethyl-2-pyrrolecarbonitrile (1.40 g, 11.9 mmol), triethylamine (2.50 ml, 17.9 mmol) and toluene (7.0 ml) was refluxed for 24 hrs as described in Example 1. After cooling, the precipitated crystals were collected by filtration and recrystallized from hexane-ethanol to give the titled compound (1.30 g, 41%).

mp. 194.3-195.7° C. IR(KBr): 2951, 2910, 1649, 1574, 1545, 1504, 1460, 1435, 1363, 1290, 1234, 1124, 1099, 1068, 864, 740 cm$^{-1}$. $^1$H-NMR(CDCl$_3$) δ: 2.31 (3H, m), 4.07 (3H, s), 6.07 (1H, d, J=4.1 Hz), 7.12 (1H, d, J=4.1 Hz), 7.40 (1H, m), 7.47-7.59 (2H, m), 8.43 (1H, dd, J=1.5, 7.8 Hz). Elemental Analysis for C$_{14}$H$_{12}$N$_2$OS Calcd. C, 65.60; H, 4.72; N, 10.93. Found C, 65.49; H, 4.54; N, 11.04.

Example 17

5-Methyl-2-(2-pyridyl)-4H-1,3-benzothiazine-4-one

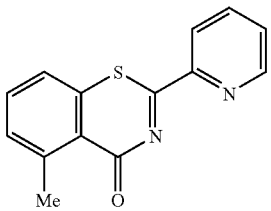

A mixture of 6-methyl-2-mercaptobenzoic acid (1.70 g, 10.1 mmol), 2-cyanopyridine (1.06 g, 10.2 mmol) and pyridine (30.0 ml) was refluxed at 135° C. for 18 hrs as described in Example 9. The reaction mixture was concentrated. The residue was subjected to a silica gel column chromatography and eluted with ethyl acetate. The resultant product was recrystallized from ethanol to give the titled compound (0.51 g, 20%).

mp. 150.8-151.3° C. IR(KBr): 3074, 2970, 1662, 1585, 1574, 1545, 1444, 1439, 1410, 1377, 1298, 1273, 1263, 1238, 1184, 1105, 1051, 955, 943, 827, 783, 733 cm$^{-1}$. $^1$H-NMR (CDCl$_3$) δ: 2.85 (3H, s), 7.38-7.54 (4H, m), 7.89-7.93 (1H, m), 8.46-8.49 (1H, m), 8.72-8.74 (1H, m). Elemental Analysis for C$_{14}$H$_{10}$N$_2$OS Calcd. C, 66.12; H, 3.96; N, 11.02. Found C, 60.10; H, 3.98; N, 11.07.

Example 18

8-Methoxy-2-(2-pyridyl)-4H-1,3-benzothiazine-4-one

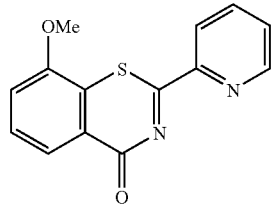

A mixture of 3-methoxy-2-mercaptobenzoic acid (1.84 g, 10.0 mmol), 2-cyanopyridine (1.05 g, 10.2 mmol) and pyridine (30.0 ml) was refluxed at 135° C. for 18 hrs as described in Example 9. The mixture was concentrated. The obtained crystals were recrystallized from ethanol to give the titled compound (0.75 g, 28%).

mp. 191.2-191.4° C. IR(KBr): 3049, 1657, 1591, 1535, 1467, 1442, 1427, 1332, 1304, 1280, 1269, 1234, 1134, 1105, 1060, 1047, 995, 941, 796, 767, 758, 742 cm$^{-1}$. $^1$H-NMR (CDCl$_3$) δ: 4.01(3H, s), 7.17 (1H, d, J=8.1 Hz), 7.51-7.59 (2H, m), 7.87-7.93 (1H, m), 8.16 (1H, d, J=8.0 Hz), 8.55 (1H, d, J=7.9 Hz), 8.75-8.76 (1H, m). Elemental Analysis for C$_{14}$H$_{10}$N$_2$O$_2$S Calcd. C, 62.21; H, 3.73; N, 10.36. Found C, 62.18; H, 3.64; N, 10.49.

Example 19

7-Fluoro-2-(2-pyridyl)-4H-1,3-benzothiazine-4-one

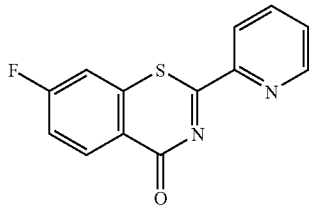

A mixture of 4-fluoro-2-mercaptobenzoic acid (5.00 g, 29.0 mmol), 2-cyanopyridine (3.05 g, 29.3 mmol) and pyridine (30.0 ml) was refluxed at 135° C. for 48 hrs as described in Example 9. The reaction mixture was concentrated. The residue was subjected to a silica gel column chromatography and eluted with hexane-ethyl acetate (2:1, v/v). The resultant product was recrystallized from ethanol to give the titled compound (0.09 g, 1%).

mp. 250.0-250.2° C. IR(KBr): 3069, 1660, 1606, 1576, 1545, 1477, 1466, 1435, 1396, 1305, 1280, 1240, 1120, 1097, 1086, 997, 941, 860, 790, 773, 738 cm$^{-1}$. $^1$H-NMR(CDCl$_3$) δ: 7.29-7.36 (2H, m), 7.54-7.58 (1H, m), 7.89-7.95 (1H, m), 8.52-8.60 (2H, m), 8.74 (1H, d, J=4.6 Hz). Elemental Analysis for C$_{13}$H$_7$N$_2$OSF Calcd. C, 60.46; H, 2.73; N, 10.85. Found C, 60.34; H, 2.65; N, 11.11.

Example 20

6-Fluoro-2-(2-pyridyl)-4H-1,3-benzothiazine-4-one

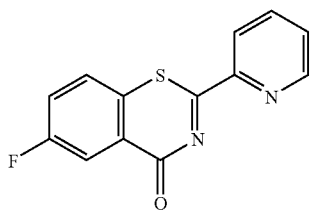

A mixture of 5-fluoro-2-mercaptobenzoic acid (1.50 g, 8.7 mmol), 2-cyanopyridine (0.92 g, 8.8 mmol) and pyridine (30.0 ml) was refluxed at 135° C. for 48 hrs as described in Example 9. The reaction mixture was concentrated. The residue was subjected to a silica gel column chromatography and eluted with hexane-ethyl acetate (2:1, v/v). The resultant product was recrystallized from ethanol to give the titled compound (0.09 g, 4%).

mp. 239.9-240.4° C. IR(KBr): 3061, 1666, 1606, 1577, 1539, 1471, 1439, 1412, 1317, 1302, 1267, 1234, 1126, 1099, 1055, 995, 950, 918, 900, 885, 819, 792, 734, 707 cm$^{-1}$. $^1$H-NMR(CDCl$_3$) δ: 7.42-7.48 (1H, m), 7.48-7.58 (1H, m), 7.62-7.66 (1H, m), 7.90-7.85 (1H, m), 8.23-8.27 (1H, m), 8.55 (1H, d, J=7.9 Hz), 8.74-8.75 (1H, m). Elemental Analysis for C$_{13}$H$_7$N$_2$OSF Calcd. C, 60.46; H, 2.73; N, 10.85. Found C, 60.48; H, 2.77; N, 10.99.

Example 21

5-Fluoro-2-(2-pyridyl)-4H-1,3-benzothiazine-4-one

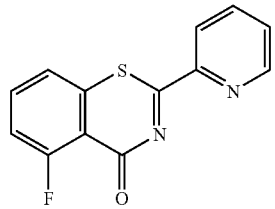

A mixture of 6-fluoro-2-mercaptobenzoic acid (5.00 g, 29.0 mmol), 2-cyanopyridine (3.05 g, 29.3 mmol) and pyridine (30.0 ml) was refluxed at 135° C. for 48 hrs as described in Example 9. The reaction mixture was concentrated. The residue was subjected to a silica gel column chromatography and eluted with hexane-ethyl acetate (2:1, v/v). The resultant product was recrystallized from ethanol to give the titled compound (0.11 g, 1%).

mp. 256.5-257.2° C. IR(KBr): 3065, 1668, 1601, 1576, 1539, 1462, 1448, 1433, 1298, 1273, 1251, 1238, 1086, 1057, 997, 945, 914, 800, 781, 738 cm$^{-1}$. $^1$H-NMR(CDCl$_3$) δ: 7.24-7.30 (1H, m), 7.41 (1H, d, J=7.9 Hz), 7.53-7.66 (2H, m), 7.89-7.95 (1H, m), 8.50 (1H, d, J=7.9 Hz), 8.73-8.74 (1H, m). Elemental Analysis for C$_{13}$H$_7$N$_2$OSF Calcd. C, 60.46; H, 2.73; N, 10.85. Found C, 60.11; H, 2.68; N, 11.04.

Example 22

2-(2-Pyridyl)-4H-pyrido[3,2-e][1,3]thiazine-4-one

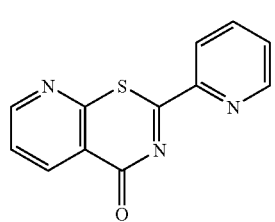

A mixture of 2-mercaptonicotinic acid (5.00 g, 32.2 mmol), 2-cyanopyridine (3.39 g, 32.5 mmol) and pyridine (30.0 ml) was refluxed at 135° C. for 72 hrs as described in Example 9. The mixture was concentrated. The residue was subjected to a silica gel column chromatography and eluted with hexane-ethyl acetate (1:1, v/v). The resultant product was recrystallized from ethanol to give the titled compound (0.10 g, 1%).

mp. 234.7-234.9° C. IR(KBr): 3069, 1666, 1568, 1543, 1467, 1439, 1402, 1307, 1290, 1236, 1217, 1114, 1074, 1041, 997, 943, 788, 761 cm$^{-1}$. $^1$H-NMR(CDCl$_3$) δ: 7.55-7.60 (2H, m), 7.90-7.96 (1H, m), 8.54 (1H, d, J=7.9 Hz), 8.75-8.78 (2H, m), 8.85-8.87 (1H, m). Elemental Analysis for C$_{12}$H$_7$N$_3$OS Calcd. C, 59.71; H, 2.29; N, 17.42. Found C, 59.75; H, 2.71; N, 17.58.

Example 23

Methyl [6-(4-oxo-4H-1,3-benzothiazin-2-yl)-2-pyridyl]acetate

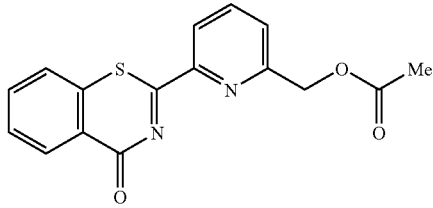

A mixture of methyl thiosalicylate (0.84 g, 5.0 mmol), 2-acetoxy-6-cyanopyridine (0.90 g, 5.0 mmol), triethylamine (1.10 ml, 7.5 mmol) and toluene (30 ml) was refluxed for 48 hrs as described in Example 1. The reaction mixture was concentrated. The precipitated crystals were collected by filtration and recrystallized from ethanol to give the titled compound (0.67 g, 43%).

mp. 180.1-180.3° C. IR(KBr): 1741, 1653, 1570, 1527, 1439, 1371, 1296, 1277, 1224, 1055, 812, 736 cm$^{-1}$. $^1$H-NMR(CDCl$_3$) δ: 2.20 (3H, s), 5.35 (2H, s), 7.58-7.72 (4H, m) 7.92 (1H, t, J=7.8 Hz), 8.47 (1H, d, J=7.8 Hz), 8.48-8.57 (1H, m). Elemental Analysis for C$_{16}$H$_{12}$N$_2$O$_3$S Calcd. C, 61.53; H, 3.87; N, 8.97. Found C, 61.59; H, 3.73; N, 9.06.

Reference Example 2

2-Mercapto-3,5-dimethylbenzoic acid

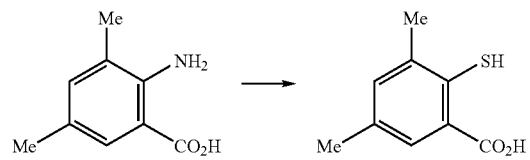

A mixture of 2-amino-3,5-dimethylbenzoic acid (5.6 g, 33.9 mmol), sodium hydroxide (1.5 g, 37.5 mmol), sodium nitrite (2.3 g, 34.0 mmol) and water (40 ml) was added dropwise to a mixture of concentrated hydrochloric acid (10 ml) and ice (10 g) under cooling with ice while adding ice in order to keep the reaction temperature under 5° C. The reaction mixture was stirred under ice-cooling condition for 30 minutes, neutralized with potassium acetate and added to a solution of potassium o-ethyl dithiocarbonate (16.9 g, 105.4 mmol) in water (50 ml) at 80° C. After stirring at the same temperature for 20 minutes, the reaction mixture was acidified (pH 3) by use of concentrated hydrochloric acid. The water layer was separated. 10% aqueous sodium hydroxide solution (30 ml) was added to the oily substance and the mixture was stirred at 80° C. for 2 hrs. Furthermore, sodium hydrogen sulfite (4.0 g) was added to the mixture, and the mixture was stirred at the same temperature for 10 minutes. The reaction mixture was filtered and the filtrate was acidified (about pH 4) by use of concentrated hydrochloric acid. The precipitate was collected by filtration and dissolved in a mixture of methanol (5 ml) and diisopropylether (80 ml), dried and concentrated under reduced pressure to give the titled compound as crystals (3.6 g, 58%).

$^1$H-NMR (CDCl$_3$) δ: 2.31 (3H, s), 2.36 (3H, s), 6.20 (1H, b s), 7.19 (1H, s), 7.86 (1H, s).

Example 24

6,8-Dimethyl-2-(2-pyridyl)-4H-1,3-benzothiazine-4-one

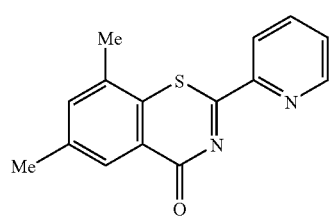

A mixture of 2-mercapto-3,5-dimethylbenzoic acid (1.6 g, 8.8 mmol), 2-cyanopyridine (1.0 g, 9.7 mmol) and pyridine (15 ml) was refluxed for 12 hrs as described in Example 9. After cooling, the precipitated crystals were collected by filtration and recrystallized from hexane-chlorobenzene to give the titled compound (1.2 g, 52%).

mp. 245.0-245.8° C. IR(KBr): 3047, 2990, 1645, 1572, 1537, 1462, 1329, 1234, 1180, 995, 792, 740 cm$^{-1}$. $^1$H-NMR (CDCl$_3$) δ: 2.46 (3H, s), 2.55 (3H, s), 7.38 (1H, s), 7.53 (1H, m), 7.91 (1H, m), 8.26 (1H, s), 8.57 (1H, d), 8.76 (1H, d). Elemental Analysis for C$_{15}$H$_{12}$N$_2$OS Calcd. C, 67.14; H, 4.51; N, 10.44. Found C, 67.20; H, 4.49; N, 10.52.

Example 25

2-(4-Methoxy-2-pyridyl)-4H-1,3-benzothiazine-4-one

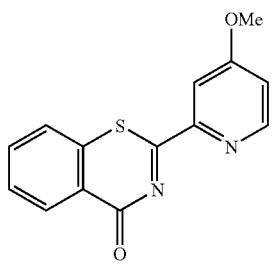

A mixture of methyl thiosalicylate (2.0 g, 11.7 mmol), 4-methoxy-2-cyanopyridine (1.5 g, 11.1 mmol), triethylamine (2.5 ml, 17.9 mmol) and toluene (5 ml) was refluxed for 12 hrs as described in Example 1. The precipitated crystals were collected by filtration and recrystallized from hexane-chlorobenzene to give the titled compound (2.4 g, 81%).

mp. 214.1-214.6° C. IR(KBr): 3080, 1655, 1591, 1570, 1533, 1475, 1305, 1028, 821 cm$^{-1}$. $^1$H-NMR(CDCl$_3$) δ: 3.97 (3H, s), 7.03 (1H, m), 7.59-7.69 (3H, m); 8.07 (1H, d, J=2.5 Hz), 8.50-8.56 (2H, m). Elemental Analysis for C$_{14}$H$_{10}$N$_2$O$_2$S Calcd. C, 62.21; H, 3.73; N, 10.36. Found C, 62.37; H, 3.70; N, 10.42.

Example 26

Ethyl 6-(4-oxo-4H-1,3-benzothiazin-2-yl)-2-pyridinecarboxylate

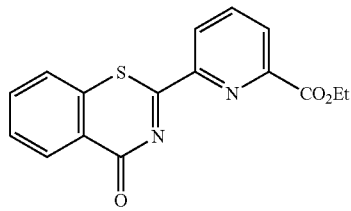

A mixture of methyl thiosalicylate (2.0 g, 11.9 mmol), ethyl 6-cyano-2-pyridinecarboxylate (2.1 g, 11.9 mmol), triethylamine (3.0 ml, 21.5 mmol) and toluene (6 ml) was refluxed for 12 hrs as described in Example 1. The precipitated crystals were collected by filtration and recrystallized from diisopropylether-tetrahydrofuran to give the titled compound (3.0 g, 80%).

mp. 170.0-172.2° C. IR(KBr): 3069, 2986, 1738, 1709, 1676, 1574, 1541, 1440, 1232, 912, 746, 729 cm$^{-1}$. $^1$H-NMR (CDCl$_3$) δ: 1.50 (3H, t), 4.54 (2H, q), 7.63-7.73 (3H, m), 8.07 (1H, m), 8.32 (1H, d), 8.56 (1H, d), 8.71 (1H, d) Elemental Analysis for C$_{16}$H$_{12}$N$_2$O$_3$S Calcd. C, 61.53; H, 3.87; N, 8.97. Found C, 61.52; H, 3.95; N, 9.14.

Example 27

Ethyl 2-(4-oxo-4H-1,3-benzothiazin-2-yl)isonicotinate

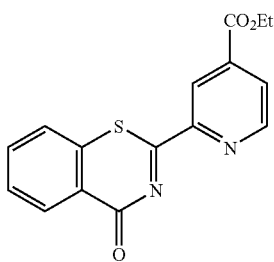

A mixture of methyl thiosalicylate (3.0 g, 17.8 mmol), ethyl 2-cyanoisonicotinate (3.1 g, 17.8 mmol), triethylamine (5.0 ml, 35.8 mmol) and toluene (10 ml) was refluxed for 8 hrs as described in Example 1. The precipitated crystals were collected by filtration and recrystallized from diisopropylether-chlorobenzene to give the titled compound (4.0 g, 71%).

mp. 235.9-236.7° C. IR(KBr): 2993, 1720, 1670, 1541, 1307, 1292, 1219, 1016, 869, 763, 734 cm$^{-1}$. $^1$H-NMR (CDCl$_3$) δ: 1.45 (3H, t), 4.48 (2H, q), 7.61-7.74 (3H, m), 8.12 (1H, m), 8.87 (1H, m), 8.88 (1H, d), 9.04 (1H, s). Elemental Analysis for C$_{16}$H$_{12}$N$_2$O$_3$S Calcd. C, 61.53; H, 3.87; N, 8.97. Found C, 61.47; H, 3.73; N, 8.99.

Example 28

Methyl 6-(4-oxo-4H-1,3-benzothiazin-2-yl)nicotinate

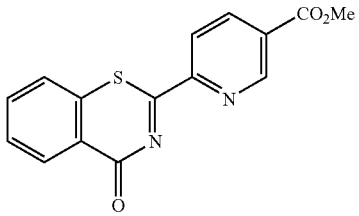

A mixture of methyl thiosalicylate (2.1 g, 12.3 mmol), methyl 6-cyanonicotinate (2.0 g, 12.3 mmol), triethylamine (3.0 ml, 21.5 mmol) and toluene (6 ml) was refluxed for 12 hrs as described in Example 1. The precipitated crystals were collected by filtration and recrystallized from diisopropylether-chlorobenzene to give the titled compound (2.1 g, 58%).

mp. 233.3-333.6° C. IR(KBr): 2951, 1728, 1660, 1572, 1537, 1439, 1294, 1277, 1114, 1095, 783, 727 cm$^{-1}$. $^1$H-NMR(CDCl$_3$) δ: 4.01 (3H, s), 7.62-7.74 (3H, m), 8.48-8.63 (3H, m), 9.30 (1H, m). Elemental Analysis for C$_{15}$H$_{10}$N$_2$O$_3$S Calcd. C, 60.39; H, 3.38; N, 9.39. Found C, 60.43; H, 3.55; N, 9.39.

Example 29

7-Chloro-2-(4-methyl-2-pyridyl)-4H-1,3-benzothiazine-4-one

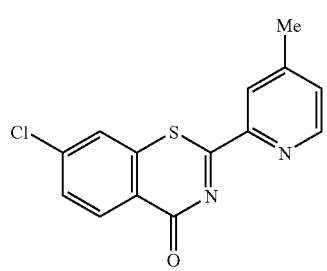

A mixture of 4-chloro-2-mercaptobenzoic acid (3.0 g, 15.9 mmol), 2-cyano-4-methylpyridine (1.9 g, 16.0 mmol) and pyridine (15 ml) was refluxed for 9 hrs as described in Example 9. After cooling, the precipitated crystals were collected by filtration, subjected to a silica gel column chromatography, eluted with ethyl acetate-methanol (5:1, v/v) and recrystallized from chlorobenzene-hexane to give the titled compound (1.47 g, 32%).

mp. 246.2-246.7° C. IR(KBr): 2959, 1664, 1585, 1566, 1535, 1379, 1292, 1275, 1093, 860, 815, 771 cm$^{-1}$. $^1$H-NMR (CDCl$_3$) δ: 2.48 (3H, s), 7.36 (1H, d, J=4.8 Hz), 7.55-7.59 (2H, m), 8.38 (1H, s), 8.47 (1H, d, J=8.3 Hz), 8.58 (1H, d, J=4.8 Hz). Elemental Analysis for C$_{14}$H$_9$N$_2$OSCl Calcd. C, 58.23; H, 3.14; N, 9.70. Found C, 58.29; H, 3.16; N, 9.73.

Example 30

7-Chloro-2-(2-pyrazyl)-4H-1,3-benzothiazine-4-one

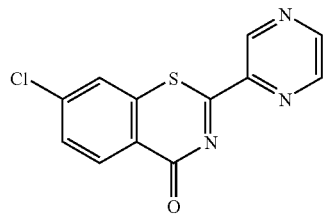

A mixture of 4-chloro-2-mercaptobenzoic acid (3.0 g, 15.9 mmol), 2-cyanopyrazine (1.8 g, 16.7 mmol) and pyridine (25 ml) was refluxed for 6 hrs as described in Example 9. After cooling, the precipitated crystals were collected by filtration, subjected to a silica gel column chromatography, eluted with ethyl acetate-methanol (5:1, v/v) and recrystallized from diisopropylether-chlorobenzene to give the titled compound (1.71 g, 39%).

mp. 240.6-240.9° C. IR(KBr): 3074, 1666, 1649, 1589, 1562, 1535, 1466, 1404, 1381, 1296, 1280, 1097, 1016, 939, 771 cm$^{-1}$. $^1$H-NMR (CDCl$_3$) δ: 7.59-7.62 (2H, m), 8.50 (1H, d, J=9.0 Hz), 8.72 (1H, s), 8.86 (1H, d, J=2.4 Hz), 9.70 (1H, d, J=1.2 Hz). Elemental Analysis for C$_{12}$H$_6$N$_3$OSCl Calcd. C, 52.27; H, 2.19; N, 15.24. Found C, 52.26; H, 2.23; N, 15.30.

Example 31

2-[6-(Propylamino)-3-pyridyl]-4H-1,3-benzothiazine-4-one

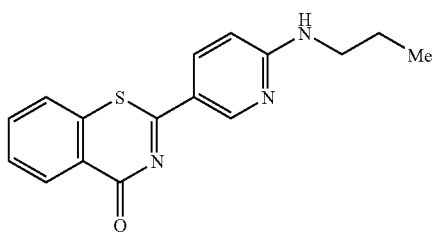

A mixture of methyl thiosalicylate (2.5 g, 15 mmol), 6-(propylamino)nicotinenitrile (1.6 g, 12.3 mmol), triethylamine (3.0 ml, 21.5 mmol) and toluene (6 ml) was refluxed for 8 hrs as described in Example 1. After cooling, the precipitated crystals were collected by filtration and recrystallized from diisopropylether-chlorobenzene to give the titled compound (0.70 g, 23%) as crystals.

mp. 210.1-210.6° C. IR (KBr): 3285, 3153, 2955, 2870, 1631, 1610, 1496, 1406, 1356, 1296, 1265, 1122, 1105, 1033, 918, 841, 738 cm$^{-1}$. $^1$H-NMR (CDCl$_3$) δ: 1.02 (3H, t, J=7.4 Hz), 1.70 (2H, m), 3.35 (2H, m), 5.29 (1H, br s), 6.46 (1H, d, J=9.0 Hz), 7.48-7.64 (3H, m), 8.29 (1H, dd, J=2.4, 9.0 Hz), 8.50 (1H, dd, J=1.6, 7.7 Hz), 8.94 (1H, d, J=2.4 Hz). Elemental Analysis for C$_{16}$H$_{15}$N$_3$OS Calcd. C, 64.62; H, 5.08; N, 14.13. Found C, 64.55; H, 4.96; N, 14.07.

Example 32

2-[6-(Benzylamino)-3-pyridyl]-4H-1,3-benzothiazine-4-one

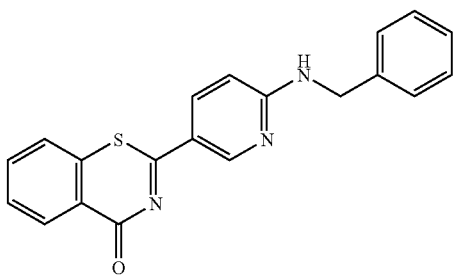

A mixture of methyl thiosalicylate (1.6 g, 9.8 mmol), 6-benzylaminonicotinenitrile (1.3 g, 6.4 mmol), triethylamine (2.0 ml, 14.3 mmol) and toluene (8 ml) was refluxed for 30 hrs as described in Example 1. After cooling, the precipitated crystals were collected by filtration and recrystallized from diisopropylether-tetrahydrofuran to give the titled compound (0.80 g, 36%) as crystals.

mp. 194.3-196.2° C. IR (KBr): 3269, 3080, 1633, 1603, 1493, 1452, 1400, 1311, 1248, 1165, 1128, 1101, 920, 821, 740 cm$^{-1}$. $^1$H-NMR (CDCl$_3$) δ: 4.63 (2H, d, J=5.8 Hz), 5.60 (1H, br s), 6.48 (1H, d, J=8.9 Hz), 7.35 (5H, m), 7.48-7.63 (3H, m), 8.28 (1H, dd, J=2.4, 8.9 Hz), 8.50 (1H, dd, J=1.7, 7.5 Hz), 8.96 (1H, d, J=2.4 Hz). Elemental Analysis for C$_{20}$H$_{15}$N$_3$OS Calcd. C, 69.54; H, 4.38; N, 12.17. Found C, 69.44; H, 4.27; N, 12.20.

Example 33

2-[6-(1-Pyrrolidinyl)-3-pyridyl]-4H-1,3-benzothiazine-4-one

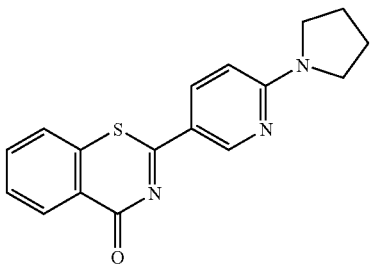

A mixture of methyl thiosalicylate (1.6 g, 9.8 mmol), 6-(1-pyrrolidinyl)nicotinenitrile (1.4 g, 8.1 mmol), triethylamine (2.0 ml, 14.3 mmol) and toluene (10 ml) was refluxed for 20 hrs as described in Example 1. After cooling, the precipitated crystals were collected by filtration and recrystallized from diisopropylether-chlorobenzene to give the titled compound (1.09 g, 43%) as crystals.

mp. 221.0-223.1° C. IR (KBr): 2966, 2872, 1637, 1595, 1506, 1458, 1313, 1259, 1236, 1170, 1126, 1103, 916, 800, 760 cm$^{-1}$. $^1$H-NMR (CDCl$_3$) δ: 2.06 (4H, m), 3.57 (4H, m), 6.42 (1H, d, J=9.1 Hz), 7.47-7.64 (3H, m), 8.31 (1H, dd, J=2.4, 9.1 Hz), 8.50 (1H, dd, J=1.2, 7.7 Hz), 8.98 (1H, d, J=2.4 Hz). Elemental Analysis for C$_{17}$H$_{15}$N$_3$OS Calcd. C, 66.00; H, 4.89; N, 13.58. Found C, 65.98; H, 4.85; N, 13.57.

Example 34

2-[6-(1-Piperidino)-3-pyridyl]-4H-1,3-benzothiazine-4-one

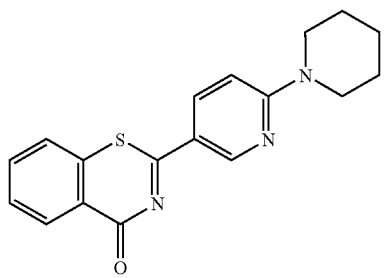

A mixture of methyl thiosalicylate (1.9 g, 11.4 mmol), 6-(1-piperidino)nicotinenitrile (1.4 g, 7.5 mmol), triethylamine (2.0 ml, 14.3 mmol) and toluene (10 ml) was refluxed for 24 hrs as described in Example 1. After cooling, the precipitated crystals were collected by filtration and recrystallized from diisopropylether-chlorobenzene to give the titled compound (0.41 g, 16%) as crystals.

mp. 191.2-191.7° C. IR (KBr): 2922, 2854, 1651, 1601, 1504, 1439, 1238, 1124, 1099, 740 cm$^{-1}$. $^1$H-NMR (CDCl$_3$) δ: 1.66-1.69 (6H, m), 3.73 (4H, m), 6.67 (1H, d, J=9.3 Hz), 7.47-7.62 (3H, m), 8.30 (1H, dd, J=2.5, 9.3 Hz), 8.50 (1H, dd, J=1.6, 7.7 Hz), 8.96 (1H, d, J=2.5 Hz). Elemental Analysis for C$_{18}$H$_{17}$N$_3$OS Calcd. C, 66.85; H, 5.30; N, 12.99. Found C, 66.87; H, 5.29; N, 12.98.

Example 35

2-[6-(4-Morpholino)-3-pyridyl]-4H-1,3-benzothiazine-4-one

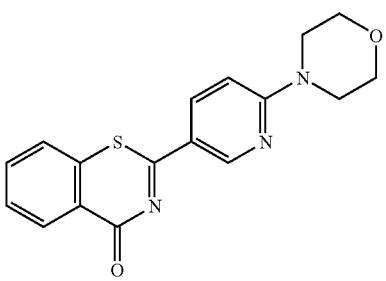

A mixture of methyl thiosalicylate (1.7 g, 10.4 mmol), 6-(4-morpholino)nicotinenitrile (1.3 g, 6.8 mmol), triethylamine (2.0 ml, 14.3 mmol) and toluene (5 ml) was refluxed for 20 hrs as described in Example 1. After cooling, the precipitated crystals were collected by filtration and recrystallized from hexane-chlorobenzene to give the titled compound (0.48 g, 21%) as crystals.

mp. 232.6-234.4° C. IR (KBr): 2912, 1664, 1604, 1504, 1433, 1236, 1116, 1049, 947, 808, 744 cm$^{-1}$. $^1$H-NMR (CDCl$_3$) δ: 3.72 (4H, t, J=4.5 Hz), 3.82 (4H, t, J=4.5 Hz), 6.68 (1H, d, J=9.1 Hz), 7.49-7.64 (3H, m), 8.35 (1H, dd, J=2.5, 9.1 Hz), 8.51 (1H, dd, J=1.6, 7.7 Hz), 8.99 (1H, d, J=2.5 Hz). Elemental Analysis for C$_{17}$H$_{15}$N$_3$O$_2$S Calcd. C, 62.75; H, 4.65; N, 12.91. Found C, 62.72; H, 4.59; N, 12.94.

Example 36

2-{6-[(4-Chlorophenyl)thio]-3-pyridyl}-4H-1,3-benzothiazine-4-one

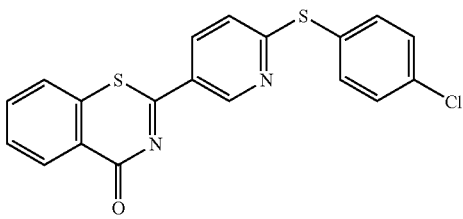

A mixture of methyl thiosalicylate (1.6 g, 9.6 mmol), 6-[(4-chlorophenyl)thio]nicotinenitrile (2.0 g, 8.1 mmol), triethylamine (2.0 ml, 14.3 mmol) and toluene (5 ml) was refluxed for 20 hrs as described in Example 1. After cooling, the precipitated crystals were collected by filtration and recrystallized from hexane-chlorobenzene to give the titled compound (1.6 g, 52%) as crystals.

mp. 221.5-222.0° C. IR (KBr): 3057, 1658, 1572, 1545, 1512, 1477, 1442, 1296, 1242, 1091, 1012, 922, 819, 734 cm$^{-1}$. $^1$H-NMR (CDCl$_3$) δ: 7.03 (1H, d, J=8.6 Hz), 7.46 (2H, d, J=8.4 Hz), 7.53 (1H, m), 7.57 (2H, d, J=8.4 Hz), 7.61-7.72 (2H, m), 8.29 (1H, dd, J=2.2, 8.6 Hz), 8.52 (1H, dd, J=1.8, 7.5 Hz), 9.13 (1H, d, J=2.2 Hz). Elemental Analysis for C$_{19}$H$_{11}$N$_2$OS$_2$Cl Calcd. C, 59.60; H, 2.90; N, 7.32. Found C, 59.50; H, 2.79; N, 7.14.

Example 37

6-(4-Oxo-4H-1,3-benzothiazin-2-yl)-N-propylnicotinamide

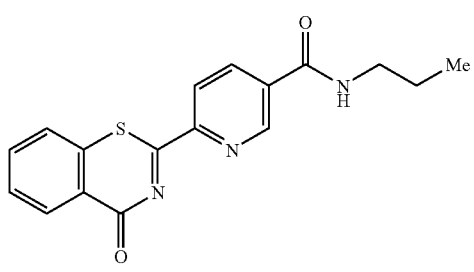

A mixture of methyl thiosalicylate (2.2 g, 13.3 mmol), 6-cyano-N-propylnicotinamide (1.2 g, 6.5 mmol), triethylamine (2.0 ml, 14.3 mmol) and toluene (4 ml) was refluxed for 5 hrs as described in Example 1. After cooling, the precipitated crystals were collected by filtration and recrystallized from diisopropylether-chloroform to give the titled compound (1.4 g, 67%) as crystals.

mp. 268.0-268.6° C. IR (KBr): 3354, 3059, 2962, 2937, 1660, 1631, 1537, 1514, 1323, 1273, 742 cm$^{-1}$. $^1$H-NMR (DMSO-d$_6$) δ: 0.93 (3H, t, J=7.3 Hz), 1.58 (2H, m), 3.27 (2H, m), 7.74 (1H, m), 7.82 (1H, m), 7.94 (1H, d, J=7.9 Hz), 8.36 (1H, d, J=7.9 Hz), 8.42-8.48 (2H, m), 8.87 (1H, m), 9.15 (1H, s). Elemental Analysis for C$_{17}$H$_{15}$N$_3$O$_2$S Calcd. C, 62.75; H, 4.65; N, 12.91. Found C, 62.72; H, 4.59; N, 12.95.

Example 38

6-(4-Oxo-4H-1,3-benzothiazin-2-yl)-2-pyridinecarboxamide

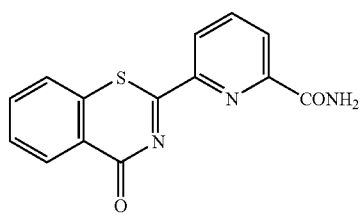

A mixture of methyl thiosalicylate (1.1 g, 6.4 mmol), 6-cyano-2-pyridinecarboxamide (0.47 g, 3.1 mmol), triethylamine (1.0 ml, 7.1 mmol) and toluene (3 ml) was refluxed for 6 hrs as described in Example. After cooling, the precipitated crystals were collected by filtration and recrystallized from hexane-ethanol to give the titled compound (0.63 g, 70%).

mp. 294.6-294.9° C. IR (KBr): 3447, 3123, 1726, 1662, 1574, 1545, 1388, 1300, 1095, 976, 742, 507 cm$^{-1}$. $^1$H-NMR (DMSO-d$_6$) δ: 7.75 (1H, m), 7.85-7.89 (2H, m), 8.00-8.03 (2H, m), 8.28-8.39 (3H, m), 8.51 (1H, dd, J=1.8, 7.1 Hz). Elemental Analysis for C$_{14}$H$_9$N$_3$O$_2$S Calcd. C, 59.35; H, 3.20; N, 14.83. Found C, 59.39; H, 3.06; N, 14.96.

Reference Example 3

2-Mercapto-4-methylbenzoic acid

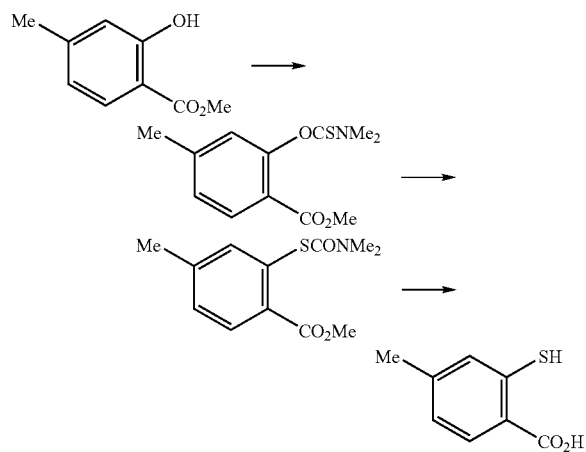

(1) Methyl 4-methylsalicylate (10.7 g, 64 mmol) was dissolved in DMF (100 ml). N,N-Dimethylthiocarbamoyl chloride (8.0 g, 65 mmol) and 1,4-diazabicyclo[2,2,2]octane (7.2 g, 65 mmol) were added thereto with the mixture stirring. The reaction mixture was stirred at room temperature for 20 hrs, poured into water and extracted with ethyl acetate. The extract was washed with water and dried, and the solvent was evaporated under reduced pressure. The residue was subjected to a silica gel column chromatography, eluted with hexane-ethyl acetate (3:1, v/v), recrystallized from ethyl acetate-hexane to give methyl 2-(N,N-dimethylaminothiocarbamoyl)oxy-4-methylbenzoate (9.1 g, 55%) as crystals (mp. 99.9-100.2° C.).

IR (KBr): 2947, 1724, 1620, 1537, 1435, 1394, 1288, 1257, 1236, 1174, 1128, 1086 cm$^{-1}$. $^1$H-NMR (CDCl$_3$) δ: 2.41 (3H, s), 3.39 (3H, s), 3.46 (3H, s), 3.82 (3H, s), 6.93 (1H, s), 7.11 (1H, d, J=8.0 Hz), 7.90 (1H, d, J=8.0 Hz). Elemental Analysis for C$_{12}$H$_{15}$NO$_3$S Calcd. C, 56.90; H, 5.97; N, 5.53. Found C, 56.91; H, 5.97; N, 5.44.

(2) Methyl 2-(N,N-dimethylaminothiocarbamoyl)oxy-4-methylbenzoate (6.7 g, 26 mmol) was melted at 190° C. for 16 hrs. After cooling the reaction mixture was subjected to a silica gel column chromatography, eluted with hexane-ethyl acetate (3:2, v/v) and recrystallized from ethyl acetate-hexane to give methyl 2-(N,N-dimethylaminocarbamoyl)thio-4-methylbenzoate (5.1 g, 75%) as crystals (mp. 79.4-80.0° C.)

IR (KBr): 2949, 1728, 1666, 1601, 1433, 1361, 1292, 1257, 1120, 1097, 1055, 908 cm$^{-1}$. $^1$H-NMR (CDCl$_3$) δ: 2.38 (3H, s), 3.07 (6H, br s), 3.86 (3H, S), 7.22 (1H, d, J=7.9 Hz), 7.43 (1H, s), 7.81 (1H, d, J=7.9 Hz). Elemental Analysis for C$_{12}$H$_{15}$NO$_3$S Calcd. C, 56.90; H, 5.97; N, 5.53. Found C, 56.74; H, 5.88; N, 5.26.

(3) A mixture of methyl 2-(N,N-dimethylaminocarbamoyl)thio-4-methylbenzoate (2.0 g, 7.9 mmol) and 10% aqueous sodium hydroxide solution (15 g, 38 mmol) was stirred at 100° C. for 14 hrs. After cooling, the reaction mixture was acidified (pH 4) by use of 1 N hydrochloric acid. The precipitated crystals were collected by filtration, dissolved in ethyl acetate and dried over anhydrous magnesium sulfate. The solvent was evaporated under reduced pressure to give 3-mercapto-4-methylbenzoic acid (1.3 g, ca. 100%) as crystals.

$^1$H-NMR (CDCl$_3$+DMSO-d$_6$) δ: 2.32 (3H, s), 5.19 (1H, br s), 6.95 (1H, d, J=8.0 Hz), 7.11 (1H, s), 7.94 (1H, d, J=8.0 Hz).

Example 39

7-Methyl-2-(2-pyridyl)-4H-1,3-benzothiazine-4-one

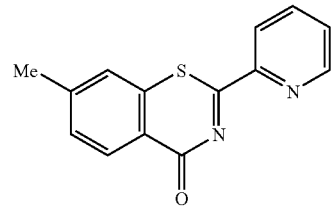

A mixture of 2-mercapto-4-methylbenzoic acid (2.0 g, 12 mmol), 2-cyanopyridine (1.4 g, 13 mmol) and pyridine (8 ml) was refluxed for 14 hrs as described in Example 9. After cooling, the precipitated crystals were collected by filtration, subjected to a silica gel column chromatography, eluted with ethyl acetate-methanol (5:1, v/v) and recrystallized from hexane-tetrahydrofuran to give the titled compound (1.4 g, 48%).

mp. 225.0-225.2° C. IR (KBr): 3076, 3001, 1658, 1606, 1568, 1539, 1464, 1305, 1282, 790 cm$^{-1}$. $^1$H-NMR (CDCl$_3$) δ: 2.49 (3H, s), 7.39 (1H, s), 7.43 (1H, d, J=8.1 Hz), 7.54 (1H, m), 7.91 (1H, m), 8.43 (1H, d, J=8.1 Hz), 8.54 (1H, d, J=7.9 Hz), 8.74 (1H, m). Elemental Analysis for C$_{14}$H$_{10}$N$_2$OS Calcd. C, 66.12; H, 3.96; N, 11.02. Found C, 66.28; H, 3.93; N, 11.03.

Example 40

2-[6-(Hydroxymethyl)-2-pyridyl]-4H-1,3-benzothiazine-4-one

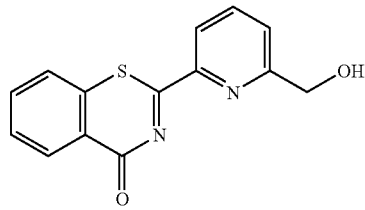

A mixture of [6-(4-oxo-4H-1,3-benzothiazin-2-yl)-2-pyridyl]methyl acetate (0.30 g, 1.00 mmol), potassium carbonate (0.004 g, 0.03 mmol) and methanol (30 ml) was stirred under nitrogen atmosphere at room temperature for 2 hrs. The reaction mixture was concentrated, dissolved in hot ethanol (10 ml) and filtered. The filtrate was concentrated under reduced pressure and the residue was recrystallized from ethanol to give the titled compound (0.19 g, 70%).

mp. 208.2-208.7° C. IR (KBr): 3385, 1628, 1589, 1570, 1525, 1444, 1302, 1089, 1062, 746 cm$^{-1}$. $^1$H-NMR (CDCl$_3$) δ: 3.40 (1H, t, J=5.2 Hz), 4.91 (2H, d, J=5.2 Hz), 7.53 (2H, d, J=7.8 Hz), 7.61-7.73 (3H, m), 7.92 (1H, t, J=7.8 Hz), 8.46 (1H, d, J=7.7 Hz), 8.54-8.57 (1H, m). Elemental Analysis for C$_{14}$H$_{10}$N$_2$O$_2$S Calcd. C, 62.21; H, 3.73; N, 10.36. Found C, 62.00; H, 3.56; N, 10.25.

Example 41

2-(6-Phenoxy-2-pyridyl)-4H-1,3-benzothiazine-4-one

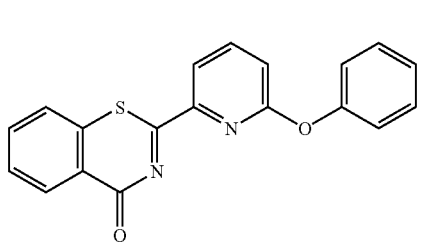

A mixture of methyl thiosalicylate (0.34 g, 2.0 mmol), 2-cyano-6-phenoxypyridine (0.40 g, 2.0 mmol), triethylamine (0.45 ml, 3.1 mmol) and toluene (30 ml) was refluxed for 48 hrs as described in Example 1. After cooling, the precipitated crystals were collected by filtration and recrystallized from ethanol to give the titled compound (0.18 g, 26%) as crystals.

mp. 160.8-161.3° C. IR(KBr): 1656, 1572, 1531, 1487, 1439, 1263, 1240, 912, 744 cm$^{-1}$. $^1$H-NMR(CDCl$_3$) δ: 7.12 (1H, d, J=8.3 Hz), 7.25-7.29 (3H, m), 7.45-7.52 (3H, m), 7.61-7.64 (2H, m), 7.88-7.90 (1H, m), 8.25 (1H, d, J=7.4 Hz), 8.51-8.54 (1H, m). Elemental Analysis for C$_{19}$H$_{12}$N$_2$O$_2$S Calcd. C, 68.66; H, 3.64; N, 8.34. Found C, 68.26; H, 3.53; N, 8.37.

Example 42

2-[6-(1-Piperidyl)-2-pyridyl]-4H-1,3-benzothiazine-4-one

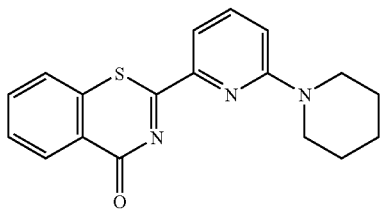

A mixture of methyl thiosalicylate (0.36 g, 2.1 mmol), 2-cyano-6-(1-piperidinyl)pyridine (0.40 g, 2.1 mmol), triethylamine (0.45 ml, 3.1 mmol) and toluene (50 ml) was refluxed for 48 hrs as described in Example 1. The solvent was concentrated under reduced pressure. The residue was subjected to a silica gel column chromatography and eluted with hexane-ethyl acetate (2:1, v/v). The obtained crystals were recrystallized from hexane-ethyl acetate to give the titled compound (0.08 g, 13%) as crystals.

mp. 178.7° C. (decomposed). IR(KBr): 1658, 1595, 1570, 1529, 1485, 1440, 1290, 1253, 1242, 1124, 1095, 1064, 976, 792 cm$^{-1}$. $^1$H-NMR(CDCl$_3$) δ: 1.70 (6H, s), 3.65 (4H, s), 6.86 (1H, d, J=8.5 Hz), 7.55-7.67 (4H, m), 7.78 (1H, d, J=7.3 Hz), 8.53 (1H, d, J=7.2 Hz). Elemental Analysis for C$_{18}$H$_{17}$N$_3$OS.0.1H$_2$O Calcd. C, 66.48; H, 5.26; N, 12.92. Found C, 66.41; H, 5.09; N, 12.67.

Reference Example 4

2-Cyano-6-methylthiopyridine

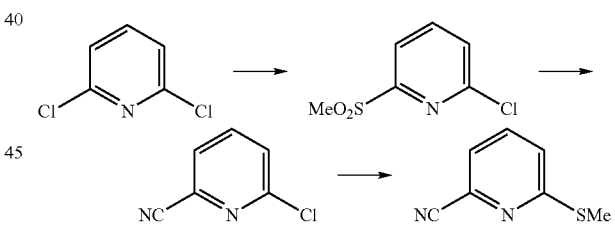

(1) 15% sodium thiomethoxide (119 ml, 254 mmol) was added to a solution of 2,6-dichloropyridine (25.0 g, 169 mmol) and tetrabutylammonium chloride (1.64 g, 5.1 mmol) in toluene (75 ml), and the mixture was stirred at 110° C. for 3 hrs. The reaction mixture was extracted with toluene, washed with saturated brine, dried and concentrated under reduced pressure. Acetic acid (120 ml) was added to the residue. 30% hydrogen peroxide solution (45 ml, 398 mmol was added dropwise to the mixture, and the mixture was stirred at 60° C. for 30 minutes and 90° C. for 18 hrs. After cooling, the reaction mixture was poured into ice-water and extracted with ethyl acetate. The extract was successively washed with saturated brine, 15% aqueous sodium hydroxide solution and saturated brine and dried, and the solvent was evaporated under reduced pressure to give 2-chloro-6-methylsulfonylpyridine (26.3 g, 81%) as crystals.

$^1$H-NMR (CDCl$_3$) δ: 3.26 (3H, s), 7.26-7.28 (1H, m), 7.93 (1H, t, J=7.8 Hz), 8.00-8.03 (1H, m).

(2) A mixture of 2-chloro-6-methylsulfonylpyridine (13.0 g, 67.8 mmol), sodium cyanide (6.69 g, 136 mmol) and DMF (150 ml) was stirred at 170° C. for 18 hrs. After cooling, the reaction mixture was poured into water and extracted with ethyl acetate. The extract was washed with saturated brine and dried, and the solvent was evaporated under reduced pressure. The residue was subjected to a silica gel column chromatography and eluted with hexane-ethyl acetate (2:1, v/v) to give 2-chloro-6-cyanopyridine (6.67 g, 71%) as crystals (mp. 82.9-83.1° C.).

IR (KBr): 2253, 1572, 1431, 1161, 1143, 912, 854, 744 cm$^{-1}$. $^1$H-NMR (CDCl$_3$) δ: 7.57 (1H, d, J=8.0 Hz), 7.65 (1H, d, J=8.1 Hz), 7.82 (1H, t, J=7.8 Hz).

(3) A mixture of 2-chloro-6-cyanopyridine (0.70 g, 5.0 mmol), sodium thiomethoxide (0.39 g, 5.5 mmol) and tetrahydrofuran (50 ml) was stirred at 90° C. for 18 hrs. The reaction mixture was concentrated under reduced pressure, combined with water and extracted with ethyl acetate. The extract was washed with saturated brine and dried, and the solvent was evaporated under reduced pressure to give the titled compound as an oil (0.76 g, 98%).

IR (Neat): 2253, 2237, 1730, 1697, 1576, 1550, 1427, 1161, 1145, 912, 742 cm$^{-1}$. $^1$H-NMR(CDCl$_3$) δ: 2.57 (3H, s), 7.36 (2H, d, J=7.8 Hz), 7.56-7.60 (1H, m).

Example 43

2-(6-Methylthio-2-pyridyl)-4H-1,3-benzothiazine-4-one

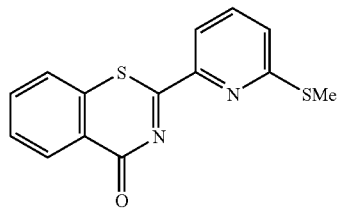

A mixture of methyl thiosalicylate (0.93 g, 5.5 mmol), 2-cyano-6-methylthiopyridine (0.83 g, 5.5 mmol), triethylamine (1.17 ml, 8.3 mmol) and toluene (30 ml) was refluxed for 48 hrs as described in Example 1. The solvent was concentrated under reduced pressure. The residue was recrystallized from ethanol to give the titled compound (0.57 g, 37%) as crystals.

mp. 207.2-207.8° C. IR(Neat): 1651, 1572, 1525, 1427, 1232, 1149, 1093, 983, 723 cm$^{-1}$. $^1$H-NMR(CDCl$_3$) δ: 2.72 (3H, s), 7.41 (1H, d, J=8.0 Hz), 7.42-7.71 (4H, m), 8.19-8.22 (1H, m), 8.54-8.57 (1H, m). Elemental Analysis for C$_{14}$H$_{10}$N$_2$OS$_2$ Calcd. C, 58.72; H, 3.52; N, 9.78. Found C, 58.76; H, 3.69; N, 9.73.

Example 44

2-(6-Methylsulfinyl-2-pyridyl)-4H-1,3-benzothiazine-4-one

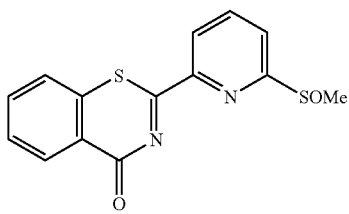

2-(6-Methylthio-2-pyridyl)-4H-1,3-benzothiazine-4-one (0.28 g, 1.0 mmol) obtained in Example 43 was dissolved in chloroform (30 ml). To the stirred mixture was added dropwise a solution of 3-chloroperbenzoic acid (ca. 70%, 0.25 g, 1.0 mmol) in chloroform (10 ml). The reaction mixture was stirred for 1 hr and concentrated under reduced pressure. The residue was subjected to a silica gel column chromatography and eluted with 10% methanol-chloroform and recrystallized from ethanol to give the titled compound (0.19 g, 64%) as crystals.

mp. 256.5° C. (decomposed). IR(Neat): 1660, 1568, 1531, 1435, 1298, 1244, 1053, 993, 817, 734 cm$^{-1}$. $^1$H-NMR (CDCl$_3$) δ: 2.99 (3H, s), 7.60-7.74 (3H, m), 8.15-8.27 (1H, m), 8.28 (1H, d, J=7.7 Hz), 8.55-8.62 (2H, m) Elemental Analysis for C$_{14}$H$_{10}$N$_2$O$_2$S$_2$ Calcd. C, 55.61; H, 3.33; N, 9.26. Found C, 55.47; H, 3.59; N, 9.13.

Example 45

2-(6-Methylsulfonyl-2-pyridyl)-4H-1,3-benzothiazine-4-one

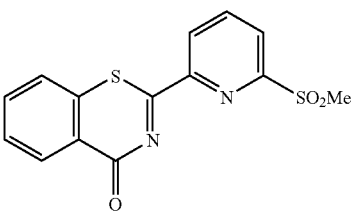

2-(6-Methylthio-2-pyridyl)-4H-1,3-benzothiazine-4-one (0.28 g, 1.0 mmol) obtained in Example 43 was dissolved in chloroform (30 ml). To the stirred mixture was added dropwise a solution of 3-chloroperbenzoic acid (ca. 70%, 0.38 g, 2.2 mmol) in chloroform (10 ml). The reaction mixture was stirred for 3 hr and concentrated under reduced pressure. The residue was subjected to a silica gel column chromatography and eluted with 10% methanol-chloroform and recrystallized from ethanol to give the titled compound (0.19 g, 61%) as crystals.

mp. 238.2-239.5° C. (decomposed). IR(Neat): 1652, 1572, 1537, 1305, 1170, 1124, 1095, 1062, 950, 775 cm$^{-1}$. $^1$H-NMR(CDCl$_3$) δ: 3.39 (3H, s), 7.63-7.74 (3H, m), 8.23 (1H, d, J=7.8 Hz), 8.31 (1H, d, J=7.8 Hz), 8.57 (1H, d, J=7.6 Hz), 8.77 (1H, d, J=7.7 Hz). Elemental Analysis for C$_{14}$H$_{10}$N$_2$O$_3$S$_2$ Calcd. C, 52.08; H, 3.25; N, 8.67. Found C, 51.83; H, 3.02; N, 8.50.

Example 46

2-{6-[(4-methylphenyl)thio]-2-pyridyl}-4H-1,3-benzothiazine-4-one

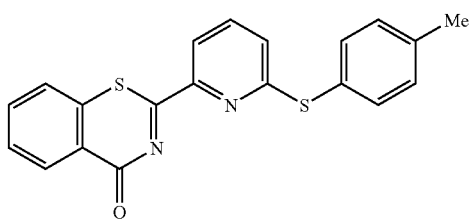

A mixture of methyl thiosalicylate (0.37 g, 2.2 mmol), 2-cyano-6-(4-methylphenyl)thiopyridine (0.50 g, 2.2 mmol), triethylamine (0.46 ml, 3.3 mmol) and toluene (30 ml) was refluxed for 48 hrs as described in Example 1. The solvent was concentrated under reduced pressure. The residue was recrystallized from ethanol to give the titled compound (0.10 g, 13%) as crystals.

mp. 176.9-178.4° C. IR(KBr): 1660, 1651, 1568, 1556, 1529, 1431, 1292, 1234, 1095, 964, 912, 742 cm$^{-1}$. $^1$H-NMR (CDCl$_3$) δ: 2.45 (3H, s), 7.08-7.11 (1H, m), 7.31 (2H, d, J=8.0 Hz), 7.57-7.67 (6H, m), 8.17-8.20 (1H, m), 8.51-8.54 (1H, m). Elemental Analysis for C$_{20}$H$_{14}$N$_2$OS$_2$ Calcd. C, 66.27; H, 3.89; N, 7.73. Found C, 66.00; H, 3.83; N, 7.68.

Example 47

[5-(4-Oxo-4H-1,3-benzothiazin-2-yl)-2-pyridyl]methyl acetate

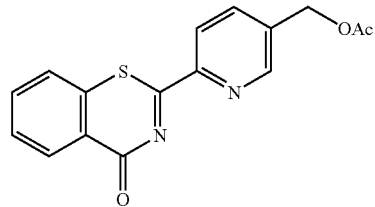

A mixture of methyl thiosalicylate (0.58 g, 3.43 mmol), a mixture of 5-acetoxy-2-cyanopyridine and 3-acetoxy-2-cyanopyridine (0.60 g, 3.43 mmol), triethylamine (0.72 ml, 5.15 mmol) and toluene (100 ml) was refluxed for 48 hrs as described in Example 1. The solvent was concentrated under reduced pressure. The residue was recrystallized from ethanol to give the titled compound (0.30 g, 29%) as crystals.

mp. 171.4-171.5° C. IR(KBr): 1730, 1649, 1537, 1267, 1053, 852, 736 cm$^{-1}$. $^1$H-NMR(CDCl$_3$) δ: 2.15 (3H, s), 5.23 (2H, s), 7.60-7.70 (3H, m), 7.89-7.92 (1H, m), 8.54-8.57 (1H, m), 8.72 (1H, d, J=1.7 Hz). Elemental Analysis for C$_{16}$H$_{12}$N$_2$O$_3$S Calcd. C, 61.53; H, 3.87; N, 8.97. Found C, 61.56; H, 3.99; N, 9.01.

Example 48

2-[5-(hydroxymethyl)-2-pyridyl]-4H-1,3-benzothiazine-4-one

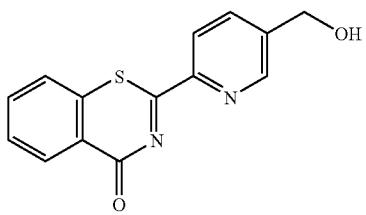

[5-(4-Oxo-4H-1,3-benzothiazin-2-yl)-2-pyridyl]methyl acetate (0.16 g, 0.5 mmol) obtained in Example 47, potassium carbonate (0.002 g, 0.02 mmol) and methanol (30 ml) was stirred under nitrogen atmosphere at room temperature for 2 hrs. The reaction mixture was concentrated under reduced pressure, dissolved in hot ethanol and filtered. The filtrate was concentrated under reduced pressure and recrystallized from ethanol to give the titled compound (0.10 g, 74%) as crystals.

mp. 246.9-247.9° C. IR(Neat): 3414, 1631, 1589, 1568, 1520, 1317, 1053, 738 cm$^{-1}$. $^1$H-NMR(CDCl$_3$) δ: 3.50 (1H, br s), 4.89 (2H, d, J=5.7 Hz), 7.60-7.69 (3H, m), 7.92-7.95 (1H, m), 8.53-8.57 (2H, m), 8.73 (1H, s). Elemental Analysis for C$_{14}$H$_{10}$N$_2$O$_2$S Calcd. C, 62.21; H, 3.73; N, 10.36. Found C, 62.23; H, 3.68; N, 10.34.

Example 49

2-[5-(trifluoromethyl)-2-pyridyl]-4H-1,3-benzothiazine-4-one

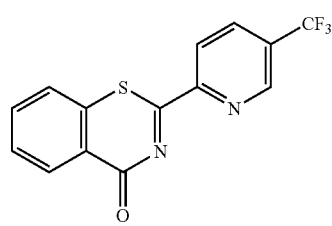

A mixture of methyl thiosalicylate (0.43 g, 2.6 mmol), 2-cyano-5-trifluoromethylpyridine (0.44 g, 2.6 mmol), triethylamine (0.60 ml, 3.8 mmol) and toluene (30 ml) was refluxed for 48 hrs as described in Example 1. The solvent was concentrated under reduced pressure. The residue was recrystallized from ethanol to give the titled compound (0.18 g, 23%) as crystals.

mp. 207.2-207.4° C. IR(KBr): 1653, 1568, 1525, 1327, 1305, 1122, 1074, 1012, 939, 871, 742 cm$^{-1}$. $^1$H-NMR (CDCl$_3$) δ: 7.63-7.73 (3H, m), 8.16-8.18 (1H, m), 8.55-8.58 (1H, m), 8.68 (1H, d, J=8.3 Hz), 9.00 (1H, s). Elemental Analysis for C$_{14}$H$_7$N$_2$OSF$_3$ Calcd. C, 54.54; H, 2.29; N, 9.09. Found C, 54.68; H, 2.32; N, 9.26.

Example 50

6-(4-Oxo-4H-1,3-benzothiazin-2-yl)-N-propyl-2-pyridinecarboxamide

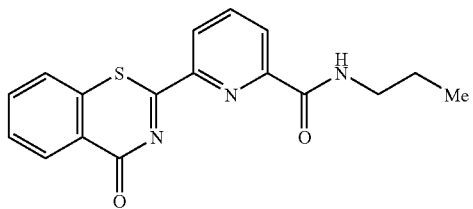

A mixture of methyl thiosalicylate (4.2 g, 25 mmol), 6-cyano-N-propyl-2-pyridinecarboxamide (2.5 g, 13 mmol), triethylamine (4.0 ml, 28 mmol) and toluene (8 ml) was refluxed for 8 hrs as described in Example 1. After cooling, the precipitated crystals were collected by filtration and recrystallized from hexane-tetrahydrofuran to give the titled compound (3.4 g, 78%) as crystals.

mp. 179.7-181.4° C. IR (KBr): 3400, 2962, 2872, 1666, 1572, 1537, 1440, 1300, 1232, 1095, 746, 733 cm$^{-1}$. $^1$H-NMR (CDCl$_3$) δ: 1.08 (3H, t, J=7.4 Hz), 1.78 (2H, m), 3.55 (2H, m), 7.62-7.74 (3H, m), 7.96 (1H, br s), 8.08 (1H, m), 8.44 (1H, d, J=7.7 Hz), 8.56 (1H, m), 8.65 (1H, d, J=7.8 Hz). Elemental Analysis for C$_{17}$H$_{15}$N$_3$O$_2$S Calcd. C, 62.75; H, 4.65; N, 12.91. Found C, 62.76; H, 4.65; N, 12.93.

Example 51

N-Benzyl-6-(4-oxo-4H-1,3-benzothiazin-2-yl)-2-pyridinecarboxamide

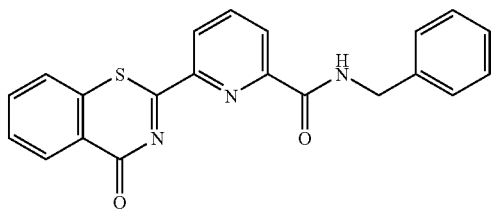

A mixture of methyl thiosalicylate (1.3 g, 7.6 mmol), N-benzyl-6-cyano-2-pyridinecarboxamide (0.88 g, 3.7 mmol), triethylamine (2.0 ml, 14 mmol) and toluene (4 ml) was refluxed for 10 hrs as described in Example 1. After cooling, the precipitated crystals were collected by filtration and recrystallized from hexane-tetrahydrofuran to give the titled compound (0.97 g, 97%) as crystals.

mp. 197.1-197.9° C. IR (KBr): 400, 3061, 1669, 1572, 1535, 1440, 1300, 1232, 1097, 746, 733 cm$^{-1}$. $^1$H-NMR (CDCl$_3$) δ: 4.80 (2H, d, J=6.2 Hz), 7.32-7.46 (5H, m) 7.57-7.69 (3H, m), 8.10 (1H, m), 8.26 (1H, m), 8.48 (1H, d, J=7.7 Hz), 8.55 (1H, d, J=7.5 Hz), 8.66 (1H, d, J=7.8 Hz). Elemental Analysis for C$_{21}$H$_{15}$N$_3$O$_2$S Calcd. C, 67.54; H, 4.05; N, 11.25. Found C, 67.47; H, 3.91; N, 11.21.

Example 52

N,N-Dimethyl-N'-[[6-(4-oxo-4H-1,3-benzothiazin-2-yl)-2-pyridyl]carbonyl]-N'-propylurea

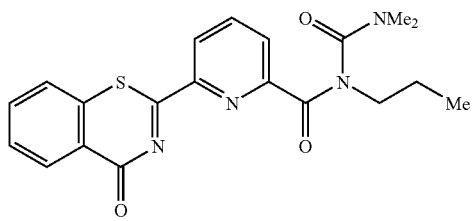

A mixture of methyl thiosalicylate (1.6 g, 9.6 mmol), N-[(6-cyano-2-pyridyl)carbonyl]-N',N'-dimethyl-N-propylurea (1.2 g, 4.7 mmol), triethylamine (2.0 ml, 14 mmol) and toluene (4 ml) was refluxed for 9 hrs as described in Example 1. After cooling, the precipitated crystals were collected by filtration and recrystallized from hexane-tetrahydrofuran to give the titled compound (1.36 g, 72%) as crystals.

mp. 190.8-192.4° C. IR (KBr): 2962, 1682, 1666, 1537, 1379, 1305, 1126, 750, 731 cm$^{-1}$. $^1$H-NMR (CDCl$_3$) δ: 1.01 (3H, t, J=7.4 Hz), 1.78 (2H, m), 2.98 (6H, s), 3.77 (2H, m), 7.61-7.71 (3H, m), 8.04 (1H, m), 8.18 (1H, d, J=7.6 Hz), 8.56 (1H, m), 8.62 (1H, m). Elemental Analysis for C$_{20}$H$_{20}$N$_4$O$_3$S Calcd. C, 60.59; H, 5.08; N, 14.13. Found C, 60.54; H, 5.15; N, 14.23.

Example 53

N-Benzyl-N',N'-dimethyl-N-[[6-(4-oxo-4H-1,3-benzothiazin-2-yl)-2-pyridyl]carbonyl]urea

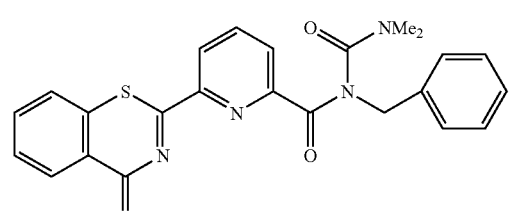

A mixture of methyl thiosalicylate (1.8 g, 10.7 mmol), N-benzyl-N-[(6-cyano-2-pyridyl)carbonyl]-N',N'-dimethylurea (1.6 g, 5.4 mmol), triethylamine (2.0 ml, 14 mmol) and toluene (4 ml) was refluxed for 8 hrs as described in Example 1. After cooling, the precipitated crystals were collected by filtration and recrystallized from hexane-chlorobenzene to give the titled compound (2.2 g, 93%) as crystals.

mp. 222.2-224.0° C. IR (KBr): 2947, 1678, 1666, 1537, 1373, 1302, 1234, 1165, 1095, 733 cm$^{-1}$. $^1$H-NMR (CDCl$_3$) δ: 2.70 (6H, br s), 5.08 (2H, s), 7.29-7.37 (3H, m), 7.47-7.49 (2H, m), 7.64-7.71 (3H, m), 8.04 (1H, m), 8.20 (1H, m), 8.55 (1H, m), 8.65 (1H, m) Elemental Analysis for C$_{24}$H$_{20}$N$_4$O$_3$S Calcd. C, 64.85; H, 4.54; N, 12.60. Found C, 64.77; H, 4.49; N, 12.57.

Example 54

7-methoxy-2-(2-pyridyl)-4H-1,3-benzothiazine-4-one

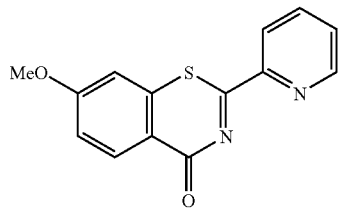

A mixture of 2-mercapto-4-methoxybenzoic acid (1.4 g, 7.9 mmol), 2-cyanopyridine (0.89 g, 8.5 mmol) and pyridine (10 ml) was refluxed for 10 hrs as described in Example 9. After cooling, the precipitated crystals were collected by filtration and recrystallized from hexane-tetrahydrofuran to give the titled compound (1.0 g, 47%) as crystals.

mp. 200.0-202.2° C. IR (KBr): 1643, 1603, 1566, 1487, 1278, 1251, 1020, 796 cm$^{-1}$. $^1$H-NMR (CDCl$_3$) δ: 3.93 (3H, s), 7.01 (1H, d, J=2.4 Hz), 7.16 (1H, dd, J=2.4, 8.9 Hz), 7.52 (1H, m), 7.90 (1H, m), 8.49 (1H, d, J=8.9 Hz), 8.53 (1H, dd, J=0.9, 7.9 Hz), 8.72 (1H, dd, J=0.7, 4.7 Hz). Elemental Analysis for C$_{14}$H$_{10}$N$_2$O$_2$S Calcd. C, 62.21; H, 3.73; N, 10.36. Found C, 62.28; H, 3.61; N, 10.41.

Example 55

2-(4-Pyridyl)-4H-1,3-benzothiazine-4-one N-oxide

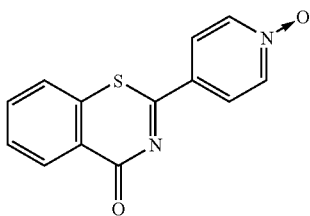

2-(4-pyridyl)-4H-1,3-benzothiazine-4-one (1.00 g, 4.1 mmol) was dissolved in chloroform (20 ml). To the mixture was added 3-chloroperbenzoic acid (ca. 77%, 0.92 g, 4.1 mmol). The reaction mixture was stirred at room temperature for 24 hr and concentrated under reduced pressure. The residue was subjected to a silica gel column chromatography and eluted with ethyl acetate-methanol (20:1, v/v) and recrystallized from diisopropylether-methanol to give the titled compound (0.18 g, 16%) as crystals.

mp. 248.2-251.7° C. IR (KBr): 3115, 1658, 1610, 1514, 1479, 1440, 1304, 1277, 1244, 1167, 1091, 842, 750 cm$^{-1}$. $^1$H-NMR (DMSO-d$_6$) δ: 7.75 (1H, m), 7.83-7.91 (2H, m), 8.12 (2H, d, J=6.4 Hz), 8.35 (1H, d, J=7.8 Hz), 8.41 (2H, d, J=6.4 Hz). Elemental Analysis for C$_{13}$H$_8$N$_2$O$_2$S Calcd. C, 60.93; H, 3.15; N, 10.93. Found C, 60.85; H, 3.08; N, 10.96.

Example 56

2-(6-Methoxy-2-pyridyl)-4H-1,3-benzothiazine-4-one

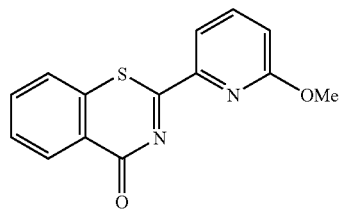

A mixture of methyl thiosalicylate (0.56 g, 3.4 mmol), 2-cyano-6-methoxypyridine (0.45 g, 3.4 mmol), triethylamine (0.70 ml, 5.0 mmol) and toluene (50 ml) was refluxed for 48 hrs as described in Example 1. The reaction mixture was concentrated under reduced pressure and recrystallized from ethanol to give the titled compound (0.12 g, 13%) as crystals.

mp. 226.0-226.1° C. IR(KBr): 1649, 1529, 1469, 1273, 1244, 1149, 1097, 1033, 808, 725 cm$^{-1}$. $^1$H-NMR(CDCl$_3$) δ: 4.10 (3H, s), 7.00 (1H, d, J=8.3 Hz), 7.59-7.68 (3H, m), 7.74-7.79 (1H, m), 8.13-8.16 (1H, m), 8.54-8.57 (1H, m). Elemental Analysis for C$_{14}$H$_{10}$N$_2$O$_2$S Calcd. C, 62.21; H, 3.73; N, 10.36. Found C, 62.12; H, 3.73; N, 10.44.

Example 57

2-[6-(Benzyloxy)-2-pyridyl]-4H-1,3-benzothiazine-4-one

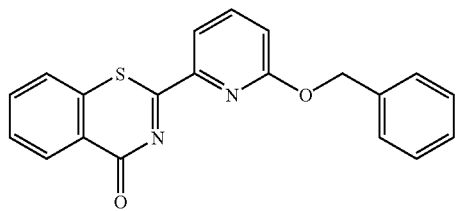

A mixture of methyl thiosalicylate (0.40 g, 2.4 mmol), 2-benzyloxy-6-cyanopyridine (0.50 g, 2.4 mmol), triethylamine (0.50 ml, 3.6 mmol) and toluene (30 ml) was refluxed for 48 hrs as described in Example 1. The reaction mixture was concentrated under reduced pressure and recrystallized from ethanol to give the titled compound (0.21 g, 26%) as crystals.

mp. 240.9-241.0° C. IR(KBr): 1637, 1572, 1529, 1504, 1442, 1256, 1128, 1097, 1030, 808, 760 cm$^{-1}$. $^1$H-NMR (CDCl$_3$) δ: 5.55 (2H, s), 7.05 (1H, d, J=8.3 Hz), 7.34-7.43 (3H, m), 7.55 (2H, d, J=6.9 Hz), 7.62-7.69 (3H, m), 7.78 (1H, t, J=8.0 Hz), 8.16 (1H, d, J=7.4 Hz), 8.54-8.57 (1H, m). Elemental Analysis for C$_{20}$H$_{14}$N$_2$O$_2$S Calcd. C, 69.35; H, 4.07; N, 8.09. Found C, 69.14; H, 3.99; N, 8.13.

Example 58

2-(6-Propoxy-2-pyridyl)-4H-1,3-benzothiazine-4-one

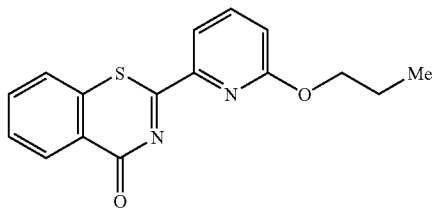

A mixture of methyl thiosalicylate (0.24 g, 1.4 mmol), 2-cyano-6-propoxypyridine (0.23 g, 1.4 mmol), triethylamine (0.30 ml, 2.1 mmol) and toluene (20 ml) was refluxed for 48 hrs as described in Example 1. The reaction mixture was concentrated under reduced pressure. The residue was subjected to a silica gel column chromatography, eluted with hexane-ethyl acetate (5:1, v/v) and recrystallized from hexane-ethyl acetate to give the titled compound (0.03 g, 7%) as crystals.

mp. 138.3-140.0° C. IR (KBr): 1651, 1595, 1574, 1537, 1446, 1294, 1277, 1238, 1028, 810, 740, 727 cm$^{-1}$. $^1$H-NMR (CDCl$_3$) δ: 1.10 (3H, t, J=7.4 Hz), 1.86-1.95 (2H, m), 4.43 (2H, t, J=6.6 Hz), 6.97 (1H, d, J=8.2 Hz), 7.62-7.77 (4H, m), 8.12 (1H, d, J=7.3 Hz), 8.53-8.56 (1H, m) Elemental Analysis for C$_{16}$H$_{14}$N$_2$O$_2$S Calcd. C, 64.41; H, 4.73; N, 9.39. Found C, 64.20; H, 4.72; N, 9.43.

Example 59

2-(6-Propylthio-2-pyridyl)-4H-1,3-benzothiazine-4-one

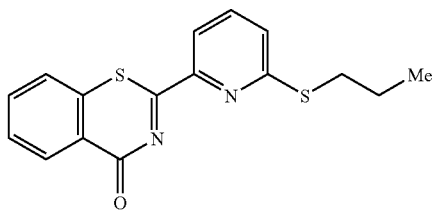

A mixture of methyl thiosalicylate (0.67 g, 4.0 mmol), 2-cyano-6-propylthiopyridine (0.72 g, 4.0 mmol), triethylamine (0.84 ml, 6.0 mmol) and toluene (50 ml) was refluxed for 48 hrs as described in Example 1. The reaction mixture was concentrated under reduced pressure and the residue was recrystallized from ethanol to give the titled compound (0.46 g, 37%) as crystals.

mp. 124.5-125.1° C. IR (KBr): 1658, 1572, 1537, 1433, 1284, 1230, 1149, 1095, 985, 742 cm$^{-1}$. $^1$H-NMR (CDCl$_3$) δ: 1.14 (3H, t, J=7.3 Hz), 1.82-1.94 (2H, m), 3.30 (2H, t, J=7.1 Hz), 7.36-7.39 (1H, m), 7.55-7.88 (4H, m), 8.19 (1H, d, J=7.6 Hz), 8.54-8.57 (1H, m). Elemental Analysis for C$_{16}$H$_{14}$N$_2$OS$_2$ Calcd. C, 61.12; H, 4.49; N, 8.91. Found C, 60.72; H, 4.22; N, 9.05.

Example 60

2-(6-Propylsulfinyl-2-pyridyl)-4H-1,3-benzothiazine-4-one

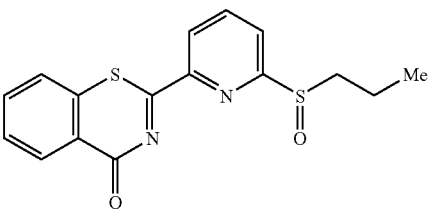

A solution of 3-chloroperbenzoic acid (ca. 50%, 0.17 g, 0.49 mmol) in ethyl acetate (20 ml) was added dropwise to a solution of
2-(6-propylthio-2-pyridyl)-4H-1,3-benzothiazine-4-one
(0.15 g, 0.48 mmol), which was obtained in Example 59, in ethyl acetate (50 ml) with stirring. The reaction mixture was stirred at room temperature for 18 hrs, washed with saturated aqueous sodium hydrogen carbonate solution (50 ml×2) and saturated brine, dried (MgSO$_4$) and concentrated under reduced pressure. The residue was recrystallized from ethyl acetate to give the titled compound (0.12 g, 76%) as crystals.

mp. 174.8-175.4° C. IR (KBr): 1653, 1570, 1533, 1437, 1298, 1057, 1041, 1030, 733 cm$^{-1}$. $^1$H-NMR(CDCl$_3$) δ: 1.11 (3H, t, J=7.4 Hz), 1.60-1.73 (1H, m) 1.97-2.04 (1H, m), 2.96-3.05 (1H, m), 3.15-3.25 (1H, m), 7.61-7.74 (3H, m), 8.16 (3H, t, J=7.8 Hz), 8.25 (1H, d, J=7.7 Hz), 8.55-8.60 (1H, m). Elemental Analysis for C$_{16}$H$_{14}$N$_2$O$_2$S$_2$ Calcd. C, 58.16; H, 4.27; N, 8.48. Found C, 58.17; H, 4.47; N, 8.62.

Example 61

2-(6-Propylsulfonyl-2-pyridyl)-4H-1,3-benzothiazine-4-one

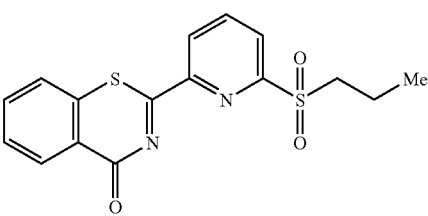

A solution of 3-chloroperbenzoic acid (ca. 50%, 0.44 g, 1.2 mmol) in ethyl acetate (10 ml) was added dropwise to a solution of
2-(6-propylsulfinyl-2-pyridyl)-4H-1,3-benzothiazine-4-one
(0.20 g, 0.64 mmol), which was obtained in Example 60, in ethyl acetate (50 ml) with stirring. The reaction mixture was stirred at room temperature for 18 hrs, washed with saturated aqueous sodium hydrogen carbonate solution (50 ml×2) and saturated brine, dried (MgSO$_4$) and concentrated under reduced pressure. The residue was recrystallized from ethanol to give the titled compound (0.09 g, 41%) as crystals.

mp. 173.8-174.5° C. IR (KBr): 1662, 1570, 1533, 1439, 1298, 1120, 1095, 1062, 993, 733 cm$^{-1}$. $^1$H-NMR (CDCl$_3$) δ:

1.10 (3H, t, J=7.4 Hz), 1.86-1.96 (2H, m), 3.49-3.52 (2H, m), 7.66-7.74 (3H, m), 8.21 (3H, t, J=7.8 Hz), 8.30-8.33 (1H, m), 8.56-8.58 (1H, m), 8.58-8.78 (1H, m). Elemental Analysis for $C_{16}H_{14}N_2O_3S_2$ Calcd. C, 55.47; H, 4.07; N, 8.09. Found C, 55.44; H, 3.84; N, 8.04.

Example 62

2-[6-(4-Phenyl-1-piperazinyl)-2-pyridyl]-4H-1,3-benzothiazine-4-one

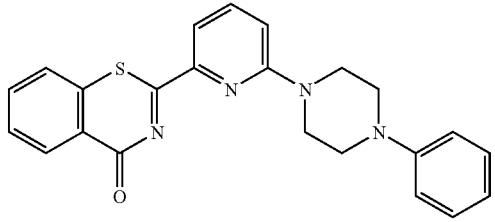

A mixture of methyl thiosalicylate (0.25 g, 1.5 mmol), 2-cyano-6-(4-phenyl-1-piperazinyl)pyridine (0.40 g, 1.5 mmol) triethylamine (0.32 ml, 2.3 mmol) and toluene (30 ml) was refluxed for 48 hrs. The reaction mixture was concentrated under reduced pressure and the crude crystals were recrystallized from ethanol to give the titled compound (0.20 g, 33%) as crystals.

mp. 245.8° C. (decomposed). IR (KBr): 1655, 1593, 1535, 1444, 1232, 1095, 1006, 937, 746 cm$^{-1}$. $^1$H-NMR (CDCl$_3$) δ: 3.36-3.40 (4H, m), 3.83-3.92 (4H, m), 6.92-6.95 (2H, m), 7.00-7.02 (2H, m), 7.29-7.34 (2H, m), 7.60-7.71 (4H, m), 7.88 (1H, d, J=7.3 Hz), 8.53-8.56 (1H, m) Elemental Analysis for $C_{23}H_{20}N_4OS$ Calcd. C, 68.98; H, 5.03; N, 13.99. Found C, 68.66; H, 4.95; N, 13.83.

Example 63

2-{6-[(4-Methylphenyl)sulfinyl]-2-pyridyl}-4H-1,3-benzothiazine-4-one

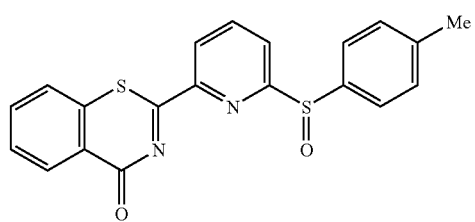

A solution of 3-chloroperbenzoic acid (ca. 70%, 0.27 g, 1.1 mmol) in chloroform (10 ml) was added dropwise to a solution of 2-[6-(4-methylphenylthio-2-pyridyl)-4H-1,3-benzothiazine-4-one (0.40 g, 1.1 mmol), which was obtained in Example 46, in chloroform (50 ml) with stirring. The reaction mixture was stirred at room temperature for 3 hrs and concentrated under reduced pressure. The residue was subjected to a silica gel column chromatography, eluted with hexane-ethyl acetate (2:1, v/v) and recrystallized from ethanol to give the titled compound (0.23 g, 54%) as crystals.

mp. 228.0-228.2° C. IR (KBr): 1660, 1570, 1533, 1437, 1298, 1049, 1030, 991, 733 cm$^{-1}$. $^1$H-NMR (CDCl$_3$) δ: 2.36 (3H, s), 7.30 (2H, d, J=8.2 Hz), 7.65-7.67 (3H, m), 7.69 (2H, d, J=8.4 Hz), 8.08 (1H, t, J=7.9 Hz), 8.25-8.28 (1H, m), 8.49-8.53 (1H m). Elemental Analysis for $C_{20}H_{14}N_2O_2S_2$ Calcd. C, 63.47; H, 3.73; N, 7.40. Found C, 63.33; H, 4.02; N, 7.40.

Example 64

2-{6-[(4-Methylphenyl)sulfonyl]-2-pyridyl}-4H-1,3-benzothiazine-4-one

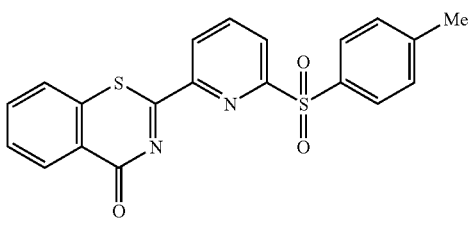

A solution of 3-chloroperbenzoic acid (ca. 70%, 0.53 g, 2.1 mmol) in chloroform (10 ml) was added dropwise to a solution of 2-{6-[(4-methylphenyl)sulfinyl]-2-pyridyl}-4H-1,3-benzothiazine-4-one (0.35 g, 11.0 mmol) in chloroform (50 ml) with stirring. The reaction mixture was stirred at room temperature for 5 hrs and concentrated under reduced pressure. The residue was subjected to a silica gel column chromatography, eluted with hexane-ethyl acetate (1:1, v/v) and recrystallized from ethanol to give the titled compound (0.25 g, 64%) as crystals.

mp. 219.6° C. (decomposed). IR (KBr): 1660, 1645, 1570, 1533, 1437, 1300, 1170, 1032, 746 cm$^{-1}$. $^1$H-NMR (CDCl$_3$) δ: 2.44 (3H, s), 7.40 (2H, d, J=8.2 Hz), 7.63-7.73 (3H, m), 8.06-8.15 (3H, m), 8.35-8.38 (1H, m), 8.52-8.55 (1H, m), 8.62-8.65 (1H, m). Elemental Analysis for $C_{20}H_{14}N_2O_3S_2$ Calcd. C, 60.90; H, 3.58; N, 7.10. Found C, 60.78; H, 3.71; N, 7.03.

Example 65

2-[(6-Methoxymethoxymethyl)-2-pyridyl]-4H-1,3-benzothiazine-4-one

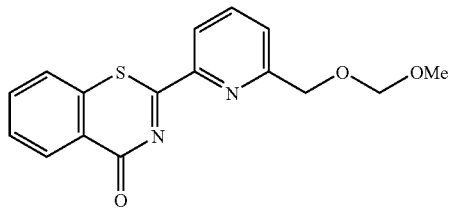

Chloromethyl methylether (0.40 g, 5.0 mmol) was added dropwise to a mixture of 2-(6-hydroxymethyl-2-pyridyl)-4H-1,3-benzothiazine-4-one (0.13 g, 0.5 mmol) obtained in Example 40 and diisopropylamine (3 ml) at room temperature. The reaction mixture was stirred for 18 hrs, diluted with water and extracted with ethyl acetate (100 ml×2). The extract was washed with 5% HCl (100 ml×2) and saturated brine, dried (MgSO$_4$) and concentrated under reduced pressure. The residue was subjected to a silica gel column chromatography, eluted with hexane-ethyl acetate (1:1, v/v) and recrystallized from ethanol to give the titled compound (0.29 g, 58%) as crystals.

mp. 159.6-159.8° C. IR (KBr): 1658, 1572, 1531, 1437, 1298, 1269, 1232, 1093, 1053, 912, 802, 738 cm$^{-1}$. $^1$H-NMR (CDCl$_3$) δ: 3.46 (3H, s), 4.84 (4H, s), 7.59-7.72 (4H, m), 7.92 (1H, t, J=7.8 Hz), 8.44 (1H, d, J=7.8 Hz), 8.52-8.57 (1H, m). Elemental Analysis for C$_{16}$H$_{14}$N$_2$O$_3$S Calcd. C, 61.13; H, 4.49; N, 8.91. Found C, 60.88; H, 4.48; N, 8.61.

Example 66 tert-Butyl 3-{3-[6-(4-oxo-4H-1,3-benzothiazin-2-yl)-2-pyridyl]propoxy}propanoate

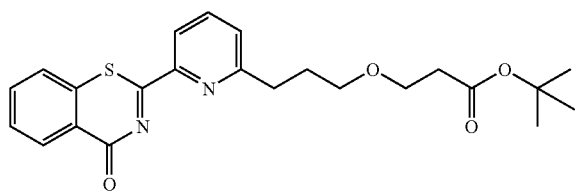

Methyl thiosalicylate (1.0 g, 6.1 mmol) and tert-butyl 3-[3-(6-cyano-2-pyridyl)propoxy]propanoate (1.6 g, 5.5 mmol) were dissolved in toluene (5.0 ml). Triethylamine (1.35 ml, 9.7 mmol) was added to the mixture and the mixture was refluxed for 14 hrs. The reaction mixture was subjected to a silica gel (110 g) column chromatography and eluted with hexane-ethyl acetate (3:2, v/v) to give the titled compound (1.7 g, 67%) as white crystals.

mp. 71.0-71.9° C. IR(KBr): 1728, 1664, 1572, 1537, 1159 cm$^{-1}$. $^1$H-NMR (CDCl$_3$) δ: 1.46 (9H, s), 2.14 (2H, m), 2.51 (2H, t, J=6.3 Hz), 2.99 (2H, t, J=7.2 Hz), 3.57 (2H, t, J=6.3 Hz), 3.71 (2H, t, J=6.3 Hz), 7.39 (1H, d, J=7.5 Hz), 7.59-7.71 (3H, m), 7.79 (1H, t, J=7.8 Hz), 8.35 (1H, d, J=7.8 Hz), 8.55 (1H, d, J=7.8 Hz). Elemental Analysis for C$_{23}$H$_{26}$N$_2$O$_4$S Calcd. C, 64.77; H, 6.14; N, 6.57. Found C, 64.51; H, 6.01; N, 6.50.

Example 67

3-{3-[6-(4-Oxo-4H-1,3-benzothiazin-2-yl)-2-pyridyl]propoxy}propionic acid

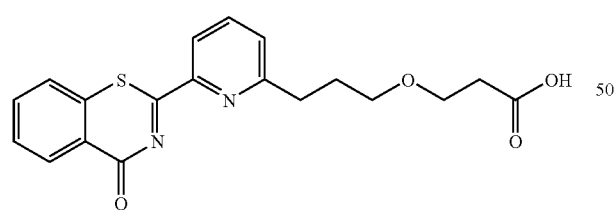

tert-Butyl 3-{3-[6-(4-oxo-4H-1,3-benzothiazin-2-yl)-2-pyridyl]propoxy}propanoate (1.70 g, 4.0 mmol) was dissolved in trifluoroacetic acid (15 ml) under ice cooling, and the mixture was stirred at 0° C. for 5 hrs. The reaction mixture was combined with isopropylether (50 ml) and stirred for 30 minutes. The precipitated crystals were collected by filtration. The crystals were recrystallized from ethanol-hexane to give the titled compound (0.57 g, 39%) as white crystals.

mp. 141.0-142.0° C. IR(KBr): 3061, 1732, 1658, 1572, 1529, 1305 cm$^{-1}$. $^1$H-NMR (CDCl$_3$) δ: 2.15 (2H, m), 2.66 (2H, t, J=6.2 Hz), 2.98 (2H, t, J=7.5 Hz), 3.59 (2H, t, J=6.3 Hz), 3.75 (2H, t, J=6.2 Hz), 7.37 (1H, d, J=7.5 Hz), 7.59-7.71 (3H, m), 7.79 (1H, t, J=7.8 Hz), 8.34 (1H, d, J=7.8 Hz), 8.54 (1H, d, J=7.8 Hz). Elemental Analysis for C$_{19}$H$_{18}$N$_2$O$_4$S Calcd. C, 61.61; H, 4.90; N, 7.56. Found C, 61.47; H, 4.94; N, 7.36.

Example 68

2-(2-Methylthio-4-pyridyl)-4H-1,3-benzothiazine-4-one

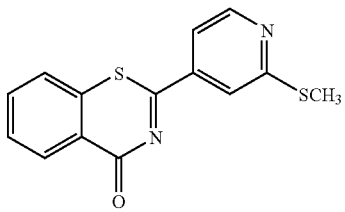

Methyl thiosalicylate (0.76 g, 4.5 mmol) and 2-methylthioisonicotinonitrile (0.34 g, 2.3 mmol) were dissolved in toluene (2.0 ml). Triethylamine (0.70 ml, 5.0 mmol) was added thereto and the mixture was refluxed for 6 hrs. The reaction mixture was cooled at room temperature and the precipitated crystals were collected and recrystallized from ethanol to give the titled compound (0.11 g, 17%) as white crystals.

mp. 173.4-173.5° C. IR(KBr): 1655, 1585, 1520, 1361, 1294 cm$^{-1}$. $^1$H-NMR (CDCl$_3$) δ: 2.59 (3H, s), 7.56-7.73 (4H, m), 7.91 (1H, s), 8.56 (1H, dd, J=7.5, 1.8 Hz), 8.63 (1H, d, J=5.3 Hz). Elemental Analysis for C$_{14}$H$_{10}$N$_2$OS$_2$ Calcd. C, 58.72; H, 3.52; N, 9.78. Found C, 58.72; H, 3.47; N, 9.88.

Reference Example 5

2-Benzyloxyisonicotinonitrile

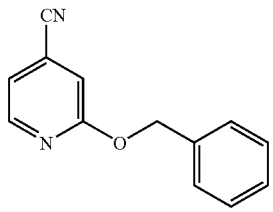

Sodium hydride (60% oil, 0.13 g, 3.3 mmol) was suspended in tetrahydrofuran (2 ml), Benzyl alcohol (0.30 g, 3.2 mmol) was added thereto and the mixture was stirred for 30 minutes.

A solution of 2-chloro-4-cyanopyridine (0.40 g, 2.9 mmol) in tetrahydrofuran (1 ml) was added to the mixture and the mixture was refluxed for 6 hrs. The reaction mixture was combined with ethyl acetate and water and stirred. The organic layer was washed with saturated brine and dried over anhydrous magnesium sulfate. The solvent was evaporated. The residue was subjected to a silica gel (30 g) column chromatography, eluted with hexane-ethyl acetate (4:1, v/v) to give the titled compound (0.37 g, 62%).

$^1$H-NMR (CDCl$_3$) δ: 5.41 (2H, m), 7.04-7.09 (2H, m), 7.33-7.45 (5H, m), 8.31 (1H, d, J=4.8 Hz).

Example 69

2-(2-Benzyloxy-4-pyridyl)-4H-1,3-benzothiazine-4-one

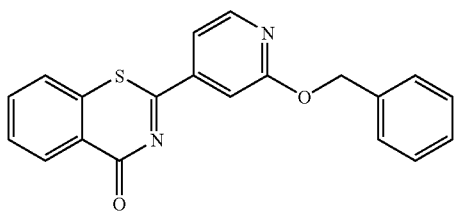

Methyl thiosalicylate (0.59 g, 3.5 mmol) and 2-(benzyloxy)isonicotinonitrile (0.37 g, 1.8 mmol) were dissolved in toluene (2.0 ml). Triethylamine (0.54 ml, 3.9 mmol) was added thereto and the mixture was refluxed for 6 hrs. The reaction mixture was subjected to a silica gel (50 g) column chromatography, eluted with hexane-ethyl acetate (2:1, v/v) and recrystallized from ethanol to give the titled compound (0.20 g, 32%) as white crystals.

mp. 116.0-116.5° C. IR(KBr): 1665, 1603, 1529, 1410, 1354, 1288 cm$^{-1}$. $^1$H-NMR (CDCl$_3$) δ: 5.46 (2H, s), 7.35-7.70 (10H, m), 8.36 (1H, d, J=5.4 Hz), 8.56 (1H, dd, J=7.5, 1.8 Hz). Elemental Analysis for C$_{20}$H$_{14}$N$_2$O$_2$S Calcd. C, 69.35; H, 4.07; N, 8.09. Found C, 69.21; H, 4.26; N; 8.09.

Example 70

2-(2-Methoxy-4-pyridyl)-4H-1,3-benzothiazine-4-one

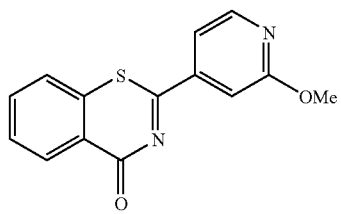

2-Chloro-4-cyanopyridine (0.40 g, 2.9 mmol) was dissolved in tetrahydrofuran (1 ml), and 12% lithium methylate in methanol (1.0 g, 3.2 mmol) was added thereto. The reaction mixture was refluxed for 6 hrs, combined with water, extracted with ethyl acetate, washed with saturated brine and dried over anhydrous magnesium sulfate. The solvent was evaporated under reduced pressure to give a mixture (0.30 g) containing 2-methoxyisonicotinonitrile. This mixture and methyl thiosalicylate (1.0 g, 5.9 mmol) were dissolved in toluene (3.0 ml), and triethylamine (1.0 ml, 7.2 mmol) was added thereto. The reaction mixture was refluxed for 8 hrs, subjected to a silica gel (60 g) column chromatography, eluted with hexane-ethyl acetate (2:1, v/v) to give the titled compound (0.05 g, 8%) as white crystals.

mp. 148.8-150.5° C. IR(KBr): 1662, 1525, 1448, 1387, 1315 cm$^{-1}$. $^1$H-NMR (CDCl$_3$) δ: 4.01 (3H, s), 7.46 (1H, s), 7.56-7.74 (4H, m) 8.35 (1H, d, J=5.4 Hz), 8.56 (1H, dd, J=7.5, 1.8 Hz). Elemental Analysis for C$_{14}$H$_{10}$N$_2$O$_2$S Calcd. C, 62.21; H, 3.73; N, 10.36. Found C, 61.95; H, 3.49; N, 10.17.

Reference Example 6

2-[N-Benzyl-N-methylamino]isonicotinonitrile

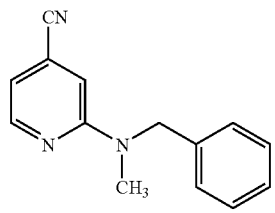

2-Chloro-4-cyanopyridine (0.40 g, 2.9 mmol) was dissolved in N-methylpyrrolidone (2.0 ml), and N-methyl-N-benzylamine (1.0 ml, 7.8 mmol) was added thereto. The reaction mixture was stirred at 100° C. for 2.5 hrs, combined with water, extracted with ethyl acetate, washed with saturated brine and dried over anhydrous magnesium sulfate. The solvent was evaporated under reduced pressure. The residue was subjected to a silica gel (50 g) column chromatography, eluted with hexane-ethyl acetate (3:1, v/v) to give the titled compound (0.47 g, 72%).

$^1$H-NMR (CDCl$_3$) δ: 3.09 (3H, s), 4.82 (2H, s), 6.67 (1H, s), 6.72 (1H, d, J=5.0 Hz), 7.08-7.35 (5H, m), 8.28 (1H, d, J=5.0 Hz).

Example 71

2-[2-(N-Benzyl-N-methylamino)-4-pyridyl]-4H-1,3-banzothiazine-4-one

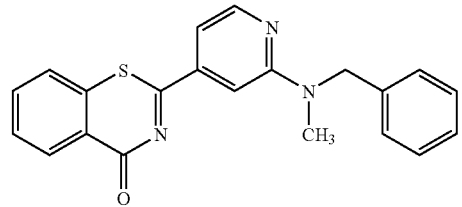

Methyl thiosalicylate (0.70 g, 4.2 mmol) and 2-[N-benzyl-N-methylamino]isonicotinonitrile (0.46 g, 2.1 mmol) were dissolved in toluene (2.0 ml), and triethylamine (0.68 ml, 4.9 mmol) was added thereto. The reaction mixture was refluxed for 8 hrs, subjected to silica gel (50 g) column chromatography, eluted with hexane-ethyl-acetate (2:1, v/v) and recrystallized from ethanol to give the titled compound (0.23 g, 15%)

mp. 145.9-146.6° C. IR(KBr): 1662, 1597, 1525, 1494, 1412, 1290 cm$^{-1}$. $^1$H-NMR (CDCl$_3$) δ: 3.14 (3H, s), 4.92 (2H, s), 7.17-7.26 (7H, m) 7.56-7.70 (3H, m), 8.34 (1H, d, J=5.2 Hz), 8.55 (1H, dd, J=7.7, 1.8 Hz). Elemental Analysis for C$_{21}$H$_{17}$N$_3$OS Calcd. C, 70.17; H, 4.77; N, 11.69. Found C, 69.92; H, 4.65; N, 11.70.

Reference Example 7

2-(Hexylamino)isonicotinonitrile

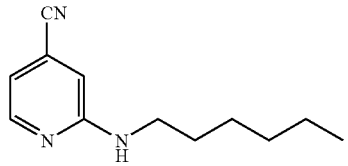

2-Chloro-4-cyanopyridine (0.40 g, 2.9 mmol) was dissolved in N-methylpyrrolidone (2.0 ml), and hexylamine (1.15 ml, 8.7 mmol) was added thereto. The reaction mixture was stirred at 100° C. for 4 hrs, combined with water, extracted with ethyl acetate, washed with saturated brine and dried over anhydrous magnesium sulfate. The solvent was evaporated under reduced pressure. The residue was subjected to a silica gel (50 g) column chromatography, eluted with hexane-ethyl acetate (3:1, v/v) to give the titled compound (0.26 g, 46%).

$^1$H-NMR (CDCl$_3$) δ: 0.90 (3H, t, J=6.9 Hz), 1.29-1.44 (6H, m), 1.61 (2H, q, J=7.2 Hz), 3.26 (2H, q, J=6.9 Hz), 4.77 (1H, br s), 6.54 (1H, s), 6.71 (1H, d, J=5.1 Hz), 8.18 (1H, d, J=5.1 Hz).

Example 72

2-[2-(Hexylamino)-4-pyridyl]-4H-1,3-benzothiazine-4-one

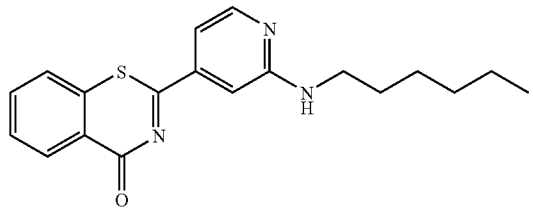

Methyl thiosalicylate (0.44 g, 2.6 mmol) and 2-(hexylamino)isonicotinonitrile (0.26 g, 1.3 mmol) were dissolved in toluene (2.0 ml), and triethylamine (0.40 ml, 2.9 mmol) was added thereto. The reaction mixture was refluxed for 14 hrs, subjected to a silica gel (50 g) chromatography, eluted with hexane-ethyl acetate (2:1, v/v) and recrystallized from ethanol to give the titled compound (0.08 g, 18%) as white crystals.

mp. 133.8-134.6° C. IR(KBr): 3375, 1649, 1601, 1518, 1292 cm$^{-1}$. $^1$H-NMR (CDCl$_3$) δ: 0.91 (3H, t, J=6.9 Hz), 1.31-1.42 (6H, m), 1.65 (2H, q, J=7.2 Hz), 3.35 (2H, q, J=6.9 Hz), 4.74 (1H, m), 7.13 (1H, s), 7.16 (1H, d, J=1.3 Hz), 7.56 (1H, d, J=7.5 Hz), 7.63-7.74 (2H, m), 8.25 (1H, d, J=5.3 Hz), 8.55 (1H, dd, J=7.5, 1.8 Hz). Elemental Analysis for C$_{19}$H$_{21}$N$_3$OS Calcd. C, 67.23; H, 6.24; N, 12.38. Found C, 66.95; H, 6.07; N, 12.37.

Reference Example 8

2-Morpholinylisonicotinonitrile

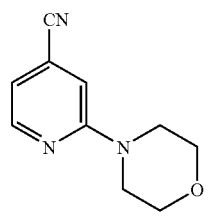

2-Chloro-4-cyanopyridine (0.40 g, 2.9 mmol) was dissolved in N-methylpyrrolidone (2.0 ml), and morpholine (0.7 ml, 8.0 mmol) was added thereto. The reaction mixture was stirred at 100° C. for 2.5 hrs and combined with water to give precipitates, which were collected by filtration and dried to give the titled compound (0.39 g, 70%).

$^1$H-NMR (CDCl$_3$) δ: 3.55 (4H, m), 3.82 (4H, m), 6.79 (1H, s), 6.80 (1H, d, J=5.7 Hz), 8.30 (1H, d, J=5.7 Hz).

Example 73

2-(2-Morpholinyl-4-pyridyl)-4H-1,3-benzothiazine-4-one

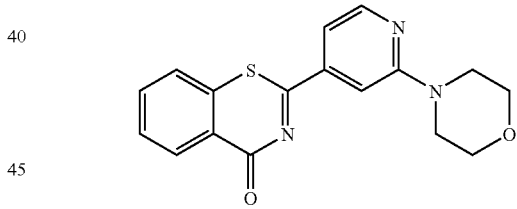

Methyl thiosalicylate (0.49 g, 2.9 mmol) and 2-morpholinylisonicotinonitrile (0.38 g, 2.0 mmol) were dissolved in toluene (2.0 ml), and triethylamine (0.48 ml, 3.4 mmol) was added thereto. The reaction mixture was refluxed for 14 hrs. After cooling, the precipitated crystals were collected by filtration and recrystallized from ethanol. The obtained crystals were recrystallized from ethyl acetate again to give the titled compound (0.16 g, 25%) as white crystals.

mp. 157.0-158.0° C. IR(KBr): 1660, 1591, 1525, 1433, 1290 cm$^{-1}$. $^1$H-NMR (CDCl$_3$) δ: 3.64 (4H, m), 3.84 (4H, m), 7.24 (1H, m), 7.41 (1H, s), 7.57 (1H, dd, J=7.4, 1.5 Hz), 7.70 (2H, m), 8.36 (1H, d, J=5.2 Hz), 8.57 (1H, dd, J=7.5, 1.4 Hz). Elemental Analysis for C$_{17}$H$_{15}$N$_3$O$_2$S Calcd. C, 62.75; H, 4.65; N, 12.91. Found C, 62.53; H, 4.47; N, 12.92.

Reference Example 9

2-[4-(4-Fluorophenyl)-1-piperazinyl]isonicotinonitrile

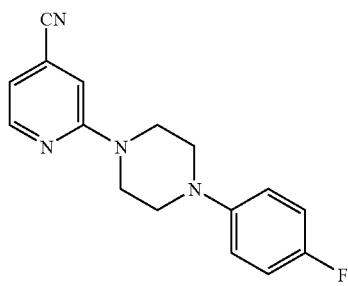

2-Chloro-4-cyanopyridine (0.40 g, 2.9 mmol) was dissolved in N-methylpyrrolidone (2.0 ml), and 1-(4-fluorophenyl)piperazine (1.0 g, 5.6 mmol) was added thereto. The reaction mixture was stirred at 100° C. for 10 hrs, combined with water to give precipitates, which were collected by filtration to give the titled compound (0.70 g, 86%).

$^1$H-NMR (CDCl$_3$) δ: 3.34 (4H, m), 3.74 (4H, m), 6.79 (1H, d, J=5.0 Hz), 6.86 (1H, s), 6.90-7.03 (4H, m), 8.30 (1H, d, J=5.0 Hz).

Example 74

2-{2-[4-(4-Fluorophenyl)-1-piperazinyl]-4-pyridyl}-4H-1,3-benzothiazine-4-one

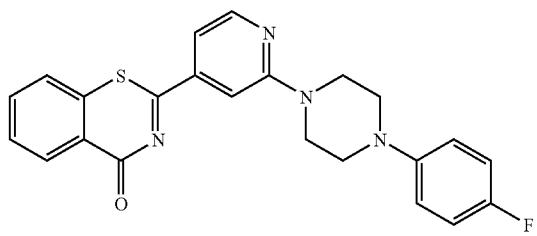

Methyl thiosalicylate (0.70 g, 4.2 mmol) and 2-[4-(4-fluorophenyl)-1-piperazinyl]isonicotinonitrile (0.69 g, 2.4 mmol) were dissolved in toluene (2.0 ml), and triethylamine (0.71 ml, 5.1 mmol) was added thereto. The reaction mixture was refluxed for 17 hrs and the precipitated crystals were collected by filtration. The filtrate was concentrated, subjected to a silica gel (50 g) column chromatography, eluted with hexane-ethyl acetate (2:1, v/v) to give crystals, which were combined with the previously obtained crystals and recrystallized from acetone-ethanol to give the titled compound (0.18 g, 17%) as white crystals.

mp. 233.0-233.6° C. IR(KBr): 1661, 1593, 1523, 1508, 1435, 1290 cm$^{-1}$. $^1$H-NMR (CDCl$_3$) δ: 3.23 (4H, m), 3.84 (4H, m), 6.95-7.00 (4H, m), 7.23 (1H, m), 7.48 (1H, s), 7.58-7.72 (3H, m), 8.37 (1H, d, J=5.2 Hz), 8.55 (1H, dd, J=7.6, 1.8 Hz). Elemental Analysis for C$_{23}$H$_{19}$N$_4$OSF Calcd. C, 66.01; H, 4.58; N, 13.39. Found C, 65.87; H, 4.77; N, 13.38.

Example 75

2-(2-Phenyl-4-pyridyl)-4H-1,3-benzothiazine-4-one

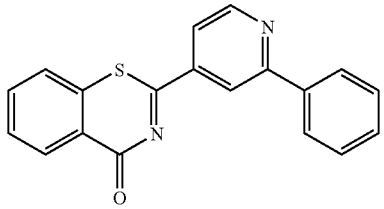

2-Chloro-4-cyanopyridine (0.40 g, 2.9 mmol), phenylboric acid (0.53 g, 4.3 mmol) and potassium carbonate (1.0 g, 7.2 mmol) were dissolved in toluene-ethanol-water (4:1:1, 30 ml), and the mixture was deairated under reduced pressure for 15 minutes. Tetrakis(triphenylphosphine)palladium (0.17 g, 0.14 mmol) was added to the mixture under nitrogen atmosphere, and the mixture was refluxed for 21 hrs. The reaction mixture was combined with ethyl acetate-water. The organic layer was washed with saturated brine and dried over anhydrous magnesium sulfate. The solvent was evaporated under reduced pressure to give crude 2-phenylisonicotinenitrile. Methyl thiosalicylate (1.10 g, 6.5 mmol) and 2-phenylisonicotinenitrile (0.50 g, 2.8 mmol) was dissolved in toluene (2.0 ml), and triethylamine (1.1 ml, 7.9 mmol) was added thereto. The reaction mixture was refluxed for 18 hrs, cooled at room temperature to give precipitated crystals, which were collected by filtration. The filtrate was concentrated, subjected to a silica gel (50 g) column chromatography and eluted with hexane-ethyl acetate (2:1, v/v) to give crystals, which were combined with the previously obtained crystals and recrystallized from ethanol to give the titled compound (0.34 g, 27%) as white crystals.

mp. 162.7-163.0° C. IR(KBr): 1665, 1591, 1525, 1286 cm$^{-1}$. $^1$H-NMR (CDCl$_3$) δ: 7.49-7.74 (6H, m), 7.92 (1H, dd, J=5.1, 1.5 Hz), 8.11 (2H, m), 8.47 (1H, s), 8.58 (1H, d, J=7.6 Hz), 8.91 (1H, d, J=5.1 Hz). Elemental Analysis for C$_{19}$H$_{12}$N$_2$OS Calcd. C, 72.13; H, 3.82; N, 8.85. Found C, 71.92; H, 3.70; N, 8.69.

Reference Example 10

2-(2-Thienyl)isonicotinonitrile

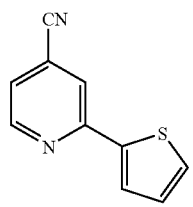

2-Chloro-4-cyanopyridine (0.50 g, 3.6 mmol) and 2-thienylboric acid (0.69 g, 5.4 mmol) were dissolved in toluene-ethanol (4:1, v/v, 25 ml), and to the mixture, a solution of potassium carbonate (1.3 g, 9.0 mmol) in water (5 ml) was added. The mixture was deairated under reduced pressure for 15 minutes. Tetrakis(triphenylphosphine)palladium (0.21 mg, 0.2 mmol) was added to the mixture under nitrogen atmosphere, and the mixture was refluxed for 20 hrs. The reaction mixture was combined with ethyl acetate and water. The organic layer was washed with saturated brine and dried over anhydrous magnesium sulfate. The solvent was evaporated under reduced pressure. The residue was subjected to a silica gel (60 g) column chromatography and eluted with hexane-ethyl acetate (3:1, v/v) to give solid, which was recrystallized from ethanol to give the titled compound (0.35 g, 52%).

$^1$H-NMR (CDCl$_3$) δ: 7.16 (1H, dd, J=5.1, 3.9 Hz), 7.34 (1H, d, J=5.1 Hz), 7.49 (1H, d, J=5.1 Hz), 7.64 (1H, d, J=3.9 Hz), 8.03 (1H, s), 8.71 (1H, d, J=5.1 Hz).

Example 75

2-[2-(2-Thienyl)-4-pyridyl]-4H-1,3-benzothiazine-4-one

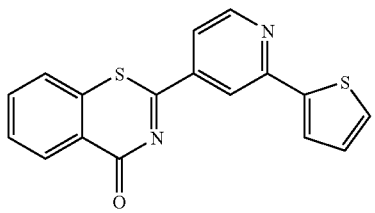

Methyl thiosalicylate (0.38 g, 2.2 mmol) and (2-thienyl) isonicotinonitrile (0.26 g, 1.4 mmol) were dissolved in toluene (2.0 ml), and triethylamine (0.39 ml, 2.8 mmol) was added thereto. The reaction mixture was refluxed for 24 hrs. The reaction mixture was subjected to a silica gel (30 g) column chromatography, eluted with hexane-ethyl acetate (2:1, v/v) and recrystallized from ethanol to give the titled compound (0.22 g, 30%) as white crystals.

mp. 160.4-161.1° C. IR(KBr): 1662, 1591, 1522, 1285 cm$^{-1}$. $^1$H-NMR (CDCl$_3$) δ: 7.16 (1H, dd, J=5.0, 3.7 Hz), 7.46 (1H, m), 7.61-7.81 (5H, m), 8.37 (1H, s), 8.57 (1H, m), 8.76 (1H, d, J=5.0 Hz). Elemental Analysis for C$_{17}$H$_{10}$N$_2$OS$_2$ Calcd. C, 63.33; H, 3.13; N, 8.69. Found C, 63.19, H, 3.19; N, 8.63.

Examples 76 and 77

2-(2-Chloro-4-pyridyl)-4H-1,3-benzothiazine-4-one and methyl 2-{[4-(4-oxo-4H-1,3-benzothiazin-2-yl)-2-pyridyl]thio}benzoate

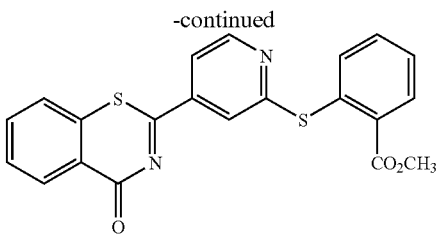

Methyl thiosalicylate (3.6 g, 21.6 mmol) and 2-chloro-4-cyanopyridine (3.0 g, 21.7 mmol) were dissolved in toluene (5.0 ml), and triethylamine (4.5 ml, 32.3 mmol) was added thereto. The reaction mixture was refluxed for 22 hrs. The reaction mixture was subjected to a silica gel (120 g) column chromatography, eluted with hexane-ethyl acetate (1:2, v/v) and recrystallized from acetone-ethyl acetate to give 2-(2-chloro-4-pyridyl)-4H-1,3-benzothiazine-4-one (0.47 g, 8.0%) as white crystals.

mp. 177.8-178.4° C. IR(KBr): 1665, 1587, 1522, 1294 cm$^{-1}$. $^1$H-NMR (CDCl$_3$) δ: 7.60 (1H, m), 7.74 (2H, m), 7.94 (1H, d, J=5.1 Hz), 8.10 (1H, s), 8.57 (1H, d, J=7.2 Hz), 8.62 (1H, d, J=5.1 Hz). Elemental Analysis for C$_{13}$H$_7$N$_2$OSCl Calcd. C, 56.83; H, 2.57; N, 10.20. Found C, 56.58; H, 2.28, N, 10.19.

The fractions eluted with ethyl acetate were collected, concentrated and recrystallized from ethyl acetate to give methyl 2-{[4-(4-oxo-4H-1,3-benzothiazin-2-yl)-2-pyridyl]thio}benzoate (0.55 g, 6.0%) as white crystals.

mp. 137.0-137.9° C. IR(KBr): 1714, 1665, 1523, 1291 cm$^{-1}$. $^1$H-NMR (CDCl$_3$) δ: 3.86 (3H, s), 7.40-7.70 (6H, m), 7.81 (1H, m), 7.94 (2H, m), 8.55 (1H, d, J=7.5 Hz), 8.67 (1H, d, J=5.1 Hz). Elemental Analysis for C$_{21}$H$_{14}$N$_2$O$_3$S$_2$ Calcd. C, 62.05; H, 3.47; N, 6.89. Found C, 61.88; H, 3.30; N, 6.68.

Reference Example 11 tert-Butyl (E)-3-(2-pyridyl)-2-propenoate

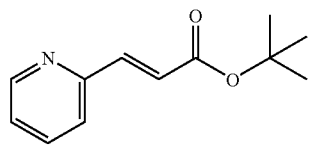

Sodium hydride (60% oil, 0.6 g, 15.7 mmol) was washed with hexane and suspended in tetrahydrofuran (5 ml). To the mixture, a solution of tert-butyl diethylphosphinoacetate (2.5 g, 9.8 mmol) in tetrahydrofuran (2 ml) was added under ice cooling condition. The reaction mixture was stirred at room temperature for 30 minutes, cooled under ice cooling condition. A solution of 2-formylpyridine (1.0 g, 9.3 mmol) in tetrahydrofuran (3.0 ml) was added to the mixture, and the mixture was stirred at 0° C. for 1.5 hrs. The reaction mixture was combined with water and extracted with ethyl acetate. The organic layer was washed with saturated brine, dried over anhydrous magnesium sulfate and concentrated under

Reference Example 12 tert-butyl 3-(2-pyridyl)propanoate

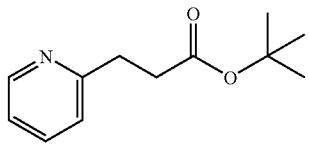

tert-Butyl (E)-3-(2-pyridyl)-2-propenoate (1.1 g, 5.4 mmol) was dissolved in ethanol (12 ml), and a solution of ammonium formate (2.0 g, 32.0 mmol) in water (3 ml) was added thereto. The reaction mixture was refluxed for 1.5 hrs, combined with ethyl acetate and water and filtered. The filtrate was extracted with ethyl acetate. The organic layer was washed with saturated brine, dried over anhydrous magnesium sulfate and concentrated under reduced pressure to give the titled compound (1.0 g, 94%).

$^1$H-NMR (CDCl$_3$) δ: 1.41 (9H, s), 2.70 (2H, t, J=7.6 Hz), 3.07 (2H, t, J=7.6 Hz), 7.11 (1H, m), 7.17 (1H, d, J=7.8 Hz), 7.58 (1H, t, J=7.8 Hz), 8.52 (1H, d, J=4.8 Hz).

Reference Example 13 tert-Butyl 3-(1-oxido-2-pyridyl)propanoate

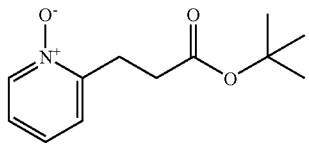

tert-Butyl 3-(2-pyridyl)propanoate (1.0 g, 5.0 mmol) was dissolved in ethyl acetate (5 ml), and 3-chloroperbenzoic acid (ca. 70%, 1.3 g, 5.2 mmol) was added thereto. The reaction mixture was subjected to a silica gel (50 g) column chromatography and eluted with ethyl acetate-ethanol (5:1, v/v) to give the titled compound (0.9 g, 80%). $^1$H-NMR (CDCl$_3$) δ: 1.41 (9H, s), 2.76 (2H, t, J=7.1 Hz), 3.17 (2H, t, J=7.1 Hz), 7.15-7.32 (3H, m), 8.24 (1H, d, J=5.7 Hz).

reduced pressure. The residue was subjected to a silica gel (60 g) column chromatography, and eluted with hexane-ethyl acetate (3:1, v/v) to give the titled compound (1.5 g, 77%).

$^1$H-NMR (CDCl$_3$) δ: 1.53 (9H, s), 6.82 (1H, d, J=15.7 Hz), 7.23 (1H, m), 7.41 (1H, d, J=7.8 Hz), 7.59 (1H, d, J=15.7 Hz), 7.70 (1H, t, J=7.8 Hz), 8.63 (1H, d, J=4.5 Hz).

Reference Example 14 tert-Butyl 3-(6-cyano-2-pyridyl)propanoate

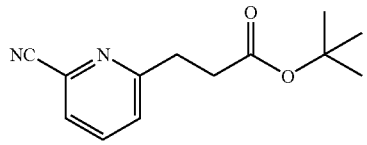

tert-Butyl 3-(1-oxido-2-pyridyl)propanoate (0.88 g, 3.9 mmol) was dissolved in nitroethane (5 ml). Trimethylsilyl cyanide (0.78 g, 7.9 mmol) and N,N-dimethylcarbamoyl chloride (0.85 g, 7.9 mmol) were added thereto. The reaction mixture was stirred at room temperature for 48 hrs, combined with ethyl acetate and water. The organic layer was washed successively with saturated aqueous sodium hydrogen carbonate solution and saturated brine and dried over anhydrous magnesium sulfate. The solvent was evaporated. The residue was subjected to a silica gel (50 g) column chromatography and eluted with hexane-ethyl acetate (3:1, v/v) to give the titled compound (0.75 g, 82%). $^1$H-NMR (CDCl$_3$) δ: 1.42 (9H, s), 2.74 (2H, t, J=7.1 Hz), 3.12 (2H, t, J=7.1 Hz), 7.41 (1H, d, J=7.8 Hz), 7.52 (1H, d, J=7.8 Hz), 7.72 (1H, t, J=7.8 Hz).

Example 78 tert-Butyl 3-[6-(4-oxo-4H-1,3-benzothiazin-2-yl)-2-pyridyl]propanoate

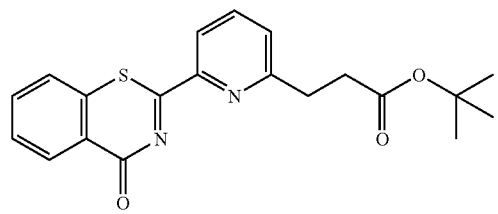

tert-Butyl 3-(6-cyano-2-pyridyl)propanoate (0.74 g, 3.2 mmol) and methyl thiosalicylate (1.1 g, 6.4 mmol) were dissolved in toluene (3 ml). Triethylamine (1.4 ml, 9.7 mmol) was added thereto. The reaction mixture was refluxed for 7.5 hrs, subjected to a silica gel (75 g) column chromatography, eluted with hexane-ethyl acetate (2:1, v/v) and recrystallized from ethanol-hexane to give the titled compound (0.68 g, 57%) as white crystals.

mp. 165.8-166.0° C. IR(KBr): 1719, 1663, 1570, 1534, 1151 cm$^{-1}$. $^1$H-NMR (CDCl$_3$) δ: 1.43 (9H, s), 2.89 (2H, t, J=7.2 Hz), 3.21 (2H, t, J=7.2 Hz), 7.42 (1H, d, J=7.7 Hz), 7.60-7.69 (3H, m), 7.80 (1H, t, J=7.7 Hz), 8.36 (1H, d, J=7.6 Hz), 8.55 (1H, d, J=7.9 Hz). Elemental Analysis for C$_{20}$H$_{20}$N$_2$O$_3$S Calcd. C, 65.20; H, 5.47; N, 7.60. Found C, 65.17; H, 5.31; N, 7.66.

Example 79

3-[6-(4-Oxo-4H-1,3-benzothiazin-2-yl)-2-pyridyl]propionic acid

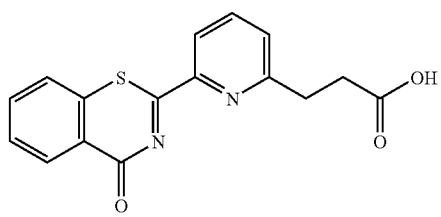

tert-Butyl 3-[6-(4-oxo-4H-1,3-benzothiazin-2-yl)-2-pyridyl]propanoate (0.50 g, 1.4 mmol) was dissolved in trifluoroacetic acid (3 ml) under ice cooling condition, and the mixture was stirred for 2.5 hrs. The reaction mixture was combined with isopropylether to give the precipitated solid, which was collected by filtration and recrystallized from tetrahydrofuran-ethanol to give the titled compound (0.33 g, 77%) as white crystals.

mp. 243.2-243.5° C. IR(KBr): 3194, 1721, 1630, 1526, 1221 cm$^{-1}$. $^1$H-NMR (DMSO-d$_6$) δ: 2.82 (1H, t, J=7.2 Hz), 3.17 (1H, t, J=7.2 Hz), 7.66 (1H, d, J=7.7 Hz), 7.72-7.94 (3H, m), 8.01 (1H, t, J=7.8 Hz), 8.19 (1H, d, J=7.7 Hz), 8.36 (1H, d, J=7.9 Hz), 12.18 (1H, s). Elemental Analysis for C$_{16}$H$_{12}$N$_2$O$_3$S Calcd. C, 61.53; H, 3.87; N, 8.97. Found C, 61.43; H, 3.67; N, 8.95.

Reference Example 15 tert-Butyl 2-pyridinecarboxylate N-oxide

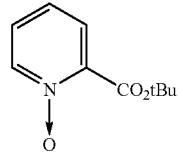

tert-Butyl 2-pyridinecarboxylate (14.0 g, 78 mmol) was dissolved in ethyl acetate (200 ml), and 3-chloroperbenzoic acid (ca. 77%, 26.2 g, 117 mmol) was added thereto. The reaction mixture was stirred at room temperature for 40 hrs. The solvent was evaporated under reduced pressure. The residue was subjected to a silica gel column chromatography and eluted with ethyl acetate-acetone (1:1, v/v) to give the titled compound (12.4 g, 81%).

$^1$H-NMR (CDCl$_3$) δ: 1.62 (9H, s), 7.23-7.29 (2H, m), 7.47 (1H, m) 8.20 (1H, m).

Reference Example 16 tert-Butyl 6-cyano-2-pyridinecarboxylate

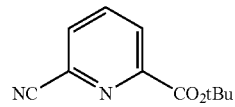

A mixture of tert-butyl 2-pyridinecarboxylate N-oxide (12.4 g, 63 mmol), trimethylsilyl cyanide (9.6 g, 96 mmol), N,N-dimethylcarbamoyl chloride (10.3 g, 95 mmol) and nitroethane (80 ml) was stirred at room temperature for 3 days. The reaction mixture was concentrated under reduced pressure. The residue was subjected to a silica gel column chromatography, eluted with hexane-ethyl acetate (3;1, v/v) and recrystallized from tetrahydrofuran-hexane to give the titled compound (11.1 g, 85%).

mp. 156.1-157.1° C. IR (KBr): 3053, 2982, 2235, 1730, 1576, 1305, 1167, 993, 846, 773 cm$^{-1}$. $^1$H-NMR (CDCl$_3$) δ: 1.64 (9H, s), 7.83 (1H, dd, J=1.0, 7.6 Hz), 7.98 (1H, dd, J=7.6, 8.0 Hz), 8.23 (1H, dd, J=1.0, 8.0 Hz). Elemental Analysis for C$_{11}$H$_{12}$N$_2$O$_2$ Calcd. C, 64.69; H 5.92; N, 13.72. Found C, 64.73; H, 5.75; N, 13.87.

Example 80 tert-Butyl 6-(4-oxo-4H-1,3-benzothiazin-2-yl)-2-pyridinecarboxylate

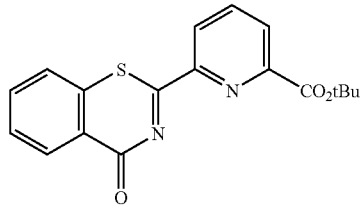

A mixture of tert-butyl 6-cyano-2-pyridinecarboxylate (1.1 g, 5.3 mmol), methyl thiosalicylate (1.8 g, 10.7 mmol), triethylamine (2.0 ml, 14.3 mmol) and toluene (4 ml) was refluxed for 12 hrs. After cooling, the precipitated crystals were collected by filtration, recrystallized from tetrahydrofuran-hexane to give the titled compound (1.3 g, 70%).

mp. 185.0-185.5° C. IR (KBr): 2976, 1738, 1664, 1539, 1304, 1149, 742, 729 cm$^{-1}$. $^1$H-NMR (CDCl$_3$) δ: 1.69 (9H, s), 7.63-7.70 (3H, m), 8.03 (1H, dd, J=7.8, 7.8 Hz), 8.24 (1H, dd, J=1.0, 7.8 Hz), 8.56 (1H, m) 8.67 (1H, dd, J=1.0, 7.8 Hz). Elemental Analysis for C$_{18}$H$_{16}$N$_2$O$_3$S Calcd. C, 63.51; H, 4.74; N, 8.23. Found C, 63.41; H, 4.74; N, 8.10.

Example 81

6-(4-Oxo-4H-1,3-benzothiazin-2-yl)-2-pyridinecarboxylic acid

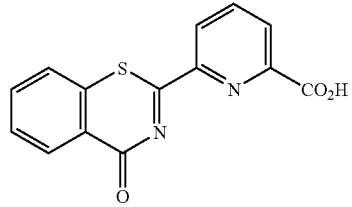

A mixture of tert-butyl 6-(4-oxo-4H-1,3-benzothiazin-2-yl)-2-pyridinecarboxylate (400 mg, 1.1 mmol) and trifluoroacetic acid (10 ml) was stirred under ice cooling condition for 3 hrs. The reaction mixture was combined with diisopropylether to precipitate crystals, which were collected by filtration and recrystallized from methanol-diisopropylether to give the titled compound (245 mg, 73%).

mp. 260.2-260.5° C. IR (KBr): 3202, 1726, 1633, 1527, 1311, 1157, 1103, 742 cm$^{-1}$. $^1$H-NMR (DMSO-d$_6$) δ: 7.73 (1H, m), 7.85 (1H, m), 7.99 (1H, d, J=7.8 Hz), 8.25-8.38 (3H, m), 8.53 (1H, dd, J=1.2, 7.5 Hz), 13.69 (1H, br s). Elemental Analysis for C$_{14}$H$_8$N$_2$O$_3$S.0.5H$_2$O Calcd. C, 57.33; H, 3.09; N, 9.55. Found C, 57.39; H, 3.37; N, 9.30.

Example 82

6-(4-Oxo-4H-1,3-benzothiazin-2-yl)-N-(2,2,2-trifluoroethyl)-2-pyridinecarboxamide

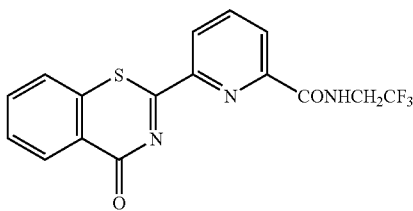

A mixture of 6-(4-oxo-4H-1,3-benzothiazin-2-yl)-2-pyridinecarboxylic acid (350 mg, 1.2 mmol), 1-ethyl 3-(3-dimethylaminopropyl)carbodiimide hydrochloride (hereinafter abbreviated as WSC) (480 mg, 2.5 mmol), 1-hydroxybenzotriazol monohydrate (hereinafter abbreviated as HOBt) (480 mg, 2.5 mmol) and N,N-dimethylformamide (hereinafter abbreviated as DMF) (15 ml) was stirred at room temperature for 9 hrs. The reaction mixture was poured into water and extracted with ethyl acetate. The extract was washed with water and dried. The solvent was evaporated under reduced pressure. The residue was subjected to a silica gel column chromatography, eluted with hexane-ethyl acetate (2:3, v/v) and recrystallized from tetrahydrofuran-hexane to give the titled compound (114 mg, 25%).

mp. 242.6-244.2° C. IR (KBr): 3404, 1691, 1664, 1537, 1290, 1267, 1167 cm$^{-1}$. $^1$H-NMR (CDCl$_3$) δ: 4.23 (2H, m), 7.64-7.75 (3H, m), 8.13 (1H, m), 8.19 (1H, br s), 8.45 (1H, d, J=7.7 Hz), 8.57 (1H, d, J=6.1 Hz), 8.71 (1H, d, J=7.9 Hz). Elemental Analysis for C$_{16}$H$_{10}$N$_3$O$_2$SF$_3$ Calcd. C, 52.60; H, 2.76; N, 11.50. Found C, 52.29; H, 2.64; N, 11.34.

Example 83

N-(2-Methoxyethyl)-6-(4-oxo-4H-1,3-benzothiazin-2-yl)-2-pyridinecarboxamide

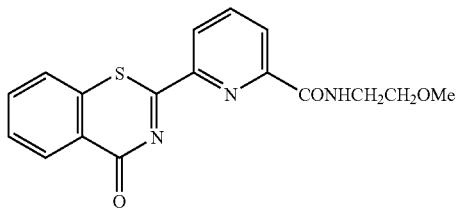

A mixture of 6-(4-oxo-4H-1,3-benzothiazin-2-yl)-2-pyridinecarboxylic acid (350 mg, 1.2 mmol), WSC (471 mg, 2.4 mmol), HOBt (332 mg, 2.4 mmol) and DMF (10 ml) was stirred at 80° C. for 17 hrs. The reaction mixture was poured into water and extracted with ethyl acetate. The extract was washed with water and dried. The solvent was evaporated. The residue was subjected to a silica gel column chromatography, eluted with ethyl acetate-methanol (50:1, v/v) and recrystallized from tetrahydrofuran-hexane to give the titled compound (167 mg, 40%).

mp. 175.5-176.7° C. IR (KBr): 3397, 2928, 1691, 1660, 1574, 1539, 1520, 1452, 1292, 1122, 746 cm$^{-1}$. $^1$H-NMR (CDCl$_3$) δ: 3.48 (3H, s), 3.65 (2H, t, J=4.9 Hz), 3.76 (2H, m), 7.65-7.73 (3H, m), 8.09 (1H, m), 8.27 (1H, br s), 8.43 (1H, dd, J=0.9, 7.7 Hz), 8.57 (1H, m), 8.66 (1H, dd, J=0.9, 7.8 Hz). Elemental Analysis for C$_{17}$H$_{15}$N$_3$O$_3$S Calcd. C, 59.81; H, 4.43; N, 12.31. Found C, 59.61,; H, 4.64; N, 11.83.

Example 84

6-Hydroxy-2-(2-pyridyl)-4H-1,3-benzothiazine-4-one

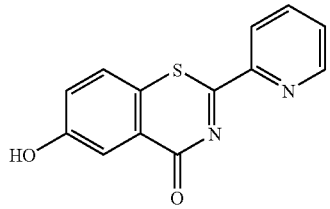

A mixture of 5-hydroxysalicylic acid (2.0 g, 11 mmol), 2-cyanopyridine (1.2 g, 11 mmol) and pyridine (10 ml) was refluxed for 1 hr. After cooling, the precipitated crystals were collected by filtration and recrystallized from dimethylsulfoxide-ethyl acetate-diethylether to give the titled compound (1.08 g, 36%)

mp. 313.3-315.0° C. IR (KBr): 3148, 1618, 1525, 1477, 1332, 1240, 1059, 792 cm$^{-1}$. $^1$H-NMR (DMSO-d$_6$) δ: 7.30 (1H, dd, J=2.7, 8.7 Hz), 7.71-7.78 (3H, m), 8.10 (1H, m), 8.34 (1H, d, J=7.9 Hz), 8.78 (1H, m), 10.43 (1H, s). Elemental Analysis for C$_{13}$H$_8$N$_2$O$_2$S Calcd. C, 60.93; H, 3.15; N, 10.93. Found C, 60.75; H, 3.05; N, 10.74.

Reference Example 17

4-Trifluoromethylthiosalicylic acid

A mixture of 2-amino-4-trifluoromethylbenzoic acid (5.0 g, 24 mmol), sodium hydroxide (1.0 g, 25 mmol), sodium nitrite (1.7 g, 24 mmol) and water (40 ml) was added dropwise to a mixture of concentrated hydrochloric acid (10 ml) and ice (10 g) while the reaction temperature had been kept at 0 to 5° C. The reaction mixture was stirred at the same temperature for 30 minutes, neutralized with potassium acetate and added to a solution of potassium O-ethyl dithocarbonate (11.7 g, 73 mmol) in water (40 ml). The reaction mixture was stirred at 80° C. for 20 minutes and acidified by use of concentrated hydrochloric acid to pH 3. The water layer was separated, and the oily substance was added to 10% aqueous sodium hydroxide solution (25 g) and stirred at 80° C. for 2 hrs. Sodium hydrosulfite (3 g) was added to the mixture, and the mixture was stirred at 80° C. for 10 minutes. The reaction mixture was filtered and the filtrate was cooled and acidified by use of concentrated hydrochloric acid to pH 4. The precipitated crystals were collected by filtration, dissolved in methanol (5 ml) and diisopropylether (100 ml) and dried. The solvent was evaporated under reduced pressure to give the titled compound (4.1 g, 77%).

$^1$H-NMR (CDCl$_3$) δ: 4.78 (1H, s), 7.44 (1H, d, J=8.2 Hz), 7.59 (1H, s), 8.24 (1H, d, J=8.2 Hz).

Example 85

2-(2-Pyridyl)-7-trifluoromethyl-4H-1,3-benzothiazine-4-one

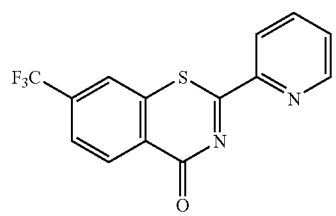

A mixture of 4-trifluoromethylthiosalicylic acid (2.5 g, 11 mmol), 2-cyanopyridine (1.2 g, 11 mmol) and pyridine (10 ml) was refluxed for 10 hrs. After cooling, the precipitated crystals were collected by filtration and recrystallized from tetrahydrofuran-hexane to give the titled compound (1.9 g, 54%).

mp. 175.8-177.0° C. IR (KBr): 3049, 1678, 1660, 1574, 1537, 1334, 1305, 1172, 1084, 792 cm$^{-1}$. $^1$H-NMR (CDCl$_3$) δ: 7.57 (1H, m), 7.83-7.87 (2H, m), 7.94 (1H, m), 8.53 (1H, dd, J=0.9, 7.9 Hz), 8.66 (1H, d, J=8.2 Hz), 8.76 (1H, m). Elemental Analysis for C$_{14}$H$_7$N$_2$OSF$_3$ Calcd. C, 54.54; H, 2.29; N, 9.09. Found C, 54.58; H, 2.14; N, 9.15.

Reference Example 18

6-[(4,4-Dimethoxybutyl)amino]nicotinenitrile

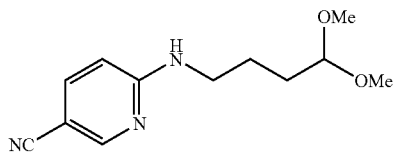

A mixture of 2-chloro-5-cyanopyridine (8.0 g, 57 mmol), 4-aminobutylaldehyde dimethylacetal (19.2 g, 144 mmol) and ethanol (120 ml) were refluxed for 15 hrs. The reaction mixture was concentrated, subjected to a column chromatography, eluted with hexane-ethyl acetate (1:1, v/v) and recrystallized from ethyl acetate-hexane to give the titled compound (11.8 g, 87%)

mp. 74.0-76.0° C. IR (KBr): 3358, 2949, 2216, 1606, 1518, 1371, 1130, 1070, 823 cm$^{-1}$. $^1$H-NMR (CDCl$_3$) δ: 1.70-1.72 (4H, m), 3.33 (6H, s), 3.36 (2H, m), 4.39 (1H, m), 5.21 (1H, br s), 6.36 (1H, d, J=8.8 Hz), 7.55 (1H, dd, J=2.2, 8.8 Hz), 8.35 (1H, d, J=2.2 Hz). Elemental Analysis for C$_{12}$H$_{17}$N$_3$O$_2$ Calcd. C, 61.26; H, 7.28; N, 17.86. Found C, 61.29; H, 6.98; N, 17.82.

Example 86

2-[6-[(4,4-Dimethoxybutyl)amino]-3-pyridyl]-4H-1,3-benzothiazine-4-one

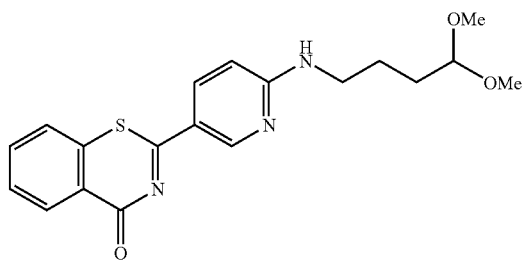

A mixture of 6-[(4,4-dimethoxybutyl)amino]nicotinenitrile (4.5 g, 19 mmol), methyl thiosalicylate (6.5 g, 38 mmol), triethylamine (6.0 ml, 43 mmol) and toluene (15 ml) was refluxed for 20 hrs. After cooling, the precipitated crystals were collected and recrystallized from tetrahydrofuran-hexane to give the titled compound (4.0 g, 56%).

mp. 157.2-158.5° C. IR (KBr): 3290, 2947, 1604, 1504, 1454, 1248, 1128, 1099, 1066, 744 cm$^{-1}$. $^1$H-NMR (CDCl$_3$) δ: 1.72-1.74 (4H, m), 3.34 (6H, s), 3.43 (2H, m), 4.41 (1H, m), 5.37 (1H, br s), 6.45 (1H, d, J=9.0 Hz), 7.49 (1H, dd, J=1.3, 7.7 Hz), 7.54-7.63 (2H, m), 8.28 (1H, dd, J=2.4, 9.0 Hz), 8.50 (1H, dd, J=1.7, 7.7 Hz), 8.93 (1H, d, J=2.4 Hz). Elemental Analysis for C$_{19}$H$_{21}$N$_3$O$_3$S Calcd. C, 61.44; H, 5.70; N, 11.31. Found C, 61.41; H, 5.90; N, 11.44.

Example 87

(tert-Butyl 3-[6-(6,8-dimethyl-4-oxo-4H-1,3-benzothiazin-2-yl)-2-pyridyl]propoxy)propanoate)

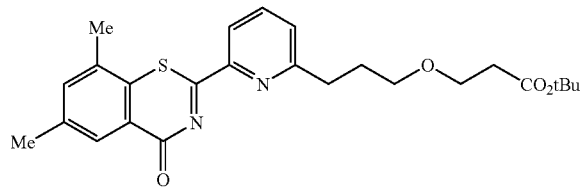

A mixture of 3,5-dimethylthiosalicylate (1.1 g, 6.1 mmol), tert-butyl 3-[3-(6-cyano-2-pyridyl)propoxy]propanoate (1.6 g, 5.5 mmol) and pyridine (10 ml) was stirred for 8 hrs. The reaction mixture was concentrated under reduced pressure. The residue was subjected to a silica gel column chromatography, eluted with hexane-ethyl acetate (2:1, v/v) and recrystallized from ethyl acetate-hexane to give the titled compound (1.4 g, 51%).

mp. 105.3-107.3° C. IR (KBr): 2974, 2930, 2868, 1730, 1659, 1537, 1454, 1365, 1323, 1159, 1115 cm$^{-1}$. $^1$H-NMR (CDCl$_3$) δ: 1.45 (9H, s), 2.12 (2H, tt, J=6.4, 7.5 Hz), 2.46 (3H, s), 2.50 (2H, t, J=6.4 Hz), 2.55 (3H, s), 2.99 (2H, t, J=7.5 Hz), 3.57 (2H, t, J=6.4 Hz), 3.70 (2H, t, J=6.4 Hz), 7.36 (1H, s), 7.38 (1H, d, J=7.5 Hz), 7.78 (1H, dd, J=7.5, 7.7 Hz), 8.26 (1H, s), 8.36 (1H, d, J=7.7 Hz). Elemental Analysis for C$_{25}$H$_{30}$N$_2$O$_4$S Calcd. C, 66.05; H, 6.65; N, 6.16. Found C, 66.06; H, 6.85; N, 6.12.

Example 88

[6-(6,8-Dimethyl-4-oxo-4H-1,3-benzothiazin-2-yl)-2-pyridyl]propoxy]propanoic acid

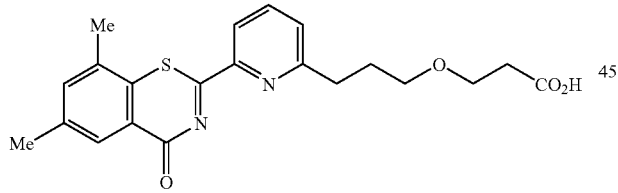

A mixture of tert-butyl 3-[6-(6,8-dimethoxy-4-oxo-4H-1,3-benzothiazin-2-yl)-2-pyridyl]propoxy]propanoate (1.1 g, 2.4 mmol) and trifluoroacetic acid (5 ml) was stirred under ice cooling condition for 3 hrs. The reaction mixture was concentrated. The residue was subjected to a silica gel column chromatography, eluted with ethyl acetate-methanol (10:1, v/v) and recrystallized from ethanol-hexane to give the titled compound (0.48 g, 49%).

mp. 156.5-157.1° C. IR (KBr): 2943, 2868, 1730, 1655, 1535, 1327, 1182, 1113, 993 cm$^{-1}$. $^1$H-NMR (CDCl$_3$) δ: 2.11 (2H, tt, J=6.2, 7.5 Hz), 2.43 (3H, s), 2.51 (3H, s), 2.63 (2H, t, J=6.2 Hz), 2.95 (2H, t, J=7.5 Hz), 3.57 (2H, t, J=6.2 Hz), 3.74 (2H, t, J=6.2 Hz), 7.33 (1H, s), 7.34 (1H, d, J=7.5 Hz), 7.76 (1H, dd, J=7.5, 7.7 Hz), 8.22 (1H, s), 8.34 (1H, d, J=7.7 Hz). Calcd. C, 61.90; H, 5.69; N, 6.87. Found C, 62.14; H, 5.48; N, 6.79.

Example 89

2-[2-(4-Methylthio)phenoxy-3-pyridyl]-4H-1,3-benzothiazine-4-one

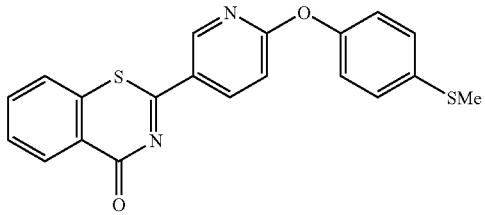

A mixture of methyl thiosalicylate (0.86 g, 5.1 mmol), 4-(4-methylthiophenoxy)benzonitrile (1.21 g, 5.0 mmol), triethylamine (1.00 ml, 7.2 mmol) and toluene (10 ml) was refluxed under nitrogen atmosphere for 16 hrs. The reaction mixture was concentrated, subjected to a silica gel column chromatography, eluted with ethyl acetate-hexane (2:1, v/v) and recrystallized from ethyl acetate-hexane to give the titled compound (0.21 g, 11%).

mp 140.5-140.6° C. IR (KBr): 1661, 1599, 1584, 1522, 1476, 1439, 1372, 1279, 1238, 1204, 1165, 1127, 1096, 1065, 1030, 1015, 924, 837, 745 cm$^{-1}$. $^1$H-NMR (CDCl$_3$) δ: 2.50 (3H, s), 6.94-7.02 (1H, m), 7.11 (2H, d, J=8.6 Hz), 7.33 (2H, d, J=8.6 Hz), 8.35-8.59 (2H, m), 8.93 (1H, d, J=2.5 Hz). Elemental Analysis for C$_{20}$H$_{14}$N$_2$O$_2$S$_2$ Calcd. C, 63.47; H, 3.73; N, 7.40. Found C, 63.20; H, 3.83; N, 7.43.

Example 90

2-[2-(4-Methyl)phenylthio-3-pyridyl]-4H-1,3-benzothiazine-4-one

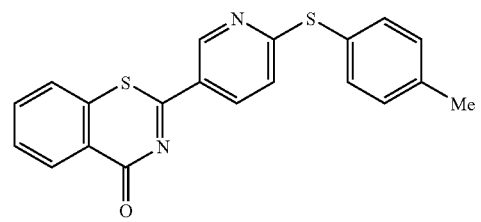

A mixture of methyl thiosalicylate (1.50 g, 8.9 mmol), 2-(4-methylphenylthio)-5-pyridinenitrile (2.00 g, 8.8 mmol), triethylamine (1.80 ml, 12.9 mmol) and toluene (10 ml) was refluxed under nitrogen atmosphere for 10 hrs. The reaction mixture was concentrated. The residue was combined with water and extracted with ethyl acetate. The extract was washed with water and dried. The solvent was evaporated. The residue was subjected to a silica gel column chromatography, eluted with ethyl acetate-hexane (3:1, v/v) and recrystallized from ethanol to give the titled compound (0.39 g, 12%).

mp 172.6-172.8° C. IR (KBr): 1661, 1578, 1516, 1448, 1360, 1289, 1238, 1111, 1096, 920 cm$^{-1}$. $^1$H-NMR (CDCl$_3$) δ: 2.40 (3H, s), 6.95 (1H, d, J=8.6 Hz), 7.25-7.74 (7H, m), 8.24 (1H, dt, J=2.0, 6.7 Hz), 8.51 (1H, d, J=7.6 Hz), 9.14 (1H, s). Elemental Analysis for C$_{20}$H$_{14}$N$_2$OS$_2$ Calcd. C, 66.27; H, 3.89; N, 7.73. Found C, 66.31; H, 3.86; N, 7.75.

Example 91

2-(6-Ethoxy-3-pyridyl)-4H-1,3-benzothiazine-4-one

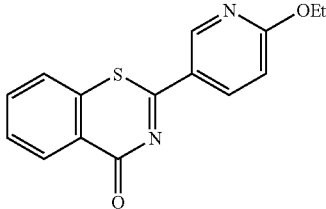

A mixture of methyl thiosalicylate (1.85 g, 11.0 mmol), 2-ethoxy-5-cyanopyridine (1.48 g, 10.0 mmol), triethylamine (1.80 ml, 12.9 mmol) and toluene (10 ml) was refluxed under nitrogen atmosphere for 18 hrs. The reaction mixture was concentrated. The residue was combined with water and extracted with ethyl acetate. The extract was washed with water and dried. The solvent was evaporated. The residue was subjected to a silica gel column chromatography, eluted with ethyl acetate-hexane (2:1, v/v) and recrystallized from chloroform-ethyl acetate to give the titled compound (0.56 g, 20%).

mp. 152.3-156.2° C. IR (KBr): 1661, 1601, 1572, 1526, 1497, 1439, 1399, 1383, 1348, 1285, 1258, 1246, 1125, 1101, 1034, 930, 835, 747 cm$^{-1}$. $^1$H-NMR (CDCl$_3$) δ: 1.42 (3H, t, J=7.1 Hz), 4.46 (2H, q, J=7.1 Hz), 6.83 (1H, d, J=8.6 Hz), 7.47-7.74 (3H, m), 8.39 (1H, dd, J=2.6, 8.9 Hz), 8.52 (1H, dd, J=1.7, 8.6 Hz), 8.96 (1H, d, J=2.6 Hz). Elemental Analysis for C$_{15}$H$_{12}$N$_2$O$_2$S Calcd. C, 63.36; H, 4.25; N, 9.85. Found C, 63.28; H, 4.15; N, 9.93.

Example 92

2-[6-(Isobutylthio)-3-pyridyl]-4H-1,3-benzothiazine-4-one

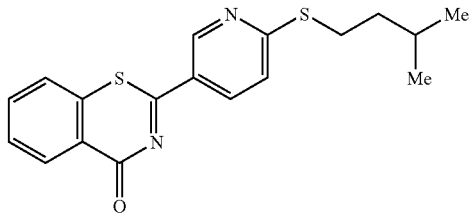

A mixture of methyl thiosalicylate (1.01 g, 6.0 mmol), 2-isobutylthio-5-cyanopyridine (1.03 g, 5.0 mmol), triethylamine (0.98 ml, 7.0 mmol) and toluene (10 ml) was refluxed under nitrogen atmosphere for 20 hrs. The reaction mixture was concentrated. The residue was subjected to a silica gel column chromatography, eluted with ethyl acetate-hexane (2:1, v/v) and recrystallized from ethyl acetate-isopropylether to give the titled compound (0.40 g, 23%).

mp. 92.8-93.1° C. IR (KBr): 1661, 1582, 1578, 1541, 1514, 1458, 1358, 1289, 1240, 1113, 1096, 1063, 1030, 922, 739 cm$^{-1}$. $^1$H-NMR (CDCl$_3$) δ: 0.95 (3H, s), 0.97 (3H, s), 1.56-1.86 (3H, m), 3.24 (2H, t, J=7.6 Hz), 7.27 (1H, d, J=9.4 Hz), 7.46-7.68 (3H, m), 8.26 (1H, dd, J=2.3, 8.6 Hz), 8.52 (1H, dd, J=1.4, 7.7 Hz), 9.16 (1H, d, J=2.3 Hz). Calcd. C, 63.13; H, 5.30; N, 8.18. Found C, 63.11; H, 5.13; N, 8.24.

Example 93

2-[6-Isopropoxy-3-pyridyl]-4H-1,3-benzothiazine-4-one

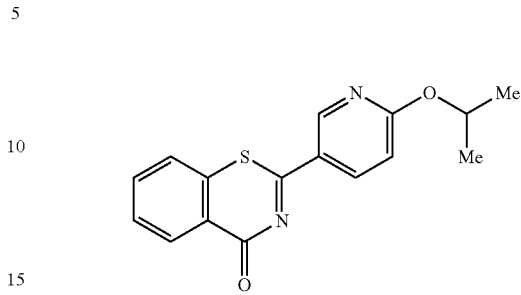

A mixture of methyl thiosalicylate (1.85 g, 11.0 mmol), 2-isopropoxy-5-cyanopyridine (1.62 g, 10.0 mmol), triethylamine (1.80 ml, 12.9 mmol) and toluene (10 ml) was refluxed under nitrogen atmosphere for 30 hrs. The reaction mixture was concentrated. The residue was subjected to a silica gel column chromatography, eluted with ethyl acetate-hexane (2:1, v/v) and recrystallized from ethyl acetate-isopropylether to give the titled compound (0.89 g, 30%).

mp. 109.7-110.4° C. IR (KBr): 1663, 1595, 1570, 1522, 1487, 1381, 1285, 1238, 1096, 1063, 1030, 947, 922, 837, 745 cm$^{-1}$. $^1$H-NMR (CDCl$_3$) δ: 1.37 (3H, s), 1.39 (3H, s), 5.38-5.47 (1H, m), 6.78 (1H, d), 7.43 (3H, m), 8.38 (1H, dd, J=2.5, 8.8 Hz), 8.52 (1H, d, J=7.6 Hz), 8.96 (1H, d, J=2.5 Hz). Elemental Analysis for C$_{16}$H$_{14}$N$_2$O$_2$S Calcd. C, 64.41; H, 4.73; N, 9.39. Found C, 64.26; H, 4.70; N, 9.26.

Example 94

2-[6-(2-Ethoxyethoxy)-3-pyridyl]-4H-1,3-benzothiazine-4-one

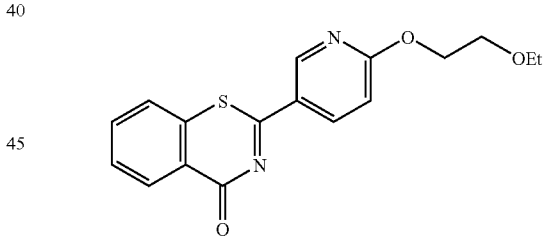

A mixture of methyl thiosalicylate (2.96 g, 17.6 mmol), 5-cyano-2-(2-ethoxy)ethoxypyridine (3.07 g, 16.0 mmol), triethylamine (2.37 ml, 17.0 mmol) and toluene (15 ml) was refluxed under nitrogen atmosphere for 40 hrs. The reaction mixture was concentrated. The residue was subjected to a silica gel column chromatography, eluted with ethyl acetate-hexane (1:1, v/v) and recrystallized from acetone-ethyl acetate-isopropylether to give the titled compound (3.01 g, 57%).

mp. 93.6-94.9° C. IR (KBr): 1661, 1597, 1522, 1487, 1391, 1287, 1238, 1125, 1098, 1046, 914, 839, 745 cm$^{-1}$. $^1$H-NMR (CDCl$_3$) δ: 1.24 (3H, t, J=7.1 Hz), 3.60 (2H, q, J=7.1 Hz), 3.72-3.88 (2H, m), 4.50-4.64 (2H, m), 6.91 (1H, d, J=8.9 Hz), 7.42-7.69 (3H, m), 8.39 (1H, dd, J=2.4, 8.9 Hz), 8.52 (1H, d, J=7.6 Hz), 8.96 (1H, s). Elemental Analysis for C$_{17}$H$_{16}$N$_2$O$_3$S Calcd. C, 62.18; H, 4.91; N, 8.53. Found C, 62.22; H, 4.91; N, 8.56.

Example 95

2-[2-[[5-(4-Oxo-4H-1,3-benzothiazin-2-yl)-2-pyridyl]oxy]-1H-isoindole-1,3(2H)-dione

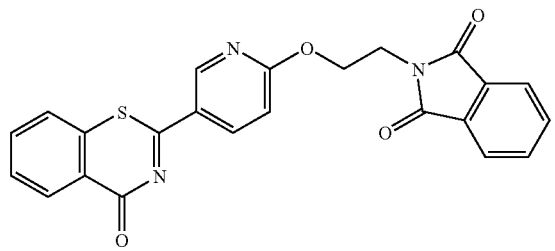

A mixture of methyl thiosalicylate (2.75 g, 16.4 mmol), 5-cyano-2-(2-succinimido)ethoxypyridine (4.00 g, 13.6 mmol), triethylamine (2.51 ml, 18.0 mmol) and toluene (20 ml) was refluxed under nitrogen atmosphere for 36 hrs. The reaction mixture was cooled, and the precipitated crystals (4.15 g) were collected by filtration and recrystallized from chloroform-methanol to give the titled compound (3.64 g, 62%)

mp. 212.4-212.6° C. IR (KBr): 1773, 1713, 1661, 1597, 1522, 1487, 1391, 1285, 1240, 1127, 1098, 1019, 912, 839, 745 cm$^{-1}$. $^1$H-NMR (CDCl$_3$) δ: 4.13 (2H, t, J=5.1 Hz), 4.70 (2H, t, J=5.1 Hz), 6.81 (1H, d, J=8.8 Hz), 7.42-7.89 (11H, m), 8.36 (1H, d, J=2.5 Hz), 8.51 (1H, d, J=7.9 Hz), 8.88 (1H, s). Elemental Analysis for C$_{23}$H$_{15}$N$_3$O$_4$S Calcd. C, 64.33; H, 3.52; N, 9.78. Found C, 63.19; H, 3.51; N, 9.65.

Example 96

Ethyl 6-{[5-(4-oxo-4H-1,3-benzothiazin-2-yl)-2-pyridyl]oxy}hexanoate

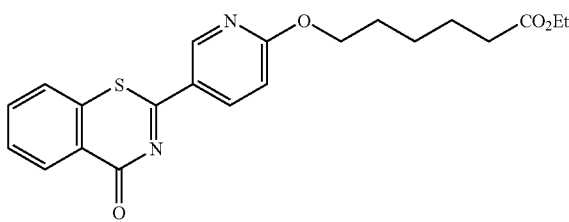

A mixture of methyl thiosalicylate (0.71 g, 4.2 mmol), ethyl 6-(5-cyanopyridin-2-yl)oxyhexanoate (1.00 g, 3.8 mmol), triethylamine (0.63 ml, 4.5 mmol) and toluene (12 ml) was refluxed under nitrogen atmosphere for 30 hrs. The reaction mixture was concentrated. The residue was subjected to a silica gel column chromatography, eluted with ethyl acetate-hexane (2:1, v/v) and recrystallized from ethyl acetate-isopropylether to give the titled compound (0.22 g, 14%).

mp. 73.6-73.9° C. IR (KBr): 1730, 1665, 1597, 1572, 1524, 1489, 1439, 1396, 1370, 1287, 1238, 1098, 1030, 922, 746 cm$^{-1}$. $^1$H-NMR (CDCl$_3$) δ: 1.25 (3H, t, J=7.1 Hz), 1.37-1.88 (6H, m), 2.33 (2H, t, J=7.4 Hz), 4.13 (2H, q, J=7.1 Hz), 4.40 (2H, t, J=6.6 Hz), 6.83 (1H, d, J=8.8 Hz), 7.36-7.64 (3H, m), 8.40 (1H, dd, J=2.6, 8.8 Hz), 8.52 (1H, dd, J=1.7, 7.7 Hz), 8.96 (1H, d, J=2.6 Hz). Elemental Analysis for C$_{21}$H$_{22}$N$_2$O$_4$S Calcd. C, 63.30; H, 5.56; N, 7.03. Found C, 63.21; H, 5.54; N, 7.10.

Example 97

Ethyl 2-{[5-(4-oxo-4H-1,3-benzothiazin-2-yl)-2-pyridyl]thio}propionate

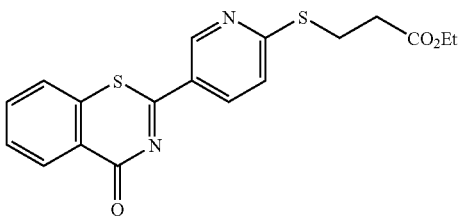

A mixture of methyl thiosalicylate (0.84 g, 5.0 mmol), ethyl 3-[2-(5-cyanopyridin-2-yl)thio]propionate (1.18 g, 5.0 mmol), triethylamine (0.84 ml, 6.0 mmol) and toluene (10 ml) was refluxed under nitrogen atmosphere for 15 hrs. The reaction mixture was diluted with ethyl acetate, washed with water, dried and concentrated under reduced pressure. The residue was subjected to a silica gel column chromatography, eluted with hexane-ethyl acetate (2:1, v/v) and recrystallized from ethyl acetate-isopropylether to give the titled compound (0.71 g, 38%).

mp. 115.7-116.0° C. IR (KBr): 1730, 1661, 1582, 1541, 1516, 1460, 1358, 1291, 1240, 1113, 1096, 1063, 1030, 922, 748, 739 cm$^{-1}$. $^1$H-NMR (CDCl$_3$) δ: 1.27 (3H, t, J=7.1 Hz), 2.80 (2H, t, J=7.0 Hz), 3.50 (2H, t, J=7.0 Hz), 4.18 (2H, q, J=7.1 Hz), 7.18-7.26 (1H, m), 7.44-7.65 (3H, m), 8.27 (1H, dd, J=2.5, 8.6 Hz), 8.53 (1H, dd, J=1.5, 7.6 Hz), 9.16 (1H, dd, J=0.6, 2.5 Hz). Elemental Analysis for C$_{18}$H$_{16}$N$_2$O$_3$S$_2$ Calcd. C, 58.04; H, 4.33; N, 7.52. Found C, 57.88; H, 4.04; N, 7.44.

Example 98 tert-Butyl 3-{3-[6-(4-oxo-4H-1,3-benzothiazin-2-yl)-3-pyridyl]propoxy}propanoate

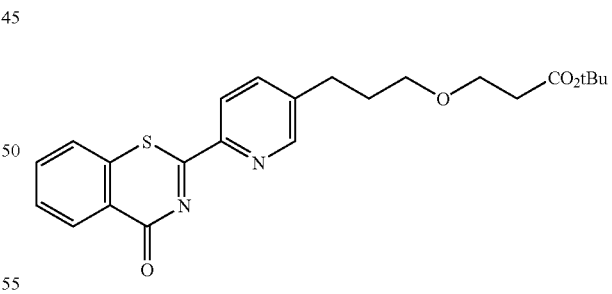

A mixture of methyl thiosalicylate (2.80 g, 16.6 mmol), a mixture of tert-butyl 3-[(2-cyanopyridin-3-yl)propoxy]propionate and tert-butyl 3-[(2-cyanopyridin-5-yl)propoxy]propionate (ca. 9:1, 4.55 g, 15.7 mmol), triethylamine (2.02 g, 20 mmol) and toluene (20 ml) was refluxed under nitrogen atmosphere for 20 hrs. The reaction mixture was concentrated under reduced pressure. The residue was subjected to a silica gel column chromatography, eluted with ethyl acetate-hexane (2:1, v/v) to give the titled compound (1.10 g, 16%).

$^1$H-NMR (CDCl$_3$) δ: 1.46 (9H, s), 1.85-1.98 (2H, m), 2.49 (2H, t, J=6.3 Hz), 2.81 (2H, t, J=7.6 Hz), 3.47 (2H, t, J=6.0

Hz), 3.67 (2H, t, J=6.3 Hz), 7.45-7.72 (4H, m), 8.46 (1H, d, J=8.0 Hz), 8.54 (1H, d, J=8.0 Hz), 8.56 (1H, s)

Example 99

3-{3-[6-(4-Oxo-4H-1,3-benzothiazin-2-yl)-3-pyridyl]propoxy}propionic acid

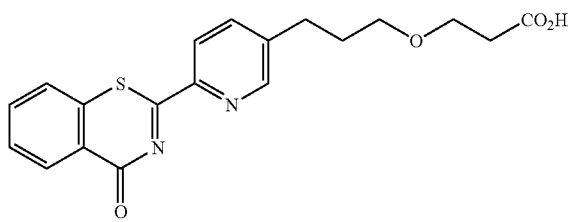

tert-Butyl 3-{3-[6-(4-oxo-4H-1,3-benzothiazin-2-yl)-3-pyridyl]propoxy}propanoate (1.0 g, 2.3 mmol) and trifluoroacetic acid (4.0 ml) was stirred under ice cooling condition for 5 hrs. The reaction mixture was concentrated under reduced pressure, diluted with chloroform, washed with water and dried. The solvent was evaporated. The residue was subjected to a silica gel column chromatography, eluted with ethyl acetate-methanol (20:1, v/v) and recrystallized from chloroform-ethyl acetate to give the titled compound (0.55 g, 66%).

mp. 145.2-146.6° C. IR (KBr): 3007, 2924, 2884, 1725, 1638, 1566, 1526, 1431, 1316, 1287, 1248, 1202, 1113, 1065, 1030, 945, 860, 748 cm$^{-1}$. $^1$H-NMR (DMSO-d$_6$) δ: 1.84 (2H, t, J=6.9 Hz), 2.44 (2H, t, J=6.2 Hz), 2.75 (2H, t, J=7.5 Hz), 3.38 (2H, t, J=6.1 Hz), 3.57 (2H, t, J=6.2 Hz), 7.58-7.91 (4H, m), 8.25 (1H, d, J=8.1 Hz), 8.33 (1H, d, J=7.9 Hz), 8.63 (1H, s), 12.13 (1H, s). Elemental Analysis for C$_{19}$H$_{18}$N$_2$O$_4$S.0.5 H$_2$O Calcd. C, 60.14; H, 5.05; N, 7.38. Found C, 60.37; H, 4.95; N, 7.27.

Reference Example 19

3-[(6-Cyano-2-pyridyl)oxy]-N,N-dimethylaminomethylene-2,2-dimethyl-1-propanesulfonamide

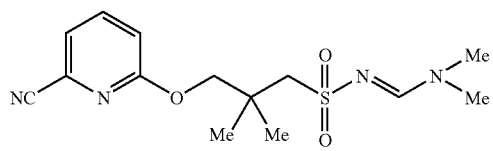

Sodium hydride (60% oil, 0.26 g, 6.5 mmol) was suspended in tetrahydrofuran (10 ml), and to the mixture, a solution of 2,2-dimethyl-3-hydroxy-1-propane-N,N-dimethylaminomethylene sulfonamide produced in accordance with M. Kuwahara et al.'s method (Chemical and Pharmaceutical Bulletin, Vol. 44, pp. 122-131, 1996) (1.34 g, 6.0 mmol) in tetrahydrofuran (15 ml) was added dropwise with stirring under ice cooling condition. The reaction mixture was stirred at the same temperature for 10 minutes. 2-Chloro-6-cyanopyridine (0.69 g, 5.0 mmol) was added to the reaction mixture. The reaction mixture was refluxed for 3 hrs, poured into ice water and extracted with ethyl acetate. The extract was washed with water and dried. The solvent was evaporated under reduced pressure. The residue was ground by isopropylether and collected by filtration to give the titled compound (1.60 g, 99%).

IR (KBr): 2236, 1628, 1447, 1335, 1271, 1208, 1117, 1022, 910, 860, 847, 810 cm$^{-1}$. $^1$H-NMR (CDCl$_3$) δ: 1.28 (6H, s), 2.99 (3H, s), 3.10 (3H, s), 3.19 (2H, s), 4.23 (2H, s), 6.98 (1H, d, J=8.4 Hz), 7.29 (1H, dd, J=0.6, 7.2 Hz), 7.66 (1H, dd, J=7.4, 8.5 Hz), 8.02 (1H, s)

Example 100

N,N-(Dimethylaminomethylene)-2,2-dimethyl-3-{[6-(4-oxo-4H-1,3-benzothiazin-2-yl)-2-pyridyl]oxy}-1-propanesulfonamide

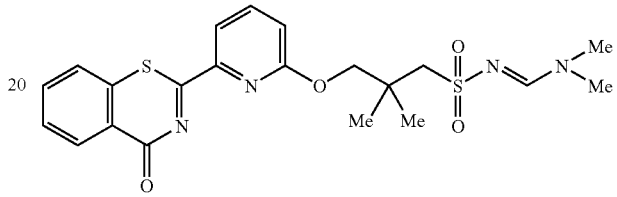

A mixture of methyl thiosalicylate (0.87 g, 5.2 mmol), 3-[(6-cyano-2-pyridyl)oxy]-N,N-dimethylaminomethylene-2,2-dimethyl-1-propanesulfonamide (1.32 g, 4.1 mmol), triethylamine (0.61 g, 6.0 mmol) and toluene (15 ml) was refluxed with stirring for 20 hrs. The reaction mixture was concentrated under reduced pressure. The residue was subjected to a silica gel column chromatography, eluted with ethyl acetate-methanol (20:1, v/v) and recrystallized from ethyl acetate to give the titled compound (0.90 g, 48%).

mp. 174.5-175.3° C. IR (KBr): 1651, 1638, 1574, 1537, 1454, 1337, 1271, 1240, 1123, 1040, 988, 910, 858, 847, 812, 729 cm$^{-1}$. $^1$H-NMR (CDCl$_3$) δ: 1.36 (6H, s), 2.89 (3H, s), 3.03 (3H, s), 3.27 (2H, s), 4.39 (2H, s), 6.99 (1H, dd, J=0.6, 8.3 Hz), 7.59-7.65 (3H, m), 7.76 (1H, dd, J=7.5, 8.2 Hz), 8.02 (1H, s), 8.13 (1H, dd, J=0.6, 7.5 Hz), 8.54 (1H, dd, J=1.4, 9.0 Hz). Elemental Analysis for C$_{21}$H$_{24}$N$_4$O$_4$S$_2$ Calcd. C, 54.76; H, 5.25; N, 12.16. Found C, 54.44; H, 5.22; N, 12.12.

Reference Example 20 tert-Butyl 3-[3-(4-pyridyl)propoxy]propanoate

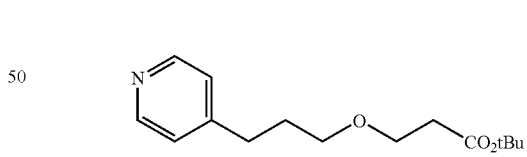

Triton B (40% methanol solution, 0.5 ml) was concentrated under reduced pressure, and 4-pyridinepropanol (10.2 g, 74.5 mmol) was added thereto. After 15 minutes, tert-butyl acrylate (9.59 g, 74.8 mmol) was added to the mixture, and the mixture was stirred at room temperature for 6 hrs. The reaction mixture was subjected to a silica gel column chromatography, eluted with hexane-ethyl acetate (1:1, v/v) to give the titled compound (17.1 g, 86%).

IR (KBr): 2978, 2868, 1730, 1603, 1556, 1159, 1113, 991 cm$^{-1}$. $^1$H-NMR (CDCl$_3$) δ: 1.46 (9H, s), 1.85-1.91 (2H, m), 2.49 (2H, t, J=6.3 Hz), 2.68 (2H, t, J=7.4 Hz), 3.44 (2H, t, J=6.2 Hz), 3.66 (2H, t, J=6.4 Hz), 7.12 (2H, d, J=5.7 Hz), 8.49 (2H, d, J=5.7 Hz).

Reference Example 21 tert-Butyl 3-[3-(4-pyridyl)propoxy]propanoate N-oxide

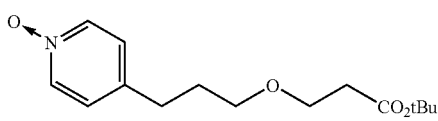

tert-Butyl 3-[3-(4-pyridyl)propoxy]propanoate (16.5 g, 62.2 mmol) was dissolved in ethyl acetate (50 ml). 3-Chloroperbenzoic acid (ca. 77%, 14.6 g, 65.2 mmol) was added to the mixture at room temperature. The reaction mixture was stirred for 23 hrs, subjected to a silica gel column chromatography and eluted with hexane-ethyl acetate (2:1, v/v) to give the titled compound (16.9 g, 96%) as an oil.

IR (KBr): 3584, 2934, 1732, 1714, 1487, 1454, 1234, 1157 cm$^{-1}$. $^1$H-NMR (CDCl$_3$) δ: 1.46 (9H, s), 1.85-1.91 (2H, m), 2.48 (2H, t, J=6.2 Hz), 2.71 (2H, t, J=7.4 Hz), 3.44 (2H, t, J=5.6 Hz), 3.66 (2H, t, J=6.2 Hz), 7.15 (2H, d, J=6.8 Hz), 8.14 (2H, d, J=6.8 Hz).

Reference Example 22 tert-Butyl 3-[3-[2-cyano-4-pyridyl]propoxy]propanoate

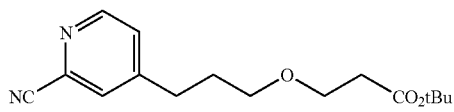

tert-Butyl 3-[3-(4-pyridyl)propoxy]propanoate N-oxide (16.0 g, 56.9 mmol) and trimethylsilyl anilide (12.4 g, 125.1 mmol) were dissolved in nitroethane (50 ml). N,N-Dimethylcarbamoyl chloride (12.8 g, 119.4 mmol) was added dropwise to the mixture. The reaction mixture was stirred at room temperature for 18 hrs and combined with saturated aqueous sodium hydrogen carbonate solution. The organic layer was separated, dried and concentrated. The residue was subjected to a silica gel column chromatography, eluted with hexane-ethyl acetate (2:1, v/v) to give the titled compound (16.2 g, 98%) as an oil.

IR (KBr): 2235, 1730, 1597, 1554, 1367, 1159, 1114 cm$^{-1}$. $^1$H-NMR (CDCl$_3$) δ: 1.47 (9H, s), 1.87-1.96 (2H, m), 2.49 (2H, t, J=6.3 Hz), 2.79 (2H, t, J=7.3 Hz), 3.46 (2H, t, J=6.0 Hz), 3.67 (2H, t, J=6.3 Hz), 7.40 (1H, d, J=5.0 Hz), 7.58 (1H, s), 8.59 (1H, d, J=5.0 Hz).

Example 101 tert-Butyl 3-[3-[2-(4-oxo-4H-1,3-benzothiazin-2-yl)-4-pyridyl]propoxy]propanoate

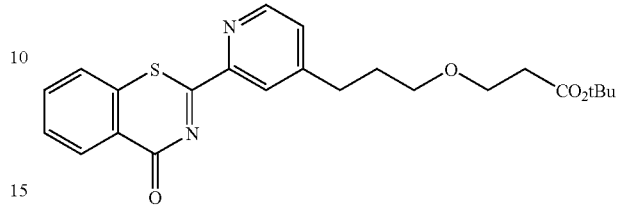

A mixture of methyl thiosalicylate (7.4 g, 43.8 mmol), tert-butyl 3-[3-[2-cyano-4-pyridyl]propoxy]propanoate (14.0 g, 48.2 mmol), triethylamine (7.1 g, 70.2 mmol) and toluene (37 ml) was refluxed under nitrogen atmosphere for 24 hrs. The reaction mixture was concentrated under reduced pressure, subjected to a column chromatography and eluted with ethyl acetate-hexane (3:2, v/v) to give the titled compound (17.7 g, 86%).

mp. 81.1-82.2° C. IR (KBr): 1728, 1664, 1572, 1537, 1366, 1281, 1159, 1115, 1096 cm$^{-1}$. $^1$H-NMR (CDCl$_3$) δ: 1.46 (9H, s), 1.92-1.97 (2H, m), 2.50 (2H, t, J=6.4 Hz), 2.82 (2H, t, J=7.5 Hz), 3.46 (2H, t, J=6.1 Hz), 3.67 (2H, t, J=6.4 Hz), 7.39 (1H, m), 7.60-7.69 (3H, m), 8.42 (1H, s), 8.56 (1H, d, J=6.7 Hz), 8.62 (1H, d, J=4.9 Hz). Elemental Analysis for C$_{23}$H$_{26}$N$_2$O$_4$S Calcd. C, 64.77; H, 6.14; N, 6.57. Found C, 64.70; H, 6.03; N, 6.44.

Example 102

3-[3-[2-(4-Oxo-4H-1,3-benzothiazin-2-yl)-4-pyridyl]propoxy]propanoic acid

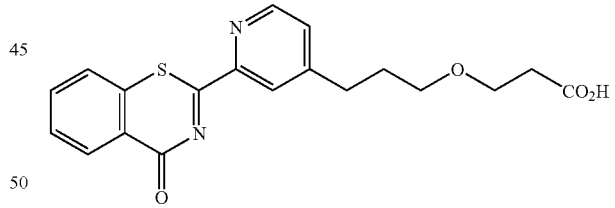

A mixture of tert-butyl 3-[3-[2-(4-oxo-4H-1,3-benzothiazin-2-yl)-4-pyridyl]propoxy]propanoate (3.9 g, 9.1 mmol) and trifluoroacetic acid (30 ml) was stirred at room temperature for 1.5 hrs. The reaction mixture was concentrated under reduced pressure to obtain crystals which were collected by filtration and recrystallized from chloroform to give the titled compound (3.0 g, 89%).

mp. 153.8-153.9° C. IR (KBr): 1732, 1714, 1661, 1570, 1537, 1470, 1441, 1283, 1100 cm$^{-1}$. $^1$H-NMR (CDCl$_3$) δ: 1.94 (2H, m), 2.65 (2H, t, J=5.7 Hz), 2.88 (2H, t, J=6.6 Hz), 3.39 (2H, t, J=5.8 Hz), 3.76 (2H, t, J=5.5 Hz), 7.36 (1H, m), 7.63-7.72 (3H, m), 8.39 (1H, s), 8.56-8.62 (2H, m). Elemental Analysis for C$_{19}$H$_{18}$N$_2$O$_4$S Calcd. C, 61.61; H, 4.90; N, 7.56. Found C, 61.31; H, 4.79; N, 7.45.

Example 103

N-Butyl-N-methyl-6-(4-oxo-4H-1,3-benzothiazin-2-yl)-2-pyridinecarboxamide

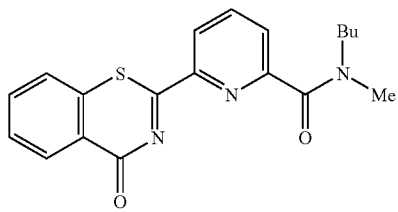

A mixture of N-butyl-N-methyl-6-(4-oxo-4H-1,3-benzothiazin-2-yl)-2-pyridinecarboxylic acid (0.45 g, 1.6 mmol), N-methylbutylamine (0.31 g, 3.5 mmol), WSC (0.63 g, 3.2 mmol), HOBt (0.44 g, 3.2 mmol) and DMF (10 ml) was stirred at 80° C. for 15 hrs. The reaction mixture was diluted and extracted with ethyl acetate. The extract was washed with water and dried. The solvent was evaporated. The residue was subjected to a silica gel column chromatography, eluted with ethyl acetate-hexane (3:2, v/v) and recrystallized from ethyl acetate-hexane to give the titled compound (0.42 g, 75%).

mp. 80.0-81.6° C. IR (KBr): 2955, 1666, 1633, 1572, 1537, 1439, 1300, 1095, 748 cm$^{-1}$. $^1$H-NMR (CDCl$_3$) δ: 0.85 (1.5H, t, J=7.3 Hz), 1.02 (1.5H, t, J=7.3 Hz), 1.23 (1H, m), 1.47 (1H, m), 1.71-1.80 (2H, m), 3.18 (1.5H, s), 3.23 (1.5H, s), 3.46 (1H, m), 3.63 (1H, m), 7.61-7.70 (3H, m), 7.87-8.04 (2H, m), 8.55-8.60 (2H, m) Elemental Analysis for C$_{19}$H$_{19}$N$_3$O$_2$S.0.75H$_2$O Calcd. C, 62.19; H, 5.63; N, 11.45. Found C, 62.37; H, 5.38; N, 11.70.

Example 104

2-[6-(1-Pyrrolidinylcarbonyl)-4H-1,3-benzothiazine-4-one

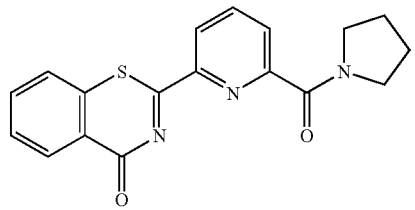

A mixture of N-butyl-N-methyl-6-(4-oxo-4H-1,3-benzothiazin-2-yl)-2-pyridinecarboxylic acid (0.45 g, 1.6 mmol), pyrrolidine (0.30 g, 4.1 mmol), WSC (0.62 g, 3.2 mmol), HOBt (0.43 g, 3.1 mmol) and DMF (10 ml) was stirred at 80° C. for 15 hrs. After cooling, the precipitates were collected by filtration, subjected to a silica gel column chromatography, eluted with ethyl acetate-methanol (3:1, v/v) and recrystallized from chlorobenzene-hexane to give the titled compound (0.28 g, 51%).

mp. 232.0-234.0° C. IR (KBr): 3493, 2970, 1660, 1622, 1572, 1537, 1421, 1302, 1097, 758 cm$^{-1}$. $^1$H-NMR (CDCl$_3$) δ: 1.95-2.09 (4H, m), 3.77 (2H, t, J=6.5 Hz), 4.03 (2H, t, J=6.5 Hz), 7.61-7.73 (3H, m), 8.03 (1H, m), 8.21 (1H, m), 8.54-8.61 (2H, m). Elemental Analysis for C$_{18}$H$_{15}$N$_3$O$_2$S Calcd. C, 64.08; H, 4.48; N, 12.45. Found C, 64.03; H, 4.38; N, 12.39.

Example 105

N,N-Diethyl-6-(4-oxo-4H-1,3-benzothiazin-2-yl)-2-pyridinecarboxamide

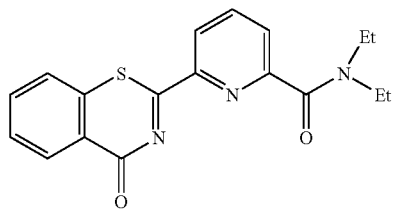

A mixture of N-butyl-N-methyl-6-(4-oxo-4H-1,3-benzothiazin-2-yl)-2-pyridinecarboxylic acid (0.45 g, 1.6 mmol), diethylamine (0.50 g, 6.8 mmol), WSC (0.62 g, 3.2 mmol), HOBt (0.43 g, 3.1 mmol) and DMF (10 ml) was stirred at 80° C. for 15 hrs. The reaction mixture was diluted with water and extracted with ethyl acetate. The extract was washed with water and dried. The solvent was evaporated. The residue was subjected to a silica gel column chromatography, eluted with ethyl acetate-hexane (2:1, v/v) and recrystallized from tetrahydrofuran-hexane to give the titled compound (0.37 g, 69%)

mp. 194.0-194.3° C. IR (KBr): 2970, 1664, 1633, 1572, 1537, 1439, 1300, 1236, 1097, 742 cm$^{-1}$. $^1$H-NMR (CDCl$_3$) δ: 1.33 (3H, t, J=7.1 Hz), 1.33 (3H, t, J=7.0 Hz), 3.51 (2H, q, J=7.0 Hz), 3.64 (2H, q, J=7.1 Hz), 7.62-7.70 (3H, m), 7.89 (1H, dd, J=1.1, 7.7 Hz), 8.01 (1H, m), 8.54-8.59 (2H, m). Elemental Analysis for C$_{18}$H$_{17}$N$_3$O$_2$S Calcd. C, 63.70; H, 5.05; N, 12.38. Found C, 63.70; H, 4.93; N, 12.40.

Example 106 tert-Butyl [[[6-(4-oxo-4H-1,3-benzothiazin-2-yl)-2-pyridyl]carbonyl]amino]hexylcarbamate A mixture of N-butyl-N-methyl-6-(4-oxo-4H-1,3-benzothiazin-2-yl)-2-pyridinecarboxylic acid (0.68 g, 2.3 mmol), tert-butyl N-(6-aminohexyl)carbamate (0.83 g, 3.8 mmol), WSC (0.92 g, 4.8 mmol), HOBt (0.65 g, 4.8 mmol) and DMF (15 ml) was stirred at 80° C. for 24 hrs. The reaction mixture was diluted with water and extracted with ethyl acetate. The extract was washed with water and dried. The solvent was evaporated. The residue was subjected to a silica gel column chromatography, eluted with ethyl acetate-hexane (3:1, v/v) and recrystallized from tetrahydrofuran-hexane to give the titled compound (0.70 g, 60%).

mp. 145.1-145.4° C. IR (KBr): 3350, 2932, 2858, 1693, 1680, 1666, 1572, 1537, 1440, 1302, 1248, 1170, 1097, 746, 733 cm$^{-1}$. $^1$H-NMR (CDCl$_3$) δ: 1.43 (9H, s), 1.43-1.56 (6H, m), 1.74 (2H, m), 3.14 (2H, m), 3.57 (2H, m), 4.55 (1H, br s), 7.65-7.73 (3H, m), 7.93 (1H, m), 8.08 (1H, m), 8.44 (1H, m), 8.57 (1H, m), 8.65 (1H, dd, J=0.6, 7.8 Hz). Elemental Analysis for $C_{25}H_{30}N_4O_4S$ Calcd. C, 62.22; H, 6.27; N, 11.61. Found C, 62.23; H, 6.39; N, 11.74.

Example 107

N-(6-Aminohexyl)-6-(4-oxo-4H-1,3-benzothiazin-2-yl)-2-pyridinecarboxamide hydrochloride

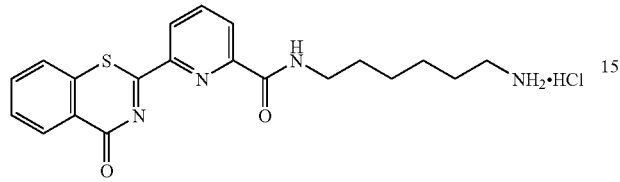

tert-Butyl [[[6-(4-oxo-4H-1,3-benzothiazin-2-yl)-2-pyridyl]carbonyl]amino]hexylcarbamate (0.30 g, 0.62 mmol) was dissolved in ethyl acetate (15 ml), and a solution of 4 N hydrochloric acid in ethyl acetate (2.0 ml, 8.0 mmol) was added thereto under ice cooling condition. The reaction mixture was stirred at the same temperature for 3 hrs. The precipitated crystals were collected by filtration and recrystallized from methanol-diethyl ether to give the titled compound (0.15 g, 56%)

mp. 95.2-97.6° C. IR (KBr): 3072, 2964, 1662, 1570, 1529, 1439, 1298, 1238, 1095, 748 cm$^{-1}$. $^1$H-NMR (DMSO-d$_6$) δ: 1.37-1.39 (4H, m), 1.60-1.63 (4H, m), 2.77 (2H, m), 3.41 (2H, m), 7.75 (1H, m), 7.84-7.92 (2H, m), 7.97 (3H, br s), 8.25-8.32 (2H, m), 8.39 (1H, d, J=8.1 Hz), 8.51 (1H, dd, J=2.3, 6.5 Hz), 8.63 (1H, t, J=6.0 Hz). Elemental Analysis for $C_{20}H_{23}N_4O_2SCl.H_2O$ Calcd. C, 54.97; H, 5.77; N, 12.82. Found C, 55.10; H, 6.19; N, 12.99.

Reference Example 23 tert-Butyl methyl(2-pyridyl)carbamate N-oxide

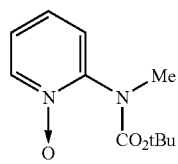

A mixture of tert-butyl methyl (2-pyridyl)carbamate (14.4 g, 69 mmol), 3-chloroperbenzoic acid (ca. 77%, 20.0 g, 89 mmol) and ethyl acetate (200 ml) was stirred at room temperature for 48 hrs. The reaction mixture was concentrated under reduced pressure, subjected to a silica gel column chromatography and eluted with ethyl acetate-methanol (10:1, v/v) to give the titled compound (14.1 g, 91%)

$^1$H-NMR (CDCl$_3$) δ: 1.41 (9H, s), 3.18 (3H, s), 7.14-7.30 (3H, m) 8.24 (1H, m).

Reference Example 24 tert-Butyl 6-cyano-2-pyridylmethylcarbamate

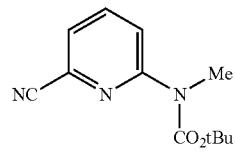

A mixture of tert-butyl methyl(2-pyridyl)carbamate N-oxide (14.1 g, 63 mmol), trimethylsilyl cyanide (12.5 g, 126 mmol), N,N-dimethylcarbamoyl chloride (13.5 g, 125 mmol) and nitroethane (120 ml) was stirred at room temperature for 48 hrs. The reaction mixture was concentrated under reduced pressure. The residue was subjected to a silica gel column chromatography, eluted with hexane-ethyl acetate (10:1, v/v) and recrystallized from ethyl acetate-hexane to give the titled compound (11.3 g, 77%).

mp. 96.4-96.6° C. IR (KBr): 2980, 2231, 1709, 1591, 1346, 1294, 1161, 808 cm$^{-1}$. $^1$H-NMR (CDCl$_3$) δ: 1.54 (9H, s), 3.42 (3H, s), 7.36 (1H, d, J=7.2 Hz), 7.70 (1H, dd, J=7.2, 8.7 Hz), 8.11 (1H, d, J=8.7 Hz). Elemental Analysis for $C_{12}H_{15}N_3O_2$ Calcd. C, 61.79; H, 6.48; N, 18.01. Found C, 61.81; H, 6.29; N, 18.12.

Example 108 tert-Butyl methyl[6-(4-oxo-4H-1,3-benzothiazin-2-yl)-2-pyridyl]carbamate

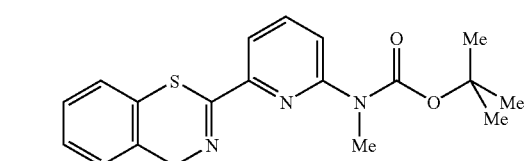

A mixture of methyl thiosalicylate (3.8 g, 22 mmol), tert-butyl 6-cyano-2-pyridylmethylcarbamate (3.5 g, 15 mmol), triethylamine (4.0 ml, 28 mmol) and toluene (10 ml) was refluxed for 14 hrs. After cooling, the precipitated crystals were collected by filtration and recrystallized from tetrahydrofuran-hexane to give the titled compound (4.6 g, 82%).

mp. 195.6-196.3° C. IR (KBr): 2972, 1703, 1651, 1574, 1537, 1344, 1153, 731 cm$^{-1}$. $^1$H-NMR (CDCl$_3$) δ: 1.57 (9H, s), 3.57 (3H, s), 7.58-7.68 (3H, m), 7.81 (1H, m), 8.10 (1H, d, J=8.4 Hz), 8.21 (1H, d, J=7.5 Hz), 8.55 (1H, m). Elemental Analysis for $C_{19}H_{19}N_3O_3S$ Calcd. C, 61.77; H, 5.18; N, 11.37. Found C, 61.88; H, 5.00; N, 11.53.

Example 109

2-(6-Methylamino-2-pyridyl)-4H-1,3-benzothiazine-4-one

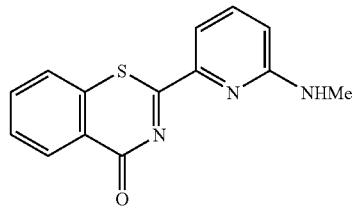

A mixture of tert-butyl methyl [6-(4-oxo-4H-1,3-benzothiazin-2-yl)-2-pyridyl]carbamate (0.60 g, 1.6 mmol) and trifluoroacetic acid (8 ml) was stirred at room temperature for 1 hr. The reaction mixture was concentrated under reduced pressure to give crystals, which were recrystallized from methanol-diethyl ether to give the titled compound (0.33 g, 74%).

mp. 206.9-208.0° C. IR (KBr): 3341, 1651, 1614, 1574, 1537, 1531, 1298, 1242, 978, 738 cm$^{-1}$. $^1$H-NMR (DMSO-d$_6$) δ: 2.93 (3H, d, J=4.3 Hz), 6.79 (1H, m), 7.06 (1H, d, J=4.3 Hz), 7.51 (1H, m), 7.62 (1H, m), 7.71 (1H, m), 7.81 (1H, m), 7.88 (1H, m), 8.34 (1H, dd, J=1.0, 7.8 Hz). Elemental Analysis for C$_{14}$H$_{11}$N$_3$OS Calcd. C, 62.43; H, 4.12; N, 15.60. Found C, 62.42; H, 3.99; N, 15.66.

Example 110

N-Methyl-N-[6-(4-oxo-4H-1,3-benzothiazin-2-yl)-2-pyridyl]acetamide

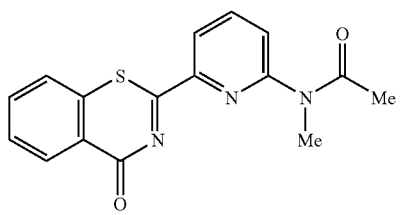

A mixture of 2-(6-methylamino-2-pyridyl)-4H-1,3-benzothiazine-4-one (0.20 g, 0.74 mmol), acetyl chloride (0.18 g, 2.22 mmol) and N,N-dimethylacetamide (10 ml) was stirred at 80° C. for 1 hr. After cooling, the reaction mixture was poured into water and extracted with ethyl acetate. The extract was washed with saturated brine and dried. The solvent was evaporated. The residue was recrystallized from tetrahydrofuran-hexane to give the titled compound (0.20 g, 86%)

mp. 218.3-220.3° C. IR (KBr): 3543, 3071, 1666, 1587, 1574, 1537, 1456, 1440, 1377, 1317, 1284, 1236, 1097, 993, 734 cm$^{-1}$. $^1$H-NMR (CDCl$_3$) δ: 2.33 (3H, s), 3.56 (3H, s), 7.60-7.76 (4H, m) 7.93 (1H, m), 8.36 (1H, d, J=7.7 Hz), 8.55 (1H, m). Elemental Analysis for C$_{16}$H$_{13}$N$_3$O$_2$S Calcd. C, 61.72; H, 4.21; N, 13.50. Found C, 61.64; H, 3.92; N, 13.42.

Example 111

N-Methyl-N-[6-(4-oxo-4H-1,3-benzothiazin-2-yl)-2-pyridyl]-2-thiophenecarboxamide

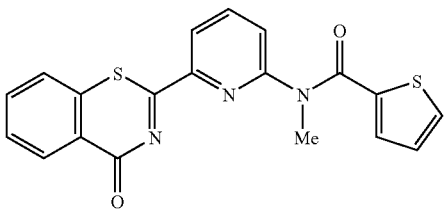

A mixture of 2-(6-methylamino-2-pyridyl)-4H-1,3-benzothiazine-4-one (0.20 g, 0.74 mmol), 2-thiophenecarbonyl chloride (0.28 g, 1.9 mmol) and N,N-dimethylacetamide (10 ml) was stirred at 80° C. for 2 hrs. After cooling, the reaction mixture was poured into water and extracted with ethyl acetate. The extract was washed successively with saturated aqueous sodium hydrogen carbonate solution and brine and dried. The solvent was evaporated. The residue was recrystallized from tetrahydrofuran-hexane to give the titled compound (0.23 g, 83%)

mp. 191.5-192.9° C. IR (KBr): 3067, 1643, 1572, 1523, 1450, 1442, 1360, 1313, 738 cm$^{-1}$. $^1$H-NMR (CDCl$_3$) δ: 3.72 (3H, s), 6.90 (1H, m), 7.06 (1H, dd, J=1.1, 3.7 Hz), 7.40-7.43 (2H, m), 7.61-7.70 (3H, m), 7.80 (1H, m), 8.35 (1H, d, J=7.6 Hz), 8.55 (1H, d, J=7.6 Hz). Elemental Analysis for C$_{19}$H$_{13}$N$_3$O$_2$S$_2$ Calcd. C, 60.14; H, 3.45; N, 11.07. Found C, 60.09; H, 3.34; N, 11.05.

Example 112

N-Methyl-N-[6-(4-oxo-4H-1,3-benzothiazin-2-yl)-2-pyridyl]-2-furamide

A mixture of 2-(6-methylamino-2-pyridyl)-4H-1,3-benzothiazine-4-one (0.20 g, 0.74 mmol), 2-furoyl chloride (0.26 g, 2.0 mmol) and N,N-dimethylacetamide (10 ml) was stirred at 80° C. for 2 hrs. After cooling, the reaction mixture was poured into water and extracted with ethyl acetate. The extract was washed successively with saturated aqueous sodium hydrogen carbonate solution and brine and dried. The solvent was evaporated. The residue was subjected to a silica gel column chromatography and eluted with hexane-ethyl acetate (1:1, v/v). The obtained crystals were recrystallized from ethyl acetate-hexane to give the titled compound (0.21 g, 63%)

mp. 186.2-187.2° C. IR (KBr): 3499, 1658, 1572, 1537, 1452, 1344, 1282, 1097, 746 cm$^{-1}$. $^1$H-NMR (CDCl$_3$) δ: 3.71 (3H, s), 6.42 (1H, dd, J=1.7, 3.5 Hz), 6.95 (1H, m), 7.29 (1H, m), 7.39 (1H, d, J=7.7 Hz), 7.57-7.71 (3H, m), 7.84 (1H, m), 8.35 (1H, d, J=7.3 Hz), 8.55 (1H, dd, J=1.5, 7.7 Hz). Elemental Analysis for C$_{19}$H$_{13}$N$_3$O$_3$S Calcd. C, 62.80; H, 3.61; N, 11.56. Found C, 62.76; H, 3.53; N, 11.61.

Example 113

N-Methyl-N-[6-(4-oxo-4H-1,3-benzothiazin-2-yl)-2-pyridyl]benzamide

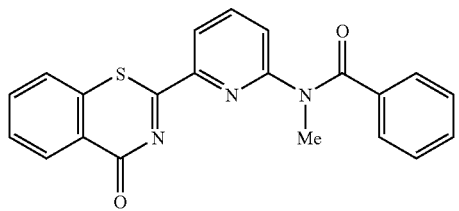

A mixture of 2-(6-methylamino-2-pyridyl)-4H-1,3-benzothiazine-4-one (0.20 g, 0.74 mmol), benzoyl chloride (0.44 g, 3.1 mmol) and N,N-dimethylacetamide (10 ml) was stirred at 80° C. for 20 hrs. After cooling, the reaction mixture was poured into water and extracted with ethyl acetate. The extract was successively washed with saturated aqueous sodium hydrogen carbonate solution and brine and dried. The solvent was evaporated. The residue was subjected to a silica gel column chromatography and eluted with hexane-ethyl acetate (1:1, v/v). The obtained crystals were recrystallized from ethyl acetate-hexane to give the titled compound (0.13 g, 38%).

mp. 234.0-235.4° C. IR (KBr): 3069, 1655, 1572, 1535, 1452, 1340, 1097, 729 cm$^{-1}$. $^1$H-NMR (CDCl$_3$) δ: 3.71 (3H, s), 7.24-7.45 (6H, m), 7.61-7.72 (4H, m), 8.25 (1H, d, J=7.6 Hz), 8.54 (1H, m). Elemental Analysis for C$_{21}$H$_{15}$N$_3$O$_2$S Calcd. C, 67.54; H, 4.05; N, 11.25. Found C, 67.59; H, 4.05; N, 11.28.

Example 114

N-Methyl-N-[6-(4-oxo-4H-1,3-benzothiazin-2-yl)-2-pyridyl]propanamide

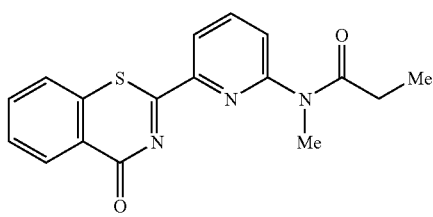

A mixture of 2-(6-methylamino-2-pyridyl)-4H-1,3-benzothiazine-4-one (0.25 g, 0.92 mmol), propionyl chloride (0.29 g, 3.1 mmol) and N,N-dimethylacetamide (10 ml) was stirred at 80° C. for 2 hrs. After cooling, the reaction mixture was poured into water and extracted with ethyl acetate. The extract was successively washed with saturated aqueous sodium hydrogen carbonate solution and brine and dried. The solvent was evaporated. The residue was recrystallized from tetrahydrofuran-hexane to give the titled compound (0.15 g, 49%).

mp. 200.6-201.2° C. IR (KBr): 3479, 3069, 2978, 2937, 1672, 1574, 1541, 1456, 1373, 1311, 1284, 1236, 1095, 810, 731 cm$^{-1}$. $^1$H-NMR (CDCl$_3$) δ: 1.21 (3H, t, J=7.3 Hz), 2.58 (2H, q, J=7.3 Hz), 3.55 (3H, s), 7.60-7.72 (3H, m), 7.79 (1H, d, J=8.0 Hz), 7.92 (1H, m), 8.35 (1H, d, J=7.6 Hz), 8.55 (1H, m). Elemental Analysis for C$_{17}$H$_{15}$N$_3$O$_2$S Calcd. C, 62.75; H, 4.65; N, 12.91. Found C, 62.36; H, 4.44; N, 12.75.

Example 115

N-methyl-N-[6-(4-oxo-4H-1,3-benzothiazin-2-yl)-2-pyridyl]cyclohexanecarboxamide

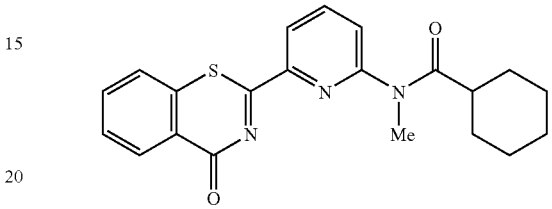

A mixture of 2-(6-methylamino-2-pyridyl)-4H-1,3-benzothiazine-4-one (0.20 g, 0.72 mmol), cyclohexanecarbonyl chloride (0.22 g, 1.5 mmol) and N,N-dimethylacetamide (10 ml) was stirred at 80° C. for 2 hrs. After cooling, the reaction mixture was poured into water and extracted with ethyl acetate. The extract was successively washed with saturated aqueous sodium hydrogen carbonate solution and brine and dried. The solvent was evaporated. The residue was subjected to a silica gel column chromatography and eluted with hexane-ethyl acetate (1:1, v/v). The obtained crystals were recrystallized from tetrahydrofuran-hexane to give the titled compound (0.20 g, 71%).

mp. 184.4-185.8° C. IR (KBr): 2932, 2854, 1666, 1572, 1537, 1452, 1284, 1238, 1095, 989, 744, 733 cm$^{-1}$. $^1$H-NMR (CDCl$_3$) δ: 1.15-1.31 (3H, m), 1.56-1.68 (3H, m), 1.79 (2H, m), 1.90 (2H, m), 2.66 (1H, m), 3.52 (3H, s), 7.59-7.72 (4H, m), 7.94 (1H, m), 8.39 (1H, d, J=7.6 Hz), 8.56 (1H, m). Elemental Analysis for C$_{21}$H$_{21}$N$_3$O$_2$S Calcd. C, 66.47; H, 5.58; N, 11.07. Found C, 66.48; H, 5.36; N, 11.24.

Example 116

6-Butoxy-2-(2-pyridyl)-4H-1,3-benzothiazine-4-one

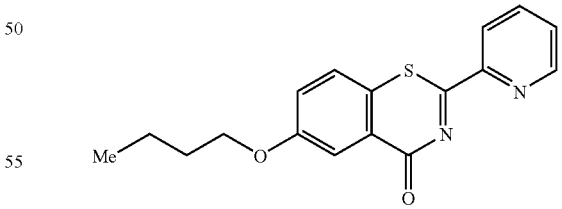

A mixture of 6-hydroxy-2-(2-pyridyl)-4H-1,3-benzothiazine-4-one (0.35 g, 1.3 mmol), 1-bromobutane (0.38 g, 2.7 mmol) and potassium carbonate (0.56 g, 4.0 mmol) and DMF (10 ml) was stirred at room temperature for 15 hrs. The reaction mixture was diluted with water and extracted with ethyl acetate. The extract was washed with water and dried. The solvent was evaporated. The obtained crystals were recrystallized from tetrahydrofuran-hexane to give the titled compound (0.35 g, 83%).

mp. 160.9-161.8° C. IR (KBr): 3053, 2951, 1660, 1643, 1599, 1537, 1469, 1344, 1282, 1234, 1057, 794 cm$^{-1}$. $^1$H-NMR (CDCl$_3$) δ: 1.00 (3H, t, J=7.3 Hz), 1.52 (2H, m), 1.82 (2H, m), 4.12 (2H, t, J=6.5 Hz), 7.29 (1H, dd, J=2.8, 8.7 Hz), 7.51-7.55 (2H, m), 7.90 (1H, m), 8.00 (1H, d, J=2.8 Hz), 8.55 (1H, d, J=7.9 Hz), 8.73 (1H, m) Elemental Analysis for C$_{17}$H$_{16}$N$_2$O$_2$S Calcd. C, 65.36; H, 5.16; N, 8.97. Found C, 65.30; H, 4.95; N, 8.85.

Example 117

6-Isobutoxy-2-(2-pyridyl)-4H-1,3-benzothiazine-4-one

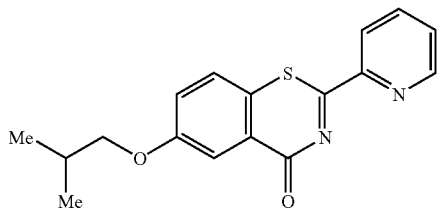

A mixture of 6-hydroxy-2-(2-pyridyl)-4H-1,3-benzothiazine-4-one (0.35 g, 1.3 mmol), isobutyl bromide (0.64 g, 4.6 mmol) and potassium carbonate (0.57 g, 4.1 mmol) and DMF (10 ml) was stirred at room temperature for 15 hrs. The reaction mixture was diluted with water and extracted with ethyl acetate. The extract was washed with water and dried. The solvent was evaporated. The residue was subjected to a silica gel column chromatography and eluted with hexane-ethyl acetate (2:1, v/v). The obtained crystals were recrystallized from ethyl acetate-hexane to give the titled compound (0.08 g, 19%).

mp. 135.5-136.5° C. IR (KBr): 2959, 1659, 1601, 1531, 1464, 1344, 1278, 1236, 1055, 792 cm$^{-1}$. $^1$H-NMR (CDCl$_3$) δ: 1.06 (6H, d, J=6.7 Hz), 2.14 (2H, m), 3.88 (2H, d, J=6.7 Hz), 7.31 (1H, dd, J=2.8, 8.8 Hz), 7.52-7.55 (2H, m), 7.91 (1H, m), 8.00 (1H, d, J=2.8 Hz), 8.55 (1H, m), 8.72 (1H, m). Elemental Analysis for C$_{17}$H$_{16}$N$_2$O$_2$S Calcd. C, 65.36; H, 5.16; N, 8.97. Found C, 65.35; H, 5.08; N, 9.02.

Example 118

6-(3-Hydroxypropoxy)-2-(2-pyridyl)-4H-1,3-benzothiazine-4-one

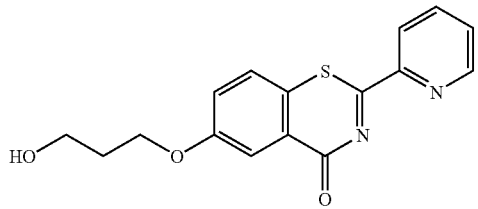

A mixture of 6-hydroxy-2-(2-pyridyl)-4H-1,3-benzothiazine-4-one (0.40 g, 1.5 mmol), 3-bromo-1-propanol (0.66 g, 4.7 mmol) and potassium carbonate (0.43 g, 3.1 mmol) and DMF (10 ml) was stirred at room temperature for 15 hrs. The reaction mixture was diluted with water and extracted with a mixture solvent of ethyl acetate and ethanol. The extract was washed with water and dried. The solvent was evaporated. The obtained crystals were recrystallized from ethanol-hexane to give the titled compound (0.27 g, 54%).

mp. 196.6-197.7° C. IR (KBr): 3370, 2951, 1628, 1599, 1518, 1467, 1354, 1282, 1236, 1064, 798 cm$^{-1}$ $^1$H-NMR (DMSO-d$_6$) δ:1.92 (2H, m), 3.60 (2H,m), 4.19 (2H, t, J=6.6 Hz), 4.60 (1H, t, J=4.9 Hz), 7.45 (1H, m), 7.72-7.85 (3H, m), 8.10 (1H, m), 8.34 (1H, d, J=7.7 Hz), 8.79 (1H, d, J=3.6 Hz). Elemental Analysis for C$_{16}$H$_{14}$N$_2$O$_3$S.0.25H$_2$O Calcd. C, 60.27; H, 4.58; N, 8.79. Found C, 60.34; H, 4.54; N, 8.67.

Example 119

6-(6-Hydroxyhexyloxy)-2-(2-pyridyl)-4H-1,3-benzothiazine-4-one

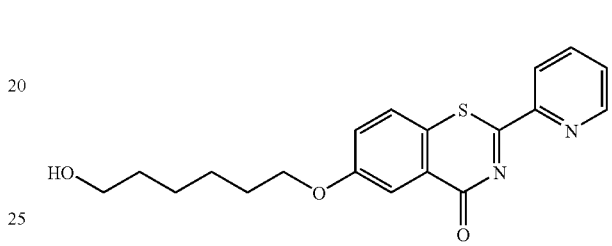

A mixture of 6-hydroxy-2-(2-pyridyl)-4H-1,3-benzothiazine-4-one (0.35 g, 1.3 mmol), 6-bromohexanol (1.28 g, 7.0 mmol) and potassium carbonate (0.38 g, 2.7 mmol) and DMF (10 ml) was stirred at room temperature for 24 hrs. The reaction mixture was diluted with water and extracted with ethyl acetate. The extract was washed with water and dried. The solvent was evaporated under reduced pressure. The obtained crystals were recrystallized from tetrahydrofuran-hexane to give the titled compound (0.44 g, 91%).

mp. 135.6-137.0° C. IR (KBr): 3451, 2939, 2866, 1651, 1643, 1599, 1537, 1471, 1348, 1282, 1236, 1060, 790 cm$^{-1}$. $^1$H-NMR (CDCl$_3$) δ: 1.26-1.67 (7H, m), 1.86 (2H, m), 3.68 (2H, m), 4.12 (2H, m), 7.29 (1H, m), 7.52-7.55 (2H, m), 7.91 (1H, m), 7.99 (1H, d, J=2.7 Hz), 8.55 (1H, d, J=7.9 Hz), 8.73 (1H, d, J=4.6 Hz). Elemental Analysis for C$_{19}$H$_{20}$N$_2$O$_3$S Calcd. C, 64.02; H, 5.66; N, 7.86. Found C, 64.03; H, 5.82; N, 7.58.

Example 120

6-(3-Phenylpropoxy)-2-(2-pyridyl)-4H-1,3-benzothiazine-4-one

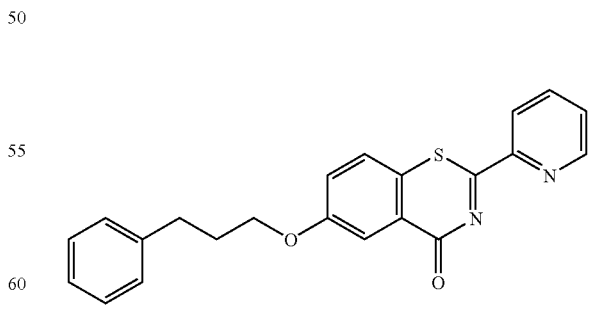

A mixture of 6-hydroxy-2-(2-pyridyl)-4H-1,3-benzothiazine-4-one (0.35 g, 1.3 mmol), 1-bromo-3-phenylpropane (0.86 g, 4.3 mmol) and potassium carbonate (0.38 g, 2.7 mmol) and DMF (10 ml) was stirred at room temperature for 20 hrs. The reaction mixture was diluted with water and extracted with ethyl acetate. The extract was washed with water and dried. The solvent was evaporated under reduced pressure. The obtained crystals were recrystallized from tetrahydrofuran-hexane to give the titled compound (0.48 g, 92%).

mp. 170.0-170.3° C. IR (KBr): 3416, 1658, 1651, 1599, 1537, 1342, 1278, 1234 cm$^{-1}$. $^1$H-NMR (CDCl$_3$) δ: 2.17 (2H, tt, J=6.3, 7.5 Hz), 2.84 (2H, t, J=7.5 Hz), 4.12 (2H, t, J=6.3 Hz), 7.20-7.32 (6H, m), 7.52-7.55 (2H, m), 7.90 (1H, m), 7.98 (1H, d, J=2.8 Hz), 8.55 (1H, d, J=7.9 Hz), 8.72 (1H, dd, J=0.6, 3.9 Hz). Elemental Analysis for C$_{22}$H$_{18}$N$_2$O$_2$S Calcd. C, 70.57; H, 4.85; N, 7.48. Found C, 70.50; H, 4.83; N, 7.51.

Example 121

6-(Benzyloxy)-2-(2-pyridyl)-4H-1,3-benzothiazine-4-one

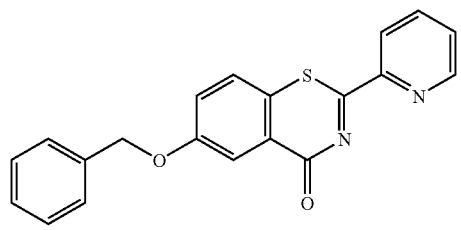

A mixture of 6-hydroxy-2-(2-pyridyl)-4H-1,3-benzothiazine-4-one (0.30 g, 1.1 mmol), benzyl bromide (0.61 g, 3.5 mmol) and potassium carbonate (0.32 g, 2.3 mmol) and DMF (10 ml) was stirred at room temperature for 2 hrs. The reaction mixture was diluted with water and extracted with ethyl acetate. The extract was washed with water and dried. The solvent was evaporated under reduced pressure. The obtained crystals were recrystallized from tetrahydrofuran-hexane to give the titled compound (0.39 g, 95%).

mp. 198.0-198.8° C. IR (KBr): 3476, 1649, 1531, 1344, 1278, 1238, 1053, 995, 788 cm$^{-1}$. $^1$H-NMR (CDCl$_3$) δ: 5.21 (2H, s), 7.35-7.57 (8H, m), 7.90 (1H, m), 8.12 (1H, d, J=2.7 Hz), 8.55 (1H, d, J=7.9 Hz), 8.73 (1H, d, J=4.4 Hz). Elemental Analysis for C$_{20}$H$_{14}$N$_2$O$_2$S Calcd. C, 69.35; H, 4.07; N, 8.09. Found C, 69.34; H, 4.11; N, 8.17.

Example 122 tert-Butyl 2-[[4-oxo-2-(2-pyridyl)-4H-1,3-benzothiazin-6-yl]oxy]acetate

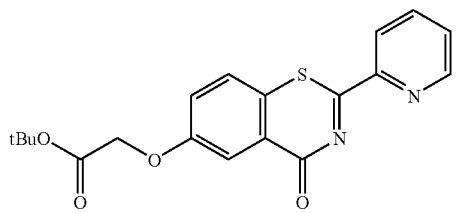

A mixture of 6-hydroxy-2-(2-pyridyl)-4H-1,3-benzothiazine-4-one (0.35 g, 1.3 mmol), tert-butyl bromoacetate (0.88 g, 4.5 mmol) and potassium carbonate (0.38 g, 2.7 mmol) and DMF (10 ml) was stirred at room temperature for 12 hrs. The reaction mixture was diluted with water and extracted with ethyl acetate. The extract was washed with water and dried. The solvent was evaporated. The residue was subjected to a silica gel column chromatography and eluted with hexane-ethyl acetate (1:1, v/v). The obtained crystals were recrystallized from tetrahydrofuran-hexane to give the titled compound (0.44 g, 87%)

mp. 183.0-184.1° C. IR (KBr): 2980, 1747, 1658, 1537, 1473, 1280, 1234, 1157, 1078, 792, 738 cm$^{-1}$. $^1$H-NMR (CDCl$_3$) δ: 1.51 (9H, s), 4.67 (2H, s), 7.39 (1H, dd, J=2.8, 8.8 Hz), 7.52 (1H, m), 7.57 (1H, d, J=8.8 Hz), 7.90-7.94 (2H, m), 8.53 (1H, dd, J=0.9, 7.9 Hz), 8.72 (1H, m). Elemental Analysis for C$_{19}$H$_{18}$N$_2$O$_4$S Calcd. C, 61.61; H, 4.90; N, 7.56. Found C, 61.67; H, 4.87; N, 7.54.

Example 123

2-[[4-Oxo-2-(2-pyridyl)-4H-1,3-benzothiazin-6-yl]oxy]acetic acid

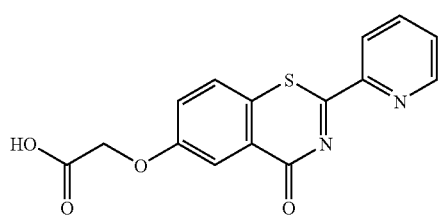

A mixture of tert-butyl 2-[[4-oxo-2-(2-pyridyl)-4H-1,3-benzothiazin-6-yl]oxy]acetate (0.30 g, 0.81 mmol) and trifluoroacetic acid (10 ml) was stirred at room temperature for 3 hrs. The reaction mixture was concentrated under reduced pressure and recrystallized from methanol-diisopropyl ether to give the titled compound (0.17 g, 67%).

mp. 250° C. (decomposed) IR (KBr): 3069, 1770, 1624, 1601, 1529, 1479, 1427, 1415, 1352, 1238, 1082, 831, 790 cm$^{-1}$. $^1$H-NMR (DMSO-d$_6$) δ: 4.89 (2H, s), 7.50 (1H, dd, J=2.8, 8.8 Hz), 7.72-7.78 (2H, m), 7.88 (1H, d, J=8.8 Hz), 8.10 (1H, m), 8.35 (1H, d, J=7.8 Hz), 8.79 (1H, d, J=4.5 Hz), 13.16 (1H, br s). Elemental Analysis for C$_{15}$H$_{10}$N$_2$O$_4$S Calcd. C, 57.32; H, 3.21; N, 8.91. Found C, 57.34; H, 2.95; N, 8.84.

Example 124 tert-Butyl 6-[[4-oxo-2-(2-pyridyl)-4H-1,3-benzothiazin-6-yl]oxy]hexanoate

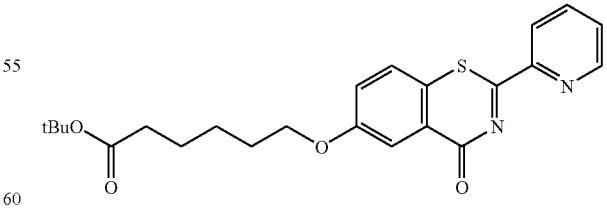

A mixture of 6-hydroxy-2-(2-pyridyl)-4H-1,3-benzothiazine-4-one (0.50 g, 1.9 mmol), tert-butyl 6-bromohexanoate (1.25 g, 4.9 mmol) and potassium carbonate (0.54 g, 3.9 mmol) and DMF (10 ml) was stirred at room temperature for 24 hrs. The reaction mixture was diluted with water and extracted with ethyl acetate. The extract was washed with water and dried. The solvent was evaporated. The obtained crystals were recrystallized from ethyl acetate-hexane to give the titled compound (0.75 g, 90%).

mp. 101.2-102.4° C. IR (KBr): 2937, 2868, 1726, 1658, 1537, 1467, 1342, 1278, 1236, 1151, 792 cm$^{-1}$. $^1$H-NMR (CDCl$_3$) δ: 1.45 (9H, s), 1.52 (2H, m), 1.67 (2H, m), 1.85 (2H, m), 2.26 (2H, t, J=7.2 Hz), 4.12 (2H, t, J=6.4 Hz), 7.29 (1H, dd, J=2.7, 8.8 Hz), 7.52-7.55 (2H, m), 7.91 (1H, m), 7.99 (1H, d, J=2.7 Hz), 8.55 (1H, d, J=7.8 Hz), 8.72 (1H, d, J=4.7 Hz). Elemental Analysis for C$_{23}$H$_{26}$N$_2$O$_4$S Calcd. C, 64.77; H, 6.14; N, 6.57. Found C, 64.69; H, 5.98; N, 6.58.

Example 125

6-[[4-Oxo-2-(2-pyridyl)-4H-1,3-benzothiazin-6-yl]oxy]hexanoic acid

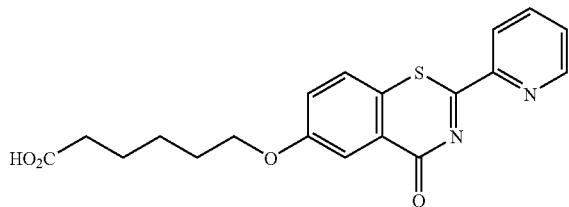

A mixture of tert-butyl 6-[[4-oxo-2-(2-pyridyl)-4H-1,3-benzothiazin-6-yl]oxy]hexanoate (0.80 g, 1.8 mmol) and trifluoroacetic acid (10 ml) was stirred under ice cooling condition for 1 hr. The reaction mixture was concentrated under reduced pressure and crystallized from diisopropyl ether to give the titled compound (0.69 g, ca. 100%).

mp. 205.4-206.3° C. IR (KBr): 3057, 2947, 1711, 1643, 1603, 1523, 1467, 1290, 1236, 1059, 802 cm$^{-1}$. $^1$H-NMR (DMSO-d$_6$) δ: 1.47 (2H, m), 1.59 (2H, m), 1.77 (2H, m), 2.25 (2H, t, J=7.2 Hz), 4.11 (2H, t, J=6.4 Hz), 7.45 (1H, dd, J=2.8, 8.8 Hz), 7.72-7.85 (3H, m), 8.10 (1H, m), 8.35 (1H, d, J=7.8 Hz), 8.79 (1H, d, J=4.7 Hz), 12.00 (1H, br s). Elemental Analysis for C$_{19}$H$_{18}$N$_2$O$_4$S.0.25H$_2$O Calcd. C, 60.87; H, 4.97; N, 7.47. Found C, 60.75; H, 4.96; N, 7.38.

Reference Example 25

2-Cyano-6-ethylthiopyridine

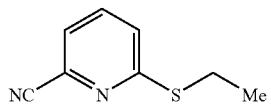

Ethyl mercaptan (0.49 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.02 g, 86%) as an oil.

IR (KBr): 2233, 1576, 1469, 1425, 1267, 1157, 1143, 978, 856, 794 cm$^{-1}$. $^1$H-NMR (CDCl$_3$) δ: 1.38 (3H, t, J=7.4 Hz), 3.20 (2H, q, J=7.3 Hz), 7.28-7.36 (2H, m), 7.55 (1H, t, J=7.6 Hz).

Example 126

2-[6-(Ethylthio)-2-pyridyl]-4H-1,3-benzothiazine-4-one

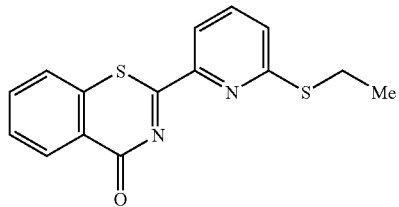

A mixture of methyl thiosalicylate (1.21 g, 7.2 mmol), 2-cyano-6-ethylthiopyridine (1.02 g, 6.2 mmol), triethylamine (1.5 ml, 10.8 mmol) and toluene (30 ml) was refluxed for 48 hrs. The reaction mixture was concentrated under reduced pressure to give precipitated crystals, which were recrystallized from ethanol to give the titled compound (0.26 g, 14%)

mp. 161.3-162.0° C. IR (KBr): 1653, 1574, 1525, 1423, 1298, 1284, 1234, 1153, 1124, 1095, 981, 812, 725 cm$^{-1}$. $^1$H-NMR (CDCl$_3$) δ: 1.51 (3H, t, J=7.4 Hz), 3.34 (2H, q, J=7.3 Hz), 7.35-7.38 (1H, m), 7.61-7.69 (4H, m), 8.18-8.21 (1H, m), 8.53-8.57 (1H, m). Elemental Analysis for C$_{15}$H$_{12}$N$_2$OS$_2$ Calcd. C, 59.97; H, 4.03; N, 9.33. Found C, 60.05; H, 3.85; N, 9.30.

Reference Example 26

2-Cyano-6-isopropylthiopyridine

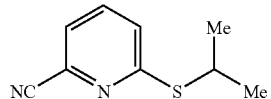

Isopropyl mercaptan (0.60 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.40 g, ca. 100%) as an oil.

IR (KBr): 2233, 1577, 1547, 1425, 1365, 1159, 1143, 1075, 1055, 978, 856, 794 cm$^{-1}$. $^1$H-NMR (CDCl$_3$) δ: 1.41 (6H, d, J=6.8 Hz), 4.00-4.15 (1H, m), 7.28-7.35 (2H, m), 7.54 (1H, t, J=7.5 Hz).

Example 127

2-[6-(Isopropylthio)-2-pyridyl)-4H-1,3-benzothiazine-4-one

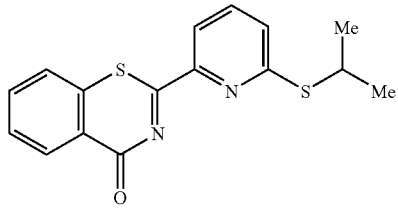

A mixture of methyl thiosalicylate (1.21 g, 7.2 mmol), 2-cyano-6-isopropylthiopyridine (1.40 g, 7.9 mmol), triethylamine (1.5 ml, 10.8 mmol) and toluene (30 ml) was refluxed for 48 hrs. The reaction mixture was concentrated under reduced pressure to give the precipitated crystals, which were recrystallized from ethyl acetate-hexane to give the titled compound (0.24 g, 10%).

mp. 185.4-185.8° C. IR (KBr): 1658, 1570, 1535, 1429, 1294, 1232, 1141, 1093, 985, 912, 744 cm$^{-1}$. $^1$H-NMR (CDCl$_3$) δ: 1.54 (6H, d, J=6.8 Hz), 4.14-4.23 (1H, m) 7.34 (1H, d, J=8.0 Hz), 7.60-7.71 (4H, m), 8.20 (1H, d, J=7.6 Hz), 8.54-8.57 (1H, m). Elemental Analysis for C$_{16}$H$_{14}$N$_2$OS$_2$ Calcd. C, 61.12; H, 4.49; N, 8.91. Found C, 61.02; H, 4.56; N, 8.91.

Reference Example 27

2-Cyano-6-tert-butylpyridine

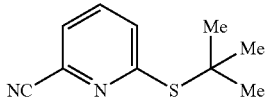

tert-Butyl mercaptan (0.72 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.19 g, 86%) as an oil.

IR (KBr): 2235, 1574, 1549, 1421, 1361, 1159, 1143, 978, 854, 794 cm$^{-1}$. $^1$H-NMR (CDCl$_3$) δ: 1.59 (9H, s), 7.31-7.38 (2H, m), 7.54 (1H, t, J=7.7 Hz).

Example 128

2-[6-(tert-Butylthio)-2-pyridyl]-4H-1,3-benzothiazine-4-one

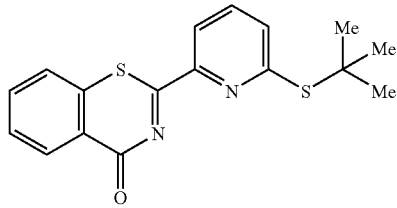

A mixture of methyl thiosalicylate (1.21 g, 7.2 mmol), 2-cyano-6-tert-butylthiopyridine (1.19 g, 6.2 mmol), triethylamine (1.5 ml, 10.8 mmol) and toluene (30 ml) was refluxed for 48 hrs. The reaction mixture was concentrated under reduced pressure to give the precipitated crystals, which were recrystallized from ethyl acetate-hexane to give the titled compound (0.15 g, 7%).

mp. 152.9-153.8° C. IR (KBr): 1660, 1570, 1531, 1427, 1294, 1232, 1136, 1093, 964, 798 cm$^{-1}$. $^1$H-NMR (CDCl$_3$) δ: 1.71 (9H, s), 7.39 (1H, d, J=7.8 Hz), 7.62-7.69 (4H, m), 8.26 (1H, d, J=7.4 Hz), 8.54-8.57 (1H, m). Elemental Analysis for C$_{17}$H$_{16}$N$_2$OS$_2$ Calcd. C, 62.16; H, 4.91; N, 8.53. Found C, 62.07; H, 5.05; N, 8.51.

Reference Example 28

2-Cyano-6-pentylthiopyridine

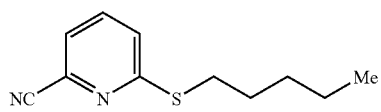

Pentyl mercaptan (0.83 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.48 g, ca. 100%) as an oil.

IR (KBr): 2235, 1574, 1549, 1454, 1427, 1159, 978, 858, 794 cm$^{-1}$. $^1$H-NMR (CDCl$_3$) δ: 0.92 (3H, t, J=7.0 Hz), 1.38-1.44 (2H, m), 1.69-1.74 (2H, m), 3.18 (2H, t, J=7.2 Hz), 7.28-7.35 (2H, m), 7.54 (1H, t, J=7.6 Hz).

Example 129

2-[6-(Pentylthio)-2-pyridyl]-4H-1,3-benzothiazine-4-one

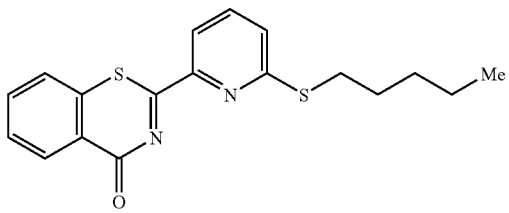

A mixture of methyl thiosalicylate (1.21 g, 7.2 mmol), 2-cyano-6-pentylthiopyridine (1.48 g, 7.2 mmol), triethylamine (1.5 ml, 10.8 mmol) and toluene (30 ml) was refluxed for 48 hrs. The reaction mixture was concentrated under reduced pressure to give the precipitated crystals, which were recrystallized from ethyl acetate-hexane to give the titled compound (1.09 g, 44%).

mp. 105.0-105.1° C. IR (KBr): 1658, 1572, 1552, 1537, 1431, 1294, 1234, 1145, 1093, 968 cm$^{-1}$. $^1$H-NMR (CDCl$_3$) δ: 0.95 (3H, t, J=7.2 Hz), 1.36-1.52 (2H, m), 1.54-1.59 (2H, m), 1.81-1.91 (2H, m), 3.31 (3H, t, J=7.5 Hz), 7.37 (1H, d, J=8.0 Hz), 7.58-7.71 (4H, m), 8.19 (1H, d, J=7.5 Hz), 8.54-8.57 (1H, m). Elemental Analysis for C$_{18}$H$_{18}$N$_2$OS$_2$ Calcd. C, 63.13; H, 5.30; N, 8.18. Found C, 63.00; H, 5.42; N, 8.28.

Reference Example 29

2-Cyano-6-isopentylthiopyridine

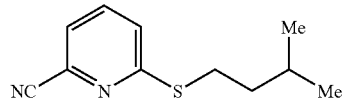

Isopentyl mercaptan (0.83 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.48 g, ca. 100%) as an oil.

IR (KBr): 2233, 1576, 1549, 1466, 1427, 1277, 1159, 1143, 1078, 978, 856, 794 cm$^{-1}$. $^1$H-NMR (CDCl$_3$) δ: 0.96 (6H, d, J=6.5 Hz), 1.55-1.62 (2H, m), 1.69-1.76 (1H, m), 3.16-3.21 (2H, m), 7.30-7.35 (2H, m), 7.54 (1H, t, J=7.6 Hz).

Example 130

2-[6-(Isopentylthio)-2-pyridyl]-4H-1,3-benzothiazine-4-one

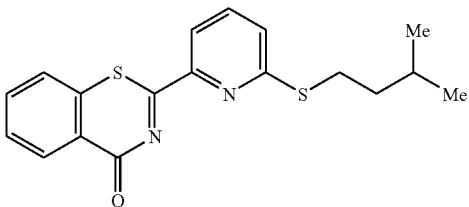

A mixture of methyl thiosalicylate (1.21 g, 7.2 mmol), 2-cyano-6-isopentylthiopyridine (1.48 g, 7.2 mmol), triethylamine (1.5 ml, 10.8 mmol) and toluene (30 ml) was refluxed for 48 hrs. The reaction mixture was concentrated under reduced pressure to give the precipitated crystals, which were recrystallized from ethyl acetate-hexane to give the titled compound (0.64 g, 26%).

mp. 103.4-105.1° C. IR (KBr): 1660, 1570, 1531, 1429, 1294, 1232, 1147, 1093, 1062, 1028, 985, 968, 798 cm$^{-1}$. $^1$H-NMR (CDCl$_3$) δ: 1.03 (6H, d, J=6.5 Hz), 1.71-1.80 (2H, m), 1.82-1.91 (1H, m), 3.30-3.35 (2H, m), 7.37 (1H, d, J=8.1 Hz), 7.57-7.69 (4H, m), 8.18-8.20 (1H, m), 8.54-8.57 (1H, m). Elemental Analysis for C$_{18}$H$_{18}$N$_2$OS$_2$ Calcd. C, 63.13; H, 5.30; N, 8.18. Found C, 62.95; H, 5.08; N, 8.16.

Reference Example 30

2-Cyano-6-(2-phenethylthio)pyridine

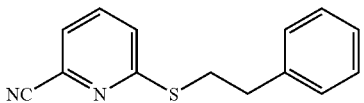

2-Phenethyl mercaptan (1.10 g, 7.9 mmol) was dissolved in tetrahydrofuran (100 ml) and added dropwise to sodium hydride (60% oil, 0.35 g, 8.7 mmol). The reaction mixture was stirred at room temperature for 1 hr. A solution of 2-chloro-6-cyanopyridine (1.00 g, 7.2 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (1.74 g, ca. 100%) as an oil.

IR (KBr): 2233, 1574, 1549, 1494, 1427, 1159, 1143, 978, 912, 856, 794 cm$^{-1}$. $^1$H-NMR (CDCl$_3$) δ: 2.98-3.03 (2H, m), 3.40-3.45 (2H, m), 7.24-7.36 (7H, m), 7.54 (1H, t, J=7.9 Hz).

Example 131

2-[6-(2-Phenethylthio)-2-pyridyl]-4H-1,3-benzothiazine-4-one

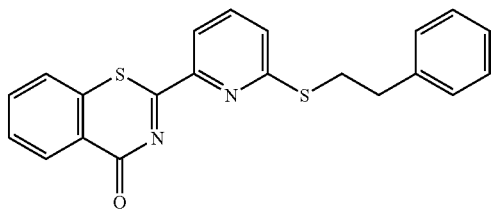

A mixture of methyl thiosalicylate (1.21 g, 7.2 mmol), 2-cyano-6-(2-phenylthio)pyridine (1.74 g, 7.2 mmol), triethylamine (1.5 ml, 10.8 mmol) and toluene (30 ml) was refluxed for 48 hrs. The reaction mixture was concentrated under reduced pressure to give the precipitated crystals, which were recrystallized from ethanol to give the titled compound (1.00 g, 37%).

mp. 167.1-168.4° C. IR (KBr): 1658, 1570, 1531, 1429, 1296, 1234, 1145, 1093, 1062, 1028, 985, 966, 744 cm$^{-1}$ $^1$H-NMR (CDCl$_3$) δ: 3.14-3.19 (2H, m), 3.57-3.62 (2H, m), 7.25-7.40 (6H, m), 7.51-7.52 (1H, m), 7.62-7.70 (3H, m), 8.20-8.23 (1H, m), 8.53-8.57 (1H, m). Elemental Analysis for C$_{21}$H$_{16}$N$_2$OS$_2$ Calcd. C, 66.99; H, 4.28; N, 7.44. Found C, 67.11; H, 4.18; N, 7.38.

Reference Example 31

Methyl 2-cyano-6-pyridylthioaectate

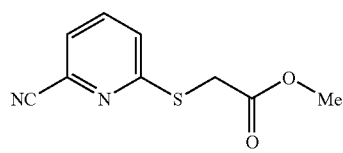

Methyl thioglycolate (0.80 g, 7.5 mmol) was dissolved in tetrahydrofuran (50 ml) and added dropwise to sodium hydride (60% oil, 0.30 g, 7.5 mmol). The reaction mixture was stirred at room temperature for 1 hr. A solution of 2-chloro-6-cyanopyridine (0.70 g, 5.0 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure. The residue was subjected to a silica gel column chromatography and eluted with hexane-ethyl acetate (2:1, v/v) to give the titled compound (0.20 g, 13%).

IR (KBr): 2235, 1730, 1572, 1554, 1518, 1504, 1433, 1141, 912, 746 cm$^{-1}$. $^1$H-NMR (CDCl$_3$) δ: 3.79 (3H, s), 3.98 (2H, s), 7.38-7.43 (2H, m) 7.82 (1H, t, J=7.9 Hz).

Example 132

Methyl [[6-(4-oxo-4H-1,3-benzothiazin-2-yl)-2-pyridyl]thio]acetic acid

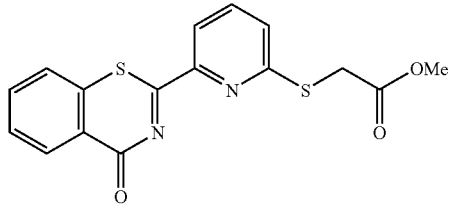

A mixture of methyl thiosalicylate (0.11 g, 0.67 mmol), methyl 2-cyano-6-pyridylthioacetate (0.14 g, 0.67 mmol), triethylamine (0.14 ml, 1.00 mmol) and toluene (20 ml) was refluxed for 48 hrs. The reaction mixture was concentrated under reduced pressure to give the precipitated crystals, which were recrystallized from methanol to give the titled compound (0.04 g, 17%).

mp. 117.1° C. (decomposed) IR (KBr): 1738, 1658, 1572, 1537, 1433, 1296, 1234, 1143, 1095, 912, 744 cm$^{-1}$. $^1$H-NMR (CDCl$_3$) δ: 3.81 (3H, s), 4.14 (2H, s), 7.46 (1H, d, J=8.0 Hz), 7.58-7.75 (4H, m), 8.26 (1H, d, J=7.6 Hz), 8.54-8.56 (1H, m). Elemental Analysis for C$_{16}$H$_{12}$N$_2$O$_3$S$_2$ Calcd. C, 55.80; H, 3.51; N, 8.13. Found C, 55.51; H, 3.51; N, 7.98.

Reference Example 32

2-Cyano-6-[2-(N,N-dimethylamino)ethyl]thiopyridine

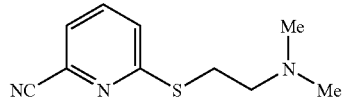

2-Dimethylaminoethanethiol (0.71 g, 5.0 mmol) was dissolved in tetrahydrofuran (100 ml) and added dropwise to sodium hydride (60% oil, 0.44 g, 11.0 mmol). The reaction mixture was stirred at room temperature for 1 hr. A solution of 2-chloro-6-cyanopyridine (0.70 g, 5.0 mmol) in tetrahydrofuran (10 ml) was added to the mixture, and the mixture was stirred at room temperature for 18 hrs. The reaction mixture was concentrated under reduced pressure, diluted with water and extracted with ethyl acetate. The extract was washed with saturated brine and dried. The solvent was evaporated under reduced pressure to give the titled compound (0.49 g, 47%).

IR (KBr): 2233, 1576, 1549, 1456, 1425, 1143, 794 cm$^{-1}$. $^1$H-NMR (CDCl$_3$) δ: 2.32 (6H, s), 2.63 (2H, t, J=7.0 Hz), 3.33 (2H, t, J=7.1 Hz), 7.33-7.36 (2H, m), 7.55 (1H, t, J=7.9 Hz).

Example 133

2-{6-[2-(N,N-Dimethylamino)ethyl]thio]-2-pyridyl}-4H-1,3-benzothiazine-4-one

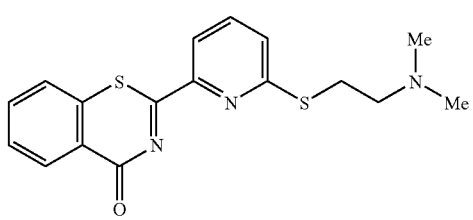

A mixture of methyl thiosalicylate (0.40 g, 2.4 mmol), 2-cyano-6-[2-(N,N-dimethylamino)ethyl]thiopyridine (0.49 g, 2.4 mmol), triethylamine (0.50 ml, 3.6 mmol) and toluene (30 ml) was refluxed for 48 hrs. The reaction mixture was concentrated under reduced pressure. The residue was subjected to a column chromatography and eluted with ethyl acetate-methanol (2:1, v/v). The obtained crystals were recrystallized from ethyl acetate-hexane to give the titled compound (0.19 g, 23%).

mp. 154.8° C. (decomposed) IR (KBr): 1655, 1570, 1527, 1431, 1296, 1234, 1095, 985, 912, 744 cm$^{-1}$ $^1$H-NMR (CDCl$_3$) δ: 2.35 (6H, s), 2.77 (2H, t, J=7.0 Hz), 3.47 (2H, t, J=7.3 Hz), 7.39 (1H, d, J=8.0 Hz), 7.58-7.71 (4H, m), 8.19-8.22 (1H, m), 8.53-8.56 (1H, m). Elemental Analysis for C$_{17}$H$_{17}$N$_3$OS$_2$ Calcd. C, 59.45; H, 4.99; N, 12.23. Found C, 59.06; H, 4.81; N, 12.04.

Reference Example 33

2-Cyano-6-ethoxypyridine

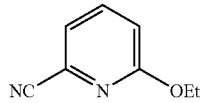

A mixture of 2-chloro-6-cyanopyridine (1.00 g, 7.2 mmol), sodium ethoxide (0.54 g, 7.9 mmol) and tetrahydrofuran (100 ml) was refluxed for 18 hrs. The reaction mixture was concentrated under reduced pressure, diluted with ice-water and extracted with ethyl acetate. The extract was washed with saturated brine and dried. The solvent was evaporated under reduced pressure. The residue was subjected to a silica gel column chromatography and eluted with hexane-ethyl acetate (5:1, v/v) to give the titled compound (0.15 g, 14%).

IR (KBr): 2235, 1608, 1589, 1564, 1448, 1389, 1334, 1275, 1209, 1163, 1111, 1037, 987, 806 cm$^{-1}$. $^1$H-NMR (CDCl$_3$) δ: 1.39 (3H, t, J=7.1 Hz), 4.39 (2H, q, J=7.1 Hz), 6.93 (1H, d, J=8.4 Hz), 7.25-7.28 (1H, m), 7.61-7.66 (1H, m).

Example 134

2-(6-Ethoxy-2-pyridyl)-4H-1,3-benzothiazine-4-one

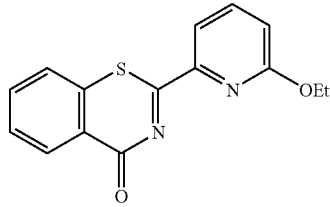

A mixture of methyl thiosalicylate (0.17 g, 1.0 mmol), 2-cyano-6-ethoxypyridine (0.15 g, 1.0 mmol), triethylamine (0.21 ml, 1.5 mmol) and toluene (30 ml) was refluxed for 48 hrs. The reaction mixture was concentrated under reduced pressure. The residue was subjected to a column chromatography and eluted with hexane-ethyl acetate (3:1, v/v). The obtained crystals were recrystallized from ethyl acetate-hexane to give the titled compound (0.04 g, 14%).

mp. 179.5-180.0° C. IR (KBr): 1651, 1593, 1574, 1523, 1440, 1383, 1332, 1294, 1273, 1238, 1095, 1032, 985, 814, 744 cm$^{-1}$. $^1$H-NMR (CDCl$_3$) δ: 1.50 (3H, t, J=7.0 Hz), 4.54 (2H, q, J=7.0 Hz), 6.95-6.98 (1H, m), 7.59-7.68 (1H, m), 7.75 (1H, t, J=7.4 Hz), 8.11-8.14 (1H, m), 8.53-8.57 (1H, m). Fab-MS m/z 285.

Example 135

4-Oxo-2-(2-pyridyl)-4H-1,3-benzothiazine-7-carboxylic acid

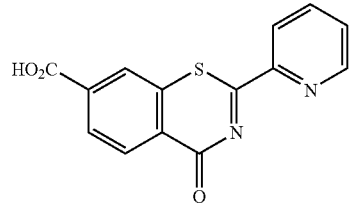

A mixture of 2-mercaptoterephthalic acid (2.0 g, 10 mmol), 2-cyanopyridine (1.3 g, 11 mmol) and pyridine (10 ml) was refluxed for 8 hrs. After cooling, the precipitated crystals were collected by filtration and recrystallized from methanol-diisopropylether to give the titled compound (1.22 g, 42%).

mp. 294.7-295.1° C. IR (KBr): 3049, 2665, 2552, 1732, 1697, 1662, 1566, 1535, 1307, 1278, 1236, 736 cm$^{-1}$. $^1$H-NMR (DMSO-d$_6$) δ: 7.77 (1H, m), 8.09-8.17 (2H, m), 8.34-8.44 (3H, m), 8.82 (1H, d, J=4.5 Hz), 13.20 (1H, br s). Elemental Analysis for C$_{14}$H$_8$N$_2$O$_3$S.1.25H$_2$O Calcd. C, 54.81; H, 3.45; N, 9.13. Found C, 55.02; H, 3.36; N, 9.31.

Example 136

2-(6-Methyl-2-pyridyl)-4H-1,3-benzothiazine-4-one

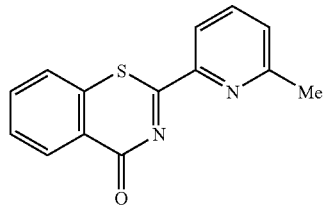

A mixture of methyl thiosalicylate (0.85 g, 5.1 mmol), 2-cyano-6-methylpyridine (0.60 g, 5.1 mmol), triethylamine (1.10 ml, 7.9 mmol) and toluene (1.1 ml) was refluxed for 9 hrs. After cooling, the precipitated crystals were collected by filtration and recrystallized from ethanol to give the titled compound (0.71 g, 55%).

mp. 169.8-170.3° C. IR (KBr): 1651, 1591, 1572, 1531, 1300 cm$^{-1}$. $^1$H-NMR (CDCl$_3$) δ: 2.69 (3H, s), 7.39 (1H, d, J=7.8 Hz), 7.60-7.71 (1H, t, J=7.8 Hz), 8.35 (1H, d, J=7.8 Hz), 8.55 (1H, d, J=7.2 Hz). Elemental Analysis for C$_{14}$H$_{10}$N$_2$OS Calcd. C, 66.12; H, 3.96; N, 11.02. Found C, 65.88; H, 3.69; N, 11.20.

Reference Example 34

2-Cyano-4-phenylpyridine

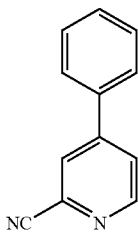

4-Phenylpyridine N-oxide (3.13 g, 18.3 mmol) was dissolved in nitroethane (30 ml), and trimethylsilyl cyanide (2.0 g, 20.2 mmol) and N,N-dimethylcarbamoyl chloride (1.7 ml, 18.5 mmol) were added thereto. The reaction mixture was stirred at room temperature for 45 hrs, concentrated under reduced pressure, combined with saturated aqueous sodium hydrogen carbonate solution and extracted with ethyl acetate. The extract was washed with saturated brine and dried. The solvent was evaporated under reduced pressure. The obtained crystals were collected by filtration, washed with diisopropyl ether and dried to give the titled compound (2.87 g, 89%). $^1$H-NMR (CDCl$_3$) δ: 7.47-7.65 (5H, m), 7.72 (1H, dd, J=1.8, 5.2 Hz), 7.91 (1H, s), 8.75 (1H, d, J=5.1 Hz).

Example 137

2-(4-Phenyl-2-pyridyl)-4H-1,3-benzothiazine-4-one

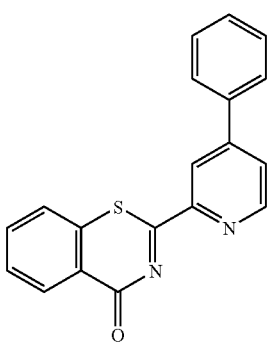

A mixture of methyl thiosalicylate (1.00 g, 5.9 mmol), 2-cyano-4-phenylpyridine (1.10 g, 5.9 mmol), triethylamine (1.30 ml, 9.0 mmol) and toluene (2.5 ml) was refluxed for 20 hrs. After cooling, the precipitated crystals were collected by filtration and recrystallized from ethanol to give the titled compound (0.99 g, 53%).

mp. 164.4-164.7° C. IR (KBr): 1655, 1570, 1533, 1296, 1283 cm$^{-1}$. $^1$H-NMR (CDCl$_3$) δ: 7.48-7.78 (9H, m), 8.57 (1H, dd, J=2.0, 7.2 Hz), 8.77 (1H, d, J=5.1 Hz), 8.80 (1H, s). Elemental Analysis for C$_{19}$H$_{12}$N$_2$OS Calcd. C, 72.13; H, 3.82; N, 8.85. Found C, 72.14; H, 3.82; N, 9.06.

Reference Example 35

2-Cyano-4-methylpyridine

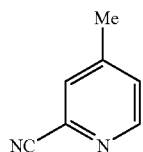

4-Methylpyridine N-oxide (2.0 g, 18.3 mmol) was dissolved in nitroethane (25 ml), and trimethylsilyl cyanide (2.0 g, 20.2 mmol) and N,N-dimethylcarbamoyl chloride (1.7 ml, 18.5 mmol) were added thereto. The reaction mixture was stirred at room temperature for 5 days, concentrated under reduced pressure, combined with saturated aqueous sodium hydrogen carbonate solution and extracted with ethyl acetate. The extract was washed with saturated brine and dried. The solvent was evaporated under reduced pressure. The obtained crystals were collected by filtration, washed with diisopropyl ether and dried to give the titled compound (0.91 g, 42%).

$^1$H-NMR (CDCl$_3$) δ: 2.43 (3H, s), 7.33 (1H, d, J=5.1 Hz), 7.53 (1H, s), 8.57 (1H, d, J=4.8 Hz).

Example 138

2-(4-Methyl-2-pyridyl)-4H-1,3-benzothiazine-4-one

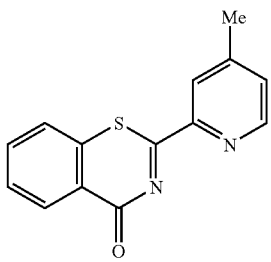

A mixture of methyl thiosalicylate (1.15 g, 6.8 mmol), 2-cyano-4-methylpyridine (0.81 g, 6.8 mmol), triethylamine (1.50 ml, 10.8 mmol) and toluene (2.0 ml) was refluxed for 8 hrs. After cooling, the precipitated crystals were collected by filtration and recrystallized from ethanol to give the titled compound (1.11 g, 64%)

mp. 199.7-199.9° C. IR (KBr): 1659, 1574, 1537, 1300, 1281 cm$^{-1}$. $^1$H-NMR (CDCl$_3$) δ: 2.48 (3H, s), 7.36 (1H, d, J=4.2 Hz), 7.60-7.72 (3H, m), 8.41 (1H, s), 8.54-8.60 (2H, m). Elemental Analysis for C$_{14}$H$_{10}$N$_2$OS Calcd. C, 66.12; H, 3.96; N, 11.02. Found C, 66.11; H, 3.70; N, 11.29.

Reference Example 36

2-(6-Chloro-2-pyridyl)-4H-1,3-benzothiazine-4-one

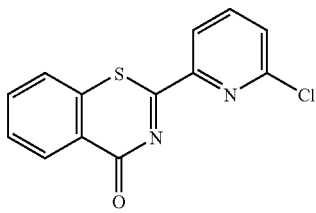

A mixture of methyl thiosalicylate (0.65 g, 3.9 mmol), 2-cyano-6-chloropyridine (0.54 g, 3.9 mmol), triethylamine (1.00 ml, 7.2 mmol) and toluene (2.0 ml) was refluxed for 6.5 hrs. After cooling, the precipitated crystals were collected by filtration and recrystallized from ethanol to give the titled compound (0.39 g, 37%).

mp. 224.3-225.0° C. IR (KBr): 1664, 1535, 1429, 1298 cm$^{-1}$. $^1$H-NMR (CDCl$_3$) δ: 7.51-7.74 (4H, m), 7.88 (1H, t, J=7.8 Hz), 8.48 (1H, d, J=7.8 Hz), 8.55 (1H, d, J=7.8 Hz). Elemental Analysis for C$_{13}$H$_7$N$_2$OSCl Calcd. C, 56.83; H, 2.57; N, 10.20. Found C, 56.80; H, 2.38; N, 10.24.

Reference Example 37

5,6,7,8-Tetrahydroquinoline N-oxide

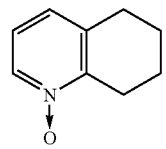

5,6,7,8-Tetrahydroquinoline (3.0 g, 22.5 mmol) was dissolved in ethyl acetate (15 ml), and 3-chloroperbenzoic acid (ca. 70%, 5.6 g, 22.5 mmol) was added thereto. The reaction mixture was stirred at room temperature for 2 days, subjected to a silica gel column chromatography and eluted with ethyl acetate-ethanol (5:1, v/v) to give the titled compound (3.4 g, 97%).

$^1$H-NMR (CDCl$_3$) δ: 1.73-1.95 (4H, m), 2.77 (2H, t, J=6.0 Hz), 2.95 (2H, t, J=6.0 Hz), 6.98-7.06 (2H, m), 8.14 (1H, d, J=5.4 Hz).

Reference Example 38

2-Cyano-5,6,7,8-tetrahydroquinoline

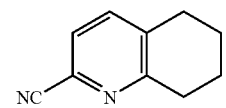

5,6,7,8-Tetrahydroquinoline N-oxide (3.0 g, 19.1 mmol) was dissolved in nitroethane (30 ml), and trimethylsilyl cyanide (2.1 g, 21.0 mmol) and N,N-dimethylcarbamoyl chloride (2.1 g, 19.1 mmol) were added thereto. The reaction mixture was stirred at room temperature for 3 days, concentrated under reduced pressure, combined with saturated aqueous sodium hydrogen carbonate solution and extracted with ethyl acetate. The extract was washed with saturated brine and dried. The solvent was evaporated under reduced pressure. The residue was subjected to a silica gel column chromatography and eluted with hexane-ethyl acetate (2:1, v/v) to give the titled compound (0.52 g, 17%).

$^1$H-NMR (CDCl$_3$) δ: 1.80-1.96 (4H, m), 2.84 (2H, t, J=6.0 Hz), 2.95 (2H, t, J=6.0 Hz), 7.40-7.48 (2H, m).

Example 139

2-(5,6,7,8-Tetrahydro-2-quinolyl)-4H-1,3-benzothiazine-4-one

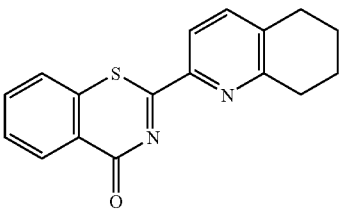

A mixture of methyl thiosalicylate (0.43 g, 2.5 mmol), 2-cyano-5,6,7,8-tetrahydroquinoline (0.40 g, 2.5 mmol), triethylamine (0.50 ml, 3.8 mmol) and toluene (2.0 ml) was refluxed for 17 hrs. After cooling, the precipitated crystals were collected by filtration and recrystallized from ethanol to give the titled compound (0.22 g, 30%)

mp. 232.3-232.8° C. IR (KBr): 1659, 1568, 1452, 1421, 1264 cm$^{-1}$. $^1$H-NMR (CDCl$_3$) δ: 1.83-2.00 (4H, m), 2.88 (2H, t, J=6.0 Hz), 3.04 (2H, t, J=6.3 Hz), 7.54-7.67 (4H, m), 8.26 (1H, d, J=7.8 Hz), 8.55 (1H, d, J=7.0 Hz). Elemental Analysis for C$_{17}$H$_{14}$N$_2$OS Calcd. C, 69.36; H, 4.79; N, 9.52. Found C, 69.32; H, 4.89; N, 9.65.

Reference Example 39

2-Cyano-6-ethylpyridine

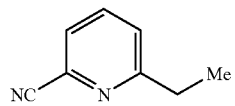

2-Ethylpyridine N-oxide (3.0 g, 24.4 mmol) was dissolved in nitroethane (30 ml), and trimethylsilyl cyanide (2.4 g, 24.0 mmol) and N,N-dimethylcarbamoyl chloride (2.4 g, 21.9 mmol) were added thereto. The reaction mixture was stirred at room temperature for 3 days, concentrated under reduced pressure, combined with saturated aqueous sodium hydrogen carbonate solution and extracted with ethyl acetate. The extract was washed with saturated brine and dried. The solvent was evaporated under reduced pressure. The residue was subjected to a silica gel column chromatography and eluted with hexane-ethyl acetate (2:1, v/v) to give the titled compound (1.0, 31%).

$^1$H-NMR (CDCl$_3$) δ: 1.32 (3H, t, J=7.5 Hz), 2.87 (2H, q, J=7.5 Hz), 7.38 (1H, d, J=7.8 Hz), 7.52 (1H, d, J=7.5 Hz), 7.73 (1H, t, J=7.8 Hz).

Example 140

2-(6-Ethyl-2-pyridyl)-4H-1,3-benzothiazine-4-one

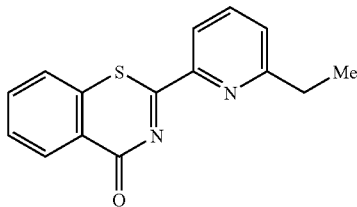

A mixture of methyl thiosalicylate (1.3 g, 7.5 mmol), 2-cyano-6-ethylpyridine (0.99 g, 7.5 mmol), triethylamine (1.60 ml, 11.5 mmol) and toluene (6.0 ml) was refluxed for 16 hrs. After cooling, the precipitated crystals were collected by filtration and recrystallized from ethanol to give the titled compound (0.45 g, 22%).

mp. 150.5-150.9° C. IR (KBr): 1653, 1572, 1533, 1439, 1306 cm$^{-1}$. $^1$H-NMR (CDCl$_3$) δ: 1.42 (3H, t, J=4.6 Hz), 2.95 (2H, q, J=7.6 Hz), 7.39 (1H, d, J=7.7 Hz), 7.59-7.70 (3H, m), 7.80 (1H, t, J=7.7 Hz), 8.35 (1H, d, J=7.7 Hz), 8.56 (1H, d, J=5.4 Hz). Elemental Analysis for C$_{15}$H$_{12}$N$_2$OS Calcd. C, 67.14; H, 4.51; N, 10.44. Found C, 67.02; H, 4.42; N, 10.35.

Reference Example 40 tert-Butyl 2-cyano-4-carbamate

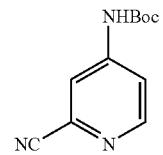

4-tert-Butoxycarbonylaminopyridine N-oxide (4.9 g, 23.1 mmol) was dissolved in nitroethane (60 ml), and trimethylsilyl cyanide (2.5 g, 25.4 mmol) and N,N-dimethylcarbamoyl chloride (2.5 g, 23.2 mmol) were added thereto. The reaction mixture was stirred at room temperature for 3 days, concentrated under reduced pressure, combined with saturated aqueous sodium hydrogen carbonate solution and extracted with ethyl acetate. The extract was washed with saturated brine and dried. The solvent was evaporated under reduced pressure. The residue was subjected to a silica gel column chromatography and eluted with hexane-ethyl acetate (2:1, v/v) to give the titled compound (1.7 g, 33%).

$^1$H-NMR (CDCl$_3$) δ: 1.54 (9H, s), 6.92 (1H, br s), 7.43 (1H, d, J=5.4 Hz), 7.86 (1H, s), 8.49 (1H, d, J=5.7 Hz).

Example 141 tert-Butyl 2-(4-oxo-4H-1,3-benzothiazin-2-yl)-4-pyridylcarbamate

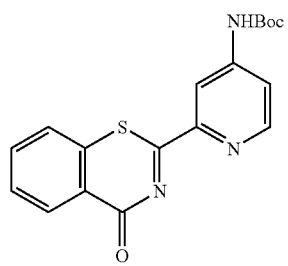

A mixture of methyl thiosalicylate (0.61 g, 3.7 mmol), 4-tert-butoxycarbonylamino-2-cyanopyridine (0.80 g, 3.7 mmol), triethylamine (0.80 ml, 5.7 mmol) and toluene (2.0 ml) was refluxed for 9 hrs. After cooling, the precipitated crystals were collected by filtration and dried to give the titled compound (0.60 g, 49%).

$^1$H-NMR (CDCl$_3$) δ: 1.54 (9H, s), 6.97 (1H, br s), 7.60-7.71 (3H, m), 8.01 (1H, d, J=3.3 Hz), 8.18 (1H, s), 8.54-8.57 (2H, m)

Example 142

2-(4-Amino-2-pyridyl)-4H-1,3-benzothiazine-4-one

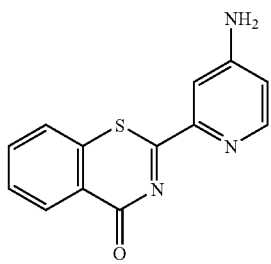

2-(4-tert-Butoxycarbonylamino-2-pyridyl)-4H-1,3-benzothiazine-4-one (100 mg, 0.28 mmol) was dissolved in trifluoroacetic acid (2.5 ml) under ice cooling condition, and the mixture was stirred for 5 hrs. The reaction mixture was combined with diisopropyl ether to precipitate crystals, which were collected by filtration, washed with diethyl ether and dried to give the titled compound (109 mg, 60%).

mp. 207.6-207.9° C. IR (KBr): 3200, 3119, 1657, 1587, 1529 cm$^{-1}$. $^1$H-NMR (DMSO-d$_6$) δ: 6.83 (1H, d, J=6.0 Hz), 7.61 (1H, s), 7.70-7.95 (3H, m), 8.17 (1H, d, J=6.0 Hz), 8.37 (1H, d, J=7.8 Hz). Elemental Analysis for C$_{13}$H$_9$N$_3$OS.H$_2$O Calcd. C, 46.45; H, 2.72; N, 10.56. Found C, 46.50; H, 2.86; N, 10.85.

Example 143

2-(4-Cyano-2-pyridyl)-4H-1,3-benzothiazine-4-one

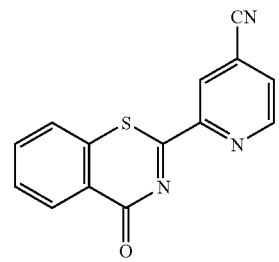

A mixture of methyl thiosalicylate (0.65 g, 3.9 mmol), 2,4-dicyanopyridine (0.50 g, 3.9 mmol), triethylamine (0.81 ml, 5.8 mmol) and toluene (2.0 ml) was refluxed for 2.5 hrs. After cooling, the precipitated crystals were collected by filtration and recrystallized from acetone-chloroform to give the titled compound (0.54 g, 53%).

mp. 283.4-283.6° C. IR (KBr): 1655, 1589, 1570, 1529, 1460, 1396 cm$^{-1}$. $^1$H-NMR (CDCl$_3$) δ: 7.63-7.78 (4H, m), 8.57 (1H, d, J=7.5 Hz), 8.80 (1H, s), 8.93 (1H, d, J=4.8 Hz). Elemental Analysis for C$_{14}$H$_7$N$_3$OS Calcd. C, 63.38; H, 2.66; N, 15.84. Found C, 63.15; H, 2.58; N, 15.63.

Reference Example 41

6-Cyano-N,N-diethylnicotinamide

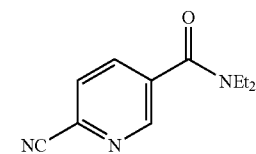

3-Diethylamidopyridine N-oxide (2.6 g, 13.5 mmol) was dissolved in nitroethane (20 ml), and trimethylsilyl cyanide (1.5 g, 14.8 mmol) and N,N-dimethylcarbamoyl chloride (1.5 g, 14.1 mmol) were added thereto. The reaction mixture was stirred at room temperature for 16 hrs, concentrated under reduced pressure, combined with saturated aqueous sodium hydrogen carbonate solution and extracted with ethyl acetate. The extract was washed with saturated brine and dried. The solvent was evaporated under reduced pressure. The residue was subjected to a silica gel column chromatography and eluted with hexane-ethyl acetate (1:1, v/v) to give the titled compound (0.36 g, 16%).

$^1$H-NMR (CDCl$_3$) δ: 1.15-1.28 (6H, m), 3.24 (2H, m), 3.57 (2H, m), 7.75 (1H, d, J=7.8 Hz), 7.85 (1H, d, J=7.8 Hz), 8.72 (1H, s).

Example 144

N,N-Diethyl-6-(4-oxo-4H-1,3-benzothiazin-2-yl)nicotinamide

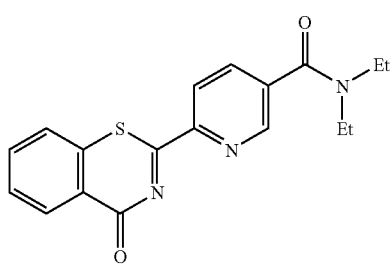

A mixture of methyl thiosalicylate (0.33 g, 2.0 mmol), 2-cyano-5-diethylamidopyridine (0.36 g, 1.8 mmol), triethylamine (0.40 ml, 2.9 mmol) and toluene (2.0 ml) was refluxed for 2.5 hrs. After cooling, the precipitated crystals were collected by filtration and recrystallized from ethanol to give the titled compound (0.34 g, 57%).

mp. 193.2-193.3° C. IR (KBr): 1661, 1626, 1537, 1439, 1284 cm$^{-1}$. $^1$H-NMR (CDCl$_3$) δ: 1.18-1.29 (6H, m), 3.31 (2H, m), 3.60 (2H, m), 7.60-7.73 (3H, m), 7.92 (1H, dd, J=1.8, 8.1 Hz), 8.58 (2H, t, J=8.4 Hz), 8.75 (1H, s). Elemental Analysis for C$_{18}$H$_{17}$N$_3$O$_2$S Calcd. C, 63.70; H, 5.05; N, 12.38. Found C, 63.53; H, 4.97; N, 12.22.

Reference Example 42

5-Acetyl-2-cyanopyridine

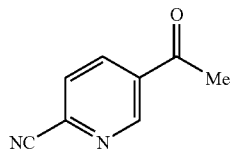

3-Acetylpyridine N-oxide (2.0 g, 14.6 mmol) was dissolved in nitroethane (20 ml), and trimethylsilyl cyanide (1.7 g, 16.7 mmol) and N,N-dimethylcarbamoyl chloride (1.8 g, 16.7 mmol) were added thereto. The reaction mixture was stirred at room temperature for 16 hrs, concentrated under reduced pressure, combined with saturated aqueous sodium hydrogen carbonate solution and extracted with ethyl acetate. The extract was washed with saturated brine and dried. The solvent was evaporated under reduced pressure. The residue was subjected to a silica gel column chromatography and eluted with hexane-ethyl acetate (3:1, v/v) to give the titled compound (0.40 g, 21%).

$^1$H-NMR (CDCl$_3$) δ: 2.67 (3H, s), 7.83 (1H, d, J=8.1 Hz), 8.36 (1H, d, J=8.1 Hz), 9.23 (1H, s).

Example 145

2-(5-Acetyl-2-pyridyl)-4H-1,3-benzothiazine-4-one

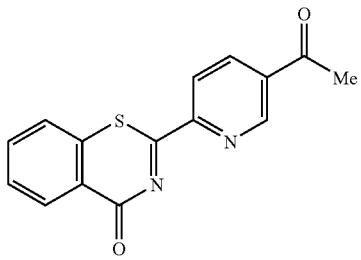

A mixture of methyl thiosalicylate (0.51 g, 3.0 mmol), 3-acetyl-2-cyanopyridine (0.40 g, 2.7 mmol), triethylamine (0.61 ml, 4.4 mmol) and toluene (2.0 ml) was refluxed for 20 hrs. After cooling, the precipitated crystals were collected by filtration and recrystallized from acetone to give the titled compound (0.30 g, 38%)

mp. 276.3-276.7° C. IR (KBr): 1684, 1651, 1589, 1537 cm$^{-1}$. $^1$H-NMR (CDCl$_3$) δ: 2.71 (3H, s), 7.63-7.75 (3H, m), 8.41 (1H, dd, J=1.8, 8.1 Hz), 8.56 (1H, d, J=8.4 Hz), 8.65 (1H, d, J=8.1 Hz), 9.25 (1H, s). Elemental Analysis for C$_{15}$H$_{10}$N$_2$O$_2$S Calcd. C, 63.81; H, 3.57; N, 9.92. Found C, 63.67; H, 3.49; N, 9.75.

Example 146

Methyl [6-(4-oxo-4H-1,3-benzothiazin-2-yl)-2-pyridyl]methanesulfonate

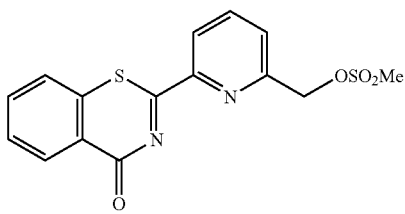

2-(6-Hydroxymethyl-2-pyridyl)-4H-1,3-benzothiazine-4-one (0.54 g, 2.0 mmol) and triethylamine (0.31 ml, 2.2 mmol) were dissolved in tetrahydrofuran (30 ml). Methanesulfonyl chloride (0.16 ml, 2.1 mmol) was added to the mixture while the mixture was stirred under ice cooling condition. The reaction mixture was stirred at room temperature for 3 hrs, diluted with water and extracted with chloroform. The extract was washed with water and dried. The solvent was evaporated under reduced pressure. The obtained crystals were recrystallized from ethanol to give the titled compound (0.64 g, 92%).

mp. 101.9-102.0° C. IR (KBr): 1653, 1591, 1570, 1531, 1439, 1348, 1300, 1277, 1170, 1022, 960, 806, 731 cm$^{-1}$. $^1$H-NMR (CDCl$_3$) δ: 3.16 (3H, s), 5.46 (2H, s), 7.61-7.74 (4H, m), 7.99 (1H, t, J=7.9 Hz), 8.53-8.57 (2H, m). Elemental Analysis for C$_{15}$H$_{12}$N$_2$O$_4$S$_2$ Calcd. C, 51.71; H, 3.47; N, 8.04. Found C, 51.88; H, 3.63; N, 8.23.

Reference Example 43 tert-Butyl (E)-3-(1-oxido-2-pyridyl)-2-propenoate

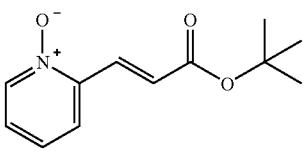

tert-Butyl (E)-3-(2-pyridyl)-2-propenoate (2.05 g, 10.0 mmol) was dissolved in ethyl acetate (10 ml), and 3-chloroperbenzoic acid (ca. 70%, 2.35 g, 10.5 mmol) was added thereto. The mixture was stirred at room temperature overnight. The reaction mixture was subjected to a silica gel (100 g) column chromatography. The fractions eluted with ethyl acetate-ethanol (5:1, v/v) were collected and concentrated to give the title compound (2.14 g, 96%).

IR (KBr): 2980, 1703, 1636, 1609, 1487, 1431, 1323, 1241, 1154 cm$^{-1}$. $^1$H-NMR (CDCl$_3$) δ: 1.53 (9H, s), 6.87 (1H, d, J=16.1 Hz), 7.22-7.28 (2H, m), 7.52 (1H, m), 7.98 (1H, d, J=16.1 Hz), 8.27 (1H, m).

Reference Example 44 tert-Butyl (E)-3-(6-cyano-2-pyridyl)-2-propenoate

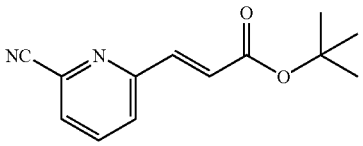

tert-Butyl (E)-3-(1-oxido-2-pyridyl)-2-propenoate (2.10 g, 9.5 mmol) was dissolved in nitroethane (10 ml), and trimethylsilyl cyanide (1.88 g, 19.0 mmol) and N,N-dimethylcarbamoyl chloride (2.04 g, 19.0 mmol) were added thereto. The reaction mixture was stirred at room temperature for 18 hrs and combined with ethyl acetate and water. The organic layer was washed with saturated aqueous sodium hydrogen carbonate solution and dried over anhydrous magnesium sulfate. The solvent was evaporated. The residue was subjected to a silica gel column chromatography. The fractions eluted with hexane-ethyl acetate (5:1, v/v) were collected and concentrated to give the titled compound (2.18 g, ca. 100%).

IR (KBr): 2980, 2253, 1713, 1647, 1582, 1471, 1370, 1319, 1152 cm$^{-1}$. $^1$H-NMR (CDCl$_3$) δ: 1.53 (9H, s), 6.93 (1H, d, J=15.6 Hz), 7.54 (1H, d, J=15.6 Hz), 7.57-7.64 (2H, m), 7.84 (1H, t, J=7.8 Hz).

Example 147 tert-Butyl (E)-3-[6-(4-oxo-4H-1,3-benzothiazin-2-yl)-2-pyridyl]-2-propenoate

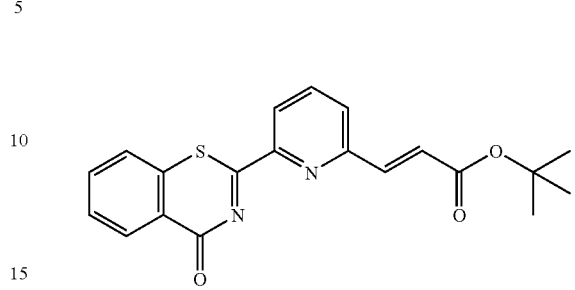

tert-Butyl (E)-3-(6-cyano-2-pyridyl)-2-propenoate (2.32 g, 10.1 mmol) and methyl thiosalicylate (1.86 g, 11.0 mmol) were dissolved in toluene (12 ml), and triethylamine (1.63 g, 25.7 mmol) was added thereto. The reaction mixture was refluxed for 38 hrs, concentrated, subjected to a silica gel column chromatography and eluted with hexane-ethyl acetate (5:2, v/v) to give the titled compound (0.78 g, 27%) as white crystals.

mp. 175.5-177.6° C. IR(KBr): 3154, 2980, 1792, 1705, 1659, 1572, 1537, 1454, 1369, 1300 cm$^{-1}$. $^1$H-NMR (CDCl$_3$) δ: 1.59 (9H, s), 7.05 (1H, d, J=15.6 Hz), 7.59-7.70 (5H, m), 7.92 (1H, t, J=7.8 Hz), 8.47-8.60 (2H, m) Elemental Analysis for C$_{20}$H$_{18}$N$_2$O$_3$S.0.25H$_2$O Calcd. C, 64.76; H, 5.03; N, 7.55. Found C, 64.64; H, 4.74; N, 7.47.

Example 148

(E)-3-[6-(4-oxo-4H-1,3-benzothiazin-2-yl)-2-pyridyl]-2-propenoic acid

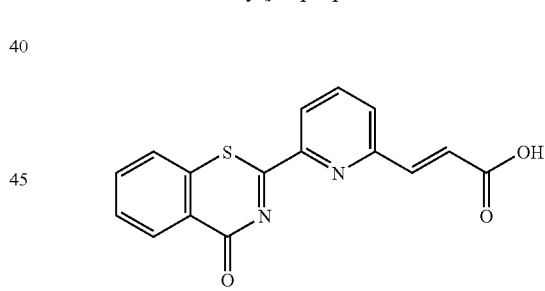

tert-Butyl (E)-3-[6-(4-oxo-4H-1,3-benzothiazin-2-yl)-2-pyridyl]-2-propenoate (0.78 g, 2.0 mmol) was dissolved in trifluoroacetic acid (4.0 ml) under ice cooling condition. The reaction mixture was stirred for 1 hr while it was warmed gradually to room temperature. The reaction mixture was concentrated under reduced pressure to precipitate crystals, which were recrystallized from methanol-diisopropyl ether to give the titled compound (0.60 g, 97%) as white crystals.

mp. 115.6-115.7° C. IR(KBr): 3214, 1715, 1647, 1572, 1534, 1443, 1385, 1308, 1225, 1101, 972 cm$^{-1}$. $^1$H-NMR (DMSO-d$_6$) δ: 7.05 (1H, d, J=15.7 Hz), 7.71-7.77 (2H, m), 7.85 (1H, m), 7.99-8.08 (2H, m), 8.18 (1H, t, J=7.7 Hz), 8.33-8.39 (2H, m). Elemental Analysis for C$_{16}$H$_{10}$N$_2$O$_3$S.0.25H$_2$O Calcd. C, 61.04; H, 3.36; N, 8.90. Found C, 61.37; H, 3.17; N, 8.94.

Example 149

2-[6-(Ethylsulfinyl)-2-pyridyl]-4H-1,3-benzothiazine-4-one

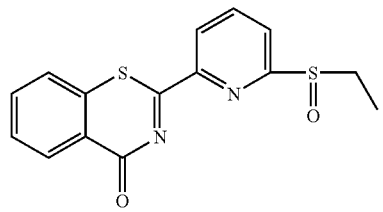

2-[6-(Ethylthio)-2-pyridyl]-4H-1,3-benzothiazine-4-one (0.10 g, 0.33 mmol) was dissolved in chloroform (50 ml). A solution of 3-chloroperbenzoic acid (ca. 77%, 0.075 g, 0.33 mmol) in chloroform (10 ml) was added dropwise to the mixture, and the mixture was stirred at room temperature for 1 hr. The solvent was evaporated and the residue was recrystallized from ethanol to give the titled compound (0.050 g, 47%) as pale yellow crystals.

mp. 181.5-182.1° C. IR(KBr): 1662, 1585, 1570, 1533, 1437, 1412, 1311, 1277, 1255, 1230, 1145, 1118, 1095, 1076, 1062, 993, 785, 758, 733 cm$^{-1}$. $^1$H-NMR (CDCl$_3$) δ: 1.29 (3H, t, J=7.3 Hz), 3.00-3.12 (1H, m), 3.25-3.37 (1H, m), 7.61-7.74 (3H, m), 8.16-8.25 (2H, m), 8.55-8.61 (2H, m). IR(KBr): 1658, 1572, 1537, 1439, 1296, 1249, 1053, 1028, 912, 746 cm$^{-1}$. Elemental Analysis for C$_{15}$H$_{12}$N$_2$O$_2$S$_2$ Calcd. C, 56.94; H, 3.82; N, 8.85. Found C, 56.88; H, 3.74; N, 8.83.

Example 150

2-[6-(Ethylsulfonyl)-2-pyridyl]-4H-1,3-benzothiazine-4-one

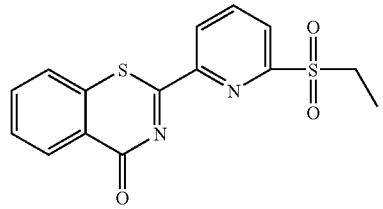

2-[6-(Ethylthio)-2-pyridyl]-4H-1,3-benzothiazine-4-one (0.10 g, 0.33 mmol) was dissolved in chloroform (30 ml). A solution of 3-chloroperbenzoic acid (ca. 77%, 0.15 g, 0.66 mmol) in chloroform (10 ml) was added dropwise to the mixture, and the mixture was stirred at room temperature for 3 hrs. The solvent was evaporated and the residue was recrystallized from ethanol to give the titled compound (0.020 g, 19%) as pale yellow crystals.

mp. 201.5-203.0° C. IR(KBr): 1662, 1585, 1570, 1533, 1437, 1412, 1311, 1277, 1255, 1230, 1145, 1118, 1095, 1076, 1062, 993, 785, 758, 733 cm$^{-1}$. $^1$H-NMR (CDCl$_3$) δ: 1.43 (3H, t, J=7.4 Hz), 3.57 (1H, q, J=7.4 Hz), 7.63-7.76 (3H, m), 8.21 (1H, t, J=7.9 Hz), 8.31-8.34 (1H, m), 8.55-8.58 (1H, m), 8.76-8.78 (1H, m). Elemental Analysis for C$_{15}$H$_{12}$N$_2$O$_3$S$_2$ Calcd. C, 54.20; H, 3.64; N, 8.43. Found C, 54.22; H, 3.63; N, 8.49.

Example 151

2-[6-(Isopropylsulfinyl)-2-pyridyl]-4H-1,3-benzothiazine-4-one

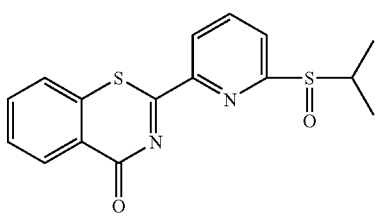

2-[6-(Isopropylthio)-2-pyridyl]-4H-1,3-benzothiazine-4-one (0.09 g, 0.29 mmol) was dissolved in chloroform (50 ml). A solution of 3-chloroperbenzoic acid (ca. 77%, 0.064 g, 0.29 mmol) in chloroform (10 ml) was added dropwise to the mixture, and the mixture was stirred at room temperature for 1 hr. The solvent was evaporated and the residue was recrystallized from ethanol to give the titled compound (0.056 g, 59%) as pale yellow crystals.

mp. 166.3-166.0° C. IR(KBr): 1666, 1572, 1537, 1435, 1298, 1246, 1298, 1246, 1095, 1055, 1028, 736 cm$^{-1}$. $^1$H-NMR (CDCl$_3$) δ: 1.11 (3H, d, J=6.8 Hz), 1.51 (3H, d, J=7.0 Hz), 3.27-3.38 (1H, m), 7.61-7.74 (3H, m), 8.15-8.22 (2H, m), 8.55-8.61 (2H, m). Elemental Analysis for C$_{16}$H$_{14}$N$_2$O$_2$S$_2$ Calcd. C, 58.16; H, 4.27; N, 8.48. Found C, 58.16; H, 4.17; N, 8.37.

Example 152

2-[6-(Isopropylsulfonyl)-2-pyridyl]-4H-1,3-benzothiazine-4-one

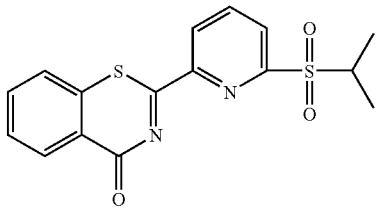

2-[6-(Isopropylthio)-2-pyridyl]-4H-1,3-benzothiazine-4-one (0.10 g, 0.32 mmol) was dissolved in chloroform (30 ml). A solution of 3-chloroperbenzoic acid (ca. 77%, 0.14 g, 0.64 mmol) in chloroform (10 ml) was added dropwise to the mixture, and the mixture was stirred at room temperature for 3 hr. The solvent was evaporated and the residue was recrystallized from ethanol to give the titled compound (0.027 g, 25%) as pale yellow crystals.

mp. 205.0-206.0° C. IR(KBr): 1662, 1570, 1535, 1439, 1298, 1118, 1095, 1062, 993, 733 cm$^{-1}$. $^1$H-NMR (CDCl$_3$) δ: 1.44 (6H, d, J=6.9 Hz), 3.87 (1H, q, J=6.9 Hz), 7.65-7.74 (3H, m), 8.20 (1H, t, J=7.8 Hz), 8.31-8.34 (1H, m), 8.56-8.58 (1H, m), 8.75-8.78 (1H, m). Elemental Analysis for C$_{16}$H$_{14}$N$_2$O$_3$S$_2$ Calcd. C, 55.47; H, 4.07; N, 8.09. Found C, 55.27; H, 4.12; N, 8.00.

Example 153

2-[6-(tert-Butylsulfinyl)-2-pyridyl]-4H-1,3-benzothiazine-4-one

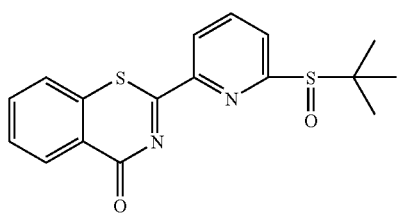

2-[6-(tert-Butylthio)-2-pyridyl]-4H-1,3-benzothiazine-one (0.15 g, 0.46 mmol) was dissolved in chloroform (30 ml), and a solution of 3-chloroperbenzoic acid (ca. 77%, 0.10 g, 0.46 mmol) in chloroform (10 ml) was added dropwise thereto. The reaction mixture was stirred at room temperature for 1 hr. The solvent was evaporated, and the residue was recrystallized from ethanol to give the titled compound (0.12 g, 75%) as white crystals.

mp. 180.5° C. (decomposed) IR(KBr): 1666, 1572, 1537, 1433, 1298, 1244, 1095, 1047, 736 cm$^{-1}$. $^1$H-NMR (CDCl$_3$) δ: 1.32 (9H, s), 7.63-7.71 (3H, m), 8.14 (1H, t, J=7.9 Hz), 8.22-8.25 (1H, m), 8.55-8.62 (2H, m). Elemental Analysis for C$_{17}$H$_{16}$N$_2$O$_2$S$_2$ Calcd. C, 59.28; H, 4.68; N, 8.13. Found C, 59.14; H, 4.84; N, 8.17.

Example 154

2-[6-(tert-Butylsulfonyl)-2-pyridyl]-4H-1,3-benzothiazine-4-one

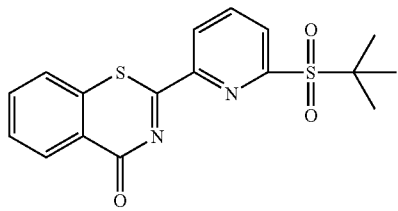

2-[6-(tert-Butylthio)-2-pyridyl]-4H-1,3-benzothiazine-4-one (0.15 g, 0.46 mmol) was dissolved in chloroform (50 ml), and a solution of 3-chloroperbenzoic acid (ca. 77%, 0.21 g, 0.92 mmol) in chloroform (10 ml) was added dropwise thereto. The reaction mixture was stirred at room temperature for 3 hrs. The solvent was evaporated and the residue was recrystallized from ethanol to give the titled compound (0.11 g, 67%) as pale yellow crystals.

mp. 233.6-234.7° C. IR(KBr): 1657, 1572, 1529, 1466, 1433, 1298, 1248, 1105, 1064, 993, 748 cm$^{-1}$. $^1$H-NMR (CDCl$_3$) δ: 1.52 (9H, s), 7.64-7.75 (3H, m), 8.19 (1H, t, J=7.9 Hz), 8.33-8.35 (1H, m), 8.55-8.58 (1H, m), 8.76-8.79 (1H, m). Elemental Analysis for C$_{17}$H$_{16}$N$_2$O$_3$S$_2$ Calcd. C, 56.65; H, 4.47; N, 7.77. Found C, 56.71; H, 4.34; N, 7.83.

Example 155

2-[6(n-Pentylsulfinyl)-2-pyridyl]-4H-1,3-benzothiazine-4-one

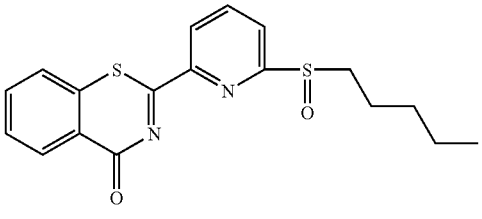

2-[6-(n-Pentylthio)-2-pyridyl]-4H-1,3-benzothiazine-4-one (0.15 g, 0.44 mmol) was dissolved in chloroform (50 ml), and a solution of 3-chloroperbenzoic acid (ca. 77%, 0.10 g, 0.46 mmol) in chloroform (10 ml) was added dropwise thereto. The reaction mixture was stirred at room temperature for 1 hr. The solvent was evaporated, and the residue was recrystallized from ethanol to give the titled compound (0.075 g, 48%) as white crystals.

mp. 146.0-147.0° C. IR(KBr): 1660, 1572, 1537, 1433, 1298, 1242, 1093, 1039, 1028, 991, 748 cm$^{-1}$. $^1$H-NMR (CDCl$_3$) δ: 0.90 (3H, t, J=7.0 Hz), 1.33-1.49 (5H, m), 1.90-1.99 (1H, m), 2.97-3.06 (1H, m), 3.17-3.27 (1H, m), 7.61-7.74 (3H, m), 8.13-8.26(2H, m), 8.58 (2H, t, J=8.1 Hz). Elemental Analysis for C$_{18}$H$_{18}$N$_2$O$_2$S$_2$ Calcd. C, 60.31; H, 5.06; N, 7.81. Found C, 60.01; H, 5.01; N, 7.82.

Example 156

2-[6-(n-Pentylsulfonyl)-2-pyridyl]-4H-1,3-benzothiazine-4-one

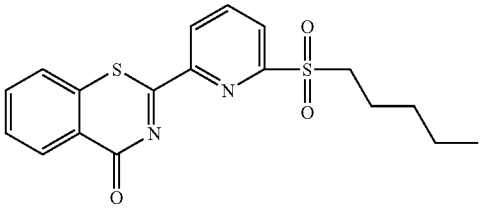

2-[6-(n-Pentylthio)-2-pyridyl]-4H-1,3-benzothiazine-4-one (0.30 g, 0.88 mmol) was dissolved in chloroform (50 ml), and a solution of 3-chloroperbenzoic acid (ca. 77%, 0.39 g, 1.75 mmol) in chloroform (10 ml) was added dropwise thereto. The reaction mixture was stirred at room temperature for 3 hrs. The solvent was evaporated, and the residue was recrystallized from ethanol to give the titled compound (0.15 g, 44%) as white crystals.

mp. 160.0-161.0° C. IR(KBr): 1660, 1587, 1572, 1537, 1462, 1439, 1408, 1302, 1278, 1249, 1095, 1064, 1028, 993, 752 cm$^{-1}$. $^1$H-NMR (CDCl$_3$) δ: 0.90 (3H, t, J=7.1 Hz), 1.32-1.51 (4H, m), 1.81-1.91(2H, m), 3.50-3.55 (2H, m), 7.65-7.74 (3H, m), 8.21 (1H, t, J=7.8 Hz), 8.30-8.33(1H, m), 8.56-8.59 (1H, m) 8.75-8.78 (1H, m). Elemental Analysis for C$_{18}$H$_{18}$N$_2$O$_3$S$_2$ Calcd. C, 57.73; H, 4.84; N, 7.48. Found C, 57.75; H, 4.87; N, 7.51.

Example 157

2-(6-Isoamylsulfinyl-2-pyridyl)-4H-1,3-benzothiazine-4-one

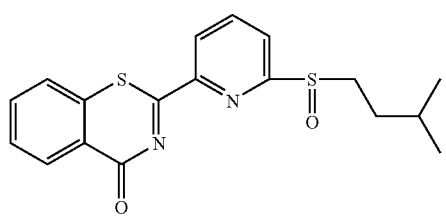

2-[6-(Isoamylthio)-2-pyridyl]-4H-1,3-benzothiazine-4-one (0.15 g, 0.44 mmol) was dissolved in chloroform (50 ml), and a solution of 3-chloroperbenzoic acid (ca. 77%, 0.10 g, 0.46 mmol) in chloroform (10 ml) was added dropwise thereto. The reaction mixture was stirred at room temperature for 1 hr. The solvent was evaporated, and the residue was recrystallized from hexane-ethyl acetate to give the titled compound (0.15 g, 96%) as pale yellow amorphous.

mp. 59.5-61.0° C. $^1$H-NMR (CDCl$_3$) δ: 0.94 (6H, t, J=6.8 Hz), 1.37-1.47 (1H, m) 1.74-1.77 (1H, m), 1.83-1.91 (1H, m), 3.01-3.09 (1H, m), 3.21-3.29 (1H, m), 7.61-7.74 (3H, m), 8.16 (2H, t, J=7.8 Hz), 8.24-8.26(1H, m), 8.56-8.61 (2H, m). IR(KBr): 1666, 1591, 1572, 1537, 1437, 1300, 1246, 1126, 1095, 1049, 1030, 993, 743 cm$^{-1}$. Fab Mass(M+1)=359.0 (theoretical value)=359.1

Example 158

2-(6-Isoamylsulfonyl-2-pyridyl)-4H-1,3-benzothiazine-4-one

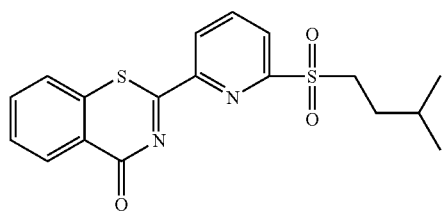

2-(6-Isoamylthio-2-pyridyl)-4H-1,3-benzothiazine-4-one (0.30 g, 0.88 mmol) was dissolved in chloroform (50 ml), and a solution of 3-chloroperbenzoic acid (ca. 77%, 0.39 g, 1.75 mmol) in chloroform (10 ml) was added dropwise thereto. The reaction mixture was stirred at room temperature for 3 hrs. The solvent was evaporated, and the residue was recrystallized from ethanol to give the titled compound (0.10 g, 31%) as pale yellow crystals.

mp. 145.5-147.0° C. IR(KBr): 1666, 1591, 1572, 1537, 1440, 1302, 1126, 1095, 1062, 1030, 995, 743 cm$^{-1}$. $^1$H-NMR (CDCl$_3$) δ: 0.96 (6H, d, J=5.8 Hz), 1.71-1.75 (2H, m) 3.52-3.57 (2H, m), 7.63-7.76 (3H, m), 8.21 (1H, t, J=7.7 Hz), 8.30-8.33(1H, m), 8.55-8.59 (1H, m), 8.77 (1H, d, J=7.8 Hz). Elemental Analysis for C$_{18}$H$_{18}$N$_2$O$_3$S$_2$ Calcd. C, 57.73; H, 4.84; N, 7.48. Found C, 57.63; H, 4.86; N, 7.51.

Reference Example 45

2-Benzylthio-6-cyanopyridine

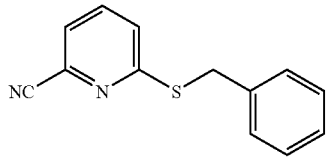

Benzyl mercaptan (0.99 g, 7.94 mmol) and sodium hydride (60% in oil, 0.35 g, 8.66 mmol) were added to THF (30 ml), and the mixture was stirred at room temperature for 1 hr. A solution of 2-chloro-6-cyanopyridine (1.00 g, 7.22 mmol) in THF (10 ml) was added dropwise to the reaction mixture, and the mixture was stirred at room temperature for 18 hrs. The reaction mixture was combined with ethyl acetate and brine. The organic layer was washed with saturated brine and dried over anhydrous magnesium sulfate. The solvent was evaporated to give the titled compound (1.63 g, 100%) as a pale pink oil.

IR(KBr): 2233, 1574, 1494, 1452, 1427, 1271, 1159, 1141, 912, 794 cm$^{-1}$. $^1$H-NMR (CDCl$_3$) δ: 4.42 (2H, s), 7.25-7.43 (7H, m), 7.54 (1H, t, J=7.9 Hz).

Example 159

2-(6-Benzylthio-2-pyridyl)-4H-1,3-benzothiazine-4-one

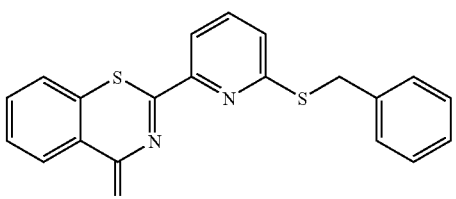

2-Benzylthio-6-cyanopyridine (1.63 g, 7.22 mmol) and methyl thiosalicylate (1.21 g, 7.22 mmol) were dissolved in toluene (30 ml), and triethylamine (1.52 ml, 10.8 mmol) was added thereto. The reaction mixture was refluxed for 48 hrs. The solvent was evaporated and the residue was recrystallized from ethanol to give the titled compound (1.03 g, 44%) as white crystals.

mp. 227.0-228.0° C. IR(KBr): 1651, 1572, 1537, 1431, 1302, 1288, 1234, 1147, 1097, 1066, 987, 972, 794 cm$^{-1}$. $^1$H-NMR (CDCl$_3$) δ: 4.62 (2H, s), 7.25-7.39 (4H, m), 7.48-7.51 (2H, m), 7.60-7.70 (4H, m), 8.22-8.24 (1H, m), 8.54-8.56 (1H, m) Elemental Analysis for C$_{20}$H$_{14}$N$_2$OS$_2$ Calcd. C, 66.27; H, 3.86; N, 7.73. Found C, 66.06; H, 3.92; N, 7.69.

Example 160

2-(6-Benzylsulfinyl-2-pyridyl)-4H-1,3-benzothiazine-4-one

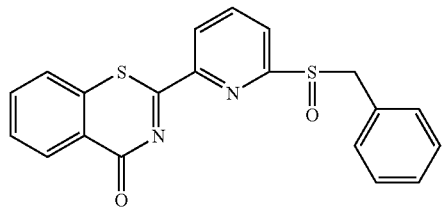

2-(6-Benzylthio-2-pyridyl)-4H-1,3-benzothiazine-4-one (0.18 g, 0.50 mmol) was dissolved in chloroform (30 ml), and a solution of 3-chloroperbenzoic acid (ca. 77%, 0.11 g, 0.50 mmol) in chloroform (10 ml) was added dropwise thereto. The reaction mixture was stirred at room temperature for 1 hr. The solvent was evaporated, and the residue was recrystallized from ethanol to give the titled compound (0.057 g, 30%) as pale yellow crystals.

mp. 208.5-210.0° C. IR(KBr): 1660, 1572, 1537, 1435, 1298, 1246, 1095, 1051, 1030, 912, 733 cm$^{-1}$. $^1$H-NMR (CDCl$_3$) δ: 4.22, 4.47 (2H, q$_{AB}$, J=13.2 Hz), 6.99-7.03 (2H, m), 7.22-7.26 (3H, m), 7.67-7.72 (3H, m), 7.79-7.82 (1H, m), 7.97 (1H, t, J=7.8 Hz), 8.53-8.57 (2H, m) Elemental Analysis for C$_{20}$H$_{14}$N$_2$O$_2$S$_2$.0.25H$_2$O Calcd. C, 62.73; H, 3.82; N, 7.31. Found C, 62.68; H, 3.88; N, 7.32.

Example 161

2-[6-(Benzylsulfonyl)-2-pyridyl]-4H-1,3-benzothiazine-4-one

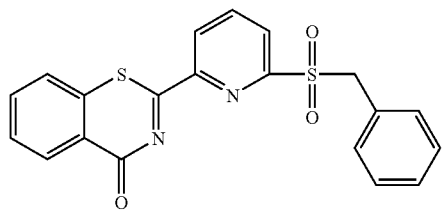

2-[6-(Benzylthio)-2-pyridyl]-4H-1,3-benzothiazine-4-one (0.30 g, 0.83 mmol) was dissolved in chloroform (30 ml), and a solution of 3-chloroperbenzoic acid (ca. 70%, 0.41 g, 1.66 mmol) in chloroform (10 ml) was added dropwise thereto. The reaction mixture was stirred at room temperature for 3 hrs. The solvent was evaporated, and the residue was recrystallized from ethanol to give the titled compound (0.10 g, 30%) as pale yellow crystals.

mp. 217.0-218.0° C. IR(KBr): 1660, 1570, 1531, 1439, 1300, 1168, 1116, 1095, 1062, 1030, 993, 733 cm$^{-1}$. $^1$H-NMR (CDCl$_3$) δ: 4.79 (2H, s), 7.22-7.28 (5H, m), 7.70-7.76 (3H, m), 8.03-8.06 (2H, m), 8.58-8.60 (1H, m), 8.70-8.73 (1H, m). Elemental Analysis for C$_{20}$H$_{14}$N$_2$O$_3$S$_2$ Calcd. C, 60.90; H, 3.58; N, 7.10. Found C, 60.78; H, 3.87; N, 7.22.

Example 162

2-[6-(2-Phenylethylsulfinyl)-2-pyridyl]-4H-1,3-benzothiazine-4-one

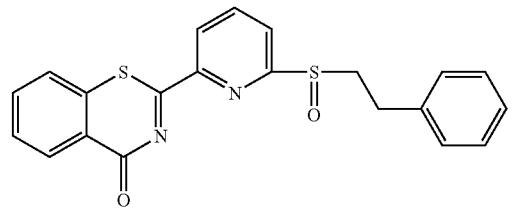

2-[6-(Phenylethylthio)-2-pyridyl]-4H-1,3-benzothiazine-4-one (0.18 g, 0.48 mmol) was dissolved in chloroform (30 ml), and a solution of 3-chloroperbenzoic acid (ca. 77%, 0.11 g, 0.48 mmol) in chloroform (10 ml) was added dropwise thereto. The reaction mixture was stirred at room temperature for 1 hr. The solvent was evaporated, and the residue was recrystallized from ethanol to give the titled compound (0.14 g, 75%) as pale yellow crystals.

mp. 164.5-165.5° C. IR(KBr): 1664, 1572, 1537, 1433, 1298, 1246, 1095, 1049, 1030, 912, 746 cm$^{-1}$. $^1$H-NMR (CDCl$_3$) δ: 2.89-2.94 (1H, m), 3.23-3.39 (2H, m), 3.48-3.53 (1H, m), 7.18-7.24 (5H, m), 7.63-7.72 (3H, m), 8.14 (1H, t, J=7.8 Hz), 8.23-8.26 (1H, m), 8.55-8.59 (2H, m). Elemental Analysis for C$_{21}$H$_{16}$N$_2$O$_2$S$_2$ Calcd. C, 64.26; H, 4.11; N, 7.14. Found C, 63.99; H, 4.00; N, 7.07.

Example 163

2-[6-(2-Phenylethyl)sulfonyl-2-pyridyl]-4H-1,3-benzothiazine-4-one

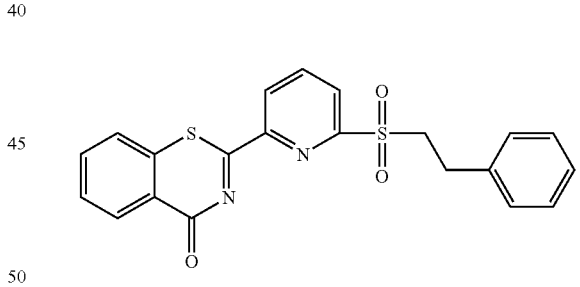

2-[6-(2-Phenylethyl)thio-2-pyridyl]-4H-1,3-benzothiazine-4-one (0.30 g, 0.80 mmol) was dissolved in chloroform (30 ml), and a solution of 3-chloroperbenzoic acid (ca. 70%, 0.39 g, 1.59 mmol) in chloroform (10 ml) was added dropwise thereto. The reaction mixture was stirred at room temperature for 3 hrs. The solvent was evaporated, and the residue was recrystallized from hexane-ethyl acetate to give the titled compound (0.014 g, 4%) as pale yellow crystals.

mp. 161.5-163.5° C. IR(KBr): 1653, 1568, 1558, 1531, 1437, 1302, 1168, 1118, 1095, 1062, 1030, 993, 742 cm$^{-1}$. $^1$H-NMR (CDCl$_3$) δ: 3.17-3.23 (2H, m), 3.84-3.89 (2H, m), 7.17-7.33 (5H, m), 7.61-7.74 (3H, m), 8.14 (1H, t, J=7.7 Hz), 8.23-8.26 (1H, m), 8.58 (1H, d, J=7.5 Hz), 8.71 (1H, d, J=7.8 Hz). Elemental Analysis for C$_{21}$H$_{16}$N$_2$O$_3$S$_2$.0.5H$_2$O Calcd. C, 60.41; H, 4.10; N, 6.70. Found C, 60.58; H, 4.06; N, 6.60.

Reference Example 46

2-Cyano-6-(3-phenylpropylthio)pyridine

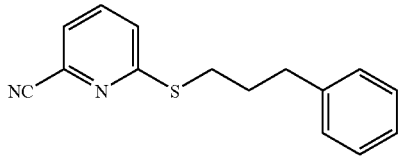

3-Phenylpropylmercaptan (1.21 g, 7.94 mmol) and sodium hydride (60%, 0.35 g, 8.66 mmol) were added to THF (30 ml), and the mixture was stirred at room temperature for 1 hr. A solution of 2-chloro-6-cyanopyridine (1.00 g, 7.22 mmol) in THF (10 ml) was added dropwise to the mixture and the mixture was stirred at room temperature for 18 hrs. The reaction mixture was combined with ethyl acetate and water. The organic layer was washed with saturated brine and dried over anhydrous magnesium sulfate. The solvent was evaporated to give the titled compound (1.84 g, 100%).

IR(KBr): 2233, 1693, 1576, 1556, 1494, 1485, 1452, 1427, 1377, 1278, 1143, 978, 796 cm$^{-1}$. $^1$H-NMR (CDCl$_3$) δ: 2.00-2.10 (2H, m), 2.77 (2H, t, J=7.3 Hz), 3.18 (2H, t, J=7.16 Hz), 7.16-7.35 (5H, m), 7.53 (1H, t, J=7.6 Hz).

Example 164

2-[6-(3-Phenylpropylthio)-2-pyridyl]-4H-1,3-benzothiazine-4-one

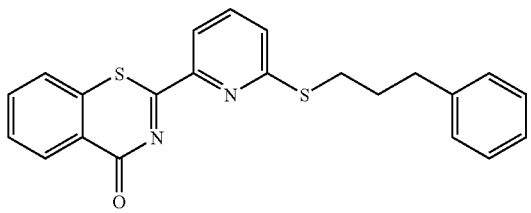

2-Cyano-6-(3-phenylpropylthio)pyridine (1.84 g, 7.22 mmol) and methyl thiosalicylate (1.21 g, 7.22 mmol) were dissolved in toluene (30 ml), and triethylamine (1.52 ml, 10.8 mmol) was added thereto. The reaction mixture was refluxed for 48 hrs. The solvent was evaporated and the residue was recrystallized from ethanol to give the titled compound (1.06 g, 38%) as pale yellow crystals.

mp. 192.5-194.0° C. IR(KBr): 1647, 1639, 1570, 1525, 1431, 1298, 1238, 1145, 1095, 1064, 985, 970, 742 cm$^{-1}$. $^1$H-NMR (CDCl$_3$) δ: 2.14-2.24 (2H, m), 2.89 (2H, t, J=7.4 Hz), 3.35 (2H, t, J=7.4 Hz), 7.22-7.28(5H, m), 7.36-7.39 (1H, m), 7.57-7.69 (1H, m), 8.18-8.21 (1H, m), 8.54-8.57 (1H, m). Elemental Analysis for C$_{22}$H$_{18}$N$_2$OS$_2$ Calcd. C, 67.66; H, 4.65; N, 7.17. Found C, 67.58; H, 4.67; N, 7.21.

Example 165

2-[6-[(3-Phenylpropyl)sulfinyl]-2-pyridyl]-4H-1,3-benzothiazine-4-one

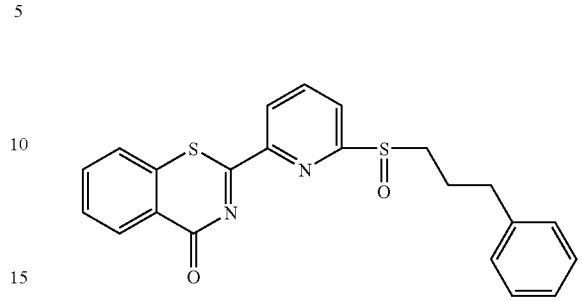

2-[6-(3-Phenylpropyl)thio-2-pyridyl]-4H-1,3-benzothiazine-4-one (0.20 g, 0.50 mmol) was dissolved in chloroform (30 ml), and a solution of 3-chloroperbenzoic acid (ca. 70%, 0.11 g, 0.50 mmol) in chloroform (10 ml) was added dropwise thereto. The reaction mixture was stirred at room temperature for 1 hr. The solvent was evaporated, and the residue was recrystallized from ethanol to give the titled compound (0.063 g, 31%) as pale yellow crystals.

mp. 164.5-165.5° C. IR(KBr): 1658, 1572, 1537, 1433, 1400, 1298, 1246, 1095, 1051, 1030, 912, 746 cm$^{-1}$. $^1$H-NMR (CDCl$_3$) δ: 1.91-1.96 (1H, m), 2.31-2.34 (1H, m), 2.76-2.85 (2H, m), 3.01-3.07 (1H, m), 3.23-3.31 (1H, m), 7.13-7.26 (5H, m), 7.52-7.75 (3H, m), 8.12-8.24 (2H, m), 8.56-8.59 (2H, m). Elemental Analysis for C$_{22}$H$_{18}$N$_2$O$_2$S$_2$.0.5H$_2$O Calcd. C, 63.59; H, 4.61; N, 6.74. Found C, 63.33; H, 4.58; N, 6.78.

Example 166

2-[6-[(3-Phenylpropyl)sulfonyl]-2-pyridyl]-4H-1,3-benzothiazine-4-one

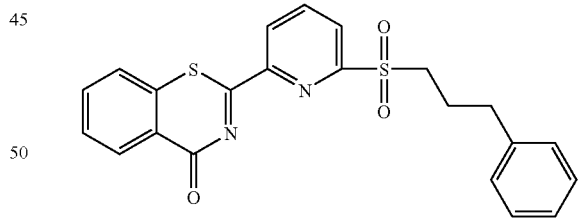

2-[6-(3-Phenylpropyl)thio-2-pyridyl]-4H-1,3-benzothiazine-4-one (0.30 g, 0.77 mmol) was dissolved in chloroform (30 ml), and a solution of 3-chloroperbenzoic acid (ca. 70%, 0.38 g, 1.54 mmol) in chloroform (10 ml) was added dropwise thereto. The reaction mixture was stirred at room temperature for 3 hrs. The solvent was evaporated, and the residue was recrystallized from n-hexane-ethyl acetate to give the titled compound (0.063 g, 19%) as pale yellow crystals.

mp. 149.5-151.0° C. IR(KBr): 1658, 1572, 1535, 1439, 1300, 1118, 1095, 1062, 993, 912, 746 cm$^{-1}$. $^1$H-NMR (CDCl$_3$) δ: 2.15-2.25 (2H, m), 2.81 (2H, t, J=6.4 Hz), 3.50-3.55 (2H, m), 7.13-7.16 (3H, m), 7.22-7.26 (3H, m), 7.58-7.61(1H, m), 7.68-7.75 (2H, m), 8.19 (1H, t, J=7.8 Hz), 8.30

(1H, d, J=7.7 Hz), 8.56-8.59 (1H, m), 8.75 (1H, d, J=7.8 Hz). Elemental Analysis for $C_{22}H_{18}N_2O_3S_2 \cdot 0.25H_2O$ Calcd. C, 61.88; H, 4.36; N, 6.56. Found C, 62.01; H, 4.25; N, 6.60.

Example 167

2-(6-Methylthiomethyl-2-pyridyl)-4H-1,3-benzothiazine-4-one

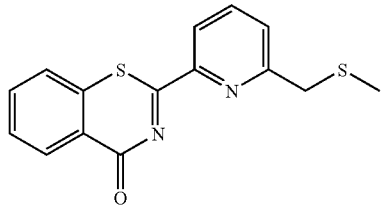

[6-(4-Oxo-4H-1,3-benzothiazin-2-yl)-2-pyridyl]methanesulfonate (0.55 g, 1.58 mmol) was dissolved in DMF (30 ml), and sodium thiomethoxide (0.13 g, 1.74 mmol) was added thereto. The mixture was stirred at 70° C. for 3 hrs. The reaction mixture was combined with ethyl acetate and water. The organic layer was washed with saturated brine and dried over anhydrous magnesium sulfate. The solvent was evaporated. The residue was recrystallized from ethanol to give the titled compound (0.35 g, 75%) as pale yellow crystals.

mp. 151.5-153.0° C. IR(KBr): 1658, 1589, 1572, 1531, 1439, 1300, 1277, 1234, 1095, 993, 744 cm$^{-1}$. $^1$H-NMR (CDCl$_3$) δ: 2.17 (3H, s), 3.90 (2H, s), 7.59-7.74(4H, m), 7.88 (1H, t, J=7.8 Hz), 8.42 (1H, d, J=7.7 Hz), 8.56 (1H, d, J=8.5 Hz). Elemental Analysis for $C_{15}H_{12}N_2OS_2$ Calcd. C, 59.97; H, 4.03; N, 9.33. Found C, 59.87; H, 3.94; N, 9.39.

Example 168

2-(6-Methylsulfinylmethyl-2-pyridyl)-4H-1,3-benzothiazine-4-one

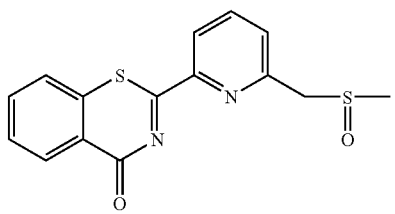

2-(6-Methylthiomethyl-2-pyridyl)-4H-1,3-benzothiazine-4-one (0.10 g, 0.33 mmol) was dissolved in chloroform (50 ml), and a solution of 3-chloroperbenzoic acid (ca. 77%, 0.075 g, 0.33 mmol) in chloroform (10 ml) was added dropwise thereto. The reaction mixture was stirred at room temperature for 1 hr. The solvent was evaporated, and the residue was recrystallized from ethyl acetate to give the titled compound (0.052 g, 50%) as pale yellow crystals.

mp. 184.5-185.5° C. IR(KBr): 1651, 1568, 1531, 1454, 1435, 1298, 1278, 1234, 1095, 1028, 995, 744 cm$^{-1}$. $^1$H-NMR (CDCl$_3$) δ: 2.68 (3H, s), 4.21, 4.32 (2H, q$_{AB}$, J=12.8 Hz), 7.59-7.70 (4H, m), 7.94 (1H, t, J=7.8 Hz), 8.51-8.57 (2H, m) Elemental Analysis for $C_{15}H_{12}N_2O_2S_2 \cdot 0.25H_2O$ Calcd. C, 56.14; H, 3.92; N, 8.73. Found C, 56.43; H, 3.74; N, 8.86.

Example 169

2-(6-Methylsulfonylmethyl-2-pyridyl)-4H-1,3-benzothiazine-4-one

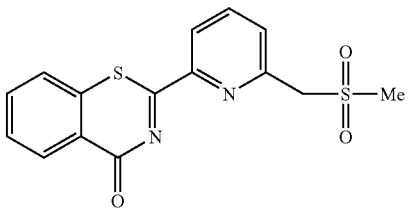

2-(6-Methylthiomethyl-2-pyridyl)-4H-1,3-benzothiazine-4-one (0.12 g, 0.40 mmol) was dissolved in chloroform (50 ml), and a solution of 3-chloroperbenzoic acid (ca. 77%, 0.18 g, 0.80 mmol) in chloroform (10 ml) was added dropwise thereto. The reaction mixture was stirred at room temperature for 3 hrs. The solvent was evaporated, and the residue was recrystallized from ethanol to give the titled compound (0.065 g, 49%) as white crystals.

mp. 230.5-231.5° C. IR(KBr): 1655, 1570, 1533, 1439, 1302, 1114, 1097, 995, 738 cm$^{-1}$. $^1$H-NMR (CDCl$_3$) δ: 3.05 (3H, s), 4.55 (2H, s), 7.60-7.74 (4H, m) 8.00 (1H, t, J=7.7 Hz), 8.54-8.59 (2H, m). Elemental Analysis for $C_{15}H_{12}N_2O_3S_2$ Calcd. C, 54.20; H, 3.64; N, 8.43. Found C, 53.95; H, 3.62; N, 8.38.

Example 170

2-[6-(4-Morpholinomethyl)-2-pyridyl]-4H-1,3-benzothiazine-4-one

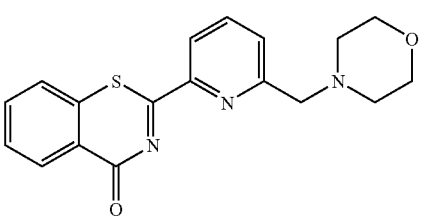

[6-(4-Oxo-4H-1,3-benzothiazin-2-yl)-2-pyridyl]methanesulfonate (0.10 g, 0.29 mmol) was dissolved in DMF (30 ml), and triethylamine (0.07 ml, 0.48 mmol) and morpholine (0.028 g, 0.32 mmol) were added thereto. The reaction mixture was stirred at 70° C. for 9 hrs and combined with ethyl acetate and water. The organic layer was washed with brine and dried over anhydrous magnesium sulfate. The solvent was evaporated and the residue was recrystallized from ethanol to give the titled compound (0.052 g, 53%) as white crystals.

mp. 191.8° C. (decomposed) IR(KBr): 1660, 1591, 1572, 1537, 1439, 1294, 1267, 1234, 1114, 1097, 1066, 995, 738 cm$^{-1}$. $^1$H-NMR (CDCl$_3$) δ: 2.59-2.62 (4H, m), 3.71-3.79 (4H, m), 3.81 (2H, s), 7.60-7.73 (4H, m), 7.88 (1H, t, J=7.7 Hz), 8.42 (1H, d, J=7.7 Hz), 8.54-8.57 (1H, m). Elemental Analysis for $C_{18}H_{17}N_3O_2S$ Calcd. C, 63.70; H, 5.05; N, 12.38. Found C, 63.96; H, 5.21; N, 12.14.

Reference Example 47

5-Cyano-2-methylthiopyridine

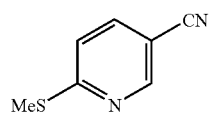

2-Chloro-5-cyanopyridine (2.10 g, 15.1 mmol) and sodium thiomethoxide (1.16 g, 16.5 mmol) were added to THF (30 ml). The reaction mixture was refluxed for 9 hrs and combined with ethyl acetate and water. The organic layer was washed with saturated brine and dried over anhydrous magnesium sulfate. The solvent was evaporated to give the titled compound (2.26 g, 100%) as pale yellow crystals.

IR(KBr): 2229, 1585, 1533, 1460, 1363, 1113, 912, 742 cm$^{-1}$. $^1$H-NMR (CDCl$_3$) δ: 2.59 (3H, s), 7.24-7.27 (1H, m), 7.64-7.67 (1H, m), 8.66-8.67 (1H, m).

Example 171

2-[6-(Methylthio)-3-pyridyl]-4H-1,3-benzothiazine-4-one

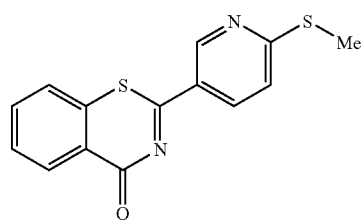

5-Cyano-2-methylthiopyridine (2.26 g, 15.0 mmol) and methyl thiosalicylate (5.05 g, 30.0 mmol) were dissolved in toluene (100 ml), and triethylamine (6.3 ml, 45.0 mmol) was added thereto. The reaction mixture was refluxed for 48 hrs. The solvent was evaporated. The residue was recrystallized from ethanol to give the titled compound (1.30 g, 31%) as pale yellow crystals.

mp. 167.9-169.9° C. IR(KBr): 1658, 1581, 1571, 1516, 1460, 1439, 1361, 1288, 1263, 1236, 1155, 1122, 1095, 1062, 1032, 925, 736 cm$^{-1}$. $^1$H-NMR (CDCl$_3$) δ: 2.64 (3H, s), 7.32 (1H, d, J=8.6 Hz), 7.54-7.72 (3H, m), 8.28-8.32 (1H, m), 8.54 (1H, d, J=7.6 Hz), 9.18 (1H, d, J=2.0 Hz). Elemental Analysis for C$_{14}$H$_{10}$N$_2$OS$_2$ Calcd. C, 58.72; H, 3.52; N, 9.78. Found C, 58.75; H, 3.81; N, 9.90.

Example 172

2-(1H-Indol-3-yl)-4H-1,3-benzothiazine-4-one

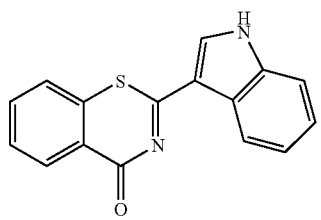

3-Cyanoindole (1.00 g, 7.0 mmol) and methyl thiosalicylate (1.20 g, 7.0 mmol) were dissolved in toluene (10 ml), and triethylamine (1.5 ml, 10.4 mmol) was added thereto. The reaction mixture was refluxed for 24 hrs. The solvent was evaporated. The residue was recrystallized from ethanol to give the titled compound (0.38 g, 20%) as pale yellow crystals.

mp. 276.5-277.0° C. IR(KBr): 1626, 1591, 1516, 1493, 1454, 1439, 1356, 1329, 1300, 1261, 1242, 1143, 1107, 1086, 1068, 908, 817, 729 cm$^{-1}$. $^1$H-NMR (CDCl$_3$) δ: 7.28-7.31 (2H, m), 7.53-7.56 (1H, m), 7.61-7.66 (1H, m), 7.71-7.75 (2H, m), 8.31 (1H, d, J=7.6 Hz), 8.49-8.51 (1H, m), 8.55 (1H, d, J=3.0 Hz), 12.41 (1H, br s). Elemental Analysis for C$_{16}$H$_{10}$N$_2$OS Calcd. C, 69.04; H, 3.62; N, 10.06. Found C, 68.91; H, 3.78; N, 10.22.

Example 173 tert-Butyl 3-[6-(7-methoxy-4-oxo-4H-1,3-benzothiazin-2-yl)-2-pyridyl]propanoate

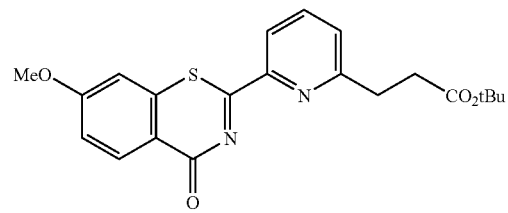

2-Mercapto-4-methoxybenzoic acid (1.26 g, 6.8 mmol) and tert-butyl 3-(6-cyano-2-pyridyl)propanoate (1.21 g, 5.2 mmol) were dissolved in pyridine (10 ml), and the reaction mixture was refluxed for 24 hrs. The reaction mixture was concentrated under reduced pressure, subjected to a silica gel column chromatography, eluted with hexane-ethyl acetate (1:1, v/v) and recrystallized from ethyl acetate-hexane to give the titled compound (0.96 g, 46%)

mp. 134.5-135.4° C. IR (KBr): 2976, 1724, 1658, 1599, 1570, 1537, 1249, 1149, 1095 cm$^{-1}$. $^1$H-NMR (CDCl$_3$) δ:

1.42 (9H, s), 2.88 (2H, t, J=7.3 Hz), 3.19 (2H, t, J=7.3 Hz), 3.93 (3H, s), 7.03 (1H, d, J=2.4 Hz), 7.15 (1H, dd, J=2.4, 8.8 Hz), 7.41 (1H, d, J=7.5 Hz), 7.79 (1H, dd, J=7.5, 7.5 Hz), 8.35 (1H, d, J=7.5 Hz), 8.47 (1H, d, J=8.8 Hz). Elemental Analysis for C$_{21}$H$_{22}$N$_2$O$_4$S Calcd. C, 63.30; H, 5.56; N, 7.03. Found C, 63.28; H, 5.52; N, 7.01.

Example 174

3-[6-(7-Methoxy-4-oxo-4H-1,3-benzothiazin-2-yl)-2-pyridyl]propionic acid

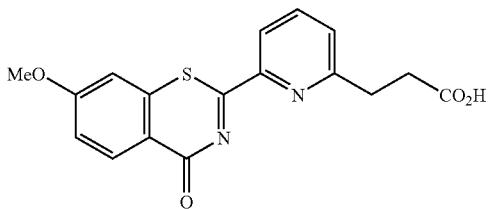

A mixture of tert-butyl 3-[6-(7-methoxy-4-oxo-4H-1,3-benzothiazin-2-yl)-2-pyridyl]propanoate (0.40 g, 1.0 mmol) obtained in Example 173 and trifluoroacetic acid (5.0 ml) was stirred at 0° C. for 2 hrs. The reaction mixture was concentrated under reduced pressure, combined with diisopropyl ether to give the crystals, which were collected by filtration and dried.

mp. 234.2-235.2° C. IR (KBr): 3136, 1714, 1630, 1591, 1560, 1527, 1277, 1224 cm$^{-1}$. $^1$H-NMR (DMSO-d$_6$) δ: 2.81 (2H, t, J=7.2 Hz), 3.13 (2H, t, J=7.2 Hz), 3.91 (3H, s), 7.25 (1H, dd, J=2.5, 8.9 Hz), 7.48 (1H, d, J=2.5 Hz), 7.63 (1H, d, J=7.6 Hz), 7.99 (1H, dd, J=7.6, 7.6 Hz), 8.15 (1H, d, J=7.6 Hz), 8.26 (1H, d, J=8.9 Hz), 12.00 (1H, br s). Elemental Analysis for C$_{17}$H$_{14}$N$_2$O$_4$S.0.25H$_2$O Calcd. C, 58.86; H, 4.21; N, 8.08. Found C, 58.86; H, 4.27; N, 8.04.

Example 175 tert-Butyl 3-[6-(7-methyl-4-oxo-4H-1,3-benzothiazin-2-yl)-2-pyridyl]propanoate

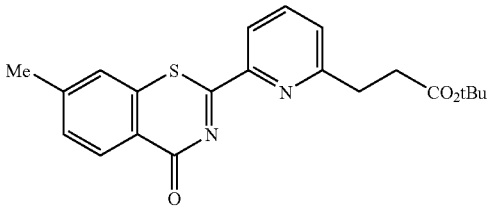

2-Mercapto-4-methylbenzoic acid (1.56 g, 9.3 mmol) and tert-butyl 3-(6-cyano-2-pyridyl)propanoate (1.46 g, 6.3 mmol) were dissolved in pyridine (15 ml), and the mixture was refluxed for 6 hrs. The reaction mixture was concentrated under reduced pressure, subjected to silica gel column chromatography, eluted with hexane-ethyl acetate (3:2, v/v) and recrystallized from ethyl acetate-hexane to give the titled compound (1.29 g, 53%).

mp. 134.8-134.9° C. IR (KBr): 2976, 2930, 1728, 1666, 1604, 1566, 1537, 1302, 1284, 1240, 1149, 1099 cm$^{-1}$. $^1$H-NMR (CDCl$_3$) δ: 1.42 (9H, s), 2.49 (3H, s), 2.88 (2H, t, J=7.3 Hz), 3.20 (2H, t, J=7.3 Hz), 7.40-7.43 (3H, m), 7.79 (1H, m), 8.35 (1H, d, J=7.7 Hz), 8.43 (1H, d, J=8.6 Hz). Elemental Analysis for C$_{21}$H$_{22}$N$_2$O$_3$S Calcd. C, 65.95; H, 5.80; N, 7.32. Found C, 65.91; H, 5.90; N, 7.25.

Example 176

3-[6-(7-Methyl-4-oxo-4H-1,3-benzothiazin-2-yl)-2-pyridyl]propionic acid

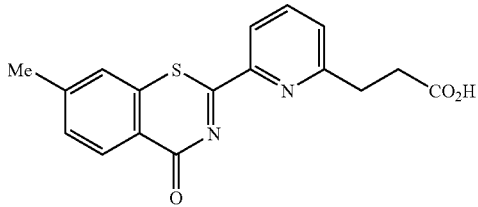

A mixture of tert-butyl 3-[6-(7-methyl-4-oxo-4H-1,3-benzothiazin-2-yl)-2-pyridyl]propanoate (0.40 g, 1.0 mmol) obtained in Example 175 and trifluoroacetic acid (5.0 ml) was stirred at 0° C. for 2 hrs. The reaction mixture was concentrated under reduced pressure and combined with diisopropyl ether to precipitate crystals, which were collected by filtration and dried to give the titled compound (0.33 g, 97%).

mp. 221.9-222.5° C. IR (KBr): 3217, 1728, 1637, 1603, 1568, 1529, 1433, 1315, 1224, 1109, 825, 779, 682 cm$^{-1}$. $^1$H-NMR (DMSO-d$_6$) δ: 2.45 (3H, s), 2.81 (2H, t, J=7.1 Hz), 3.13 (2H, t, J=7.1 Hz), 7.52 (1H, d, J=8.2 Hz), 7.64 (1H, d, J=7.6 Hz), 7.71 (1H, s), 7.99 (1H, dd, J=8.1, 8.2 Hz), 8.15 (1H, d, J=7.6 Hz), 8.23 (1H, d, J=8.1 Hz), 12.00 (1H, br s). Elemental Analysis for C$_{17}$H$_{14}$N$_2$O$_3$S Calcd. C, 62.56; H, 4.32; N, 8.58. Found C, 62.12; H, 4.10; N, 8.51.

Example 177 tert-Butyl 3-[6-(4-oxo-7-trifluoromethyl-4H-1,3-benzothiazin-2-yl)-2-pyridyl]propanoate

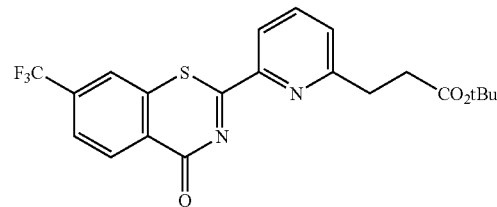

2-Mercapto-4-trifluoromethylbenzoic acid (1.59 g, 7.2 mmol) and tert-butyl 3-(6-cyano-2-pyridyl)propanoate (1.32 g, 5.7 mmol) were dissolved in pyridine (15 ml), and the mixture was refluxed for 15 hrs. The reaction mixture was concentrated under reduced pressure, subjected to a silica gel column chromatography, eluted with hexane-ethyl acetate (3:1, v/v) and recrystallized from ethyl acetate-hexane to give the titled compound (0.85 g, 34%).

mp. 148.5-149.4° C. IR (KBr): 2978, 1726, 1672, 1572, 1537, 1329, 1309, 1238, 1172, 1134, 1084 cm$^{-1}$. $^1$H-NMR (CDCl$_3$) δ: 1.42 (9H, s), 2.88 (2H, t, J=7.2 Hz), 3.21 (2H, t, J=7.2 Hz), 7.46 (1H, d, J=7.6 Hz), 7.79-7.84 (2H, m), 7.90 (1H, s), 8.35 (1H, d, J=7.6 Hz), 8.65 (1H, d, J=8.3 Hz).

Elemental Analysis for $C_{21}H_{19}N_2O_3SF_3$ Calcd. C, 57.79; H, 4.39; N, 6.42. Found C, 57.89; H, 4.28; N, 6.56.

Example 178

3-[6-(4-Oxo-7-trifluoromethyl-4H-1,3-benzothiazin-2-yl)-2-pyridyl]propionic acid

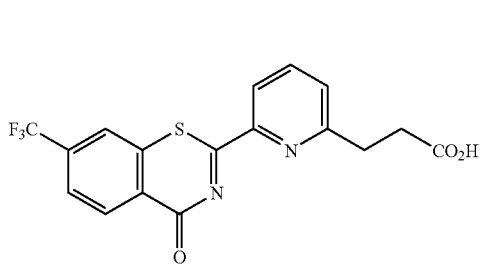

A mixture of tert-butyl 3-[6-(4-oxo-7-trifluoromethyl-4H-1,3-benzothiazin-2-yl)-2-pyridyl]propanoate (0.35 g, 0.8 mmol) and trifluoroacetic acid (5.0 ml) was stirred at 0° C. for 2 hrs. The reaction mixture was concentrated under reduced pressure and combined with diisopropyl ether to precipitate crystals, which were collected by filtration and dried to give the titled compound (0.27 g, 88%).

mp. 192.9-193.1° C. IR (KBr): 3053, 2918, 1711, 1662, 1614, 1539, 1336, 1309, 1172, 1120, 1086, 817 cm$^{-1}$. $^1$H-NMR (DMSO-d$_6$) δ: 2.81 (2H, t, J=7.1 Hz), 3.14 (2H, t, J=7.1 Hz), 7.67 (1H, d, J=7.4 Hz), 7.99-8.04 (2H, m), 8.18 (1H, d, J=7.4 Hz), 8.45-8.51 (2H, m), 12.00 (1H, br s). Elemental Analysis for $C_{17}H_{11}N_2O_3SF_3 \cdot 0.75H_2O$ Calcd. C, 51.84; H, 3.20; N, 7.11. Found C, 51.99; H, 2.92; N, 7.00.

Example 179 tert-Butyl 3-[6-(7-chloro-4-oxo-4H-1,3-benzothiazin-2-yl)-2-pyridyl]propanoate

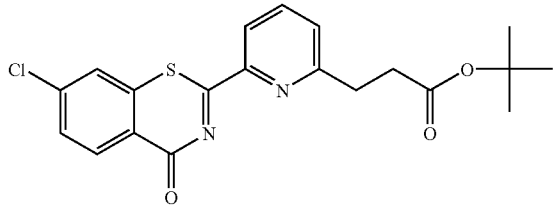

tert-Butyl 3-(6-cyano-2-pyridyl)propanoate (1.6 g, 6.9 mmol) and 4-chlorothiosalicylic acid (2.6 g, 13.7 mmol) were dissolved in pyridine (15 ml), and the mixture was refluxed for 13 hrs. The solvent was evaporated. The residue was subjected to a silica gel column chromatography. The fractions eluted with hexane-ethyl acetate (3:1, v/v) were collected, concentrated and recrystallized from hexane-ethyl acetate to give the titled compound (1.4 g, 51%) as pale yellow crystals.

mp. 167.9-168.2° C. $^1$H-NMR (CDCl$_3$) δ: 1.42 (9H, s), 2.87 (2H, t, J=7.2 Hz), 3.20 (2H, t, J=7.2 Hz), 7.43 (1H, d, J=7.3 Hz), 7.56 (1H, dd, J=2.0, 8.5 Hz), 7.62 (1H, d, J=2.0 Hz), 7.80 (1H, dd, J=7.3, 7.5 Hz), 8.34 (1H, d, J=7.5 Hz), 8.47 (1H, d, J=8.5 Hz). IR(KBr): 2976, 2932, 1726, 1678, 1585, 1570, 1535, 1379, 1271, 1149, 1093 cm$^{-1}$. Elemental Analysis for $C_{20}H_{19}N_2O_3SCl$ Calcd. C, 59.62; H, 4.75; N, 6.95. Found C, 59.65; H, 4.96; N, 7.15.

Example 180

3-[6-(7-Chloro-4-oxo-4H-1,3-benzothiazin-2-yl)-2-pyridyl]propionic acid

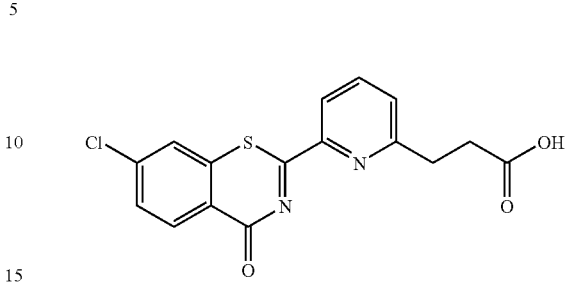

tert-Butyl 3-[6-(7-chloro-4-oxo-4H-1,3-benzothiazin-2-yl)-2-pyridyl]propanoate (0.60 g, 1.5 mmol) was dissolved in trifluoroacetic acid (5 ml), and the mixture was stirred at 0° C. for 2 hrs. The solvent was evaporated and the residue was crystallized from diisopropyl ether to give the titled compound (0.49 g, 96%) as white crystals.

mp. 224.4-224.7° C. $^1$H-NMR (DMSO-d$_6$) δ: 2.80 (2H, t, J=7.1 Hz), 3.13 (2H, t, J=7.1 Hz), 7.65 (1H, d, J=7.7 Hz), 7.73 (1H, dd, J=2.0, 8.5 Hz), 8.00 (1H, m), 8.13-8.17 (2H, m), 8.31 (1H, d, J=8.5 Hz), 12.20 (1H, br s). IR(KBr): 3051, 2922, 1709, 1664, 1585, 1566, 1529, 1379, 1261, 1230, 1095 cm$^{-1}$. Elemental Analysis for $C_{16}H_{11}N_2O_3SCl \cdot 0.25H_2O$ Calcd. C, 54.71; H, 3.30; N, 7.97. Found C, 54.85; H, 3.14; N, 7.82.

Reference Example 48

Methyl 2-[[(dimethylamino)carbothioyl]oxy]-4-fluorobenzoate

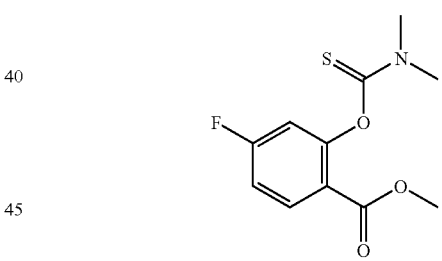

4-Fluorosalicylic acid (10.0 g, 64 mmol) was dissolved in methanol (300 ml), and concentrated sulfuric acid (6.3 g, 64 mmol) was added thereto. The reaction mixture was refluxed for 48 hrs. The solvent was evaporated, and the residue was neutralized with 2 N aqueous sodium hydroxide solution. Ethyl acetate was added to the mixture. The organic layer was washed with saturated brine and dried over anhydrous magnesium sulfate. The solvent was evaporated to give methyl 4-fluorosalicylate (10.0 g, 92%) as white crystals. Methyl 4-fluorosalicylate (10.0 g, 58 mmol) and N,N-dimethylthiocarbamoyl chloride (9.6 g, 77 mmol) were dissolved in DMF (100 ml), and 1,4-diazabicyclo[2.2.2]octane (8.5 g, 75 mmol) was added thereto. The reaction mixture was stirred at room temperature for 7 hrs. The reaction mixture was combined with ethyl acetate and water. The organic layer was washed with saturated brine and dried over anhydrous magnesium sulfate. The solvent was evaporated. The residue was subjected to a silica gel column chromatography. The fractions eluted with ethylacetate-hexane (1:5, v/v) were collected, concentrated and recrystallized from ethyl acetate-hexane to give the titled compound (12.1 g, 80%) as white crystals.

mp. 106.8-107.2° C. $^1$H-NMR (CDCl$_3$) δ: 3.39 (3H, s), 3.46 (3H, s), 3.83 (3H, s), 6.87 (1H, m), 7.02 (1H, m), 8.03 (1H, m). IR(KBr): 2949, 1728, 1606, 1539, 1496, 1396, 1286, 1257, 1151, 1113, 1086 cm$^{-1}$ Elemental Analysis for C$_{11}$H$_{12}$NO$_3$SF Calcd. C, 51.35; H, 4.70; N, 5.44. Found C, 51.47; H, 4.93; N, 5.41.

Reference Example 49

Methyl 2-[[(dimethylamino)carbonyl]thio]-4-fluorobenzoate

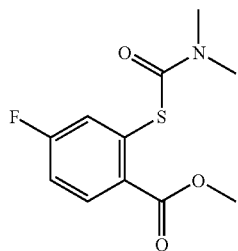

Methyl 2-[[(dimethylamino)carbothioyl]oxy]-4-fluorobenzoate (4.7 g, 18 mmol) was melted at 190° C. and stirred at the same temperature for 18 hrs. The mixture was subjected to a silica gel column chromatography. The fractions eluted with ethylacetate-hexane (1:3, v/v) were collected and concentrated to give the titled compound (4.3 g, 91%).

$^1$H-NMR (CDCl$_3$) δ: 3.05 (3H, s), 3.10 (3H, s), 3.87 (3H, s), 7.10 (1H, m), 7.38 (1H, dd, J=2.6, 8.8 Hz), 7.94 (1H, dd, J=5.8, 8.8 Hz).

Reference Example 50

4-Fluorothisalicylic acid

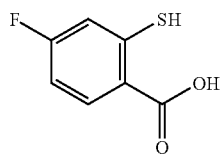

A mixture of methyl 2-[[(dimethylamino)carbonyl]thio]-4-fluorobenzoate (4.7 g, 18 mmol) and 10% aqueous sodium hydroxide solution (36 g, 90 mmol) was stirred at 100° C. for 14 hrs. The reaction mixture was acidified (pH 3) by the addition of 6 N hydrochloric acid, and the precipitates were collected. The precipitates were dissolved in ethyl acetate, dried over anhydrous magnesium sulfate. The solvent was evaporated to give the titled compound (2.7 g, 87%) as pale yellow crystals.

$^1$H-NMR (CDCl$_3$+DMSO-d$_6$) δ: 5.50 (1H, br s), 6.83 (1H, m), 7.02 (1H, dd, J=2.5, 9.3 Hz), 8.10 (1H, m).

Example 181 tert-Butyl 3-[6-(7-fluoro-4-oxo-4H-1,3-benzothiazin-2-yl)-2-pyridyl]propanoate

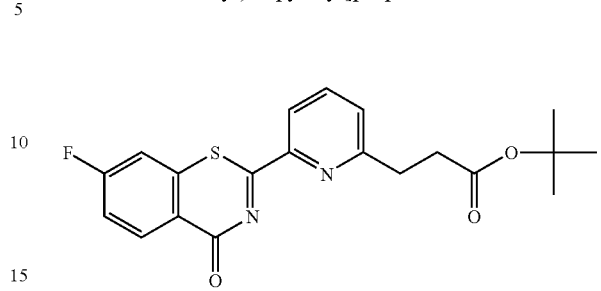

tert-Butyl 3-(6-cyano-2-pyridyl)propanoate (1.5 g, 6.5 mmol) and 4-fluorothiosalicylic acid (1.7 g, 9.7 mmol) were dissolved in pyridine (10 ml), and the mixture was refluxed for 15 hrs. The solvent was evaporated, and the residue was subjected to a silica gel column chromatography. The fractions eluted with hexane-ethyl acetate (3:1, v/v) were collected, concentrated and recrystallized from hexane-ethyl acetate to give the titled compound (1.36 g, 54%) as white crystals.

mp. 158.5-159.5° C. $^1$H-NMR (CDCl$_3$) δ: 1.42 (9H, s), 2.87 (2H, t, J=7.2 Hz), 3.20 (2H, t, J=7.2 Hz), 7.29-7.34 (2H, m), 7.43 (1H, d, J=7.6 Hz), 7.81 (1H, m), 8.34 (1H, d, J=7.6 Hz), 8.58 (1H, dd, J=5.8, 9.5 Hz). IR(KBr): 3061, 2976, 2930, 1730, 1672, 1599, 1581, 1547, 1240, 1151 cm$^{-1}$. Elemental Analysis for C$_{20}$H$_{19}$N$_2$O$_3$SF Calcd. C, 62.16; H, 4.96; N, 7.25. Found C, 62.05; H, 4.95; N, 7.15.

Example 182

3-[6-(7-Fluoro-4-oxo-4H-1,3-benzothiazin-2-yl)-2-pyridyl]propionic acid

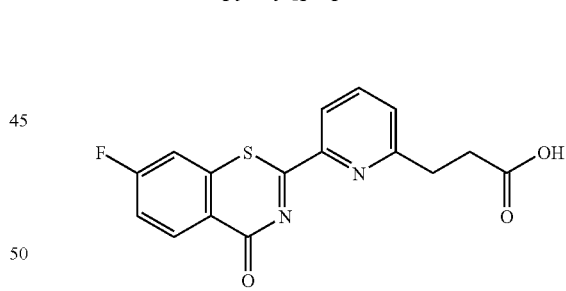

tert-Butyl 3-[6-(7-fluoro-4-oxo-4H-1,3-benzothiazin-2-yl)-2-pyridyl]propanoate (0.50 g, 1.3 mmol) was dissolved in trifluoroacetic acid (5 ml), and the mixture was stirred at 0° C. for 2 hrs. The solvent was evaporated, and the residue was crystallized from diethyl ether to give the titled compound (0.43 g, 99%) as white crystals.

mp. 215.0-217.0° C. $^1$H-NMR (DMSO-d$_6$) δ: 2.81 (2H, t, J=7.2 Hz), 3.13 (2H, t, J=7.2 Hz), 7.56 (1H, m), 7.66 (1H, d, J=7.7 Hz), 7.92 (1H, m), 8.01 (1H, m), 8.17 (1H, d, J=7.7 Hz), 8.40 (1H, m), 12.22 (1H, s). IR(KBr): 3136, 1714, 1630, 1591, 1560, 1527, 1277, 1224 cm$^{-1}$. Elemental Analysis for C$_{16}$H$_{11}$N$_2$O$_3$SF.0.25H$_2$O Calcd. C, 57.39; H, 3.46; N, 8.37. Found C, 57.04; H, 3.12; N, 8.13.

Example 183 tert-Butyl 3-[2-(7-chloro-4-oxo-4H-1,3-benzothiazin-2-yl)-4-pyridyl]propanoate

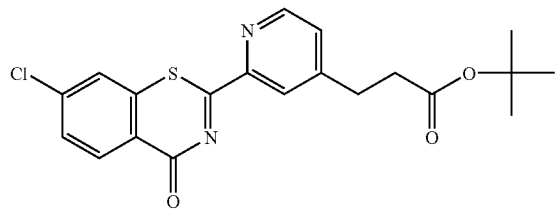

4-Chlorothiosalicylic acid (2.3 g, 12.2 mmol) and tert-butyl 3-(2-cyano-4-pyridyl)propanoate (1.4 g, 6.0 mmol) were dissolved in pyridine (20 ml), and the mixture was refluxed for 16 hrs. The solvent was evaporated and the residue was subjected to a silica gel column chromatography. The fraction eluted with hexane-ethyl acetate (2:1, v/v) were collected, concentrated and recrystallized from hexane-tetrahydrofuran to give the titled compound (1.3 g, 52%) as white crystals.

mp. 151.8-152.1° C. $^1$H-NMR (CDCl$_3$) δ: 1.42 (9H, s), 2.64 (2H, t, J=7.4 Hz), 3.02 (2H, t, J=7.4 Hz), 7.42 (1H, dd, J=1.5, 4.8 Hz), 7.56-7.60 (2H, m), 8.40 (1H, s), 8.48 (1H, d, J=8.2 Hz), 8.62 (1H, d, J=4.8 Hz). IR(KBr): 2976, 1726, 1666, 1585, 1566, 1537, 1278, 1151, 1093 cm$^{-1}$. Elemental Analysis for C$_{20}$H$_{19}$N$_2$O$_3$SCl Calcd. C, 59.62; H, 4.75; N, 6.95. Found C, 59.54; H, 4.45; N, 6.97.

Example 184 tert-Butyl 3-[2-(7-fluoro-4-oxo-4H-1,3-benzothiazin-2-yl)-4-pyridyl]propanoate

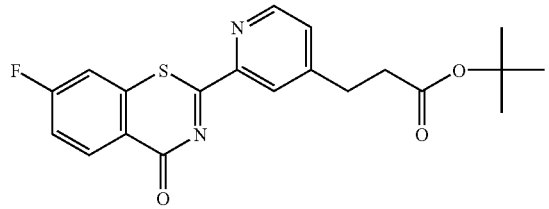

4-Fluorothiosalicylic acid (1.9 g, 11.3 mmol) and tert-butyl 3-(2-cyano-4-pyridyl)propanoate (1.3 g, 5.6 mmol) were dissolved in pyridine (20 ml), and the mixture was refluxed for 18 hrs. The solvent was evaporated, and the residue was subjected to a silica gel column chromatography. The fractions eluted with hexane-ethyl acetate (2:1, v/v) were collected, concentrated and recrystallized from hexane-tetrahydrofuran to give the titled compound (1.2 g, 54%) as white crystals.

mp. 137.6-138.1° C. $^1$H-NMR (CDCl$_3$) δ: 1.42 (9H, s), 2.64 (2H, t, J=7.5 Hz), 3.02 (2H, t, J=7.5 Hz), 7.29-7.35 (2H, m), 7.42 (1H, dd, J=1.2, 4.8 Hz), 8.40 (1H, s), 8.58 (1H, m), 8.62 (1H, d, J=5.0 Hz). IR(KBr): 2978, 2932, 1726, 1666, 1601, 1577, 1541, 1477, 1277, 1240, 1151 cm$^{-1}$. Elemental Analysis for C$_{20}$H$_{19}$N$_2$O$_3$SF Calcd. C, 62.16; H, 4.96; N, 7.25. Found C, 62.29; H, 5.15; N, 7.31.

Example 185

3-[2-(7-Chloro-4-oxo-4H-1,3-benzothiazin-2-yl)-4-pyridyl]propionic acid

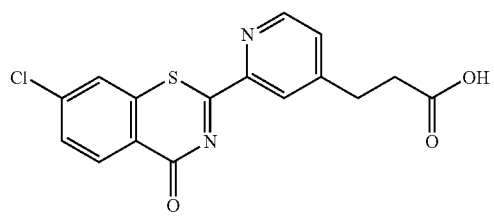

tert-Butyl 3-[2-(7-chloro-4-oxo-4H-1,3-benzothiazin-2-yl)-4-pyridyl]propanoate (1.00 g, 2.4 mmol) was dissolved in trifluoroacetic acid (10 ml), and the mixture was stirred at 0° C. for 2 hrs. The solvent was evaporated, and the residue was recrystallized from hexane-tetrahydrofuran-methanol to give the titled compound (0.66 g, 76%) as white crystals.

mp. 262.9-263.5° C. $^1$H-NMR (DMSO-d$_6$) δ: 2.68 (2H, t, J=7.0 Hz), 3.00 (2H, t, J=7.0 Hz), 7.64 (1H, s), 7.73 (1H, m), 8.11 (1H, m), 8.21 (1H, m), 8.30 (1H, m), 8.68 (1H, m), 12.26 (1H, s). IR(KBr): 3065, 1718, 1626, 1560, 1525, 1388, 1302, 1184, 1101 cm$^{-1}$. Elemental Analysis for C$_{16}$H$_{11}$N$_2$O$_3$SCl Calcd. C, 55.41; H, 3.20; N, 8.08. Found C, 55.28; H, 3.07; N, 8.01.

Example 186

3-[2-(7-Fluoro-4-oxo-4H-1,3-benzothiazin-2-yl)-4-pyridyl]propionic acid

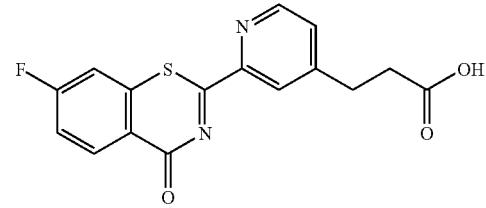

tert-Butyl 3-[2-(7-fluoro-4-oxo-4H-1,3-benzothiazin-2-yl)-4-pyridyl]propanoate (0.92 g, 2.3 mmol) was dissolved in trifluoroacetic acid (10 ml), and the mixture was stirred at 0° C. for 2 hrs. The solvent was evaporated, and the residue was recrystallized from diisopropyl ether-methanol to give the titled compound (0.56 g, 71%) as white crystals.

mp. 240.0° C. (decomposed) $^1$H-NMR (DMSO-d$_6$) δ: 2.69 (2H, t, J=7.2 Hz), 3.00 (2H, t, J=7.2 Hz), 7.57 (1H, m), 7.65 (1H, m), 7.91 (1H, m), 8.22 (1H, s), 8.39 (1H, m), 8.68 (1H, m), 12.26 (1H, s). IR(KBr): 2930, 1720, 1630, 1601, 1576, 1537, 1475, 1292, 1224, 1192, 1097 cm$^{-1}$. Elemental Analysis for C$_{16}$H$_{11}$N$_2$O$_3$SF Calcd. C, 58.17; H, 3.36; N, 8.48. Found C, 58.22; H, 3.30; N, 8.46.

Reference Example 51

4-Bromosalicylic acid

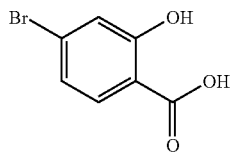

4-Aminosalicylic acid (15.0 g, 98 mmol) and hydrobromic acid (47%, 100 ml) were mixed with water (100 ml). A solution of sodium nitrite (6.8 g, 98 mmol) in water (50 ml) was added dropwise to the mixture at 0° C., and the mixture was stirred at the same temperature for 30 minutes. A mixture of cuprous bromide (16.9 g, 117 mmol) and hydrobromic acid (47%, 45 ml) was added dropwise to the mixture at 0° C., and the mixture was stirred at the same temperature for 1 hr. The reaction mixture was combined with ethyl acetate and extracted. The organic layer was washed with saturated brine and dried over anhydrous magnesium sulfate. The solvent was evaporated to give the titled compound (15.5 g, 73%) as a gray solid.

$^1$H-NMR (DMSO-d$_6$) δ: 7.09 (1H, dd, J=0.9, 8.4 Hz), 7.19 (1H, d, J=0.9 Hz), 7.69 (1H, d, J=8.4 Hz), 10.33 (1H, br s).

Reference Example 52

Methyl 4-bromo-2-[[(dimethylamino)carbothioyl]oxy]benzoate

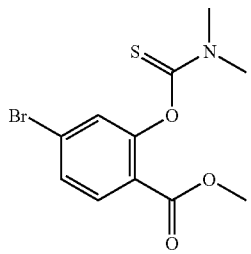

4-Bromosalicylic acid (15.5 g, 71 mmol) was dissolved in methanol (500 ml), and concentrated sulfuric acid (9.7 g, 99 mmol) was added thereto. The reaction mixture was refluxed for 24 hrs, and the solvent was evaporated. The residue was neutralized with 2 N aqueous sodium hydroxide solution and extracted with ethyl acetate. The organic layer was washed with saturated brine and dried over anhydrous magnesium sulfate. The solvent was evaporated. The residue was subjected to a silica gel column chromatography. The fractions eluted with ethyl acetate-hexane (1:20, v/v) were collected and concentrated to give methyl 4-bromosalicylate (8.7 g, 52%). Methyl 4-bromosalicylate (8.7 g, 37 mmol) and N,N-dimethylthiocarbamoyl chloride (6.0 g, 48 mmol) were dissolved in DMF (80 ml), and 1,4-diazabicyclo[2.2.2]octane (5.5 g, 49 mmol) was added thereto. The reaction mixture was stirred at room temperature for 24 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with ethyl acetate-hexane (1:4, v/v) were collected, concentrated and recrystallized from ethyl acetate-hexane to give the titled compound (10.6 g, 88%) as white crystals.

mp. 117.5-118.3° C. $^1$H-NMR (CDCl$_3$) δ: 3.38 (3H, s), 3.45 (3H, s), 3.83 (3H, s), 7.31 (1H, d, J=1.9 Hz), 7.45 (1H, dd, J=1.9, 8.4 Hz), 7.86 (1H, d, J=8.4 Hz). IR(KBr): 2947, 1712, 1595, 1550, 1394, 1286, 1207, 1116 cm$^{-1}$ Elemental Analysis for C$_{11}$H$_{12}$NO$_3$SBr Calcd. C, 41.52; H, 3.80; N, 4.40. Found C, 41.65; H, 3.71; N, 4.39.

Reference Example 53

Methyl 4-bromo-2-[[(dimethylamino)carbonyl]thio]benzoate

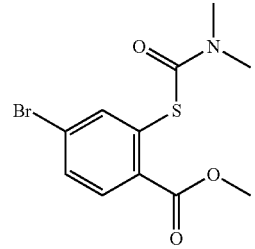

Methyl 4-bromo-2-[[(dimethylamino)carbothioyl]oxy]benzoate (5.4 g, 17 mmol) was melted with heating at 190° C. and stirred at the same temperature for 6 hrs. The mixture was subjected to a silica gel column chromatography. The fractions eluted with ethyl acetate-hexane (1:2, v/v) were collected and concentrated to give the titled compound (3.2 g, 59%).

$^1$H-NMR (CDCl$_3$) δ: 3.04 (3H, br s), 3.11 (3H, br s), 3.87 (3H, s), 7.55 (1H, dd, J=2.0, 8.4 Hz), 7.78 (1H, d, J=8.4 Hz), 7.79 (1H, d, J=2.0 Hz).

Reference Example 54

4-Bromothiosalicylic acid

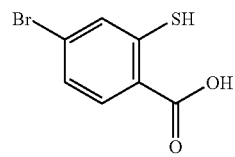

A mixture of methyl 4-bromo-2-[[(dimethylamino)carbonyl]thio]benzoate (3.2 g, 10 mmol) and 10% aqueous sodium hydroxide solution (20 g, 50 mmol) was stirred at 100° C. for 14 hrs. The reaction mixture was acidified (pH 3) by the addition of 6 N hydrochloric acid. The precipitates were collected by filtration, dissolved in ethyl acetate and dried over anhydrous magnesium sulfate. The solvent was evaporated to give the titled compound (2.3 g, 100%) as white crystals.

$^1$H-NMR (DMSO-d$_6$) δ: 7.37 (1H, dd, J=1.8, 8.5 Hz), 7.80-7.85 (2H, m).

Example 187 tert-Butyl 3-[2-(7-bromo-4-oxo-4H-1,3-benzothiazin-2-yl)-4-pyridyl]propanoate

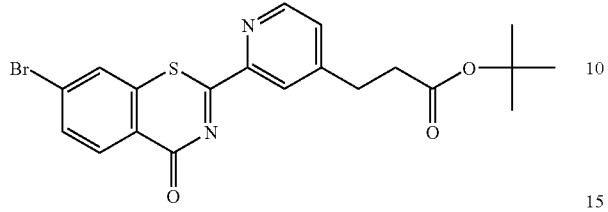

tert-Butyl 3-(2-cyano-4-pyridyl)propanoate (1.3 g, 5.6 mmol) and 4-bromothiosalicylic acid (1.8 g, 8.0 mmol) were dissolved in pyridine (20 ml), and the mixture was refluxed for 18 hrs. The solvent was evaporated, and the residue was subjected to a silica gel column chromatography. The fractions eluted with hexane-ethyl acetate (3:2, v/v) were collected, concentrated and recrystallized from hexane-tetrahydrofuran to give the titled compound (0.63 g, 25%) as white crystals.

mp. 172.9-173.7° C. $^1$H-NMR (CDCl$_3$) δ: 1.42 (9H, s), 2.64 (2H, t, J=7.5 Hz), 3.02 (2H, t, J=7.5 Hz), 7.42 (1H, d, J=4.9 Hz), 7.71-7.76 (2H, m), 8.38-8.40 (2H, m), 8.62 (1H, d, J=4.9 Hz). IR(KBr): 2978, 2932, 1726, 1660, 1579, 1562, 1529, 1367, 1278, 1157 cm$^{-1}$. Elemental Analysis for C$_{20}$H$_{19}$N$_2$O$_3$SBr Calcd. C, 53.70; H, 4.28; N, 6.26. Found C, 53.86; H, 4.05; N, 6.28.

Example 188

3-[2-(7-Bromo-4-oxo-4H-1,3-benzothiazin-2-yl)-4-pyridyl]propionic acid

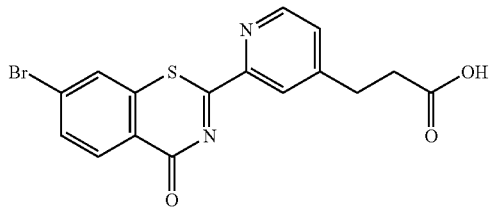

tert-Butyl 3-[2-(7-bromo-4-oxo-4H-1,3-benzothiazin-2-yl)-4-pyridyl]propanoate (0.49 g, 1.1 mmol) was dissolved in trifluoroacetic acid (5 ml), and the mixture was stirred at 0° C. for 2 hrs. The solvent was evaporated, and the residue was recrystallized from diisopropyl ether-tetrahydrofuran to give the titled compound (0.38 g, 89%) as white crystals.

mp. 257.5-259.1° C. $^1$H-NMR (DMSO-d$_6$) δ: 2.68 (2H, t, J=7.3 Hz), 3.00 (2H, t, J=7.3 Hz), 7.65 (1H, d, J=4.9 Hz), 7.87 (1H, m), 8.21-8.27 (3H, m), 8.69 (1H, d, J=4.9 Hz), 12.23 (1H, br s). IR(KBr): 3059, 1718, 1626, 1577, 1560, 1523, 1385, 1302, 1184 cm$^{-1}$. Elemental Analysis for C$_{16}$H$_{11}$N$_2$O$_3$SBr Calcd. C, 49.12; H, 2.83; N, 7.16. Found C, 49.40; H, 2.83; N, 7.21.

Reference Example 55

4-Methyl-2-pyridinecarbaldehyde

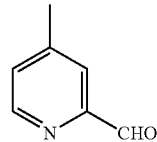

Diisobutyl aluminium hydride in toluene (1.5 M, 43.5 ml, 65 mmol) was added dropwise to a solution of 2-cyano-4-methylpyridine (7.0 g, 59 mmol) in dichloromethane (180 ml) at −78° C., and the mixture was stirred at the same temperature for 2 hrs. The reaction mixture was combined with concentrated hydrochloric acid (28 ml) and water (112 ml), and the water layer and the organic layer were separated. The organic layer was extracted with 2 N hydrochloric acid. The water layer was combined, neutralized with sodium hydrogen carbonate and extracted with diethyl ether. The extract was washed with saturated brine and dried over anhydrous magnesium sulfate. The solvent was evaporated to give the titled compound (2.7 g, 37%).

Reference Example 56 tert-Butyl (E)-3-(4-methyl-2-pyridyl)-2-propenoate

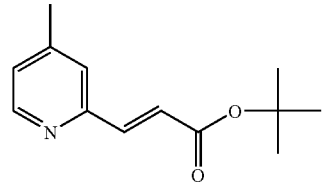

A solution of tert-butyl diethylphosphonoacetate (6.2 g, 24 mmol) in tetrahydrofuran (20 ml) was added dropwise to a mixture of sodium hydride (60% in oil, 1.1 g, 26 mmol) and tetrahydrofuran (120 ml) at 0° C., and the mixture was stirred at the same temperature for 30 minutes. Successively, a solution of 4-methyl-2-pyridinecarbaldehyde (1.5 g, 12 mmol) in tetrahydrofuran (30 ml) was added dropwise to the mixture at 0° C., and the mixture was stirred at room temperature for 1 hr. The reaction mixture was combined with water and extracted with ethyl acetate. The organic layer was washed with saturated brine and dried over anhydrous magnesium sulfate. The solvent was evaporated. The residue was subjected to a silica gel column chromatography. The fractions eluted with ethylacetate-hexane (1:5, v/v) were collected and concentrated to give the titled compound (1.9 g, 70%).

$^1$H-NMR (CDCl$_3$) δ: 1.52 (9H, s), 2.36 (3H, s), 6.80 (1H, d, J=15.7 Hz), 7.07 (1H, d, J=4.8 Hz), 7.24 (1H, s), 7.55 (1H, d, J=15.7 Hz), 8.48 (1H, d, J=4.8 Hz).

149

Reference Example 57 tert-Butyl 3-(4-methyl-2-pyridyl)propanoate

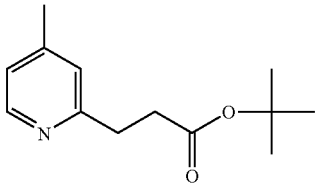

tert-Butyl (E)-3-(4-methyl-2-pyridyl)-2-propenoate (1.9 g, 8.5 mmol) was dissolved in methanol (80 ml), and 10% palladium-carbon (200 mg) was added thereto. The mixture was stirred under hydrogen atmosphere at room temperature for 3 hrs. Palladium-carbon was filtered off, and the filtrate was concentrated to give the titled compound (1.8 g, 90%).

$^1$H-NMR (CDCl$_3$) δ: 1.41 (9H, s), 2.31 (3H, s), 2.68 (2H, t, J=7.6 Hz), 3.02 (2H, t, J=7.6 Hz), 6.93 (1H, d, J=4.8 Hz), 6.99 (1H, s), 8.36 (1H, d, J=4.8 Hz).

Reference Example 58 tert-Butyl 3-(4-methyl-2-pyridyl)propanoate N-oxide

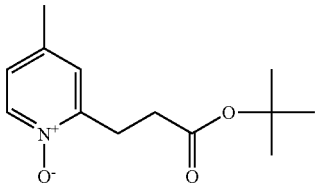

tert-Butyl 3-(4-methyl-2-pyridyl)propanoate (1.8 g, 8.3 mmol) and 3-chloroperbenzoic acid (ca. 77%, 2.4 g, 10.8 mmol) were dissolved in ethyl acetate (50 ml), and the mixture was stirred at room temperature for 4 hrs. The solvent was evaporated, and the residue was subjected to a silica gel column chromatography. The fractions eluted with methanol-ethyl acetate (1:4, v/v) were collected and concentrated to give the titled compound (1.7 g, 88%).

$^1$H-NMR (CDCl$_3$) δ: 1.41 (9H, s), 2.31 (3H, s), 2.75 (2H, t, J=7.1 Hz), 3.14 (2H, t, J=7.1 Hz), 6.95 (1H, dd, J=2.3, 6.6 Hz), 7.10 (1H, d, J=2.3 Hz), 8.13 (1H, d, J=6.6 Hz).

Reference Example 59 tert-Butyl 3-(6-cyano-4-methyl-2-pyridyl)propanoate

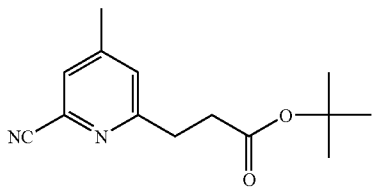

tert-Butyl 3-(4-methyl-2-pyridyl)propanoate N-oxide (1.7 g, 7.3 mmol) was dissolved in nitroethane (40 ml), and trim-

150 ethylsilyl cyanide (1.4 g, 14.7 mmol) and N,N-dimethylcarbamoyl chloride (1.2 g, 11.3 mmol) were added thereto. The mixture was stirred at room temperature for 22 hrs. The solvent was evaporated, and the residue was subjected to a silica gel column chromatography. The fractions eluted with ethyl acetate-hexane (1:4, v/v) were collected and concentrated to give the titled compound (1.4 g, 79%).

$^1$H-NMR (CDCl$_3$) δ: 1.42 (9H, s), 2.37 (3H, s), 2.71 (2H, t, J=7.1 Hz), 3.05 (2H, t, J=7.1 Hz), 7.21 (1H, s), 7.34 (1H, s) IR(KBr): 2978, 2932, 2233, 1726, 1604, 1367, 1151 cm$^{-1}$.

Example 189 tert-Butyl 3-[4-methyl-6-(4-oxo-4H-1,3-benzothiazin-2-yl)-2-pyridyl]propanoate

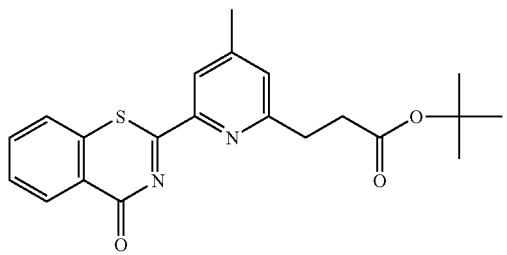

tert-Butyl 3-(6-cyano-4-methyl-2-pyridyl)propanoate (0.72 g, 2.9 mmol) and methyl thiosalicylate (0.99 g, 5.9 mmol) were dissolved in toluene (4 ml), and triethylamine (2.0 ml, 14.3 mmol) was added thereto. The mixture was refluxed for 14 hrs. The solvent was evaporated, and the residue was subjected to a silica gel column chromatography. The fractions eluted with ethyl acetate-hexane (1:2, v/v) were collected, concentrated and recrystallized from ethyl acetate-hexane to give the titled compound (0.61 g, 54%) as white crystals.

mp. 168.5-169.3° C. $^1$H-NMR (CDCl$_3$) δ: 1.43 (9H, s), 2.42 (3H, s), 2.86 (2H, t, J=7.2 Hz), 3.14 (2H, t, J=7.2 Hz), 7.23 (1H, s), 7.60-7.68 (3H, m), 8.22 (1H, s), 8.55 (1H, m) IR(KBr): 2976, 2928, 1726, 1655, 1572, 1531, 1365, 1298, 1153, 1095, 758 cm$^{-1}$. Elemental Analysis for C$_{21}$H$_{22}$N$_2$O$_3$S Calcd. C, 65.95; H, 5.80; N, 7.32. Found C, 66.01; H, 5.75; N, 7.32.

Example 190 tert-Butyl 3-[6-(7-chloro-4-oxo-4H-1,3-benzothiazin-2-yl)-4-methyl-2-pyridyl]propanoate

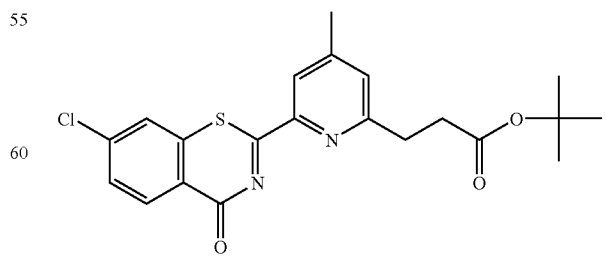

tert-Butyl 3-(6-cyano-4-methyl-2-pyridyl)propanoate (0.69 g, 2.8 mmol) and 4-chlorothiosalicylic acid (1.05 g, 5.7 mmol) were dissolved in pyridine (10 ml). The mixture was refluxed for 22 hrs. The solvent was evaporated, and the residue was subjected to a silica gel column chromatography. The fractions eluted with hexane-ethyl acetate (3:1, v/v) were collected, concentrated and recrystallized from hexane-ethyl acetate to give the titled compound (0.33 g, 28%) as white crystals.

mp. 162.3-163.0° C. $^1$H-NMR (CDCl$_3$) δ: 1.42 (9H, s), 2.42 (3H, s), 2.85 (2H, t, J=7.2 Hz), 3.14 (2H, t, J=7.2 Hz), 7.24 (1H, s), 7.55 (1H, dd, J=1.9, 8.5 Hz), 7.61 (1H, d, J=1.9 Hz), 8.20 (1H, s), 8.47 (1H, d, J=8.5 Hz). IR(KBr): 2976, 2930, 1724, 1666, 1585, 1566, 1537, 1282, 1153, 1093 cm$^{-1}$. Elemental Analysis for C$_{21}$H$_{21}$N$_2$O$_3$SCl Calcd. C, 60.50; H, 5.08; N, 6.72. Found C, 60.64; H, 5.02; N, 6.65.

Example 191

3-[4-Methyl-6-(4-oxo-4H-1,3-benzothiazin-2-yl)-2-pyridyl]propionic acid

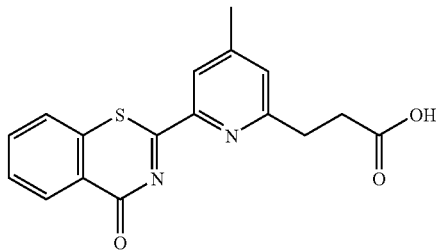

tert-Butyl 3-[4-methyl-6-(4-oxo-4H-1,3-benzothiazin-2-yl)-2-pyridyl]propanoate (0.44 g, 1.1 mmol) was dissolved in trifluoroacetic acid (5 ml), and the mixture was stirred at 0° C. for 2 hrs. The solvent was evaporated, and the residue was recrystallized from diisopropyl ether-methanol to give the titled compound (0.33 g, 87%) as white crystals.

mp. 244.6-245.5° C. $^1$H-NMR (DMSO-d$_6$) δ: 2.44 (3H, s), 2.79 (2H, t, J=7.1 Hz), 3.07 (2H, t, J=7.1 Hz), 7.48 (1H, s), 7.71 (1H, m), 7.83 (1H, m), 7.92 (1H, d, J=7.8 Hz), 8.03 (1H, s), 8.34 (1H, dd, J=1.0, 7.8 Hz), 12.19 (1H, s). IR(KBr): 3223, 1728, 1637, 1570, 1527, 1440, 1307, 1224, 835, 752 cm$^{-1}$. Elemental Analysis for C$_{17}$H$_{14}$N$_2$O$_3$S Calcd. C, 62.56; H, 4.32; N, 8.58. Found C, 62.48; H, 4.32; N, 8.50.

Example 192

3-[6-(7-Chloro-4-oxo-4H-1,3-benzothiazin-2-yl)-4-methyl-2-pyridyl]propionic acid

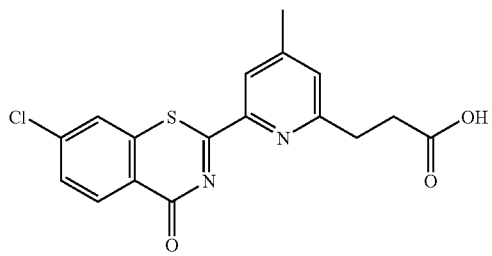

tert-Butyl 3-[6-(7-chloro-4-oxo-4H-1,3-benzothiazin-2-yl)-4-methyl-2-pyridyl]propanoate (0.25 g, 0.61 mmol) was dissolved in trifluoroacetic acid (5 ml), and the mixture was stirred at 0° C. for 2 hrs. The solvent was evaporated, and the residue was recrystallized from hexane-tetrahydrofuran to give the titled compound (0.16 g, 74%) as white crystals.

mp. 232.2-233.2° C. $^1$H-NMR (DMSO-d$_6$) δ: 2.43 (3H, s), 2.78 (2H, t, J=7.2 Hz), 3.07 (2H, t, J=7.2 Hz), 7.48 (1H, s), 7.73 (1H, dd, J=2.0, 8.5 Hz), 8.01 (1H, s), 8.13 (1H, d, J=2.0 Hz), 8.30 (1H, d, J=8.5 Hz), 12.17 (1H, s). IR(KBr): 2922, 1695, 1655, 1560, 1535, 1381, 1309, 1095 cm$^{-1}$. Elemental Analysis for C$_{17}$H$_{13}$N$_2$O$_3$SCl Calcd. C, 56.59; H, 3.63; N, 7.76. Found C, 56.41; H, 3.37; N, 7.74.

Reference Example 60

6-(2-Thienyl)-2-pyridinecarbonitrile

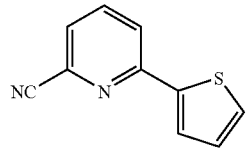

6-Chloro-2-pyridinecarbonitrile (1.2 g, 8.6 mmol) and 2-thiopheneboric acid (1.9 g, 15.3 mmol) were dissolved in toluene (100 ml)-ethanol (25 ml), and potassium carbonate (3.0 g, 21.7 mmol) and water (25 ml) were added thereto. The mixture was deairated under reduced pressure for 10 minutes. Tetrakis(triphenylphosphine)palladium (0) (0.5 g, 0.43 mmol) was added to the reaction mixture under argon atmosphere, and the mixture was refluxed for 16 hrs. The reaction mixture was combined with ethyl acetate and water. The organic layer was separated, washed with saturated brine and dried over anhydrous magnesium sulfate. The solvent was evaporated, and the residue was subjected to a silica gel column chromatography. The fractions eluted with hexane-ethyl acetate (4:1, v/v) were collected, concentrated and recrystallized from hexane-ethyl acetate to give the titled compound (1.3 g, 85%)

mp. 88.2-88.6° C. $^1$H-NMR (CDCl$_3$) δ: 7.13 (1H, dd, J=3.7, 5.0 Hz), 7.47 (1H, dd, J=0.9, 5.0 Hz), 7.52 (1H, m), 7.66 (1H, dd, J=1.0, 3.7 Hz), 7.76-7.83 (2H, m) IR(KBr): 3105, 3061, 2235, 1585, 1452, 1423, 860 cm$^{-1}$. Elemental Analysis for C$_{10}$H$_6$N$_2$S Calcd. C, 64.49; H, 3.25; N, 15.04. Found C, 64.44; H, 3.14; N, 15.08.

Reference Example 61

6-(2-Furyl)-2-pyridinecarbonitrile

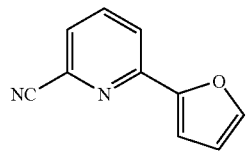

6-Chloro-2-pyridinecarbonitrile (0.90 g, 6.5 mmol) and 2-furanboric acid (1.1 g, 9.8 mmol) were dissolved in toluene (80 ml)-ethanol (205 ml), and potassium carbonate (2.2 g, 15.9 mmol) and water (20 ml) were added thereto. The mixture was deairated under reduced pressure for 10 minutes. Tetrakis(triphenylphosphine)palladium (0) (0.36 g, 0.31 mmol) was added to the reaction mixture under argon atmosphere, and the mixture was refluxed for 13 hrs. The reaction mixture was combined with ethyl acetate and water. The organic layer was separated, washed with saturated brine and dried over anhydrous magnesium sulfate. The solvent was evaporated, and the residue was subjected to a silica gel column chromatography. The fractions eluted with hexane-ethyl acetate (5:1, v/v) were collected, concentrated and recrystallized from hexane-ethyl acetate to give the titled compound (0.97 g, 87%).

mp. 90.2-90.3° C. $^1$H-NMR (CDCl$_3$) δ: 6.57 (1H, dd, J=1.6, 3.5 Hz), 7.20 (1H, m), 7.51 (1H, dd, J=1.6, 6.9 Hz), 7.56 (1H, dd, J=0.6, 1.6 Hz), 7.80-7.89 (2H, m). IR(KBr): 3155, 3057, 2237, 1604, 1574, 1491, 1440, 1168, 1006, 922, 804 cm$^{-1}$. Elemental Analysis for C$_{10}$H$_6$N$_2$O Calcd. C, 70.58; H, 3.55; N, 16.46. Found C, 70.63; H, 3.48; N, 16.66.

Example 193

2-[6-(2-Thienyl)-2-pyridyl]-4H-1,3-benzothiazin-4-one

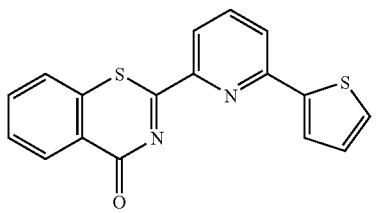

6-(2-Thienyl)-2-pyridinecarbonitrile (0.56 g, 3.0 mmol) and methyl thiosalicylate (0.77 g, 4.6 mmol) were dissolved in toluene (4 ml), and triethylamine (2.0 ml, 14.3 mmol) was added thereto. The reaction mixture was refluxed for 10 hrs. After cooling, the precipitates were collected by filtration and recrystallized from tetrahydrofuran-hexane to give the titled compound (0.84 g, 86%) as pale yellow crystals.

mp. 222.2-223.4° C. $^1$H-NMR (CDCl$_3$) δ: 7.16 (1H, m), 7.48 (1H, d, J=5.1 Hz), 7.62-7.71 (4H, m), 7.81-7.90 (2H, m), 8.35 (1H, t, J=7.2 Hz), 8.55 (1H, d, J=7.6 Hz). IR(KBr): 3065, 1655, 1572, 1535, 1454, 1302, 1278, 1238, 1099, 806 cm$^{-1}$. Elemental Analysis for C$_{17}$H$_{10}$N$_2$OS$_2$ Calcd. C, 63.33; H, 3.13; N, 8.69. Found C, 63.38; H, 3.32; N, 8.87.

Example 194

2-[6-(2-Furyl)-2-pyridyl]-4H-1,3-benzothiazine-4-one

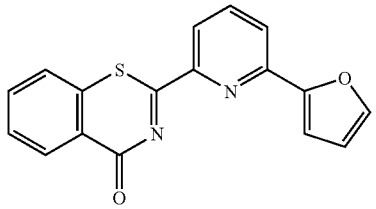

6-(2-Furyl)-2-pyridinecarbonitrile (0.60 g, 3.5 mmol) and methyl thiosalicylate (1.01 g, 6.0 mmol) were dissolved in toluene (4 ml), and triethylamine (2.0 ml, 14.3 mmol) was added thereto. The reaction mixture was refluxed for 12 hrs. After cooling, the precipitates were collected by filtration and recrystallized from tetrahydrofuran-hexane to give the titled compound (0.75 g, 69%) as pale yellow crystals.

mp. 217.9-218.4° C. $^1$H-NMR (CDCl$_3$) δ: 6.60 (1H, dd, J=1.7, 3.4 Hz), 7.27 (1H, d, J=3.4 Hz), 7.59-7.72 (4H, m), 7.86-7.94 (2H, m), 8.36 (1H, m), 8.55 (1H, m). IR(KBr): 3123, 1666, 1574, 1537, 1493, 1440, 1300, 1236, 1095, 908 cm$^{-1}$. Elemental Analysis for C$_{17}$H$_{10}$N$_2$O$_2$S.0.25H$_2$O Calcd. C, 65.69; H, 3.40; N, 9.01. Found C, 65.94; H, 3.26; N, 9.18.

Reference Example 62

2-(1,3-Oxazol-5-yl)pyridine

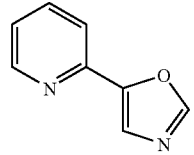

Picolinaldehyde (2.5 g, 23 mmol) and toluenesulfonylmethyl isocyanide (5.3 g, 27 mmol) were dissolved in methanol (30 ml), and potassium carbonate (3.5 g, 25 mmol) was added thereto. The mixture was refluxed for 30 minutes. The solvent was evaporated, and ethyl acetate and water were added to the residue. The organic layer was washed with saturated brine and dried over anhydrous magnesium sulfate. The solvent was evaporated. The residue was subjected to a silica gel column chromatography. The fractions eluted with hexane-ethyl acetate (2:3, v/v) were collected and concentrated to give the titled compound.

$^1$H-NMR (CDCl$_3$) δ: 7.25 (1H, m), 7.66-7.80 (3H, m), 7.97 (1H, s), 8.65 (1H, m).

Reference Example 63

2-(1,3-Oxazol-5-yl)pyridine N-oxide

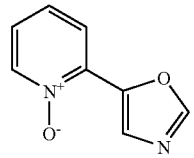

2-(1,3-Oxazol-5-yl)pyridine (2.8 g, 19 mmol) and 3-chloroperbenzoic acid (77%, 13.6 g, 58 mmol) were dissolved in ethyl acetate, and the mixture was stirred at room temperature for 6 days. The solvent was evaporated, and the residue was subjected to a silica gel column chromatography. The fractions eluted with methanol-ethyl acetate (1:4, v/v) were collected and concentrated to give the titled compound (1.1 g, 34%).

$^1$H-NMR (CDCl$_3$) δ: 7.22 (1H, m), 7.36 (1H, m), 7.87 (1H, dd, J=1.9, 8.1 Hz), 8.04 (1H, s), 8.33 (1H, d, J=6.4 Hz), 8.54 (1H, s).

Reference Example 64

6-(1,3-Oxazol-5-yl)-2-pyridinecarbonitrile

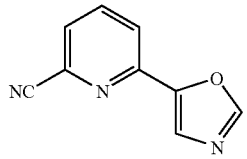

2-(1,3-Oxazol-5-yl)pyridine N-oxide (1.0 g, 6.6 mmol) was dissolved in nitroethane (15 ml), and trimethylsilyl cyanide (2.7 g, 27.2 mmol) and N,N-dimethylcarbamoyl chloride (3.0 g, 27.8 mmol) were added thereto. The mixture was stirred at room temperature for 5 days. The solvent was evaporated, and the residue was subjected to a silica gel column chromatography. The fractions eluted with ethyl acetate-hexane (1:1, v/v) were collected, concentrated and recrystallized from hexane-ethyl acetate to give the titled compound (0.84 g, 75%).

mp. 147.8-148.1° C. $^1$H-NMR (CDCl$_3$) δ: 7.62 (1H, dd, J=1.3, 7.3 Hz), 7.82 (1H, s), 7.86 (1H, dd, J=1.3, 8.1 Hz), 7.93 (1H, dd, J=7.3, 8.1 Hz), 8.01 (1H, s). IR(KBr): 3163, 3063, 2235, 1597, 1574, 1496, 1448, 1122, 958, 814 cm$^{-1}$. Elemental Analysis for C$_9$H$_5$N$_3$O Calcd. C, 63.16; H, 2.94; N, 24.55. Found C, 63.04; H, 2.65; N, 24.46.

Example 195

2-(1,3-Oxazol-5-yl)-2-pyridyl]-4H-1,3-benzothiazine-4-one

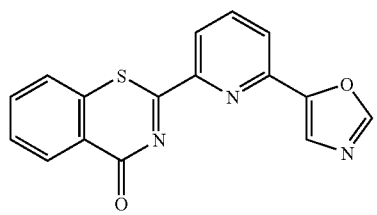

6-(1,3-Oxazol-5-yl)-2-pyridinecarbonitrile (0.72 g, 4.2 mmol) and methyl thiosalicylate (1.54 g, 9.1 mmol) were dissolved in toluene (6 ml), and triethylamine (1.5 ml, 10.7 mmol) was added thereto. The mixture was refluxed for 8 hrs. After cooling, the precipitates were collected by filtration and recrystallized from hexane-chlorobenzene to give the titled compound (1.24 g, 95%) as pale yellow crystals.

mp. 271.3-272.7° C. $^1$H-NMR (DMSO-d$_6$) δ: 7.73 (1H, m), 7.83 (1H, m), 7.92 (1H, d, J=7.4 Hz), 7.99 (1H, s), 8.09 (1H, d, J=7.4 Hz), 8.20 (1H, m), 8.29 (1H, d, J=7.4 Hz), 8.35 (1H, d, J=7.7 Hz), 8.66 (1H, s). IR(KBr): 3128, 2649, 1570, 1529, 1487, 1439, 1304, 1093, 815, 752 cm$^{-1}$. Elemental Analysis for C$_{16}$H$_9$N$_3$O$_2$S Calcd. C, 62.53; H, 2.95; N, 13.67. Found C, 62.51; H, 2.66; N, 13.62.

Reference Example 65

6-(Pyrazol-1-yl)-2-pyridinecarbonitrile

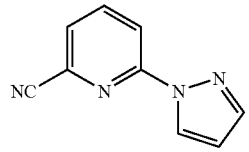

6-Chloro-2-pyridinecarbonitrile (1.0 g, 7.2 mmol) and pyrazole (2.4 g, 35.9 mmol) were dissolved in DMF (10 ml), and potassium carbonate (3.0 g, 21.7 mmol) was added thereto. The mixture was stirred at 100° C. for 18 hrs. The reaction mixture was combined with ethyl acetate and water, the organic layer was washed with saturated brine and dried over anhydrous magnesium sulfate. The solvent was evaporated, and the residue was subjected to a silica gel column chromatography. The fractions eluted with hexane-ethyl acetate (3:1, v/v) were collected, concentrated and recrystallized from hexane-ethyl acetate to give the titled compound (0.98 g, 80%).

mp. 120.9-122.1° C. $^1$H-NMR (CDCl$_3$) δ: 6.51 (1H, m), 7.57 (1H, d, J=7.4 Hz), 7.76 (1H, d, J=0.6 Hz), 7.94 (1H, m), 8.24 (1H, d, J=8.4 Hz), 8.56 (1H, d, J=2.5 Hz). IR(KBr): 3092, 2235, 1593, 1527, 1469, 1392, 945, 806, 750 cm$^{-1}$. Elemental Analysis for C$_9$H$_6$N$_4$ Calcd. C, 63.52; H, 3.55; N, 32.92. Found C, 63.51; H, 3.34; N, 32.68.

Example 196

2-[6-(1H-Pyrazol-1-yl)-2-pyridyl]-4H-1,3-benzothiazine-4-one

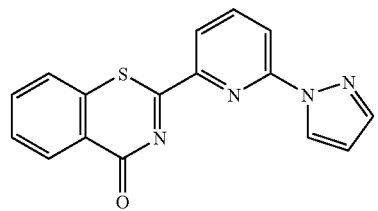

6-(Pyrazol-1-yl)-2-pyridinecarbonitrile (0.68 g, 4.0 mmol) and methyl thiosalicylate (1.00 g, 5.9 mmol) were dissolved in toluene (5 ml), and triethylamine (2.0 ml, 14.3 mmol) was added thereto. The mixture was refluxed for 8 hrs. After cooling, the precipitates were collected by filtration and recrystallized from hexane-tetrahydrofuran to give the titled compound (0.82 g, 67%) as pale yellow crystals.

mp. 253.0-254.0° C. $^1$H-NMR (CDCl$_3$) δ: 6.56 (1H, m), 7.62-7.73 (3H, m), 7.80 (1H, s), 8.02 (1H, dd, J=7.8, 7.8 Hz), 8.22 (1H, d, J=7.8 Hz), 8.41 (1H, d, J=7.5 Hz), 8.55 (1H, m), 8.72 (1H, d, J=2.5 Hz). IR(KBr): 3074, 1658, 1574, 1537, 1469, 1402, 1060, 933, 814, 742 cm$^{-1}$. Elemental Analysis for C$_{16}$H$_{10}$N$_4$OS Calcd. C, 62.73; H, 3.29; N, 18.29. Found C, 62.73; H, 3.06; N, 18.26.

Reference Example 66

6-Phenyl-2-pyridinecarbonitrile

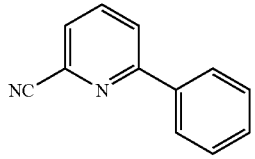

6-Chloro-2-pyridinecarbonitrile (0.80 g, 5.7 mmol) and phenylboric acid (1.05 g, 8.6 mmol) were dissolved in toluene (60 ml)-ethanol (15 ml), and potassium carbonate (2.00 g, 14.4 mmol) and water (15 ml) were added thereto. The mixture was deairated under reduced pressure for 10 minutes. Tetrakis(triphenylphosphine)palladium (0) (0.33 g, 0.29 mmol) was added to the reaction mixture under argon atmosphere, and the mixture was refluxed for 16 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with hexane-ethyl acetate (4:1, v/v) were collected, concentrated and recrystallized from hexane-ethyl acetate to give the titled compound (0.90 g, 86%).

mp. 65.2-66.1° C. $^1$H-NMR (CDCl$_3$) δ: 7.48-7.51 (3H, m), 7.62 (1H, dd, J=1.1, 7.3 Hz), 7.85-7.93 (2H, m), 8.01-8.04 (2H, m) IR(KBr): 3067, 2235, 1581, 1556, 1448, 817, 762 cm$^{-1}$. Elemental Analysis for C$_{12}$H$_8$N$_2$ Calcd. C, 79.98; H, 4.47; N, 15.55. Found C, 79.86; H, 4.61; N, 15.42.

Reference Example 67

6-(4-Methoxyphenyl)-2-pyridinecarbonitrile

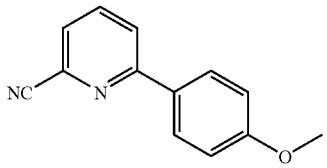

6-Chloro-2-pyridinecarbonitrile (0.70 g, 5.0 mmol) and 4-methoxyphenylboric acid (1.17 g, 7.7 mmol) were dissolved in toluene (60 ml)-ethanol (15 ml), and potassium carbonate (1.75 g, 12.6 mmol) and water (15 ml) were added thereto. The mixture was deairated under reduced pressure for 10 minutes. Tetrakis(triphenylphosphine)palladium (0) (0.29 g, 0.25 mmol) was added to the reaction mixture under argon atmosphere, and the mixture was refluxed for 16 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with hexane-ethyl acetate (4:1, v/v) were collected, concentrated and recrystallized from hexane-ethyl acetate to give the titled compound (0.94 g, 88%).

mp. 86.3-86.6° C. $^1$H-NMR (CDCl$_3$) δ: 3.46 (3H, s), 7.01 (2H, m), 7.54 (1H, dd, J=1.3, 7.1 Hz), 7.79-7.89 (2H, m), 8.00 (2H, m) IR(KBr): 2972, 2235, 1608, 1585, 1518, 1448, 1440, 1315, 1265, 1178, 1024 cm$^{-1}$. Elemental Analysis for C$_{13}$H$_{10}$N$_2$O Calcd. C, 74.27; H, 4.79; N, 13.33. Found C, 74.39; H, 5.00; N, 13.14.

Example 197

2-(6-Phenyl-2-pyridyl)-4H-1,3-benzothiazine-4-one

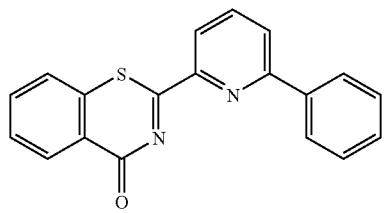

6-Phenyl-2-pyridinecarbonitrile (0.72 g, 4.0 mmol) and methyl thiosalicylate (1.20 g, 7.1 mmol) were dissolved in toluene (4 ml), and triethylamine (2.0 ml, 14.3 mmol) was added thereto. The mixture was refluxed for 8 hrs. After cooling, the precipitates were collected by filtration and recrystallized from hexane-tetrahydrofuran to give the titled compound (0.73 g, 57%) as white crystals.

mp. 195.4-197.0° C. $^1$H-NMR (CDCl$_3$) δ: 7.46-7.57 (3H, m), 7.62-7.69 (3H, m), 7.95-7.97 (2H, m), 8.16 (2H, d, J=7.0 Hz), 8.45 (1H, dd, J=1.8, 6.6 Hz), 8.56 (1H, d, J=7.5 Hz). IR(KBr): 3063, 1658, 1572, 1537, 1446, 1296, 1234, 1097, 956, 763 cm$^{-1}$. Elemental Analysis for C$_{19}$H$_{12}$N$_2$OS Calcd. C, 72.13; H, 3.82; N, 8.85. Found C, 72.29; H, 3.75; N, 8.81.

Example 198

2-[6-(4-Methoxyphenyl)-2-pyridyl]-4H-1,3-benzothiazine-4-one

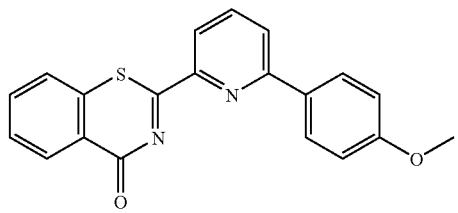

6-(4-Methoxyphenyl)-2-pyridinecarbonitrile (0.81 g, 3.8 mmol) and methyl thiosalicylate (1.07 g, 6.3 mmol) were dissolved in toluene (4 ml), and triethylamine (2.0 ml, 14.3 mmol) was added thereto. The mixture was refluxed for 8 hrs. After cooling, the precipitates were collected by filtration and recrystallized from hexane-tetrahydrofuran to give the titled compound (0.87 g, 65%) as pale yellow crystals.

mp. 200.1-201.1° C. $^1$H-NMR (CDCl$_3$) δ: 3.90 (3H, s), 7.06 (2H, d, J=8.8 Hz), 7.59-7.69 (3H, m), 7.89-7.91 (2H, m), 8.13 (2H, d, J=8.8 Hz), 8.36 (1H, m), 8.56 (1H, d, J=7.7 Hz). IR(KBr): 3067, 3003, 2982, 2835, 1657, 1574, 1531, 1518, 1450, 1313, 1257 cm$^{-1}$. Elemental Analysis for C$_{20}$H$_{14}$N$_2$O$_2$S Calcd. C, 69.35; H, 4.07; N, 8.09. Found C, 69.26; H, 4.01; N, 7.92.

Reference Example 68

6-Cyano-2,2'-bipyridyl

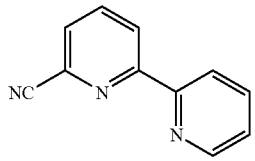

2,2'-Bipyridyl N-oxide (2.8 g, 16 mmol) was dissolved in nitroethane (50 ml), and trimethylsilyl cyanide (6.4 g, 65 mmol) and N,N-dimethylcarbamoyl chloride (3.7 g, 35 mmol) were added thereto. The mixture was stirred at room temperature for 36 hrs. The solvent was evaporated, and the residue was subjected to a silica gel column chromatography. The fractions eluted with hexane-ethyl acetate (3:1, v/v) were collected, concentrated and recrystallized from hexane-ethyl acetate to give the titled compound (1.2 g, 43%) as white crystals.

mp. 135.9-136.8° C. $^1$H-NMR (CDCl$_3$) δ: 7.37 (1H, m) 7.70 (1H, dd, J=0.9, 7.6 Hz), 7.86 (1H, m), 7.95 (1H, m), 8.47 (1H, dd, J=0.9, 7.9 Hz), 8.65-8.70 (2H, m). IR(KBr): 3491, 2237, 1581, 1431, 987, 775 cm$^{-1}$. Elemental Analysis for C$_{11}$H$_7$N$_3$ Calcd. C, 72.92; H, 3.89; N, 23.19. Found C, 72.80; H, 3.81; N, 22.97.

Example 199

2-[6-(2,2'-Bipyridyl)]-4H-1,3-benzothiazine-4-one

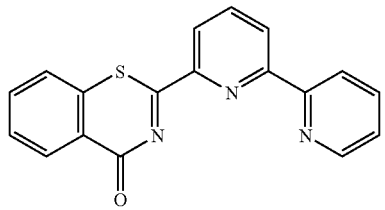

6-Cyano-2,2'-bipyridyl (0.90 g, 4.9 mmol) and methyl thiosalicylate (1.26 g, 7.5 mmol) were dissolved in toluene (5 ml), and triethylamine (2.0 ml, 14.3 mmol) was added thereto. The mixture was refluxed for 12 hrs. After cooling, the precipitates were collected by filtration and recrystallized from hexane-tetrahydrofuran to give the titled compound (1.34 g, 85%) as white crystals.

mp. 222.1-223.9° C. $^1$H-NMR (CDCl$_3$) δ: 7.38 (1H, m), 7.60-7.72 (3H, m), 7.92 (1H, m), 8.02 (1H, m), 8.51-8.73 (5H, m). IR(KBr): 3520, 3063, 1666, 1574, 1537, 1431, 1313, 1284, 779 cm$^{-1}$. Elemental Analysis for C$_{18}$H$_{11}$N$_3$OS Calcd. C, 68.12; H, 3.49; N, 13.24. Found C, 67.90; H, 3.30; N, 13.10.

Reference Example 69

4,4'-Dimethyl-2,2'-bipyridyl N-oxide

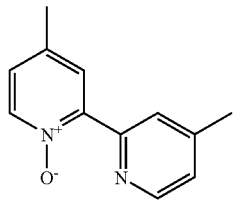

4,4'-Dimethyl-2,2'-bipyridyl (4.8 g, 26 mmol) and 3-chloroperbenzoic acid (77%, 8.7 g, 39 mmol) were dissolved in chloroform (25 ml), and the mixture was stirred at room temperature for 24 hrs. The solvent was evaporated, and the residue was subjected to a silica gel column chromatography. The fractions eluted with ethylacetate-methanol (4:1, v/v) were collected, concentrated and crystallized from dimethyl ether to give the titled compound (3.7 g, 71%).

$^1$H-NMR (CDCl$_3$) δ: 2.39 (3H, s), 2.44 (3H, s), 7.06 (1H, dd, J=2.5, 6.7 Hz), 7.16 (1H, dd, J=0.7, 4.9 Hz), 7.93 (1H, d, J=2.5 Hz), 8.20 (1H, d, J=6.7 Hz), 8.56 (1H, d, J=4.9 Hz), 8.72 (1H, s).

Reference Example 70

6-Cyano-4,4'-dimethyl-2,2'-bipyridyl

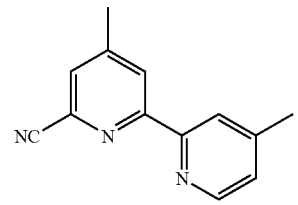

4,4'-Dimethyl-2,2'-bipyridyl N-oxide (3.7 g, 18 mmol) was dissolved in nitroethane (50 ml), and trimethylsilyl cyanide (5.5 g, 55 mmol) and N,N-dimethylcarbamoyl chloride (2.9 g, 27 mmol) were added thereto. The mixture was stirred at room temperature for 36 hrs. The solvent was evaporated, and the residue was subjected to a silica gel column chromatography. The fractions eluted with hexane-ethyl acetate (5:1, v/v) were collected, concentrated and recrystallized from hexane-ethyl acetate to give the titled compound (3.4 g, 87%) as white crystals.

mp. 132.1-132.4° C. $^1$H-NMR (CDCl$_3$) δ: 2.46 (3H, s), 2.49 (3H, s), 7.18 (1H, dd, J=0.9, 4.9 Hz), 7.51 (1H, d, J=0.6 Hz), 8.28 (1H, d, J=0.9 Hz), 8.47 (1H, d, J=0.6 Hz), 8.52 (1H, d, J=4.9 Hz). IR(KBr): 2918, 2231, 1597, 1554, 1377, 991, 871, 833 cm$^{-1}$ Elemental Analysis for C$_{13}$H$_{11}$N$_3$ Calcd. C, 74.62; H, 5.30; N, 20.08. Found C, 74.62; H, 5.20; N, 20.06.

Example 200

2-[6-(4,4'-Dimethyl-2,2'-bipyridyl)]-4H-1,3-benzothiazine-4-one

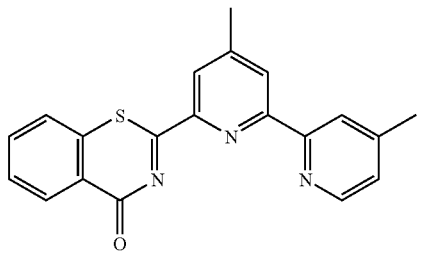

6-Cyano-4,4'-dimethyl-2,2'-bipyridyl (1.00 g, 4.8 mmol) and methyl thiosalicylate (1.25 g, 7.4 mmol) were dissolved in toluene (5 ml), and triethylamine (2.0 ml, 14.3 mmol) was added thereto. The mixture was refluxed for 9 hrs. After cooling, the precipitates were collected by filtration and recrystallized from hexane-tetrahydrofuran to give the titled compound (1.22 g, 74%) as white crystals.

mp. 234.9-235.2° C. $^1$H-NMR (CDCl$_3$) δ: 2.53 (3H, s), 2.54 (3H, s), 7.20 (1H, m) 7.61-7.70 (3H, m), 8.38 (2H, m), 8.48 (1H, s), 8.55-8.58 (2H, m). IR(KBr): 3051, 1660, 1593, 1572, 1537, 1439, 1298, 1284, 1095, 738 cm$^{-1}$. Elemental Analysis for C$_{20}$H$_{15}$N$_3$OS Calcd. C, 69.54; H, 4.38; N, 12.17. Found C, 69.44; H, 4.29; N, 12.17.

Example 201

N-(2-Hydroxyethyl)-6-(4-oxo-4H-1,3-benzothiazin-2-yl)-2-pyridinecarboxamide

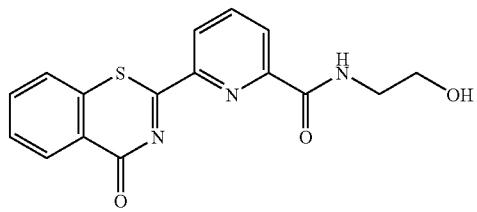

6-(4-Oxo-4H-1,3-benzothiazin-2-yl)-2-pyridinecarboxylic acid (1.00 g, 3.5 mmol) was dissolved in DMF (20 ml). 2-Aminoethanol (0.51 g, 8.3 mmol), WSC (1.34 g, 7.0 mmol) and HOBt (0.95 g, 7.0 mmol) were added thereto, and the mixture was stirred at 80° C. for 6 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with ethyl acetate-methanol (4:1, v/v) were collected, concentrated and recrystallized from diisopropyl ether-methanol to give the titled compound (0.12 g, 10%) as pale yellow crystals.

mp. 213.8-215.2° C. $^1$H-NMR (DMSO-d$_6$) δ: 3.51 (2H, dt, J=5.7, 5.6 Hz), 3.62 (2H, t, J=5.7 Hz), 4.89 (1H, br s), 7.75 (1H, m), 7.83-7.90 (2H, m), 8.25-8.39 (3H, m), 8.50 (1H, m), 8.55 (1H, t, J=5.6 Hz). IR(KBr): 3383, 3327, 2949, 2934, 1657, 1535, 1439, 1300, 1093, 748 cm$^{-1}$. Elemental Analysis for C$_{16}$H$_{13}$N$_3$O$_3$S Calcd. C, 58.70; H, 4.00; N, 12.84. Found C, 58.48; H, 3.87; N, 12.64.

Reference Example 71 tert-Butyl 2-pyridylmethylcarbamate

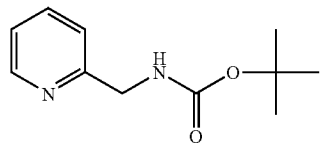

2-Aminomethylpyridine (6.0 g, 55 mmol) and di-tert-butyl dicarbonate (13.3 g, 61 mmol) were dissolved in tetrahydrofuran (150 ml), and the mixture was stirred at 0° C. for 1 hr and at room temperature for 3 hrs. The solvent was evaporated and the residue was subjected to a silica gel column chromatography. The fractions eluted with hexane-ethyl acetate (2:3, v/v) were collected and concentrated to give the titled compound (11.4 g, 98%).

$^1$H-NMR (CDCl$_3$) δ: 1.46 (9H, s), 4.44 (2H, d, J=5.3 Hz), 5.57 (1H, br s), 7.17 (1H, dd, J=5.0, 7.3 Hz), 7.27 (1H, d, J=6.0 Hz), 7.65 (1H, m), 8.53 (1H, d, J=5.0 Hz).

Reference Example 72 tert-Butyl 2-pyridylmethylcarbamate N-oxide

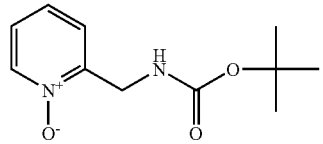

tert-Butyl 2-pyridylmethylcarbamate (11.4 g, 54 mmol) and 3-chloroperbenzoic acid (77%, 5.9 g, 71 mmol) were dissolved in ethyl acetate (150 ml), and the mixture was stirred at room temperature for 15 hrs. The solvent was evaporated, and the residue was subjected to a silica gel column chromatography. The fractions eluted with methanol-ethyl acetate (1:5, v/v) were collected and concentrated to give the titled compound (11.1 g, 90%).

$^1$H-NMR (CDCl$_3$) δ: 1.42 (9H, s), 4.47 (2H, d, J=6.4 Hz), 5.88 (1H, br s), 7.22-7.25 (2H, m), 7.40 (1H, m), 8.23 (1H, m).

Reference Example 73 tert-Butyl (6-cyano-2-pyridyl)methylcarbamate

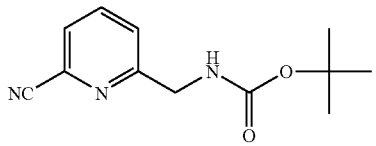

tert-Butyl 2-pyridylmethylcarbamate N-oxide (3.0 g, 13.3 mmol) was dissolved in nitroethane (50 ml), and trimethylsilyl cyanide (2.8 g, 28.6 mmol) and N,N-dimethylcarbamoyl chloride (1.7 g, 16.2 mmol) were added thereto. The mixture was stirred at room temperature for 24 hrs. The solvent was evaporated, and the residue was subjected to a silica gel column chromatography. The fractions eluted with ethyl acetate-hexane (2:1, v/v) were collected, concentrated and recrystallized from hexane-ethyl acetate to give the titled compound (1.8 g, 58%) as white crystals.

mp. 85.9-86.5° C. $^1$H-NMR (CDCl$_3$) δ: 1.46 (9H, s) 4.47 (2H, d, J=5.7 Hz), 5.48 (1H, br s), 7.51 (1H, d, J=7.8 Hz), 7.59 (1H, d, J=7.3 Hz), 7.81 (1H, dd, J=7.3, 7.8 Hz). IR(KBr): 3350, 2978, 2237, 1712, 1693, 1514, 1452, 1367, 1282, 1250, 1171 cm$^{-1}$. Elemental Analysis for C$_{12}$H$_{15}$N$_3$O$_2$ Calcd. C, 61.79; H, 6.48; N, 18.01. Found C, 61.79; H, 6.59; N, 18.01.

Example 202 tert-Butyl [6-(4-Oxo-4H-1,3-benzothiazin-2-yl)-2-pyridyl]methylcarbamate

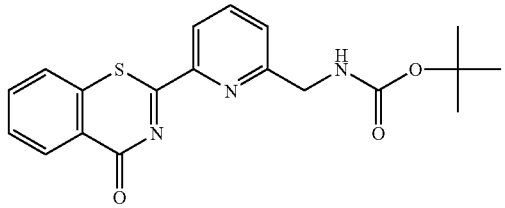

tert-Butyl (6-cyano-2-pyridyl)methylcarbamate (1.6 g, 6.8 mmol) and methyl thiosalicylate (1.8 g, 10.9 mmol) were dissolved in toluene (6 ml), and triethylamine (3.0 ml, 21.5 mmol) was added thereto. The mixture was refluxed for 20 hrs. After cooling, the precipitates were collected by filtration and dissolved in chloroform. The solution was subjected to a silica gel column chromatography. The fractions eluted with chloroform-methanol (20:1, v/v) were collected, concentrated and recrystallized from hexane-chloroform to give the titled compound (1.8 g, 72%) as pale yellow crystals.

mp. 160.0-162.1° C. $^1$H-NMR (CDCl$_3$) δ: 1.50 (9H, s), 4.57 (2H, d, J=5.7 Hz), 5.47 (1H, br s), 7.51 (1H, d, J=7.7 Hz), 7.60-7.71 (3H, m), 7.87 (1H, m), 8.42 (1H, d, J=7.7 Hz), 8.54 (1H, m). IR(KBr): 3350, 2976, 1711, 1658, 1572, 1537, 1439, 1290, 1250, 1170, 1097 cm$^{-1}$. Elemental Analysis for C$_{19}$H$_{19}$N$_3$O$_3$S Calcd. C, 61.77; H, 5.18; N, 11.37. Found C, 61.54; H, 5.00; N, 11.30.

Example 203

2-[6-(Aminomethyl)-2-pyridyl]-4H-1,3-benzothiazine-4-one trifluoroacetic acid salt

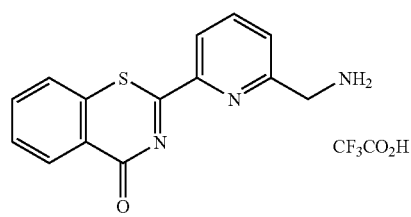

tert-Butyl (6-(4-Oxo-4H-1,3-benzothiazin-2-yl)-2-pyridyl]methylcarbamate (0.25 g, 0.67 mmol) was dissolved in trifluoroacetic acid (4 ml), and the mixture was stirred at room temperature for 2 hrs. The solvent was evaporated and the residue was recrystallized from methanol-diisopropyl ether to give the titled compound (0.22 g, 85%) as white crystals.

mp. 184.5-186.5° C. $^1$H-NMR (DMSO-d$_6$) δ: 4.39 (2H, s), 7.75 (1H, m), 7.83-7.88 (3H, m), 8.19 (1H, m), 8.34-8.40 (2H, m), 8.55 (3H, s). IR(KBr): 3535, 2995, 1685, 1647, 1527, 1201, 1128, 796 cm$^{-1}$. Elemental Analysis for C$_{16}$H$_{12}$N$_3$O$_3$SF$_3$.0.25H$_2$O Calcd. C, 49.55; H, 3.25; N, 10.83. Found C, 49.58; H, 3.26; N, 10.83.

Example 204

N-[[6-(4-Oxo-4H-1,3-benzothiazin-2-yl)-2-pyridyl]methyl]acetamide

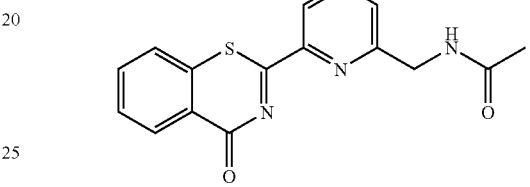

2-[6-(Aminomethyl)-2-pyridyl]-4H-1,3-benzothiazine-4-one trifluoroacetic acid salt (350 mg, 0.91 mmol) was dissolved in N,N-dimethylacetamide (10 ml), and acetyl chloride (150 mg, 1.91 mmol) was added thereto. The reaction mixture was stirred at 60° C. for 3 hrs and combined with ethyl acetate, tetrahydrofuran and water. The organic layer was washed with saturated brine and dried over anhydrous magnesium sulfate. The solvent was evaporated, and the residue was subjected to a silica gel column chromatography. The fractions eluted with methanol-ethyl acetate (1:10, v/v) were collected, concentrated and recrystallized from methanol-diisopropyl ether to give the titled compound (81 mg, 28%) as white crystals.

mp. 199.2-200.4° C. $^1$H-NMR (CDCl$_3$) δ: 2.17 (3H, s) 4.69 (2H, d, J=5.3 Hz), 6.73 (1H, br s), 7.51 (1H, d, J=7.6 Hz), 7.58-7.69 (3H, m), 7.85 (1H, m), 8.38 (1H, d, J=7.7 Hz), 8.54 (1H, dd, J=1.8, 7.4 Hz). IR(KBr): 3285, 3080, 1651, 1572, 1537, 1294, 738 cm$^{-1}$ Elemental Analysis for C$_{16}$H$_{13}$N$_3$O$_2$S Calcd. C, 61.72; H, 4.21; N, 13.50. Found C, 61.59; H, 4.18; N, 13.26.

Example 205

N-[[6-(4-Oxo-4H-1,3-benzothiazin-2-yl)-2-pyridyl]methyl]propanamide

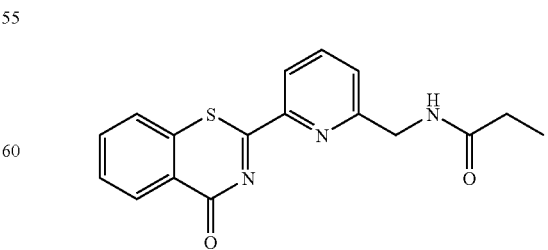

2-[6-(Aminomethyl)-2-pyridyl]-4H-1,3-benzothiazine-4-one trifluoroacetic acid salt (500 mg, 1.3 mmol) was dissolved in N,N-dimethylacetamide (10 ml), and propionyl chloride (370 mg, 4.0 mmol) was added thereto. The reaction mixture was stirred at 60° C. for 16 hrs and combined with ethyl acetate and water. The organic layer was washed with saturated brine and dried over anhydrous magnesium sulfate. The solvent was evaporated, and the residue was subjected to a silica gel column chromatography. The fractions eluted with methanol-ethyl acetate (1:20, v/v) were collected, concentrated and recrystallized from hexane-tetrahydrofuran to give the titled compound (224 mg, 53%) as white crystals.

mp. 199.0-199.8° C. $^1$H-NMR (CDCl$_3$) δ: 1.29 (3H, t, J=7.5 Hz), 2.42 (2H, q, J=7.5 Hz) 4.70 (2H, d, J=5.2 Hz), 6.74 (1H, br s), 7.51 (1H, d, J=7.6 Hz), 7.60-7.70 (3H, m), 7.86 (1H, m), 8.39 (1H, d, J=7.6 Hz), 8.54 (1H, m). IR(KBr): 3285, 3071, 1651, 1572, 1537, 1439, 1302, 1236, 734 cm$^{-1}$ Elemental Analysis for C$_{17}$H$_{15}$N$_3$O$_2$S Calcd. C, 62.75; H, 4.65; N, 12.91. Found C, 62.74; H, 4.89; N, 12.86.

Example 206

2-Methyl-N-[[6-(4-oxo-4H-1,3-benzothiazin-2-yl)-2-pyridyl]methyl]propanamide

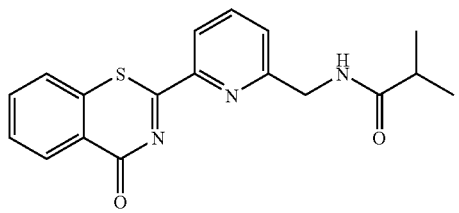

2-[6-(Aminomethyl)-2-pyridyl]-4H-1,3-benzothiazine-4-one trifluoroacetic acid salt (450 mg, 1.1 mmol) was dissolved in N,N-dimethylacetamide (10 ml), and isobutyryl chloride (365 mg, 3.9 mmol) was added thereto. The reaction mixture was stirred at 60° C. for 16 hrs and combined with ethyl acetate and water. The organic layer was washed with saturated brine and dried over anhydrous magnesium sulfate. The solvent was evaporated, and the residue was subjected to a silica gel column chromatography. The fractions eluted with methanol-ethyl acetate (1:30, v/v) were collected, concentrated and recrystallized from hexane-ethanol to give the titled compound (231 mg, 58%) as white crystals.

mp. 188.6-189.2° C. $^1$H-NMR (CDCl$_3$) δ: 1.30 (6H, d, J=6.9 Hz), 2.58 (1H, sept, J=6.9 Hz) 4.70 (2H, d, J=5.1 Hz), 6.79 (1H, br s), 7.50 (1H, d, J=7.7 Hz), 7.58-7.70 (3H, m), 7.87 (1H, m), 8.41 (1H, d, J=7.7 Hz), 8.55 (1H, m). IR(KBr): 3433, 3273, 3071, 2966, 1649, 1589, 1572, 1537, 1440, 1302, 1240 cm$^{-1}$ Elemental Analysis for C$_{18}$H$_{17}$N$_3$O$_2$S.1.0H$_2$O Calcd. C, 60.49; H, 5.36; N, 11.76. Found C, 60.74; H, 5.27; N, 11.72.

Example 207

N-[[6-(4-Oxo-4H-1,3-benzothiazin-2-yl)-2-pyridyl]methyl]benzamide

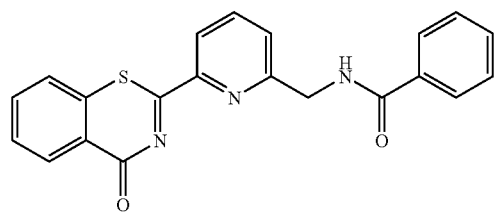

2-[6-(Aminomethyl)-2-pyridyl]-4H-1,3-benzothiazine-4-one trifluoroacetic acid salt (330 mg, 0.86 mmol) was dissolved in N,N-dimethylacetamide (10 ml), and benzoyl chloride (264 mg, 1.87 mmol) was added thereto. The reaction mixture was stirred at 60° C. for 14 hrs and combined with ethyl acetate and water. The organic layer was washed with saturated brine and dried over anhydrous magnesium sulfate. The solvent was evaporated, and the residue was subjected to a silica gel column chromatography. The fractions eluted with hexane-ethyl acetate (1:3, v/v) were collected, concentrated and recrystallized from hexane-tetrahydrofuran to give the titled compound (125 mg, 39%) as white crystals.

mp. 213.9-214.7° C. $^1$H-NMR (CDCl$_3$) δ: 4.90 (2H, d, J=5.1 Hz), 7.51-7.67 (8H, m), 7.88 (1H, m), 8.00 (2H, m), 8.31 (1H, d, J=7.7 Hz), 8.54 (1H, m). IR(KBr): 3344, 1651, 1572, 1537, 1296, 754 cm$^{-1}$ Elemental Analysis for C$_{21}$H$_{15}$N$_3$O$_2$S Calcd. C, 67.54; H, 4.05; N, 11.25. Found C, 67.35; H, 4.13; N, 11.16.

Example 208

N-[[6-(4-Oxo-4H-1,3-benzothiazin-2-yl)-2-pyridyl]methyl]-2-thiophenecarboxamide

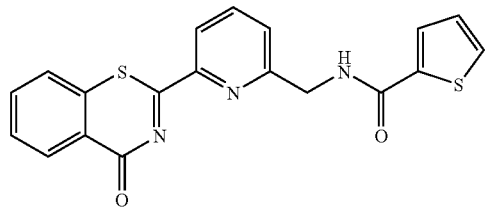

2-[6-(Aminomethyl)-2-pyridyl]-4H-1,3-benzothiazine-4-one trifluoroacetic acid salt (350 mg, 0.91 mmol) was dissolved in N,N-dimethylacetamide (10 ml), and 2-thenoyl chloride (400 mg, 2.72 mmol) was added thereto. The reaction mixture was stirred at 60° C. for 15 hrs and combined with ethyl acetate and water. The organic layer was washed with saturated brine and dried over anhydrous magnesium sulfate. The solvent was evaporated, and the residue was subjected to a silica gel column chromatography. The fractions eluted with hexane-ethylacetate (1:4, v/v) were collected, concentrated and recrystallized from hexane-tetrahydrofuran to give the titled compound (151 mg, 43%) as white crystals.

mp. 208.5-209.0° C. $^1$H-NMR (CDCl$_3$) δ: 4.86 (2H, d, J=5.1 Hz), 7.16 (1H, dd, J=3.7, 4.9 Hz), 7.45 (1H, m), 7.52-7.57 (3H, m), 7.60-7.69 (2H, m), 7.75 (1H, dd, J=1.1, 3.7 Hz), 7.88 (1H, m), 8.37 (1H, d, J=7.5 Hz), 8.53 (1H, m). IR(KBr) 3325, 1643, 1572, 1531, 1298, 1267, 734 cm$^{-1}$ Elemental Analysis for C$_{19}$H$_{13}$N$_3$O$_2$S$_2$ Calcd. C, 60.14; H, 3.45; N, 11.07. Found C, 60.11; H, 3.41; N, 11.17.

Example 209

2,2,2-Trifluoro-N-[[6-(4-oxo-4H-1,3-benzothiazin-2-yl)-2-pyridyl]methyl]acetamide

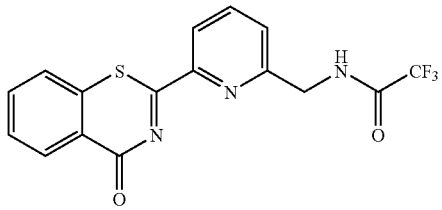

2-[6-(Aminomethyl)-2-pyridyl]-4H-1,3-benzothiazine-4-one trifluoroacetic acid salt (350 mg, 0.91 mmol) was dissolved in pyridine (10 ml), and methanesulfonyl chloride (576 mg, 5.04 mmol) was added thereto. The reaction mixture was stirred at room temperature for 3 hrs. The solvent was evaporated, and the residue was subjected to a silica gel column chromatography. The fractions eluted with hexane-ethyl acetate (1:1, v/v) were collected, concentrated and recrystallized from hexane-tetrahydrofuran to give the titled compound (228 mg, 68%) as pale yellow crystals.

mp. 226.4-227.4° C. $^1$H-NMR (CDCl$_3$) δ: 4.80 (2H, d, J=5.0 Hz), 7.51 (1H, d, J=7.7 Hz), 7.59 (1H, m), 7.64-7.71 (2H, m), 7.88-7.93 (2H, m), 8.42 (1H, d, J=7.7 Hz), 8.54 (1H, dd, J=1.8, 7.5 Hz). IR(KBr): 3269, 3105, 1711, 1655, 1570, 1533, 1439, 1298, 1174, 738 cm$^{-1}$ Elemental Analysis for C$_{16}$H$_{10}$N$_3$O$_2$SF$_3$ Calcd. C, 52.60; H, 2.78; N, 11.50. Found C, 52.74; H, 2.95; N, 11.55.

Example 210

3-(Methylthio)-N-[[6-(4-oxo-4H-1,3-benzothiazin-2-yl)-2-pyridyl]methyl]propanamide

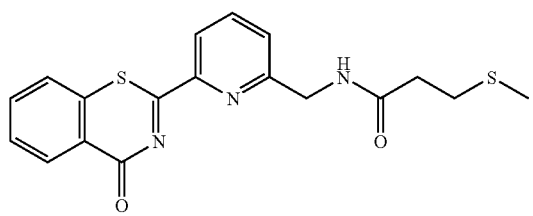

2-[6-(Aminomethyl)-2-pyridyl]-4H-1,3-benzothiazine-4-one trifluoroacetic acid salt (0.80 g, 2.1 mmol) was dissolved in N,N-dimethylacetamide (10 ml), and 3-methylthiopropionyl chloride (0.86 g, 6.2 mmol) was added thereto. The reaction mixture was stirred at 60° C. for 15 hrs and combined with ethyl acetate and water. The organic layer was washed with saturated brine and dried over anhydrous magnesium sulfate. The solvent was evaporated, and the residue was subjected to a silica gel column chromatography. The fractions eluted with methanol-ethyl acetate (1:10, v/v) were collected, concentrated and recrystallized from diisopropyl ether-tetrahydrofuran to give the titled compound (0.18 g, 24%) as white crystals.

mp. 191.6-192.8° C. $^1$H-NMR (CDCl$_3$) δ: 2.18 (3H, s), 2.69 (2H, t, J=7.0 Hz), 2.92 (2H, t, J=7.0 Hz), 4.72 (2H, d, J=5.2 Hz), 6.95 (1H, m), 7.53 (1H, d, J=7.7 Hz), 7.61-7.70 (3H, m), 7.86 (1H, m), 8.39 (1H, d, J=7.8 Hz), 8.55 (1H, m). IR(KBr): 3283, 3078, 1660, 1651, 1572, 1531, 1440, 1300, 1097, 734 cm$^{-1}$ Elemental Analysis for C$_{18}$H$_{17}$N$_3$O$_2$S$_2$ Calcd. C, 58.20; H, 4.61; N, 11.31. Found C, 58.05; H, 4.48; N, 11.30.

Example 211

N-[[6-(4-Oxo-4H-1,3-benzothiazin-2-yl)-2-pyridyl]methyl]methanesulfonamide

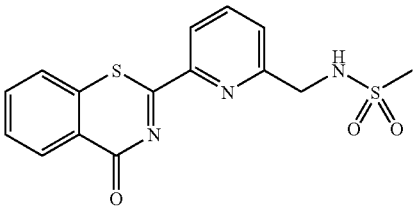

2-[6-(Aminomethyl)-2-pyridyl]-4H-1,3-benzothiazine-4-one trifluoroacetic acid salt (450 mg, 1.1 mmol) and methanesulfonyl chloride (205 mg, 1.7 mmol) were dissolved in ethyl acetate (10 ml) and water (5 ml), and sodium hydrogen carbonate (250 mg, 3.0 mmol) was added thereto. The mixture was stirred at room temperature for 1 hr. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with ethyl acetate-methanol (20:1, v/v) were collected, concentrated and recrystallized from hexane-tetrahydrofuran to give the titled compound (88 mg, 21%) as white crystals.

mp. 188.1-189.5° C. $^1$H-NMR (CDCl$_3$) δ: 3.03 (3H, s), 4.60 (2H, d, J=5.7 Hz), 5.64 (1H, m), 7.56 (1H, d, J=7.7 Hz), 7.60-7.71 (3H, m), 7.91 (1H, m), 8.46 (1H, d, J=7.7 Hz), 8.54 (1H, m). IR(KBr): 3271, 1658, 1572, 1531, 1440, 1317, 1149, 1097, 748, 736 cm$^{-1}$ Elemental Analysis for C$_{15}$H$_{13}$N$_3$O$_3$S$_2$ Calcd. C, 51.86; H, 3.77; N, 12.10. Found C, 51.76; H, 3.69; N, 12.00.

Example 212

N-[[6-(4-Oxo-4H-1,3-benzothiazin-2-yl)-2-pyridyl]methyl]ethanesulfonamide

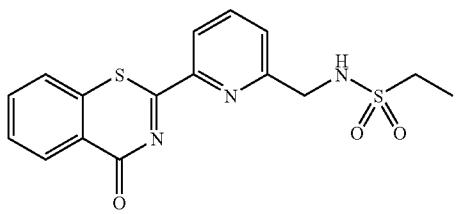

2-[6-(Aminomethyl)-2-pyridyl]-4H-1,3-benzothiazine-4-one trifluoroacetic acid salt (500 mg, 1.3 mmol) and ethanesulfonyl chloride (270 mg, 2.1 mmol) were dissolved in ethyl acetate (10 ml) and water (5 ml), and sodium hydrogen carbonate (270 mg, 3.2 mmol) was added thereto. The mixture was stirred at room temperature for 3 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with ethyl acetate-hexane (2:1, v/v) were collected, concentrated and recrystallized from hexane-tetrahydrofuran to give the titled compound (101 mg, 21%) as pale yellow crystals.

mp. 170.0-171.0° C. $^1$H-NMR (CDCl$_3$) δ: 1.41 (3H, t, J=7.3 Hz), 3.11 (2H, q, J=7.3 Hz), 4.58 (2H, d, J=5.7 Hz), 5.52 (1H, t, J=5.7 Hz), 7.56 (1H, d, J=7.7 Hz), 7.61-7.71 (3H, m), 7.91 (1H, m), 8.46 (1H, d, J=7.8 Hz), 8.55 (1H, m). IR(KBr): 3269, 1658, 1572, 1531, 1440, 1319, 1143, 1097, 736 cm$^{-1}$ Elemental Analysis for C$_{16}$H$_{15}$N$_3$O$_3$S$_2$ Calcd. C, 53.17; H, 4.18; N, 11.63. Found C, 53.19; H, 4.32; N, 11.71.

Example 213

N-[[6-(4-Oxo-4H-1,3-benzothiazin-2-yl)-2-pyridyl]methyl]benzenesulfonamide

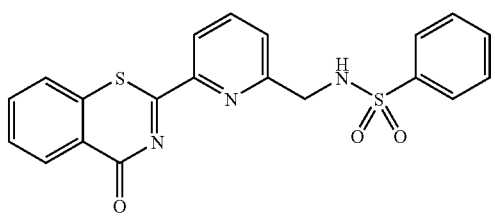

2-[6-(Aminomethyl)-2-pyridyl]-4H-1,3-benzothiazine-4-one trifluoroacetic acid salt (400 mg, 1.0 mmol) and benzenesulfonyl chloride (300 mg, 1.7 mmol) were dissolved in ethyl acetate (10 ml) and water (5 ml), and sodium hydrogen carbonate (225 mg, 2.6 mmol) was added thereto. The mixture was stirred at room temperature for 2 hrs. The reaction mixture was combined with ethyl acetate and water. The organic layer was washed with saturated brine and dried over anhydrous magnesium sulfate. The solvent was evaporated, and the residue was subjected to a silica gel column chromatography. The fractions eluted with ethyl acetate-hexane (1:1, v/v) were collected, concentrated and recrystallized from hexane-tetrahydrofuran to give the titled compound (162 mg, 38%) as white crystals.

mp. 206.7-207.5° C. $^1$H-NMR (CDCl$_3$) δ: 4.44 (2H, d, J=5.7 Hz), 5.84 (1H, t, J=5.7 Hz), 7.38-7.49 (4H, m), 7.65-7.70 (3H, m), 7.79 (1H, m), 7.86-7.90 (2H, m), 8.35 (1H, d, J=7.5 Hz), 8.55 (1H, m) IR(KBr): 3254, 3063, 1658, 1651, 1572, 1537, 1444, 1327, 1304, 1161, 1095 cm$^{-1}$ Elemental Analysis for C$_{20}$H$_{15}$N$_3$O$_3$S$_2$ Calcd. C, 58.66; H, 3.69; N, 10.26. Found C, 58.70; H, 3.67; N, 10.13.

Example 214

Diethyl [6-(4-oxo-4H-1,3-benzothiazin-2-yl)-2-pyridyl]methylamidophosphate

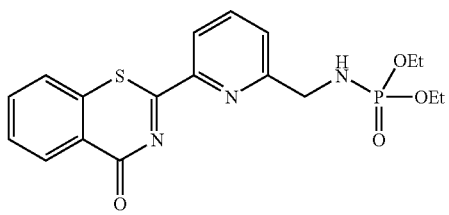

2-[6-(Aminomethyl)-2-pyridyl]-4H-1,3-benzothiazine-4-one trifluoroacetic acid salt (400 mg, 1.0 mmol) and diethyl chlorophosphate (360 mg, 2.1 mmol) were dissolved in acetonitrile (15 ml), and potassium carbonate (430 mg, 3.1 mmol) was added thereto. The mixture was stirred at room temperature for 15 hrs. The solvent was evaporated, and the residue was subjected to a silica gel column chromatography. The fractions eluted with ethyl acetate-methanol (8:1, v/v) were collected, concentrated and recrystallized from diisopropyl ether-methanol to give the titled compound (225 mg, 53%) as white crystals.

mp. 135.2-135.8° C. $^1$H-NMR (CDCl$_3$) δ: 1.36 (6H, m), 3.84 (1H, m), 4.13 (4H, m), 4.37 (2H, dd, J=6.3, 9.1 Hz), 7.55 (1H, d, J=7.7 Hz), 7.63-7.71 (3H, m), 7.89 (1H, m), 8.45 (1H, d, J=7.7 Hz), 8.55 (1H, m). IR(KBr): 3223, 2982, 1660, 1572, 1537, 1440, 1300, 1236, 1057, 1030, 966 cm$^{-1}$ Elemental Analysis for C$_{18}$H$_{20}$N$_3$O$_4$SP Calcd. C, 53.33; H, 4.97; N, 10.36. Found C, 53.18; H, 4.87; N, 10.65.

Example 215

O,O-Diethyl [6-(4-oxo-4H-1,3-benzothiazin-2-yl)-2-pyridyl]methylamidothiophosphate

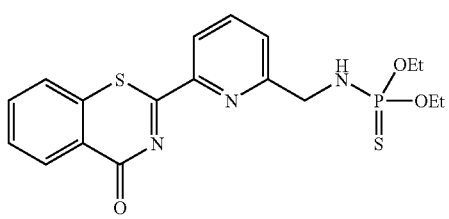

2-[6-(Aminomethyl)-2-pyridyl]-4H-1,3-benzothiazine-4-one trifluoroacetic acid salt (400 mg, 1.0 mmol) and diethyl chlorothiophosphate (410 mg, 2.2 mmol) were dissolved in acetonitrile (15 ml), and potassium carbonate (430 mg, 3.1

Example 216

N,N-Dimethyl-N'-[[6-(4-oxo-4H-1,3-benzothiazin-2-yl)-2-pyridyl]methyl]urea

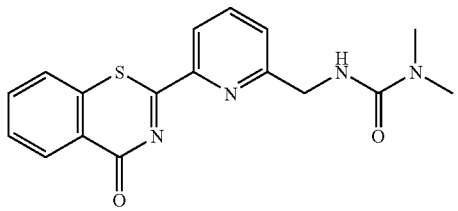

A mixture of 2-[6-(aminomethyl)-2-pyridyl]-4H-1,3-benzothiazine-4-one trifluoroacetic acid salt (0.40 g, 1.0 mmol) and potassium carbonate (0.43 g, 3.1 mmol) was stirred at room temperature for 20 minutes. Successively, N,N-dimethylcarbamoyl chloride (0.47 g, 4.3 mmol) was added to the mixture, and the mixture was stirred at room temperature for 5 hrs. The precipitates were filtered, and the filtrate was concentrated. The residue was subjected to a silica gel column chromatography. The fractions eluted with chloroform-ethanol (40:1, v/v) were collected, concentrated and recrystallized from chloroform-hexane to give the titled compound (0.24 g, 68%) as white crystals.

mp. 175.2-176.3° C. $^1$H-NMR (CDCl$_3$) δ: 3.07 (6H, s), 4.69 (2H, s), 5.75 (1H, br s), 7.53-7.70 (4H, m), 7.88 (1H, m), 8.42 (1H, d, J=7.7 Hz), 8.56 (1H, m). IR(KBr): 3350, 2828, 1643, 1572, 1529, 1440, 1298, 1234, 1097, 734 cm$^{-1}$ Elemental Analysis for C$_{17}$H$_{16}$N$_4$O$_2$S·0.5H$_2$O Calcd. C, 58.44; H, 4.90; N, 16.03. Found C, 58.58; H, 4.63; N, 16.01.

Reference Example 74 tert-Butyl 2-(2-pyridyl)ethylcarbamate

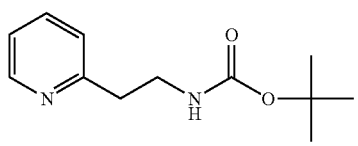

2-(2-Aminoethyl)pyridine (10.2 g, 83 mmol) and di-tert-butyl dicarbonate (20.0 g, 91 mmol) were dissolved in tetrahydrofuran (130 ml), and the mixture was stirred at 0° C. for 30 minutes and at room temperature for 3 hrs. The solvent was evaporated, and the residue was subjected to a silica gel column chromatography. The fraction eluted with hexane-ethyl acetate (1:2, v/v) were collected and concentrated to give the titled compound (18.5 g, 99%).

$^1$H-NMR (CDCl$_3$) δ: 1.43 (9H, s), 2.97 (2H, t, J=6.4 Hz), 3.54 (2H, m), 5.15 (1H, br s), 7.12-7.17 (2H, m), 7.61 (1H, m), 8.53 (1H, dd, J=0.6, 4.8 Hz).

Reference Example 75 tert-Butyl 2-(4-pyridyl)ethylcarbamate

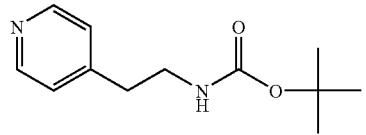

4-(2-Aminoethyl)pyridine (4.4 g, 36 mmol) and di-tert-butyl dicarbonate (8.8 g, 40 mmol) were dissolved in tetrahydrofuran (60 ml), and the mixture was stirred at 0° C. for 30 minutes and at room temperature for 3 hrs. The solvent was evaporated, and the residue was subjected to a silica gel column chromatography. The fraction eluted with ethyl acetate were collected and concentrated to give the titled compound (6.9 g, 81%).

$^1$H-NMR (CDCl$_3$) δ: 1.43 (9H, s), 2.80 (2H, t, J=6.9 Hz), 3.40 (2H, m), 4.60 (1H, br s), 7.13 (2H, d, J=6.0 Hz), 8.51 (2H, d, J=6.0 Hz).

Reference Example 76 tert-Butyl 2-(2-pyridyl)ethylcarbamate N-oxide

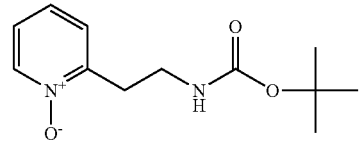

tert-Butyl 2-(2-pyridyl)ethylcarbamate (18.5 g, 83 mmol) and 3-chloroperbenzoic acid (77%, 24.5 g, 109 mmol) were dissolved in ethyl acetate (200 ml), and the mixture was stirred at room temperature for 15 hrs. The solvent was evaporated, and the residue was subjected to a silica gel column chromatography. The fractions eluted with methanol-ethyl acetate (1:4, v/v) were collected and concentrated to give the titled compound (19.6 g, 99%).

$^1$H-NMR (CDCl$_3$) δ: 1.41 (9H, s), 3.16 (2H, t, J=6.4 Hz), 3.53 (2H, m), 5.40 (1H, br s), 7.18-7.26 (3H, m), 8.26 (1H, m).

Reference Example 77 tert-Butyl 2-(4-pyridyl)ethylcarbamate N-oxide

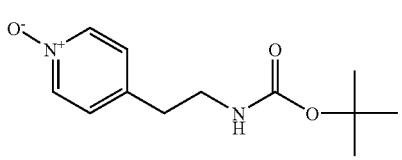

tert-Butyl 2-(4-pyridyl)ethylcarbamate (6.9 g, 31 mmol) and 3-chloroperbenzoic acid (77%, 9.1 g, 40 mmol) were dissolved in ethyl acetate (100 ml), and the mixture was stirred at room temperature for 3 hrs. The solvent was evaporated, and the residue was subjected to a silica gel column chromatography. The fractions eluted with methanol-ethyl acetate (1:3, v/v) were collected and concentrated to give the titled compound (7.4 g, 99%).

$^1$H-NMR (CDCl$_3$) δ: 1.42 (9H, s), 2.82 (2H, t, J=6.8 Hz), 3.38 (2H, m), 4.90 (1H, br s), 7.12 (2H, d, J=6.9 Hz), 8.13 (2H, d, J=6.9 Hz).

Reference Example 78 tert-Butyl 2-(6-cyano-2-pyridyl)ethylcarbamate

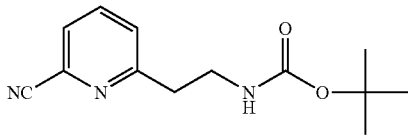

tert-Butyl 2-(2-pyridyl)ethylcarbamate N-oxide (6.2 g, 26 mmol) was dissolved in nitroethane (80 ml), and trimethylsilyl cyanide (7.8 g, 78 mmol) and N,N-dimethylcarbamoyl chloride (5.5 g, 51 mmol) were added thereto. The mixture was stirred at room temperature for 48 hrs. The solvent was evaporated, and the residue was subjected to a silica gel column chromatography. The fractions eluted with ethyl acetate-hexane (1:2, v/v) were collected, concentrated and recrystallized from hexane-ethyl acetate to give the titled compound (5.3 g, 83%).

mp. 79.1-80.3° C. $^1$H-NMR (CDCl$_3$) δ: 1.42 (9H, s) 3.04 (2H, t, J=6.4 Hz), 3.56 (2H, m), 4.92 (1H, br s), 7.40 (1H, d, J=7.8 Hz), 7.56 (1H, d, J=7.6 Hz), 7.75 (1H, dd, J=7.6, 7.8 Hz). IR(KBr): 3350, 2976, 2932, 2235, 1697, 1589, 1514, 1452, 1365, 1275, 1250 cm$^{-1}$ Elemental Analysis for C$_{13}$H$_{17}$N$_3$O$_2$ Calcd. C, 63.14; H, 6.93; N, 16.99. Found C, 63.12; H, 6.90; N, 17.02.

Reference Example 79 tert-Butyl 2-(2-cyano-4-pyridyl)ethylcarbamate

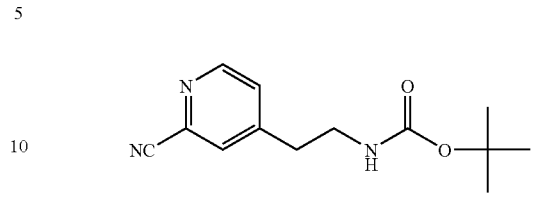

tert-Butyl 2-(4-pyridyl)ethylcarbamate N-oxide (7.4 g, 31 mmol) was dissolved in nitroethane (100 ml), and trimethylsilyl cyanide (9.2 g, 92 mmol) and N,N-dimethylcarbamoyl chloride (6.7 g, 62 mmol) were added thereto. The mixture was stirred at room temperature for 10 hrs. The solvent was evaporated, and the residue was subjected to a silica gel column chromatography. The fractions eluted with ethyl acetate-hexane (1:1, v/v) were collected, concentrated and recrystallized from hexane-ethyl acetate to give the titled compound (6.6 g, 86%)

mp. 70.5-71.2° C. $^1$H-NMR (CDCl$_3$) δ: 1.42 (9H, s) 2.88 (2H, t, J=6.8 Hz), 3.41 (2H, m), 4.63 (1H, br s), 7.37 (1H, dd, J=1.3, 4.9 Hz), 7.55 (1H, d, J=1.3 Hz), 8.62 (1H, d, J=4.9 Hz). IR(KBr): 3337, 2976, 2934, 2237, 1697, 1599, 1518, 1365, 1275, 1250, 1169 cm$^{-1}$ Elemental Analysis for C$_{13}$H$_{17}$N$_3$O$_2$ Calcd. C, 63.14; H, 6.93; N, 16.99. Found C, 63.33; H, 6.98; N, 17.05.

Example 217 tert-Butyl 2-[6-(4-oxo-4H-1,3-benzothiazin-2-yl)-2-pyridyl]ethylcarbamate

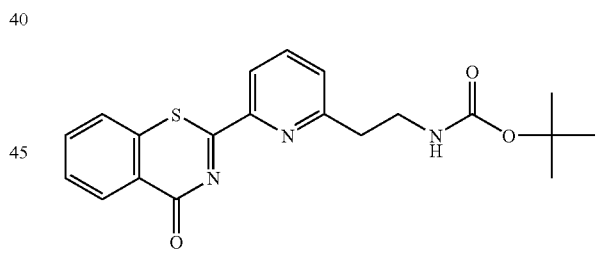

tert-Butyl 2-(6-cyano-2-pyridyl)ethylcarbamate (2.0 g, 8.1 mmol) and methyl thiosalicylate (2.0 g, 12 mmol) were dissolved in toluene (10 ml), and triethylamine (5.0 ml, 36 mmol) was added thereto. The mixture was refluxed for 14 hrs. The solvent was evaporated, and the residue was subjected to a silica gel column chromatography. The fractions eluted with ethyl acetate-hexane (3:2, v/v) were collected, concentrated and recrystallized from hexane-tetrahydrofuran to give the titled compound (2.0 g, 64%) as white crystals.

mp. 170.2-170.8° C. $^1$H-NMR (CDCl$_3$) δ: 1.45 (9H, s), 3.12 (2H, t, J=6.3 Hz), 3.69 (2H, m), 5.27 (1H, br s), 7.40 (1H, d, J=7.6 Hz), 7.61-7.72 (3H, m), 7.83 (1H, m), 8.39 (1H, d, J=7.7 Hz), 8.56 (1H, m). IR(KBr): 3350, 2976, 2930, 1705, 1660, 1572, 1535, 1300, 1248, 1170, 736 cm$^{-1}$. Elemental Analysis for C$_{20}$H$_{21}$N$_3$O$_3$S Calcd. C, 62.64; H, 5.52; N, 10.96. Found C, 62.67; H, 5.45; N, 11.08.

Example 218 tert-Butyl 2-[2-(4-oxo-4H-1,3-benzothiazin-2-yl)-4-pyridyl]ethylcarbamate

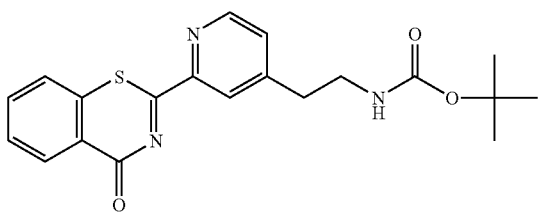

tert-Butyl 2-(2-cyano-4-pyridyl)ethylcarbamate (3.0 g, 12 mmol) and methyl thiosalicylate (3.6 g, 21 mmol) were dissolved in toluene (12 ml), and triethylamine (6.0 ml, 43 mmol) was added thereto. The mixture was refluxed for 8 hrs. The solvent was evaporated, and the residue was subjected to a silica gel column chromatography. The fractions eluted with ethyl acetate-hexane (2:1, v/v) were collected, concentrated and recrystallized from hexane-ethanol to give the titled compound (3.3 g, 71%) as white crystals.

mp. 159.8-161.0° C. $^1$H-NMR (CDCl$_3$) δ: 1.41 (9H, s), 2.93 (2H, t, J=6.9 Hz), 3.46 (2H, m), 4.58 (1H, br s), 7.41 (1H, m), 7.60-7.69 (3H, m), 8.41 (1H, s), 8.55 (1H, dd, J=1.4, 8.0 Hz), 8.64 (1H, d, J=4.9 Hz). IR(KBr): 3350, 2976, 2930, 1705, 1660, 1572, 1535, 1300, 1248, 1170, 736 cm$^{-1}$. Elemental Analysis for C$_{20}$H$_{21}$N$_3$O$_3$S Calcd. C, 62.64; H, 5.52; N, 10.96. Found C, 62.67; H, 5.62; N, 10.88.

Example 219 tert-Butyl 2-[2-(7-chloro-4-oxo-4H-1,3-benzothiazin-2-yl)-4-pyridyl]ethylcarbamate

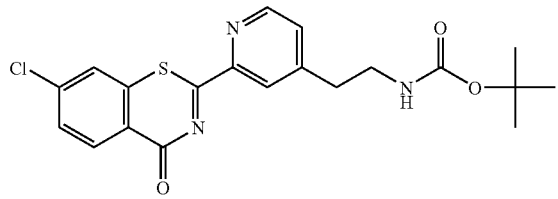

tert-Butyl 2-(2-cyano-4-pyridyl)ethylcarbamate (1.5 g, 6.0 mmol) and 4-chlorothiosalicylic acid (2.3 g, 12.1 mmol) were dissolved in pyridine (10 ml), and the mixture was refluxed for 18 hrs. The solvent was evaporated, and the residue was subjected to a silica gel column chromatography. The fractions eluted with hexane-ethyl acetate (1:1, v/v) were collected, concentrated and recrystallized from hexane-tetrahydrofuran to give the titled compound (0.48 g, 19%) as white crystals.

mp. 168.2-169.2° C. $^1$H-NMR (CDCl$_3$) δ: 1.42 (9H, s), 2.94 (2H, t, J=6.9 Hz), 3.46 (2H, m), 4.60 (1H, br s), 7.42 (1H, d, J=4.0 Hz), 7.56-7.60 (2H, m), 8.38 (1H, s), 8.48 (1H, d, J=8.3 Hz), 8.64 (1H, d, J=4.9 Hz). IR(KBr): 3377, 2980, 1685, 1655, 1585, 1560, 1531, 1381, 1284, 1165, 729 cm$^{-1}$ Elemental Analysis for C$_{20}$H$_{20}$N$_3$O$_3$SCl Calcd. C, 57.48; H, 4.82; N, 10.05. Found C, 57.67; H, 4.88; N, 9.86.

Example 220

2-[6-(2-Aminoethyl)-2-pyridyl]-4H-1,3-benzothiazine-4-one trifluoroacetic acid salt

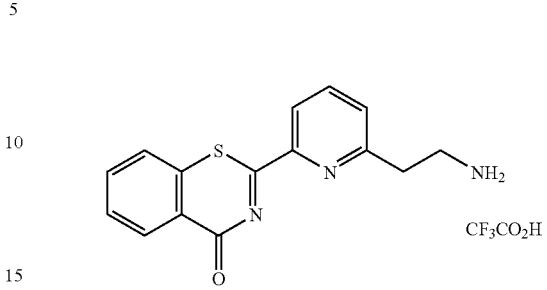

tert-Butyl 2-[6-(4-oxo-4H-1,3-benzothiazin-2-yl)-2-pyridyl]ethylcarbamate (0.35 g, 0.91 mmol) was dissolved in trifluoroacetic acid (4 ml), and the mixture was stirred at room temperature for 2 hrs. The solvent was evaporated, and the residue was recrystallized from methanol-diisopropyl ether to give the titled compound (0.33 g, 91%) as white crystals.

mp. 206.2-207.1° C. $^1$H-NMR (DMSO-d$_6$) δ: 3.22 (2H, t, J=7.0 Hz), 3.37 (2H, t, J=7.0 Hz), 7.70-7.77 (2H, m), 7.82-7.91 (2H, m), 7.99 (3H, br s), 8.08 (1H, m), 8.25 (1H, d, J=7.8 Hz), 8.37 (1H, d, J=7.9 Hz). IR(KBr): 3130, 1676, 1662, 1574, 1541, 1483, 1203, 1184, 1120, 817, 798 cm$^{-1}$. Elemental Analysis for C$_{17}$H$_{14}$N$_3$O$_3$SF$_3$ Calcd. C, 51.38; H, 3.55; N, 10.57. Found C, 51.41; H, 3.80; N, 10.62.

Example 221

2-[4-(2-Aminoethyl)-2-pyridyl]-4H-1,3-benzothiazine-4-one trifluoroacetic acid salt

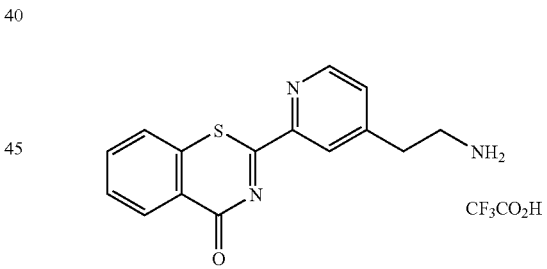

tert-Butyl 2-[2-(4-oxo-4H-1,3-benzothiazin-2-yl)-4-pyridyl]ethylcarbamate (0.82 g, 2.1 mmol) was dissolved in trifluoroacetic acid (10 ml), and the mixture was stirred at room temperature for 2 hrs. The solvent was evaporated, and the residue was recrystallized from methanol-diisopropyl ether to give the titled compound (0.75 g, 89%) as white crystals.

mp. 209.0-210.7° C. $^1$H-NMR (DMSO-d$_6$) δ: 3.06 (2H, t, J=7.2 Hz), 3.21 (2H, m) 7.68-7.77 (2H, m), 7.82-7.95 (5H, m), 8.31 (1H, s), 8.37 (1H, d, J=7.8 Hz), 8.76 (1H, d, J=4.6 Hz). IR(KBr): 2990, 1678, 1635, 1521, 1203, 1174, 1145, 833 cm$^{-1}$. Elemental Analysis for C$_{17}$H$_{14}$N$_3$O$_3$SF$_3$ Calcd. C, 51.38; H, 3.55; N, 10.57. Found C, 51.28; H, 3.48; N, 10.64.

Example 222

2-[4-(2-Aminoethyl)-2-pyridyl]-4H-1,3-benzothiazine-4-one hydrochloride salt

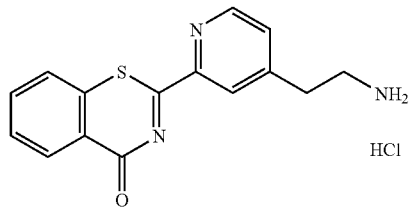

tert-Butyl 2-[2-(4-oxo-4H-1,3-benzothiazin-2-yl)-4-pyridyl]ethylcarbamate (0.40 g, 1.0 mmol) was dissolved in ethyl acetate (20 ml), and 4 N hydrochloric acid in ethyl acetate (2 ml) was added thereto dropwise at 0° C. The mixture was stirred at the same temperature for 1 hr. The precipitates were collected by filtration and recrystallized from diisopropyl ether-methanol to give the titled compound (0.04 g, 12%) as white crystals.

mp. 238° C. (decomposed) $^1$H-NMR (DMSO-$d_6$) δ: 3.12 (2H, m), 3.17 (2H, m), 7.71 (1H, d, J=4.9 Hz), 7.76 (1H, d, J=7.8 Hz), 7.85 (1H, m), 7.93 (1H, d, J=8.0 Hz), 8.10 (3H, br s), 8.30 (1H, s), 8.37 (1H, d, J=7.8 Hz), 8.76 (1H, d, J=4.9 Hz). IR(KBr): 2889, 2739, 2640, 1633, 1518, 1304, 1099 cm$^{-1}$ Elemental Analysis for $C_{15}H_{14}N_3OSCl \cdot 0.25H_2O$ Calcd. C, 55.55; H, 4.51; N, 12.96. Found C, 55.71; H, 4.43; N, 12.91.

Example 223

2-[4-(2-Aminoethyl)-2-pyridyl]-7-chloro-4H-1,3-benzothiazine-4-one trifluoroacetic acid salt

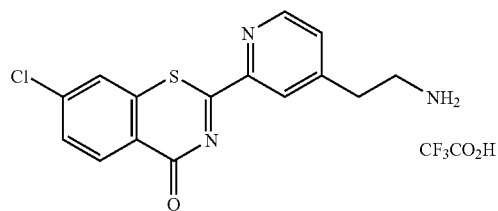

tert-Butyl 2-[2-(7-chloro-4-oxo-4H-1,3-benzothiazin-2-yl)-4-pyridyl]ethylcarbamate (0.36 g, 0.86 mmol) was dissolved in trifluoroacetic acid (10 ml), and the mixture was stirred at room temperature for 3 hrs. The solvent was evaporated, and the residue was recrystallized from methanol-diisopropyl ether to give the titled compound (0.33 g, 89%) as white crystals.

mp. 212° C. (decomposed) $^1$H-NMR (DMSO-$d_6$) δ: 3.06 (2H, t, J=7.2 Hz), 3.20 (2H, m), 7.70 (1H, dd, J=1.5, 4.9 Hz), 7.78 (1H, dd, J=2.0, 8.5 Hz), 7.87 (3H, br s), 8.18 (1H, d, J=2.0 Hz), 8.30 (1H, d, J=1.5 Hz), 8.34 (1H, d, J=8.5 Hz), 8.76 (1H, d, J=4.9 Hz). IR(KBr): 3047, 1693, 1635, 1560, 1520, 1203, 1165, 1138 cm$^{-1}$. Elemental Analysis for $C_{17}H_{13}N_3O_3SF_3Cl$ Calcd. C, 47.28; H, 3.03; N, 9.73. Found C, 47.27; H, 3.23; N, 9.79.

Example 224

N-[2-[6-(4-Oxo-4H-1,3-benzothiazin-2-yl)-2-pyridyl]ethyl]benzamide

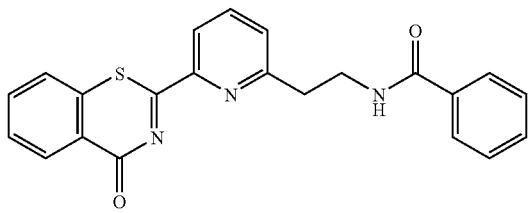

2-[6-(2-Aminoethyl)-2-pyridyl]-4H-1,3-benzothiazine-4-one trifluoroacetic acid salt (0.53 g, 1.3 mmol) was dissolved in N,N-dimethylacetamide (10 ml), and benzoyl chloride (0.38 g, 2.7 mmol) and potassium carbonate (0.18 g, 1.3 mmol) were added thereto. The reaction mixture was stirred at 60° C. for 4 hrs, combined with ethyl acetate and water. The organic layer was successively washed with saturated aqueous sodium hydrogen carbonate solution and saturated brine, and dried over anhydrous magnesium sulfate. The solvent was evaporated, and the residue was subjected to a silica gel column chromatography. The fractions eluted with methanol-ethyl acetate (1:20, v/v) were collected, concentrated and recrystallized from hexane-ethanol to give the titled compound (0.13 g, 26%) as white crystals.

mp. 201.7-202.6° C. $^1$H-NMR (CDCl$_3$) δ: 3.27 (2H, t, J=6.0 Hz), 4.04 (2H, t, J=6.0 Hz), 7.37-7.47 (6H, m), 7.60-7.70 (2H, m), 7.81-7.85 (3H, m), 8.40 (1H, d, J=7.4 Hz), 8.55 (1H, m). IR(KBr): 3325, 1643, 1572, 1529, 1439, 1302, 736 cm$^{-1}$ Elemental Analysis for $C_{22}H_{17}N_3O_2S$ Calcd. C, 68.20; H, 4.42; N, 10.85. Found C, 68.40; H, 4.35; N, 10.78.

Example 225

N-[2-[2-(4-Oxo-4H-1,3-benzothiazin-2-yl)-4-pyridyl]ethyl]benzamide

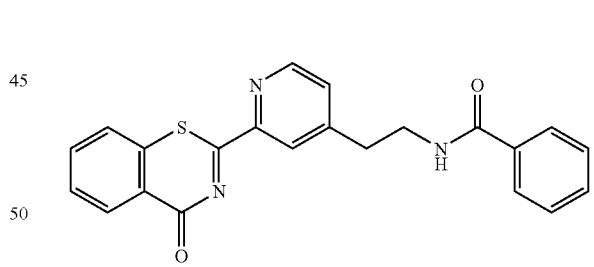

2-[4-(2-Aminoethyl)-2-pyridyl]-4H-1,3-benzothiazine-4-one trifluoroacetic acid salt (0.50 g, 1.2 mmol) was dissolved in N,N-dimethylacetamide (10 ml), and benzoyl chloride (0.36 g, 2.6 mmol) and potassium carbonate (0.17 g, 1.2 mmol) were added thereto. The reaction mixture was stirred at 60° C. for 5 hrs, combined with ethyl acetate and water. The organic layer was successively washed with saturated aqueous sodium hydrogen carbonate solution and saturated brine, and dried over anhydrous magnesium sulfate. The solvent was evaporated, and the residue was subjected to a silica gel column chromatography. The fractions eluted with methanol-ethyl acetate (1:20, v/v) were collected, concentrated and recrystallized from hexane-chloroform to give the titled compound (0.17 g, 36%) as white crystals.

mp. 216.8-219.3° C. ¹H-NMR (CDCl₃) δ: 3.07 (2H, t, J=6.9 Hz), 3.80 (2H, m), 6.54 (1H, m), 7.41-7.48 (4H, m), 7.62-7.77 (5H, m), 8.41 (1H, s), 8.52 (1H, m), (1H, d, J=4.9 Hz). IR(KBr): 3287, 3061, 1657, 1643, 1572, 1531, 1304, 1282, 742 cm⁻¹ Elemental Analysis for C₂₂H₁₇N₃O₂S Calcd. C, 68.20; H, 4.42; N, 10.85. Found C, 67.91; H, 4.33; N, 10.81.

Example 226

N-[2-[6-(4-Oxo-4H-1,3-benzothiazin-2-yl)-2-pyrizyl]ethyl]acetamide

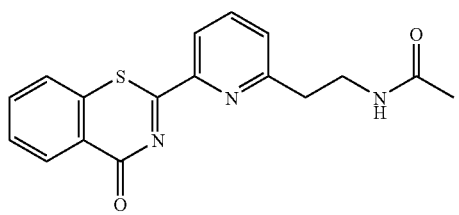

2-[6-(2-Aminoethyl)-2-pyridyl]-4H-1,3-benzothiazine-4-one trifluoroacetic acid salt (0.58 g, 1.4 mmol) was dissolved in N,N-dimethylacetamide (10 ml), and acetyl chloride (0.38 g, 4.8 mmol) and potassium carbonate (0.20 g, 1.4 mmol) were added thereto. The reaction mixture was stirred at 60° C. for 8 hrs, combined with ethyl acetate and water. The organic layer was washed with saturated brine, and dried over anhydrous magnesium sulfate. The solvent was evaporated, and the residue was subjected to a silica gel column chromatography. The fractions eluted with methanol-ethyl acetate (1:8, v/v) were collected, concentrated and recrystallized from diisopropyl ether-methanol to give the titled compound (0.15 g, 31%) as pale yellow crystals.

mp. 206.7-207.9° C. ¹H-NMR (CDCl₃) δ: 2.04 (3H, s), 3.14 (2H, t, J=6.1 Hz), 3.83 (2H, m), 6.53 (1H, br s), 7.41 (1H, d, J=7.6 Hz), 7.58-7.70 (3H, m), 7.83 (1H, m), 8.37 (1H, d, J=7.7 Hz), 8.55 (1H, dd, J=1.5, 7.7 Hz). IR(KBr): 3325, 1643, 1572, 1529, 1439, 1302, 736 cm⁻¹ Elemental Analysis for C₁₇H₁₅N₃O₂S Calcd. C, 62.75; H, 4.65; N, 12.91. Found C, 62.63; H, 4.63; N, 12.94.

Example 227

N-[2-[6-(4-Oxo-4H-1,3-benzothiazin-2-yl)-2-pyridyl]ethyl]-N'-phenylurea

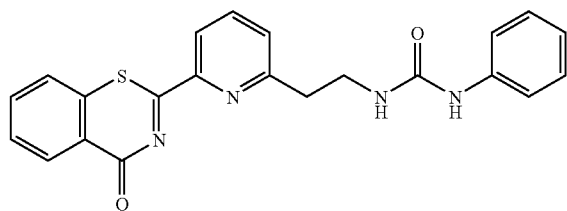

A mixture of 2-[6-(2-aminoethyl)-2-pyridyl]-4H-1,3-benzothiazine-4-one trifluoroacetic acid salt (0.40 g, 1.0 mmol), potassium carbonate (0.41 g, 3.0 mmol) and acetonitrile (15 ml) was stirred at room temperature for 20 minutes. Successively phenyl isocyanate (0.47 g, 4.0 mmol) was added to the mixture, and the mixture was refluxed for 4 hrs. After cooling, the precipitates were collected by filtration and dissolved in chlorobenzene and water. The organic layer was dried over magnesium sulfate. The solvent was evaporated, and the residue was recrystallized from hexane-chlorobenzene to give the titled compound (0.07 g, 17%) as pale yellow crystals.

mp. 234.8-236.4° C. ¹H-NMR (DMSO-d₆) δ: 3.08 (2H, t, J=6.6 Hz), 3.61 (2H, m), 6.21 (1H, m), 6.87 (1H, m), 7.19 (2H, m), 7.36 (2H, d, J=7.7 Hz), 7.66 (1H, d, J=7.6 Hz), 7.73 (1H, m), 7.81-7.88 (2H, m), 8.04 (1H, m), 8.22 (1H, d, J=7.7 Hz), 8.36 (1H, d, J=7.6 Hz), 8.46 (1H, s). IR(KBr): 3422, 3325, 2943, 1687, 1641, 1597, 1570, 1541, 1496, 1440, 1311 cm⁻¹ Elemental Analysis for C₂₂H₁₈N₄O₂S·0.5H₂O Calcd. C, 64.22; H, 4.65; N, 13.62. Found C, 64.27; H, 4.40; N, 13.61.

Example 228

N-Ethyl-N'-[2-[6-(4-oxo-4H-1,3-benzothiazin-2-yl)-2-pyridyl]ethyl]urea

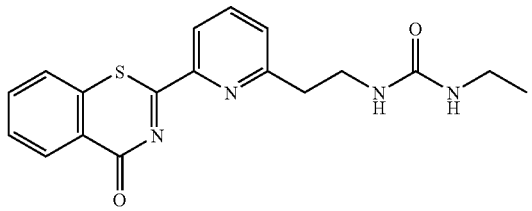

A mixture of 2-[6-(2-aminoethyl)-2-pyridyl]-4H-1,3-benzothiazine-4-one trifluoroacetic acid salt (0.45 g, 1.1 mmol), potassium carbonate (0.47 g, 3.4 mmol) and acetonitrile (26 ml) was stirred at room temperature for 20 minutes. Successively ethyl isocyanate (0.36 g, 5.1 mmol) was added to the mixture, and the mixture was refluxed for 3 hrs. After cooling, the precipitates were collected by filtration, dissolved in chloroform and subjected to a silica gel column chromatography. The fractions eluted with chloroform-ethanol (15:1, v/v) were collected, concentrated and recrystallized from chloroform-hexane to give the titled compound (0.25 g, 63%) as white crystals.

mp. 240.3-242.4° C. ¹H-NMR (DMSO-d₆) δ: 0.96 (3H, t, J=7.1 Hz), 2.95-3.04 (4H, m), 3.49 (2H, m), 5.83 (1H, t, J=5.4 Hz), 5.88 (1H, t, J=5.6 Hz), 7.61 (1H, d, J=7.5 Hz), 7.75 (1H, m), 7.85 (1H, m), 7.95 (1H, d, J=7.6 Hz), 8.02 (1H, m), 8.20 (1H, d, J=7.6 Hz), 8.36 (1H, dd, J=0.8, 7.8 Hz). IR(KBr): 3319, 1660, 1622, 1572, 1539, 1302, 1095, 744 cm⁻¹ Elemental Analysis for C₁₈H₁₈N₄O₂S Calcd. C, 61.00; H, 5.12; N, 15.81. Found C, 60.85; H, 5.11; N, 15.81.

Example 229

N,N-Dimethyl-N'-[2-[6-(4-oxo-4H-1,3-benzothiazin-2-yl)-2-pyridyl]ethyl]urea

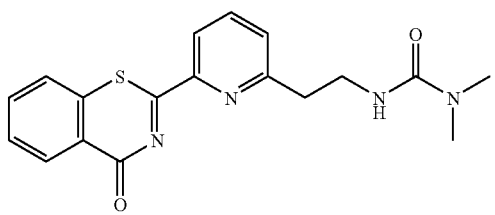

A mixture of 2-[6-(2-aminoethyl)-2-pyridyl]-4H-1,3-benzothiazine-4-one trifluoroacetic acid salt (0.45 g, 1.1 mmol), potassium carbonate (0.46 g, 3.3 mmol) and acetonitrile (20 ml) was stirred at room temperature for 20 minutes. Successively N,N-dimethylcarbamoyl chloride (0.47 g, 4.3 mmol) was added to the mixture, and the mixture was stirred at room temperature for 3 hrs. The precipitates were filtered, and the filtrate was concentrated. The residue was subjected to a silica gel column chromatography. The fractions eluted with chloroform-ethanol (20:1, v/v) were collected, concentrated and recrystallized from chloroform-hexane to give the titled compound (0.31 g, 77%) as white crystals.

mp. 190.2-191.0° C. $^1$H-NMR (CDCl$_3$) δ: 2.89 (6H, s), 3.16 (2H, t, J=6.2 Hz), 3.81 (2H, m), 5.17 (1H, m), 7.43 (1H, d, J=7.6 Hz), 7.59-7.71 (3H, m), 7.84 (1H, m), 8.38 (1H, d, J=7.8 Hz), 8.54 (1H, m). IR(KBr): 3352, 2928, 1655, 1637, 1570, 1533, 1439, 1300, 1232, 1097, 736 cm$^{-1}$ Elemental Analysis for C$_{18}$H$_{18}$N$_4$O$_2$S.0.25H$_2$O Calcd. C, 60.23; H, 5.20; N, 15.61. Found C, 60.36; H, 5.15; N, 15.56.

Example 230

N,N-Diethyl-N'-[2-[6-(4-oxo-4H-1,3-benzothiazin-2-yl)-2-pyridyl]ethyl]urea

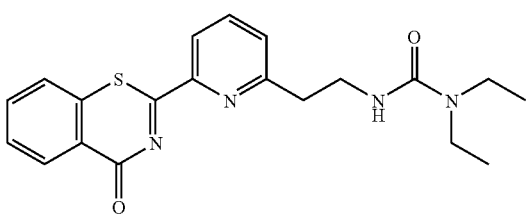

A mixture of 2-[6-(2-aminoethyl)-2-pyridyl]-4H-1,3-benzothiazine-4-one trifluoroacetic acid salt (0.40 g, 1.0 mmol), potassium carbonate (0.41 g, 3.0 mmol) and acetonitrile (20 ml) was stirred at room temperature for 20 minutes. Successively N,N-diethylcarbamoyl chloride (0.54 g, 4.0 mmol) was added to the mixture, and the mixture was stirred at room temperature for 4 hrs. The precipitates were filtered, and the filtrate was concentrated. The residue was subjected to a silica gel column chromatography. The fractions eluted with chloroform-ethanol (30:1, v/v) were collected, concentrated and recrystallized from ethanol-hexane to give the titled compound (0.12 g, 31%) as white crystals.

mp. 174.9-175.6° C. $^1$H-NMR (CDCl$_3$) δ: 1.06 (6H, t, J=7.1 Hz), 3.15-3.26 (6H, m), 3.82 (2H, m), 5.06 (1H, m), 7.42 (1H, d, J=7.7 Hz), 7.58-7.70 (3H, m), 7.83 (1H, m), 8.38 (1H, d, J=7.7 Hz), 8.56 (1H, m). IR(KBr): 3358, 2972, 2930, 1658, 1643, 1572, 1531, 1439, 1282, 1097, 736 cm$^{-1}$ Elemental Analysis for C$_{20}$H$_{22}$N$_4$O$_2$S Calcd. C, 62.80; H, 5.80; N, 14.65. Found C, 62.88; H, 5.73; N, 14.64.

Reference Example 80 tert-Butyl 2-pyridylcarbamate

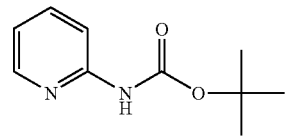

2-Aminopyridine (6.0 g, 63.7 mmol) and di-tert-butyl dicarbonate (14.4 g, 65.9 mol) were dissolved in tetrahydrofuran (150 ml), and the mixture was refluxed for 12 hrs. After cooling, the precipitates were filtered, and the filtrate was concentrated. The residue was subjected to a silica gel column chromatography. The fractions eluted with hexane-ethyl acetate (15:1, v/v) were collected and concentrated to give the titled compound (7.5 g, 60%).

$^1$H-NMR (CDCl$_3$) δ: 1.54 (9H, s), 6.94 (1H, m), 7.65 (1H, m), 7.96 (1H, d, J=8.4 Hz), 8.29 (1H, d, J=4.6 Hz), 8.70 (1H, br s).

Reference Example 81 tert-Butyl 2-pyridylcarbamate N-oxide

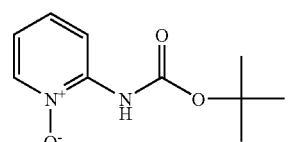

tert-Butyl 2-pyridylcarbamate (7.4 g, 38 mmol) and 3-chloroperbenzoic acid (77%, 11.2 g, 50 mmol) were dissolved in ethyl acetate (100 ml), and the mixture was stirred at room temperature for 20 hrs. The solvent was evaporated, and the residue was subjected to a silica gel column chromatography. The fractions eluted with methanol-ethyl acetate (1:20, v/v) were collected and concentrated to give the titled compound (7.6 g, 95%).

$^1$H-NMR (CDCl$_3$) δ: 1.54 (9H, s), 6.91 (1H, m), 7.29 (1H, m), 8.15 (1H, dd, J=1.6, 8.5 Hz), 8.20 (1H, m), 9.30 (1H, br s)

Reference Example 82

N'-(6-Cyano-2-pyridyl)-N,N-dimethylurea

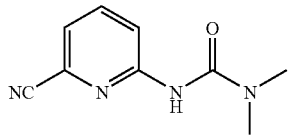

tert-Butyl 2-pyridylcarbamate N-oxide (7.6 g, 36 mmol) was dissolved in nitroethane (100 ml), and trimethylsilyl cyanide (14.5 g, 146 mmol) and N,N-dimethylcarbamoyl chloride (15.8 g, 147 mmol) were added thereto. The mixture was stirred at room temperature for 3 days and at 50° C. for 24 hrs. The solvent was evaporated, and the residue was subjected to a silica gel column chromatography. The fractions eluted with ethyl acetate-hexane (1:1, v/v) were collected and concentrated. The residue was crystallized from hexane to give tert-butyl 6-cyano-2-pyridyl [(dimethylamino)carbonyl] carbamate (3.3 g) Furthermore, this compound (3.3 g) was dissolved in trifluoroacetic acid (20 ml), and the mixture was stirred at 0° C. for 3 hrs. The solvent was evaporated, and the residue was subjected to a silica gel. The fractions eluted with hexane-ethyl acetate (1:1, v/v) were collected, concentrated and recrystallized from hexane-ethyl acetate to give the titled compound (1.0 g, 15%).

mp. 124.6-124.8° C. $^1$H-NMR (CDCl$_3$) δ: 3.06 (6H, s), 7.31 (1H, br s), 7.32 (1H, d, J=7.4 Hz), 7.74 (1H, dd, J=7.4, 8.6 Hz), 8.33 (1H, d, J=8.6 Hz). IR(KBr): 3408, 2941, 2235, 1666, 1574, 1529, 1452, 1400, 1307, 1174, 983 cm$^{-1}$. Elemental Analysis for C$_9$H$_{10}$N$_4$O Calcd. C, 56.83; H, 5.30; N, 29.46. Found C, 56.82; H, 5.37; N, 29.60.

Example 231

N,N-Dimethyl-N'-[6-(4-oxo-4H-1,3-benzothiazin-2-yl)-2-pyridyl]urea

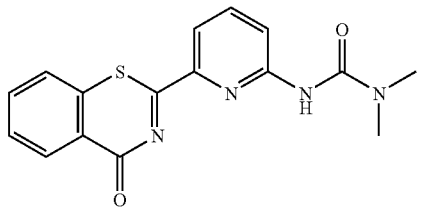

N'-(6-Cyano-2-pyridyl)-N,N-dimethylurea (0.72 g, 3.8 mmol) and methyl thiosalicylate (0.89 g, 5.2 mmol) were dissolved in toluene (4 ml), and triethylamine (2.0 ml, 14.3 mmol) was added thereto. The mixture was refluxed for 8 hrs. After cooling, the precipitates were collected and recrystallized from diisopropyl ether-methanol to give the titled compound (0.62 g, 50%) as white crystals.

mp. 230.1-230.3° C. $^1$H-NMR (CDCl$_3$) δ: 3.13 (6H, s), 7.28 (1H, s), 7.52 (1H, d, J=7.2 Hz), 7.59-7.64 (2H, m), 7.81 (1H, m), 8.14 (1H, d, J=7.5 Hz), 8.27 (1H, d, J=8.3 Hz), 8.52 (1H, m). IR(KBr): 3485, 1651, 1579, 1529, 1456, 1404, 1300, 989, 808, 738 cm$^{-1}$. Elemental Analysis for C$_{16}$H$_{14}$N$_4$O$_2$S Calcd. C, 58.88; H, 4.32; N, 17.17. Found C, 58.74; H, 4.08; N, 17.06.

Example 232 tert-Butyl 6-(8-methyl-4-oxo-4H-1,3-benzothiazin-2-yl)-2-pyridinecarboxylate

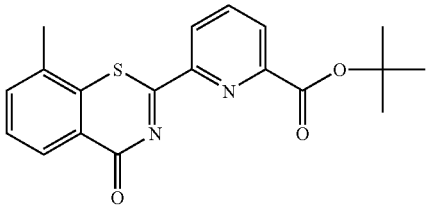

tert-Butyl 6-cyano-2-pyridinecarboxylate (3.2 g, 15 mmol) and 3-methylthiosalicylic acid (4.7 g, 28 mmol) were dissolved in pyridine (40 ml), and the mixture was refluxed for 16 hrs. The solvent was evaporated, and the residue was subjected to a silica gel column chromatography. The fractions eluted with hexane-tetrahydrofuran (2:1, v/v) were collected, concentrated and recrystallized from hexane-tetrahydrofuran to give the titled compound (3.1 g, 56%) as pale yellow crystals.

mp. 204.3-204.7° C. $^1$H-NMR (CDCl$_3$) δ: 1.69 (9H, s), 2.60 (3H, s), 7.53-7.55 (2H, m), 8.03 (1H, dd, J=7.8, 7.8 Hz), 8.25 (1H, dd, J=0.9, 7.8 Hz), 8.44 (1H, m), 8.69 (1H, dd, J=0.9, 7.8 Hz). IR(KBr): 2974, 2932, 1712, 1658, 1579, 1541, 1327, 1311, 1182, 1153, 771 cm$^{-1}$. Elemental Analysis for C$_{19}$H$_{18}$N$_2$O$_3$S Calcd. C, 64.39; H, 5.12; N, 7.90. Found C, 64.29; H, 4.87; N, 7.78.

Example 233

6-(8-Methyl-4-oxo-4H-1,3-benzothiazin-2-yl)-2-pyridinecarboxylic acid

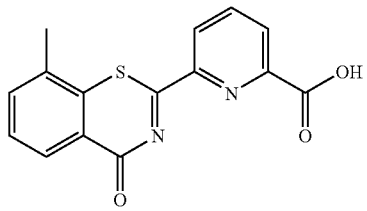

tert-Butyl 6-(8-methyl-4-oxo-4H-1,3-benzothiazin-2-yl)-2-pyridinecarboxylate (0.50 g, 1.4 mmol) was dissolved in trifluoroacetic acid (5 ml), and the mixture was stirred at 0° C. for 4 hrs. The solvent was evaporated, and the residue was crystallized from diethyl ether to give the titled compound (0.39 g, 94%) as pale yellow crystals.

mp. 260.5-260.8° C. $^1$H-NMR (DMSO-d$_6$) δ: 2.55 (3H, s), 7.62 (1H, m), 7.73 (1H, d, J=7.1 Hz), 8.21-8.34 (3H, m), 8.54 (1H, m), 13.70 (1H, br s). IR(KBr): 3067, 1697, 1672, 1543, 1471, 1307, 1099, 773 cm$^{-1}$. Elemental Analysis for C$_{15}$H$_{10}$N$_2$O$_3$S Calcd. C, 60.39; H, 3.38; N, 9.39. Found C, 60.10; H, 3.32; N, 9.27.

Example 234 tert-Butyl 6-[[[6-(8-methyl-4-oxo-4H-1,3-benzothiazin-2-yl)-2-pyridyl]carbonyl]amino]hexylcarbamate

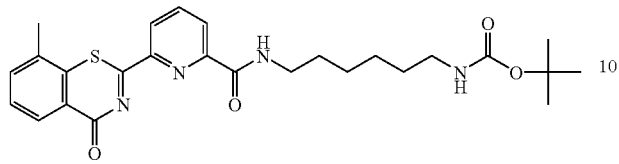

6-(8-Methyl-4-oxo-4H-1,3-benzothiazin-2-yl)-2-pyridinecarboxylic acid (1.5 g, 5.0 mmol) was dissolved in DMF (15 ml) and N-(tert-butoxycarbonyl)-1,6-diaminohexane (2.1 g, 10.0 mmol), WSC (3.0 g, 15.5 mmol) and HOBt (2.0 g, 14.9 mmol) were added thereto. The reaction mixture was stirred at 80° C. for 10 hrs and combined with ethyl acetate and water. The organic layer was washed with saturated brine and dried over magnesium sulfate. The solvent was evaporated and the residue was subjected to a silica gel column chromatography. The fractions eluted with ethyl acetate-hexane (4:1, v/v) were collected, concentrated and recrystallized from hexane-tetrahydrofuran to give the titled compound (1.1 g, 45%) as white crystals.

mp. 170.7-171.5° C. $^1$H-NMR (DMSO-d$_6$) δ: 1.43 (9H, s), 1.43-1.55 (6H, m), 1.74 (2H, m), 2.60 (3H, s), 3.13 (2H, m), 3.57 (2H, m), 4.52 (1H, br s), 7.55 (1H, m), 7.56 (1H, s), 7.98 (1H, m), 8.08 (1H, m), 8.41-8.45 (2H, m), 8.66 (1H, dd, J=0.9, 7.8 Hz). IR(KBr): 3350, 2932, 2858, 1680, 1666, 1537, 1448, 1307, 1271, 1250, 1172 cm$^{-1}$. Elemental Analysis for C$_{26}$H$_{32}$N$_4$O$_4$S Calcd. C, 62.88; H, 6.49; N, 11.28. Found C, 62.78; H, 6.51; N, 11.09.

Example 235

N-(6-Aminohexyl)-6-(8-methyl-4-oxo-4H-1,3-benzothiazin-2-yl)-2-pyridinecarboxamide hydrochloride salt

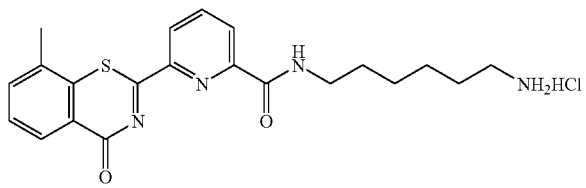

tert-Butyl 6-[[[6-(8-methyl-4-oxo-4H-1,3-benzothiazin-2-yl)-2-pyridyl]carbonyl]amino]hexylcarbamate (0.30 g, 0.60 mmol) was dissolved in dioxane (10 ml), and 4 N hydrochloric acid in dioxane (1.0 ml. 4.00 mol) was added thereto. The reaction mixture was stirred at room temperature for 24 hrs. The precipitates were collected by filtration and recrystallized from diisopropyl ether-methanol to give the titled compound (0.05 g, 20%) as pale yellow crystals.

mp. 240° C. $^1$H-NMR (CDCl$_3$) δ: 1.40 (4H, m), 1.57-1.64 (4H, m), 2.59 (3H, s), 2.76 (2H, m), 3.43 (2H, m), 7.64 (1H, m), 7.74 (1H, d, J=7.3 Hz), 7.96 (3H, br s), 8.22-8.31 (3H, m), 8.49 (1H, m), 8.60 (1H, m). IR(KBr): 3337, 2858, 1651, 1529, 1317, 758 cm$^{-1}$. Elemental Analysis for C$_{21}$H$_{25}$N$_4$O$_2$SCl.0.25H$_2$O Calcd. C, 57.66; H, 5.88; N, 12.81. Found C, 57.61; H, 5.58; N, 12.75.

Reference Example 83

2-(2-Pyridylmethyl)-1H-isoindole-1,3(2H)-dione

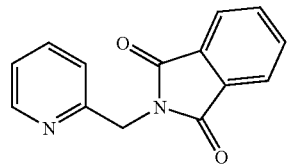

2-Aminomethylpyridine (4.0 g, 37 mmol) and phthalic anhydride (5.5 g, 37 mmol) were dissolved in toluene (100 ml), and triethylamine (3.7 g, 36 mmol) was added thereto. The mixture was refluxed for 3 hrs. The solvent was evaporated, and the residue was recrystallized from hexane-ethanol to give the titled compound (7.6 g, 86%).
$^1$H-NMR (CDCl$_3$) δ: 5.01 (2H, s), 7.16 (1H, dd, J=4.9, 7.4 Hz), 7.27 (1H, d, J=8.4 Hz), 7.63 (1H, m), 7.72 (2H, m), 7.88 (2H, m), 8.52 (1H, d, J=4.6 Hz).

Reference Example 84

2-(2-Pyridylmethyl)-1H-isoindole-1,3(2H)-dione N-oxide

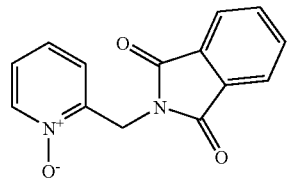

2-(2-Pyridylmethyl)-1H-isoindole-1,3(2H)-dione (7.5 g, 32 mmol) and 3-chloroperbenzoic acid (77%, 14.3 g, 64 mmol) were dissolved in chloroform (250 ml), and the mixture was stirred at room temperature for 20 hrs. The solvent was evaporated, and the residue was washed with ethyl acetate to give the titled compound (8.0 g, 99%) as white crystals. $^1$H-NMR (CDCl$_3$) δ: 5.16 (2H, s), 7.15 (1H, m), 7.24-7.26 (2H, m) 7.77 (2H, m), 7.90 (2H, m), 8.33 (1H, m).

Reference Example 85

6-[(1,3-Dioxo-1,3-dihydro-2H-isoindol-2-yl)methyl]-2-pyridinecarbonitrile

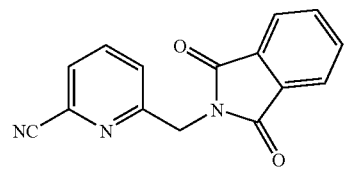

2-(2-Pyridylmethyl)-1H-isoindole-1,3(2H)-dione N-oxide (8.0 g, 31 mmol) was dissolved in mixed solvent of nitroethane (80 ml) and chloroform (150 ml), and trimethylsilyl cyanide (9.3 g, 94 mmol) and N,N-dimethylcarbamoyl chloride (6.8 g, 63 mmol) were added thereto. The mixture was stirred at room temperature for 4 hrs and at 60° C. for 24 hrs. The solvent was evaporated, and the residue was subjected to a silica gel column chromatography. The fractions eluted with hexane-ethyl acetate (2:1, v/v) were collected, concentrated and recrystallized from hexane-tetrahydrofuran to give the titled compound (1.8 g, 22%) as white crystals.

mp. 204.7-204.9° C. $^1$H-NMR (CDCl$_3$) δ: 5.05 (2H, s) 7.50 (1H, d, J=8.0 Hz), 7.59 (1H, d, J=7.6 Hz), 7.74-7.82 (3H, m), 7.87-7.93 (2H, m). IR(KBr): 3080, 2245, 1776, 1713, 1421, 1396, 1323, 1111, 950 cm$^{-1}$ Elemental Analysis for C$_{15}$H$_9$N$_3$O$_2$ Calcd. C, 68.44; H, 3.45; N, 15.96. Found C, 68.43; H, 3.40; N, 15.88.

Example 236

2-[[6-(4-Oxo-4H-1,3-benzothiazin-2-yl)-2-pyridyl]methyl]-1H-isoindole-1,3(2H)-dione

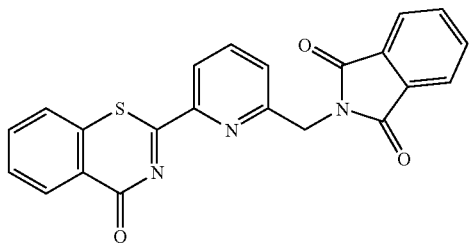

6-[(1,3-Dioxo-1,3-dihydro-2H-isoindol-2-yl)methyl]-2-pyridinecarbonitrile (1.25 g, 4.7 mmol) and methyl thiosalicylate (1.59 g, 9.4 mmol) were dissolved in toluene (10 ml), and triethylamine (5.0 ml, 35.8 mmol) was added thereto. The reaction mixture was refluxed for 15 hrs. After cooling, the precipitates were collected by filtration and recrystallized from hexane-chloroform to give the titled compound (1.48 g, 78%) as white crystals.

mp. 280.4-281.1° C. $^1$H-NMR (CDCl$_3$) δ: 5.16 (2H, s), 7.24 (1H, dd, J=1.3, 7.2 Hz), 7.52-7.63 (3H, m), 7.81-7.84 (2H, m), 7.88 (1H, m), 7.94-7.99 (2H, m), 8.39 (1H, d, J=7.8 Hz), 8.48 (1H, dd, J=1.5, 6.8 Hz). IR(KBr): 3026, 1766, 1709, 1658, 1572, 1531, 1425, 1394, 1296, 949, 723 cm$^{-1}$. Elemental Analysis for C$_{22}$H$_{13}$N$_3$O$_3$S Calcd. C, 66.15; H, 3.28; N, 10.52. Found C, 66.17; H, 3.20; N, 10.51.

Example 237

N-Butyl-4-oxo-2-(2-pyridyl)-4H-1,3-benzothiazine-7-carboxamide

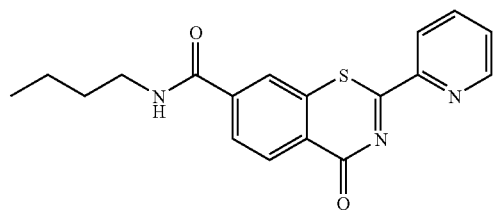

N,N'-carbonyldiimidazole (570 mg, 3.5 mmol) was added to a mixture of 4-oxo-2-(2-pyridyl)-4H-1,3-benzothiazine-7-carboxylic acid (800 mg, 2.8 mmol) and tetrahydrofuran (20 ml), and the mixture was stirred at 60° C. for 2 hrs. Successively, butylamine (410 mg, 5.6 mmol) was added to the reaction mixture, and the mixture was stirred at 60° C. for 30 minutes. The solvent was evaporated, and the residue was subjected to a silica gel column chromatography. The fractions eluted with hexane-ethyl acetate (1:3, v/v) were collected, concentrated and recrystallized from hexane-tetrahydrofuran to give the titled compound (478 mg, 50%) as white crystals.

mp. 193.5-194.2° C. $^1$H-NMR (CDCl$_3$) δ: 0.98 (3H, t, J=7.3 Hz), 1.46 (2H, m), 1.64 (2H, m), 3.50 (2H, m), 6.47 (1H, br s), 7.55 (1H, m), 7.86-7.93 (2H, m), 8.07 (1H, d, J=1.4 Hz), 8.50 (1H, d, J=7.8 Hz), 8.55 (1H, d, J=8.2 Hz), 8.73 (1H, d, J=3.9 Hz). IR(KBr): 3358, 2961, 2932, 2872, 1658, 1643, 1556, 1518, 1467, 1307, 1284 cm$^{-1}$ Elemental Analysis for C$_{18}$H$_{17}$N$_3$O$_2$S Calcd. C, 63.70; H, 5.05; N, 12.38. Found C, 63.69; H, 4.97; N, 12.50.

Example 238

2-(2-Pyridyl)-7-(1-pyrrolidinylcarbonyl)-4H-1,3-benzothiazine-4-one

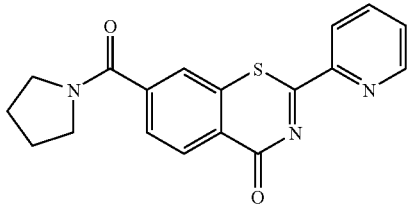

N,N'-carbonyldiimidazole (445 mg, 2.7 mmol) was added to a mixture of 4-oxo-2-(2-pyridyl)-4H-1,3-benzothiazine-7-carboxylic acid (600 mg, 2.1 mmol) and tetrahydrofuran (20 ml), and the mixture was stirred at 60° C. for 2 hrs. Successively, pyrrolidine (300 mg, 4.2 mmol) was added to the reaction mixture, and the mixture was stirred at 60° C. for 1 hr. The solvent was evaporated, and the residue was subjected to a silica gel column chromatography. The fractions eluted with ethyl acetate were collected, concentrated and recrystallized from hexane-tetrahydrofuran to give the titled compound (83 mg, 11%) as white crystals.

mp. 173.6-174.2° C. $^1$H-NMR (CDCl$_3$) δ: 1.94 (2H, m), 1.99 (2H, m), 3.43 (2H, t, J=6.4 Hz), 3.69 (2H, t, J=6.7 Hz), 7.56 (1H, m), 7.72 (1H, dd, J=1.5, 8.1 Hz), 7.76 (1H, d, J=1.1 Hz), 7.92 (1H, m), 8.53-8.58 (2H, m), 8.75 (1H, d, J=4.5 Hz). IR(KBr): 2972, 2876, 1660, 1626, 1560, 1529, 1433, 1302, 1278, 1236, 794 cm$^{-1}$ Elemental Analysis for C$_{18}$H$_{15}$N$_3$O$_2$S.0.5H$_2$O Calcd. C, 62.41; H, 4.66; N, 12.13. Found C, 63.69; H, 4.97; N, 12.14.

Example 239

N-Cyclopropyl-4-oxo-2-(2-pyridyl)-4H-1,3-benzothiazine-7-carboxamide

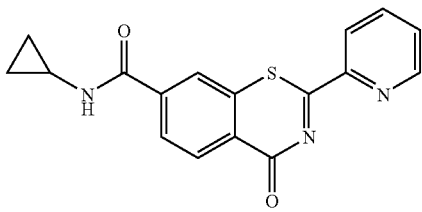

N,N'-carbonyldiimidazole (520 mg, 3.2 mmol) was added to a mixture of 4-oxo-2-(2-pyridyl)-4H-1,3-benzothiazine-7-carboxylic acid (700 mg, 2.4 mmol) and tetrahydrofuran (20 ml), and the mixture was stirred at 60° C. for 2 hrs. Successively, cyclopropylamine (700 mg, 12.2 mmol) was added to the reaction mixture, and the mixture was stirred at 60° C. for 1 hr. The solvent was evaporated, and the residue was subjected to a silica gel column chromatography. The fractions eluted with ethyl acetate were collected, concentrated and recrystallized from diisopropyl ether-methanol to give the titled compound (45 mg, 5%) as pale yellow crystals.

mp. 272.1-274.1° C. $^1$H-NMR (DMSO-$d_6$+CDCl$_3$) δ: 0.71 (2H, m), 0.83 (2H, m), 2.96 (1H, m), 7.60 (1H, m), 7.95 (1H, m), 8.08 (1H, dd, J=1.5, 8.3 Hz), 8.20 (1H, d, J=1.5 Hz), 8.48-8.53 (2H, m), 8.76 (1H, d, J=4.2 Hz), 8.28 (1H, br s). IR(KBr): 3354, 3331, 3072, 1655, 1635, 1560, 1520, 1471, 1298, 1286, 1109 cm$^{-1}$ Elemental Analysis for $C_{17}H_{13}N_3O_2S$ Calcd. C, 63.14; H, 4.05; N, 12.99. Found C, 62.93; H, 3.99; N, 13.00.

Example 240

7-(4-Morpholinocarbonyl)-2-(2-pyridyl)-4H-1,3-benzothiazine-4-one

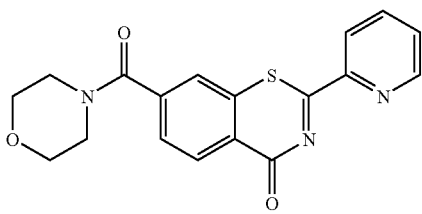

N,N'-carbonyldiimidazole (710 mg, 4.4 mmol) was added to a mixture of 4-oxo-2-(2-pyridyl)-4H-1,3-benzothiazine-7-carboxylic acid (750 mg, 2.6 mmol) and tetrahydrofuran (20 ml), and the mixture was stirred at 60° C. for 2 hrs. Successively, morpholine (700 mg, 8.0 mmol) was added to the reaction mixture, and the mixture was stirred at 60° C. for 1 hr. The solvent was evaporated, and the residue was subjected to a silica gel column chromatography. The fractions eluted with methanol-ethyl acetate (1:20, v/v) were collected, concentrated and recrystallized from hexane-tetrahydrofuran to give the titled compound (436 mg, 47%) as white crystals.

mp. 217.6-218.8° C. $^1$H-NMR (CDCl$_3$) δ: 3.45 (2H, m), 3.68-3.81 (6H, m), 7.55-7.67 (3H, m), 7.93 (1H, m), 8.53 (1H, d, J=7.8 Hz), 8.57 (1H, d, J=8.3 Hz), 8.75 (1H, s). IR(KBr): 3528, 2972, 2912, 2858, 1660, 1639, 1560, 1529, 1435, 1280, 1113 cm$^{-1}$ Elemental Analysis for $C_{18}H_{15}N_3O_3S \cdot 0.25H_2O$ Calcd. C, 60.41; H, 4.37; N, 11.74. Found C, 60.42; H, 4.10; N, 11.79.

Example 241

7-Bromo-2-(2-pyridyl)-4H-1,3-benzothiazine-4-one

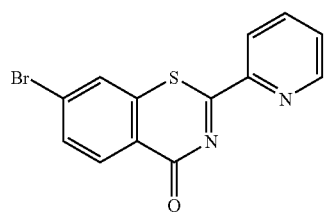

2-Cyanopyridine (0.29 g, 2.8 mmol) and 4-bromothiosalicylic acid (0.8 g, 3.4 mmol) were dissolved in pyridine (6 ml), and the mixture was refluxed for 8 hrs. The solvent was evaporated, and the residue was subjected to silica gel column chromatography. The fractions eluted with chloroform-ethyl acetate (5:1, v/v) were collected, concentrated and recrystallized from hexane-chloroform to give the titled compound (0.33 g, 36%) as white crystals.

mp. 230.7-232.2° C. $^1$H-NMR (CDCl$_3$) δ: 7.57 (1H, m), 7.71-7.77 (2H, m), 7.93 (1H, m), 8.39 (1H, d, J=8.5 Hz), 8.53 (1H, d, J=7.9 Hz), 8.75 (1H, d, J=4.4 Hz). IR(KBr): 1660, 1579, 1564, 1531, 1377, 1280, 736 cm$^{-1}$. Elemental Analysis for $C_{13}H_7N_2OSBr$ Calcd. C, 48.92; H, 2.21; N, 8.78. Found C, 48.92; H, 2.22; N, 8.53.

Example 242

6-(4-Oxo-4H-1,3-benzothiazin-2-yl)-s-pyridinecarbonitrile

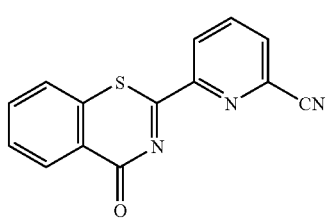

2,6-Pyridinecarbonitrile (1.00 g, 7.7 mmol) and methyl thiosalicylate (1.54 g, 9.1 mmol) were dissolved in toluene (6 ml), and triethylamine (3.0 ml, 21.5 mmol) was added thereto. The mixture was refluxed for 1 hr. After cooling, the precipitates were collected by filtration and recrystallized from hexane-chlorobenzene to give the titled compound (1.07 g, 52%) as pale yellow crystals.

mp. 263.7-264.2° C. $^1$H-NMR (CDCl$_3$) δ: 7.74 (1H, m), 7.82 (1H, m), 7.97 (1H, d, J=7.9 Hz), 8.32-8.37 (3H, m), 8.60 (1H, m). IR(KBr): 3078, 2241, 1666, 1572, 1537, 1439, 1302, 1097, 995, 815, 742 cm$^{-1}$. Elemental Analysis for $C_{14}H_7N_3OS$ Calcd. C, 63.38; H, 2.66; N, 15.84. Found C, 63.51; H, 2.96; N, 15.69.

Reference Example 86

Diethyl 2-pyridylmethylphoapshonate

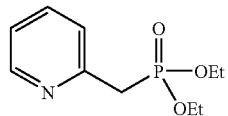

A solution of lithium diisopropylamide (69 mmol) in tetrahydrofuran (145 ml) was produced. To the solution, a solution of 2-picoline (5.0 g, 53 mmol) in tetrahydrofuran (20 ml) was added dropwise at −78° C. The mixture was stirred at the same temperature for 10 minutes. Successively, a solution of diethyl chlorophosphate (13.8 g, 80 mmol) in tetrahydrofuran (20 ml) was added dropwise to the mixture at −78° C., and the mixture was stirred at the same temperature for 30 minutes. The reaction mixture was combined with aqueous ammonium chloride solution and extracted with ethyl acetate. The organic layer was washed with saturated brine and dried over anhydrous magnesium sulfate. The solvent was evaporated, and the residue was subjected to a silica gel column chromatography. The fractions eluted with ethyl acetate-methanol (8:1, v/v) were collected and concentrated to give the titled compound (3.6 g, 29%).

$^1$H-NMR (CDCl$_3$) δ: 1.26 (6H, t, J=7.0 Hz), 3.38 (1H, s), 3.45 (1H, s), 4.09 (4H, q, J=7.0 Hz), 7.16 (1H, m), 7.39 (1H, m) 7.64 (1H, m), 8.54 (1H, d, J=4.6 Hz).

Reference Example 87

Diethyl 2-pyridylmethylphosphonate N-oxide

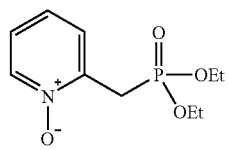

Diethyl 2-pyridylmethylphosphonate (3.1 g, 13 mmol) and 3-chloroperbenzoic acid (77%, 4.0 g, 18 mmol) were dissolved in ethyl acetate (50 ml), and the mixture was stirred at room temperature for 4 hrs. The solvent was evaporated, and the residue was subjected to a silica gel column chromatography. The fractions eluted with methanol-ethyl acetate (1:3, v/v) were collected and concentrated to give the titled compound (2.9 g, 88%).

$^1$H-NMR (CDCl$_3$) δ: 1.30 (6H, t, J=7.0 Hz), 3.66 (1H, s), 3.73 (1H, s), 4.16 (4H, q, J=7.0 Hz), 7.16-7.27 (2H, m), 7.54 (1H, m), 8.27 (1H, d, J=5.7 Hz).

Reference Example 88

Diethyl (6-cyano-2-pyridyl)methylphosphonate

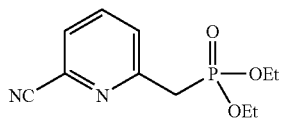

Diethyl 2-pyridylmethylphosphonate N-oxide (2.9 g, 12 mmol) was dissolved in nitroethane (30 ml), and trimethylsilyl cyanide (2.6 g, 26 mmol) and N,N-dimethylcarbamoyl chloride (2.7 g, 25 mmol) were added thereto. The mixture was stirred at room temperature for 30 hrs. The solvent was evaporated, and the residue was subjected to a silica gel column chromatography. The fractions eluted with ethyl acetate-methanol (20:1, v/v) were collected and concentrated to give the titled compound (1.5 g, 49%).

$^1$H-NMR (CDCl$_3$) δ: 1.29 (6H, t, J=7.0 Hz), 3.41 (1H, s), 3.49 (1H, s), 4.11 (4H, m), 7.58-7.64 (2H, m), 7.79 (1H, m). IR(KBr): 2984, 2237, 1587, 1450, 1249, 1053, 1026, 968 cm$^{-1}$.

Example 243

Diethyl [6-(4-oxo-4H-1,3-benzothiazin-2-yl)-2-pyridyl]methylphosphonate

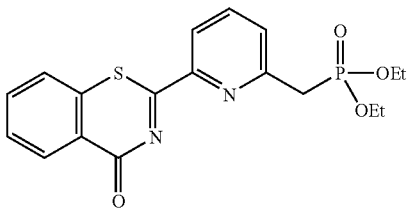

Diethyl (6-cyano-2-pyridyl)methylphosphonate (1.4 g, 5.8 mmol) and methyl thiosalicylate (1.9 g, 11.6 mmol) were dissolved in toluene (8 ml), and triethylamine (4.0 ml, 28.6 mmol) was added thereto. The mixture was refluxed for 13 hrs. The solvent was evaporated, and the residue was subjected to a silica gel column chromatography. The fractions eluted with ethyl acetate-methanol (10:1, v/v) were collected, concentrated and recrystallized from diisopropyl ether-ethanol to give the titled compound (510 mg, 22%) as pale yellow crystals.

mp. 115.5-116.5° C. $^1$H-NMR (CDCl$_3$) δ: 1.29 (6H, t, J=7.0 Hz), 3.50 (1H, s), 3.58 (1H, s), 4.12 (4H, m), 7.60-7.72 (4H, m), 7.86 (1H, m), 8.43 (1H, d, J=7.8 Hz), 8.55 (1H, m). IR(KBr): 2982, 1662, 1572, 1537, 1302, 1275, 1250, 1051, 1028, 966 cm$^{-1}$. Elemental Analysis for C$_{18}$H$_{19}$N$_2$O$_4$SP Calcd. C, 55.38; H, 4.91; N, 7.18. Found C, 55.34; H, 4.89; N, 7.21.

Example 244

[6-(4-Oxo-4H-1,3-benzothiazin-2-yl)-2-pyridyl]methylphosphoric acid

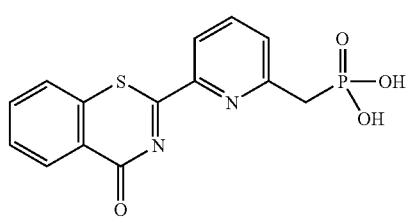

Diethyl [6-(4-oxo-4H-1,3-benzothiazin-2-yl)-2-pyridyl]methylphosphonate (0.20 g, 0.51 mmol) and iodetrimethylsilane (0.31 g, 1.58 mmol) were dissolved in dichloromethane (10 ml), and the mixture was stirred at room temperature for 1 hr. The reaction mixture was combined with methanol, and the solvent was evaporated. The residue was recrystallized from diisopropyl ether-methanol to give the titled compound (0.05 g, 30%) as pale yellow crystals.

mp. 254.0° C. (decomposed) $^1$H-NMR (DMSO-d$_6$) δ: 3.31 (1H, s), 3.38 (1H, s), 7.69-7.75 (2H, m), 7.84 (1H, m), 7.95 (1H, d, J=7.9 Hz), 8.03 (1H, m), 8.21 (1H, d, J=8.0 Hz), 8.36 (1H, dd, J=1.1, 7.9 Hz), 10.90 (2H, br s). IR(KBr): 2905, 1589, 1570, 1529, 1440, 1317, 1012, 929 cm$^{-1}$. Elemental Analysis for C$_{14}$H$_{11}$N$_2$O$_4$PS.0.25H$_2$O Calcd. C, 49.63; H, 3.42; N, 8.27. Found C, 49.80; H, 3.36; N, 8.26.

Reference Example 89

Diethyl (E)-2-(2-pyridyl)ethenylphosphonate

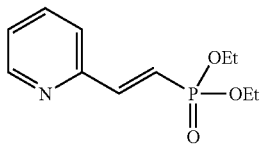

A solution of tetraethyl methylenediphosphonate (3.7 g, 13 mmol) in tetrahydrofuran (5 ml) was added dropwise to a mixture of sodium hydride (60% in oil, 750 mg, 18 mmol) and tetrahydrofuran (15 ml) at 0° C., and the mixture was stirred at the same temperature for 20 minutes. Successively, a solution of 2-pyridinecarbaldehyde (1.3 g, 12 mmol) in tetrahydrofuran (5 ml) was added dropwise to the mixture at 0° C., and the mixture was stirred at room temperature for 30 minutes. The reaction mixture was combined with water and extracted with ethyl acetate. The organic layer was washed with brine and dried over anhydrous magnesium sulfate. The solvent was evaporated, and the residue was subjected to a silica gel column chromatography. The fractions eluted with ethyl acetate-methanol (20:1, v/v) were collected and concentrated to give the titled compound (2.7 g, 94%).

$^1$H-NMR (CDCl$_3$) δ: 1.33 (6H, t, J=7.0 Hz), 4.13 (4H, q, J=7.0 Hz), 6.88 (1H, dd, J=17.1, 19.3 Hz), 7.27 (1H, m), 7.38 (1H, d, J=7.7 Hz), 7.52 (1H, dd, J=17.1, 21.7 Hz), 7.72 (1H, m), 8.64 (1H, d, J=4.0 Hz).

Reference Example 90

Diethyl 2-(2-pyridyl)ethylphosphanate

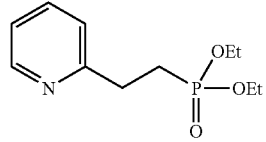

Diethyl (E)-2-(2-pyridyl)ethenylphosphonate (2.7 g, 11.2 mmol) was dissolved in ethanol (80 ml), and 10% palladium-carbon (300 mg) was added thereto. The mixture was stirred under hydrogen atmosphere at room temperature for 3 hrs. Palladium-carbon was filtered off, and the filtrate was concentrated to give the titled compound (2.7 g, 100%).

$^1$H-NMR (CDCl$_3$) δ: 1.30 (6H, t, J=7.0 Hz), 2.24 (2H, m), 3.08 (2H, m), 4.09 (4H, m), 7.13 (1H, m), 7.19 (1H, d, J=7.7 Hz), 7.60 (1H, m), 8.53 (1H, d, J=4.5 Hz).

Reference Example 91

Diethyl 2-(2-pyridyl)ethylphosphonate N-oxide

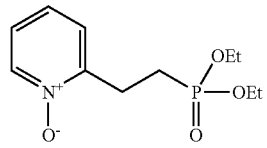

Diethyl 2-(2-pyridyl)ethylphosphonate (2.7 g, 11 mmol) and 3-chloroperbenzoic acid (77%, 3.2 g, 14 mmol) were dissolved in ethyl acetate (50 ml), and the mixture was stirred at room temperature for 4 hrs. The solvent was evaporated, and the residue was subjected to a silica gel column chromatography. The fractions eluted with methanol-ethyl acetate (1:3, v/v) were collected and concentrated to give the titled compound (2.8 g, 99%).

$^1$H-NMR (CDCl$_3$) δ: 1.29 (6H, t, J=7.0 Hz), 2.23-2.34 (2H, m), 3.13-3.23 (2H, m), 4.08 (4H, m), 7.16-7.25 (2H, m), 7.32 (1H, m), 8.24 (1H, m).

Reference Example 92

Diethyl 2-(6-cyano-2-pyridyl)ethylphosphonate

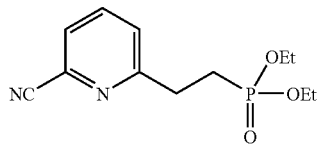

Diethyl 2-(2-pyridyl)ethylphosphonate N-oxide (2.8 g, 11 mmol) was dissolved in nitroethane (30 ml), and trimethylsilyl cyanide (2.2 g, 22 mmol) and N,N-dimethylcarbamoyl chloride (2.4 g, 22 mmol) were added thereto. The mixture was stirred at room temperature for 28 hrs. The solvent was evaporated, and the residue was subjected to a silica gel

Example 245

Diethyl 2-[6-(4-oxo-4H-1,3-benzothiazin-2-yl)-2-pyridyl]ethylphosphonate

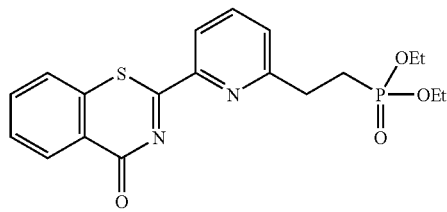

Diethyl 2-(6-cyano-2-pyridyl)ethylphosphonate (0.80 g, 2.9 mmol) and methyl thiosalicylate (1.00 g, 5.9 mmol) were dissolved in toluene (4 ml), and triethylamine (2.0 ml, 14.3 mmol) was added thereto. The mixture was refluxed for 5 hrs. After cooling, the precipitated crystals were collected by filtration and recrystallized from diisopropyl ether-ethanol to give the titled compound (0.61 g, 50%) as white crystals.

mp. 148.8-149.8° C. $^1$H-NMR (CDCl$_3$) δ: 1.33 (6H, t, J=7.0 Hz), 2.43 (2H, m), 3.21 (2H, m), 4.15 (4H, m), 7.43 (1H, d, J=7.5 Hz), 7.61-7.71 (3H, m), 7.82 (1H, m), 8.38 (1H, d, J=7.5 Hz), 8.55 (1H, m). IR(KBr): 2978, 1655, 1574, 1537, 1305, 1286, 1242, 1049, 1026, 966 cm$^{-1}$. Elemental Analysis for C$_{19}$H$_{21}$N$_2$O$_4$SP Calcd. C, 56.43; H, 5.23; N, 6.93. Found C, 56.40; H, 5.01; N, 6.88.

Example 246

2-[6-(4-oxo-4H-1,3-benzothiazin-2-yl)-2-pyridyl]ethylphosphoric acid

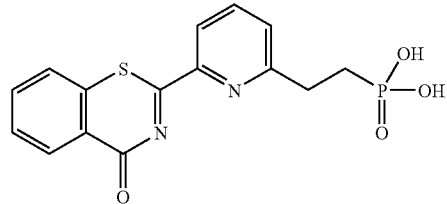

Diethyl 2-[6-(4-oxo-4H-1,3-benzothiazin-2-yl)-2-pyridyl]ethylphosphonate (0.42 g, 1.0 mmol) and iodetrimethylsilane (0.65 g, 3.2 mmol) were dissolved in dichloromethane (10 ml), and the mixture was stirred at 0° C. for 1 hr. The reaction mixture was combined with methanol, and the solvent was evaporated. The residue was recrystallized from diisopropyl ether-methanol to give the titled compound (0.21 g, 60%) as pale yellow crystals.

mp. 235.3-237.2° C. $^1$H-NMR (DMSO-d$_6$) δ: 2.02-2.14 (2H, m), 3.04-3.13 (2H, m) 7.67-7.74 (2H, m), 7.82 (1H, m), 7.95-8.03 (2H, m), 8.19 (1H, d, J=7.7 Hz), 8.35 (1H, d, J=7.8 Hz). IR(KBr): 2808, 2305, 1631, 1570, 1525, 1163, 1014, 933 cm$^{-1}$. Elemental Analysis for C$_{15}$H$_{13}$N$_2$O$_4$PS.1.0H$_2$O Calcd. C, 49.18; H, 4.13; N, 7.65. Found C, 49.42; H, 4.33; N, 7.48.

Reference Example 93

Diethyl (E)-2-(4-pyridyl)ethenylphosphate

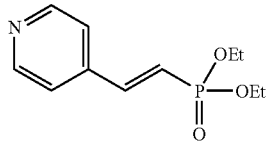

A solution of tetraethyl methylenediphosphonate (13.3 g, 46 mmol) in tetrahydrofuran (30 ml) was added dropwise to a solution of sodium hydride (60% in oil, 2.6 g, 65 mmol) and tetrahydrofuran (10 ml) at 0° C., and the mixture was stirred at the same temperature for 30 minutes. Successively, a solution of 4-pyridinecarbaldehyde (4.6 g, 43 mmol) in tetrahydrofuran (30 ml) was added dropwise to the mixture at 0° C., and the mixture was stirred at room temperature for 1 hr. The reaction mixture was combined with water and extracted with ethyl acetate. The organic layer was washed with saturated brine and dried over magnesium sulfate. The solvent was evaporated to give the titled compound (10.3 g, 100%).

$^1$H-NMR (CDCl$_3$) δ: 1.37 (6H, m), 4.17 (4H, m), 6.51 (1H, dd, J=17.4, 17.4 Hz), 7.40 (2H, m), 7.44 (1H, dd, J=17.4, 22.0 Hz), 8.66 (2H, m)

Reference Example 94

Diethyl 2-(4-pyridyl)ethylphosphonate

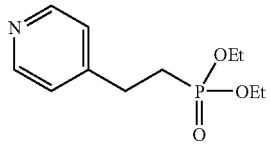

Diethyl (E)-2-(4-pyridyl)ethenylphosphonate (10.3 g, 42 mmol) was dissolved in ethanol (25 ml), and 10% palladium-carbon (1.0 g) was added thereto. The mixture was stirred under hydrogen atmosphere at room temperature for 5 hrs. Palladium-carbon was filtered off, and the filtrate was concentrated to give the titled compound (10.3 g, 100%).

$^1$H-NMR (CDCl$_3$) δ: 1.32 (6H, m), 2.05 (2H, m), 2.93 (2H, m), 4.09 (4H, m), 7.19 (2H, d, J=5.8 Hz), 8.53 (2H, d, J=5.8 Hz).

197

Reference Example 95

Diethyl 2-(4-pyridyl)ethylphosphonate N-oxide

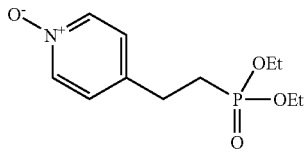

Diethyl 2-(4-pyridyl)ethylphosphonate (10.3 g, 42 mmol) and 3-chloroperbenzoic acid (77%, 12.3 g, 54 mmol) were dissolved in ethyl acetate (200 ml), and the mixture was stirred at room temperature for 5 hrs. The solvent was evaporated, and the residue was subjected to a silica gel column chromatography. The fractions eluted with ethanol-ethyl acetate (1:1, v/v) were collected and concentrated to give the titled compound (9.9 g, 99%).

$^1$H-NMR (CDCl$_3$) δ: 1.32 (6H, t, J=7.0 Hz), 2.03 (2H, m), 2.94 (2H, m), 4.09 (4H, q, J=7.0 Hz), 7.16 (2H, d, J=5.7 Hz), 8.17 (2H, d, J=5.7 Hz).

Reference Example 96

Diethyl 2-(2-cyano-4-pyridyl)ethylphosphonate

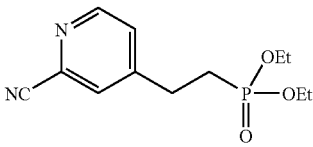

Diethyl 2-(4-pyridyl)ethylphosphonate N-oxide (9.9 g, 38 mmol) was dissolved in nitroethane (200 ml), and trimethylsilyl cyanide (7.5 g, 75 mmol) and N,N-dimethylcarbamoyl chloride (6.1 g, 56 mmol) were added thereto. The mixture was stirred at room temperature for 12 hrs. The solvent was evaporated, and the residue was subjected to a silica gel column chromatography. The fractions eluted with ethyl acetate-methanol (15:1) were collected and concentrated to give the titled compound (7.3 g, 71%).

$^1$H-NMR (CDCl$_3$) δ: 1.31 (6H, t, J=7.0 Hz), 2.06 (2H, m), 2.98 (2H, m), 4.10 (4H, m), 7.38 (1H, dd, J=0.7, 5.0 Hz), 7.57 (1H, d, J=0.7 Hz), 8.62 (1H, d, J=5.0 Hz).

198

Example 247

Diethyl 2-[2-(4-oxo-4H-1,3-benzothiazin-2-yl)-4-pyridyl]ethylphosphonate

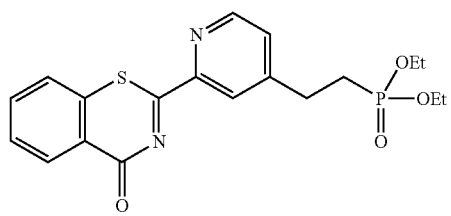

Diethyl 2-(2-cyano-4-pyridyl)ethylphosphonate (1.4 g, 5.4 mmol) and methyl thiosalicylate (1.8 g, 10.9 mmol) were dissolved in toluene (8 ml), and triethylamine (4.0 ml, 28.6 mmol) was added thereto. The mixture was refluxed for 6 hrs. The solvent was evaporated, and the residue was subjected to a silica gel column chromatography. The fractions eluted with ethyl acetate-methanol (10:1, v/v) were collected, concentrated and recrystallized from hexane-ethyl acetate to give the titled compound (0.96 g, 43%) as white crystals.

mp. 102.0-103.2° C. $^1$H-NMR (CDCl$_3$) δ: 1.33 (6H, t, J=7.0 Hz), 2.11 (2H, m), 3.03 (2H, m), 4.13 (4H, m), 7.42 (1H, dd, J=1.6, 4.9 Hz), 7.61-7.70 (3H, m), 8.43 (1H, d, J=1.0 Hz), 8.56 (1H, m), 8.65 (1H, d, J=4.9 Hz). IR(KBr): 2982, 2934, 1662, 1570, 1533, 1280, 1236, 1053, 1030, 966, 812 cm$^{-1}$. Elemental Analysis for C$_{19}$H$_{21}$N$_2$O$_4$SP Calcd. C, 56.43; H, 5.23; N, 6.93. Found C, 56.23; H, 5.30; N, 6.58.

Example 248

Diethyl 2-[2-(7-chloro-4-oxo-4H-1,3-benzothiazin-2-yl)-4-pyridyl]ethylphosphonate

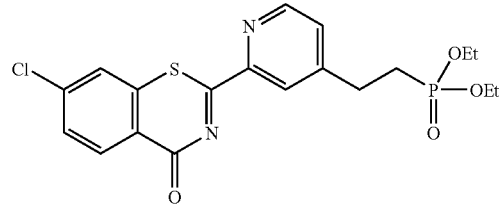

Diethyl 2-(2-cyano-4-pyridyl)ethylphosphonate (1.7 g, 6.4 mmol) and 4-chlorothiosalicylic acid (2.4 g, 12.8 mmol) were dissolved in pyridine (30 ml), and the mixture was refluxed for 13 hrs. The solvent was evaporated, and the residue was subjected to a silica gel column chromatography. The fractions eluted with ethyl acetate-chloroform (1:1, v/v) were collected, concentrated and recrystallized from hexane-tetrahydrofuran to give the titled compound (0.43 g, 15%) as white crystals.

mp. 137.7-139.1° C. $^1$H-NMR (CDCl$_3$) δ: 1.33 (6H, t, J=7.1 Hz), 2.11 (2H, m), 3.04 (2H, m), 4.14 (4H, m), 7.42 (1H, d, J=4.8 Hz), 7.56-7.60 (2H, m), 8.40 (1H, s), 8.49 (1H, d, J=8.2 Hz), 8.64 (1H, d, J=4.8 Hz). IR(KBr): 2982, 1666, 1585, 1566, 1537, 1278, 1240, 1093, 1055, 1028, 964 cm$^{-1}$. Elemental Analysis for C$_{19}$H$_{20}$N$_2$O$_4$SPCl.0.25H$_2$O Calcd. C, 51.47; H, 4.66; N, 6.32. Found C, 51.67; H, 4.40; N, 5.97.

Example 249

2-[6-[(Ethylthio)methyl]-2-pyridyl]-4H-1,3-benzothiazine-4-one

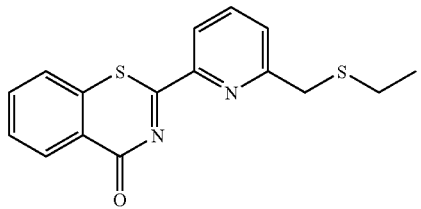

Ethyl mercaptan (0.25 g, 3.30 mmol) and sodium hydride (60% in oil, 0.15 g, 3.60 mmol) were dissolved in DMF (30 ml), and 6-(4-oxo-4H-1,3-benzothiazin-2-yl)-2-pyridylmethanesulfonate (1.05 g, 3.00 mmol) was added thereto. The reaction mixture was stirred at room temperature for 18 hrs and combined with ethyl acetate and water. The organic layer was washed with saturated brine and dried over magnesium sulfate. The solvent was evaporated, and the residue was recrystallized from n-hexane-ethyl acetate to give the titled compound (0.23 g, 24%) as pale yellow crystals.

mp. 142.0-143.5° C. $^1$H-NMR (CDCl$_3$) δ: 1.32 (3H, t, J=7.3 Hz), 2.59 (2H, q, J=7.3 Hz), 3.95 (2H, s), 7.61-7.73 (4H, m), 7.87 (1H, t, J=7.8 Hz), 8.41 (1H, d, J=7.7 Hz), 8.54-8.56 (1H, m). IR(KBr): 1658, 1589, 1570, 1531, 1439, 1300, 1095, 993, 742 cm$^{-1}$. Elemental Analysis for C$_{16}$H$_{14}$N$_2$OS$_2$ Calcd. C, 61.12; H, 4.49; N, 8.91. Found C, 60.87; H, 4.41; N, 8.67.

Example 250

2-[6-[(Ethylsulfinyl)methyl]-2-pyridyl]-4H-1,3-benzothiazine-4-one

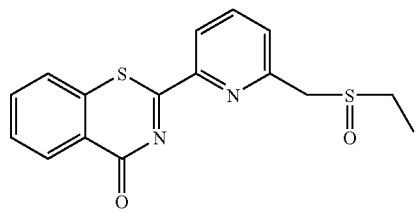

2-[6-[(Ethylthio)methyl]-2-pyridyl]-4H-1,3-benzothiazine-4-one (0.10 g, 0.32 mmol) was dissolved in chloroform (50 ml), and a solution of 3-chloroperbenzoic acid (ca. 77%, 0.071 g, 0.32 mmol) in chloroform (10 ml) was added dropwise thereto. The mixture was stirred at room temperature for 1 hr. The solvent was evaporated, and the residue was recrystallized from n-hexane-ethyl acetate to give the titled compound (0.095 g, 91%) as pale yellow crystals.

mp. 188.5-190.0° C. $^1$H-NMR (CDCl$_3$) δ: 1.29 (3H, s), 3.11, 3.30 (2H, q$_{AB}$, J=13.8 Hz), 4.21, 4.32 (2H, q$_{AB}$, J=12.8 Hz), 7.59-7.70 (4H, m), 7.94 (1H, t, J=7.8 Hz), 8.51-8.57 (2H, m). IR(KBr): 1652, 1568, 1531, 1454, 1437, 1298, 1095, 1028, 995, 744 cm$^{-1}$. Elemental Analysis for C$_{16}$H$_{14}$N$_2$O$_2$S$_2$ Calcd. C, 58.16; H, 4.27; N, 8.48. Found C, 57.93; H, 4.18; N, 8.20.

Example 251

2-[6-[(Ethylsulfonyl)methyl]-2-pyridyl]-4H-1,3-benzothiazine-4-one

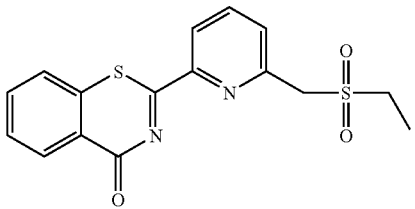

2-[6-[(Ethylthio)methyl]-2-pyridyl]-4H-1,3-benzothiazine-4-one (0.10 g, 0.32 mmol) was dissolved in chloroform (50 ml), and a solution of 3-chloroperbenzoic acid (ca. 77%, 0.14 g, 0.64 mmol) in chloroform (10 ml) was added dropwise thereto. The mixture was stirred at room temperature for 3 hrs. The solvent was evaporated, and the residue was recrystallized from n-hexane-ethyl acetate to give the titled compound (0.043 g, 39%) as white crystals.

mp. 188.5-190.0° C. $^1$H-NMR (CDCl$_3$) δ: 1.43 (3H, s), 3.57 (2H, q, J=7.3 Hz), 4.55 (2H, s), 7.59-7.70 (4H, m), 7.94 (1H, t, J=7.8 Hz), 8.51-8.57 (2H, m). IR(KBr): 1652, 1568, 1531, 1454, 1437, 1298, 1114, 1095, 995, 744 cm$^{-1}$. Elemental Analysis for C$_{16}$H$_{14}$N$_2$O$_3$S$_2$ Calcd. C, 55.47; H, 4.07; N, 8.09. Found C, 55.53; H, 4.18; N, 8.21.

Example 252

2-[6-[(n-Propylthio)methyl]-2-pyridyl]-4H-1,3-benzothiazine-4-one

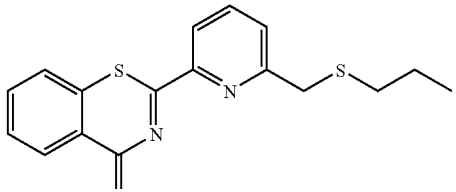

n-Propyl mercaptan (0.25 g, 3.30 mmol) and sodium hydride (60% in oil, 0.15 g, 3.60 mmol) were dissolved in DMF (30 ml), and 6-(4-oxo-4H-1,3-benzothiazin-2-yl)-2-pyridylmethanesulfonate (1.05 g, 3.00 mmol) was added thereto. The reaction mixture was stirred at room temperature for 18 hrs, combined with ethyl acetate and water. The organic layer was washed with saturated brine and dried over anhydrous magnesium sulfate. The solvent was evaporated, and the residue was recrystallized from n-hexane-ethyl acetate to give the titled compound (0.20 g, 20%) as pale yellow crystals.

mp. 111.5-113.0° C. ¹H-NMR (CDCl₃) δ: 0.99 (2H, t, J=7.3 Hz), 1.62-1.74 (2H, m), 2.55 (2H, t, J=7.3 Hz), 3.92 (2H, s), 7.60-7.71 (4H, m), 7.87 (1H, t, J=7.8 Hz), 8.41 (1H, d, J=7.7 Hz), 8.54-8.57 (1H, m). IR(KBr): 1666, 1572, 1537, 1439, 1300, 1095, 993, 746 cm⁻¹. Elemental Analysis for $C_{17}H_{16}N_2OS_2$ Calcd. C, 62.16; H, 4.91; N, 8.53. Found C, 62.20; H, 4.69; N, 8.44.

Example 253

2-[6-(n-Propylsulfinyl)methyl]-2-pyridyl]-4H-1,3-benzothiazine-4-one

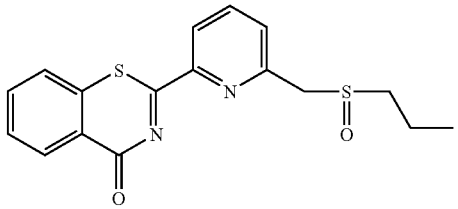

0.2-[6-[(n-Propylthio)methyl]-2-pyridyl]-4H-1,3-benzothiazine-4-one (0.080 g, 0.24 mmol) was dissolved in chloroform (50 ml), and a solution of 3-chloroperbenzoic acid (ca. 77%, 0.055 g, 0.24 mmol) in chloroform (10 ml) was added dropwise thereto. The mixture was stirred at room temperature for 1 hr. The solvent was evaporated, and the residue was recrystallized from n-hexane-ethyl acetate to give the titled compound (0.071 g, 85%) as pale yellow crystals.

mp. 171.0-173.0° C. ¹H-NMR (CDCl₃) δ: 1.05 (3H, t, J=7.3 Hz), 1.68-1.70 (2H, m), 3.10, 3.19 (2H, $q_{AB}$, J=13.8 Hz), 4.16-4.25 (2H, $q_{AB}$, J=12.8 Hz), 7.60-7.71 (4H, m), 7.87 (1H, t, J=7.8 Hz), 8.41 (1H, d, J=7.7 Hz), 8.54-8.57 (1H, m). IR(KBr): 1664, 1572, 1537, 1438, 1300, 1095, 993, 746 cm⁻¹. Elemental Analysis for $C_{17}H_{16}N_2O_2S_2$ Calcd. C, 59.28; H, 4.68; N, 8.13. Found C, 59.15; H, 4.72; N, 8.41.

Example 254

2-[6-[(n-Propylsulfonyl)methyl)-2-pyridyl]-4H-1,3-benzothiazine-4-one

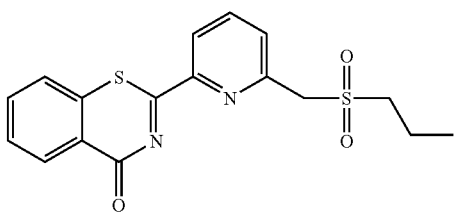

2-[6-[(n-Propylthio)methyl]-2-pyridyl]-4H-1,3-benzothiazine-4-one (0.10 g, 0.30 mmol) was dissolved in chloroform (50 ml), and a solution of 3-chloroperbenzoic acid (ca. 77%, 0.14 g, 0.61 mmol) in chloroform (10 ml) was added dropwise thereto. The mixture was stirred at room temperature for 3 hrs. The solvent was evaporated, and the residue was recrystallized from n-hexane-ethyl acetate to give the titled compound (0.080 g, 73%) as white crystals.

mp. 177.0-179.0° C. ¹H-NMR (CDCl₃) δ: 1.07 (3H, t, J=7.3 Hz), 1.80-1.81 (2H, m), 3.55 (2H, m), 4.52 (2H, s), 7.60-7.71 (4H, m), 7.87 (1H, t, J=7.8 Hz), 8.41 (1H, d, J=7.7 Hz), 8.54-8.58 (1H, m). IR(KBr): 1664, 1572, 1537, 1438, 1300, 1114, 1095, 993, 746 cm⁻¹. Elemental Analysis for $C_{17}H_{16}N_2O_3S_2$ Calcd. C, 56.65; H, 4.47; N, 7.77. Found C, 56.45; H, 4.72; N, 7.80.

Example 255

2-[6-[(Benzylthio)methyl]-2-pyridyl]-4H-1,3-benzothiazine-4-one

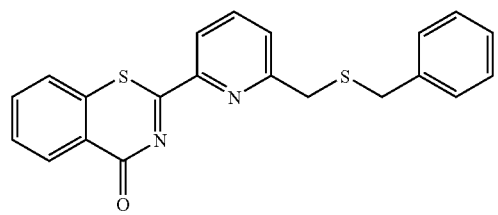

Benzyl mercaptan (0.41 g, 3.30 mmol) and sodium hydride (60% in oil, 0.15 g, 3.60 mmol) were dissolved in DMF (30 ml), and 6-(4-oxo-4H-1,3-benzothiazin-2-yl)-2-pyridyl-methanesulfonate (1.05 g, 3.00 mmol) was added thereto. The reaction mixture was stirred at room temperature for 18 hrs and combined with ethyl acetate and water. The organic layer was washed with saturated brine and dried over anhydrous magnesium sulfate. The solvent was evaporated, and the residue was recrystallized from n-hexane-ethyl acetate to give the titled compound (0.18 g, 16%) as pale yellow crystals.

mp. 126.0-128.0° C. ¹H-NMR (CDCl₃) δ: 3.80 (2H, s), 3.83 (2H, s), 7.25-7.41 (5H, m) 7.61-7.69 (4H, m), 7.84 (1H, t, J=7.8 Hz), 8.41 (1H, d, J=7.7 Hz), 8.55-8.58 (1H, m). IR(KBr): 1658, 1572, 1537, 1439, 1300, 1095, 993, 742 cm⁻¹. Elemental Analysis for $C_{21}H_{16}N_2OS_2$ Calcd. C, 66.99; H, 4.28; N, 7.44. Found C, 66.89; H, 4.20; N, 7.55.

Example 256

2-[6-[(Benzylsulfinyl)methyl]-2-pyridyl]-4H-1,3-benzothiazine-4-one

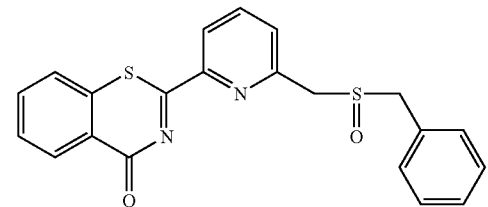

2-[6-[(Benzylthio)methyl]-2-pyridyl]-4H-1,3-benzothiazine-4-one (0.080 g, 0.22 mmol) was dissolved in chloroform (50 ml), and a solution of 3-chloroperbenzoic acid (ca. 77%, 0.037 g, 0.22 mmol) in chloroform (10 ml) was added dropwise thereto. The mixture was stirred at room temperature for 1 hr. The solvent was evaporated, and the residue was recrystallized from n-hexane-ethyl acetate to give the titled compound (0.053 g, 64%) as pale yellow crystals.

mp. 187.0-189.0° C. ¹H-NMR (CDCl₃) δ: 4.15, 4.24 (2H, $q_{AB}$, J=13.8 Hz), 4.23, 4.32 (2H, $q_{AB}$, J=12.6 Hz), 7.25-7.41 (5H, m), 7.61-7.69 (4H, m), 7.84 (1H, t, J=7.8 Hz), 8.41 (1H, d, J=7.7 Hz), 8.55-8.58 (1H, m). IR(KBr): 1660, 1572, 1537, 1439, 1300, 1095, 993, 742 cm$^{-1}$. Elemental Analysis for C$_{21}$H$_{16}$N$_2$O$_2$S$_2$ Calcd. C, 64.26; H, 4.11; N, 7.14. Found C, 64.49; H, 4.20; N, 7.35.

Example 257

2-[6-[(Benzylsulfonyl)methyl]-2-pyridyl]-4H-1,3-benzothiazine-4-one

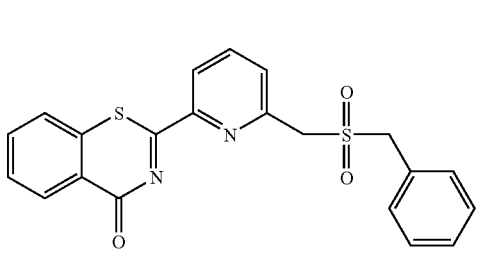

2-[6-[(Benzylthio)methyl]-2-pyridyl]-4H-1,3-benzothiazine-4-one (0.13 g, 0.35 mmol) was dissolved in chloroform (50 ml), and a solution of 3-chloroperbenzoic acid (ca. 77%, 0.16 g, 0.71 mmol) in chloroform (10 ml) was added dropwise thereto. The mixture was stirred at room temperature for 3 hrs. The solvent was evaporated, and the residue was recrystallized from n-hexane-ethyl acetate to give the titled compound (0.084 g, 54%) as white crystals.

mp. 246.0-248.0° C. $^1$H-NMR (CDCl$_3$) δ: 4.46 (2H, s), 4.53 (2H, s), 7.25-7.43 (5H, m), 7.61-7.69 (4H, m), 7.84 (1H, t, J=7.8 Hz), 8.41 (1H, d, J=7.7 Hz), 8.55-8.58 (1H, m). IR(KBr): 1658, 1572, 1537, 1439, 1300, 1115, 1095, 993, 742 cm$^{-1}$. Elemental Analysis for C$_{21}$H$_{16}$N$_2$O$_3$S$_2$ Calcd. C, 61.74; H, 3.95; N, 6.86. Found C, 62.01; H, 4.21; N, 6.58.

Example 258

Methyl ({[6-(4-oxo-4H-1,3-benzothiazin-2-yl)-2-pyridyl]methyl}thio)acetate

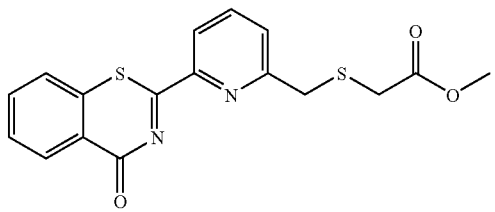

Methyl thioglycolate (0.35 g, 3.30 mmol) and sodium hydride (60% in oil, 0.15 g, 3.60 mmol) were dissolved in DMF (30 ml), and 6-(4-oxo-4H-1,3-benzothiazin-2-yl)-2-pyridylmethanesulfonate (1.05 g, 3.00 mmol) was added thereto. The reaction mixture was stirred at room temperature for 18 hrs and combined with ethyl acetate and water. The organic layer was washed with saturated brine and dried over anhydrous magnesium sulfate. The solvent was evaporated and the residue was recrystallized from ethanol to give the titled compound (0.55 g, 51%) as pale yellow crystals.

mp. 108.0-110.0° C. $^1$H-NMR (CDCl$_3$) δ: 3.35 (2H, s), 3.73 (3H, s), 4.06 (2H, s), 7.59-7.71 (4H, m), 7.88 (1H, t, J=7.8 Hz), 8.42 (1H, d, J=7.7 Hz), 8.55 (1H, d, J=8.5 Hz). IR(KBr): 1730, 1658, 1651, 1572, 1537, 1435, 1300, 1097, 993, 744 cm$^{-1}$. Elemental Analysis for C$_{17}$H$_{14}$N$_2$O$_3$S$_2$ Calcd. C, 56.96; H, 3.94; N, 7.82. Found C, 56.84; H, 3.99; N, 7.70.

Example 259

Methyl ({[6-(4-oxo-4H-1,3-benzothiazin-2-yl)-2-pyridyl]methyl}sulfinyl)acetate

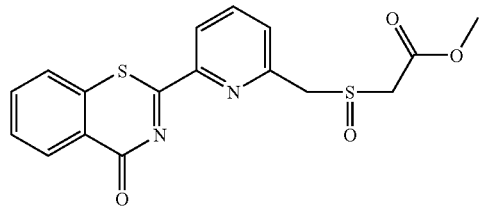

Methyl ({[6-(4-oxo-4H-1,3-benzothiazin-2-yl)-2-pyridyl]methyl}thio)acetate (0.10 g, 0.28 mmol) was dissolved in chloroform (50 ml), and a solution of 3-chloroperbenzoic acid (ca. 77%, 0.064 g, 0.28 mmol) in chloroform (10 ml) was added dropwise thereto. The mixture was stirred at room temperature for 1 hr. The solvent was evaporated, and the residue was recrystallized from ethanol to give the titled compound (0.096 g, 92%) as pale yellow crystals.

mp. 149.5-151.0° C. $^1$H-NMR (CDCl$_3$) δ: 3.70, 4.00 (2H, q$_{AB}$, J=14.3 Hz), 3.83 (3H, s), 4.38, 4.55 (2H, q$_{AB}$, J=13.1 Hz), 7.60-7.73 (4H, m), 7.95 (1H, t, J=7.8 Hz), 8.52-8.58 (2H, m). IR(KBr): 1732, 1651, 1570, 1531, 1435, 1277, 1234, 1097, 912, 742 cm$^{-1}$. Elemental Analysis for C$_{17}$H$_{14}$N$_2$O$_4$S$_2$ Calcd. C, 54.53; H, 3.77; N, 7.48. Found C, 54.43; H, 3.73; N, 7.26.

Example 260

Methyl ({[6-(4-oxo-4H-1,3-benzothiazin-2-yl)-2-pyridyl]methyl}sulfonyl)acetate

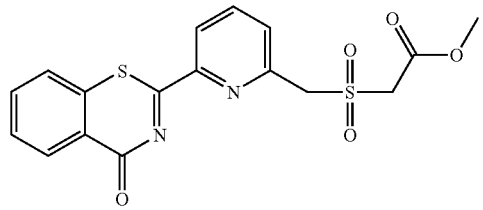

Methyl ({[6-(4-oxo-4H-1,3-benzothiazin-2-yl)-2-pyridyl]methyl}thio)acetate (0.20 g, 0.56 mmol) was dissolved in chloroform (50 ml), and a solution of 3-chloroperbenzoic acid (ca. 77%, 0.25 g, 1.12 mmol) in chloroform (10 ml) was added dropwise thereto. The mixture was stirred at room temperature for 3 hrs. The solvent was evaporated, and the residue was recrystallized from ethanol to give the titled compound (0.043 g, 20%) as white crystals.

mp. 205.0-207.0° C. $^1$H-NMR (CDCl$_3$) δ: 3.73 (3H, s), 4.35 (2H, s), 4.66 (2H, s), 7.59-7.71 (4H, m), 7.88 (1H, t, J=7.8 Hz), 8.42 (1H, d, J=7.7 Hz), 8.55 (1H, d, J=8.5 Hz). IR(KBr): 1732, 1655, 1570, 1533, 1439, 1302, 1114, 1097, 995, 738 cm$^{-1}$. Elemental Analysis for C$_{17}$H$_{14}$N$_2$O$_5$S$_2$ Calcd. C, 52.30; H, 3.64; N, 8.43. Found C, 52.15; H, 3.62; N, 8.38.

Example 261

2-[6-(Methylsulfinyl)-3-pyridyl]-4H-1,3-benzothiazine-4-one

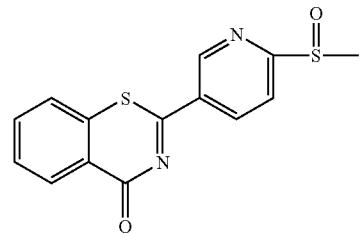

2-[6-(Methylthio)-3-pyridyl]-4H-1,3-benzothiazine-4-one (0.28 g, 1.00 mmol) was dissolved in chloroform (30 ml), and a solution of 3-chloroperbenzoic acid (ca. 77%, 0.23 g, 1.00 mmol) in chloroform (10 ml) was added dropwise thereto. The mixture was stirred at room temperature for 1 hr. The solvent was evaporated, and the residue was recrystallized from ethanol to give the titled compound (0.085 g, 28%) as pale yellow crystals.

mp. 195.0-196.5° C. $^1$H-NMR (CDCl$_3$) δ: 2.93 (3H, s), 7.59-7.61 (1H, m), 7.69-7.75 (2H, m), 8.21-8.24 (1H, m), 8.56-8.59 (1H, m), 8.69-8.72 (1H, m), 9.37-9.38 (1H, m). IR(KBr): 1660, 1572, 1520, 1439, 1361, 1299, 1095, 1053, 923, 742 cm$^{-1}$. Elemental Analysis for C$_{14}$H$_{10}$N$_2$O$_2$S$_2$ Calcd. C, 55.61; H, 3.33; N, 9.26. Found C, 55.49; H, 3.27; N, 9.39.

Example 262

2-[6-(Methylsulfonyl)-3-pyridyl]-4H-1,3-benzothiazine-4-one

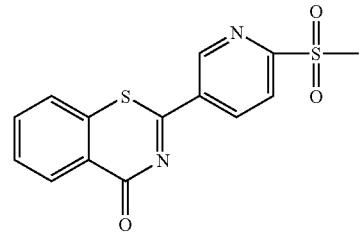

2-[6-(Methylthio)-3-pyridyl]-4H-1,3-benzothiazine-4-one (0.56 g, 2.00 mmol) was dissolved in chloroform (30 ml), and a solution of 3-chloroperbenzoic acid (ca. 77%, 0.90 g, 4.00 mmol) in chloroform (10 ml) was added dropwise thereto. The mixture was stirred at room temperature for 3 hrs. The solvent was evaporated, and the residue was recrystallized from ethanol to give the titled compound (0.090 g, 14%) as pale yellow crystals.

mp. 205.0-207.0° C. $^1$H-NMR (CDCl$_3$) δ: 3.31 (3H, s), 7.60-7.63 (1H, m), 7.71-7.77 (2H, m), 8.25-8.28 (1H, m), 8.57-8.60 (1H, m), 8.72-8.76 (1H, m), 9.44-9.45 (1H, m). IR(KBr): 1658, 1572, 1520, 1439, 1292, 1238, 1163, 1095, 912, 742 cm$^{-1}$. Elemental Analysis for C$_{14}$H$_{10}$N$_2$O$_3$S$_2$ Calcd. C, 52.82; H, 3.17; N, 8.80. Found C, 52.89; H, 3.47; N, 8.99.

Example 263

2-[2-(Methylsulfinyl)-4-pyridyl]-4H-1,3-benzothiazine-4-one

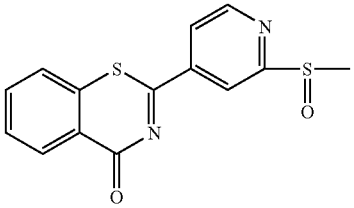

2-[2-(Methylthio)-4-pyridyl]-4H-1,3-benzothiazine-4-one (0.28 g, 1.00 mmol) was dissolved in chloroform (30 ml), and a solution of 3-chloroperbenzoic acid (ca. 77%, 0.23 g, 1.00 mmol) in chloroform (10 ml) was added dropwise thereto. The mixture was stirred at room temperature for 1 hr. The solvent was evaporated, and the residue was recrystallized from ethanol to give the titled compound (0.096 g, 32%) as pale yellow crystals.

mp. 172.5-174.0° C. $^1$H-NMR (CDCl$_3$) δ: 2.93 (3H, s), 7.60-7.62 (1H, m), 7.70-7.76 (2H, m), 8.21-8.23 (1H, m), 8.56-8.59 (1H, m), 8.64-8.65 (1H, m), 8.84-8.86 (1H, m). IR(KBr): 1666, 1587, 1572, 1518, 1439, 1290, 1242, 1093, 1049, 956, 744 cm$^{-1}$. Elemental Analysis for C$_{14}$H$_{10}$N$_2$O$_2$S$_2$ Calcd. C, 55.61; H, 3.33; N, 9.26. Found C, 55.45; H, 3.35; N, 9.24.

Example 264

2-[2-(Methylsulfonyl)-4-pyridyl]-4H-1,3-benzothiazine-4-one

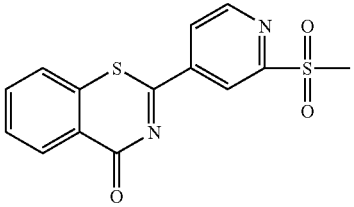

2-[2-(Methylthio)-4-pyridyl]-4H-1,3-benzothiazine-4-one (0.56 g, 2.00 mmol) was dissolved in chloroform (30 ml), and a solution of 3-chloroperbenzoic acid (ca. 77%, 0.90 g, 4.00 mmol) in chloroform (10 ml) was added dropwise thereto. The mixture was stirred at room temperature for 3 hrs. The solvent was evaporated, and the residue was recrystallized from ethanol to give the titled compound (0.030 g, 5%) as pale yellow crystals.

mp. 189.5-191.5° C. $^1$H-NMR (CDCl$_3$) δ: 3.31 (3H, s), 7.61-7.64 (1H, m), 7.70-7.78 (2H, m), 8.34-8.36 (1H, m), 8.56-8.59 (1H, m), 8.72-8.73 (1H, m) 8.96 (1H, d, J=5.0 Hz). IR(KBr): 1666, 1589, 1572, 1520, 1440, 1294, 1147, 1095, 956, 744 cm$^{-1}$. Elemental Analysis for C$_{14}$H$_{10}$N$_2$O$_3$S$_2$.0.25H$_2$O Calcd. C, 52.08; H, 3.27; N, 8.67. Found C, 52.38; H, 3.21; N, 8.42.

Example 265

2-(6-{[4-(4-Fluorophenyl)-1-piperazinyl]methyl}-2-pyridyl)-4H-1,3-benzothiazine-4-one

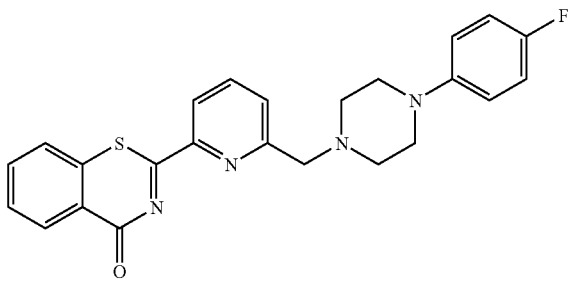

6-(4-Oxo-4H-1,3-benzothiazin-2-yl)-2-pyridylmethane-sulfonate (0.30 g, 0.86 mmol), triethylamine (0.20 ml, 1.42 mmol) and 1-(4-fluorophenyl)piperazine (0.17 g, 0.95 mmol) were dissolved in DMF (30 ml), and the mixture was stirred at 70° C. for 18 hrs. The reaction mixture was combined with ethyl acetate and water. The organic layer was washed with saturated brine and dried over anhydrous magnesium sulfate. The solvent was evaporated, and the residue was recrystallized from n-hexane-ethyl acetate to give the titled compound (0.19 g, 50%) as pale yellow crystals.

mp. 156.0-157.0° C. $^1$H-NMR (CDCl$_3$) δ: 2.78 (2H, t, J=4.7 Hz), 3.18 (2H, t, J=4.7 Hz), 3.88 (2H, s), 6.88-6.99 (4H, m), 7.61-7.75 (4H, m), 7.89 (1H, t, J=7.7 Hz), 8.55 (1H, d, J=7.7 Hz), 8.54-8.55 (1H, m). IR(KBr): 1658, 1589, 1572, 1531, 1439, 1300, 1277, 1234, 1095, 993, 744 cm$^{-1}$. Elemental Analysis for C$_{24}$H$_{21}$FN$_4$OS Calcd. C, 66.65; H, 4.89; N, 12.99. Found C, 66.55; H, 4.80; N, 13.01.

Example 266

2-(6-(1-Piperidinomethyl)-2-pyridyl]-4H-1,3-benzothiazine-4-one

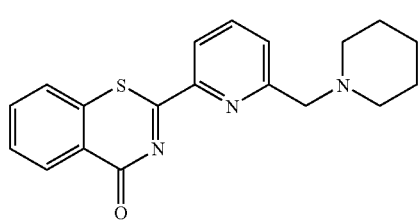

6-(4-Oxo-4H-1,3-benzothiazin-2-yl)-2-pyridylmethane-sulfonate (0.30 g, 0.86 mmol), triethylamine (0.20 ml, 1.42 mmol) and piperidine (0.081 g, 0.95 mmol) were dissolved in DMF (30 ml), and the mixture was stirred at 70° C. for 18 hrs. The reaction mixture was combined with ethyl acetate and water. The organic layer was washed with saturated brine and dried over anhydrous magnesium sulfate. The solvent was evaporated, and the residue was recrystallized from n-hexane-ethyl acetate to give the titled compound (0.16 g, 54%) as pale yellow crystals.

mp. 162.0-163.0° C. $^1$H-NMR (CDCl$_3$) δ: 1.65-1.62 (6H, m), 2.53-2.55 (4H, m), 3.78 (2H, s), 7.60-7.74 (4H, m), 7.86 (1H, t, J=7.7 Hz), 8.40 (1H, d, J=7.7 Hz), 8.54-8.56 (1H, m). IR(KBr): 1660, 1589, 1572, 1531, 1439, 1300, 1277, 1234, 1095, 993, 744 cm$^{-1}$. Elemental Analysis for C$_{19}$H$_{19}$N$_3$OS Calcd. C, 67.63; H, 5.68; N, 12.45. Found C, 67.61; H, 5.72; N, 12.45.

Example 267

2-{6-[(4-Phenyl-1-piperidyl)methyl]-2-pyridyl}-4H-1,3-benzothiazine-4-one

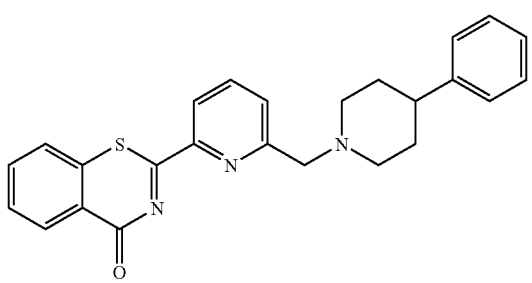

6-(4-Oxo-4H-1,3-benzothiazin-2-yl)-2-pyridylmethane-sulfonate (0.30 g, 0.86 mmol), triethylamine (0.20 ml, 1.42 mmol) and 4-phenylpiperidine (0.15 g, 0.95 mmol) were dissolved in DMF (30 ml), and the mixture was stirred at 70° C. for 18 hrs. The reaction mixture was combined with ethylacetate and water. The organic layer was washed with saturated brine and dried over anhydrous magnesium sulfate. The solvent was evaporated, and the residue was recrystallized from n-hexane-ethyl acetate to give the titled compound (0.16 g, 76%) as pale yellow crystals.

mp. 207.0-208.0° C. $^1$H-NMR (CDCl$_3$) δ: 1.83-1.89 (4H, m), 2.27-2.36 (2H, m), 3.10 (2H, d, J=11.5 Hz), 3.86 (2H, s), 7.18-7.31 (5H, m) 7.62-7.68 (3H, m), 7.75 (1H, d, J=7.8 Hz), 7.88 (1H, t, J=7.7 Hz), 8.42 (1H, d, J=7.7 Hz), 8.54-8.57(1H, m). IR(KBr): 1662, 1589, 1570, 1533, 1439, 1289, 1095, 993, 744 cm$^{-1}$. Elemental Analysis for C$_{25}$H$_{23}$N$_3$OS Calcd. C, 72.61; H, 5.61; N, 10.16. Found C, 72.55; H, 5.60; N, 10.10.

Example 268

2-{6-[(4-Benzyl-1-piperidyl)methyl]-2-pyridyl}-4H-1,3-benzothiazine-4-one

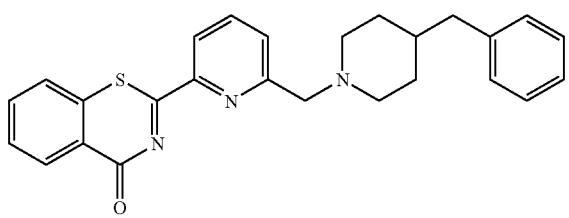

6-(4-Oxo-4H-1,3-benzothiazin-2-yl)-2-pyridylmethane-sulfonate (0.30 g, 0.86 mmol), triethylamine (0.20 ml, 1.42 mmol) and 4-benzylpiperidine (0.17 g, 0.95 mmol) were dissolved in DMF (30 ml), and the mixture was stirred at 70° C. for 18 hrs. The reaction mixture was combined with ethyl acetate and water. The organic layer was washed with saturated brine and dried over anhydrous magnesium sulfate. The solvent was evaporated, and the residue was recrystallized from n-hexane-ethyl acetate to give the titled compound (0.25 g, 67%) as pale yellow crystals.

mp. 151.0-153.0° C. $^1$H-NMR (CDCl$_3$) δ: 2.04-2.15 (2H, m), 2.56 (2H, d, J=6.7 Hz), 2.94(2H, d, J=11.1 Hz), 3.77 (2H, s), 7.13-7.29 (5H, m), 7.59-7.71 (4H, m), 7.85 (1H, t, J=7.8 Hz), 8.39 (1H, d, J=7.7 Hz), 8.54 (1H, d, J=8.5 Hz). IR(KBr): 1660, 1589, 1572, 1537, 1439, 1296, 1097, 910, 736 cm$^{-1}$. Elemental Analysis for C$_{26}$H$_{25}$N$_3$OS Calcd. C, 73.04; H, 5.89; N, 9.83. Found C, 72.87; H, 5.94; N, 9.79.

Example 269

2-(6-{[4-(4-Chlorophenyl)-4-hydroxy-1-piperidyl]methyl}-2-pyridyl)-4H-1,3-benzothiazine-4-one

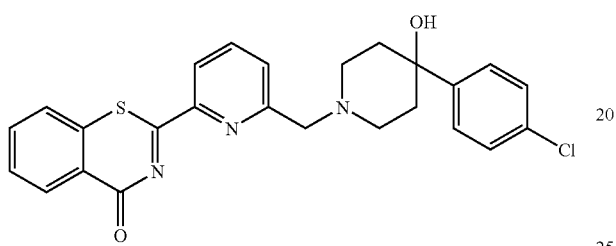

6-(4-Oxo-4H-1,3-benzothiazin-2-yl)-2-pyridylmethanesulfonate (0.30 g, 0.86 mmol), triethylamine (0.20 ml, 1.42 mmol) and 4-(4-chlorophenyl)-4-hydroxypiperidine (0.20 g, 0.95 mmol) were dissolved in DMF (30 ml), and the mixture was stirred at 70° C. for 18 hrs. The reaction mixture was combined with ethyl acetate and water. The organic layer was washed with saturated brine and dried over anhydrous magnesium sulfate. The solvent was evaporated, and the residue was recrystallized from n-hexane-ethylacetate to give the titled compound (0.20 g, 49%) as pale yellow crystals.

mp. 151.0-153.0° C. $^1$H-NMR (CDCl$_3$) δ: 1.75-1.79 (2H, m), 2.14-2.24 (2H, m), 2.66-2.73 (2H, m), 2.87-2.95 (2H, m), 3.89 (2H, s), 7.33 (2H, d, J=8.6 Hz), 7.47 (2H, d, J=8.6 Hz), 7.60-7.75 (4H, m), 7.88 (1H, t, J=7.8 Hz), 8.42 (1H, d, J=7.7 Hz), 8.53-8.57 (1H, m). IR(KBr): 1651, 1572, 1537, 1439, 1302, 1097, 910, 734 cm$^{-1}$. Elemental Analysis for C$_{25}$H$_{22}$ClN$_3$O$_2$S Calcd. C, 64.72; H, 4.78; N, 9.06. Found C, 64.43; H, 4.74; N, 8.86.

Reference Example 97

2-Cyano-6-(2-pyrimidinyl)thiopyridine

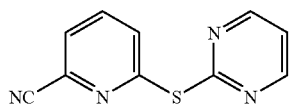

2-Mercaptopyridine (0.89 g, 7.94 mmol) and sodium hydride (60% in oil, 0.35 g, 8.66 mmol) were dissolved in DMF (30 ml), and 2-chloro-6-cyanopyridine (1.05 g, 3.00 mmol) was added thereto. The reaction mixture was stirred at 70° C. for 18 hrs and combined with ethyl acetate and water. The organic layer was washed with saturated brine and dried over anhydrous magnesium sulfate. The solvent was evaporated, and the residue was recrystallized from n-hexane-ethyl acetate to give the titled compound (1.32 g, 85%).

$^1$H-NMR (CDCl$_3$) δ: 7.10 (1H, t, J=4.8 Hz), 7.63-7.66 (1H, m), 8.85 (1H, t, J=4.8 Hz), 8.05-8.08 (1H, m), 8.56 (1H, d, J=4.8 Hz). IR(KBr): 2231, 1572, 1550, 1433, 1371, 1167, 1147, 1086, 983, 798 cm$^{-1}$.

Example 270

2-[6-(2-Pyrimidinylthio)-2-pyridyl]-4H-1,3-benzothiazine-4-one

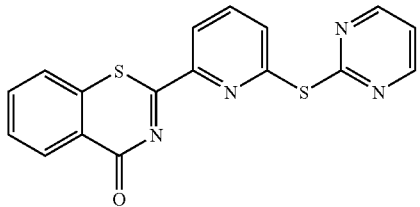

2-Cyano-6-(2-pyrimidinyl)thiopyridine (1.30 g, 6.07 mmol) and methyl thiosalicylate (1.53 g, 9.10 mmol) were dissolved in toluene (100 ml), and triethylamine (1.70 ml, 12.1 mmol) was added thereto. The mixture was refluxed for 18 hrs. The solvent was evaporated, and the residue was recrystallized from ethanol to give the titled compound (0.11 g, 5%) as pale yellow crystals.

mp. 245.2-245.8° C. $^1$H-NMR (CDCl$_3$) δ: 7.10 (1H, t, J=4.8 Hz), 7.60-7.66 (3H, m), 8.93 (1H, t, J=7.8 Hz), 8.03-8.06 (1H, m), 8.49-8.59 (4H, m) IR(KBr): 1666, 1554, 1535, 1431, 1383, 1296, 1095, 1062, 802, 746 cm$^{-1}$. Elemental Analysis for C$_{17}$H$_{10}$N$_4$OS$_2$ Calcd. C, 58.27; H, 2.88; N, 15.99. Found C, 58.28; H, 3.09; N, 15.85.

Reference Example 98

2-Cyano-6-(1-methyl-1H-imidazol-2-yl)thiopyridine

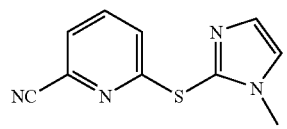

2-Mercapto-1-methyl-1H-imidazole (0.91 g, 7.94 mmol) and sodium hydride (60% in oil, 0.35 g, 8.66 mmol) were dissolved in DMF (30 ml), and 2-chloro-6-cyanopyridine (1.05 g, 3.00 mmol) was added thereto. The reaction mixture was stirred at 70° C. for 18 hrs and combined with ethyl acetate and water. The organic layer was washed with saturated brine and dried over anhydrous magnesium sulfate. The solvent was evaporated, and the residue was recrystallized from n-hexane-ethyl acetate to give the titled compound (1.71 g, ca. 100%) as pale yellow crystals.

$^1$H-NMR (CDCl$_3$) δ: 3.79 (3H, s), 7.21-7.23 (1H, m), 7.63-7.66 (1H, m), 8.85 (1H, t, J=4.8 Hz), 8.25 (1H, d, J=7.6 Hz), 8.56 (1H, d, J=4.8 Hz). IR(KBr): 2231, 1570, 1550, 1433, 1373, 1167, 1152, 1086, 983, 798 cm$^{-1}$.

Example 271

2-{6-[(1-Methyl-1H-imidazol-2-yl)thio]-2-pyridyl}-4H-1,3-benzothiazine-4-one

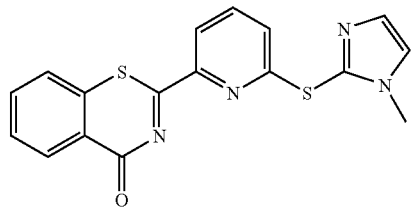

2-Cyano-6-(1-methyl-1H-imidazol-2-yl)thiopyridine (1.56 g, 7.22 mmol) and methyl thiosalicylate (1.53 g, 9.10 mmol) were dissolved in toluene (100 ml), and triethylamine (1.70 ml, 12.1 mmol) was added thereto. The reaction mixture was refluxed for 18 hrs. The solvent was evaporated, and the residue was recrystallized from ethanol to give the titled compound (0.14 g, 5%) as pale yellow crystals.

mp. 171.9-172.3° C. $^1$H-NMR (CDCl$_3$) δ: 3.79 (3H, s), 7.22-7.29 (2H, m), 7.34 (1H, s), 7.53-7.55 (1H, m), 7.60-7.76 (3H, m), 8.25 (1H, d, J=7.6 Hz), 8.53 (1H, d, J=1.6 Hz). IR(KBr): 1658, 1556, 1537, 1433, 1296, 1095, 964, 746 cm$^{-1}$. Elemental Analysis for C$_{17}$H$_{12}$N$_4$OS$_2$ Calcd. C, 57.93; H, 3.43; N, 15.90. Found C, 58.18; H, 3.10; N, 15.75.

Example 272

2-{6-[(2-Pyridylthio)methyl]-2-pyridyl}-4H-1,3-benzothiazine-4-one

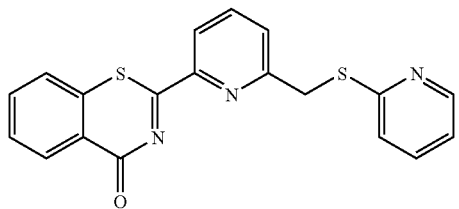

2-mercaptopyridine (0.21 g, 1.89 mmol) and sodium hydride (60% in oil, 0.083 g, 2.06 mmol) were dissolved in DMF (30 ml), and 6-(4-oxo-4H-1,3-benzothiazin-2-yl)-2-pyridylmethanesulfonate (0.60 g, 1.72 mmol) was added thereto. The reaction mixture was stirred at room temperature for 18 hrs and combined with ethyl acetate and water. The organic layer was washed with saturated brine and dried over anhydrous magnesium sulfate. The solvent was evaporated, and the residue was recrystallized from ethanol to give the titled compound (0.54 g, 87%) as pale yellow crystals.

mp. 151.3-151.9° C. $^1$H-NMR (CDCl$_3$) δ: 4.70 (2H, s), 6.99-7.03 (1H, m), 7.25-7.28 (1H, m), 7.48-7.53 (1H, m), 7.59-7.70 (4H, m), 7.80 (1H, d, J=7.5 Hz), 8.46 (1H, d, J=4.1 Hz), 8.47-8.55 (1H, m). IR(KBr): 1660, 1589, 1574, 1537, 1452, 1439, 1300, 1097, 993, 744 cm$^{-1}$. Elemental Analysis for C$_{19}$H$_{13}$N$_3$OS$_2$ Calcd. C, 62.79; H, 3.61; N, 11.56. Found C, 62.87; H, 3.43; N, 11.46.

Example 273

2-{6-[(4-pyridylthio)methyl]-2-pyridyl}-4H-1,3-benzothiazine-4-one

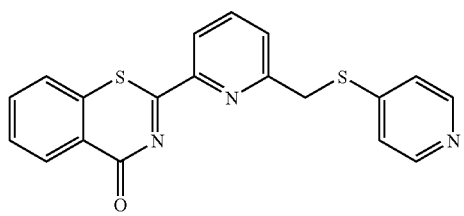

4-Mercaptopyridine (0.21 g, 1.89 mmol) and sodium hydride (60% in oil, 0.083 g, 2.06 mmol) were dissolved in DMF (30 ml), and 6-(4-oxo-4H-1,3-benzothiazin-2-yl)-2-pyridylmethanesulfonate (0.60 g, 1.72 mmol) was added thereto. The reaction mixture was stirred at room temperature for 18 hrs and combined with ethyl acetate and water. The organic layer was washed with saturated brine and dried over anhydrous magnesium sulfate. The solvent was evaporated, and the residue was recrystallized from ethanol to give the titled compound (0.11 g, 17%) as pale yellow crystals.

mp. 181.9-182.5° C. $^1$H-NMR (CDCl$_3$) δ: 4.45 (2H, s), 7.31-7.33 (2H, m), 7.61-7.71 (4H, m), 7.89 (1H, t, J=7.7 Hz), 8.41-8.45 (3H, s), 8.54-8.56 (1H, m). IR(KBr): 1658, 1572, 1535, 1452, 1439, 1300, 1095, 993, 742 cm$^{-1}$. Elemental Analysis for C$_{19}$H$_{13}$N$_3$OS$_2$ Calcd. C, 62.79; H, 3.61; N, 11.56. Found C, 62.89; H, 3.50; N, 11.44.

Reference Example 99

2-Cyano-6-(4-pyridylthio)pyridine

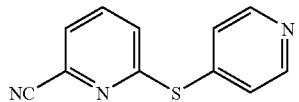

4-Mercaptopyridine (0.88 g, 7.94 mmol) and sodium hydride (60% in oil, 0.35 g, 8.66 mmol) were dissolved in THF (30 ml), and the mixture was stirred at room temperature for 1 hr. A solution of 2-chloro-6-cyanopyridine (1.00 g, 7.22 mmol) in THF (10 ml) was added to the mixture, and the mixture was stirred at room temperature for 18 hrs. The mixture was combined with ethyl acetate and water. The organic layer was washed with saturated brine and dried over anhydrous magnesium sulfate. The solvent was evaporated to give the titled compound (1.54 g, ca. 100%) as an oil.

$^1$H-NMR (CDCl$_3$) δ: 7.63-7.68 (2H, m), 7.82(1H, t, J=7.5 Hz), 8.36 (1H, d, J=7.7 Hz), 8.55-8.68 (3H, m). IR(KBr): 2237, 1556, 1427, 1271, 1138, 983, 800 cm$^{-1}$.

Example 274

2-[6-(4-Pyridylthio)-2-pyridyl]-4H-1,3-benzothiazine-4-one

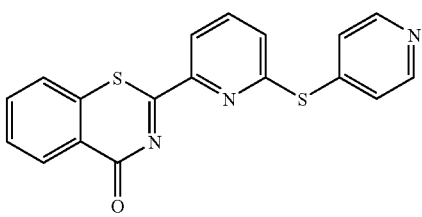

2-Cyano-6-(4-pyridylthio)pyridine (1.54 g, 7.22 mmol) and methyl thiosalicylate (1.34 g, 7.94 mmol) were dissolved in toluene (50 ml), and triethylamine (1.52 ml, 10.83 mmol) was added thereto. The mixture was refluxed for 18 hrs. The solvent was evaporated, and the residue was recrystallized from ethanol to give the titled compound (0.053 g, 2%) as pale yellow crystals.

mp. 245.2-245.8° C. $^1$H-NMR (CDCl$_3$) δ: 7.49-7.54 (4H, m), 7.62-7.68 (2H, m), 7.82 (1H, t, J=7.5 Hz), 8.36 (1H, d, J=7.7 Hz), 8.54 (1H, d, J=7.7 Hz), 8.55-8.68 (2H, m). IR(KBr): 1664, 1568, 1531, 1427, 1294, 1157, 1095, 794 cm$^{-1}$. Elemental Analysis for C$_{18}$H$_{11}$N$_3$OS$_2$.0.25H$_2$O Calcd. C, 61.08; H, 3.27; N, 11.87. Found C, 60.87; H, 3.31; N, 11.90.

Reference Example 100

(6-Cyano-2-pyridyl)thioacetic acid

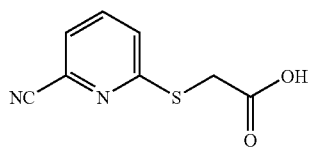

A mixture of thioglycolic acid (6.91 g, 75.0 mmol), sodium hydride (60% in oil, 6.00 g, 150.0 mmol) and DMF (100 ml) was stirred at room temperature for 1 hr. 2-Chloro-6-cyanopyridine (7.00 g, 50.0 mmol) was added thereto, and the mixture was stirred at room temperature for 18 hrs. The reaction mixture was combined with ethyl acetate and 10% hydrochloric acid. The organic layer was washed with saturated brine and dried over anhydrous magnesium sulfate. The solvent was evaporated to give the titled compound (4.56 g, 47%) as pale yellow crystals.

$^1$H-NMR (CDCl$_3$) δ: 3.95 (2H, s), 7.38-7.43 (2H, m), 7.61 (1H, t, J=7.9 Hz), 12.84 (1H, br s). IR(KBr): 3152, 2235, 1730, 1572, 1554, 1433, 1141, 746 cm$^{-1}$.

Reference Example 101 tert-Butyl (6-cyano-2-pyridyl)thioacetate

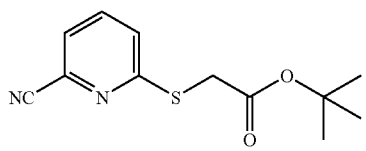

(6-Cyano-2-pyridyl)thioacetic acid (4.56 g, 23.5 mmol) and concentrated sulfuric acid (1 ml) were added to dichloromethane (300 ml), and isobutene was added thereto. The reaction mixture was sealed and stirred at room temperature for 18 hrs. Water was added to the reaction mixture. The organic layer was washed with saturated brine, dried over anhydrous magnesium sulfate. The solvent was evaporated to give the titled compound (5.77 g, 98%) as a pale yellow oil.

$^1$H-NMR (CDCl$_3$) δ: 1.45 (9H, s), 3.95 (2H, s), 7.38-7.43 (2H, m), 7.61 (1H, t, J=7.9 Hz). IR(KBr): 2235, 1732, 1572, 1554, 1433, 1141, 746 cm$^{-1}$.

Example 275 tert-Butyl [{6-(4-oxo-4H-1,3-benzothiazin-2-yl)-2-pyridyl]thio}acetate

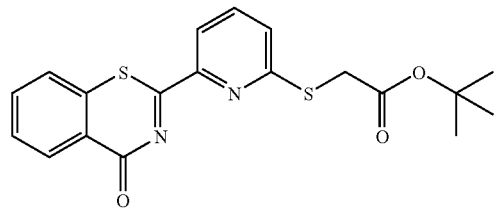

tert-Butyl (6-cyano-2-pyridyl)thioacetate (3.00 g, 10.2 mmol) and methyl thiosalicylate (2.02 g, 12.0 mmol) were dissolved in toluene (50 ml), and triethylamine (2.52 ml, 18.0 mmol) was added thereto. The mixture was refluxed for 18 hrs. The solvent was evaporated, and the residue was recrystallized from ethanol to give the titled compound (2.02 g, 52%) as pale yellow crystals.

mp. 169.5-170.0° C. $^1$H-NMR (CDCl$_3$) δ: 1.45 (9H, s), 4.09 (2H, s), 7.44-7.47 (1H, m), 7.61-7.74 (4H, m), 8.23-8.26 (1H, m), 8.54-8.57 (1H, m). IR(KBr): 1730, 1660, 1570, 1573, 1433, 1367, 1296, 1234, 1095, 744 cm$^{-1}$. Elemental Analysis for C$_{19}$H$_{18}$N$_2$O$_3$S$_2$ Calcd. C, 59.05; H, 4.69; N, 7.25. Found C, 59.18; H, 4.86; N, 6.98.

Example 276

[6-(4-Oxo-4H-1,3-benzothiazin-2-yl)-2-pyridyl]thioacetic acid

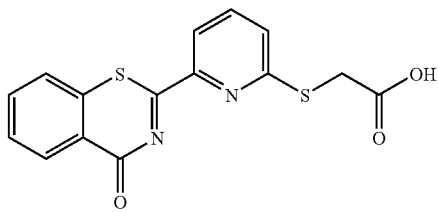

tert-Butyl {[6-(4-oxo-4H-1,3-benzothiazin-2-yl)-2-pyridyl]thio}acetate (0.30 g, 0.78 mmol) was dissolved in trifluoroacetic acid (5 ml), and the mixture was stirred for 0.5 hr. Diisopropyl ether was added to the mixture. The obtained precipitates were recrystallized from ethanol to give the titled compound (0.21 g, 83%) as pale yellow crystals.

mp. 258.0-260.0° C. $^1$H-NMR (DMSO-$d_6$) δ: 4.41 (2H, s), 7.70-7.75 (2H, m), 7.86 (2H, d, J=3.8 Hz), 7.95 (1H, t, J=7.7 Hz), 8.08 (1H, d, J=7.6 Hz), 8.37 (1H, d, J=7.9 Hz), 12.88 (1H, br s). IR(KBr): 3152, 1732, 1633, 1568, 1525, 1433, 1315, 1246, 1211, 985, 748 cm$^{-1}$. Elemental Analysis for $C_{15}H_{10}N_2O_3S_2$ Calcd. C, 54.53; H, 3.05; N, 8.48. Found C, 54.52; H, 2.79; N, 8.18.

Example 277

Ethyl {[6-(4-oxo-4H-1,3-benzothiazin-2-yl)-2-pyridyl]thio}acetate

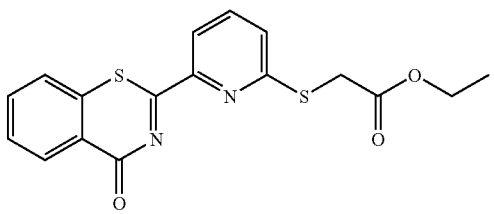

Ethyl (6-cyano-2-pyridyl)thioacetate (0.48 g, 2.15 mmol) and methyl thiosalicylate (0.40 g, 2.34 mmol) were dissolved in toluene (50 ml), and triethylamine (0.51 ml, 3.66 mmol) was added thereto. The mixture was refluxed for 18 hrs. The solvent was evaporated, and the residue was recrystallized from ethanol to give the titled compound (0.40 g, 52%) as pale yellow crystals.

mp. 124.5-125.0° C. $^1$H-NMR (CDCl$_3$) δ: 1.29 (3H, t, J=7.1 Hz), 4.14 (2H, s), 4.25 (2H, q, J=7.1 Hz), 7.45-7.48 (1H, m), 7.60-7.75 (4H, m), 8.23-8.26 (1H, m), 8.55-8.57 (1H, m). IR(KBr): 1736, 1655, 1570, 1533, 1431, 1294, 1143, 1095, 1028, 746 cm$^{-1}$. Elemental Analysis for $C_{17}H_{14}N_2O_3S_2$ Calcd. C, 56.96; H, 3.94; N, 7.82. Found C, 56.87; H, 3.90; N, 7.94.

Example 278 tert-Butyl {[6-(4-oxo-4H-1,3-benzothiazin-2-yl)-2-pyridyl]sulfinyl}acetate

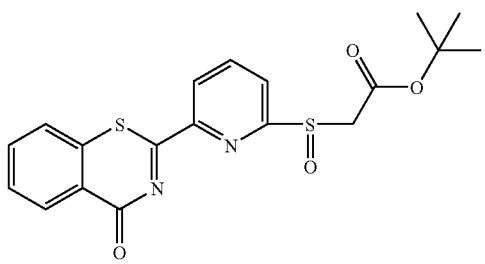

tert-Butyl {[6-(4-oxo-4H-1,3-benzothiazin-2-yl)-2-pyridyl]thio}acetate (0.34 g, 1.00 mmol) was dissolved in chloroform (20 ml), and a solution of 3-chloroperbenzoic acid (ca. 77%, 0.23 g, 1.00 mmol) in chloroform (10 ml) was added thereto. The mixture was stirred at room temperature for 1 hr. The solvent was evaporated, and the residue was recrystallized from n-hexane-ethyl acetate to give the titled compound (0.30 g, 75%) as pale yellow crystals.

mp. 158.8-159.1° C. $^1$H-NMR (CDCl$_3$) δ: 1.44 (9H, s), 3.89, 4.17 (2H, q$_{AB}$, J=14.0 Hz), 7.63-7.73 (3H, m), 8.19 (1H, t, J=7.8 Hz), 8.26-8.28 (1H, m), 8.55-8.64 (2H, m). IR(KBr): 1724, 1664, 1572, 1537, 1437, 1369, 1298, 1248, 1095, 734 cm$^{-1}$. Elemental Analysis for $C_{19}H_{18}N_2O_4S_2$ Calcd. C, 56.70; H, 4.51; N, 6.96. Found C, 56.40; H, 4.33; N, 6.79.

Example 279

[6-(4-Oxo-4H-1,3-benzothiazin-2-yl)-2-pyridyl]sulfinylacetic acid

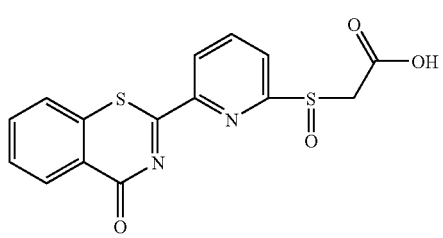

tert-Butyl [[6-(4-oxo-4H-1,3-benzothiazin-2-yl)-2-pyridyl]sulfinyl]acetate (0.12 g, 0.30 mmol) was dissolved in trifluoroacetic acid (5 ml), and the mixture was stirred for 0.5 hr. Diisopropyl ether was added to the mixture. The obtained crystals were recrystallized from ethanol to give the titled compound (0.081 g, 79%) as pale yellow crystals.

mp. 186.5-188.0° C. $^1$H-NMR (DMSO-$d_6$) δ: 4.02, 4.23 (2H, q$_{AB}$, J=14.5 Hz), 7.73 (1H, t, J=7.7 Hz), 7.84 (1H, t, J=7.9 Hz), 7.94 (1H, d, J=7.8 Hz), 8.23 (1H, d, J=7.3 Hz), 8.34-8.47 (2H, m), 13.38 (1H, br s). IR(KBr): 2850, 1722, 1658, 1570, 1529, 1437, 1288, 1236, 1184, 1095, 734 cm$^{-1}$. Elemental Analysis for $C_{15}H_{10}N_2O_4S_2$ Calcd. C, 52.01; H, 2.91; N, 8.09. Found C, 51.85; H, 2.96; N, 8.02.

Example 280 tert-Butyl {[6-(4-oxo-4H-1,3-benzothiazin-2-yl)-2-pyridyl]sulfonyl}acetate

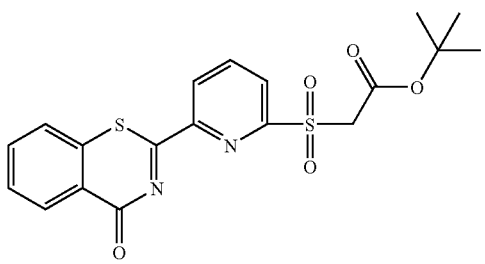

tert-Butyl {[6-(4-oxo-4H-1,3-benzothiazin-2-yl)-2-pyridyl]thio}acetate (1.00 g, 2.59 mmol) was dissolved in chloroform (50 ml), and a solution of 3-chloroperbenzoic acid (ca. 77%, 1.16 g, 5.18 mmol) in chloroform (10 ml) was added to thereto. The mixture was stirred at room temperature for 3 hrs. The solvent was evaporated, and the residue was recrystallized from n-hexane-ethyl acetate to give the titled compound (0.13 g, 12%) as pale yellow crystals.

mp. 159.0-160.0° C. $^1$H-NMR (CDCl$_3$) δ: 1.30 (9H, s), 4.54 (2H, s), 7.66-7.75 (4H, m), 8.23 (1H, t, J=7.8 Hz), 8.30-8.33 (1H, m), 8.56-8.59 (1H, m), 8.77-8.80 (1H, m). IR(KBr): 1726, 1662, 1570, 1535, 1439, 1332, 1300, 1170, 1095, 733 cm$^{-1}$. Elemental Analysis for C$_{19}$H$_{18}$N$_2$O$_5$S$_2$ Calcd. C, 54.53; H, 4.34; N, 6.69. Found C, 54.36; H, 4.29; N, 6.65.

Example 281

[6-(4-Oxo-4H-1,3-benzothiazin-2-yl)-2-pyridyl]sulfonylacetic acid

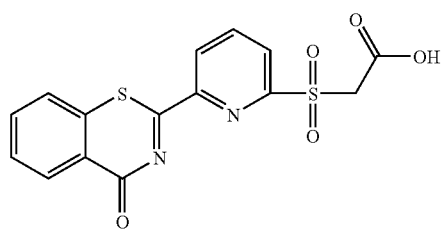

tert-Butyl {[6-(4-oxo-4H-1,3-benzothiazin-2-yl)-2-pyridyl]sulfonyl}acetate (0.10 g, 0.24 mmol) was dissolved in trifluoroacetic acid (5 ml), and the mixture was stirred for 0.5 hr. Diisopropyl ether was added to the mixture. The obtained precipitates were recrystallized from ethanol to give the titled compound (0.048 g, 55%) as pale yellow crystals.

mp. 192.0-193.5° C. $^1$H-NMR (DMSO-d$_6$) δ: 4.80 (2H, s), 7.77 (1H, t, J=7.4 Hz), 7.85 (1H, t, J=7.5 Hz), 8.00 (1H, d, J=7.9 Hz), 8.39 (2H, d, J=7.8 Hz), 8.47 (1H, t, J=7.8 Hz), 8.65 (1H, t, J=7.7 Hz), 13.49 (1H, br s). IR(KBr): 3071, 1739, 1655, 1572, 1537, 1440, 1340, 1315, 1180, 1095, 733 cm$^{-1}$. Elemental Analysis for C$_{15}$H$_{10}$N$_2$O$_5$S$_2$ Calcd. C, 49.72; H, 2.78; N, 7.73. Found C, 49.52; H, 2.83; N, 7.55.

Reference Example 102

(6-Cyano-2-pyridyl)thioacetamide

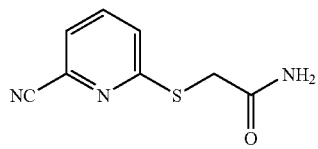

A mixture of (6-cyano-2-pyridyl)thioacetic acid (0.95 g, 4.89 mmol), isobutyl chloroformate (1.05 ml, 7.33 mmol), triethylamine (1.03 ml, 7.33 mmol) and THF (150 ml) was stirred under ice cooling condition for 2 hrs. 28% ammonium solution (100 ml) was added to the mixture, and the mixture was stirred under ice cooling condition for 2 hrs. The reaction mixture was combined with ethyl acetate. The organic layer was washed with saturated brine and dried over magnesium sulfate. The solvent was evaporated to give the titled compound (0.49 g, 52%) as pale yellow crystals $^1$H-NMR (CDCl$_3$) δ: 3.85 (2H, s), 5.44(1H, br s), 6.54(1H, br s), 7.43-7.47(2H, m), 7.64-7.69 (1H, m), 12.84(1H, br s). IR(KBr): 3385, 3171, 2231, 1647, 1572, 1545, 1425, 1145, 796 cm$^{-1}$.

Example 282

2-[[6-(4-Oxo-4H-1,3-benzothiazin-2-yl)-2-pyridyl]thioacetamide

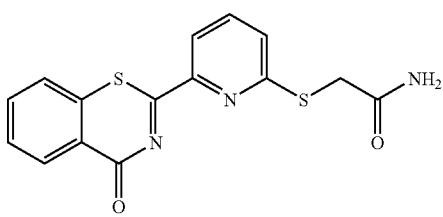

(6-Cyano-2-pyridyl)thioacetamide (0.47 g, 2.43 mmol) and methyl thiosalicylate (0.45 g, 2.67 mmol) were dissolved in toluene (50 ml), and triethylamine (0.51 ml, 3.64 mmol) was added thereto. The mixture was refluxed for 18 hrs. The solvent was evaporated, and the residue was recrystallized from ethanol to give the titled compound (0.33 g, 41%) as white crystals.

mp. 256.7-257.0° C. $^1$H-NMR (DMSO-d$_6$) δ: 4.00 (2H, s), 7.26(1H, br s), 7.68-7.77 (3H, m), 7.83-7.97 (3H, m), 8.06 (1H, d, J=6.0 Hz), 8.36 (1H, d, J=7.9 Hz). IR(KBr): 3379, 3173, 1666, 1633, 1570, 1535, 1435, 1367, 1302, 1248, 1095, 752 cm$^{-1}$. Elemental Analysis for C$_{15}$H$_{11}$N$_3$O$_2$S$_2$ Calcd. C, 54.69; H, 3.37; N, 12.76. Found C, 54.63; H, 3.27; N, 12.71.

Example 283

2-{[6-(4-Oxo-4H-1,3-benzothiazin-2-yl)-2-pyridyl]sulfinyl}acetamide

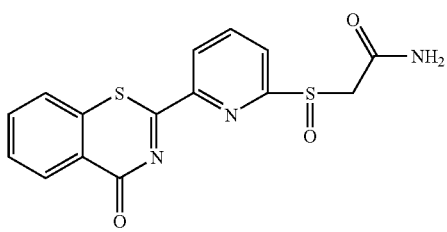

2-{[6-(4-Oxo-4H-1,3-benzothiazin-2-yl)-2-pyridyl]thio}acetamide (0.12 g, 0.36 mmol) was dissolved in chloroform (300 ml), and a solution of 3-chloroperbenzoic acid (77%, 0.082 g, 0.36 mmol) in chloroform (10 ml) was added dropwise thereto. The mixture was stirred at room temperature for 1 hr. The solvent was evaporated, and the residue was recrystallized from ethanol to give the titled compound (0.071 g, 57%) as white crystals.

$^1$H-NMR (DMSO-d$_6$) δ: 3.82, 4.03 (2H, q$_{AB}$, J=13.8 Hz), 7.47 (1H, br s), 7.75 (2H, t, J=7.8 Hz), 7.86 (1H, t, J=7.1 Hz), 7.98 (1H, d, J=7.9 Hz), 8.23 (1H, d, J=7.5 Hz), 8.36-8.48 (3H, m). IR(KBr): 3360, 1685, 1647, 1570, 1529, 1439, 1307, 1298, 1246, 1099, 746 cm$^{-1}$. Elemental Analysis for C$_{15}$H$_{11}$N$_3$O$_3$S$_2$.0.25H$_2$O Calcd. C, 51.49; H, 3.31; N, 12.01. Found C, 51.53; H, 3.06; N, 11.85.

Reference Example 103

6-Cyano-2-methylthiopyrimidine

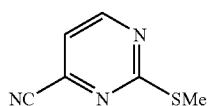

A mixture of 2-chloro-6-cyanopyrimidine (2.20 g, 15.8 mmol), sodium thiomethoxide (1.22 g, 17.3 mmol) and THF (100 ml) was refluxed for 2 hrs. The reaction mixture was combined with ethyl acetate and water. The organic layer was washed with saturated brine and dried over anhydrous magnesium sulfate. The solvent was evaporated to give the titled compound (1.57 g, 66%) as pale yellow crystals.

$^1$H-NMR (CDCl$_3$) δ: 2.58 (3H, s), 7.26(1H, d, J=4.8 Hz), 8.70 (1H, d, J=4.8 Hz). IR(KBr): 2241, 1554, 1537, 1396, 1348, 1197, 862 cm$^{-1}$.

Example 284

2-[2-(Methylthio)-6-pyrimidinyl]-4H-1,3-benzothiazine-4-one

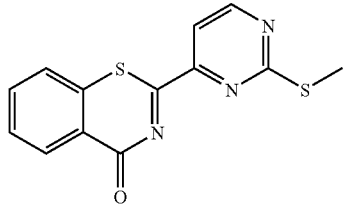

6-Cyano-2-methylthiopyrimidine (1.37 g, 9.06 mmol) and methyl thiosalicylate (3.05 g, 18.1 mmol) were dissolved in toluene (30 ml), and triethylamine (3.80 ml, 27.2 mmol) was added thereto. The mixture was refluxed for 18 hrs. The solvent was evaporated, and the residue was recrystallized from ethanol to give the titled compound (1.40 g, 54%) as pale yellow crystals.

mp. 223.5-224.0° C. $^1$H-NMR (CDCl$_3$) δ: 2.70 (3H, s), 7.62-7.76 (3H, m), 8.03(1H, d, J=5.0 Hz), 8.54-8.57 (1H, m), 8.78 (1H, d, J=5.0 Hz). IR(KBr): 1655, 1533, 1412, 1346, 1284, 1203, 1093, 748 cm$^{-1}$. Elemental Analysis for C$_{13}$H$_9$N$_3$OS$_2$ Calcd. C, 54.34; H, 3.16; N, 14.62. Found C, 54.57; H, 3.27; N, 14.76.

Example 285

2-[2-(Methylsulfinyl)-6-pyrimidinyl]-4H-1,3-benzothiazine-4-one

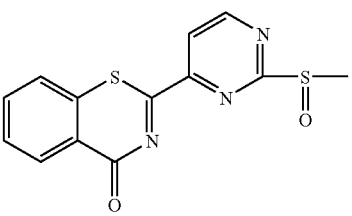

2-[2-(Methylthio)-6-pyrimidinyl]-4H-1,3-benzothiazine-4-one (0.30 g, 1.50 mmol) was dissolved in chloroform (100 ml), and a solution of 3-chloroperbenzoic acid (ca. 77%, 0.23 g, 1.50 mmol) in chloroform (10 ml) was added dropwise thereto. The mixture was stirred at room temperature for 1 hr. The solvent was evaporated, and the residue was recrystallized from ethanol to give the titled compound (0.18 g, 55%) as pale yellow crystals.

mp. 250.5-252.0° C. $^1$H-NMR (CDCl$_3$) δ: 3.08 (3H, s), 7.65-7.79 (3H, m), 8.50(1H, d, J=5.0 Hz), 8.56-8.59 (1H, m), 9.16 (1H, d, J=5.0 Hz). IR(KBr): 1664, 1566, 1535, 1439, 1377, 1292, 1062, 729 cm$^{-1}$. Elemental Analysis for C$_{13}$H$_9$N$_3$O$_2$S$_2$ Calcd. C, 51.47; H, 2.99; N, 13.85. Found C, 51.45; H, 3.06; N, 13.87.

Example 286

2-[2-(Methylsulfonyl)-6-pyrimidinyl]-4H-1,3-benzothiazine-4-one

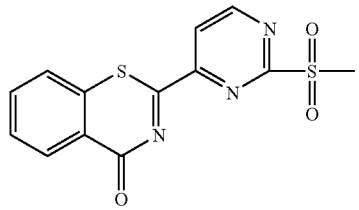

2-[2-(Methylthio)-6-pyrimidinyl]-4H-1,3-benzothiazine-4-one (0.30 g, 1.05 mmol) was dissolved in chloroform (50 ml), and a solution of 3-chloroperbenzoic acid (ca. 77%, 0.47 g, 2.10 mmol) in chloroform (10 ml) was added dropwise thereto. The mixture was stirred at room temperature for 3 hrs. The solvent was evaporated, and the residue was recrystallized from ethanol to give the titled compound (0.030 g, 9%) as pale yellow crystals.

mp. 269.5-270.0° C. $^1$H-NMR (CDCl$_3$) δ: 3.49 (3H, s), 7.66-7.80 (3H, m), 8.57-8.60 (1H, m), 8.64(1H, d, J=5.2 Hz), 9.20 (1H, d, J=5.2 Hz). IR(KBr): 1662, 1570, 1539, 1425, 1307, 1290, 1140, 1060, 993, 758 cm$^{-1}$. Elemental Analysis for $C_{13}H_9N_3O_3S_2$ Calcd. C, 48.89; H, 2.84; N, 13.16. Found C, 48.68; H, 2.77; N, 13.01.

Reference Example 104

2-Cyano-6-methylthiopyrazine

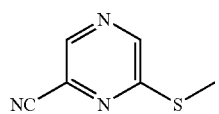

A mixture of 2-chloro-6-cyanopyrazine (1.40 g, 10.0 mmol) sodium thiomethoxide (0.78 g, 11.0 mmol) and THF (100 ml) was refluxed for 2 hrs. The reaction mixture was combined with ethyl acetate and water. The organic layer was washed with saturated brine and dried over magnesium sulfate. The solvent was evaporated to give the titled compound (1.25 g, 83%) as pale yellow crystals.

$^1$H-NMR (CDCl$_3$) δ: 2.61 (3H, s), 8.49 (1H, s), 8.60 (1H, s) IR(KBr): 2241, 1670, 1521, 1390, 1190, 1167, 1138, 1108, 887, 734 cm$^{-1}$.

Example 287

2-[6-(Methylthio)-2-pyrazinyl]-4H-1,3-benzothiazine-4-one

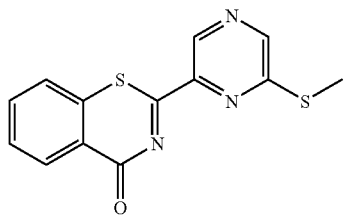

2-Cyano-6-methylthiopyrazine (0.80 g, 5.29 mmol) and methyl thiosalicylate (1.34 g, 7.94 mmol) were dissolved in toluene (100 ml), and triethylamine (1.48 ml, 10.6 mmol) was added thereto. The mixture was refluxed for 18 hrs. The solvent was evaporated, and the residue was recrystallized from ethanol to give the tilted compound (0.35 g, 23%) as pale yellow crystals.

mp. 202.4-202.9° C. $^1$H-NMR (CDCl$_3$) δ: 2.73 (3H, s), 7.60-7.74 (3H, m), 8.55-8.58 (1H, m), 8.67 (1H, s), 9.29 (1H, s). IR(KBr): 1649, 1570, 1527, 1439, 1292, 1124, 1095, 1062, 1003, 916, 733 cm$^{-1}$. Elemental Analysis for $C_{13}H_9N_3OS_2$ Calcd. C, 54.34; H, 3.16; N, 14.62. Found C, 54.28; H, 3.09; N, 14.55.

Example 288

2-[6-(Methylsulfinyl)-2-pyrazinyl]-4H-1,3-benzothiazine-4-one

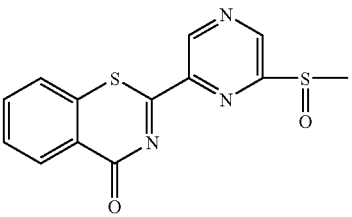

2-[6-(Methylthio)-2-pyrazinyl]-4H-1,3-benzothiazine-4-one (0.14 g, 0.50 mmol) was dissolved in chloroform (50 ml), and a solution of 3-chloroperbenzoic acid (ca. 77%, 0.11 g, 0.50 mmol) was added dropwise thereto. The mixture was stirred at room temperature for 1 hr. The solvent was evaporated, and the residue was recrystallized from ethanol to give the titled compound (0.12 g, 79%) as pale yellow crystals.

mp. 228.5-230.5° C. $^1$H-NMR (CDCl$_3$) δ: 3.06 (3H, s), 7.60-7.63 (1H, m), 7.67-7.78 (2H, m), 8.56-8.59 (1H, m), 9.47 (1H, s), 9.81 (1H, s). IR(KBr): 1658, 1570, 1529, 1288, 1059, 1010, 968, 736 cm$^{-1}$. Elemental Analysis for $C_{13}H_9N_3O_2S_2$ Calcd. C, 51.47; H, 2.99; N, 13.85. Found C, 51.33; H, 3.04; N, 13.95.

Example 289

2-[6-(Methylsulfonyl)-2-pyrazinyl]-4H-1,3-benzothiazine-4-one

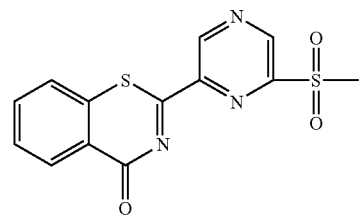

2-[6-(Methylthio)-2-pyrazinyl]-4H-1,3-benzothiazine-4-one (0.14 g, 1.0 mmol) was dissolved in chloroform (30 ml), and a solution of 3-chloroperbenzoic acid (ca. 77%, 0.22 g, 0.66 mmol) was added dropwise thereto. The mixture was stirred at room temperature for 3 hr. The solvent was evaporated, and the residue was recrystallized from ethanol to give the titled compound (0.040 g, 25%) as pale yellow crystals.

mp. 232.0-233.0° C. $^1$H-NMR (CDCl$_3$) δ: 3.40 (3H, s), 7.63-7.80 (3H, m), 8.57-8.60 (1H, m), 9.52 (1H, s), 9.96 (1H, s). IR(KBr): 1660, 1572, 1531, 1331, 1290, 1091, 1014, 978, 740 cm$^{-1}$. Elemental Analysis for C$_{13}$H$_9$N$_3$O$_3$S$_2$ Calcd. C, 48.89; H, 2.84; N, 13.16. Found C, 48.83; H, 2.78; N, 13.29.

Reference Example 105

2-Cyano-6-dimethylaminopyrazine

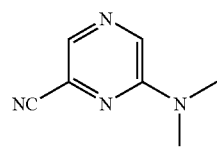

2-Chloro-6-cyanopyrazine (0.85 g, 6.09 mmol) and 1.67 N dimethylamine in acetonitrile (4.00 ml, 6.70 mmol) were added to THF (100 ml), and the mixture was stirred at room temperature for 2 hrs. The reaction mixture was combined with ethyl acetate and water. The organic layer was washed with saturated brine and dried over anhydrous magnesium sulfate. The solvent was evaporated to give the titled compound (0.50 g, 55%) as pale yellow crystals.

$^1$H-NMR (CDCl$_3$) δ: 3.16 (6H, s), 8.07 (1H, s), 8.18 (1H, s) IR(KBr): 2233, 1738, 1680, 1591, 1521, 1367, 1242, 1150, 993, 846 cm$^{-1}$.

Example 290

2-[6-(Dimethylamino)-2-pyrazinyl]-4H-1,3-benzothiazine-4-one

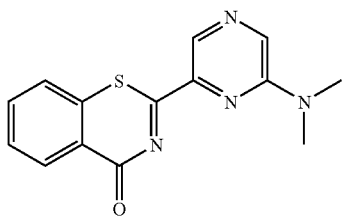

2-Cyano-6-dimethylaminopyrazine (0.50 g, 3.37 mmol) and methyl thiosalicylate (1.14 g, 6.75 mmol) was dissolved in toluene (100 ml), and triethylamine (1.42 ml, 10.1 mmol) was added thereto. The mixture was refluxed for 18 hrs. The solvent was evaporated, and the residue was recrystallized from ethanol to give the titled compound (0.31 g, 32%) as pale yellow crystals.

mp. 248.0-249.0° C. $^1$H-NMR (CDCl$_3$) δ: 3.25 (6H, s), 7.57-7.68 (3H, m), 8.24 (1H, m), 8.53-8.56 (1H, m), 8.90 (1H, s). IR(KBr): 1657, 1581, 1570, 1537, 1435, 1290, 1236, 1093, 989, 756 cm$^{-1}$. Elemental Analysis for C$_{14}$H$_{12}$N$_4$OS Calcd. C, 59.14; H, 4.25; N, 19.70. Found C, 59.01; H, 4.17; N, 19.54.

Reference Example 106 tert-Butyl [methyl(6-cyano-2-pyrazinyl)amino]acetate

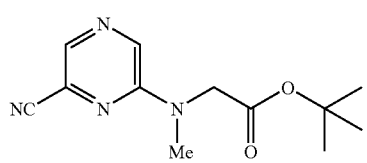

2-Chloro-6-cyanopyrazine (2.09 g, 15.0 mmol), sarcosine tert-butyl ester hydrochloride salt (2.72 g, 15.0 mmol) and triethylamine (2.38 ml, 17.0 mmol) were added to DMF (30 ml), and the mixture was stirred at room temperature for 18 hrs. The reaction mixture was combined with ethyl acetate and water. The organic layer was washed with saturated brine and dried over anhydrous magnesium sulfate. The solvent was evaporated to give the titled compound (1.00 g, 27%) as pale yellow crystals.

$^1$H-NMR (CDCl$_3$) δ: 1.46 (9H, s), 3.21 (3H, s), 4.18 (2H, s), 8.16 (1H, s), 8.23 (1H, s). IR(KBr): 2233, 1734, 1576, 1521, 1419, 1367, 1226, 1153, 993, 842 cm$^{-1}$.

Example 291 tert-Butyl {methyl[6-(4-oxo-4H-1,3-benzothiazin-2-yl)-2-pyrazinyl]amino}acetate

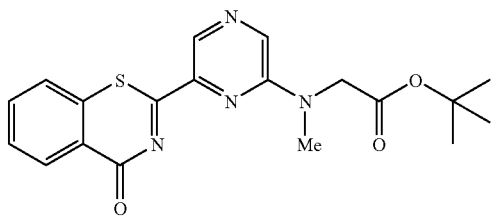

tert-Butyl [methyl(6-cyano-2-pyrazinyl)amino]acetate (1.00 g, 4.03 mmol) and methyl thiosalicylate (1.36 g, 8.06 mmol) were dissolved in toluene (50 ml), and triethylamine (1.70 ml, 12.1 mmol) was added thereto. The mixture was refluxed for 18 hrs. The solvent was evaporated, and the residue was recrystallized from ethanol to give the titled compound (0.41 g, 26%) as pale yellow crystals.

mp. 189.0-190.5° C. $^1$H-NMR (CDCl$_3$) δ: 1.47 (9H, s), 3.30 (3H, s), 4.29 (2H, s) 7.56-7.71 (3H, m), 8.30 (1H, s), 8.55 (1H, d, J=7.6 Hz), 8.99 (1H, s). IR(KBr): 1736, 1660, 1570, 1537, 1439, 1369, 1294, 1224, 1097, 734 cm$^{-1}$. Elemental Analysis for C$_{19}$H$_{20}$N$_4$O$_3$S Calcd. C, 59.36; H, 5.24; N, 14.57. Found C, 59.21; H, 5.13; N, 14.38.

Example 292

{Methyl[6-(4-oxo-1,3-benzothiazin-2-yl)-2-pyrazinyl]amino}acetic acid

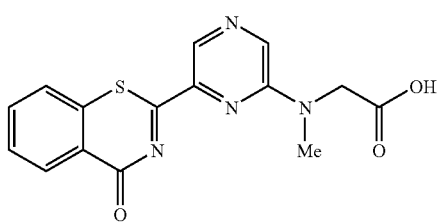

tert-Butyl {methyl[6-(4-oxo-4H-1,3-benzothiazin-2-yl)-2-pyrazinyl]amino}acetate (0.20 g, 0.52 mmol) was dissolved in trifluoroacetic acid (5 ml), and the mixture was stirred for 0.5 hr. Diisopropyl ether was added thereto. The obtained precipitates were recrystallized from ethanol to give the titled compound (0.15 g, 87%) as pale yellow crystals mp. 283.0° C. (decomposed) $^1$H-NMR (DMSO-d$_6$) δ: 3.24 (3H, s), 4.43 (2H, s), 7.70-7.75 (1H, m), 7.79-7.88 (2H, m), 8.35 (1H, d, J=7.3 Hz), 8.67 (1H, s) 12.83 (1H, br s). IR(KBr): 3082, 2513, 1703, 1653, 1587, 1572, 1541, 1435, 1421, 1294, 1271, 999, 752 cm$^{-1}$. Elemental Analysis for C$_{15}$H$_{12}$N$_4$O$_3$S Calcd. C, 54.87; H, 3.68; N, 17.06. Found C, 54.67; H, 3.54; N, 16.89.

Reference Example 107 tert-Butyl [methyl(6-cyano-2-pyrimidinyl)amino]acetate

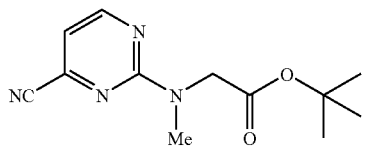

2-Chloro-6-cyanopyrimidine (1.45 g, 10.4 mmol), sarcosine tert-butyl ester hydrochloric acid (1.89 g, 10.4 mmol) and triethylamine (1.60 ml, 11.4 mmol) were added to DMF (30 ml), and the mixture was stirred at room temperature for 18 hrs. The reaction mixture was combined with ethyl acetate and water. The organic layer was washed with saturated brine and dried over anhydrous magnesium sulfate. The solvent was evaporated to give the titled compound (1.99 g, 77%) as pale yellow crystals.

$^1$H-NMR (CDCl$_3$) δ: 1.47 (9H, s), 3.24 (3H, d, J=5.5 Hz), 4.22 (2H, d, J=8.7 Hz), 6.80 (1H, d, J=4.7 Hz), 8.43-8.51 (1H, m). IR(KBr): 2237, 1736, 1574, 1537, 1410, 1365, 1226, 1153, 1033, 815 cm$^{-1}$.

Example 293 tert-Butyl {methyl[6-(4-oxo-4H-1,3-benzothiazin-2-yl)-2-pyrimidinyl]amino}acetate

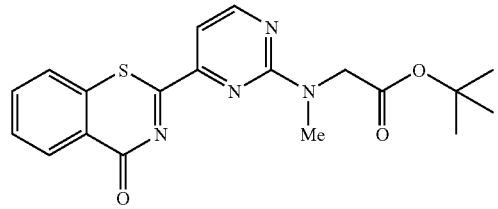

tert-Butyl [methyl(6-cyano-2-pyrimidinyl)amino]acetate (1.63 g, 6.56 mmol) and methyl thiosalicylate (3.31 g, 19.7 mmol) were dissolved in toluene (50 ml), and triethylamine (2.76 ml, 19.7 mmol) was added thereto. The mixture was refluxed for 18 hrs. The solvent was evaporated, and the residue was recrystallized from ethanol to give the titled compound (1.20 g, 39%) as pale yellow crystals.

mp. 186.5-188.0° C. $^1$H-NMR (CDCl$_3$) δ: 1.47 (9H, s), 3.36 (3H, s), 4.33 (2H, s), 7.60-7.73 (4H, m), 8.53-8.61 (2H, m). IR(KBr): 1738, 1660, 1568, 1539, 1408, 1365, 1294, 1209, 1153, 1097, 734 cm$^{-1}$. Elemental Analysis for C$_{19}$H$_{20}$N$_4$O$_3$S Calcd. C, 59.36; H, 5.24; N, 14.57. Found C, 59.17; H, 5.08; N, 14.39.

Example 294

{Methyl[6-(4-oxo-4H-1,3-benzothiazin-2-yl)-2-pyrimidinyl]amino}acetic acid

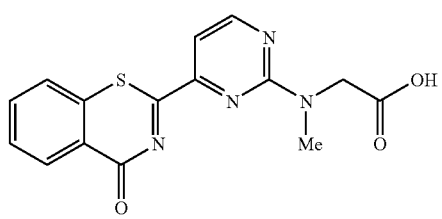

tert-Butyl {methyl[6-(4-oxo-4H-1,3-benzothiazin-2-yl)-2-pyrimidinyl]amino}acetate (0.20 g, 0.52 mmol) was dissolved in trifluoroacetic acid (5 ml), and the mixture was stirred for 0.5 hr. Diisopropyl ether was added thereto. The obtained crystals were recrystallized from ethanol to give the titled compound (0.15 g, 87%) as pale yellow crystals.

mp. 215.0° C. (decomposed) $^1$H-NMR (DMSO-d$_6$) δ: 3.27 (3H, d, J=19.4 Hz), 4.40 (2H, d, J=14.6 Hz), 7.43 (1H, d, J=4.9 Hz), 7.72-7.77 (1H, m), 7.81-7.93 (2H, m), 8.35 (1H, d, J=7.3 Hz), 8.67-8.72 (1H, m), 12.73 (1H, br s). IR(KBr): 3082, 2515, 1703, 1653, 1589, 1572, 1541, 1435, 1421, 1294, 1271, 752 cm$^{-1}$. Elemental Analysis for C$_{15}$H$_{12}$N$_4$O$_3$S Calcd. C, 54.87; H, 3.68; N, 17.06. Found C, 54.61; H, 3.50; N, 16.89.

Reference Example 108 tert-Butyl [(6-cyano-2-pyrimidinyl)amino]acetate

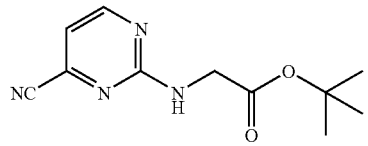

2-Chloro-6-cyanopyrimidine (2.09 g, 15.0 mmol), glycine tert-butyl ester hydrochloride salt (2.52 g, 15.0 mmol) and triethylamine (2.38 ml, 17.0 mmol) were dissolved in DMF (30 ml), and the mixture was stirred at room temperature for 18 hrs. The reaction mixture was combined with ethyl acetate and water. The organic layer was washed with saturated brine and dried over anhydrous magnesium sulfate. The solvent was evaporated to give the titled compound (1.07 g, 45%) as pale yellow crystals.

$^1$H-NMR (CDCl$_3$) δ: 1.49 (9H, s), 4.08 (2H, d, J=5.6 Hz), 5.90 (1H, br s), 6.88 (1H, d, J=4.7 Hz), 8.46 (1H, d, J=4.7 Hz). IR(KBr): 3261, 2984, 2243, 1734, 1601, 1570, 1535, 1417, 1367, 1228, 1155, 848, 733 cm$^{-1}$.

Example 295 tert-Butyl {[6-(4-oxo-4H-1,3-benzothiazin-2-yl)-2-pyrimidinyl]amino}acetate

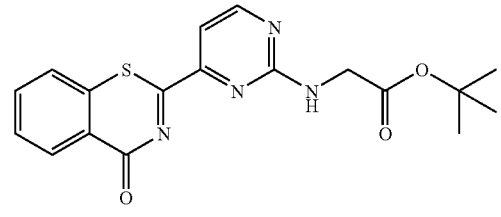

tert-Butyl [(6-cyano-2-pyrimidinyl)amino]acetate (1.00 g, 4.03 mmol) and methyl thiosalicylate (2.34 g, 13.9 mmol) were dissolved in toluene (50 ml), and triethylamine (1.95 ml, 13.9 mmol) was added thereto. The mixture was refluxed for 18 hrs. The solvent was evaporated, and the residue was recrystallized from ethanol to give the titled compound (1.03 g, 60%) as pale yellow crystals.

mp. 247.0-248.0° C. $^1$H-NMR (CDCl$_3$) δ: 1.51 (9H, s), 4.20 (2H, d, J=5.5 Hz), 5.84 (1H, br s), 7.61-7.74 (4H, m), 8.53-8.57 (2H, m). IR(KBr): 3261, 2976, 1741, 1651, 1591, 1568, 1531, 1408, 1219, 1143, 1095, 733 cm$^{-1}$. Elemental Analysis for C$_{18}$H$_{18}$N$_4$O$_3$S Calcd. C, 58.36; H, 4.90; N, 15.12. Found C, 58.13; H, 4.77; N, 14.98.

Example 296

{[6-(4-Oxo-4H-1,3-benzothiazin-2-yl)-2-pyrimidinyl]amino}acetic acid

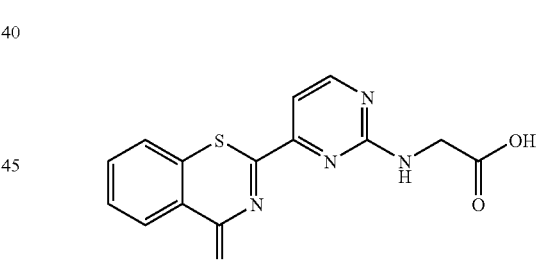

tert-Butyl {[6-(4-oxo-4H-1,3-benzothiazin-2-yl)-2-pyrimidinyl]amino}acetate (0.20 g, 0.54 mmol) was dissolved in trifluoroacetic acid (5 ml), and the mixture was stirred for 0.5 hr. Diisopropyl ether was added thereto. The obtained precipitates were recrystallized from ethanol to give the titled compound (0.13 g, 75%) as pale yellow crystals mp. 283.0-284.0° C. $^1$H-NMR (DMSO-d$_6$) δ: 4.04 (2H, d, J=12.3 Hz), 7.43 (1H, d, J=4.8 Hz), 7.75 (1H, t, J=6.9 Hz), 7.85 (1H, t, J=7.6 Hz), 7.98 (1H, br s), 8.36 (1H, d, J=7.4 Hz), 8.64 (1H, d, J=4.8 Hz), 12.58 (1H, br s). IR(KBr): 3254, 2995, 2567, 1730, 1705, 1653, 1603, 1568, 1537, 1437, 1425, 1398, 1294, 1275, 1095, 823, 752 cm$^{-1}$. Elemental Analysis for C$_{14}$H$_{10}$N$_4$O$_3$S Calcd. C, 53.50; H, 3.21; N, 17.82. Found C, 53.67; H, 3.10; N, 17.89.

Reference Example 109

2-Cyano-6-[2-(dimethylamino)ethylthio]pyrazine

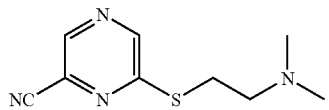

2-Dimethylaminoethanethiol hydrochloride salt (1.46 g, 10.0 mmol) and sodium hydride (60% in oil, 0.88 g, 22.0 mmol) were added to THF (50 ml), and 2-chloro-6-cyanopyrazine (1.40 g, 10.0 mmol) was added thereto. The mixture was stirred at room temperature for 18 hrs. The reaction mixture was combined with ethyl acetate and water. The organic layer was washed with saturated brine and dried over anhydrous magnesium sulfate. The solvent was evaporated, and the residue was recrystallized from n-hexane-ethyl acetate to give the titled compound (1.00 g, 48%) as pale yellow crystals.

$^1$H-NMR (CDCl$_3$) δ: 2.32 (6H, s), 2.62-2.67 (2H, m), 3.31-3.38 (2H, m), 8.48 (1H, s), 8.58 (1H, s). IR(KBr): 2233, 1576, 1549, 1456, 1143, 794 cm$^{-1}$.

Example 297

2-(6-{[2-Dimethylamino]ethyl}thio)-2-pyrazinyl]-4H-1,3-benzothiazine-4-one

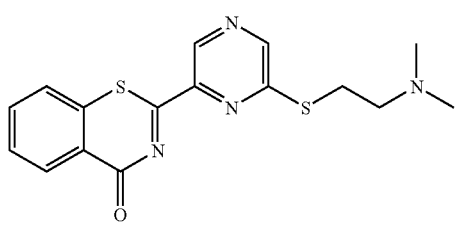

2-Cyano-6-[2-(dimethylamino)ethylthio]pyrazine (1.00 g, 4.80 mmol) and methyl thiosalicylate (1.61 g, 9.60 mmol) were dissolved in toluene (50 ml), and triethylamine (1.70 ml, 12.0 mmol) was added thereto. The mixture was refluxed for 18 hrs. The solvent was evaporated, and the residue was recrystallized from ethanol to give the titled compound (0.45 g, 27%) as pale yellow crystals.

mp. 160.5° C. (decomposed) $^1$H-NMR (CDCl$_3$) δ: 2.38 (6H, s), 2.77 (2H, t, J=6.9 Hz), 3.47 (2H, t, J=6.9 Hz) 7.59-7.72 (3H, m), 8.55-8.58 (1H, m), 8.65 (1H, s), 9.29 (1H, s). IR(KBr): 1655, 1572, 1537, 1435, 1286, 1091, 912, 744 cm$^{-1}$. Elemental Analysis for C$_{16}$H$_{16}$N$_4$OS$_2$ Calcd. C, 55.79; H, 4.68; N, 16.27. Found C, 55.40; H, 4.50; N, 16.08.

Reference Example 110

4-Chloro-2-cyanopyridine

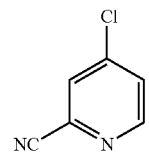

4-Chloropyridine N-oxide (7.53 g, 58.1 mmol) and N,N-dimethylcarbamoyl chloride (9.36 g, 87.0 mmol) were added to acetonitrile (200 ml), and trimethylsilyl cyanide (11.5 g, 116 mmol) was added dropwise thereto. The mixture was stirred at room temperature for 18 hrs. The reaction mixture was combined with ethyl acetate and water. The organic layer was successively washed with saturated aqueous sodium hydrogen carbonate solution and saturated brine and dried over magnesium sulfate. The solvent was evaporated, and the residue was subjected to a silica gel (200 g) column chromatography. The fractions eluted with n-hexane-ethyl acetate (3:1, v/v) were collected, concentrated to give the titled compound (8.05 g, 99%) as a pale yellow oil.

$^1$H-NMR (CDCl$_3$) δ: 7.54-7.56 (1H, m), 7.72(1H, s), 8.63 (1H, d, J=5.3 Hz). IR(KBr): 2239, 1568, 1549, 1462, 1379, 1288, 1215, 844, 704 cm$^{-1}$.

Reference Example 111

2-Cyano-4-methylthiopyridine

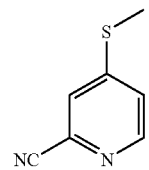

4-Chloro-2-cyanopyridine (2.18 g, 15.7 mmol) and sodium thiomethoxide (2.20 g, 31.4 mmol) were dissolved in THF (100 ml), and the mixture was refluxed for 2 hrs. The reaction mixture was combined with ethyl acetate and water. The organic layer was washed with saturated brine and dried over anhydrous magnesium sulfate. The solvent was evaporated to give the titled compound (2.36 g, 99%) as pale yellow crystals.

$^1$H-NMR (CDCl$_3$) δ: 2.53 (3H, s), 7.25-7.27 (1H, m), 7.45(1H, s), 8.46 (1H, d, J=5.3 Hz). IR(KBr): 2233, 1574, 1537, 1462, 1386, 1292, 1099, 987, 962, 844 cm$^{-1}$.

Example 298

2-[4-(Methylthio)-2-pyridyl]-4H-1,3-benzothiazine-4-one

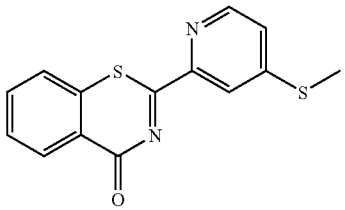

2-Cyano-4-methylthiopyridine (2.36 g, 15.7 mmol) and methyl thiosalicylate (5.28 g, 31.4 mmol) were dissolved in toluene (100 ml), and triethylamine (9.9 ml, 70.7 mmol) was added thereto. The mixture was refluxed for 18 hrs. The solvent was evaporated, and the residue was recrystallized from ethanol to give the titled compound (3.00 g, 68%) as pale yellow crystals.

mp. 213.0-214.0° C. $^1$H-NMR (CDCl$_3$) δ: 2.59 (3H, s), 7.30-7.32 (1H, m), 7.62-7.70 (3H, m), 8.34 (1H, s), 8.47-8.49 (1H, m), 8.54-8.55 (1H, m). IR(KBr): 1651, 1570, 1531, 1456, 1296, 1277, 1255, 1240, 1101, 1066, 831, 734 cm$^{-1}$. Elemental Analysis for C$_{14}$H$_{10}$N$_2$OS$_2$ Calcd. C, 58.72; H, 3.52; N, 9.78. Found C, 58.66; H, 3.39; N, 9.55.

Example 299

2-[4-(Methylsulfinyl)-2-pyridyl]-4H-1,3-benzothiazine-4-one

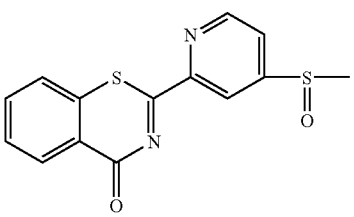

2-[4-(Methylthio)-2-pyridyl]-4H-1,3-benzothiazine-4-one (0.28 g, 1.00 mmol) was dissolved in chloroform (50 ml), and a solution of 3-chloroperbenzoic acid (Ca. 77%, 0.23 g, 1.00 mmol) in chloroform (10 ml) was added dropwise thereto. The mixture was stirred at room temperature for 1 hr. The solvent was evaporated, and the residue was recrystallized from ethanol to give the titled compound (0.23 g, 77%) as pale yellow crystals.

mp. 205.0-206.0° C. $^1$H-NMR (CDCl$_3$) δ: 2.87 (3H, s), 7.63-7.73 (3H, m), 8.04-8.07 (1H, m), 8.58-8.59 (1H, m), 8.96 (1H, d, J=4.9 Hz). IR(KBr): 1657, 1570, 1529, 1292, 1236, 1062, 1030, 914, 723 cm$^{-1}$. Elemental Analysis for C$_{14}$H$_{10}$N$_2$O$_2$S$_2$ Calcd. C, 55.61; H, 3.33; N, 9.26. Found C, 55.55; H, 3.04; N, 9.05.

Example 300

2-[4-(Methylsulfonyl)-2-pyridyl]-4H-1,3-benzothiazine-4-one

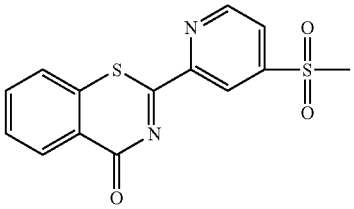

2-[4-(Methylthio)-2-pyridyl]-4H-1,3-benzothiazine-4-one (0.28 g, 1.00 mmol) was dissolved in chloroform (30 ml), and a solution of 3-chloroperbenzoic acid (ca. 77%, 0.46 g, 2.00 mmol) in chloroform (10 ml) was added dropwise thereto. The mixture was stirred at room temperature for 3 hrs. The solvent was evaporated, and the residue was recrystallized from ethanol to give the titled compound (0.14 g, 45%) as pale yellow crystals.

mp. 300.0-301.0° C. $^1$H-NMR (DMSO-d$_6$) δ: 3.46 (3H, s), 7.74-7.79 (1H, m), 7.84-7.87 (1H, m), 7.84-7.87 (1H, m), 8.27-8.29 (1H, m), 8.38-8.40 (1H, m), 8.71 (1H, s), 9.15 (1H, d, J=4.9 Hz). IR(KBr): 1651, 1570, 1525, 1439, 1296, 1143, 1089, 981, 783 cm$^{-1}$. Elemental Analysis for C$_{14}$H$_{10}$N$_2$O$_3$S$_2$ Calcd. C, 52.82; H, 3.17; N, 8.80. Found C, 52.83; H, 3.88; N, 8.56.

Reference Example 112

3-Pyridyl)propyl acetate

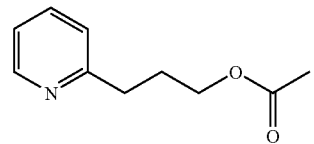

2-Pyridinepropanol (2.0 g, 14.6 mmol) was dissolved in pyridine (5 ml), and acetic anhydride (3.0 g, 29.2 mmol) was added thereto. The reaction mixture was stirred at room temperature for 2.5 hrs, and subjected to a silica gel (75 g) column chromatography. The fractions eluted with hexane-ethyl acetate (3:1, v/v) were collected and concentrated to give the titled compound (2.6 g, 99%).

$^1$H-NMR (CDCl$_3$) δ: 2.03 (3H, s), 2.11 (2H, m), 2.88 (2H, t, J=7.5 Hz), 4.12 (2H, t, J=6.3 Hz), 7.11-7.15 (2H, m), 7.61 (1H, t, J=7.8 Hz), 8.54 (1H, d, J=5.1 Hz).

Reference Example 113

3-(1-Oxide-2-pyridyl)propyl acetate

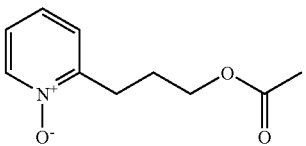

(3-Pyridyl)propyl acetate (2.6 g, 14.5 mmol) was dissolved in ethyl acetate (15 ml), and 3-chloroperbenzoic acid (ca. 77%, 3.7 g, 15.0 mmol) was added thereto. The reaction mixture was stirred at room temperature for 14 hrs and subjected to a silica gel (80 g) column chromatography. The fractions eluted with ethyl acetate-ethanol (3:1, v/v) were collected and concentrated to give the titled compound (2.8 g, 99%).

$^1$H-NMR (CDCl$_3$) δ: 2.05 (3H, s), 2.11 (2H, m), 3.01 (2H, t, J=7.5 Hz), 4.15 (2H, t, J=6.3 Hz), 7.13-7.27 (3H, m), 8.25 (1H, d, J=6.0 Hz).

Reference Example 114

3-(6-Cyano-2-pyridyl)propyl acetate

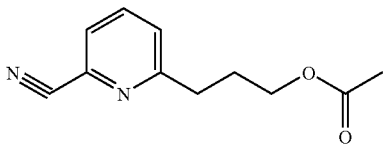

3-(1-Oxide-2-pyridyl)propyl acetate (2.8 g, 14.3 mmol) was dissolved in nitroethane (15 ml), and trimethylsilyl cyanide (2.9 g, 28.7 mmol) and N,N-dimethylcarbamoyl chloride (3.1 g, 28.6 mmol) were added thereto. The reaction mixture was stirred at room temperature for 39 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to a silica gel (50 g) column chromatography. The fractions eluted with hexane-ethyl acetate (3:1, v/v) were collected and concentrated to give the titled compound (2.5 g, 86%).

$^1$H-NMR (CDCl$_3$) δ: 2.05 (3H, s), 2.11 (2H, m), 2.92 (2H, t, J=7.5 Hz), 4.13 (2H, t, J=6.3 Hz), 7.38 (1H, d, J=7.8 Hz), 7.54 (1H, d, J=7.8 Hz), 7.74 (1H, t, J=7.8 Hz).

Example 301

3-[6-(4-Oxo-4H-1,3-benzothiazin-2-yl)-2-pyridyl]propyl acetate

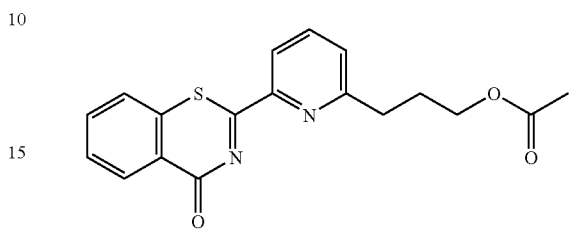

3-(6-Cyano-2-pyridyl)propyl acetate (1.5 g, 7.3 mmol) and methyl thiosalicylate (1.9 g, 11.0 mmol) were dissolved in toluene (5 ml), and triethylamine (2.1 ml, 15.1 mmol) was added thereto. The reaction mixture was refluxed for 16 hrs and kept at room temperature to precipitate crystals. The crystals were washed with toluene and recrystallized from ethanol to give the titled compound (1.4 g, 56%) as white crystals.

mp. 141.3-141.6° C. $^1$H-NMR (CDCl$_3$) δ: 2.07 (3H, s), 2.24 (2H, m), 3.01 (2H, t, J=7.2 Hz), 4.24 (2H, t, J=7.2 Hz), 7.39 (1H, d, J=7.5 Hz), 7.60-7.69 (3H, m), 7.81 (1H, t, J=7.7 Hz), 8.37 (1H, d, J=7.8 Hz), 8.55 (1H, d, J=7.8 Hz). IR(KBr): 1729, 1657, 1572, 1537, 1240 cm$^{-1}$. Elemental Analysis for $C_{18}H_{16}N_2O_3S$ Calcd. C, 63.51; H, 4.74; N, 8.23. Found C, 63.26; H, 4.47; N, 8.04.

Reference Example 115

6-(3-Hydroxypropyl)-2-pyridinecarbonitrile

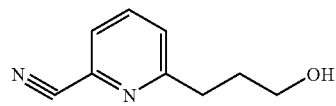

3-(6-Cyano-2-pyridyl)propyl acetate (3.0 g, 14.7 mmol) was dissolved in methanol (15 ml), and potassium carbonate (0.08 g, 0.58 mmol) was added thereto. The reaction mixture was stirred at room temperature for 22 hrs and concentrated to give the titled compound (2.2 g, 92%).

$^1$H-NMR (CDCl$_3$) δ: 1.94-2.08 (2H, m), 2.98 (2H, t, J=7.5 Hz), 3.71 (2H, t, J=6.2 Hz), 7.41 (1H, d, J=7.9 Hz), 7.55 (1H, d, J=7.0 Hz), 7.75 (1H, t, J=7.8 Hz).

Example 302

2-[6-(3-Hydroxypropyl)-2-pyridyl]-4H-1,3-benzothiazine-4-one

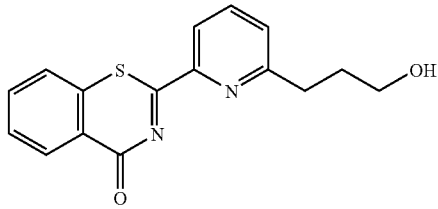

6-(3-Hydroxypropyl)-2-pyridinecarbonitrile (2.2 g, 13.6 mmol) and methyl thiosalicylate (3.7 g, 22.0 mmol) were dissolved in toluene (15 ml), and triethylamine (3.0 ml, 21.7 mmol) was added thereto. The reaction mixture was refluxed for 30 hrs and subjected to a silica gel (170 g) column chromatography. The fractions eluted with ethyl acetate were collected and concentrated to give the titled compound (0.61 g, 15%) as white crystals.

mp. 145.5-146.0° C. $^1$H-NMR (CDCl$_3$) δ: 2.05-2.18 (2H, m), 3.06 (2H, t, J=7.3 Hz), 3.79 (2H, q, J=7.6 Hz), 7.42 (1H, d, J=7.6 Hz), 7.60-7.69 (3H, m), 7.82 (1H, t, J=7.8 Hz), 8.38 (1H, d, J=7.8 Hz), 8.53 (1H, d, J=7.9 Hz). IR(KBr): 3520, 1643, 1572, 1534, 1306 cm$^{-1}$. Elemental Analysis for C$_{16}$H$_{14}$N$_2$O$_2$S Calcd. C, 64.41; H, 4.73; N, 9.39. Found C, 64.28; H, 4.70; N, 9.50.

Reference Example 116

Ethyl 5-(2-pyridyl)-4-pentenoate

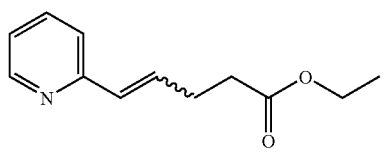

2-Pyridinecarbaldehyde (3.0 g, 28.0 mmol) and (4-ethoxy-4-oxobutyl)triphenylphosphonium (16.7 g, 36.5 mmol) were dissolved in 1,4-dioxane (60 ml), and a solution of potassium carbonate (5.8 g, 42.0 mmol) in water (6 ml) was added thereto. The reaction mixture was refluxed for 18 hrs and combined with ethyl acetate and water. The organic layer was washed with saturated brine and dried over anhydrous magnesium sulfate. The solvent was evaporated, and the residue was subjected to a silica gel. (100 g) column chromatography. The fractions eluted with hexane-ethyl acetate (4:1, v/v) were collected and concentrated to give Z-form of the titled compound (2.3 g, 40%). And the fractions eluted with hexane-ethyl acetate (2:1, v/v) were collected and concentrated to give E-form of the titled compound (1.2 g, 21%)

(Z-form)

$^1$H-NMR (CDCl$_3$) δ: 1.24 (3H, t, J=7.2 Hz), 2.49 (2H, t, J=7.2 Hz), 2.96 (2H, m), 4.12 (2H, q, J=7.2 Hz), 5.86 (1H, dt, J=7.2, 11.8 Hz), 6.46 (1H, d, J=11.8 Hz), 7.11 (1H, m), 7.23 (1H, t, J=7.8 Hz), 7.63 (1H, t, J=7.8 Hz), 8.60 (1H, d, J=5.7 Hz).

(E-form)

$^1$H-NMR (CDCl$_3$) δ: 1.26 (3H, t, J=7.2 Hz), 2.34-2.63 (4H, m), 4.12 (2H, q, J=7.2 Hz), 6.52 (1H, d, J=15.9 Hz), 6.73 (1H, dt, J=6.6, 15.9 Hz), 7.11 (1H, m), 7.24 (1H, t, J=7.8 Hz), 7.60 (1H, t, J=7.8 Hz), 8.53 (1H, d, J=5.7 Hz).

Reference Example 117

Ethyl 5-(2-pyridyl)valerate

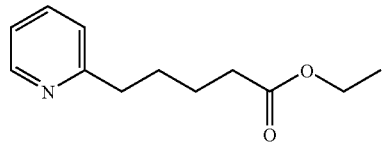

Ethyl 5-(2-pyridyl)-4-pentenoate (1.7 g, 8.2 mmol) was dissolved in ethanol (20 ml), and 10% palladium-carbon (0.22 g) and a solution of ammonium formate (3.1 g, 49.0 mmol) in water (5 ml) were added thereto. The reaction mixture was refluxed for 2 hrs. Palladium-carbon was filtered off, and the reaction mixture was combined with ethyl acetate and water. The organic layer was washed with saturated brine and dried over anhydrous magnesium sulfate. The solvent was evaporated to give the titled compound (1.6 g, 94%).

$^1$H-NMR (CDCl$_3$) δ: 1.24 (3H, t, J=7.2 Hz), 1.66-1.81 (4H, m) 2.31 (2H, t, J=7.5 Hz), 2.81 (2H, t, J=7.2 Hz), 4.12 (2H, q, J=7.2 Hz), 7.08-7.18 (2H, m), 7.59 (1H, t, J=7.8 Hz), 8.52 (1H, d, J=6.0 Hz).

Reference Example 118

Ethyl 5-(1-oxide-2-pyridyl)valerate

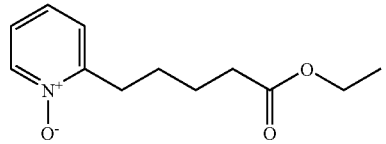

Ethyl 5-(2-pyridyl)valerate (0.75 g, 3.2 mmol) was dissolved in ethyl acetate (5 ml), and 3-chloroperbenzoic acid (0.72 g, 3.3 mmol) was added thereto. The reaction mixture was stirred at room temperature for 15 hrs and subjected to a silica gel (40 g) column chromatography. The fractions eluted with ethyl acetate-ethanol (3:1, v/v) were collected and concentrated to give the titled compound (0.51 g, 64%).

$^1$H-NMR (CDCl$_3$) δ: 1.25 (3H, t, J=7.2 Hz), 1.68-1.84 (4H, m), 2.37 (2H, t, J=7.2 Hz), 2.95 (2H, t, J=7.2 Hz), 4.13 (2H, q, J=7.2 Hz), 7.11-7.26 (3H, m), 8.25 (1H, d, J=6.0 Hz).

Reference Example 119

Ethyl 5-(6-cyano-2-pyridyl)valerate

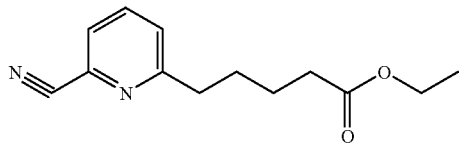

Ethyl 5-(1-oxide-2-pyridyl)valerate (0.49 g, 2.2 mmol) was dissolved in nitroethane (4 ml), and trimethylsilyl cyanide (0.45 g, 4.5 mmol) and N,N-dimethylcarbamoyl chloride (0.48 g, 4.5 mmol) were added thereto. The reaction mixture was stirred at room temperature for 18 hrs and combined with ethyl acetate and water. The organic layer was washed with saturated aqueous sodium hydrogen carbonate solution and saturated brine and dried over anhydrous magnesium sulfate. The solvent was evaporated, and the residue was subjected to a silica gel (20 g) column chromatography. The fractions eluted with hexane-ethyl acetate (3:1, v/v) were collected and concentrated to give the titled compound (0.35 g, 69%).

$^1$H-NMR (CDCl$_3$) δ: 1.25 (3H, t, J=7.2 Hz), 1.65-1.82 (4H, m), 2.32 (2H, t, J=7.2 Hz), 2.86 (2H, t, J=7.2 Hz), 4.13 (2H, q, J=7.2 Hz), 7.36 (1H, d, J=7.8 Hz), 7.52 (1H, d, J=7.8 Hz), 7.72 (1H, t, J=7.8 Hz).

Example 303

Ethyl 5-[6-(4-oxo-4H-1,3-benzothiazin-2-yl)-2-pyridyl]valerate

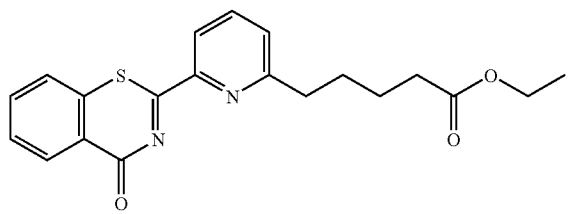

Ethyl 5-(6-cyano-2-pyridyl)valerate (0.34 g, 1.5 mmol) and methyl thiosalicylate (0.40 g, 2.4 mmol) were dissolved in toluene (2 ml), and triethylamine (0.43 ml, 3.1 mmol) was added thereto. The reaction mixture was refluxed for 14 hrs and subjected to a silica gel (25 g) column chromatography. The fractions eluted with hexane-ethyl acetate (3:1, v/v) were collected and concentrated. The residue was recrystallized from ethanol-hexane to give the titled compound (0.41 g, 76%) as white crystals.

mp. 87.0-88.0° C. $^1$H-NMR (CDCl$_3$) δ: 1.26 (3H, t, J=7.2 Hz), 1.47-1.93 (4H, m), 2.40 (2H, t, J=7.2 Hz), 2.94 (2H, t, J=7.5 Hz), 4.14 (2H, q, J=7.2 Hz), 7.38 (1H, d, J=7.5 Hz), 7.61-7.68 (3H, m), 7.80 (1H, t, J=7.8 Hz), 8.35 (1H, d, J=7.8 Hz), 8.55 (1H, d, J=7.8 Hz). IR(KBr): 1728, 1658, 1572, 1534, 1238 cm$^{-1}$. Elemental Analysis for C$_{20}$H$_{20}$N$_2$O$_3$S Calcd. C, 65.20; H, 5.47; N, 7.60. Found C, 65.10; H, 5.34; N, 7.58.

Example 304

5-[6-(4-Oxo-4H-1,3-benzothiazin-2-yl)-2-pyridyl]valeric acid

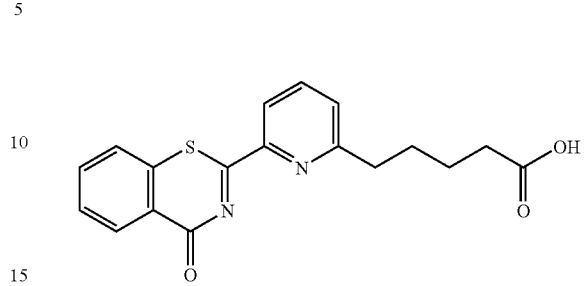

2-(Trimethylsilyl)ethyl 5-[6-(4-oxo-4H-1,3-benzothiazin-2-yl)-2-pyridyl]valerate (0.23 g, 0.52 mmol) was dissolved in N,N-dimethylformamide (2 ml), and 1.0 M tetrabutylammonium fluoride in tetrahydrofuran (1.3 ml, 1.3 mmol) was added thereto. The reaction mixture was stirred for 15 minutes and concentrated under reduced pressure. Trifluoroacetic acid (2.5 ml) was added to the residue, and the mixture was stirred at room temperature for 1 hr. The reaction mixture was subjected to a silica gel (25 g) column chromatography. The fractions eluted with hexane-ethyl acetate (3:1, v/v) were collected and concentrated. The residue was recrystallized from ethanol-acetone to give the titled compound (0.10 g, 55%) as white crystals.

mp. 161.9-162.3° C. $^1$H-NMR (DMSO-d$_6$) δ: 1.28-1.98 (4H, m), 2.47 (2H, t, J=7.2 Hz), 2.94 (2H, t, J=7.2 Hz), 7.37 (1H, d, J=7.8 Hz), 7.59-7.70 (3H, m), 7.79 (1H, t, J=7.8 Hz), 8.34 (1H, d, J=7.8 Hz), 8.55 (1H, d, J=6.9 Hz). IR(KBr): 3200, 1718, 1655, 1570, 1528, 1304 cm$^{-1}$. Elemental Analysis for C$_{18}$H$_{16}$N$_2$O$_3$S Calcd. C, 63.51; H, 4.74; N, 8.23. Found C, 63.45; H, 4.85; N, 8.49.

Reference Example 120

2-(Trimethylsilyl)ethyl 5-[6-(4-oxo-4H-1,3-benzothiazin-2-yl)-2-pyridyl]valerate

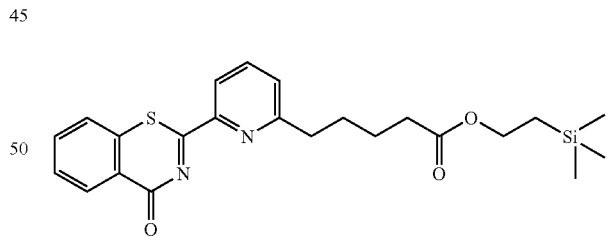

2-(Trimethylsilyl)ethyl 5-(6-cyano-2-pyridyl)valerate (1.0 g, 3.3 mmol) and methyl thiosalicylate (0.85 g, 5.0 mmol) were dissolved in toluene (4 ml), and triethylamine (0.85 ml, 8.4 mmol) was added thereto. The reaction mixture was refluxed for 10 hrs and subjected to a silica gel (75 g) column chromatography. The fractions eluted with hexane-ethyl acetate (4:1, v/v) were collected and concentrated to give the titled compound (0.38 g, 27%) as white crystals.

$^1$H-NMR (CDCl$_3$) δ: 0.03 (9H, s), 0.98 (2H, m), 1.74-1.93 (4H, m) 2.39 (2H, t, J=7.2 Hz), 2.94 (2H, t, J=7.2 Hz), 4.16 (2H, m), 7.37 (1H, d, J=7.0 Hz), 7.60-7.69 (3H, m), 7.79 (1H, t, J=7.8 Hz), 8.36 (1H, d, J=7.8 Hz), 8.55 (1H, d, J=7.8 Hz).

Reference Example 121

2-(Trimethylsilyl)ethyl 5-(6-cyano-2-pyridyl)valerate

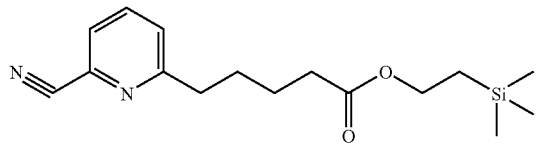

2-(Trimethylsilyl)ethyl 5-(1-oxide-2-pyridyl)valerate (0.94 g, 3.2 mmol) was dissolved in nitroethane (5 ml), and trimethylsilyl cyanide (0.64 g, 6.5 mmol) and N,N-dimethylcarbamoyl chloride (0.69 g, 6.4 mmol) were added thereto. The reaction mixture was stirred at room temperature for 15 hrs and combined with ethyl acetate and saturated aqueous sodium hydrogen carbonate solution. The organic layer was successively washed with saturated aqueous sodium hydrogen carbonate solution and saturated brine and dried over anhydrous magnesium sulfate. The solvent was evaporated, and the residue was subjected to silica gel (50 g) column chromatography. The fractions eluted with hexane-ethyl acetate (3:1, v/v) were collected and concentrated to give the titled compound (1.0 g, 86%).

$^1$H-NMR (CDCl$_3$) δ: 0.04 (9H, s), 0.98 (2H, m), 1.57-1.82 (4H, m), 2.33 (2H, t, J=7.2 Hz), 2.85 (2H, t, J=7.2 Hz), 4.16 (2H, m), 7.36 (1H, d, J=7.5 Hz), 7.52 (1H, d, J=7.5 Hz), 7.72 (1H, t, J=7.8 Hz).

Reference Example 122

2-(Trimethylsilyl)ethyl 5-(1-oxide-2-pyridyl)valerate

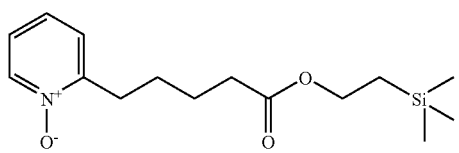

2-(Trimethylsilyl)ethyl 5-(2-pyridyl)valerate (1.1 g, 4.1 mmol) was dissolved in ethyl acetate (10 ml), and 3-chloroperbenzoic acid (ca. 77%, 1.1 g, 4.8 mmol) was added thereto. The reaction mixture was stirred at room temperature for 15 hrs and subjected to a silica gel (50 g) column chromatography. The fractions eluted with ethyl acetate-acetone (2:1, v/v) were collected and concentrated to give the titled compound (1.0 g, 83%).

$^1$H-NMR (CDCl$_3$) δ: 0.04 (9H, s), 0.98 (2H, m), 1.71-1.81 (4H, m), 2.36 (2H, t, J=7.2 Hz), 2.95 (2H, t, J=7.2 Hz), 4.17 (2H, m), 7.14-7.26 (3H, m), 8.26 (1H, d, J=6.0 Hz).

Reference Example 123

2-(Trimethylsilyl)ethyl 5-(2-pyridyl)valerate

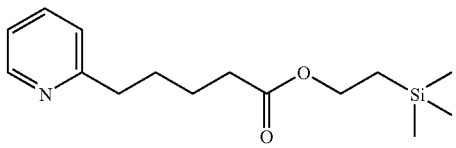

5-(2-Pyridyl)valeric acid (1.5 g, 8.4 mmol) was dissolved in N,N-dimethylformamide (25 ml), and trimethylsilylethanol (2.0 g, 16.7 mmol), WSC (3.2 g, 16.7 mmol) and HOBt (2.3 g, 16.7 mmol) were added thereto successively. The mixture was stirred at room temperature for 6 hrs. The solvent was evaporated, and the residue was combined with ethyl acetate and water. The organic layer was washed with saturated brine and dried over anhydrous magnesium sulfate. The solvent was evaporated, and the residue was subjected to a silica gel (60 g) column chromatography. The fractions eluted with hexane-ethyl acetate (2:1, v/v) were collected and concentrated to give the titled compound (1.1 g, 49%).

$^1$H-NMR (CDCl$_3$) δ: 0.03 (9H, s), 0.97 (2H, m), 1.67-1.81 (4H, m), 2.32 (2H, t, J=7.5 Hz), 2.81 (2H, t, J=7.5 Hz), 4.15 (2H, m), 7.07-7.15 (2H, m), 7.58 (1H, t, J=7.8 Hz), 8.52 (1H, d, J=5.4 Hz).

Reference Example 124

5-(2-Pyridyl)valeric acid

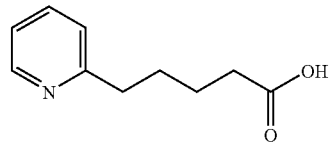

Ethyl 5-(2-pyridyl)valerate (3.6 g, 17.2 mmol) was dissolved in ethanol (12 ml), and 2 M aqueous sodium hydroxide solution (12.9 ml, 25.8 mmol) was added thereto. The reaction mixture was stirred at room temperature for 1.5 hrs. The solvent was evaporated, and the residue was combined with ethanol and filtered to remove the insolubles. The filtrate was concentrated to give the titled compound (2.5 g, 82%)

$^1$H-NMR (DMSO-d$_6$) δ: 1.17-1.72 (4H, m), 2.23 (2H, t, J=7.2 Hz), 2.72 (2H, t, J=7.2 Hz), 7.16-7.25 (2H, m), 7.68 (1H, t, J=7.8 Hz), 8.46 (1H, d, J=7.8 Hz).

Example 305

2-{6-[2-(1H-1,2,3,4-tetrazol-5-yl)ethyl]-2-pyridyl}-4H-1,3-benzothiazine-4-one

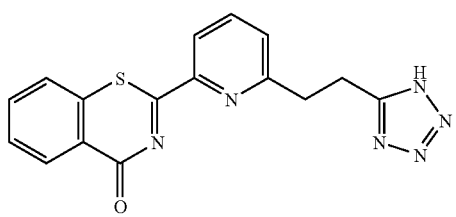

3-[6-(4-oxo-4H-1,3-benzothiazin-2-yl)-2-pyridyl]propionitrile (0.25 g, 0.85 mmol) and trimethylsilylazide (0.20 g, 1.7 mol) were dissolved in toluene (5 ml), and dibutyltin (IV) oxide (0.02 g, 0.08 mmol) was added thereto. The reaction mixture was refluxed for 48 hrs and kept at room temperature. The precipitated crystals were collected by filtration, washed with toluene and recrystallized from ethanol to give the titled compound (0.20 g, 68%) as white crystals.

mp. 156.6-157.0° C. $^1$H-NMR (DMSO-$d_6$) δ: 3.37-3.49 (4H, m), 7.67 (1H, d, J=7.6 Hz), 7.75 (1H, t, J=6.6 Hz), 7.84-7.89 (2H, m), 8.03 (1H, t, J=7.7 Hz), 8.20 (1H, d, J=7.6 Hz), 8.36 (1H, d, J=7.8 Hz), 16.10 (1H, bs). IR(KBr): 3119, 3057, 1658, 1620, 1589, 1523, 1439, 1311 cm$^{-1}$. Elemental Analysis for $C_{16}H_{12}N_6OS$ Calcd. C, 57.13; H, 3.60; N, 24.98. Found C, 57.31; H, 3.50; N, 24.75.

Example 306

3-[6-(4-Oxo-4H-1,3-benzothiazin-2-yl)-2-pyridyl]propionitrile

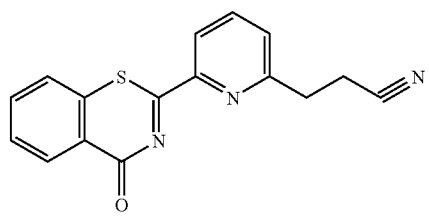

6-(2-Cyanoethyl)-2-pyridinecarbonitrile (0.28 g, 1.8 mmol) and methyl thiosalicylate (0.36 g, 2.1 mmol) were dissolved in toluene (2 ml), and triethylamine (0.37 ml, 2.7 mmol) was added thereto. The reaction mixture was refluxed for 6 hrs and kept at room temperature. The precipitated crystals were collected, washed with toluene and recrystallized from ethanol to give the titled compound (0.28 g, 54%) as white crystals.

mp. 156.6-157.0° C. $^1$H-NMR (CDCl$_3$) δ: 3.02 (2H, t, J=7.2 Hz), 3.29 (2H, t, J=7.2 Hz), 7.46 (1H, d, J=7.5 Hz), 7.61-7.71 (3H, m), 7.88 (1H, t, J=7.8 Hz), 8.44 (1H, d, J=7.8 Hz), 8.56 (1H, d, J=7.8 Hz). IR(KBr): 2247, 1659, 1574, 1537, 1439 cm$^{-1}$. Elemental Analysis for $C_{16}H_{11}N_3OS \cdot 0.5H_2O$ Calcd. C, 63.56; H, 4.00; N, 13.90. Found C, 63.81; H, 3.83; N, 13.79.

Reference Example 125

6-(2-Cyanoethyl)-2-pyridinecarbonitrile

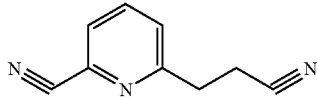

3-(1-Oxide-2-pyridyl)propionitrile (0.42 g, 2.8 mmol) was dissolved in nitroethane (4 ml), and trimethylsilyl cyanide (0.68 g, 6.9 mmol) and N,N-dimethylcarbamoyl chloride (0.74 g, 6.9 mmol) were added thereto. The reaction mixture was stirred at room temperature for 19 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to a silica gel (20 g) column chromatography. The fractions eluted with hexane-ethyl acetate (3:1, v/v) were collected and concentrated to give the titled compound (0.30 g, 67%).

$^1$H-NMR (CDCl$_3$) δ: 2.90 (2H, t, J=7.2 Hz), 3.19 (2H, t, J=7.2 Hz), 7.47 (1H, d, J=7.8 Hz), 7.62 (1H, d, J=7.8 Hz), 7.82 (1H, t, J=7.8 Hz).

Reference Example 126

3-(1-Oxide-2-pyridyl)propionitrile

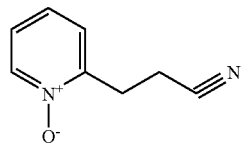

3-(2-Pyridyl)propionitrile (0.41 g, 3.1 mmol) was dissolved in ethyl acetate (5 ml), and 3-chloroperbenzoic acid (ca. 77%, 0.82 g, 3.7 mmol) was added thereto. The reaction mixture was stirred at room temperature for 21 hrs and subjected to a silica gel (20 g) column chromatography. The fractions eluted with ethyl acetate-acetone (1:1, v/v) were collected and concentrated to give the titled compound (0.42 g, 91%).

$^1$H-NMR (CDCl$_3$) δ: 2.98 (2H, t, J=6.9 Hz), 3.22 (2H, t, J=6.9 Hz), 7.23-7.39 (3H, m), 8.27 (1H, d, J=7.8 Hz).

Reference Example 127

3-(2-Pyridyl)propionitrile

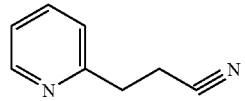

(E)-3-(2-Pyridyl)acrylonitrile (0.50 g, 3.8 mmol) was dissolved in 2-propanol (10 ml), and sodium borohydride (0.50 g, 13.2 mmol) was added thereto. The reaction mixture was stirred at 80° C. for 14 hrs and cooled under ice cooling condition, combined with water, concentrated to the half amount and extracted with ethyl acetate. The organic layer was washed with saturated brine and dried over anhydrous magnesium sulfate. The solvent was evaporated, and the residue was subjected to a silica gel (25 g) column chromatography. The fractions eluted with hexane-ethyl acetate (1:1, v/v) were collected and concentrated to give the titled compound (0.42 g, 82%).

$^1$H-NMR (CDCl$_3$) δ: 2.85 (2H, t, J=7.2 Hz), 3.13 (2H, t, J=7.2 Hz), 7.17-7.25 (2H, m), 7.66 (1H, t, J=7.8 Hz), 8.56 (1H, d, J=4.2 Hz).

Reference Example 128

3-(2-Pyridyl)acrylonitrile

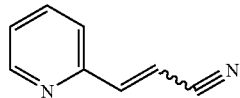

Sodium hydride (ca. 60%, 1.0 g, 28.1 mmol) was suspended in tetrahydrofuran (12 ml), and a solution of diethyl cyanoethylphosphonate (4.7 g, 26.8 mmol) in tetrahydrofuran (12 ml) was added thereto under ice cooling condition. The reaction mixture was stirred for 1 hr. A solution of 2-pyridinecarbaldehyde (2.7 g, 25.0 mmol) in tetrahydrofuran (10 ml) was added to the mixture, and the mixture was stirred at 0° C. to room temperature for 6 hrs. The reaction mixture was combined with water under ice cooling condition, concentrated to the half amount and extracted with ethyl acetate. The organic layer was washed with saturated brine and dried over magnesium sulfate. The solvent was evaporated, and the residue was subjected to a silica gel (100 g) column chromatography. The fractions eluted with hexane-ethyl acetate (2:1, v/v) were collected and concentrated to give Z-form of the titled compound (0.50 g, 15%). And simultaneously, the fractions eluted with hexane-ethyl acetate (3:2, v/v) were collected and concentrated to give E-form of the titled compound.

(Z-form)

$^1$H-NMR (CDCl$_3$) δ: 5.67 (1H, d, J=12.1 Hz), 7.28 (1H, d, J=12.1 Hz), 7.33 (1H, m), 7.78-7.86 (2H, m), 8.74 (1H, d, J=4.8 Hz).

(E-form)

$^1$H-NMR (CDCl$_3$) δ: 6.60 (1H, d, J=16.1 Hz), 7.30-7.35 (2H, m), 7.40 (1H, d, J=16.1 Hz), 7.74 (1H, t, J=7.8 Hz), 8.64 (1H, d, J=5.4 Hz).

Example 307

7-[6-(4-Oxo-4H-1,3-benzothiazin-2-yl)-2-pyridyl]heptanoic acid

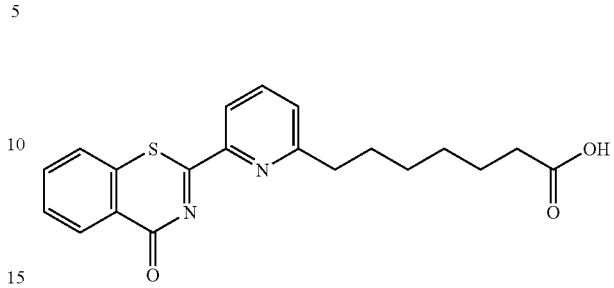

2-(Trimethylsilyl)ethyl 7-[6-(4-oxo-4H-1,3-benzothiazin-2-yl)-2-pyridyl]heptanoate (0.50 g, 1.1 mmol) was dissolved in N,N-dimethylformamide (4 ml), and 1.0 M tetrabutylammonium fluoride solution in tetrahydrofuran (2.6 ml, 2.6 mmol) was added thereto. The reaction mixture was stirred for 30 minutes and concentrated under reduced pressure. Trifluoroacetic acid (5 ml) was added to the residue, and the mixture was stirred at room temperature for 1 hr. The reaction mixture was subjected to a silica gel (40 g) column chromatography. The fractions eluted with hexane-ethyl acetate (1:1, v/v) were collected and concentrated. The residue was recrystallized from ethanol-hexane to give the titled compound (0.24 g, 61%) as white crystals.

mp. 148.6-150.6° C. $^1$H-NMR (DMSO-d$_6$) δ: 1.43-1.48 (4H, m), 1.69 (2H, t, J=7.2 Hz), 1.86 (2H, t, J=7.2 Hz), 2.38 (2H, t, J=7.5 Hz), 2.91 (2H, t, J=7.5 Hz), 7.36 (1H, d, J=7.5 Hz), 7.59-7.68 (3H, m), 7.79 (1H, t, J=7.8 Hz), 8.34 (1H, d, J=7.8 Hz), 8.55 (1H, d, J=6.9 Hz). IR(KBr): 3053, 1703, 1659, 1570, 1537, 1298 cm$^{-1}$. Elemental Analysis for C$_{20}$H$_{20}$N$_2$O$_3$S.0.25H$_2$O Calcd. C, 64.41; H, 5.54; N, 7.51. Found C, 64.63; H, 5.32; N, 7.46.

Reference Example 129

2-(Trimethylsilyl)ethyl 7-[6-(4-oxo-4H-1,3-benzothiazin-2-yl)-2-pyridyl]heptanoate

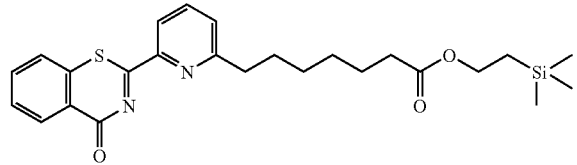

2-(Trimethylsilyl)ethyl 7-(6-cyano-2-pyridyl)heptanoate (0.52 g, 1.6 mmol) and methyl thiosalicylate (0.43 g, 2.5 mmol) were dissolved in toluene (2 ml), and triethylamine (0.44 ml, 2.3 mmol) was added thereto. The reaction mixture was refluxed for 16 hrs and subjected to a silica gel (35 g) column chromatography. The fractions eluted with hexane-ethyl acetate (4:1, v/v) were collected and concentrated to give the titled compound (0.38 g, 27%) as a yellow oil.

$^1$H-NMR (CDCl$_3$) δ: 0.03 (9H, s), 0.98 (2H, m), 1.40-1.45 (4H, m) 1.67 (2H, t, J=7.2 Hz), 1.86 (2H, t, J=7.2 Hz), 2.30 (2H, t, J=7.5 Hz), 2.91 (2H, t, J=7.5 Hz), 4.16 (2H, m), 7.36 (1H, d, J=7.5 Hz), 7.61-7.68 (3H, m), 7.79 (1H, t, J=7.8 Hz), 8.34 (1H, d, J=7.8 Hz), 8.55 (1H, d, J=7.2 Hz).

Reference Example 130

2-(Trimethylsilyl)ethyl 7-(6-Cyano-2-pyridyl)heptanoate

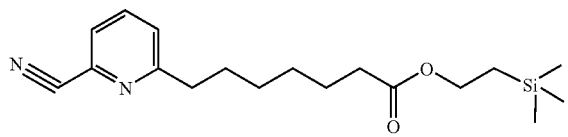

2-(Trimethylsilyl)ethyl 7-(1-oxide-2-pyridyl)heptanoate (0.54 g, 1.7 mmol) was dissolved in nitroethane (3 ml), and trimethylsilyl cyanide (0.33 g, 3.3 mmol) and N,N-dimethylcarbamoyl chloride (0.36 g, 3.4 mmol) were added thereto. The reaction mixture was stirred at room temperature for 18 hrs and combined with ethyl acetate and saturated aqueous sodium hydrogen carbonate solution. The organic layer was successively washed with saturated aqueous sodium hydrogen carbonate solution and saturated brine and dried over anhydrous magnesium sulfate. The solvent was evaporated, and the residue was subjected to a silica gel (40 g) column chromatography. The fractions eluted with hexane-ethylacetate (3:1, v/v) were collected and concentrated to give the titled compound (0.52 g, 94%).

$^1$H-NMR (CDCl$_3$) δ: 0.04 (9H, s), 0.98 (2H, m), 1.34-1.37 (4H, m), 1.59 (2H, t, J=7.2 Hz), 1.74 (2H, t, J=7.2 Hz), 2.27 (2H, t, J=7.2 Hz), 2.82 (2H, t, J=7.2 Hz), 4.16 (2H, m), 7.38 (1H, d, J=7.8 Hz), 7.52 (1H, d, J=7.8 Hz), 7.72 (1H, t, J=7.8 Hz).

Reference Example 131

2-(Trimethylsilyl)ethyl 7-(1-oxide-2-pyridyl)heptanoate

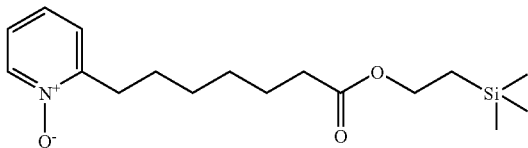

2-(Trimethylsilyl)ethyl 7-(2-pyridyl)heptanoate (0.77 g, 2.5 mmol) was dissolved in ethyl acetate (7 ml), and 3-chloroperbenzoic acid (ca. 77%, 0.61 g, 2.8 mmol) was added thereto. The reaction mixture was stirred at room temperature for 14 hrs and subjected to a silica gel (25 g) column chromatography. The fractions eluted with ethyl acetate-acetone (1:1, v/v) were collected and concentrated to give the titled compound (0.55 g, 67%)

$^1$H-NMR (CDCl$_3$) δ: 0.04 (9H, s), 0.98 (2H, m), 1.39-1.44 (4H, m), 1.62-1.76 (4H, m), 2.28 (2H, t, J=7.5 Hz), 2.92 (2H, t, J=7.5 Hz), 4.16 (2H, m), 7.12-7.22 (3H, m), 8.26 (1H, t, J=6.0 Hz).

Reference Example 132

(2-Trimethylsilyl)ethyl 7-(2-pyridyl)heptanoate

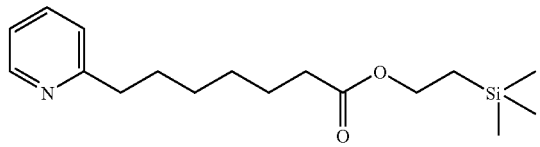

7-(2-pyridyl)heptanoic acid (0.89 g, 4.3 mmol) was dissolved in N,N-dimethylformamide (20 ml), and trimethylsilylethanol (1.5 g, 12.9 mmol), WSC (2.5 g, 12.9 mmol) and HOBt (1.7 g, 12.9 mmol) were successively added thereto. The reaction mixture was stirred at room temperature for 13 hrs. The solvent was evaporated, and the residue was combined with ethyl acetate and water. The organic layer was washed with saturated brine and dried over anhydrous magnesium sulfate. The solvent was evaporated, and the residue was subjected to a silica gel (40 g) column chromatography. The fractions eluted with hexane-ethyl acetate (3:1, v/v) were collected and concentrated to give the titled compound (0.78 g, 59%).

$^1$H-NMR (CDCl$_3$) δ: 0.04 (9H, s), 0.97 (2H, m), 1.34-1.39 (4H, m), 1.6-1.75 (4H, m), 2.26 (2H, t, J=7.5 Hz), 2.78 (2H, t, J=7.5 Hz), 4.16 (2H, m), 7.07-7.14 (2H, m), 7.58 (1H, t, J=7.7 Hz), 8.51 (1H, d, J=5.7 Hz).

Reference Example 133

7-(2-Pyridyl)heptanoic acid

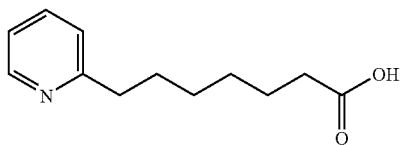

7-(2-Pyridyl)-6-heptenoic acid (0.97 g, 4.7 mmol) was dissolved in ethanol (15 ml), and 10% palladium-carbon (0.16 g) and a solution of ammonium formate (1.7 g, 27.0 mmol) in water (2 ml) were added thereto. The reaction mixture was refluxed for 2 hrs. Palladium-carbon was filtered off. The reaction mixture was combined with water, concentrated under reduced pressure to the half amount and extracted with ethyl acetate. The organic layer was washed with saturated brine and dried over magnesium sulfate. The solvent was concentrated under reduced pressure to give the titled compound (0.89 g, 91%).

$^1$H-NMR (DMSO-d$_6$) δ: 1.29 (4H, m), 1.45-1.50 (2H, m), 1.60-1.65 (2H, m), 2.18 (2H, t, J=7.5 Hz), 2.70 (2H, t, J=7.5 Hz), 7.15-7.28 (2H, m), 7.67 (1H, t, J=7.6 Hz), 8.46 (1H, d, J=4.6 Hz).

Reference Example 134

7-(2-Pyridyl)-6-heptenoic acid

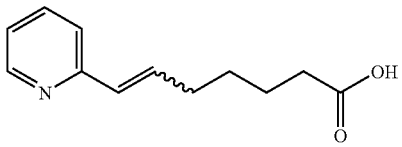

(5-Carboxypentyl)triphenyl phosphonium (13.7 g, 30.0 mmol) was suspended in tetrahydrofuran (50 ml), and potassium tert-butoxide (6.3 g, 56.0 mmol) was added thereto under ice cooling condition. The mixture was stirred for 1 hr. Successively, a solution of 2-pyridinecarbaldehyde (2.0 g, 18.7 mmol) in tetrahydrofuran (10 ml) was added to the mixture, and the mixture was stirred at 0° C. for 3 hrs. The reaction mixture was combined with 2 N aqueous sodium hydroxide solution (50 ml), washed with diethyl ether, neutralized with 6 N HCl and extracted with ethyl acetate. The organic layer was washed with saturated brine and dried over magnesium sulfate. The solvent was evaporated, and the residue was subjected to a silica gel (100 g) column chromatography. The fractions eluted with hexane-ethyl acetate (1:1, v/v) were collected and concentrated to give Z-form of the titled compound (2.0 g, 52%). And the fractions eluted with hexane-ethyl acetate (1:2, v/v) were collected and concentrated to give a mixture of E-form and Z-form of the titled compound (0.97 g, 25%)

(Z-form)
$^1$H-NMR (CDCl$_3$) δ: 1.40-1.75 (4H, m), 2.35 (2H, m), 2.56 (2H, t, J=7.2 Hz), 5.88 (1H, dt, J=7.5 & 11.8 Hz), 6.49 (1H, d, J=11.8 Hz), 7.14 (1H, m), 7.23 (1H, d, J=7.8 Hz), 7.66 (1H, t, J=7.8 Hz), 8.60 (1H, d, J=5.7 Hz).

(E-form)
$^1$H-NMR (CDCl$_3$) δ: 1.50-1.80 (4H, m), 2.20-2.42 (4H, m), 6.52 (1H, d, J=15.8 Hz), 6.73 (1H, dt, J=6.7 & 15.9 Hz), 7.12 (1H, m), 7.27 (1H, t, J=7.8 Hz), 7.63 (1H, t, J=7.8 Hz), 8.55 (1H, d, J=7.8 Hz).

Example 308

3-[2-(4-Oxo-4H-1,3-benzothiazin-2-yl)-4-pyridyl]propionic acid

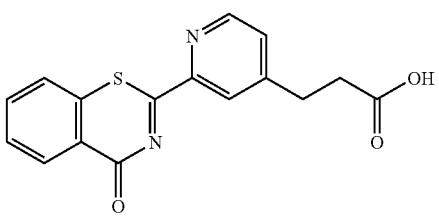

tert-Butyl 3-[2-(4-oxo-4H-1,3-benzothiazin-2-yl)-4-pyridyl]propionate (0.45 g, 1.2 mmol) was dissolved in trifluoroacetic acid (3.0 ml), and the mixture was stirred at room temperature for 2.5 hrs. Isopropyl ether was added to the reaction mixture to precipitate crystals, which were collected by filtration and washed with ethanol-hexane to give the titled compound (0.32 g, 84%) as white crystals.

mp. 215.3-215.9° C. $^1$H-NMR (DMSO-d$_6$) δ: 2.69 (2H, t, J=7.4 Hz), 3.01 (2H, t, J=7.4 Hz), 7.65 (1H, t, J=7.4 Hz), 7.75 (1H, t, J=7.6 Hz), 7.84 (1H, m), 7.90 (1H, m), 8.25 (1H, s), 8.36 (1H, d, J=7.9 Hz), 8.69 (1H, d, J=4.9 Hz). IR(KBr): 3086, 3055, 1714, 1653, 1591, 1568, 1522, 1444 cm$^{-1}$. Elemental Analysis for C$_{16}$H$_{12}$N$_2$O$_3$S Calcd. C, 61.53; H, 3.87; N, 8.97. Found C, 61.42; H, 3.96; N, 8.92.

Example 309 tert-butyl 3-[2-(4-oxo-4H-1,3-benzothiazin-2-yl)-4-pyridyl]propionate

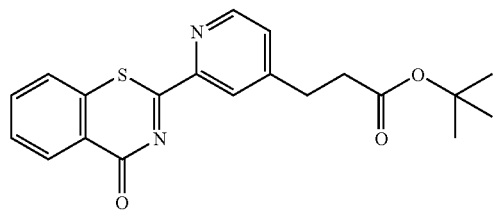

tert-Butyl 3-(2-cyano-4-pyridyl)propionate (0.51 g, 2.2 mmol) and methyl thiosalicylate (0.55 g, 3.3 mmol) were dissolved in toluene (2 ml), and triethylamine (0.47 ml, 3.4 mmol) was added thereto. The mixture was refluxed for 8 hrs and subjected to a silica gel (30 g) column chromatography. The fractions eluted with hexane-ethyl acetate (3:1, v/v) were collected and concentrated to give the titled compound (0.56 g, 69%) as white crystals.

mp. 135.8-136.7° C. $^1$H-NMR (CDCl$_3$) δ: 1.43 (9H, s), 2.65 (2H, t, J=7.6 Hz), 3.03 (2H, t, J=7.6 Hz), 7.41 (1H, t, J=4.9 Hz), 7.60-7.70 (3H, m), 8.43 (1H, s), 8.56 (1H, d, J=8.1 Hz), 8.63 (1H, d, J=4.7 Hz). IR(KBr): 1726, 1664, 1572, 1537, 1365 cm$^{-1}$. Elemental Analysis for C$_{20}$H$_{20}$N$_2$O$_3$S Calcd. C, 65.20; H, 5.47; N, 7.60. Found C, 65.16; H, 5.52; N, 7.51.

Reference Example 135 tert-Butyl 3-(2-Cyano-4-pyridyl)propionate

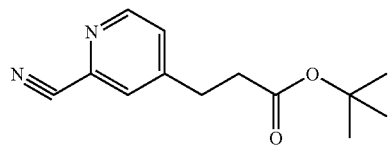

tert-Butyl 3-(4-pyridyl)propionate (0.58 g, 2.8 mmol) was dissolved in ethyl acetate (4 ml), and 3-chloroperbenzoic acid (ca. 77%, 0.65 g, 2.9 mmol) was added thereto. The reaction mixture was stirred at room temperature for 18 hrs and subjected to a silica gel (35 g) column chromatography. The fractions eluted with ethyl acetate-ethanol (3:1, v/v) were collected and concentrated. The residue was dissolved in nitroethane (4 ml), and trimethylsilyl cyanide (0.50 g, 5.1 mmol) and N,N-dimethylcarbamoyl chloride (0.54 g, 5.1 mmol) were added thereto. The reaction mixture was stirred at room temperature for 16 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to a silica gel (30 g) column chromatography. The fractions eluted with hexane-ethyl acetate (4:1, v/v) were collected and concentrated to give the titled compound (0.52 g, 79%).

$^1$H-NMR (CDCl$_3$) δ: 1.42 (9H, s), 2.59 (2H, t, J=7.4 Hz), 2.97 (2H, t, J=7.4 Hz), 7.37 (1H, d, J=7.8 Hz), 7.56 (1H, s), 8.61 (1H, d, J=7.8 Hz).

Reference Example 136 tert-Butyl 3-(4-pyridyl)propionate

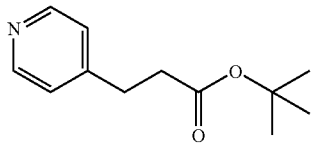

tert-Butyl (E)-3-(4-Pyridyl)acrylate (0.88 g, 4.3 mmol) was dissolved in ethanol (10 ml), and 10% palladium-carbon (0.17 g) and a solution of ammonium formate (1.4 g, 21.4 mmol) in water (2.5 ml) were added thereto. The reaction mixture was refluxed for 3 hrs. Palladium-carbon was filtered off. The reaction mixture was combined with water, concentrated under reduced pressure to the half amount and extracted with ethyl acetate. The organic layer was washed with saturated brine and dried over magnesium sulfate. The solvent was evaporated, and the residue was subjected to a silica gel (20 g) column chromatography. The fractions eluted with hexane-ethyl acetate (3:1, v/v) were collected and concentrated to give the titled compound (0.58 g, 65%).

$^1$H-NMR (CDCl$_3$) δ: 1.41 (9H, s), 2.56 (2H, t, J=7.5 Hz), 2.91 (2H, t, J=7.5 Hz), 7.13 (2H, d, J=6.0 Hz), 8.50 (2H, d, J=6.0 Hz).

Reference Example 137 tert-Butyl (E)-3-(4-pyridyl)acrylate

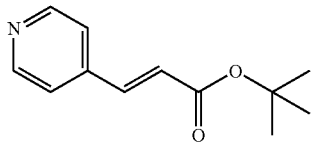

Sodium hydride (0.43 g, 10.8 mmol) was suspended in tetrahydrofuran (5 ml), and a solution of tert-butyl diethylphosphonoacetate (2.5 g, 9.8 mmol) in tetrahydrofuran (2 ml) was added thereto under ice cooling condition. The mixture was stirred for 0.5 hr. Successively, a solution of 4-pyridinecalbaldehyde (1.0 g, 9.3 mmol) in tetrahydrofuran (3 ml) was added to the mixture, and the mixture was stirred at 0° C. for 2 hrs. The reaction mixture was combined with water, concentrated under reduced pressure to the half amount and extracted with ethyl acetate. The organic layer was washed with saturated brine and dried over magnesium sulfate. The solvent was evaporated to give the titled compound (1.8 g, 92%).

$^1$H-NMR (CDCl$_3$) δ: 1.54 (9H, s), 6.52 (1H, d, J=16.0 Hz), 7.35 (2H, d, J=4.5 Hz), 7.49 (1H, d, J=16.0 Hz), 8.64 (2H, d, J=4.5 Hz).

Example 310

(E)-3-[2-(4-Oxo-4H-1,3-benzothiazin-2-yl)-4-pyridyl]acrylic acid

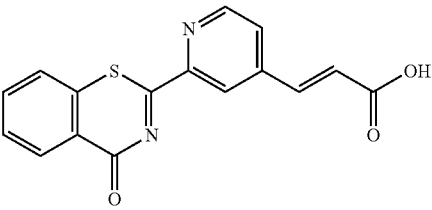

tert-Butyl (E)-3-[2-(4-oxo-4H-1,3-benzothiazin-2-yl)-4-pyridyl]acrylate (0.14 g, 0.44 mmol) was dissolved in trifluoroacetic acid (2.0 ml), and the mixture was stirred at room temperature for 2.5 hrs. Isopropyl ether was added to the reaction mixture to precipitate crystals, which were collected by filtration and recrystallized from tetrahydrofuran-ethanol to give the titled compound (0.088 g, 64%) as white crystals.

mp. 284.3-285.0° C. $^1$H-NMR (DMSO-d$_6$) δ: 6.91 (1H, d, J=16.1 Hz), 7.73 (1H, d, J=16.1 Hz), 7.73 (1H, m), 7.83 (1H, t, J=7.2 Hz), 7.92 (1H, m), 8.05 (1H, d, J=7.9 Hz), 8.37 (1H, d, J=7.9 Hz), 8.50 (1H, s), 8.83 (1H, d, J=5.0 Hz). IR(KBr): 3113, 3061, 1711, 1626, 1572, 1532, 1315 cm$^{-1}$. Elemental Analysis for C$_{16}$H$_{10}$N$_2$O$_3$S Calcd. C, 61.93; H, 3.25; N, 9.03. Found C, 61.68; H, 3.23; N, 8.99.

Example 311 tert-Butyl (E)-3-[2-(4-oxo-4H-1,3-benzothiazin-2-yl)-4-pyridyl]acrylate

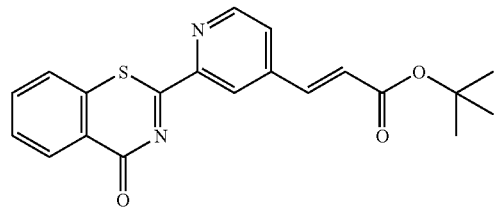

tert-Butyl (E)-3-(2-cyano-4-pyridyl)acrylate (0.84 g, 3.2 mmol) and methyl thiosalicylate (0.74 g, 4.4 mmol) were dissolved in toluene (3 ml), and triethylamine (0.77 ml, 5.5 mmol) was added thereto. The reaction mixture was refluxed for 7 hrs and subjected to a silica gel (50 g) column chromatography. The fractions eluted with hexane-ethyl acetate (3:1, v/v) were collected and concentrated. The residue was recrystallized from ethyl acetate-isopropyl ether to give the titled compound (0.16 g, 17%) as white crystals.

mp. 196.0-196.7° C. $^1$H-NMR (CDCl$_3$) δ: 1.56 (9H, s), 6.72 (1H, d, J=16.1 Hz), 7.55-7.71 (5H, m), 8.56 (1H, d, J=8.0 Hz), 8.64 (1H, s), 8.74 (1H, d, J=4.9 Hz). IR(KBr): 1711, 1661, 1572, 1537, 1367, 1325 cm$^{-1}$. Elemental Analysis for C$_{20}$H$_{18}$N$_2$O$_3$S Calcd. C, 65.55; H, 4.95; N, 7.64. Found C, 65.48; H, 4.91; N, 7.58.

Reference Example 138 tert-Butyl (E)-3-(2-cyano-4-pyridyl)acrylate

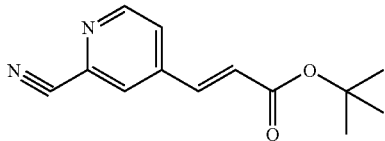

tert-Butyl (E)-3-(4-pyridyl)acrylate (0.88 g, 4.3 mmol) was dissolved in ethyl acetate (4 ml), and 3-chloroperbenzoic acid (ca. 77%, 0.95 g, 4.3 mmol) was added thereto. The reaction mixture was stirred at room temperature for 45 hrs and subjected to a silica gel (40 g) column chromatography. The fractions eluted with ethyl acetate-ethanol (4:1) were collected and concentrated. The residue was dissolved in nitroethane (5 ml), and trimethylsilyl cyanide (0.63 g, 6.3 mmol) and N,N-dimethylcarbamoyl chloride (0.68 g, 6.3 mmol) were added thereto. The reaction mixture was stirred at room temperature for 20 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to silica gel (30 g) column chromatography. The fractions eluted with hexane-ethyl acetate (5:1, v/v) were collected and concentrated to give the titled compound (0.73 g, 99%).

$^1$H-NMR (CDCl$_3$) δ: 1.54 (9H, s), 6.58 (1H, d, J=16.0 Hz), 7.47 (1H, d, J=16.0 Hz), 7.55 (1H, d, J=5.1 Hz), 7.75 (1H, s), 8.74 (1H, d, J=5.1 Hz).

Example 312 ({3-[6-(4-Oxo-4H-1,3-benzothiazin-2-yl)-2-pyridyl]propanoyl}amino)acetic acid

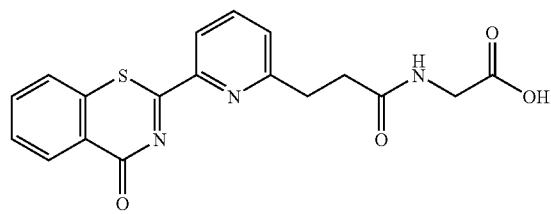

tert-Butyl ({3-[6-(4-Oxo-4H-1,3-benzothiazin-2-yl)-2-pyridyl]propanoyl}amino)acetate (0.27 g, 0.63 mmol) was dissolved in trifluoroacetic acid (1.5 ml), and the mixture was stirred at room temperature for 2.5 hrs. Isopropyl ether was added to the reaction mixture to precipitate crystals, which were collected by filtration and recrystallized from tetrahydrofuran-ethanol to give the titled compound (0.12 g, 49%) as white crystals.

mp. 219.2-219.8° C. $^1$H-NMR (DMSO-d$_6$) δ: 2.71 (2H, t, J=7.3 Hz), 3.14 (2H, t, J=7.3 Hz), 3.78 (2H, d, J=5.9 Hz), 7.64 (1H, t, J=7.3 Hz), 7.73 (1H, t, J=7.3 Hz), 7.83 (1H, t, J=7.3 Hz), 7.93-8.03 (2H, m), 8.19 (1H, d, J=7.7 Hz), 8.29 (1H, m), 8.36 (1H, d, J=7.9 Hz), 12.47 (1H, bs). IR(KBr): 3055, 1759, 1651, 1589, 1514, 1439 cm$^{-1}$. Elemental Analysis for C$_{11}$H$_{15}$N$_3$O$_4$S Calcd. C, 58.53; H, 4.09; N, 11.38. Found C, 58.40; H, 4.22; N, 11.15.

Reference Example 139 tert-Butyl ({3-[6-(4-oxo-4H-1,3-benzothiazin-2-yl)-2-pyridyl]propanoyl}amino)acetate

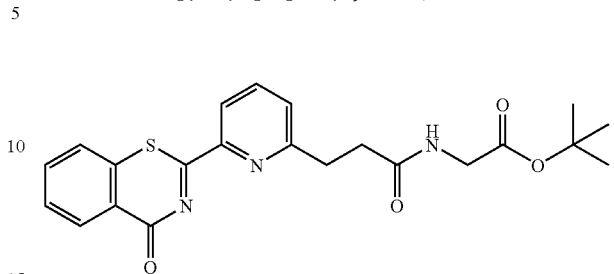

3-[6-(4-oxo-4H-1,3-benzothiazin-2-yl)-2-pyridyl]propionic acid (0.20 g, 0.64 mmol) as dissolved in N,N-dimethylformamide (3 ml), and glycine tert-butyl ester (0.11 g, 0.67 mmol), WSC (0.25 g, 1.3 mmol) and HOBt (0.18 g, 1.3 mmol) were added successively thereto. The reaction mixture was stirred at room temperature for 17 hrs, concentrated under reduced pressure and combined with ethyl acetate and water. The organic layer was washed with saturated brine and dried over anhydrous magnesium sulfate. The solvent was evaporated, and the residue was subjected to a silica gel (15 g) column chromatography. The fractions eluted with hexane-ethylacetate (1:1, v/v) were collected and concentrated to give the titled compound (0.27 g, 99%) as white crystals.

$^1$H-NMR (CDCl$_3$) δ: 1.44 (9H, s), 2.90 (2H, t, J=7.2 Hz), 3.30 (2H, t, J=7.2 Hz), 3.96 (2H, d, J=4.9 Hz), 6.31 (1H, bs), 7.43 (1H, d, J=7.6 Hz), 7.62-7.69 (3H, m), 7.80 (1H, t, J=7.8 Hz), 8.34 (1H, d, J=7.6 Hz), 8.56 (1H, d, J=7.5 Hz).

Example 313

1-{3-[6-(4-Oxo-4H-1,3-benzothiazin-2-yl)-2-pyridyl]propanoyl}proline

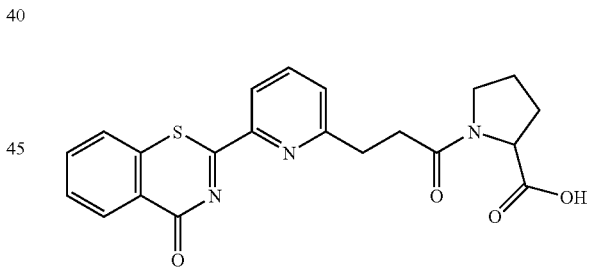

tert-Butyl 1-{3-[6-(4-oxo-4H-1,3-benzothiazin-2-yl)-2-pyridyl]propanoyl}-2-pyrrolidinecarboxylate (0.25 g, 0.68 mmol) was dissolved in trifluoroacetic acid (2 ml), and the mixture was stirred at room temperature for 2.5 hrs. Isopropyl ether was added to the reaction mixture to precipitate crystals, which were collected by filtration and recrystallized from ethanol-hexane to give the titled compound (0.13 g, 45%) as white crystals.

mp. 210.5-211.0° C. $^1$H-NMR (DMSO-d$_6$) δ: 1.70-2.20 (4H, m), 2.80-2.90 (2H, m), 3.10-3.16 (2H, m), 3.30-3.70 (2H, m), 4.24 & 4.61 (1H, m), 7.66-7.75 (2H, m), 7.81-7.95 (2H, m), 8.00 (1H, t, J=7.8 Hz), 8.18 (1H, d, J=7.7 Hz), 8.36 (1H, d, J=7.8 Hz), 12.45 (1H, bs). IR(KBr): 3248, 1736, 1659, 1572, 1537, 1439 cm$^{-1}$. Elemental Analysis for C$_{21}$H$_{19}$N$_3$O$_4$S.0.25H$_2$O Calcd. C, 60.93; H, 4.75; N, 10.15. Found C, 60.92; H, 4.71; N, 10.22.

Reference Example 140 tert-Butyl 1-{3-[6-(4-oxo-4H-1,3-benzothiazin-2-yl)-2-pyridyl]propanoyl}-2-pyrrolidinecarboxylate

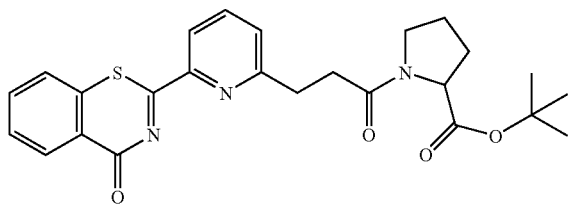

3-[6-(4-oxo-4H-1,3-benzothiazin-2-yl)-2-pyridyl]propionic acid (0.25 g, 0.80 mmol) was dissolved in N,N-dimethylformamide (3 ml), and proline tert-butyl ester (0.15 g, 0.88 mmol), WSC (0.31 g, 1.6 mmol) and HOBt (0.22 g, 1.6 mmol) were successively added thereto. The reaction mixture was stirred for 18 hrs, concentrated under reduced pressure and combined with ethyl acetate and water. The organic layer was washed with saturated brine and dried over magnesium sulfate. The solvent was evaporated, and the residue was recrystallized from isopropyl ether to give the titled compound (0.29 g, 78%) as white crystals.

$^1$H-NMR (CDCl$_3$) δ: 1.45 (9H, d, J=3.3 Hz), 1.92-2.16 (4H, m) 2.90-2.97 (2H, m), 3.24-3.32 (2H, m), 3.55-3.75 (2H, m), 4.42 (1H, m), 7.46 (1H, d, J=7.6 Hz), 7.60-7.70 (3H, m), 7.78 (1H, t, J=7.7 Hz), 8.32 (1H, d, J=7.8 Hz), 8.57 (1H, d, J=8.0 Hz).

Example 314

(Methyl{3-[6-(4-oxo-4H-1,3-benzothiazin-2-yl)-2-pyridyl]propanoyl}amino)acetic acid

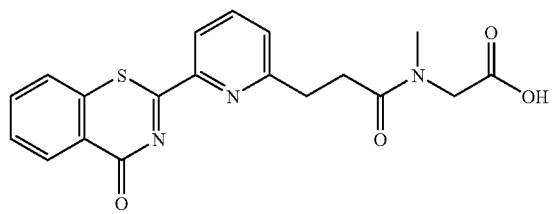

tert-Butyl (methyl{3-[6-(4-oxo-4H-1,3-benzothiazin-2-yl)-2-pyridyl]propanoyl}amino)acetate (0.32 g, 0.73 mmol) was dissolved in trifluoroacetic acid (1.0 ml), and the mixture was stirred at room temperature for 2.5 hrs. Isopropyl ether was added to the reaction mixture to precipitate crystals, which were collected by filtration and recrystallized from ethanol-hexane to give the titled compound (0.25 g, 83%) as white crystals.

mp. 194.5-194.8° C. $^1$H-NMR (DMSO-d$_6$) δ: 2.78-2.95 (4H, m), 3.33 (2H, s), 4.02 & 4.24 (3H, s), 7.65-7.83 (3H, m), 7.90-8.02 (2H, m), 8.17 (1H, d, J=7.7 Hz), 8.35 (1H, d, J=7.9 Hz), 12.69 (1H, bs). IR(KBr): 3055, 1759, 1651, 1603, 1589, 1514, 1439 cm$^{-1}$. Elemental Analysis for C$_{19}$H$_{17}$N$_3$O$_4$S Calcd. C, 59.52; H, 4.47; N, 10.96. Found C, 59.53; H, 4.53; N, 11.12.

Reference Example 141 tert-Butyl (methyl(3-[6-(4-oxo-4H-1,3-benzothiazin-2-yl)-2-pyridyl]propanoyl]amino)acetate

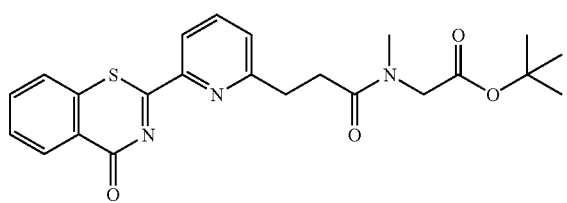

3-[6-(4-oxo-4H-1,3-benzothiazin-2-yl)-2-pyridyl]propionic acid (0.35 g, 1.1 mmol) was dissolved in N,N-dimethylformamide (4 ml), and N-methylglycine tert-butyl ester (0.24 g, 1.3 mmol), WSC (0.43 g, 2.2 mmol) and HOBt (0.31 g, 2.3 mmol) were successively added thereto. The reaction mixture was stirred for 20 hrs, concentrated under reduced pressure and combined with ethyl acetate and water. The organic layer was washed with saturated brine and dried over anhydrous magnesium sulfate. The solvent was evaporated, and the residue was recrystallized from ethanol-hexane to give the titled compound (0.33 g, 67%) as white crystals.

$^1$H-NMR (CDCl$_3$) δ: 1.45 & 1.47 (9H, s), 2.85-3.05 (2H, m), 3.01 & 3.16 (3H, s), 3.28 (2H, m), 4.04 & 4.05 (2H, s), 7.47 (1H, d, J=7.5 Hz), 7.60-7.69 (3H, s), 7.79 (1H, t, J=7.7 Hz), 8.34 (1H, d, J=7.8 Hz), 8.56 (1H, d, J=7.9 Hz).

Example 315

Ethyl 2-methyl-3-[6-(4-oxo-4H-1,3-benzothiazin-2-yl)-2-pyridyl]propionate

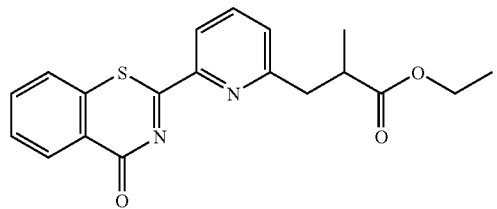

Ethyl 3-(6-cyano-2-pyridyl)-2-methylpropionate (0.79 g, 3.6 mmol) and methyl thiosalicylate (1.2 g, 7.3 mmol) were dissolved in toluene (3 ml), and triethylamine (0.76 ml, 5.4 mmol) was added thereto. The reaction mixture was refluxed for 21 hrs and subjected to a silica gel (70 g) column chromatography. The fractions eluted with hexane-ethyl acetate (2:1, v/v) were collected and concentrated to give the titled compound (0.89 g, 70%) as white crystals.

mp. 120.2-120.7° C. $^1$H-NMR (CDCl$_3$) δ: 1.21 (3H, t, J=7.1 Hz), 1.31 (3H, d, J=6.9 Hz), 3.00 (1H, dd, J=14.0 & 5.9 Hz), 3.21-3.37 (2H, m), 4.08-4.20 (2H, m), 7.41 (1H, d, J=7.5 Hz), 7.60-7.70 (3H, m), 7.80 (1H, t, J=7.8 Hz), 8.37 (1H, d, J=7.8 Hz), 8.57 (1H, d, J=8.0 Hz). IR(KBr): 1728, 1651, 1591, 1574, 1537, 1452 cm$^{-1}$. Elemental Analysis for C$_{19}$H$_{18}$N$_2$O$_3$S Calcd. C, 64.39; H, 5.12; N, 7.90. Found C, 64.36; H, 5.10; N, 7.88.

Reference Example 142

Ethyl 3-(6-cyano-2-pyridyl)-2-methylpropionate

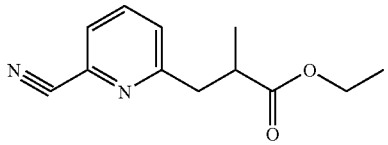

Ethyl 2-methyl-3-(2-pyridyl)propionate (1.0 g, 5.2 mmol) was dissolved in ethyl acetate (4 ml), and 3-chloroperbenzoic acid (ca. 77%, 1.2 g, 5.2 mmol) was added thereto. The reaction mixture was stirred at room temperature for 14 hrs and subjected to a silica gel (50 g) column chromatography. The fractions eluted with ethyl acetate-ethanol (4:1, v/v) were collected and concentrated. The residue was dissolved in acetonitrile (10 ml), and trimethylsilyl cyanide (0.95 g, 9.6 mmol) and N,N-dimethylcarbamoyl chloride (0.77 g, 7.2 mmol) were added thereto. The reaction mixture was stirred at room temperature for 16 hrs and combined with ethyl acetate and water. The organic layer was washed with saturated aqueous sodium hydrogen carbonate solution and saturated brine and dried over anhydrous magnesium sulfate. The solvent was evaporated, and the residue was subjected to a silica gel (50 g) column chromatography. The fractions eluted with hexane-ethyl acetate (4:1, v/v) were collected and concentrated to give the titled compound (0.80 g, 76%).

$^1$H-NMR (CDCl$_3$) δ: 1.22 (3H, t, J=7.3 Hz), 1.23 (3H, d, J=7.1 Hz), 2.90 (1H, dd, J=13.7 & 6.0 Hz), 3.03-3.27 (2H, m), 4.11 (2H, q, J=7.1 Hz), 7.38 (1H, d, J=7.8 Hz), 7.53 (1H, d, J=7.8 Hz), 7.72 (1H, t, J=7.8 Hz).

Reference Example 143

Ethyl 2-methyl-3-(2-pyridyl)propionate

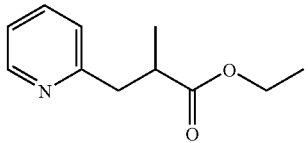

Ethyl 2-methyl-3-(2-pyridyl)acrylate (7.8 g, 41.0 mmol) was dissolved in ethanol (80 ml), and 10% palladium-carbon (1.0 g) and a solution of ammonium formate (11.2 g, 178 mmol) in water (20 ml) was added thereto. The mixture was refluxed for 2 hrs. Palladium-carbon was filtered off. The reaction mixture was combined with water, concentrated under reduced pressure to the half amount and extracted with ethyl acetate. The organic layer was washed with saturated brine and dried over anhydrous magnesium sulfate. The solvent was evaporated to give the titled compound (7.2 g, 91%).

$^1$H-NMR (CDCl$_3$) δ: 1.18 (3H, d, J=7.1 Hz), 1.19 (3H, t, J=7.1 Hz), 2.83 (1H, dd, J=13.5 & 7.0 Hz), 3.03 (1H, m), 3.19 (1H, dd, J=13.5 & 7.4 Hz), 4.10 (2H, q, J=7.1 Hz), 7.09-7.15 (2H, m), 7.58 (1H, d, J=7.1 Hz), 8.53 (1H, d, J=4.7 Hz).

Reference Example 144

Ethyl 2-methyl-3-(2-pyridyl)acrylate

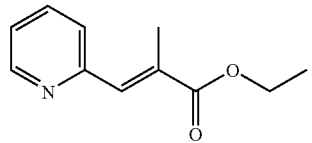

Sodium hydride (ca. 60%, 2.0 g, 50.0 mmol) was suspended in tetrahydrofuran (20 ml), and a solution of ethyl 2-(diethylphosphono)propionate (11.7 g, 49.1 mmol) in tetrahydrofuran (8 ml) was added thereto under ice cooling condition. The mixture was stirred for 0.5 hr. Successively, a solution of 2-pyridinecarbaldehyde (5.0 g, 46.7 mmol) in tetrahydrofuran (8 ml) was added to the mixture. The mixture was stirred at 0° C. for 14 hrs, combined with water, concentrated under reduced pressure to the half amount and extracted with ethyl acetate. The organic layer was washed with saturated brine and dried over anhydrous magnesium sulfate. The solvent was evaporated, and the residue was subjected to a silica gel (80 g) column chromatography. The fractions eluted with hexane-ethyl acetate (3:1, v/v) were collected and concentrated to give the titled compound (7.8 g, 87%).

$^1$H-NMR (CDCl$_3$) δ: 1.35 (3H, t, J=7.1 Hz), 2.33 (3H, d, J=1.4 Hz), 4.29 (2H, q, J=7.1 Hz), 7.20 (1H, m), 7.38 (1H, d, J=7.8 Hz), 7.64 (1H, d, J=1.4 Hz), 7.71 (1H, t, J=7.8 Hz), 8.68 (1H, d, J=4.8 Hz).

Example 316

2-{4-[2-(1H-1,2,3,4-Tetrazol-5-yl)ethyl]-2-pyridyl}-4H-1,3-benzothiazine-4-one

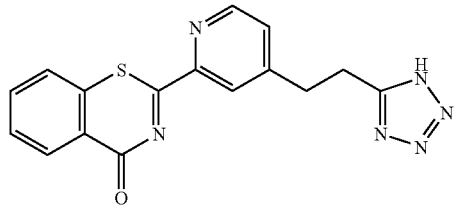

3-[2-(4-Oxo-4H-1,3-benzothiazin-2-yl)-4-pyridyl]propionitrile (0.25 g, 0.85 mmol) and trimethylsilyl azide (0.20 g, 1.7 mmol) were dissolved in toluene (5 ml), and dibutyltin (IV) oxide (0.02 g, 0.08 mmol) was added thereto. The reaction mixture was refluxed for 48 hrs and kept at room temperature. The precipitated crystals were collected by filtration and washed with toluene. The obtained crystals were recrystallized from ethanol to give the titled compound (0.13 g, 44%) as white crystals.

mp. 250.0° C. (decomp.) $^1$H-NMR (DMSO-d$_6$) δ: 3.25-3.34 (4H, m), 7.63 (1H, d, J=3.7 Hz), 7.73 (1H, t, J=7.0 Hz), 7.81-7.93 (2H, m), 8.29 (1H, s), 8.36 (1H, d, J=7.0 Hz), 8.69 (1H, d, J=5.2 Hz), 16.10 (1H, bs). IR(KBr): 3140, 3063, 1657, 1612, 1601, 1587, 1529, 1518, 1441, 1319 cm$^{-1}$. Elemental Analysis for C$_{16}$H$_{12}$N$_6$OS Calcd. C, 57.13; H, 3.60; N, 24.98. Found C, 57.31; H, 3.50; N, 24.75.

Example 317

3-[2-(4-Oxo-4H-1,3-benzothiazin-2-yl)-4-pyridyl]propionitrile

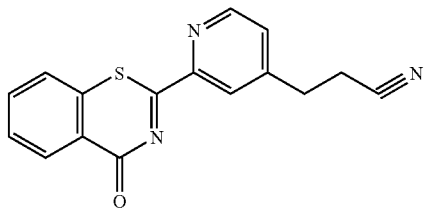

4-(2-Cyanoethyl)-2-pyridinecarbonitrile (0.70 g, 4.5 mmol) and methyl thiosalicylate (1.1 g, 6.2 mmol) were dissolved in toluene (3.5 ml), and triethylamine (1.2 ml, 8.9 mmol) was added thereto. The reaction mixture was refluxed for 8 hrs and kept at room temperature. The precipitated crystals were collected by filtration and washed with toluene. The obtained crystals were recrystallized from tetrahydrofuran-ethanol to give the titled compound (0.66 g, 51%) as white crystals mp. 178.3-179.0° C. $^1$H-NMR (CDCl$_3$) δ: 2.77 (2H, t, J=7.2 Hz), 3.10 (2H, t, J=7.2 Hz), 7.48 (1H, d, J=5.0 Hz), 7.60-7.72 (3H, m), 8.44 (1H, s), 8.58 (1H, d, J=8.0 Hz), 8.72 (1H, d, J=4.9 Hz). IR(KBr): 2247, 1659, 1599, 1570, 1537, 1439, 1298 cm$^{-1}$. Elemental Analysis for C$_{16}$H$_{11}$N$_3$OS.0.5H$_2$O Calcd. C, 63.56; H, 4.00; N, 13.90. Found C, 63.81; H, 3.83; N, 13.79.

Reference Example 145

4-(2-Cyanoethyl)-2-pyridinecarbonitrile

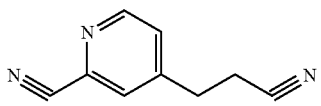

3-(1-Oxide-2-pyridyl)propionitrile (0.89 g, 5.9 mmol) was dissolved in acetonitrile (10 ml), and trimethylsilyl cyanide (1.2 g, 12.1 mmol) and N,N-dimethylcarbamoyl chloride (1.1 g, 10.3 mmol) were added thereto. The reaction mixture was stirred at room temperature for 16 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to a silica gel (20 g) column chromatography. The fractions eluted with hexane-ethyl acetate (2:1, v/v) were collected and concentrated to give the titled compound (0.71 g, 76%).

$^1$H-NMR (CDCl$_3$) δ: 2.72 (2H, t, J=7.1 Hz), 3.05 (2H, t, J=7.1 Hz), 7.45 (1H, d, J=5.0 Hz), 7.60 (1H, s), 8.71 (1H, d, J=5.0 Hz).

Reference Example 146

3-(1-Oxide-2-pyridyl)propionitrile

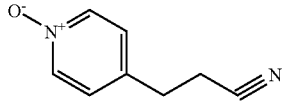

3-(4-Pyridyl)propionitrile (0.88 g, 6.7 mmol) was dissolved in ethyl acetate (8 ml), and 3-chloroperbenzoic acid (ca. 77%, 1.5 g, 6.7 mmol) was added thereto. The reaction mixture was stirred at room temperature for 48 hrs and subjected to a silica gel (25 g) column chromatography. The fractions eluted with ethyl acetate-ethanol (3:1, v/v) were collected and concentrated to give the titled compound (0.89 g, 91%).

$^1$H-NMR (CDCl$_3$) δ: 2.67 (2H, t, J=7.1 Hz), 2.97 (2H, t, J=7.1 Hz), 7.18 (2H, d, J=6.8 Hz), 8.19 (2H, d, J=6.8 Hz).

Reference Example 147

3-(4-Pyridyl)propionitrile

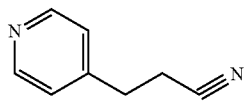

3-(4-Pyridyl)acrylonitrile (1.3 g, 10.0 mmol) was dissolved in ethanol (10 ml), and 10% palladium-carbon (0.13 g) and a solution of ammonium formate (2.5 g, 40.0 mmol) in water (3 ml) were added thereto. The reaction mixture was refluxed for 2.5 hrs. Palladium-carbon was filtered off, and the reaction mixture was combined with ethyl acetate and water. The organic layer was washed with saturated brine and dried over anhydrous magnesium sulfate. The reaction mixture was subjected to a silica gel (25 g) column chromatography. The fractions eluted with hexane-ethyl acetate (1:1, v/v) were collected and concentrated to give the titled compound (0.88 g, 67%)

$^1$H-NMR (CDCl$_3$) δ: 2.67 (2H, t, J=7.3 Hz), 2.97 (2H, t, J=7.3 Hz), 7.18 (2H, d, J=6.0 Hz), 8.59 (2H, d, J=6.0 Hz).

Reference Example 148

3-(4-Pyridyl)acrylonitrile

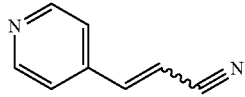

Sodium hydride (ca. 60%, 1.0 g, 28.1 mmol) was dissolved in tetrahydrofuran (10 ml), and a solution of diethyl cyanomethylphosphonate (4.7 g, 26.8 mmol) in tetrahydrofuran (5 ml) was added under ice cooling condition. The mixture was stirred for 1 hr. Successively, a solution of 2-pyridinecarbaldehyde (2.7 g, 25.0 mmol) in tetrahydrofuran (5 ml) was added to the mixture, and the mixture was stirred at 0° C. to room temperature for 3 hrs. The reaction mixture was combined with water under ice cooling condition, concentrated under reduced pressure to the half amount and extracted with ethyl acetate. The organic layer was washed with saturated brine and dried over magnesium sulfate. The solvent was evaporated, and the residue was subjected to a silica gel (100 g) column chromatography. The fractions eluted with hexane-ethyl acetate (2:1, v/v) were collected and concentrated to give the titled compound (a mixture of E-form and Z-form, 2.5 g, 77%).

$^1$H-NMR (CDCl$_3$) δ: 5.70 (0.18H, d, J=12.1 Hz), 6.10 (0.82H, d, J=16.7 Hz), 7.12 (0.18H, d, J=12.1 Hz), 7.29 (0.82H, d, J=16.7 Hz), 7.30-7.39 (1.6H, m), 7.63 (0.4H, d, J=6.2 Hz), 8.70 (1.6H, d, J=6.2 Hz), 8.75 (0.4H, d, J=6.2 Hz).

Example 318

Ethyl 2-methyl-3-[2-(4-oxo-4H-1,3-benzothiazin-2-yl)-4-pyridyl]propionate

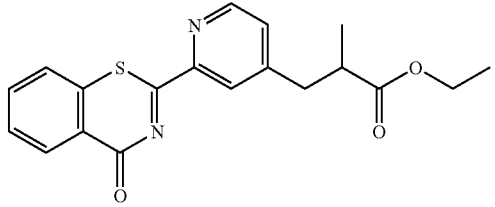

Ethyl 3-(2-cyano-4-pyridyl)-2-methylpropionate (0.50 g, 2.3 mmol) and methyl thiosalicylate (0.96 g, 5.7 mmol) were dissolved in toluene (2 ml), and triethylamine (11.0 ml, 5.7 mmol) was added thereto. The reaction mixture was refluxed for 8 hrs and combined with isopropyl ether to precipitate crystals, which were collected by filtration and recrystallized from ethyl acetate to give the titled compound (0.43 g, 53%) as white crystals.

mp. 120.3-120.7° C. $^1$H-NMR (CDCl$_3$) δ: 1.19-1.26 (5H, m), 2.75-2.89 (2H, m), 3.14 (1H, dd, J=12.5 & 6.5 Hz), 4.11 (2H, q, J=7.1 Hz), 7.37 (1H, d, J=4.9 Hz), 7.60-7.70 (3H, m), 8.42 (1H, s), 8.56 (1H, d, J=7.9 Hz), 8.63 (1H, d, J=5.1 Hz). IR(KBr): 1728, 1661, 1599, 1572, 1537, 1439, 1298 cm$^{-1}$. Elemental Analysis for C$_{19}$H$_{18}$N$_2$O$_3$S Calcd. C, 64.39; H, 5.12; N, 7.90. Found C, 64.31; H, 5.26; N, 7.69.

Reference Example 149

Ethyl 3-(2-cyano-4-pyridyl)-2-methylpropionate

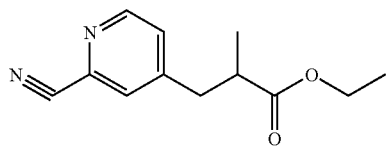

Ethyl 2-methyl-3-(4-pyridyl)propionate (5.9 g, 30.5 mmol) was dissolved in ethyl acetate (25 ml) and 3-Chloroperbenzoic acid (ca. 77%, 7.5 g, 33.4 mmol) was added thereto. The reaction mixture was stirred at room temperature for 14 hrs and subjected to a silica gel (120 g) column chromatography. The fractions eluted with ethyl acetate-ethanol (3:1, v/v) were collected and concentrated. The residue was dissolved in acetonitrile (18 ml), and trimethylsilyl cyanide (4.5 g, 45.0 mmol) and N,N-dimethylcarbamoyl chloride (3.5 g, 32.5 mmol) were added thereto. The reaction mixture was stirred at room temperature for 18 hrs and combined with ethyl acetate and water. The organic layer was successively washed with saturated aqueous sodium hydrogen carbonate solution and saturated brine and dried over anhydrous magnesium sulfate. The solvent was evaporated, and the residue was subjected to a silica gel (50 g) column chromatography. The fractions eluted with hexane-ethylacetate (4:1, v/v) were collected and concentrated to give the titled compound (3.7 g, 76%).

$^1$H-NMR (CDCl$_3$) δ: 1.20 (3H, t, J=7.1 Hz), 1.22 (3H, d, J=6.7 Hz), 2.71-2.82 (2H, m), 3.06 (1H, m), 4.10 (2H, q, J=7.1 Hz), 7.34 (1H, d, J=5.0 Hz), 7.54 (1H, s), 8.60 (1H, d, J=5.0 Hz).

Reference Example 150

N,N-Dimethyl-2-(2-methyl-4-pyridyl)ethenamine

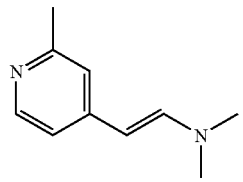

n-Butyl lithium in hexane (1.6 M, 35 ml, 56 mmol) was added dropwise to a solution of 2,4-lutidine (5.0 g, 46 mmol) in tetrahydrofuran (50 ml) at −78° C., and the mixture was stirred at the same temperature for 30 minutes. Successively, diethylamine (5.1 g, 69 mmol) was added to the mixture, and the mixture was stirred at −78° C., and the mixture was stirred at the same temperature for 30 minutes. Furthermore, DMF (6.8 g, 93 mmol) was added to the mixture at −78° C., and the mixture was stirred at the same temperature for 1 hr. The reaction mixture was combined with aqueous ammonium chloride solution and extracted with ethyl acetate. The organic layer was washed with saturated brine and dried over anhydrous magnesium sulfate. The solvent was evaporated to give the titled compound (7.5 g, 99%).

$^1$H-NMR (CDCl$_3$) δ: 2.43 (3H, s), 2.86 (6H, s), 4.96 (1H, m), 6.76-6.84 (2H, m), 6.99 (1H, d, J=13.7 Hz), 8.16 (1H, m).

Reference Example 151

2-Methylisonicotinaldehyde

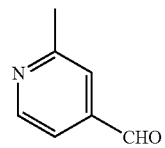

A solution of N,N-dimethyl-2-(2-methyl-4-pyridyl)ethenamine (6.4 g, 39 mmol) in methanol (25 ml) was added dropwise to a mixture of sodium periodate (25.2 g, 117 mmol) and methanol (25 ml) at room temperature. The mixture was stirred at the same temperature for 1 hr. The precipitates were filtered off, and the filtrate was concentrated. The residue was combined with water and extracted with ethyl acetate. The organic layer was washed with saturated brine and dried over magnesium sulfate. The solvent was evaporated to give the titled compound (3.7 g, 78%).

$^1$H-NMR (CDCl$_3$) δ: 2.68 (3H, s), 7.51 (1H, d, J=4.9 Hz), 7.56 (1H, s), 8.76 (1H, d, J=4.9 Hz), 10.05 (1H, s).

Reference Example 152 tert-Butyl (E)-3-(2-methyl-4-pyridyl)-2-propenoate

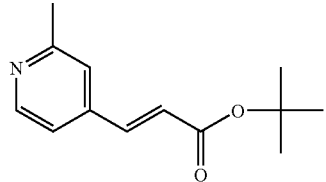

A solution of tert-butyl diethylphosphonoacetate (12.4 g, 49 mmol) in tetrahydrofuran (30 ml) was added dropwise to a mixture of sodium hydride (60% in oil, 2.3 g, 57 mmol) and tetrahydrofuran (100 ml) at 0° C., and the mixture was stirred at the same temperature for 30 minutes. Successively, a solution of 2-methylisonicotinaldehyde (5.0 g, 41 mmol) in tetrahydrofuran (20 ml) was added to the mixture at 0° C., and the mixture was stirred at room temperature for 1 hr. The reaction mixture was combined with water and extracted with ethyl acetate. The organic layer was washed with saturated brine and dried over anhydrous magnesium sulfate. The solvent was evaporated, and the residue was subjected to a silica gel column chromatography. The fractions eluted with ethyl acetate-hexane (2:3, v/v) were collected and concentrated to give the titled compound (4.4 g, 48%).

$^1$H-NMR (CDCl$_3$) δ: 1.53 (9H, s), 2.57 (3H, s), 6.49 (1H, d, J=16.1 Hz), 7.16 (1H, d, J=5.1 Hz), 7.20 (1H, s), 7.46 (1H, d, J=16.1 Hz), 8.51 (1H, d, J=5.1 Hz).

Reference Example 153 tert-Butyl 3-(2-methyl-4-pyridyl)propanoate

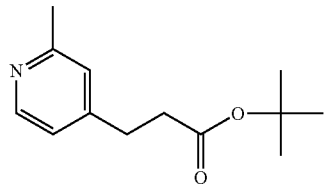

tert-Butyl (E)-3-(2-methyl-4-pyridyl)-2-propenoate (4.4 g, 20 mmol) was dissolved in methanol (100 ml), and 10% palladium-carbon (0.45 g) was added thereto. The mixture was stirred under hydrogen atmosphere for 3 hrs. Palladium-carbon was filtered off, and the filtrate was concentrated to give the titled compound (4.4 g, 99%).

$^1$H-NMR (CDCl$_3$) δ: 1.41 (9H, s), 2.52 (3H, s), 2.54 (2H, t, J=7.5 Hz), 2.86 (2H, t, J=7.5 Hz), 6.94 (1H, d, J=5.1 Hz), 7.00 (1H, s), 8.37 (1H, d, J=5.1 Hz).

Reference Example 154 tert-Butyl 3-(2-methyl-4-pyridyl)propanoate N-oxide

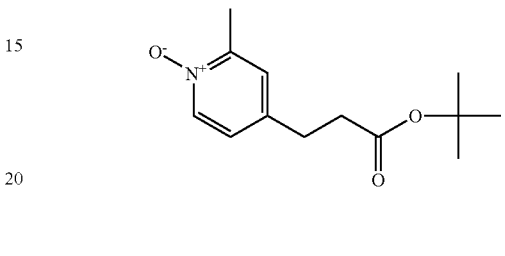

tert-Butyl 3-(2-methyl-4-pyridyl)propanoate (4.3 g, 19 mmol) and 3-chloroperbenzoic acid (77%, 5.3 g, 23 mmol) were dissolved in ethyl acetate (100 ml), and the mixture was stirred at room temperature for 20 hrs. The solvent was evaporated, and the residue was subjected to a silica gel column chromatography. The fractions eluted with ethanol-ethyl acetate (1:3, v/v) were collected and concentrated to give the titled compound (4.4 g, 94%).

$^1$H-NMR (CDCl$_3$) δ: 1.41 (9H, s), 2.50 (3H, s), 2.54 (2H, t, J=7.3 Hz), 2.86 (2H, t, J=7.3 Hz), 6.99 (1H, d, J=6.6 Hz), 7.10 (1H, s), 8.17 (1H, d, J=6.6 Hz).

Reference Example 155 tert-Butyl 3-(2-cyano-6-methyl-4-pyridyl)propanoate

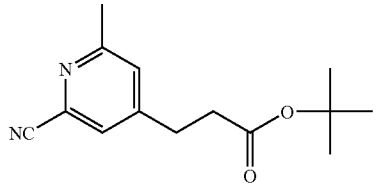

tert-Butyl 3-(2-methyl-4-pyridyl)propanoate N-oxide (4.4 g, 18 mmol) was dissolved in acetonitrile (150 ml), and trimethylsilyl cyanide (3.7 g, 37 mmol) and N,N-dimethylcarbamoyl chloride (3.0 g, 28 mmol) were added thereto. The mixture was stirred at room temperature for 48 hrs. The solvent was evaporated, and the residue was combined with water and extracted with ethyl acetate. The organic layer was washed with saturated brine and dried over magnesium sulfate. The solvent was evaporated, and the residue was subjected to a silica gel column chromatography. The fractions eluted with ethyl acetate-hexane (1:5, v/v) were collected and concentrated to give the titled compound (2.8 g, 62%).

$^1$H-NMR (CDCl$_3$) δ: 1.41 (9H, s), 2.56 (2H, t, J=7.4 Hz), 2.56 (3H, s), 2.91 (2H, t, J=7.4 Hz), 7.21 (1H, s), 7.37 (1H, s)

Example 319 tert-Butyl 3-[2-methyl-6-(4-oxo-4H-1,3-benzothiazin-2-yl)-4-pyridyl]propanoate

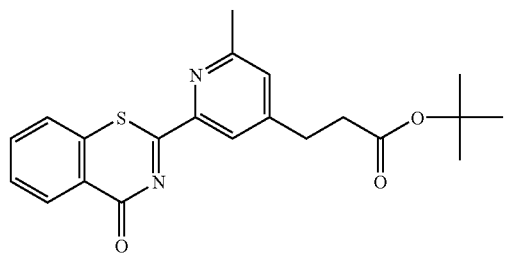

tert-Butyl 3-(2-cyano-6-methyl-4-pyridyl)propanoate (1.2 g, 4.8 mmol) and methyl thiosalicylate (1.6 g, 9.9 mmol) were dissolved in toluene (10 ml), and triethylamine (4.0 ml, 28.6 mmol) was added thereto. The mixture was refluxed for 24 hrs. The solvent was evaporated, and the residue was subjected to a silica gel column chromatography. The fractions eluted with ethyl acetate-hexane (1:2, v/v) were collected, concentrated and recrystallized from tetrahydrofuran-hexane to give the titled compound (1.2 g, 66%)

mp. 129.4-130.5° C. $^1$H-NMR (CDCl$_3$) δ: 1.42 (9H, s), 2.62 (2H, t, J=7.5 Hz), 2.64 (3H, s), 2.97 (2H, t, J=7.5 Hz), 7.25 (1H, s), 7.59-7.68 (3H, m), 8.23 (1H, s), 8.55 (1H, m). IR: 2976, 2932, 1728, 1660, 1572, 1537, 1493, 1367, 1292, 1151, 1097 cm$^{-1}$. Elemental Analysis for C$_{21}$H$_{22}$N$_2$O$_3$S Calcd. C, 65.95; H, 5.80; N, 7.32. Found C, 65.89; H, 5.89; N, 7.14.

Example 320 tert-Butyl 3-[2-(7-chloro-4-oxo-4H-1,3-benzothiazin-2-yl)-6-methyl-4-pyridyl]propanoate

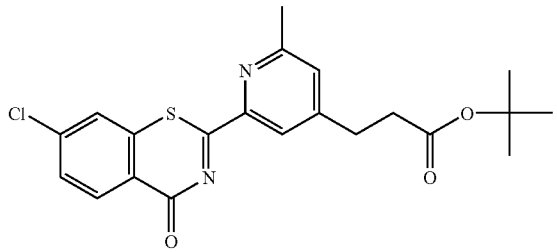

tert-Butyl 3-(2-cyano-6-methyl-4-pyridyl)propanoate (1.6 g, 6.5 mmol) and 4-chlorothiosalicylic acid (2.4 g, 13.1 mmol) were dissolved in pyridine (20 ml). The mixture was refluxed for 24 hrs. The solvent was evaporated, and residue was subjected to a silica gel column chromatography. The fractions eluted with hexane-ethyl acetate (2:1, v/v) were collected, concentrated and recrystallized from hexane-ethyl acetate to give the titled compound (1.2 g, 46%) as pale yellow crystals.

mp. 186.4-187.6° C. $^1$H-NMR (CDCl$_3$) δ: 1.42 (9H, s), 2.61 (2H, t, J=7.5 Hz), 2.63 (3H, s), 2.97 (2H, t, J=7.5 Hz), 7.26 (1H, s), 7.56 (1H, dd, J=1.9, 8.4 Hz), 7.60 (1H, d, J=1.9 Hz), 8.20 (1H, s), 8.47 (1H, d, J=8.4 Hz). IR: 2976, 1726, 1664, 1585, 1564, 1535, 1379, 1284, 1151, 1095 cm$^{-1}$. Elemental Analysis for C$_{21}$H$_{21}$N$_2$O$_3$SCl Calcd. C, 60.50; H, 5.08; N, 6.72. Found C, 60.45; H, 5.20; N, 6.59.

Example 321

3-[2-Methyl-6-(4-oxo-4H-1,3-benzothiazin-2-yl)-4-pyridyl]propionic acid

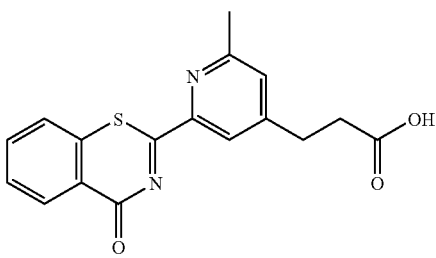

tert-Butyl 3-[2-methyl-6-(4-oxo-4H-1,3-benzothiazin-2-yl)-4-pyridyl]propanoate (0.96 g, 2.5 mmol) was dissolved in trifluoroacetic acid (8 ml), and the mixture was stirred at 0° C. for 2 hrs. The solvent was evaporated, and the residue was recrystallized from diisopropyl ether-ethanol to give the titled compound (0.74 g, 90%) as white crystals.

mp. 233.2-234.7° C. $^1$H-NMR (DMSO-d$_6$) δ: 2.57 (3H, s), 2.66 (2H, t, J=7.3 Hz), 2.95 (2H, t, J=7.3 Hz), 7.49 (1H, s), 7.71 (1H, m), 7.81 (1H, m), 7.92 (1H, d, J=7.9 Hz), 8.05 (1H, s), 8.34 (1H, d, J=7.9 Hz), 12.30 (1H, br s). IR: 3051, 1722, 1518, 1439, 1307, 1188 cm$^{-1}$. Elemental Analysis for C$_{17}$H$_{14}$N$_2$O$_3$S Calcd. C, 62.56; H, 4.32; N, 8.58. Found C, 62.52; H, 4.24; N, 8.43.

Example 322

3-[2-(7-Chloro-4-oxo-4H-1,3-benzothiazin-2-yl)-6-methyl-4-pyridyl]propionic acid

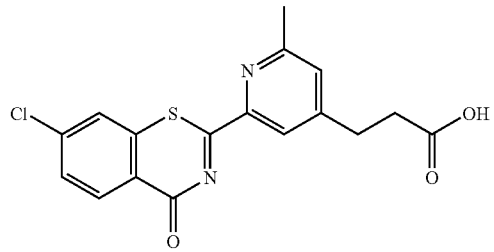

tert-Butyl 3-[2-(7-chloro-4-oxo-4H-1,3-benzothiazin-2-yl)-6-methyl-4-pyridyl]propanoate (0.90 g, 2.5 mmol) was dissolved in trifluoroacetic acid (8 ml), and the mixture was stirred at 0° C. for 2 hrs. The solvent was evaporated, and the residue was recrystallized from diisopropyl ether-ethanol to give the titled compound (0.74 g, 82%) as pale yellow crystals.

mp. 273.5° C. (decomposed) $^1$H-NMR (DMSO-d$_6$) δ: 2.57 (3H, s), 2.66 (2H, t, J=7.3 Hz), 2.95 (2H, t, J=7.3 Hz), 7.51 (1H, s), 7.74 (1H, dd, J=2.0, 8.6 Hz), 8.04 (1H, s), 8.15 (1H, d, J=2.0 Hz), 8.31 (1H, d, J=8.5 Hz), 12.22 (1H, br s). IR: 3084, 3024, 1724, 1628, 1560, 1523, 1302, 1182 cm$^{-1}$. Elemental Analysis for C$_{17}$H$_{13}$N$_2$O$_3$SCl Calcd. C, 56.59; H, 3.63; N, 7.76. Found C, 56.48; H, 3.60; N, 7.62.

Reference Example 156

N-(2-Chloroethyl)-N'-(4-pyridyl)urea

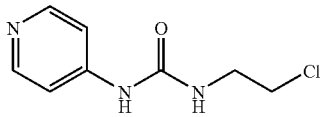

2-Chloroethylisocyanate (10.0 g, 94 mmol) was added dropwise to a mixture of 4-aminopyridine (6.0 g, 63 mmol) and toluene (40 mL) at 0° C., and the mixture was stirred at room temperature for 6 hrs. The precipitates were collected by filtration and washed with diisopropyl ether to give the titled compound (11.1 g, 87%) as white crystals.

$^1$H-NMR (DMSO-d$_6$) δ: 3.43 (2H, m), 3.66 (2H, t, J=6.1 Hz), 6.67 (1H, t, J=5.6 Hz), 7.37 (2H, d, J=6.2 Hz), 8.29 (2H, d, J=6.2 Hz), 9.19 (1H, s).

Reference Example 157

1-(4-Pyridyl)-2-imidazolidinone

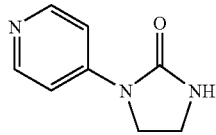

Sodium hydride (60% in oil, 2.4 g, 60 mmol) was added to a mixture of N-(2-chloroethyl)-N'-(4-pyridyl)urea (11.1 g, 55 mmol), tetrahydrofuran (40 ml) and DMF (40 ml) at 0° C., and the mixture was stirred at room temperature for 2 hrs. The reaction mixture was combined with methanol. The solvent was evaporated, and the residue was combined with water and extracted with ethyl acetate. The organic layer was washed with saturated brine and dried over magnesium sulfate. The residue was recrystallized from tetrahydrofuran-hexane to give the titled compound (2.4 g, 27%) as white crystals.

$^1$H-NMR (CDCl$_3$) δ: 3.64 (2H, t, J=7.2 Hz), 3.94 (2H, t, J=7.2 Hz), 5.39 (1H, br s), 7.48 (2H, d, J=5.0 Hz), 8.47 (2H, d, J=5.0 Hz).

Reference Example 158 tert-Butyl [2-oxo-3-(4-pyridyl)-1-imidazolidinyl]acetate

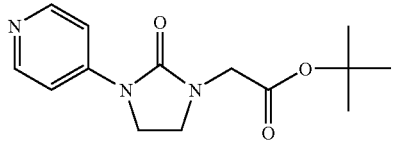

Sodium hydride (60% in oil, 0.40 g, 10.1 mmol) was added to a mixture of 1-(4-pyridyl)-2-imidazolidinone (1.5 g, 9.2 mmol) and DMF (20 ml) at 0° C., and the mixture was stirred at room temperature for 30 minutes. Successively, tert-butyl bromoacetate (2.2 g, 11.2 mmol) was added to the mixture, and the mixture was stirred at room temperature for 2 hrs. The reaction mixture was combined with water and extracted with ethyl acetate. The organic layer was washed with saturated brine and dried over magnesium sulfate. The solvent was evaporated, and the residue was subjected to a silica gel column chromatography. The fractions eluted with ethyl acetate-methanol (5:1, v/v) were collected, concentrated and recrystallized from tetrahydrofuran-hexane to give the titled compound (1.7 g, 68%) as white crystals.

mp. 146.8-147.7° C. $^1$H-NMR (CDCl$_3$) δ: 1.48 (9H, s), 3.67 (2H, m), 3.87 (2H, m), 3.97 (2H, s), 7.48 (2H, m), 8.46 (2H, m). IR: 2980, 2934, 1739, 1711, 1595, 1510, 1471, 1442, 1392, 1282, 1234, 1153 cm$^{-1}$. Elemental Analysis for C$_{14}$H$_{19}$N$_3$O$_3$ Calcd. C, 60.63; H, 6.91; N, 15.15. Found C, 60.57; H, 6.92; N, 15.04.

Reference Example 159 tert-Butyl [2-oxo-3-(4-pyridyl)-1-imidazolidinyl]acetate N-oxide

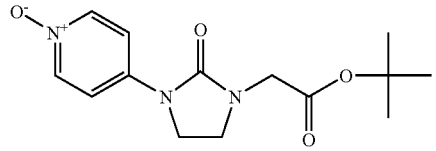

tert-Butyl [2-oxo-3-(4-pyridyl)-1-imidazolidinyl]acetate (1.6 g, 5.9 mmol) and 3-chloroperbenzoic acid (77%, 2.0 g, 8.9 mmol) were dissolved in chloroform (30 ml), and the mixture was stirred at room temperature for 45 hrs. The solvent was evaporated, and the residue was subjected to a silica gel column chromatography. The fractions eluted with methanol-ethyl acetate (2:3, v/v) were collected and concentrated to give the titled compound (1.6 g, 95%) as white crystals.

$^1$H-NMR (CDCl$_3$) δ: 1.48 (9H, s), 3.69 (2H, m), 3.86 (2H, m), 3.96 (2H, s), 7.53 (2H, d, J=7.5 Hz), 8.13 (2H, d, J=7.5 Hz).

Reference Example 160 tert-Butyl [3-(2-cyano-4-pyridyl)-2-oxo-imidazolidinyl]acetate

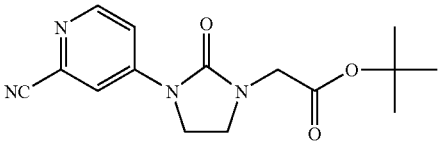

tert-Butyl [2-oxo-3-(4-pyridyl)-1-imidazolidinyl]acetate N-oxide (1.6 g, 5.6 mmol) was dissolved in nitroethane (50 ml), and trimethylsilyl cyanide (1.1 g, 11.5 mmol) and N,N-dimethylcarbamoyl chloride (1.0 g, 9.3 mmol) were added thereto. The mixture was stirred at room temperature for 14 hrs. The solvent was evaporated, and the residue was subjected to a silica gel column chromatography. The fractions eluted with ethyl acetate-hexane (4:1, v/v) were collected, concentrated and recrystallized from ethyl acetate-hexane to give the titled compound (0.93 g, 54%) as pale yellow crystals.

mp. 139.0-140.1° C. $^1$H-NMR (CDCl$_3$) δ: 1.49 (9H, s), 3.70 (2H, m), 3.89 (2H, m), 3.98 (2H, s), 7.61 (1H, dd, J=2.3, 5.7 Hz), 8.00 (1H, d, J=2.3 Hz), 8.51 (1H, d, J=5.7 Hz). IR: 2978, 2935, 2235, 1718, 1591, 1477, 1437, 1392, 1280, 1234, 1155 cm$^{-1}$. Elemental Analysis for C$_{15}$H$_{18}$N$_4$O$_3$ Calcd. C, 59.59; H, 6.00; N, 18.53. Found C, 59.39; H, 6.00; N, 18.58.

Example 323 tert-Butyl (2-oxo-3-[2-(4-oxo-4H-1,3-benzothiazin-2-yl)-4-pyridyl]-1-imidazolidinyl]acetate

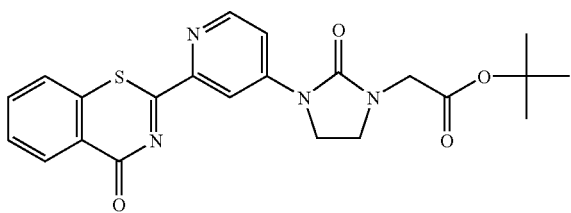

tert-Butyl [3-(2-cyano-4-pyridyl)-2-oxo-1-imidazolidinyl]acetate (0.80 g, 2.6 mmol) and methyl thiosalicylate (1.33 g, 7.8 mmol) were dissolved in toluene (6 ml), and triethylamine (2.0 ml, 14.3 mmol) was added thereto. The mixture was refluxed for 8 hrs. The solvent was evaporated, and the residue was subjected to a silica gel column chromatography. The fractions eluted with ethyl acetate-hexane (3:1, v/v) were collected, concentrated and recrystallized from tetrahydrofuran-hexane to give the titled compound (0.68 g, 58%).

mp. 192.3-194.0° C. $^1$H-NMR (CDCl$_3$) δ: 1.49 (9H, s), 3.72 (2H, m), 4.00 (2H, s), 4.02 (2H, m), 7.60-7.69 (3H, m), 7.96 (1H, d, J=0.6 Hz), 8.53-8.56 (3H, m). IR: 2978, 2932, 1738, 1714, 1660, 1593, 1572, 1537, 1477, 1435, 1280, 1232, 1155 cm$^{-1}$. Elemental Analysis for C$_{22}$H$_{22}$N$_4$O$_4$S Calcd. C, 60.26; H, 5.06; N, 12.78. Found C, 60.29; H, 5.12; N, 12.58.

Example 324

[2-Oxo-3-[2-(4-oxo-4H-1,3-benzothiazin-2-yl)-4-pyridyl]-1-imidazolidinyl]acetic acid

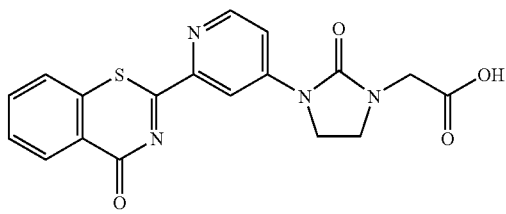

tert-Butyl [2-oxo-3-[2-(4-oxo-4H-1,3-benzothiazin-2-yl)-4-pyridyl]-1-imidazolidinyl]acetate (0.31 g, 0.70 mmol) was dissolved in trifluoroacetic acid (5 ml), and the mixture was stirred at 0° C. for 2 hrs. The solvent was evaporated and the residue was recrystallized from diethyl ether-methanol to give the titled compound (0.22 g, 81%) as white crystals.

mp. 271.0-273.0° C. $^1$H-NMR (DMSO-d$_6$) δ: 3.63 (2H, m), 4.00 (2H, m), 4.01 (2H, s), 7.72-7.91 (4H, m), 8.35 (1H, d, J=7.7 Hz), 8.57-8.61 (2H, m), 12.93 (1H, br s). IR: 2899, 1738, 1711, 1622, 1591, 1525, 1487, 1444, 1288, 1195 cm$^{-1}$. Elemental Analysis for C$_{18}$H$_{14}$N$_4$O$_4$S.0.25H$_2$O Calcd. C, 55.88; H, 3.78; N, 14.48. Found C, 56.10; H, 3.76; N, 14.35.

Reference Example 161

1-Ethyl-3-(4-pyridyl)-2-imidazolidinone

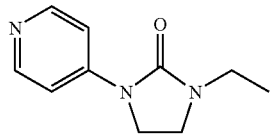

Sodium hydride (60% in oil, 0.25 g, 6.3 mmol) was added to a mixture of 1-(4-pyridyl)-2-imidazolidinone (0.94 g, 5.7 mmol) and DMF (15 ml) at 0° C., and the mixture was stirred at room temperature for 30 minutes. Successively, iodemethane (1.51 g, 9.6 mol) was added to the reaction mixture, and the mixture was stirred at room temperature for 2 hrs. The reaction mixture was combined with water and extracted with ethyl acetate. The organic layer was washed with saturated brine and dried over anhydrous magnesium sulfate. The solvent was evaporated, and the residue was crystallized from diisopropyl ether to give the titled compound (0.71 g, 65%) as pale yellow crystals.

$^1$H-NMR (CDCl$_3$) δ: 1.19 (3H, t, J=7.2 Hz), 3.38 (2H, q, J=7.2 Hz), 3.55 (2H, m), 3.80 (2H, m), 7.47 (2H, m), 8.44 (2H, m).

Reference Example 162

1-Ethyl-3-(4-pyridyl)-2-imidazolidinone N-oxide

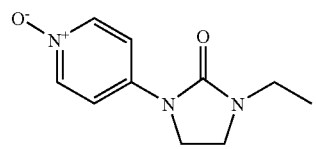

1-Ethyl-3-(4-pyridyl)-2-imidazolidinone (0.71 g, 3.7 mmol) and 3-chloroperbenzoic acid (77%, 1.67 g, 7.4 mmol) were dissolved in ethyl acetate (20 ml), and the mixture was stirred at room temperature for 40 hrs. The solvent was evaporated, and the residue was subjected to a silica gel column chromatography. The fractions eluted with methanol-ethyl acetate (2:3, v/v) were collected and concentrated to give the titled compound (0.57 g, 73%) as white crystals.

$^1$H-NMR (CDCl$_3$) δ: 1.19 (3H, t, J=7.2 Hz), 3.38 (2H, q, J=7.2 Hz), 3.56 (2H, m), 3.81 (2H, m), 7.54 (2H, d, J=7.6 Hz), 8.13 (2H, d, J=7.6 Hz).

Reference Example 163

4-(3-Ethyl-2-oxo-1-imidazolidinyl)-2-pyridinecarbonitrile

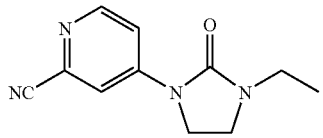

1-Ethyl-3-(4-pyridyl)-2-imidazolidinone N-oxide (0.56 g, 2.7 mmol) was dissolved in nitroethane (20 ml), and trimethylsilyl cyanide (0.55 g, 5.5 mmol) and N,N-dimethylcarbamoyl chloride (0.44 g, 4.1 mmol) were added thereto. The mixture was stirred at room temperature for 20 hrs. The solvent was evaporated, and the residue was subjected to a silica gel column chromatography. The fractions eluted with ethyl acetate-hexane (5:1, v/v) were collected, concentrated and recrystallized from tetrahydrofuran-hexane to give the titled compound (0.17 g, 29%) as white crystals.

$^1$H-NMR (CDCl$_3$) δ: 1.20 (3H, t, J=7.2 Hz), 3.40 (2H, q, J=7.2 Hz), 3.60 (2H, m), 3.82 (2H, m), 7.60 (1H, dd, J=2.0, 5.7 Hz), 8.00 (1H, d, J=2.0 Hz), 8.49 (1H, d, J=5.7 Hz).

Example 325

2-[4-(3-Ethyl-2-oxo-1-imidazolidinyl)-2-pyridyl]-4H-1,3-benzothiazine-4-one

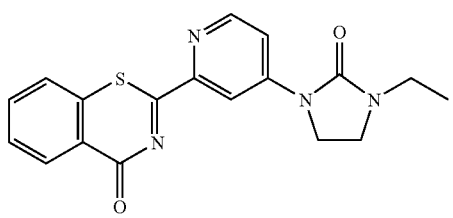

4-(3-Ethyl-2-oxo-1-imidazolidinyl)-2-pyridinecarbonitrile (0.16 g, 0.76 mmol) and methyl thiosalicylate (0.42 g, 2.5 mmol) was dissolved in toluene (4 ml), and triethylamine (2.0 ml, 14.3 mmol) was added thereto. The mixture was refluxed for 9 hrs. The solvent was evaporated, and the residue was subjected to a silica gel column chromatography. The fractions eluted with ethyl acetate were collected, concentrated and recrystallized from tetrahydrofuran-hexane to give the titled compound (0.14 g, 51%) as white crystals.

mp. 211.5-213.0° C. $^1$H-NMR (CDCl$_3$) δ: 1.21 (3H, t, J=7.2 Hz), 3.40 (2H, q, J=7.2 Hz), 3.60 (2H, m), 3.97 (2H, m), 7.60-7.71 (3H, m), 7.93 (1H, d, J=2.1 Hz), 8.52-8.58 (3H, m). IR: 3495, 2976, 1707, 1653, 1591, 1527, 1479, 1437, 1273, 991 cm$^{-1}$. Elemental Analysis for C$_{16}$H$_{16}$N$_4$O$_2$S Calcd. C, 61.35; H, 4.58; N, 15.90. Found C, 61.30; H, 4.71; N, 15.84.

Example 326

2-(6-Oxo-1,6-dihydro-2-pyridyl)-4H-1,3-benzothiazine-4-one

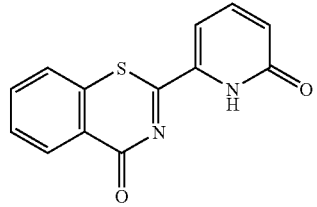

2-(6-(Benzyloxy)-2-pyridyl)-4H-1,3-benzothiazine-4-one (0.15 g, 0.43 mmol) was dissolved in trifluoroacetic acid (10 ml), and the mixture was stirred at room temperature for 15 hrs. The solvent was evaporated, and the residue was recrystallized from chloroform-hexane to give the titled compound (0.07 g, 69%).

mp. 214.2-215.3° C. $^1$H-NMR (CDCl$_3$) δ: 6.89 (1H, d, J=9.1 Hz), 7.22 (1H, d, J=6.9 Hz), 7.52-7.57 (2H, m), 7.65-7.75 (2H, m), 8.52 (1H, d, J=8.1 Hz), 9.85 (1H, br s). IR: 3437, 1666, 1645, 1606, 1523, 1440, 1298, 806 cm$^{-1}$. Elemental Analysis for C$_{13}$H$_8$N$_2$O$_2$S Calcd. C, 60.93; H, 3.15; N, 10.93. Found C, 60.72; H, 3.07; N, 10.80.

Example 327 tert-Butyl 3-[6-(4-oxo-4H-1,3-benzothiazin-2-yl)-3-pyridyl]propanoate

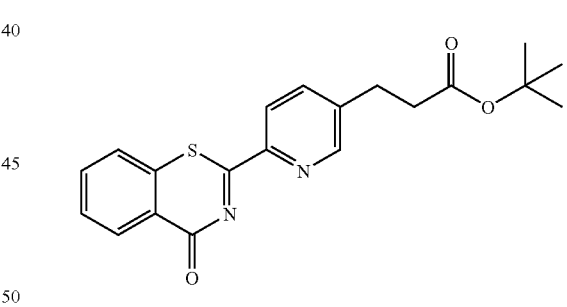

tert-Butyl 3-(6-cyano-3-pyridyl)propanoate (0.46 g, 1.97 mmol) and methyl thiosalicylate (0.50 g, 2.96 mmol) were dissolved in toluene (30 ml), and triethylamine (0.55 ml, 3.94 mmol) was added thereto. The mixture was refluxed for 18 hrs. The solvent was evaporated, and the residue was recrystallized from ethanol to give the titled compound (0.71 g, 98%) as white crystals.

mp. 160.0-161.0° C. $^1$H-NMR (CDCl$_3$) δ: 1.42 (9H, s), 2.62 (2H, t, J=7.5 Hz), 3.03 (2H, t, J=7.4 Hz), 7.59-7.68 (3H, m), 7.74-7.77 (1H, m), 8.47 (1H, d, J=8.2 Hz), 8.53-8.56 (1H, m), 8.60 (1H, d, J=1.7 Hz). IR(KBr): 1722, 1658, 1591, 1572, 1531, 1435, 1363, 1307, 1282, 1159, 1097, 1024, 935, 852, 748 cm$^{-1}$. Elemental Analysis for C$_{20}$H$_{20}$N$_2$O$_3$S Calcd. C, 65.20; H, 5.47; N, 7.60. Found C, 65.17; H, 5.55; N, 7.54.

Example 328

3-[6-(4-Oxo-4H-1,3-benzothiazin-2-yl)-3-pyridyl]propionic acid

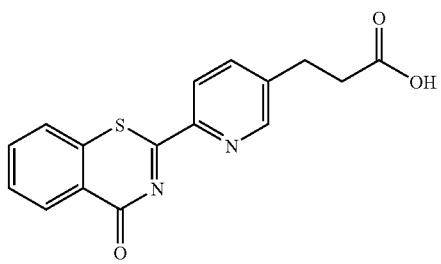

tert-Butyl 3-[6-(4-oxo-4H-1,3-benzothiazin-2-yl)-3-pyridyl]propanoate (0.21 g, 0.56 mmol) was dissolved in trifluoroacetic acid (5 ml), and the mixture was stirred at room temperature for 0.5 hr. Diisopropyl ether was added to the reaction mixture to give crystals, which were recrystallized from ethanol to give the titled compound (0.12 g, 68%) as white crystals.

mp. 232.2-232.4° C. $^1$H-NMR (DMSO-$d_6$) δ: 2.67 (2H, t, J=7.5 Hz), 2.97 (2H, t, J=7.4 Hz), 7.72 (2H, t, J=7.1 Hz), 7.80-7.86 (1H, m), 7.91 (1H, d, J=7.8 Hz), 7.97-8.00 (1H, m), 8.28 (1H, d, J=8.1 Hz), 8.35 (1H, d, J=7.4 Hz), 8.71 (1H, d, J=1.6 Hz), 12.2 (1H, br s). IR(KBr): 3514, 3024, 2706, 1712, 1699, 1635, 1568, 1518, 1460, 1442, 1311, 1294, 1228, 1178, 1157, b1134, 1103, 1028, 947, 852, 752 cm$^{-1}$. Elemental Analysis for $C_{16}H_{12}N_2O_3S$ Calcd. C, 61.53; H, 3.87; N, 8.97. Found C, 61.41; H, 3.66; N, 8.87

Example 329

3-[6-(4-Oxo-4H-1,3-benzothiazin-2-yl)-3-pyridyl]propanamide

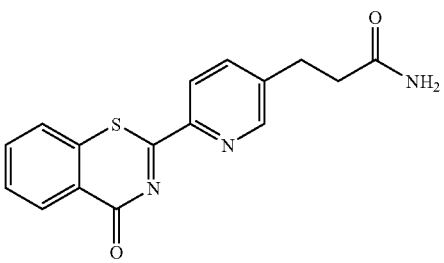

3-[6-(4-Oxo-4H-1,3-benzothiazin-2-yl)-3-pyridyl]propionic acid (0.31 g, 1.00 mmol), isobutyl chloroformate (0.22 ml, 1.50 mmol) and triethylamine (0.22 ml, 1.50 mmol) were dissolved in THF (10 ml), and the mixture was stirred under ice cooling condition for 1 hr. 25% aqueous ammonium solution was added to the mixture, and the mixture was stirred under ice cooling condition for 0.5 hr. The obtained precipitates were recrystallized from ethanol to give the titled compound (0.17 g, 55%) as white crystals.

mp. 247.5-247.8° C. $^1$H-NMR (DMSO-$d_6$) δ: 2.47 (2H, t, J=7.4 Hz), 2.96 (2H, t, J=7.4 Hz), 6.83 (1H, br s), 7.33 (1H, br s), 7.70-7.75 (1H, m), 7.80-7.85 (1H, m), 7.90-7.96 (2H, m), 8.28 (1H, d, J=8.0 Hz), 8.35 (1H, d, J=7.8 Hz), 8.67 (1H, d, J=1.8 Hz). IR(KBr): 3393, 3179, 1682, 1647, 1570, 1527, 1439, 1307, 1286, 1244, 1203, 1286, 1244, 1203, 1128, 1099, 1068, 1032, 966, 945, 850, 756 cm$^{-1}$. Elemental Analysis for $C_{16}H_{13}N_3O_2S$ Calcd. C, 61.72; H, 4.21; N, 13.50. Found C, 61.64; H, 4.05; N, 13.23.

Example 330

3-[6-(4-Oxo-4H-1,3-benzothiazin-2-yl)-2-pyridyl]propanamide

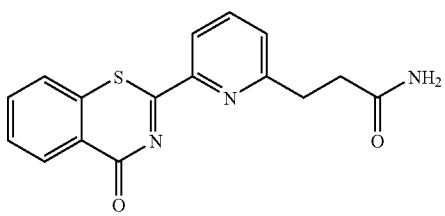

3-[6-(4-Oxo-4H-1,3-benzothiazin-2-yl)-2-pyridyl]propionic acid (0.31 g, 1.00 mmol), isobutyl chloroformate (0.22 ml, 1.50 mmol) and triethylamine (0.22 ml, 1.50 mmol) were dissolved in THF (10 ml), and the mixture was stirred under ice cooling condition for 1 hr. 25% aqueous ammonium solution was added to the mixture, and the mixture was stirred under ice cooling condition for 0.5 hr. The obtained precipitates were recrystallized from ethanol to give the titled compound (0.20 g, 65%) as white crystals.

mp. 236.3-236.5° C. $^1$H-NMR (DMSO-$d_6$) δ: 2.62 (2H, t, J=7.3 Hz), 3.11 (2H, t, J=7.7 Hz), 6.84 (1H, br s), 7.40 (1H, br s), 7.63 (1H, d, J=7.7 Hz), 7.73-7.75 (1H, m), 7.84-7.86 (1H, m), 7.94 (1H, d, J=7.7 Hz), 8.00 (1H, t, J=7.8 Hz), 8.18 (1H, d, J=7.7 Hz), 8.34-8.37 (1H, m). IR(KBr): 3385, 3200, 1651, 1628, 1570, 1537, 1440, 1298, 1126, 1095, 1064, 1028, 995, 815, 548 cm$^{-1}$. Elemental Analysis for $C_{16}H_{13}N_3O_2S$ Calcd. C, 61.72; H, 4.21; N, 13.50. Found C, 61.42; H, 4.02; N, 13.28.

Example 331

3-[6-(4-Oxo-4H-1,3-benzothiazin-2-yl)-4-pyridyl]propanamide

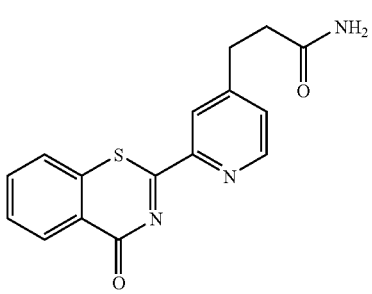

3-[6-(4-Oxo-4H-1,3-benzothiazin-2-yl)-4-pyridyl]propionic acid (0.31 g, 1.00 mmol), isobutyl chloroformate (0.22 ml, 1.50 mmol) and triethylamine (0.22 ml, 1.50 mmol) were dissolved in THF (10 ml), and the mixture was stirred under ice cooling condition for 1 hr. 25% aqueous ammonium solution was added to the mixture, and the mixture was stirred under ice cooling condition for 0.5 hr. The obtained precipitates were recrystallized from ethanol to give the titled compound (0.15 g, 49%) as white crystals.

mp. 237.0-239.7° C. $^1$H-NMR (DMSO-d$_6$) δ: 2.48 (2H, t, J=7.7 Hz), 2.99 (2H, t, J=7.4 Hz), 6.83 (1H, br s), 7.36 (1H, br s), 7.61-7.62 (1H, m), 7.73 (1H, t, J=7.2 Hz), 7.84 (1H, t, J=7.7 Hz), 7.84 (1H, t, J=7.7 Hz), 7.92 (1H, d, J=7.9 Hz), 8.23 (1H, s), 8.36 (1H, d, J=7.8 Hz), 8.68 (1H, d, J=4.9 Hz). IR(KBr): 3404, 3300, 3200, 1662, 1599, 1572, 1537, 1439, 1408, 1304, 1280, 1230, 1165, 1095, 1068, 1030, 999, 835, 742 cm$^{-1}$. Elemental Analysis for $C_{16}H_{13}N_3O_2S$ Calcd. C, 61.72; H, 4.21; N, 13.50. Found C, 61.66; H, 4.26; N, 13.48.

Example 332

2,2-Dimethyl-3-hydroxy-3-[2-(4-oxo-4H-1,3-benzothiazin-2-yl)-4-pyridyl]propionic acid

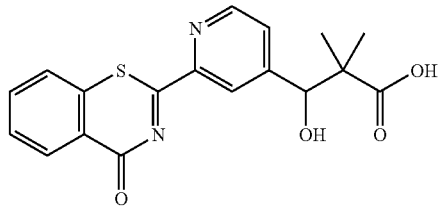

2-(Trimethylsilyl)ethyl 2,2-dimethyl-3-hydroxy-3-[2-(4-oxo-4H-1,3-benzothiazin-2-yl)-4-pyridyl]propionate (0.11 g, 0.24 mmol) was dissolved in tetrahydrofuran (2 ml), and 1.0 M tetrabutylammonium fluoride in tetrahydrofuran (0.58 ml, 0.58 mmol) was added thereto. The reaction mixture was stirred for 2 hrs and concentrated under reduced pressure. Trifluoroacetic acid (1.5 ml) was added to the residue, and the mixture was stirred at room temperature for 13 hrs. Diisopropyl ether was added to the mixture. The precipitated solid was collected by filtration and recrystallized from ethanol-hexane to give the titled compound (0.044 g, 51%) as white crystals.

mp. 235.3-235.8° C. IR: 3358, 3073, 1714, 1693, 1682, 1591, 1631, 1523, 1467 cm$^{-1}$. $^1$H-NMR (DMSO-d$_6$) δ: 0.96 (3H, s), 1.09 (3H, s), 4.99 (1H, d, J=4.3 Hz), 5.99 (1H, d, J=4.3 Hz), 7.65 (1H, d, J=4.4 Hz), 7.74 (1H, t, J=7.5 Hz), 7.84 (1H, t, J=7.0 Hz), 7.92 (1H, m), 8.32 (1H, s), 8.37 (1H, d, J=7.8 Hz), 8.74 (1H, d, J=4.9 Hz).

Reference Example 164

2-(Trimethylsilyl)ethyl 2,2-dimethyl-3-hydroxy-3-[2-(4-oxo-4H-1,3-benzothiazin-2-yl)-4-pyridyl]propionate

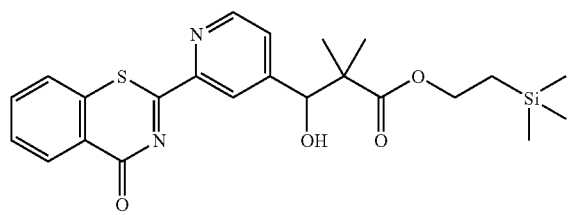

2-(Trimethylsilyl)ethyl 2,2-dimethyl-3-(2-cyano-4-pyridyl)propionate (0.53 g, 1.7 mmol) and methyl thiosalicylate (0.44 g, 2.6 mmol) were dissolved in toluene (2 ml), and triethylamine (0.41 ml, 3.0 mmol) was added thereto. The reaction mixture was refluxed for 50 hrs and subjected to a silica gel (30 g) column chromatography. The fractions eluted with hexane-ethyl acetate (3:1, v/v) were collected and concentrated to give the titled compound (0.12 g, 16%) as white crystals. $^1$H-NMR (CDCl$_3$) δ: 0.05 (9H, s), 1.02 (2H, m), 1.16 (3H, s), 1.19 (3H, s), 3.65 (1H, d, J=4.4 Hz), 4.25 (2H, m), 5.01 (1H, d, J=4.4 Hz), 7.57-7.70 (4H, m), 8.45 (1H, s), 8.55 (1H, d, J=8.1 Hz), 8.70 (1H, d, J=4.7 Hz).

Reference Example 165

2-(Trimethylsilyl)ethyl 2,2-dimethyl-3-(2-cyano-4-pyridyl)propionate

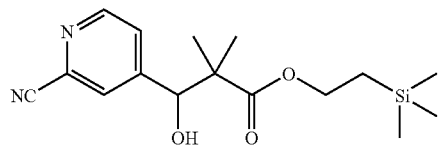

2-(Trimethylsilyl)ethyl 2,2-dimethyl-3-hydroxy-3-(4-pyridyl)propionate (0.60 g, 2.0 mmol) was dissolved in ethyl acetate (4 ml), and 3-chloroperbenzoic acid (ca. 77%, 0.50 g, 2.2 mmol) was added thereto. The reaction mixture was stirred at room temperature for 16 hrs and subjected to a silica gel (35 g) column chromatography. The fractions eluted with ethyl acetate-ethanol (4:1, v/v) were collected and concentrated. The residue was dissolved in acetonitrile (4 ml), and trimethylsilyl cyanide (0.39 g, 3.9 mmol) and N,N-dimethylcarbamoyl chloride (0.38 g, 3.5 mmol) were added thereto. The reaction mixture was stirred at room temperature for 50 hrs and combined with ethyl acetate and water. The organic layer was successively washed with saturated aqueous sodium hydrogen carbonate solution, 1 N hydrochloric acid and saturated brine and dried over anhydrous magnesium sulfate. The solvent was evaporated, and the residue was subjected to a silica gel (20 g) column chromatography. The fractions eluted with hexane-ethyl acetate (3:1, v/v) were collected and concentrated to give the titled compound (0.54 g, 85%).

$^1$H-NMR (CDCl$_3$) δ: 0.05 (9H, s), 0.97 (2H, m), 0.98 (3H, s), 1.16 (3H, s), 4.16 (2H, m), 5.01 (1H, s), 7.44 (1H, d, J=5.4 Hz), 7.64 (1H, s), 8.64 (1H, d, J=5.4 Hz).

Reference Example 166

2-(Trimethylsilyl)ethyl 2,2-dimethyl-3-hydroxy-3-(4-pyridyl)propionate

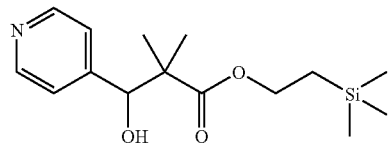

1.6 M n-butyl lithium in hexane (14.0 ml, 22.4 mmol) was added to a solution of diisopropylamine (2.3 g, 22.4 mmol) in tetrahydrofuran (15 ml) under ice cooling condition, and the mixture was stirred for 30 minutes. The reaction mixture was cooled to −78° C., and a solution of 2-(trimethylsilyl)ethyl isobutyrate (4.0 g, 21.2 mmol) in tetrahydrofuran (5 ml) was added dropwise to the mixture. The reaction mixture was stirred for 45 minutes. Successively, a solution of 4-pyridinecarbaldehyde (2.5 g, 23.3 mmol) in tetrahydrofuran (10 ml) was added to the mixture, and the mixture was stirred with warming from −78° C. to room temperature for 2.5 hrs. The reaction mixture was combined with saturated aqueous ammonium chloride solution and extracted with ethylacetate. The organic layer was washed with saturated brine and dried over anhydrous magnesium sulfate. The solvent was evaporated, and the residue was subjected to a silica gel (100 g) column chromatography. The fraction eluted with hexane-ethyl acetate (3:1, v/v) were collected and concentrated to give the titled compound (3.2 g, 51%) as a colorless oil.

$^1$H-NMR (CDCl$_3$) δ: 0.05 (9H, s), 1.00 (2H, m), 1.12 (3H, s), 1.14 (3H, s), 3.60 (1H, d, J=4.4 Hz), 4.21 (2H, m), 4.86 (1H, d, J=4.4 Hz), 7.24 (2H, d, J=6.0 Hz), 8.55 (2H, d, J=6.0 Hz).

Example 333

2,2-Dimethyl-3-[2-(4-oxo-4H-1,3-benzothiazin-2-yl)-4-pyridyl]propionate

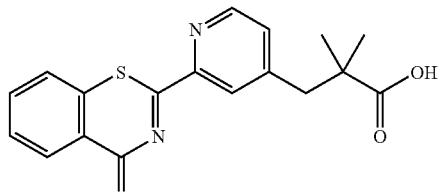

2-(Trimethylsilyl)ethyl 2,2-dimethyl-3-[2-(4-oxo-4H-1,3-benzothiazin-2-yl)-4-pyridyl]propionate (0.41 g, 0.93 mmol) was dissolved in tetrahydrofuran (5 ml), and 1.0 M tetrabutylammonium fluoride in tetrahydrofuran (2.2 ml, 2.2 mmol) was added thereto. The reaction mixture was stirred for 2 hrs. The reaction mixture was concentrated under reduced pressure. Trifluoroacetic acid (1.5 ml) was added to the mixture, and the mixture was stirred at room temperature for 13 hrs. Diisopropyl ether was added to the reaction mixture to precipitate solid, which was collected by filtration and recrystallized from ethanol-hexane to give the titled compound (0.10 g, 32%) as white crystals.

mp. 212.3-212.9° C. IR: 3514, 3056, 1714, 1620, 1520, 1470, 1318 cm$^{-1}$. $^1$H-NMR (DMSO-d$_6$) δ: 1.15 (6H, s), 3.00 (2H, s), 7.54 (1H, d, J=4.9 Hz), 7.76 (1H, t, J=7.9 Hz), 7.84 (1H, t, J=7.2 Hz), 7.92 (1H, m), 8.18 (1H, s), 8.37 (1H, d, J=7.8 Hz), 8.71 (1H, d, J=4.9 Hz), 12.52 (1H, br s).

Reference Example 167

2-(Trimethylsilyl)ethyl 2,2-dimethyl-3-[2-(4-oxo-4H-1,3-benzothiazin-2-yl)-4-pyridyl]propionate

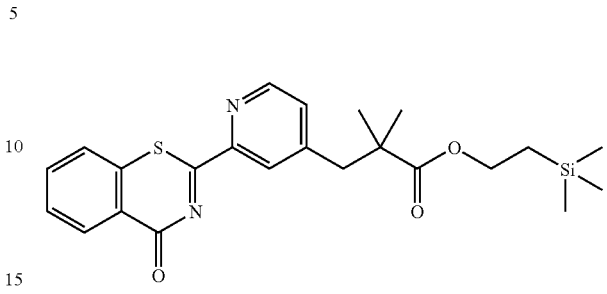

2-(Trimethylsilyl)ethyl 2,2-dimethyl-3-(2-cyano-4-pyridyl)propionate (0.68 g, 2.2 mmol) and methyl thiosalicylate (0.60 g, 3.6 mmol) were dissolved in toluene (2.5 ml), and triethylamine (0.56 ml, 4.0 mmol) was added thereto. The reaction mixture was refluxed for 16 hrs and subjected to a silica gel (30 g) column chromatography. The fractions eluted with hexane-ethyl acetate (5:1, v/v) were collected and concentrated to give the titled compound (0.52 g, 53%) as white crystals.

$^1$H-NMR (CDCl$_3$) δ: 0.03 (9H, s), 0.99 (2H, m), 1.23 (6H, s), 2.98 (2H, s), 4.18 (2H, m), 7.34 (1H, d, J=4.9 Hz), 7.60-7.71 (3H, m), 8.35 (1H, s), 8.55 (1H, d, J=8.0 Hz), 8.61 (1H, d, J=4.9 Hz).

Reference Example 168

2-(Trimethylsilyl)ethyl 2,2-dimethyl-3-(2-cyano-4-pyridyl)propionate

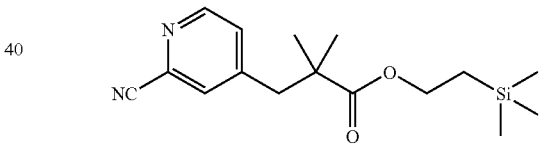

2-(Trimethylsilyl)ethyl 2,2-dimethyl-3-(4-pyridyl)propionate (0.77 g, 2.8 mmol) was dissolved in ethyl acetate (4 ml), and 3-chloroperbenzoic acid (ca. 77%, 0.68 g, 3.0 mmol) was added thereto. The reaction mixture was stirred at room temperature for 5 hrs and subjected to a silica gel (35 g) column chromatography. The fractions eluted with ethyl acetate-ethanol (4:1, v/v) were collected and concentrated. The residue was dissolved in acetonitrile (6 ml), and trimethylsilyl cyanide (0.49 g, 4.9 mmol) and N,N-dimethylcarbamoyl chloride(0.45 g, 4.2 mmol) were added thereto. The reaction mixture was stirred at room temperature for 14 hrs and combined with ethyl acetate and water. The organic layer was successively washed with saturated aqueous sodium hydrogen carbonate solution, 1 N hydrochloric acid and saturated brine and dried over magnesium sulfate. The solvent was evaporated, and the residue was subjected to a silica gel (30 g) column chromatography. The fractions eluted with hexane-ethyl acetate (5:1, v/v) were collected and concentrated to give the titled compound (0.69 g, 91%).

$^1$H-NMR (CDCl$_3$) δ: 0.05 (9H, s), 0.97 (2H, m), 1.20 (6H, s), 2.90 (2H, s), 4.16 (2H, m), 7.30 (1H, d, J=5.0 Hz), 7.50 (1H, s), 8.59 (1H, d, J=5.0 Hz).

Reference Example 169

2-(Trimethylsilyl)ethyl
2,2-dimethyl-3-(4-pyridyl)propionate

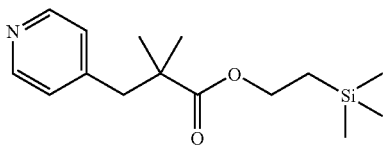

4-Pyridinemethanol (1.0 g, 9.2 mmol) was dissolved in tetrahydrofuran (10 ml), and triethylamine (1.5 ml, 10.9 mmol) and methanesulfonyl chloride (0.75 ml, 9.7 mmol) were successively added thereto under ice cooling condition. The mixture was stirred for 1 hr to produce mesylate. On the other hand, diisopropylamine (0.89 g, 8.8 mmol) was dissolved in tetrahydrofuran (10 ml), and 1.6 M n-butyl lithium in hexane (5.5 ml, 8.8 mmol) was added thereto under ice cooling condition. The reaction mixture was stirred for 30 minutes and cooled to −78° C. A solution of 2-(trimethylsilyl)ethyl isobutyrate (1.6 g, 8.3 mmol) in tetrahydrofuran (5 ml) was added dropwise to the mixture at −78° C., and the mixture was stirred for 1 hr. Successively, a solution of the mesylate produced above in tetrahydrofuran (10 ml) was added dropwise to the mixture at −78° C., and the mixture was stirred for 3 hrs while it was warmed to room temperature. The reaction mixture was filtered to remove the insolubles. The filtrate was combined with saturated aqueous ammonium chloride solution and extracted with ethyl acetate. The organic layer was washed with saturated brine and dried over magnesium sulfate. The solvent was evaporated, and the residue was subjected to a silica gel (30 g) column chromatography. The fractions eluted with hexane-ethyl acetate (3:1, v/v) were collected and concentrated to give the titled compound (0.77 g, 30%) as a colorless oil.

$^1$H-NMR (CDCl$_3$) δ: 0.03 (9H, s), 0.93 (2H, m), 1.18 (6H, s), 2.84 (2H, s), 4.15 (2H, m), 7.06 (2H, d, J=6.0 Hz), 8.48 (2H, d, J=6.0 Hz).

Example 334 tert-Butyl 3-[2-(6-(4-oxo-4H-1,3-benzothiazin-2-yl)-2-pyridyl)ethoxy]propanoate

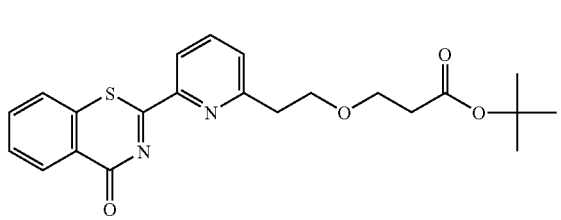

tert-Butyl 3-[(2-cyano-6-pyridyl)]ethoxypropanoate (2.76 g, 10 mmol) and methyl thiosalicylate (2.02 g, 12 mmol) were dissolved in toluene (25 ml), and triethylamine (1.81 ml, 13 mmol) was added thereto. The mixture was refluxed under nitrogen atmosphere for 20 hrs. The solvent was evaporated, and the residue was subjected to a silica gel column chromatography. The titled compound (1.55 g, 38%) was given as crystals from the fractions eluted with ethyl acetate-hexane (1:2, v/v).

mp. 67.7-68.5° C. $^1$H-NMR (CDCl$_3$) δ: 1.41 (9H, s), 2.48 (2H, t, J=6.4 Hz), 3.16 (2H, t, J=6.5 Hz), 3.74 (2H, t, J=6.4 Hz), 3.94 (2H, t, J=6.5 Hz), 7.45 (1H, dd, J=0.7, 7.9 Hz), 7.52-7.66 (3H, m), 7.79 (1H, t, J=7.7 Hz), 8.36 (1H, dd, J=0.7, 7.9 Hz), 8.54 (1H, dd, J=1.2, 7.5 Hz). IR(KBr): 1728, 1663, 1591, 1572, 1535, 1439, 1366, 1298, 1258, 1159, 1113, 1098, 995 cm$^{-1}$. Elemental Analysis for C$_{22}$H$_{24}$N$_2$O$_4$S.0.2 H$_2$O Calcd. C, 63.50; H, 5.91; N, 6.73. Found C, 64.06; H, 5.86; N, 6.64.

Example 335

3-[2-(6-(4-Oxo-4H-1,3-benzothiazin-2-yl)-2-pyridyl)ethoxy]propionic acid

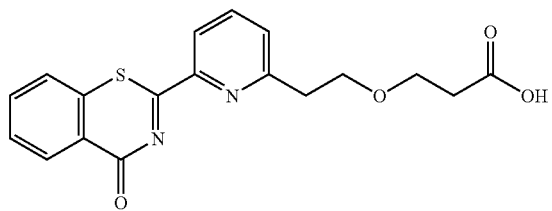

A mixture of tert-butyl 3-[2-(6-(4-oxo-4H-1,3-benzothiazin-2-yl)-2-pyridyl)ethoxy]propionate (0.41 g, 1.0 mmol) and trifluoroacetic acid (5 ml) was stirred at 0° C. for 2 hrs. The reaction mixture was concentrated under reduced pressure. The residue was recrystallized from ethyl acetate-hexane to give the titled compound (0.30 g, 85%).

mp. 236.6-236.7° C. $^1$H-NMR (CDCl$_3$) δ: 2.42 (2H, t, J=6.3 Hz), 3.09 (2H, t, J=6.6 Hz), 3.64 (2H, t, J=6.3 Hz), 3.84 (2H, t, J=6.6 Hz), 7.47-7.89 (5H, m), 8.17 (1H, d, J=7.7 Hz), 8.33 (1H, dd, J=1.3, 7.9 Hz), 12.10 (1H, br). IR(KBr): 3059, 1713, 1655, 1572, 1534, 1443, 1397, 1306, 1238, 1115, 1084, 1059, 1032, 995, 924 cm$^{-1}$. Elemental Analysis for C$_{18}$H$_{16}$N$_2$O$_4$S Calcd. C, 60.66; H, 4.53; N, 7.86. Found C, 60.22; H, 4.50; N, 7.66.

Example 336 tert-Butyl 3-[(6-(4-oxo-4H-1,3-benzothiazin-2-yl)-2-pyridyl)methoxy]propanoate

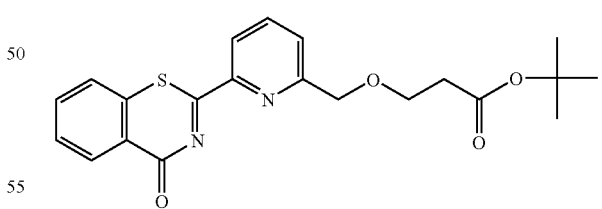

tert-Butyl 3-[(2-cyano-6-pyridyl)]methoxypropanoate (2.62 g, 10 mmol) and methyl thiosalicylate (1.85 g, 11 mmol) were dissolved in toluene (30 ml), and triethylamine (1.70 ml, 12 mmol) were added thereto. The reaction mixture was refluxed under nitrogen atmosphere for 15 hrs. The solvent was evaporated, and the residue was subjected to a silica gel column chromatography. The titled compound (2.92 g, 71%) was given from the fraction eluted with ethyl acetate-hexane (1:2, v/v) and recrystallized from ethyl acetate-isopropyl ether.

mp. 84.7-84.9° C. $^1$H-NMR (CDCl$_3$) δ: 1.36 (9H, s), 2.51 (2H, t, J=6.2Hz), 3.77 (2H, t, J=6.2 Hz), 4.64 (2H, s), 7.42-7.61 (4H, m), 7.78 (1H, t, J=7.8 Hz), 8.27 (1H, d, J=7.7 Hz), 8.38 (1H, d, J=7.8 Hz). IR(KBr): 1730, 1667, 1574, 1537, 1441, 1368, 1163, 1096, 1065, 1030, 995, 846, 802, 750 cm$^{-1}$. Elemental Analysis for C$_{21}$H$_{22}$N$_2$O$_4$S Calcd. C, 63.30; H, 5.56; N, 7.03. Found C, 63.15; H, 5.44; N, 7.28.

Example 337

3-[(6-(4-oxo-4H-1,3-benzothiazin-2-yl)-2-pyridyl)methoxy]propionic acid

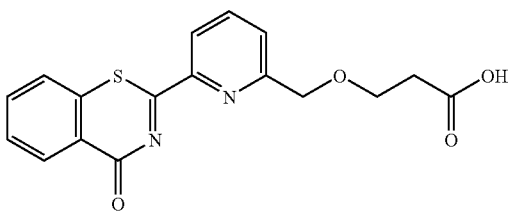

A mixture of tert-butyl 3-[(6-(4-oxo-4H-1,3-benzothiazin-2-yl)-2-pyridyl)methoxy]propanoate (2.80 g, 6.8 mmol) and trifluoroacetic acid (15 ml) was stirred at 0° C. for 3 hrs. The mixture was concentrated under reduced pressure, and the residue was crystallized from ethyl acetate-hexane to give the titled compound (1.78 g, 74%), which was recrystallized from ethanol to give prisms (1.66 g, 69%)

mp. 176.6-176.7° C. $^1$H-NMR (CDCl$_3$) δ: 2.57 (2H, t, J=6.2 Hz), 3.79 (2H, t, J=6.2 Hz), 4.68 (2H, s), 7.59-7.77 (3H, m), 7.89 (1H, d, J=7.4 Hz), 8.08 (1H, t, J=7.7 Hz), 8.23 (1H, d, J=7.4 Hz), 8.32 (1H, dd, J=1.1, 7.8 Hz) IR(KBr): 3063, 1738, 1647, 1590, 1570, 1526, 1477, 1437, 1304, 1273, 1194, 1121, 1103, 1063, 1046, 995, 866, 802 cm$^{-1}$. Elemental Analysis for C$_{17}$H$_{14}$N$_2$O$_4$S Calcd. C, 59.64; H, 4.12; N, 8.18. Found C, 59.60; H, 3.82; N, 8.07.

Example 338 tert-Butyl 3-[6-(8-methyl-4-oxo-4H-1,3-benzothiazin-2-yl)-2-pyridyl]propanoate

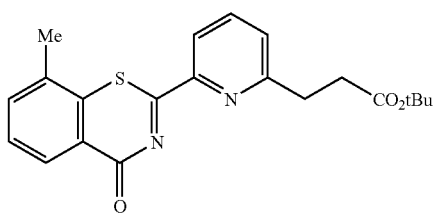

A mixture of 3-methylthiosalicylic acid (2.52 g, 15 mmol), tert-butyl 3-(6-cyano-2-pyridyl)propanoate (2.32 g, 10 mmol) and pyridine (30 ml) was refluxed under nitrogen atmosphere for 20 hrs and concentrated under reduced pressure. The residue was subjected to a silica gel (100 g) column chromatography. The titled compound (2.79 g, 73%) was given from the fractions eluted with hexane-ethyl acetate (2:1, v/v), which were recrystallized from ethyl acetate-isopropyl ether.

mp. 109.9-110.0° C. $^1$H-NMR (CDCl$_3$) δ: 1.41 (9H, s), 2.61 (3H, s), 2.88 (2H, t, J=7.3 Hz), 3.21 (2H, t, J=7.3 Hz), 7.42 (1H, d, J=7.7 Hz), 7.44-7.53 (2H, m), 7.80 (1H, t, J=7.8 Hz), 8.38 (1H, d, J=7.8 Hz), 8.43 (1H, dd, J=2.6, 6.8 Hz). IR(KBr): 2976, 1728, 1661, 1537, 1454, 1366, 1308, 1152, 1098, 993, 912, 847, 814 cm$^{-1}$. Elemental Analysis for C$_{21}$H$_{22}$N$_2$O$_3$S Calcd. C, 65.95; H, 5.80; N, 7.32. Found C, 65.96; H, 5.71; N, 7.24.

Example 339 tert-Butyl 3-[2-cyano-6-(4-oxo-4H-1,3-benzothiazin-2-yl)-3-pyridyl]propanoate

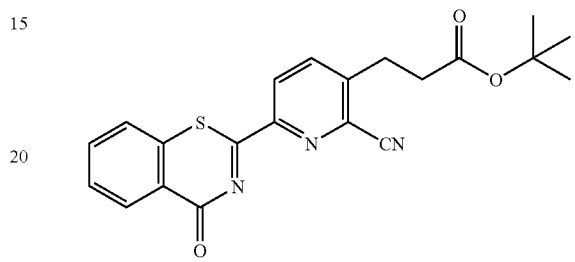

tert-Butyl 3-(2,6-dicyano-3-pyridyl)propanoate (0.31 g, 1.20 mmol) and methyl thiosalicylate (0.40 g, 2.40 mmol) were dissolved in toluene (30 ml), and triethylamine (0.75 ml, 5.41 mmol) was added thereto. The mixture was refluxed for 18 hrs, and the solvent was evaporated. The residue was washed with hexane-ethyl acetate to give the titled compound (0.12 g, 25%) as white amorphous solid.

mp. 196.3-196.8° C. $^1$H-NMR (CDCl$_3$) δ: 1.41 (9H, s), 2.73 (2H, t, J=7.2 Hz), 3.25 (2H, t, J=7.1 Hz), 7.64-7.75 (3H, m), 7.99 (1H, d, J=8.2 Hz), 8.55 (1H, d, J=7.7 Hz), 8.65 (1H, d, J=8.2 Hz). IR(KBr): 2233, 1712, 1651, 1570, 1529, 1444, 1369, 1348, 1300, 1267, 1161, 1138, 1084, 1064, 979, 856, 750 cm$^{-1}$.

Example 340

3-[2-Cyano-6-(4-oxo-4H-1,3-benzothiazin-2-yl)-3-pyridyl]propanoate

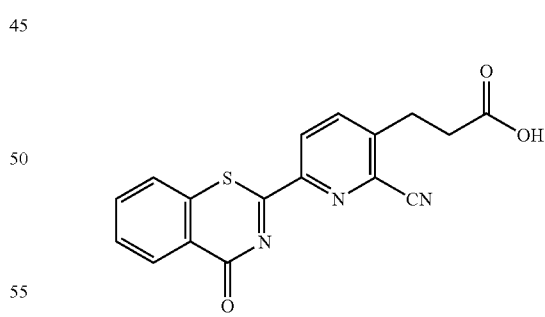

tert-Butyl 3-[2-cyano-6-(4-oxo-4H-1,3-benzothiazin-2-yl)-3-pyridyl]propanoate (0.06 g, 0.15 mmol) was dissolved in trifluoroacetic acid (3 ml), and the mixture was stirred at room temperature for 0.5 hr. The reaction mixture was combined with diisopropyl ether to give precipitates, which were recrystallized from ethanol to give the titled compound (0.037 g, 74%) as white crystals.

mp. 283.8° C. (decomposed) $^1$H-NMR (DMSO-d$_6$) δ: 2.78 (2H, t, J=7.3 Hz), 3.15 (2H, t, J=7.2 Hz), 7.72-7.78(1H, m), 7.83-7.88 (1H, m), 7.99 (1H, d, J=7.3 Hz), 8.30 (1H, d, J=8.3

Hz), 8.35-8.38 (1H, m), 8.54 (1H, d, J=8.3 Hz), 12.3 (1H, br s). IR(KBr): 3078, 1732, 1620, 1614, 1591, 1568, 1518, 1442, 1429, 1315, 1271, 1207, 1161, 1130, 1109, 1032, 989, 862, 752 cm$^{-1}$. Fab Mass(M+1)=338.1 (theoretical value)=338.1

Example 341 tert-Butyl 3-[2-(methylthio)-6-(4-oxo-4H-1,3-benzothiazin-2-yl)-4-pyridyl]propanoate

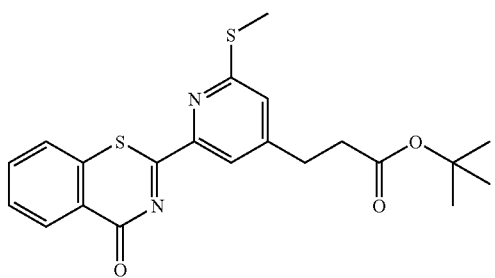

tert-Butyl 3-[2-cyano-6-(methylthio)-4-pyridyl]propanoate (0.70 g, 2.50 mmol) and methyl thiosalicylate (0.84 g, 5.00 mmol) were dissolved in toluene (50 ml), and triethylamine (1.40 ml, 10.0 mmol) was added thereto. The reaction mixture was refluxed for 18 hrs, and the solvent was evaporated. The residue was recrystallized from hexane-ethyl acetate to give the titled compound (0.59 g, 57%) as pale yellow crystals.

mp. 125.5-126.5° C. $^1$H-NMR (CDCl$_3$) δ: 1.43 (9H, s), 2.60 (2H, t, J=7.4 Hz), 2.71 (3H, s), 2.94 (2H, t, J=7.5 Hz), 7.28 (1H, s), 7.60-7.70 (3H, m), 8.09 (1H, s), 8.54-8.57 (1H, m). IR(KBr): 2974, 1726, 1660, 1593, 1572, 1537, 1439, 1392, 1365, 1294, 1257, 1234, 1149, 1095, 1030, 864, 746 cm$^{-1}$. Elemental Analysis for C$_{21}$H$_{22}$N$_2$O$_3$S$_2$ Calcd. C, 60.84; H, 5.35; N, 6.76. Found C, 60.56; H, 5.43; N, 6.52.

Example 342

3-[2-(Methylthio)-6-(4-oxo-4H-1,3-benzothiazin-2-yl)-4-pyridyl]propionic acid

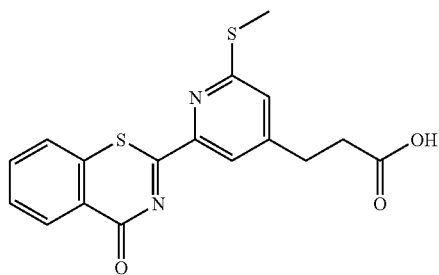

tert-Butyl 3-[2-(methylthio)-6-(4-oxo-4H-1,3-benzothiazin-2-yl)-4-pyridyl]propanoate (0.12 g, 0.29 mmol) was dissolved in trifluoroacetic acid (5 ml), and the mixture was stirred at room temperature for 0.5 hr. Diisopropyl ether was combined with the reaction mixture to give precipitates, which were recrystallized from ethanol to give the titled compound (0.09 g, 87%) as pale yellow crystals.

mp. 235.5-236.5° C. $^1$H-NMR (DMSO-d$_6$) δ: 2.66 (2H, t, J=7.5 Hz), 2.67 (3H, s), 2.94 (2H, t, J=7.3 Hz), 7.56 (1H, s), 7.70-7.75 (1H, m), 7.80-7.85 (1H, m), 7.92-7.96 (2H, m), 8.34-8.37 (1H, m), 12.2 (1H, br s). IR(KBr): 3067, 1732, 1637, 1595, 1574, 1537, 1431, 1307, 1277, 1234, 1190, 1180, 1163, 1101, 1016, 891, 866, 740 cm$^{-1}$ Elemental Analysis for C$_{17}$H$_{14}$N$_2$O$_3$S$_2$ Calcd. C, 56.96; H, 3.94; N, 7.82. Found C, 56.77; H, 3.89; N, 7.64.

Example 343 tert-Butyl 3-[2-(methylsulfinyl)-6-(4-oxo-4H-1,3-benzothiazin-2-yl)-4-pyridyl]propanoate

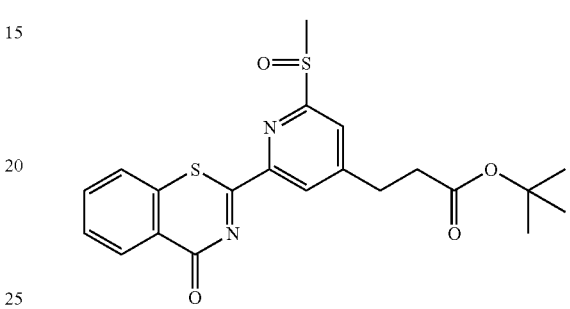

tert-Butyl 3-[2-(methylthio)-6-(4-oxo-4H-1,3-benzothiazin-2-yl)-4-pyridyl]propanoate (0.22 g, 0.53 mmol) was dissolved in chloroform (50 ml), and a solution of 3-chloroperbenzoic acid (77%, 0.12 g, 0.53 mmol) in chloroform (10 ml) was added dropwise thereto. The mixture was stirred at room temperature for 1 hr. The solvent was evaporated, and the residue was recrystallized from hexane-ethyl acetate to give the titled compound (0.17 g, 86%) as white crystals.

mp. 219.5-220.0° C. $^1$H-NMR (CDCl$_3$) δ: 1.44 (9H, s), 2.70 (2H, t, J=7.5 Hz), 2.97 (3H, s), 3.13 (2H, t, J=7.5 Hz), 7.59-7.72 (3H, m), 8.12 (1H, d, J=1.2 Hz), 8.47 (1H, d, J=1.1 Hz), 8.55-8.58 (1H, m). IR(KBr): 2976, 1722, 1662, 1589, 1572, 1537, 1439, 1367, 1292, 1147, 1095, 1062, 1030, 738 cm$^{-1}$. Elemental Analysis for C$_{21}$H$_{22}$N$_2$O$_4$S$_2$·0.25H$_2$O Calcd. C, 57.98; H, 5.21; N, 6.44. Found C, 58.08; H, 5.15; N, 6.25.

Example 344

3-[2-(methylsulfinyl)-6-(4-oxo-4H-1,3-benzothiazin-2-yl)-4-pyridyl]propionic acid

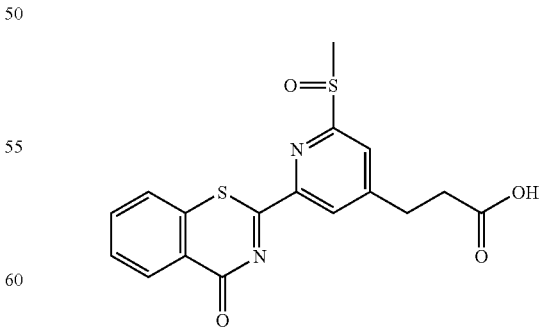

tert-Butyl 3-[2-(methylsulfinyl)-6-(4-oxo-4H-1,3-benzothiazin-2-yl)-4-pyridyl]propanoate (0.12 g, 0.28 mmol) was dissolved in trifluoroacetic acid (5 ml), and the mixture was stirred at room temperature for 0.5 hr. Diisopropyl ether was combined with the reaction mixture to give precipitates, which were recrystallized from ethanol to give the titled compound (0.095 g, 91%) as white crystals.

mp. 265.5-266.0° C. $^1$H-NMR (DMSO-$d_6$) δ: 2.74 (2H, t, J=7.3 Hz), 2.93 (3H, s), 3.13 (2H, t, J=7.2 Hz), 7.75-7.78 (1H, m), 7.83-7.88 (1H, m), 7.96 (1H, d, J=7.4 Hz), 8.12 (1H, d, J=1.1 Hz), 8.34-8.39 (1H, m), 12.3 (1H, br s). IR(KBr): 2955, 1722, 1657, 1589, 1570, 1537, 1439, 1413, 1340, 1294, 1221, 1176, 1155, 1126, 1097, 1068, 1018, 993, 877, 750 cm$^{-1}$. Elemental Analysis for $C_{17}H_{14}N_2O_4S_2$ Calcd. C, 54.53; H, 3.77; N, 7.48. Found C, 54.38; H, 3.98; N, 7.28.

Example 345 tert-Butyl 3-[2-(methylsulfonyl)-6-(4-oxo-4H-1,3-benzothiazin-2-yl)-4-pyridyl]propanoate

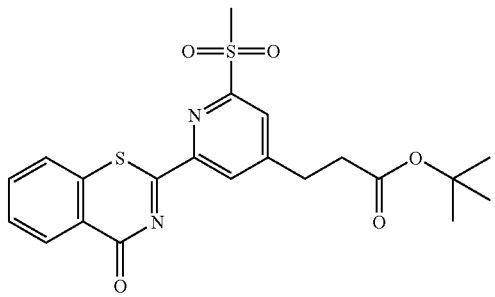

tert-Butyl 3-[2-(methylthio)-6-(4-oxo-4H-1,3-benzothiazin-2-yl)-4-pyridyl]propanoate (0.20 g, 0.48 mmol) was dissolved in chloroform (50 ml), and a solution of 3-chloroperbenzoic acid (77%, 0.22 g, 0.97 mmol) in chloroform (10 ml) was added dropwise thereto. The mixture was stirred at room temperature for 3 hrs. The solvent was evaporated, and the residue was recrystallized from hexane-ethyl acetate to give the titled compound (0.060 g, 28%) as white crystals.

mp. 223.0° C. (decomposed) $^1$H-NMR (CDCl$_3$) δ: 1.44 (9H, s), 2.70 (2H, t, J=7.4 Hz), 3.15 (2H, t, J=7.3 Hz), 3.37 (3H, s), 7.62-7.74 (3H, m), 8.16 (1H, d, J=0.8 Hz), 8.55-8.59 (1H, m), 8.63 (1H, d, J=0.8 Hz). IR(KBr): 2976, 1720, 1664, 1591, 1570, 1535, 1439, 1367, 1306, 1292, 1234, 1149, 1128, 1095, 1066, 1030, 960, 748 cm$^{-1}$. Elemental Analysis for $C_{21}H_{22}N_2O_5S_2$ Calcd. C, 56.48; H, 4.97; N, 6.27. Found C, 56.30; H, 5.00; N, 6.18.

Example 346

3-[2-(Methylsulfonyl)-6-(4-oxo-4H-1,3-benzothiazin-2-yl)-4-pyridyl]propionic acid

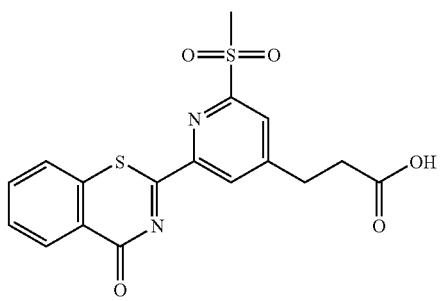

tert-Butyl 3-[2-(methylsulfonyl)-6-(4-oxo-4H-1,3-benzothiazin-2-yl)-4-pyridyl]propanoate (0.20 g, 0.45 mmol) was dissolved in trifluoroacetic acid (5 ml), and the mixture was stirred at room temperature for 0.5 hr. Diisopropyl ether was combined with the reaction mixture to give precipitates, which were recrystallized from ethanol to give the titled compound (0.11 g, 63%) as pale yellow crystals.

mp. 305.5-306.0° C. $^1$H-NMR (DMSO-$d_6$) δ: 2.75 (2H, t, J=7.2 Hz), 3.15 (2H, t, J=7.1 Hz), 3.45 (3H, s), 7.76-7.79 (1H, m), 7.84-7.89 (1H, m), 7.99 (1H, d, J=7.6 Hz), 8.28 (1H, d, J=0.9 Hz), 8.37-8.40 (1H, m), 8.52 (1H, d, J=0.9 Hz), 12.2 (1H, br s). IR(KBr) 3069, 1741, 1630, 1591, 1568, 1533, 1462, 1439, 1423, 1400, 1305, 1238, 1170, 1155, 1130, 1101, 1066, 1030, 1010, 906, 756 cm$^{-1}$. Elemental Analysis for $C_{17}H_{14}N_2O_5S_2$ Calcd. C, 52.30; H, 3.61; N, 7.17. Found C, 52.16; H, 3.72; N, 6.98.

Example 347

2-(2-Methyl-1,3-thiazol-4-yl)-4H-1,3-benzothiazin-4-one

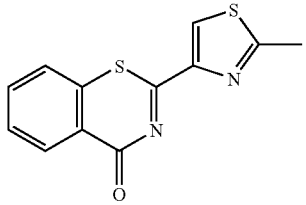

2-Methyl-1,3-thiazole-4-carbonitrile (0.46 g, 3.7 mmol) and methyl thiosalicylate (1.26 g, 7.4 mmol) were dissolved in toluene (6 ml), and triethylamine (3.0 ml, 21.5 mmol) was added thereto. The mixture was refluxed for 15 hrs. After cooling, the precipitates were collected by filtration and recrystallized from ethanol to give the titled compound (0.75 g, 78%) as white crystals.

mp. 219.0-220.0° C. $^1$H-NMR (CDCl$_3$) δ: 2.83 (3H, s), 7.55-7.70 (3H, m), 8.44 (1H, s), 8.55 (1H, m). IR(KBr): 3098, 1645, 1574, 1531, 1288, 1159, 740 cm$^{-1}$. Elemental Analysis for $C_{12}H_8N_2OS_2$ Calcd. C, 55.36; H, 3.10; N, 10.76. Found C, 55.53; H, 3.25; N, 10.71.

Example 348

2-(1,3-thiazol-2-yl)-4H-1,3-benzothiazin-4-one

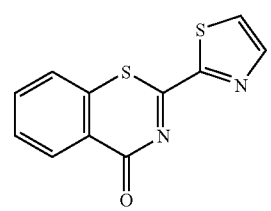

1,3-Thiazole-2-carbonitrile (0.32 g, 2.9 mmol) and methyl thiosalicylate (0.98 g, 5.8 mmol) were dissolved in toluene (4 ml), and triethylamine (2.0 ml, 14.3 mmol) was added thereto. The reaction mixture was refluxed for 2 hrs. After cooling, the precipitates were collected by filtration and recrystallized from diisopropyl ether-ethanol to give the titled compound (0.51 g, 70%) as yellow crystals.

mp. 229.1-229.8° C. $^1$H-NMR (CDCl$_3$) δ: 7.60 (1H, m), 7.63 (1H, m), 7.68 (1H, m), 7.73 (1H, m), 8.10 (1H, m), 8.55 (1H, d, J=7.8 Hz). IR(KBr): 3126, 1666, 1655, 1535, 1292,

Example 349

2-(4-Methyl-1,3-thiazol-2-yl)-4H-1,3-benzothiazin-4-one

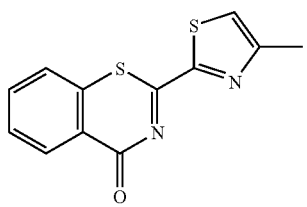

4-Methyl-1,3-thiazole-2-carbonitrile (0.27 g, 2.2 mmol) and methyl thiosalicylate (0.75 g, 4.4 mmol) were dissolved in toluene (4 ml), and triethylamine (2.0 ml, 14.3 mmol) was added thereto. The reaction mixture was refluxed for 6 hrs. After cooling, the precipitates were collected by filtration and recrystallized from ethanol to give the titled compound (0.28 g, 49%) as yellow crystals.

mp. 209.6-210.7° C. $^1$H-NMR (CDCl$_3$) δ: 2.58 (3H, s), 7.30 (1H, s), 7.56 (1H, d, J=7.6 Hz), 7.60-7.71 (2H, m), 8.54 (1H, dd, J=0.7, 7.6 Hz). IR(KBr): 3098, 1658, 1525, 1504, 1286, 738 cm$^{-1}$. Elemental Analysis for C$_{12}$H$_8$N$_2$OS$_2$ Calcd. C, 55.39; H, 3.10; N, 10.76. Found C, 55.23; H, 3.11; N, 10.55.

Example 350

2-[4-(1-Benzoyl-2-pyrrolidinyl)-2-pyridyl]-4H-1,3-benzothiazin-4-one

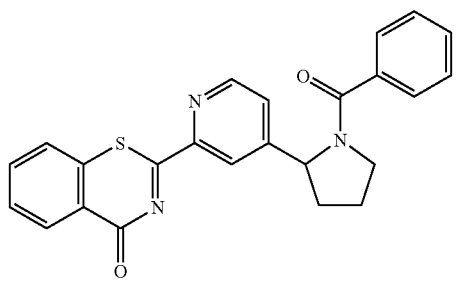

4-(1-Benzoyl-2-pyrrolidinyl)-2-pyridinecarbonitrile (0.42 g, 1.5 mmol) and methyl thiosalicylate (1.03 g, 6.1 mmol) were dissolved in toluene (4 ml), and triethylamine (2.0 ml, 14.3 mmol) was added thereto. The mixture was refluxed for 14 hrs. The solvent was evaporated, and the residue was subjected to a silica gel column chromatography. The fractions eluted with ethyl acetate-hexane (4:1, v/v) were collected and concentrated to give the titled compound (0.52 g, 82%) as amorphous crystals.

$^1$H-NMR (CDCl$_3$) δ: 1.95-2.02 (3H, m), 2.40 (0.16H, m), 2.56 (0.83H, m), 3.72 (0.83H, m), 3.83-3.91 (1H, m), 4.04 (0.16H, m), 5.01 (0.16H, m), 5.32 (0.83H, m), 7.15 (0.83H, s), 7.30 (0.16H, s), 7.43-7.51 (3H, m), 7.60-7.71 (5H, m), 8.14 (0.16H, m), 8.49 (0.83H, s), 8.55 (1H, d, J=8.0 Hz), 8.67 (1H, d, J=4.8 Hz). IR(KBr): 3057, 2974, 2876, 1658, 1631, 1572, 1537, 1408, 1294, 1095 cm$^{-1}$. Elemental Analysis for C$_{24}$H$_{19}$N$_3$O$_2$S.0.25H$_2$O Calcd. C, 68.96; H, 4.70; N, 10.05. Found C, 68.71; H, 4.79; N, 9.71.

Example 351

2-[4-(1-Acetyl-2-pyrrolidinyl)-2-pyridyl]-4H-1,3-benzothiazine-4-one

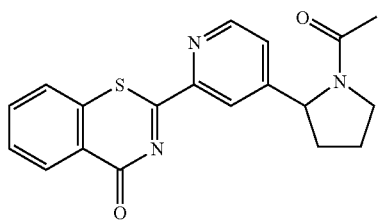

4-(1-Acetyl-2-pyrrolidinyl)-2-pyridinecarbonitrile (0.32 g, 1.5 mmol) and methyl thiosalicylate (1.02 g, 6.0 mmol) were dissolved in toluene (4 ml), and triethylamine (2.0 ml, 14.3 mmol) was added thereto. The mixture was refluxed for 24 hrs. The solvent was evaporated, and the residue was subjected to a silica gel column chromatography. The fractions eluted with ethyl acetate-methanol (8:1, v/v) were collected, concentrated and recrystallized from diethyl ether-methanol to give the titled compound (0.25 g, 48%) as white crystals.

mp. 206.2-207.4° C. $^1$H-NMR (CDCl$_3$) δ: 1.64 (1H, s), 1.84-2.07 (3H, m), 2.17 (2H, s), 2.39 (0.67H, m), 2.50 (0.33H, m), 3.67 (0.67H, m), 3.77-3.85 (1.33H, m), 5.03 (0.33H, m), 5.18 (0.67H, m), 7.32-7.35 (1H, m), 7.60-7.71 (3H, m), 8.33 (0.67H, s), 8.45 (0.33H, s), 8.53-8.56 (1H, m), 8.64 (0.67H, d, J=4.9 Hz), 8.72 (0.33H, d, J=4.9 Hz). IR(KBr): 3437, 2974, 2876, 1651, 1570, 1535, 1439, 1415, 1296, 1282, 1095 cm$^{-1}$. Elemental Analysis for C$_{19}$H$_{17}$N$_3$O$_2$S Calcd. C, 64.94; H, 4.88; N, 11.96. Found C, 64.64; H, 4.98; N, 11.81.

Example 352 tert-Butyl 2-[2-(4-oxo-4H-1,3-benzothiazin-2-yl)-4-pyridyl]-1-pyrrolidinecarboxylate

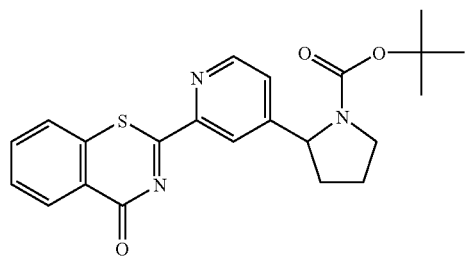

tert-Butyl 2-(2-cyano-4-pyridyl)-1-pyrrolidinecarboxylate (1.6 g, 6.0 mmol) and methyl thiosalicylate (3.0 g, 18.3 mmol) were dissolved in toluene (10 ml), and triethylamine (5.0 ml, 35.8 mmol) was added thereto. The mixture was refluxed for 18 hrs. The solvent was evaporated, and the residue was subjected to a silica gel column chromatography. The fractions eluted with ethyl acetate-hexane (1:1, v/v) were collected, concentrated and recrystallized from hexane-tetrahydrofuran to give the titled compound (1.5 g, 63%) as white crystals.

mp. 194.8-195.8° C. $^1$H-NMR (CDCl$_3$) δ: 1.19 (5.4H, s), 1.46 (3.6H, s), 1.80-1.96 (3H, m), 2.41 (1H, m), 3.59 (0.4H, m), 3.67 (1.6H, m), 4.85 (0.6H, m), 4.96 (0.4H, m), 7.36 (1H, m), 7.61-7.71 (3H, m), 8.40 (1H, s), 8.56 (1H, d, J=7.5 Hz), 8.65 (1H, d, J=4.6 Hz). IR(KBr): 2974, 1693, 1666, 1537, 1392, 1165 cm$^{-1}$. Elemental Analysis for C$_{22}$H$_{23}$N$_3$O$_3$S Calcd. C, 64.53; H, 5.66; N, 10.26. Found C, 64.48; H, 5.64; N, 10.13.

Example 353

2-[4-(2-Pyrrolidinyl)-2-pyridyl]-4H-1,3-benzothiazine-4-one trifluoroacetic acid salt

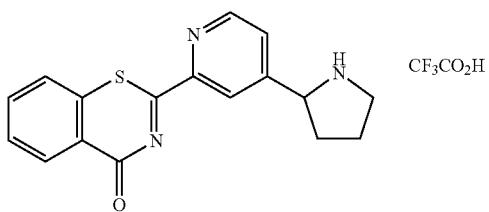

tert-Butyl 2-[2-(4-oxo-4H-1,3-benzothiazin-2-yl)-4-pyridyl]-1-pyrrolidinecarboxylate (0.35 g, 0.85 mmol) was dissolved in trifluoroacetic acid (5 ml), and the mixture was stirred at room temperature for 3 hrs. The solvent was evaporated, and the residue was recrystallized from diisopropyl ether-methanol to give the titled compound (0.31 g, 85%) as white crystals.

mp. 187.5-189.0° C. $^1$H-NMR (DMSO-d$_6$) δ: 1.97-2.21 (3H, m), 2.56 (1H, m), 3.33-3.50 (2H, m), 4.80 (1H, m), 7.75 (1H, m), 7.83-7.88 (2H, m), 7.95 (1H, d, J=8.0 Hz), 8.37 (1H, d, J=7.9 Hz), 8.52 (1H, s), 8.89 (1H, d, J=4.9 Hz), 9.48 (2H, br s). IR(KBr): 2984, 2762, 1660, 1535, 1203, 1172, 1124, 827 cm$^{-1}$. Elemental Analysis for C$_{19}$H$_{16}$N$_3$O$_3$SF$_3$ Calcd. C, 53.90; H, 3.81; N, 9.92. Found C, 53.74; H, 3.91; N, 9.96.

Example 354

2-[4-(2-Pyrrolidinyl)-2-pyridyl]-4H-1,3-benzothiazine-4-one hydrochloride salt

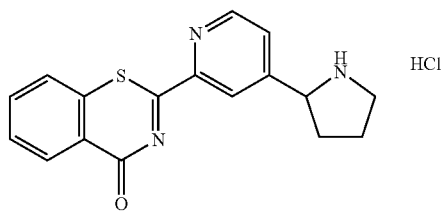

tert-Butyl 2-[2-(4-oxo-4H-1,3-benzothiazin-2-yl)-4-pyridyl]-1-pyrrolidinecarboxylate (0.40 g, 0.97 mmol) was dissolved in ethyl acetate (25 ml), and 4 N hydrogen chloride-ethyl acetate solution (8 ml) was added dropwise thereto at room temperature. The mixture was stirred at the same temperature for 30 minutes. The precipitates were collected by filtration and recrystallized from diethyl ether-methanol to give the titled compound (0.10 g, 31%) as white crystals.

mp. 219.4-221.4° C. $^1$H-NMR (DMSO-d$_6$) δ: 2.00-2.15 (3H, m), 2.52 (1H, m), 3.34-3.47 (2H, m), 4.77 (1H, m), 7.74 (1H, m), 7.86 (1H, m), 7.93-7.96 (2H, m), 8.38 (1H, m), 8.49 (1H, s), 8.88 (1H, d, J=5.0 Hz), 9.49 (1H, br s), 10.27 (1H, br s). Elemental Analysis for C$_{17}$H$_{16}$N$_3$OSCl.0.25H$_2$O Calcd. C, 58.28; H, 4.75; N, 11.99. Found C, 58.18; H, 4.84; N, 11.94.

Example 355 tert-Butyl 3-[2-cyano-6-(4-oxo-4H-1,3-benzothiazin-2-yl)-4-pyridyl]propanoate

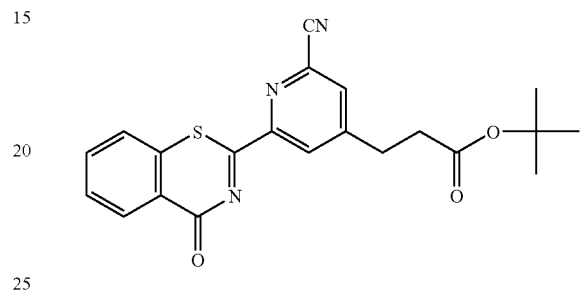

tert-Butyl 3-(2,6-dicyano-4-pyridyl)propanoate (1.4 g, 5.5 mmol) and methyl thiosalicylate (1.7 g, 10.1 mmol) were dissolved in toluene (10 ml), and triethylamine (5.0 ml, 35.8 mmol) was added thereto. The mixture was refluxed for 3 hrs. The solvent was evaporated, and the residue was subjected to a silica gel column chromatography. The fractions eluted with ethyl acetate-hexane (2:3, v/v) were collected, concentrated and recrystallized from hexane-tetrahydrofuran to give the titled compound (0.79 g, 36%) as white crystals.

mp. 189.9-190.7° C. $^1$H-NMR (CDCl$_3$) δ: 1.43 (9H, s), 2.67 (2H, t, J=7.2 Hz), 3.08 (2H, t, J=7.2 Hz), 7.64-7.73 (3H, m), 7.79 (1H, d, J=1.4 Hz), 8.56 (1H, m), 8.61 (1H, d, J=1.4 Hz). IR(KBr): 2978, 2932, 1724, 1664, 1572, 1537, 1294, 1151 cm$^{-1}$. Elemental Analysis for C$_{21}$H$_{19}$N$_3$O$_3$S Calcd. C, 64.10; H, 4.87; N, 10.68. Found C, 64.13; H, 5.10; N, 10.44.

Example 356

3-[2-Cyano-6-(4-oxo-4H-1,3-benzothiazin-2-yl)-4-pyridyl]propanoate

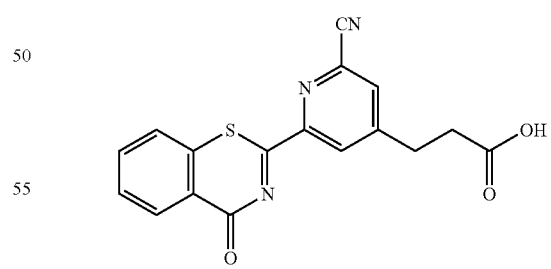

tert-Butyl 3-[2-cyano-6-(4-oxo-4H-1,3-benzothiazin-2-yl)-4-pyridyl]propanoate (0.41 g, 1.05 mmol) was dissolved in trifluoroacetic acid (5 ml), and the mixture was stirred at 0° C. for 2 hrs. The solvent was evaporated, and the residue was recrystallized from methanol to give the titled compound (0.27 g, 76%) as pale yellow crystals.

mp. 271.0-272.7° C. $^1$H-NMR (DMSO-d$_6$) δ: 2.74 (2H, t, J=7.3 Hz), 3.06 (2H, t, J=7.3 Hz), 7.74 (1H, m), 7.85 (1H, m), 7.97 (1H, d, J=8.0 Hz), 8.32 (1H, s), 8.35 (1H, d, J=7.9 Hz), 8.50 (1H, s), 12.29 (1H, br s). IR(KBr): 3074, 1724, 1635, 1589, 1535, 1440, 1317, 1161, 887 cm$^{-1}$. Elemental Analysis for $C_{17}H_{11}N_3O_3S \cdot 0.25H_2O$ Calcd. C, 59.73; H, 3.39; N, 12.29. Found C, 59.82; H, 3.69; N, 11.97.

Experimental Example 1

Inhibitory Activity on Heart Muscle Cell Apoptosis

Newborn rats (within 1 day after birth) were obtained from pregnant Wister rats purchased from Charles River, anesthetized under ether, and sterilized with 70% ethanol, and then their hearts were excised with tweezers. The excised hearts were washed with a phosphate-buffered physiological saline (T900; Takara) and cut into pieces with surgical scissors. These tissue pieces were washed 4 to 5 times with a phosphate-buffered physiological saline to remove a majority of blood-derived non-heart muscle cells. To the tissue pieces derived from 10 newborns, 5 ml of enzyme solution (1.25 mg trypsin (Difco) and 0.25 mg collagenase (Sigma) per ml of phosphate-buffered saline (PBS)) was added and the mixture was stirred with a stirrer at 37° C. for 15 minutes. Another 2.5 ml enzyme solution was then added twice repeatedly at a 15-minutes interval. Then, Medium 199 (Gibco) containing 10% fetal calf serum (Biowiker) was added in a half volume of the enzyme solution to terminate the enzyme reaction. The cells were filtered through a Cell Strainer (Falcon) and then centrifuged at 400×g for 5 minutes, whereby the cells were collected.

The cells thus collected from 10 newborns were suspended in 50 ml Medium 199 containing 10% fetal calf serum, plated onto 100 mm Petri dishes (Iwaki) in a volume of 10 ml/dish and cultured for 1 hour in a $CO_2$ incubator set at 5% $CO_2$ and 37° C. The cells were then recovered, filtered through a Cell Strainer and centrifuged at 400×g for 5 minutes to collect the primary heart muscle cells derived from newborn rats.

Then, the heart muscle cells from 10 newborn rats were suspended in 2 ml low-isotonic solution (prepared by dissolving 8.29 g $NH_4Cl$, 1.0 g $KHCO_3$, 37 mg EDTA/2Na (ethylenediaminetetraacetic acid disodium) (Dojindo) in 1 L of water) and left for 3 minutes to disrupt erythrocytes. After 10 ml Medium 199 containing 10% fetal calf serum was added thereto, the primary heart muscle cells from newborn rats were collected by centrifugation at 400×g for 5 minutes. The cells were suspended in Medium 199 containing 10% fetal calf serum and then filtered through a cell strainer. After 0.3% trypan blue was added to, and mildly mixed with, an aliquot of the resulting cell suspension, the number of heart muscle cells was counted on an erythrocyte counting plate.

The primary heart muscle cells from newborn rats were suspended at a density of $3 \times 10^6$ cells/ml in Medium 199 containing 10% fetal calf serum, put onto a 96-well plate in a volume of 0.1 ml/well, and then cultured in a $CO_2$ incubator set at 5% $CO_2$ and 37° C. After the plate was stirred with a micromixer (Taiyo Kagaku Kogyo), the medium was exchanged 3 times with serum-free Medium 199, and then test compounds were added thereto. The cells were cultured for additional 4 days to induce apoptosis. Then, fetal calf serum was added thereto at a concentration of 10%, and the cells were further cultured for about 17 hours in a $CO_2$ incubator set at 5% $CO_2$ and 37° C. Finally, the number of viable cells was determined with Cell Counting Kit (Dojindo) using WST-8 (2-(2-methoxy-4-nitrophenyl)-3-(4-nitrophenyl)-5-(2,4-disulfophenyl)-2H-tetrazolium, monosodium salt) as the coloring substrate to determine the inhibition of the heart muscle cell apoptosis.

The above-mentioned experiment was triplicated in an independent manner.

The Mean minimal effective concentration (±SD) was shown for each test compound (Compounds 1 to 5 obtained in Reference Examples) in Table 1. In Table 1, the minimal effective concentration is defined as the concentration required to increase the mean viable cell number by 50% as compared with that in the absence of test compounds.

TABLE 1

| Ex. Compound No. | Minimal Effective Concentration (µM) |
|---|---|
| 7 | 0.021 |
| 10 | 0.023 |
| 19 | 0.025 |
| 20 | 0.038 |
| 21 | 0.030 |
| 28 | 0.025 |
| 29 | 0.035 |
| 30 | 0.012 |
| 37 | 0.037 |
| 38 | 0.013 |
| 39 | 0.037 |
| 40 | 0.044 |
| 43 | 0.053 |
| 47 | 0.017 |
| 48 | 0.043 |
| 49 | 0.043 |
| 50 | 0.020 |
| 51 | 0.034 |
| 52 | 0.010 |
| 53 | 0.032 |
| 54 | 0.037 |
| 55 | 0.016 |
| 56 | 0.039 |
| 57 | 0.033 |
| 58 | 0.091 |
| 60 | 0.019 |
| 61 | 0.010 |
| 63 | 0.046 |
| 64 | 0.052 |
| 65 | 0.045 |
| 67 | 0.031 |
| 68 | 0.018 |
| 70 | 0.017 |
| 73 | 0.024 |
| 75 | 0.035 |
| 76 | 0.036 |
| 77 | 0.039 |
| 79 | 0.061 |
| 80 | 0.035 |
| 81 | 0.012 |
| 82 | 0.011 |
| 83 | 0.027 |
| 85 | 0.040 |
| 99 | 0.043 |
| 100 | 0.036 |
| 102 | 0.036 |
| 103 | 0.042 |
| 104 | 0.019 |
| 105 | 0.028 |
| 106 | 0.052 |
| 107 | 0.012 |
| 111 | 0.037 |
| 112 | 0.051 |
| 113 | 0.022 |
| 115 | 0.052 |
| 126 | 0.032 |
| 127 | 0.040 |
| 128 | 0.081 |
| 133 | 0.06 |
| 134 | 0.095 |

This result shows that Example Compounds have the inhibitory activity on heart muscle cell apoptosis.

Formulation Example 1

| Capsule | |
|---|---|
| (1) Compound obtained in Example 45 | 20 mg |
| (2) lactose | 60 mg |
| (3) microcrystalline cellulose | 9 mg |
| (4) magnesium stearate | 1 mg |
| 1 capsule | 100 mg |

(1), (2), (3) and ½ of (4) were mixed and granulated. The remained (4) was added thereto, and the whole of them is enclosed into gelatin capsules.

Formulation Example 2

| | |
|---|---|
| (1) Compound obtained in Example 45 | 30 mg |
| (2) lactose | 48 mg |
| (3) corn starch | 18 mg |
| (4) microcrystalline cellulose | 3.5 mg |
| (5) magnesium stearate | 0.5 mg |
| 1 tablet | 100 mg |

(1), (2), (3), ⅔ of (4) and ½ of (5) were mixed and granulated. The remained (4) and (5) were added thereto, and they were compressed to form tablets.

INDUSTRIAL APPLICABILITY

This invention provides novel 1,3-benzothiazinone derivatives having an excellent apoptosis inhibitory effect and MIF binding effect and the like. They are safe and useful drugs for preventing and/or treating heart disease, nervous degenerative disease, cerebrovascular disease, central nervous infectious disease, traumatorathy, demyelinating disease, bone and articular disease, kidney ischemia, liver disease, osteomyelodysplasia, AIDS, cancer, and the like.

The invention claimed is:

1. 3-[6-(4-Oxo-4H-1,3-benzothiazin-2-yl)-2-pyridyl]propionic acid or a salt thereof.
2. 3-[6-(7-Chloro-4-oxo-4H-1,3-benzothiazin-2-yl)-4-methyl-2-pyridyl]propionic acid or a salt thereof.
3. 3-[2-(7-Chloro-4-oxo-4H-1,3-benzothiazin-2-yl)-4-pyridyl]propionic acid or a salt thereof.
4. 3-[2-Methyl-6-(4-oxo-4H-1,3-benzothiazin-2-yl)-4-pyridyl]propionic acid or a salt thereof.
5. 3-[2-(7-Chloro-4-oxo-4H-1,3-benzothiazin-2-yl)-6-methyl-4-pyridyl]propionic acid or a salt thereof.
6. 3-[6-(7-Chloro-4-oxo-4H-1,3-benzothiazin-2-yl)-2-pyridyl]propionic acid or a salt thereof.
7. 3-[2-(4-Oxo-4H-1,3-benzothiazin-2-yl)-4-pyridyl]propionic acid or a salt thereof.
8. 2-(6-Propylsulfonyl-2-pyridyl)-4H-1,3-benzothiazin-4-one or a salt thereof.
9. 2-(6-Methylsulfonyl-2-pyridyl)-4H-1,3-benzothiazin-4-one or a salt thereof.
10. 6-(4-Oxo-4H-1,3-benzothiazin-2-yl)-2-pyridinecarboxamide or a salt thereof.
11. N-(6-Aminohexyl)-6-(4-oxo-4H-1,3-benzothiazin-2-yl)-2-pyridinecarboxamide or a salt thereof.

* * * * *